US012161648B2

(12) United States Patent
Spradlin et al.

(10) Patent No.: US 12,161,648 B2
(45) Date of Patent: Dec. 10, 2024

(54) COVALENT TARGETING OF E3 LIGASES

(71) Applicants: The Regents of the University of California, Oakland, CA (US); Novartis AG, Basel (CH)

(72) Inventors: Jessica Spradlin, Berkeley, CA (US); Carl C. Ward, Berkeley, CA (US); Daniel K. Nomura, Walnut Creek, CA (US); Markus Schirle, Cambridge, MA (US); John A. Tallarico, Cambridge, MA (US); Jeffrey McKenna, Cambridge, MA (US); Thomas John Maimone, Richmond, CA (US); Xirui Hu, Cambridge, MA (US)

(73) Assignees: The Regents of the University of California, Oakland, CA (US); Novartis AG, Basel (CH)

( * ) Notice: Subject to any disclaimer, the term of this patent is extended or adjusted under 35 U.S.C. 154(b) by 839 days.

(21) Appl. No.: 17/282,277

(22) PCT Filed: Oct. 9, 2019

(86) PCT No.: PCT/US2019/055461
§ 371 (c)(1),
(2) Date: Apr. 1, 2021

(87) PCT Pub. No.: WO2020/076996
PCT Pub. Date: Apr. 16, 2020

(65) Prior Publication Data
US 2021/0369731 A1     Dec. 2, 2021

Related U.S. Application Data

(60) Provisional application No. 62/743,337, filed on Oct. 9, 2018.

(51) Int. Cl.
| | |
|---|---|
| *A61K 31/551* | (2006.01) |
| *A61K 31/365* | (2006.01) |
| *A61K 31/4535* | (2006.01) |
| *A61K 47/55* | (2017.01) |
| *A61P 35/00* | (2006.01) |

(52) U.S. Cl.
CPC .......... *A61K 31/551* (2013.01); *A61K 31/365* (2013.01); *A61K 31/4535* (2013.01); *A61K 47/55* (2017.08); *A61P 35/00* (2018.01)

(58) Field of Classification Search
CPC ................ A61K 31/551; A61K 31/365; A61K 31/4535; A61K 47/55; A61P 35/00; C07D 519/00; C07D 493/04; C07D 495/14
See application file for complete search history.

(56) References Cited

U.S. PATENT DOCUMENTS

| | | | |
|---|---|---|---|
| 2015/0119435 A1 | 4/2015 | Crews et al. | |
| 2017/0029437 A1 | 2/2017 | Bradner et al. | |
| 2018/0163202 A1* | 6/2018 | Yang | C12N 15/113 |
| 2018/0228907 A1* | 8/2018 | Crew | A61K 47/55 |

FOREIGN PATENT DOCUMENTS

| | | |
|---|---|---|
| CN | 101928747 A | 12/2010 |
| WO | WO-2017/091673 A2 | 6/2017 |
| WO | WO-2017/091673 A3 | 6/2017 |
| WO | WO-2017/091673 A8 | 6/2017 |
| WO | WO-2017/180417 A1 | 10/2017 |
| WO | WO-2018/052945 A1 | 3/2018 |
| WO | WO-2020/146779 A1 | 7/2020 |

OTHER PUBLICATIONS

Backus, K.M. et al. (Jun. 23, 2016). "Proteome-wide covalent ligand discovery in native biological systems," *Nature* 534(7608):570-574.
Bateman, L.A. et al. (Jun. 29, 2017). "Chemoproteomics-enabled covalent ligand screen reveals a cysteine hotspot in reticulon 4 that impairs ER morphology and cancer pathogenicity," *Chem Commun* 53(53):7234-7237.
Burslem, G.M .et al. (Sep. 13, 2017). "Small-Molecule Modulation of Protein Homeostasis," *Chem Rev* 117(17):11269-11301.
Grossman, E.A. et al. (Nov. 16, 2017). "Covalent Ligand Discovery against Druggable Hotspots Targeted by Anti-cancer Natural Products," *Cell Chem Biol* 24(11):1368-1376.e4.
Han, J. et al. (Aug. 2013). "ZNF313 is a novel cell cycle activator with an E3 ligase activity inhibiting cellular senescence by destabilizing p21(WAF1.)," *Cell Death Differ* 20(8):1055-1067.
Henning, N.J. et al. (Apr. 15, 2021). "Discovery of a Covalent FEM1B Recruiter for Targeted Protein Degradation Application," *bioRxiv* 15 pages.
International Search Report mailed on Feb. 5, 2020, for PCT Application No. PCT/US2019/055461, filed Oct. 9, 2019, 8 pages.
Kitagawa, K. et al. (2009). "Ubiquitin-mediated control of oncogene and tumor suppressor gene products," *Cancer Sci* 100(8):1374-1381.
Lai, A.C. et al. (Feb. 2017). "Induced protein degradation: an emerging drug discovery paradigm," *Nat Rev Drug Discov* 16(2):101-114.
Lee, M-G. et al. (Oct. 28, 2014). "XAF1 directs apoptotic switch of p53 signaling through activation of HIPK2 and ZNF313," *PNAS USA* 111(43):15532-15537.

(Continued)

*Primary Examiner* — Alicia L Otton
*Assistant Examiner* — David M Shim
(74) *Attorney, Agent, or Firm* — Mintz, Levin, Cohn, Ferris, Glovsky and Popeo, P.C.

(57) ABSTRACT

Disclosed herein, inter alia, are compositions and methods for targeting E3 ligases. In an aspect is a targeted protein degrader including 1) a targeted protein binder and 2) an E3 Ubiquitin ligase binder, wherein the E3 Ubiquitin ligase is human RNF4 or human RNF114. In an aspect is provided a pharmaceutical composition including a compound as described herein, including embodiments, and a pharmaceutically acceptable excipient.

13 Claims, 55 Drawing Sheets
Specification includes a Sequence Listing.

(56) References Cited

OTHER PUBLICATIONS

Luo, M. et al. (Apr. 15, 2021). "Chemoproteomics-enabled discovery of covalent RNF114-based degraders that mimic natural product function," *Cell Chem Biol* 28(4):559-566.e15.

Nomura, D.K. et al. ((2019). "Target Identification of Bioactive Covalently Acting Natural Products," *Curr Top Microbiol Immunol* 420:351-374.

Spradlin, J.N. et al. (Jul. 2019). "Harnessing the anti-cancer natural product nimbolide for targeted protein degradation," *Nat Chem Biol* 15(7):747-755.

Spradlin, J.N. et al. (Apr. 6, 2021). "Reimagining Druggability Using Chemoproteomic Platforms," *Acc. Chem Res* 54(7):1801-1813.

Tong, B. et al. (Jul. 17, 2020). "A Nimbolide-Based Kinase Degrader Preferentially Degrades Oncogenic BCR-ABL," *ACS Chem Biol* 15(7):1788-1794.

Tong, B. et al. (Sep. 23, 2020). "Bardoxolone conjugation enables targeted protein degradation of $BRD_4$," *Sci Rep* 10(1):15543.

Ward, C.C. et al. (Nov. 15, 2019). "Covalent Ligand Screening Uncovers a RNF4 E3 Ligase Recruiter for Targeted Protein Degradation Applications," *ACS Chem Biol* 14(11):2430-2440.

Weerapana, E. et al. (Dec. 9, 2010). "Quantitative reactivity profiling predicts functional cysteines in proteomes," *Nature* 468(7325):790-795.

Winter, G. E. et al. (Jun. 19, 2015). "Drug Development. Phthalimide conjugation as a strategy for in vivo target protein degradation," *Science* 348(6241):1376-1381.

Written Opinion mailed on Feb. 5, 2020, for PCT Application No. PCT/US2019/055461, filed Oct. 9, 2019, 8 pages.

Zengerle, M. et al. (Aug. 21, 2015). "Selective Small Molecule Induced Degradation of the BET Bromodomain Protein BRD4," *ACS Chem Biol* 10(8):1770-1777.

Lin, B. et al. (Nov. 2017). "Negative regulation of the RLH signaling by the E3 ubiquitin ligase RNF114," *Cytokine* 99:186-193.

Extended European Search Report mailed on May 27, 2022, for EP Patent Application No. 19872219.1, 12 pages.

Häkli, M. et al. (Feb. 27, 2004). "Transcriptional coregulator SNURF (RNF4) possesses ubiquitin E3 ligase activity," *FEBS Lett* 560(1-3):56-62.

Zhou, B. et al. (Jan. 25, 2018). "Discovery of a Small-Molecule Degrader of Bromodomain and Extra-Terminal (BET) Proteins with Picomolar Cellular Potencies and Capable of Achieving Tumor Regression," *Journal of Medicinal Chemistry* 61(2):462-481.

\* cited by examiner

TRH 1-23 reacts with C132 and C135 of RNF4

RNF4 C132

RNF4 C135

TRH 1-23 reactivity with C132/135 of RNF4

RNF4 auto-ubiquitination activity

CCW 28-3: an RNF4 recruiter-based degrader gel-based ABPP of CCW 28-3 against RNF4

CCW 28-3 degradation of BRD4 in 231MFP breast cancer cells

DKM 2-76

TRH 1-74

μM  -  100  10  1

RNF4

IA-rhodamine

RNF4 silver staining

μM  -  100  10  1

RNF4

IA-rhodamine

RNF4 silver staining

YP 1-44 (μM)   -   100  10   1

TRH 1-23 (μM)   -   100  10   1 nimbolide nimbolide effects on breast cancer cell proliferation and survival isoTOP-ABPP analysis of nimbolide in 231MFP breast cancer cell proteomes *in vitro* isoTOP-ABPP analysis of nimbolide in 231MFP breast cancer cells *in situ* nimbolide-alkyne probe labeling of 231MFP cell proteomes nimbolide-alkyne probe labeling of RNF114 nimbolide-based degraders

XH1 does not affect BRD4 degradation proteosome inhibitor rescue of XH2-mediate BRD4 degradation in 231MFP breast cancer cells dose-response of MZ1 versus XH2

E1 inhibitor rescue of XH2-mediate BRD4 degradation in 231MFP breast cancer cells developing a RNF114 probe JNS27 covalent ligand screening hits

RNF114 autoubiquitination activity

FIG. 16A (cont.)

FIG. 19D
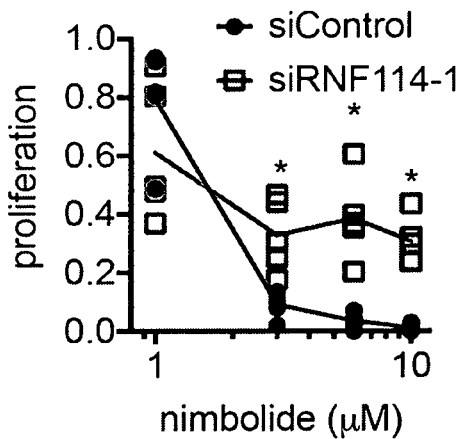
FIG. 20A
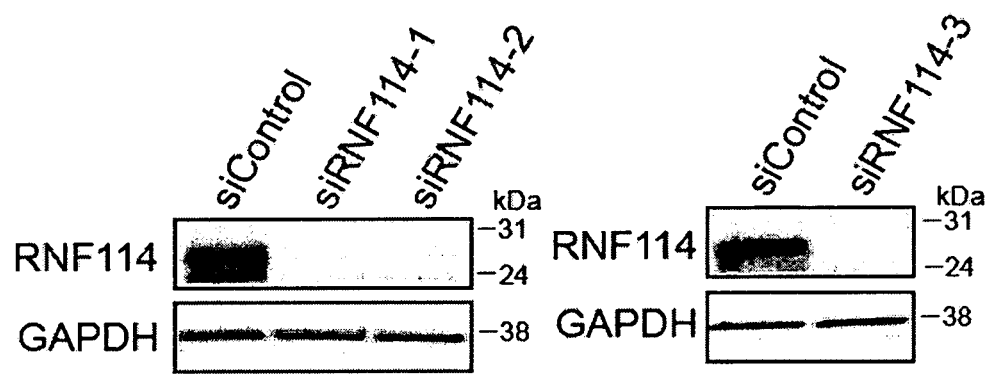
FIG. 20B
FIG. 20C
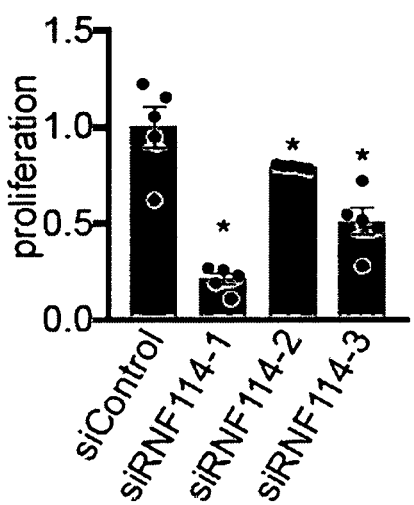
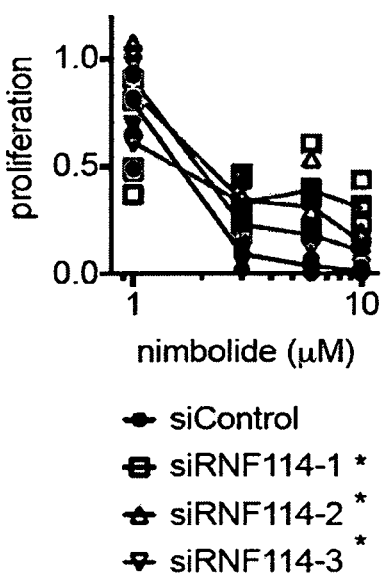

IC50 0.73 ± 0.13 µM nimbolide-alkyne in situ labeling,
anti-Flag pulldown in RNF114-Flag cells,
CuAAC with rhodamine-azide nimbolide-alkyne in situ labeling,
CuAAC with biotin-azide,
avidin pulldown XH2 IC50 against RNF114
0.24 ± 0.12

SEQUENCE LISTING

<160> NUMBER OF SEQ ID NOS: 16

<210> SEQ ID NO 1
<211> LENGTH: 190
<212> TYPE: PRT
<213> ORGANISM: Artificial Sequence
<220> FEATURE:
<223> OTHER INFORMATION: Synthetic polypeptide

<400> SEQUENCE: 1

Met Ser Thr Arg Lys Arg Gly Gly Ala Ile Asn Ser Arg Gln Ala
1               5                   10                  15

Gln Lys Arg Thr Arg Glu Ala Thr Ser Thr Pro Glu Ile Ser Leu Glu
                20                  25                  30

Ala Glu Pro Ile Glu Leu Val Glu Thr Ala Gly Asp Glu Ile Val Asp
            35                  40                  45

Leu Thr Cys Glu Ser Leu Glu Pro Val Val Asp Leu Thr His Asn
    50                  55                  60

Asp Ser Val Val Ile Val Asp Glu Arg Arg Pro Arg Arg Asn Ala
65                  70                  75                  80

Arg Arg Leu Pro Gln Asp His Ala Asp Ser Cys Val Val Ser Ser Asp
                85                  90                  95

Asp Glu Glu Leu Ser Arg Asp Arg Asp Val Tyr Val Thr Thr His Thr
            100                 105                 110

Pro Arg Asn Ala Arg Asp Glu Gly Ala Thr Gly Leu Arg Pro Ser Gly
        115                 120                 125

Thr Val Ser Cys Pro Ile Cys Met Asp Gly Tyr Ser Glu Ile Val Gln
    130                 135                 140

Asn Gly Arg Leu Ile Val Ser Thr Glu Cys Gly His Val Phe Cys Ser
145                 150                 155                 160

Gln Cys Leu Arg Asp Ser Leu Lys Asn Ala Asn Thr Cys Pro Thr Cys
                165                 170                 175

Arg Lys Lys Ile Asn His Lys Arg Tyr His Pro Ile Tyr Ile
            180                 185                 190

<210> SEQ ID NO 2
<211> LENGTH: 228
<212> TYPE: PRT
<213> ORGANISM: Artificial Sequence
<220> FEATURE:
<223> OTHER INFORMATION: Synthetic polypeptide

<400> SEQUENCE: 2

Met Ala Ala Gln Gln Arg Asp Cys Gly Gly Ala Ala Gln Leu Ala Gly
1               5                   10                  15

Pro Ala Ala Glu Ala Asp Pro Leu Gly Arg Phe Thr Cys Pro Val Cys
                20                  25                  30

Leu Glu Val Tyr Glu Lys Pro Val Gln Val Pro Cys Gly His Val Phe
            35                  40                  45

```
Cys Ser Ala Cys Leu Gln Glu Cys Leu Lys Pro Lys Pro Val Cys
        50                  55                  60

Gly Val Cys Arg Ser Ala Leu Ala Pro Gly Val Arg Ala Val Glu Leu
65                  70                  75                  80

Glu Arg Gln Ile Glu Ser Thr Glu Thr Ser Cys His Gly Cys Arg Lys
                85                  90                  95

Asn Phe Phe Leu Ser Lys Ile Arg Ser His Val Ala Thr Cys Ser Lys
            100                 105                 110

Tyr Gln Asn Tyr Ile Met Glu Gly Val Lys Ala Thr Ile Lys Asp Ala
            115                 120                 125

Ser Leu Gln Pro Arg Asn Val Pro Asn Arg Tyr Thr Phe Pro Cys Pro
        130                 135                 140

Tyr Cys Pro Glu Lys Asn Phe Asp Gln Glu Gly Leu Val Glu His Cys
145                 150                 155                 160

Lys Leu Phe His Ser Thr Asp Thr Lys Ser Val Val Cys Pro Ile Cys
                165                 170                 175

Ala Ser Met Pro Trp Gly Asp Pro Asn Tyr Arg Ser Ala Asn Phe Arg
            180                 185                 190

Glu His Ile Gln Arg Arg His Arg Phe Ser Tyr Asp Thr Phe Val Asp
        195                 200                 205

Tyr Asp Val Asp Glu Glu Asp Met Met Asn Gln Val Leu Gln Arg Ser
    210                 215                 220

Ile Ile Asp Gln
225

<210> SEQ ID NO 3
<211> LENGTH: 1362
<212> TYPE: PRT
<213> ORGANISM: Artificial Sequence
<220> FEATURE:
<223> OTHER INFORMATION: Synthetic polypeptide

<400> SEQUENCE: 3

Met Ser Ala Glu Ser Gly Pro Gly Thr Arg Leu Arg Asn Leu Pro Val
1               5                   10                  15

Met Gly Asp Gly Leu Glu Thr Ser Gln Met Ser Thr Thr Gln Ala Gln
            20                  25                  30

Ala Gln Pro Gln Pro Ala Asn Ala Ala Ser Thr Asn Pro Pro Pro Pro
        35                  40                  45

Glu Thr Ser Asn Pro Asn Lys Pro Lys Arg Gln Thr Asn Gln Leu Gln
    50                  55                  60

Tyr Leu Leu Arg Val Val Leu Lys Thr Leu Trp Lys His Gln Phe Ala
65                  70                  75                  80

Trp Pro Phe Gln Gln Pro Val Asp Ala Val Lys Leu Asn Leu Pro Asp
                85                  90                  95

Tyr Tyr Lys Ile Ile Lys Thr Pro Met Asp Met Gly Thr Ile Lys Lys
            100                 105                 110

Arg Leu Glu Asn Asn Tyr Tyr Trp Asn Ala Gln Glu Cys Ile Gln Asp
        115                 120                 125

Phe Asn Thr Met Phe Thr Asn Cys Tyr Ile Tyr Asn Lys Pro Gly Asp
    130                 135                 140

Asp Ile Val Leu Met Ala Glu Ala Leu Glu Lys Leu Phe Leu Gln Lys
145                 150                 155                 160

Ile Asn Glu Leu Pro Thr Glu Glu Thr Glu Ile Met Ile Val Gln Ala
                165                 170                 175
```

-continued

```
Lys Gly Arg Gly Arg Gly Arg Lys Glu Thr Gly Thr Ala Lys Pro Gly
                180                 185                 190

Val Ser Thr Val Pro Asn Thr Thr Gln Ala Ser Thr Pro Pro Gln Thr
            195                 200                 205

Gln Thr Pro Gln Pro Asn Pro Pro Val Gln Ala Thr Pro His Pro
        210                 215                 220

Phe Pro Ala Val Thr Pro Asp Leu Ile Val Gln Thr Pro Val Met Thr
225                 230                 235                 240

Val Val Pro Pro Gln Pro Leu Gln Thr Pro Pro Val Pro Pro Gln
                245                 250                 255

Pro Gln Pro Pro Ala Pro Ala Pro Gln Pro Val Gln Ser His Pro
            260                 265                 270

Pro Ile Ile Ala Ala Thr Pro Gln Pro Val Lys Thr Lys Lys Gly Val
        275                 280                 285

Lys Arg Lys Ala Asp Thr Thr Thr Pro Thr Thr Ile Asp Pro Ile His
    290                 295                 300

Glu Pro Pro Ser Leu Pro Pro Glu Pro Lys Thr Thr Lys Leu Gly Gln
305                 310                 315                 320

Arg Arg Glu Ser Ser Arg Pro Val Lys Pro Pro Lys Lys Asp Val Pro
                325                 330                 335

Asp Ser Gln Gln His Pro Ala Pro Glu Lys Ser Ser Lys Val Ser Glu
            340                 345                 350

Gln Leu Lys Cys Cys Ser Gly Ile Leu Lys Glu Met Phe Ala Lys Lys
        355                 360                 365

His Ala Ala Tyr Ala Trp Pro Phe Tyr Lys Pro Val Asp Val Glu Ala
    370                 375                 380

Leu Gly Leu His Asp Tyr Cys Asp Ile Ile Lys His Pro Met Asp Met
385                 390                 395                 400

Ser Thr Ile Lys Ser Lys Leu Glu Ala Arg Glu Tyr Arg Asp Ala Gln
                405                 410                 415

Glu Phe Gly Ala Asp Val Arg Leu Met Phe Ser Asn Cys Tyr Lys Tyr
            420                 425                 430

Asn Pro Pro Asp His Glu Val Val Ala Met Ala Arg Lys Leu Gln Asp
        435                 440                 445

Val Phe Glu Met Arg Phe Ala Lys Met Pro Asp Glu Pro Glu Glu Pro
    450                 455                 460

Val Val Ala Val Ser Ser Pro Ala Val Pro Pro Thr Lys Val Val
465                 470                 475                 480

Ala Pro Pro Ser Ser Ser Asp Ser Ser Ser Asp Ser Ser Ser Asp Ser
                485                 490                 495

Asp Ser Ser Thr Asp Asp Ser Glu Glu Glu Arg Ala Gln Arg Leu Ala
            500                 505                 510

Glu Leu Gln Glu Gln Leu Lys Ala Val His Glu Gln Leu Ala Ala Leu
        515                 520                 525

Ser Gln Pro Gln Gln Asn Lys Pro Lys Lys Glu Lys Asp Lys Lys
    530                 535                 540

Glu Lys Lys Lys Glu Lys His Lys Arg Lys Glu Glu Val Glu Glu Asn
545                 550                 555                 560

Lys Lys Ser Lys Ala Lys Glu Pro Pro Lys Lys Thr Lys Lys Asn
                565                 570                 575

Asn Ser Ser Asn Ser Asn Val Ser Lys Lys Glu Pro Ala Pro Met Lys
            580                 585                 590
```

```
Ser Lys Pro Pro Pro Thr Tyr Glu Ser Glu Glu Asp Lys Cys Lys
        595                 600                 605

Pro Met Ser Tyr Glu Lys Arg Gln Leu Ser Leu Asp Ile Asn Lys
610                 615                 620

Leu Pro Gly Glu Lys Leu Gly Arg Val Val His Ile Ile Gln Ser Arg
625                 630                 635                 640

Glu Pro Ser Leu Lys Asn Ser Asn Pro Asp Glu Ile Glu Ile Asp Phe
                645                 650                 655

Glu Thr Leu Lys Pro Ser Thr Leu Arg Glu Leu Glu Arg Tyr Val Thr
                660                 665                 670

Ser Cys Leu Arg Lys Lys Arg Lys Pro Gln Ala Glu Lys Val Asp Val
        675                 680                 685

Ile Ala Gly Ser Ser Lys Met Lys Gly Phe Ser Ser Ser Glu Ser Glu
        690                 695                 700

Ser Ser Ser Glu Ser Ser Ser Asp Ser Glu Asp Ser Glu Thr Glu
705                 710                 715                 720

Met Ala Pro Lys Ser Lys Lys Gly His Pro Gly Arg Glu Gln Lys
                725                 730                 735

Lys His His His His His Gln Gln Met Gln Gln Ala Pro Ala Pro
            740                 745                 750

Val Pro Gln Gln Pro Pro Pro Gln Gln Pro Pro Pro Pro
        755                 760                 765

Pro Pro Gln Gln Gln Gln Pro Pro Pro Pro Pro Pro Ser
        770                 775                 780

Met Pro Gln Gln Ala Ala Pro Ala Met Lys Ser Ser Pro Pro Phe
785                 790                 795                 800

Ile Ala Thr Gln Val Pro Val Leu Glu Pro Gln Leu Pro Gly Ser Val
                805                 810                 815

Phe Asp Pro Ile Gly His Phe Thr Gln Pro Ile Leu His Leu Pro Gln
                820                 825                 830

Pro Glu Leu Pro Pro His Leu Pro Gln Pro Glu His Ser Thr Pro
        835                 840                 845

Pro His Leu Asn Gln His Ala Val Val Ser Pro Pro Ala Leu His Asn
        850                 855                 860

Ala Leu Pro Gln Gln Pro Ser Arg Pro Ser Asn Arg Ala Ala Ala Leu
865                 870                 875                 880

Pro Pro Lys Pro Ala Arg Pro Ala Val Ser Pro Ala Leu Thr Gln
                885                 890                 895

Thr Pro Leu Leu Pro Gln Pro Pro Met Ala Gln Pro Pro Gln Val Leu
        900                 905                 910

Leu Glu Asp Glu Glu Pro Pro Ala Pro Pro Leu Thr Ser Met Gln Met
        915                 920                 925

Gln Leu Tyr Leu Gln Gln Leu Gln Lys Val Gln Pro Pro Thr Pro Leu
        930                 935                 940

Leu Pro Ser Val Lys Val Gln Ser Gln Pro Pro Pro Leu Pro Pro
945                 950                 955                 960

Pro Pro His Pro Ser Val Gln Gln Gln Leu Gln Gln Pro Pro Pro
                965                 970                 975

Pro Pro Pro Pro Gln Pro Gln Pro Pro Gln Gln His Gln Pro
                980                 985                 990

Pro Pro Arg Pro Val His Leu Gln  Pro Met Gln Phe Ser  Thr His Ile
        995                 1000                 1005
```

```
Gln Gln Pro Pro Pro Pro Gln Gly Gln Gln Pro Pro His Pro Pro
    1010                1015                1020

Pro Gly Gln Gln Pro Pro Pro Gln Pro Ala Lys Pro Gln Gln
    1025                1030                1035

Val Ile Gln His His His Ser Pro Arg His His Lys Ser Asp Pro
    1040                1045                1050

Tyr Ser Thr Gly His Leu Arg Glu Ala Pro Ser Pro Leu Met Ile
    1055                1060                1065

His Ser Pro Gln Met Ser Gln Phe Gln Ser Leu Thr His Gln Ser
    1070                1075                1080

Pro Pro Gln Gln Asn Val Gln Pro Lys Lys Gln Glu Leu Arg Ala
    1085                1090                1095

Ala Ser Val Val Gln Pro Gln Pro Leu Val Val Val Lys Glu Glu
    1100                1105                1110

Lys Ile His Ser Pro Ile Ile Arg Ser Glu Pro Phe Ser Pro Ser
    1115                1120                1125

Leu Arg Pro Glu Pro Pro Lys His Pro Glu Ser Ile Lys Ala Pro
    1130                1135                1140

Val His Leu Pro Gln Arg Pro Glu Met Lys Pro Val Asp Val Gly
    1145                1150                1155

Arg Pro Val Ile Arg Pro Glu Gln Asn Ala Pro Pro Pro Gly
    1160                1165                1170

Ala Pro Asp Lys Asp Lys Gln Lys Gln Glu Pro Lys Thr Pro Val
    1175                1180                1185

Ala Pro Lys Lys Asp Leu Lys Ile Lys Asn Met Gly Ser Trp Ala
    1190                1195                1200

Ser Leu Val Gln Lys His Pro Thr Thr Pro Ser Ser Thr Ala Lys
    1205                1210                1215

Ser Ser Ser Asp Ser Phe Glu Gln Phe Arg Arg Ala Ala Arg Glu
    1220                1225                1230

Lys Glu Glu Arg Glu Lys Ala Leu Lys Ala Gln Ala Glu His Ala
    1235                1240                1245

Glu Lys Glu Lys Glu Arg Leu Arg Gln Glu Arg Met Arg Ser Arg
    1250                1255                1260

Glu Asp Glu Asp Ala Leu Glu Gln Ala Arg Arg Ala His Glu Glu
    1265                1270                1275

Ala Arg Arg Arg Gln Glu Gln Gln Gln Gln Arg Gln Glu Gln
    1280                1285                1290

Gln Gln Gln Gln Gln Gln Gln Ala Ala Ala Val Ala Ala Ala Ala
    1295                1300                1305

Thr Pro Gln Ala Gln Ser Ser Gln Pro Gln Ser Met Leu Asp Gln
    1310                1315                1320

Gln Arg Glu Leu Ala Arg Lys Arg Glu Gln Glu Arg Arg Arg Arg
    1325                1330                1335

Glu Ala Met Ala Ala Thr Ile Asp Met Asn Phe Gln Ser Asp Leu
    1340                1345                1350

Leu Ser Ile Phe Glu Glu Asn Leu Phe
    1355                1360

<210> SEQ ID NO 4
<211> LENGTH: 58
<212> TYPE: DNA
<213> ORGANISM: Artificial Sequence
<220> FEATURE:
```

<223> OTHER INFORMATION: Synthetic polynucleotide

<400> SEQUENCE: 4
ccggccatgg ctgccgtaag aatttctcga gaaattctta cggcagccat ggttttg    58

<210> SEQ ID NO 5
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 5
gcaagctgac cctgaagttc at    22

<210> SEQ ID NO 6
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 6
aatgttccaa accg    14

<210> SEQ ID NO 7
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 7
ttgcagtgtt ccac    14

<210> SEQ ID NO 8
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 8
cccaccgtgt tcttcgacat t    21

<210> SEQ ID NO 9
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 9
ggacccgtat gctttaggat ga    22

<210> SEQ ID NO 10
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 10
gugugaaggc caccauuaa    19

```
<210> SEQ ID NO 11
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 11
gcuuagaggu guacgagaa                                              19

<210> SEQ ID NO 12
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 12
gcacggauac caaaucugu                                              19

<210> SEQ ID NO 13
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 13
agaccagcau gacagauuu                                              19

<210> SEQ ID NO 14
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 14
cugagaaguc gucgggcga                                              19

<210> SEQ ID NO 15
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 15
tgtccgtcag aacccatgc                                              19

<210> SEQ ID NO 16
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 16
aaagtcgaag ttccatcgct c                                           21
```

COVALENT TARGETING OF E3 LIGASES

CROSS-REFERENCES TO RELATED APPLICATIONS

This application is the national stage filing under 35 U.S.C. § 371 of International Application No. PCT/US2019/055461 filed Oct. 9, 2019, which claims the benefit of U.S. Provisional Application No. 62/743,337, filed Oct. 9, 2018, which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 052103-517N01US_Sequence_Listing_ST25.txt, created Mar. 16, 2021, 18,717 bytes, machine format IBM-PC, MS Windows operating system, is hereby incorporated by reference.

BACKGROUND

Targeted protein degradation has arisen as a powerful strategy for the treatment of diseases. This approach employs bifunctional degraders consisting of a protein targeting ligand linked to an E3 ligase recruiter which brings the E3 ligase to particular protein substrates to ubiquitinate and degrade these substrates in a proteasome-dependent manner. One challenge with this approach, however, is the relatively few E3 ligase recruiters that currently exist for targeted protein degradation applications. Described herein, inter alia, are solutions to these and other problems in the art.

BRIEF SUMMARY

In an aspect is a targeted protein degrader including 1) a targeted protein binder and 2) an E3 Ubiquitin ligase binder, wherein the E3 Ubiquitin ligase is human RNF4 or human RNF114.

In an aspect is provided a pharmaceutical composition including a compound as described herein, including embodiments, and a pharmaceutically acceptable excipient.

In an aspect is provided a method of reducing (e.g., reducing relative to a control) the level of a cellular protein, said method including contacting the cellular protein with a targeted protein degrader. In embodiments, the targeted protein degrader is a compound described herein.

In an aspect is provided a method of treating cancer, the method including contacting a cellular protein associated with cancer with a targeted protein degrader (e.g., a compound described herein).

In an aspect is provided a method of treating cancer, the method including administering to a subject in need thereof a therapeutically effective amount of a targeted protein degrader as described herein, including embodiments.

In an aspect is provided a method of reducing the level of a cellular protein, the method including contacting the cellular protein with a targeted protein degrader and thereby form a targeted protein degrader-cellular protein complex; wherein the targeted protein degrader includes: (i) a monovalent E3 Ubiquitin ligase binder; (ii) a monovalent targeted protein binder; and (iii) a binder linker directly bonded to the monovalent E3 Ubiquitin ligase binder and the targeted protein binder.

In an aspect is provided a method of identifying a cellular protein contacted by a targeted protein binder including: (A) contacting a first sample of a cell proteome or cell with the targeted protein binder thereby forming a cellular protein-targeted protein binder complex; (B) contacting both the resulting first sample of a cell proteome or cell of step A and a second sample of the cell proteome or cell that has not been contacted with the targeted protein binder, with a compound having the formula:

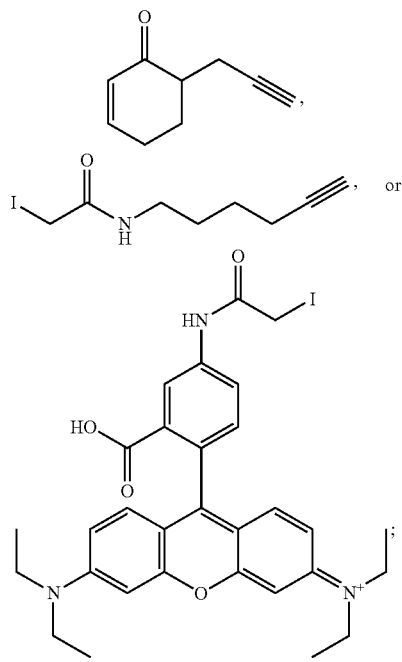

(C) contacting the resulting first sample of step B with a first detectable agent and the resulting second sample of step B with a second detectable agent; (D) measuring the level of the first detectable agent and second detectable agent bound to selected proteins; and (E) identifying the cellular protein in a cellular protein-targeted protein binder complex by measuring a difference between the level of the first detectable agent and second detectable agent, each bound to the cellular protein capable of forming the cellular protein-targeted protein binder complex.

In an aspect is a method of making an E3 Ubiquitin ligase-E3 Ubiquitin ligase binder-cellular protein complex including: (A) contacting the E3 Ubiquitin ligase with an E3 Ubiquitin ligase binder and thereby forming an E3 Ubiquitin ligase-E3 Ubiquitin ligase binder complex; and (B) contacting the E3 Ubiquitin ligase-E3 Ubiquitin ligase binder complex with the cellular protein and thereby forming an E3 Ubiquitin ligase-E3 Ubiquitin ligase binder-cellular protein complex.

In an aspect is provided a method of making a cellular protein-E3 Ubiquitin ligase binder-E3 Ubiquitin ligase complex including: (A) contacting the cellular protein with an E3 Ubiquitin ligase binder and thereby forming a cellular protein-E3 Ubiquitin ligase binder complex; and (B) contacting the cellular protein-E3 Ubiquitin ligase binder complex with the E3 Ubiquitin ligase and thereby forming a cellular protein-E3 Ubiquitin ligase binder-E3 Ubiquitin ligase complex.

In an aspect is provided a method of inhibiting the formation of a cellular protein-E3 Ubiquitin ligase complex including contacting the E3 Ubiquitin ligase with an E3

Ubiquitin ligase binder and thereby inhibiting the formation of a cellular protein-E3 Ubiquitin ligase complex.

BRIEF DESCRIPTION OF THE DRAWINGS

(FIG. 1A) Gel-based ABPP labeling of E3 ligases MDM2, RNF4, and UBE3A. Pure protein was labeled with IA-rhodamine for 30 min at room temperature, followed by SDS/PAGE and visualization by in-gel fluorescence. (FIG. 1B) Schematic of gel-based ABPP screen of covalent ligands (50 μM) against IA-rhodamine labeling of pure RNF4, looking for compounds that inhibit probe labeling resulting in loss of fluorescence. (FIGS. 1C-1D) Gel-based ABPP screen of cysteine-reactive covalent ligands against IA-rhodamine labeling of RNF4. Covalent ligands were pre-incubated with pure RNF4 protein for 30 min prior to IA-rhodamine labeling (250 nM) for 1 h. Proteins were subjected to SDS/PAGE and visualized by in-gel fluorescence. Highlighted were potential hits from this screen. (FIG. 1E) Structures and gel-based ABPP confirmation of reproducible RNF4 screening hits, performed as described in (FIGS. 1C-1D). Gels were also silver stained.

(FIG. 2A) LC-MS/MS analysis of TRH 1-23 covalent adduct on RNF4. RNF4 was incubated with TRH 1-23 (50 μM) for 30 min at RT. RNF4 was digested with trypsin and tryptic digests were analyzed by LC-MS/MS and we searched for the TRH 1-23 modified adduct. Shown are the MS/MS spectra of TRH 1-23-modified C132 and C135 RNF4 tryptic peptide. Highlighted in the peptide sequence is the cysteine that was modified. Peptide sequences correspond to residues 118-147 of SEQ ID NO:1. (FIG. 2B) Schematic of TRH 1-23 reactivity with C132 or C135 of RNF4. (FIG. 2C) TRH 1-23 does not inhibit RNF4 autoubiquitination assay. RNF4 was pre-incubated with TRH 1-23 (100 μM) followed by addition of UBA1, E2 enzyme, and ATP for 40 min at 37 C. The reaction was quenched and subjected to SDS/PAGE and Western blotting for RNF4. Gel shown in (FIG. 2C) is a representative gel from n=3.

(FIGS. 3A-3B) Analogs of TRH 1-23 were tested against IA-rhodamine labeling of RNF4 using gel-based ABPP. (FIG. 3C) CCW16 was tested against IA-rhodamine labeling of RNF4 using gel-based ABPP. For (FIGS. 3A-3C), covalent ligands were pre-incubated with pure RNF4 protein for 30 min prior to IA-rhodamine labeling for 1 h. Proteins were subjected to SDS/PAGE and visualized by in-gel fluorescence. In (FIG. 3C), gels were quantified by densitometry to calculate IC50 values. Gel shown in (FIG. 3C) is a representative gel from n=3.

(FIG. 4A) Structure of CCW 28-3, an RNF4-recruiter-based degrader linked to BRD4 inhibitor JQ1. (FIG. 4B) Gel-based ABPP analysis of CCW 28-3 against pure human RNF4. CCW 28-3 was pre-incubated with pure RNF4 protein for 30 min prior to IA-rhodamine labeling for 1 h. Proteins were subjected to SDS/PAGE and visualized by in-gel fluorescence. Gels were quantified by densitometry to calculate IC50 values. (FIG. 4C) CCW 28-3 treatment in 231MFP breast cancer cells leads to BRD4 degradation. 231MFP breast cancer cells were treated with vehicle DMSO or CCW 28-3 for 3 h. Proteins were subjected to SDS/PAGE and Western blotting for BRD4 and GAPDH loading control. (FIGS. 4D, 4E) CCW 28-3 treatment in 231MFP breast cancer cells leads to proteasome-, E1 inhibitor-, and BRD4 inhibitor-dependent BRD4 degradation. Vehicle DMSO or proteasome inhibitor bortezomib (BTZ) (10 μM), E1 inhibitor TAK-243 (10 μM), or BRD4 inhibitor JQ1 (10 μM) were pre-incubated for 30 min prior to treatment with MZ1 (1 μM) or CCW 28-3 (1 μM) for 3 h. Proteins were subjected to SDS/PAGE and Western blotting for BRD4 and actin loading control. (FIG. 4F) RNF4 wild-type and knockout Hela cells were treated with CCW 28-3 (10 μM) for 5 h and subjected to SDS/PAGE and Western blotting for BRD4, RNF4, and GAPDH. Blots in (FIGS. 4B-4F) were quantified by densitometry. Data in (FIGS. 4B-4F) are from representative gels from n=3. Bar graphs are average±sem, n=3-5/group. Significance is expressed as *p<0.05 compared to vehicle-treated controls and #p<0.05 compared to CCW 28-3 treated groups in (B, D-E) and CCW 28-3 treated wild-type cells in (FIG. 4F).

(FIG. 8A) Structure of nimbolide. Nimbolide possesses a cyclic enone that is potentially cysteine-reactive. (FIGS. 8B-8C) 231MFP and HCC38 breast cancer cell proliferation in serum-containing media and serum-free cell survival. Cells were treated with DMSO vehicle or nimbolide and cell viability was assessed after 48 h by Hoechst stain. Data shown in (FIGS. 8B-8C) are average±sem, n=6/group. Significance is expressed as *p<0.05 compared to vehicle-treated controls.

(FIG. 9A) Schematic of isoTOP-ABPP in which 231MFP breast cancer cell proteomes or cells were pre-treated with DMSO or nimbolide (10 μM, 30 min in vitro or 1.5 h in situ) prior to labeling of proteomes in vitro with IA-alkyne (100 μM, 1 h), followed by appendage of isotopically light (for DMSO-treated) or heavy (for nimbolide-treated) TEV protease cleavable biotin-azide tags by copper-catalyzed azide-alkyne cycloaddition (CuAAC). Control and treated proteomes were subsequently combined in a 1:1 ratio, probe-labeled proteins were avidin-enriched, digested with trypsin, and probe-modified tryptic peptides were eluted by TEV protease, analyzed by LC-MS/MS, and light to heavy probe-modified peptide ratios were quantified. (FIG. 9B) isoTOP-ABPP analysis of nimbolide (10 µM) in 231MFP breast cancer cell proteomes in vitro analyzed as described in (FIG. 9A). Three targets that showed light/heavy ratios >5 included C308 of PTOV1, C8 of RNF114, and C123 of PFKP. (FIG. 9C) isoTOP-ABPP analysis of nimbolide (10 µM) in 231MFP breast cancer cells in situ analyzed as described in (FIG. 9A). (FIG. 9D) RNF114 was stably knocked down using a short-hairpin RNA oligonucleotide in 231MFP cells. RNF114 knockdown in shRNF114 cells was confirmed by qPCR in comparison to shControl cells. Cell proliferation was assessed 48 h after seeding cells by Hoechst stain. (FIG. 9E) 231MFP shControl and shRNF114 sensitivity to nimbolide. 231MFP shControl and shRNF114 cells were treated with DMSO vehicle or nimbolide and cell proliferation was assessed after 48 h by Hoechst stain. % proliferation with nimbolide treatment was normalized against respective shControl or shRNF114 control groups. Data shown in (FIGS. 9D-9E) are average±sem. Data shown in (FIGS. 9B-9E) are from n=6/group. Significance in (FIGS. 9D, 9E) is expressed as *p<0.05 compared to shControl groups.

(FIG. 10A) Nimbolide targets an intrinsically disordered region within RNF114 as assessed by PONDR. (FIG. 10B) Route for synthesis of the alkyne-functionalized nimbolide probe. (FIG. 10C) Nimbolide probe labeling of 231MFP breast cancer cell proteomes. 231MFP proteomes were pre-incubated with DMSO or nimbolide (10 µM, 30 min) prior to labeling with the nimbolide-alkyne probe (1 µM, 1 h), followed by CuAAC-appendage of rhodamine-azide, SDS/PAGE, and analysis of in-gel fluorescence. Nimbolide-competed bands correspond to the molecular weights of PTOV1 and RNF114. (FIG. 10D) Gel-based ABPP analysis of pure human RNF114 protein labeled with nimbolide probe. In the upper two panels, pure RNF114 protein was pre-incubated with DMSO vehicle or nimbolide (100 µM, 30 min) prior to labeling with the nimbolide probe (10 µM, 1 h) in PBS. In the lower two panels, pure wild-type and C8A mutant RNF114 protein were labeled with the nimbolide probe (10 µM, 1 h) in PBS with 1 mg/ml BSA. For both experiments, shown are nimbolide-alkyne labeling and silver staining of RNF114. (FIG. 10E) Pure RNF114 protein was labeled with nimbolide (100 µM, 1 h) and subjected to tryptic digestion and LC-MS/MS analysis. Shown is the nimbolide-modified adduct on C8 of RNF114. Peptide sequence corresponds to residues 7-26 of SEQ ID NO:2. Data shown in (FIGS. 10C-10D) are from n=3/group.

(FIG. 11A) RNF114 ubiquitination assay with pure GST-Ube1, GST-UBE2D1, and RNF114 protein, Flag-Ubiquitin and ATP with or without addition of p21 and blotting against Flag-ubiquitin (left) or p21 (right). DMSO or Nimbolide (100 µM) was pre-incubated with RNF114, before the addition of the E1 and E2 enzymes, Flag-ubiquitin and ATP to start the reaction. (FIG. 11B) RNF114 autoubiquitination assay with DMSO or nimbolide (100 M) treatment with wild-type or C8A mutant RNF114. (FIG. 11C) In an in vitro incubation of pure RNF114 and p21 protein, Flag-RNF114 pulldown and p21 enrichment was inhibited by nimbolide (100 µM). D) 231MFP cells were treated with nimbolide (100 µM). Shown are p21 levels in DMSO control or nimbolide-treated cells. Gels shown in (FIGS. 11A-11D) are representative images from n=3/group. Data shown in (FIG. 11C) are average±sem. Data shown in (FIG. 11C) are from n=3/group. Significance in (FIG. 11C) is expressed as *p<0.05 compared to the p21/RNF114 group in (FIG. 11C) or against vehicle-treated control groups for each time point in (FIG. 11D).

(FIG. 12A) Route for synthesizing XH1 and XH2, nimbolide-based degraders consisting of nimbolide as an RNF114 recruiter, linkers, and the BRD4 inhibitor JQ1. (FIGS. 12B, 12C) BRD4 levels in 231MFP breast cancer cells pre-treated with DMSO vehicle or proteasome inhibitor bortezomib (BTZ) (1 µM) 30 min prior to and also during treatment with XH1 (FIG. 12B) or XH2 (FIG. 12C) treatment (100 nM) for 12 h. (FIG. 12D) BRD4 levels in 231MFP breast cancer cells treated with MZ1 versus XH2 treatment for 12 h. (FIGS. 12E-12G) BRD4 levels in 231MFP breast cancer cells pre-treated with DMSO vehicle or E3 ligase inhibitor TAK-243 (10 µM) (E), JQ1 (1 µM) (F), or emetine (75 µM) (FIG. 12G) for 30 min prior to and also during XH2 treatment (100 nM) for 12 h. Long and short BRD4 isoforms and GAPDH loading controls were visualized by SDS/PAGE and Western blotting and quantified by densitometry in (FIGS. 12B-12G). Gels shown in (B-G) are representative images from n=3/group. Data shown in (B, C, E-G) are average±sem. Significance in (FIGS. 12B, 12C, 12E-12G) is expressed as *p<0.05 compared to the vehicle-treated control groups and #p<0.05 compared to XH2-treated groups.

(FIG. 13A) Gel-based ABPP analysis of nimbolide competition against IA-alkyne (10 µM) or JNS27 (50 µM) labeling of pure RNF114 protein. Structures of IA-alkyne and JNS27 probes are shown with reactive moieties highlighted in red. Shown also is gel-based ABPP analysis of nimbolide (50 µM) competition against JNS27 labeling of wild-type and C8A mutant RNF114 protein. In these experiments, DMSO or nimbolide was pre-incubated for 30 min prior to probe labeling for 1 h. (FIG. 13B) Upon screening a library of cysteine-reactive covalent ligands against JNS27 labeling of RNF114, EN62 was one of the top hits. Shown is the structure of EN62 with the acrylamide reactive moiety highlighted in red. Shown also is a gel-based ABPP analysis of EN62 against JNS27 labeling of pure RNF114. (FIG. 13C) RNF114 autoubiquitination assay with DMSO or EN62 (50 µM) treatment with wild-type or C8A mutant RNF114. (FIG. 13D) IsoTOP-ABPP analysis of EN62 in 231MFP breast cancer cell proteomes in vitro. DMSO or EN62 (50 µM) were pre-incubated with 231MFP proteomes 30 min prior to IA-alkyne labeling (100 µM) for 1 h, followed by the isoTOP-ABPP method. (FIG. 13E) 231MFP cell survival with EN62 after 48 h assessed by Hoechst stain. (FIG. 13F) 231MFP tumor xenograft growth in C.B-17 female SCID mice treated with vehicle (18:1:1 saline:PEG40:ethanol) or EN62 (50 mg/kg ip, once per day, initiated 17 days after subcutaneous injection of 231MFP cells). Gels shown in (FIGS. 13A-13C) are representative images from n=3/group. Data shown in (FIGS. 13D, 13F) are average±sem, n=3-8/group. Significance in (FIGS. 13E-13F) is expressed as *p<0.05 compared to the vehicle-treated controls.

(FIGS. 17A-17B) 231MFP breast cancer cell proliferation in serum-containing media (FIG. 17A) and serum-free cell survival (FIG. 17B). Data shown in FIGS. 17A-17B are average±sem, n=6 biologically independent samples/group. (FIG. 17C) Percent of propidium iodide and Annexin-V-positive (PI+/Annexin-V+) cells assessed by flow cytometry after treating 231MFP cells with DMSO vehicle or nimbolide for 24 or 48 h. Shown are representative FACS data from n=3 biologically independent samples/group. Quantitation of percentage of late-stage apoptotic cells defined as defined as FITC+/PI+ cells are shown in FIG. 18D. Statistical significance was calculated with unpaired two-tailed Student's t-tests. Significance is expressed as *p=7.75×10$^{-14}$ and 1.14×10$^{-13}$ for 100 and 10 µM, respectively in FIG. 17A and *p=3.88×10$^{-8}$ and 1.53×10$^{-7}$ for 100 and 10 µM, respectively in FIG. 17B compared to vehicle-treated controls.

(FIGS. 18A-18B) HCC38 breast cancer cell proliferation in serum-containing media (FIG. 18A) and serum-free cell survival (FIG. 18B). Cells were treated with DMSO vehicle or nimbolide and cell viability was assessed after 48 h. (FIG. 18C) Shown is the gating strategy for the flow cytometry data. We used two gating steps—the first step we gated by forward and side scatter. The second gate was based on separation into quadrants by cell death stains (PI/annexin). (FIGS. 18D-18E) Percent of propidium iodide and Annexin-V-positive (PI+/Annexin-V+) cells assessed by flow cytometry after treating 231MFP (FIG. 18D) and HCC38 (FIG. 18E) cells with DMSO vehicle or nimbolide for 24 or 48 h. Representative FACS data from 231MFP cells in FIG. 18D in shown in FIG. 17C and from HCC38 cells are shown in (FIG. 18E) on the left panels. Bar graphs in FIGS. 18D-18E are percentage of late-stage apoptotic cells defined as defined as PI+/Annexin-V+ cells. Data shown in FIGS. 18A-18B and FIGS. 18D-18E are average±sem, n=6 in FIGS. 18A-18B and n=3 in FIGS. 18D-18E biologically independent samples/group. Statistical significance was calculated with unpaired two-tailed Student's t-tests. Significance is expressed as *p=1.64×10$^{-13}$ and 2.05×10$^{-13}$ for 100 and 10 µM, respectively for FIG. 18A and *p=2.09×10$^{-11}$ and 7.07×10$^{-12}$ for 100 and 10 µM, respectively for FIG. 18B, *p=9.05×10$^{-5}$ and 1.87×10$^{-5}$ for 10 and 100 µM, respectively for 24 h data for FIG. 18D, *p=0.00139, 0.000142, and 7.97×10$^{-9}$ for 1, 10 and 100 µM, respectively for 48 h data for FIG. 18E, *p=0.00424, 0.0182, and 2.22×10$^{-11}$ for 1, 10 and 100 µM, respectively for 24 h data for FIG. 18E, and *p=6.68×10$^{-6}$, 4.70×10$^{-7}$, and 9.00×10$^{-11}$ for 1, 10 and 100 µM, respectively for 48 h data for FIG. 18E, compared to vehicle-treated controls.

FIGS. 19A-19D. isoTOP-ABPP analysis of nimbolide in 231MFP breast cancer cell proteomes reveal RNF114 as a target. (FIG. 19A) isoTOP-ABPP analysis of nimbolide (10 µM) in 231MFP breast cancer cells in situ analyzed as described in FIG. 19A. Light vs heavy isotopic probe-modified peptide ratios are shown in the left plot where the primary target with the highest ratio was C8 of RNF114. Shown on the right is a representative MS1 light vs heavy peak for the probe-modified peptide bearing C8 of RNF114. (FIG. 19B) RNF114 knockdown by short interfering RNA (siRNA) targeting RNF114 validated by Western blotting of RNF114 compared to siControl 231MFP cells. GAPDH expression is shown as a loading control. Shown gel is a representative gel from n=3 biological replicates/group. (FIG. 19C) 231MFP cell proliferation after 24 h in siControl and siRNF114 cells. (FIG. 19D) Nimbolide effects on 231MFP siControl and siRNF114 231MFP breast cancer cells. Nimbolide effects on 231MFP siControl and siRNF114 231MFP breast cancer cells. Cells were treated with DMSO vehicle or nimbolide for 24 h after which proliferation was assessed. Data for siControl or siRNF114 group was normalized to the respective DMSO vehicle control in each group. Individual biologically independent sample data is shown and the lines indicate mean values. Data shown in FIG. 19C is average±sem. Data shown in FIGS. 19A-19B are from n=3, in FIGS. 18D-18E are from n=5 biologically independent samples/group. Statistical significance in FIGS. 18D-18E was calculated with unpaired two-tailed Student's t-tests. Significance in FIG. 18D is expressed as *p=4.52×10$^{-5}$ compared to siControl cells. Significance in FIG. 18E is expressed as *p=1.90×10$^{-5}$, 2.72×10$^{-4}$, and 0.00101 for 10, 6, and 3 µM, respectively compared to the corresponding nimbolide treatment concentration from siControl groups.

FIGS. 20A-20D. Elucidating the Role of RNF114 in nimbolide-mediated effects. (FIG. 20A) RNF114 knockdown by 3 independent siRNAs targeting RNF114 validated by Western blotting of RNF114 compared to siControl 231MFP cells. GAPDH expression is shown as a loading control. (FIG. 20B) 231MFP cell proliferation after 24 h in siControl and siRNF114 cells assessed by Hoechst stain. (FIG. 20C) Nimbolide effects on 231MFP siControl and siRNF114 231MFP breast cancer cells. Cells were treated with DMSO vehicle or nimbolide for 24 h after which proliferation was assessed by Hoechst stain. Data for each siControl or siRNF114 group was normalized to the respective DMSO vehicle control in each group. Individual biologically independent sample data is shown and the lines indicate mean values. (FIG. 20D) Gel-based ABPP analysis of nimbolide, JNS27, and iodoacetamide competition against IA-rhodamine labeling of recombinant human RNF114 protein. RNF114 protein was pre-treated with DMSO vehicle or nimbolide, JNS27, or iodoacetamide for 30 min prior to labeling of RNF114 with IA-rhodamine (100 nM) for 30 min. RNF114 IA-rhodamine labeling was assessed by SDS/PAGE and in-gel fluorescence. Data shown are from an n=1 biological replicates. Data shown are from n=3 biologically independent samples/group. Gels shown in FIG. 20A and FIG. 20D are representative gels from n=3 biologically independent samples/group. Data shown in FIG. 20B are average±sem, n=5 for FIG. 20B biologically independent samples/group. Statistical significance was calculated with unpaired two-tailed Student's t-tests in FIG. 20B, FIG. 20C. Significance is expressed in FIG. 20B as *p=4.52×10$^{-5}$, 0.0429, and 0.00230 for siRNF114-1, siRNF114-2, and siRNF114-3, respectively compared to siControl cells. Significance in FIG. 20C is expressed as *p=1.90×10$^{-5}$, 0.000272, 0.00101 for 10, 6, and 3 µM, respectively for siRNF114-1; *p=0.000626, 0.00139, 3.66× 10$^{-5}$ for 10, 6, and 3 µM, respectively for siRNF114-2; and *p=0.00134, 9.15×10$^{-5}$, 0.00769 for 10, 6, and 3 µM, respectively for siRNF114-3 compared to corresponding concentration of nimbolide treatment in siControl cells. Significance in FIG. 20F is expressed as *p=0.0188 compared to vehicle-treated controls.

(FIG. 21A) Nimbolide targets an intrinsically disordered region within RNF114 as assessed by PONDR. (FIG. 21B) Route for synthesis of the alkyne-functionalized nimbolide probe. (FIG. 21C) Gel-based ABPP analysis of pure human RNF114 protein labeled with nimbolide probe. In the upper two panels, pure RNF114 protein was pre-incubated with DMSO vehicle or nimbolide (100 µM, 30 min) prior to labeling with the nimbolide probe (10 µM, 1 h) in PBS. In the lower two panels, pure wild-type and C8A mutant RNF114 protein were labeled with the nimbolide probe (10 µM, 1 h) in PBS with 1 mg/ml BSA. (FIG. 21D) Gel-based ABPP analysis of nimbolide competition against IA-alkyne (10 µM) or JNS27 (50 µM) labeling of pure RNF114 protein. Structures of IA-alkyne and JNS27 probes are shown with reactive moieties highlighted in red. Shown also is gel-based ABPP analysis of nimbolide (50 µM) competition against JNS27 labeling of wild-type and C8A mutant RNF114 protein. In these experiments, DMSO or nimbolide was pre-incubated for 30 min prior to probe labeling for 1 h. (FIG. 21E) Nimbolide-alkyne labeling of Flag-RNF114 in 231MFP cells. 231MFP cells stably expressing a Flag-tagged RNF114 were treated with DMSO vehicle or nimbolide-alkyne for 2 h. RNF114 was subsequently enriched from harvested cell lysates and then rhodamine-azide was appended onto probe-labeled proteins by CuAAC, after which nimbolide-alkyne labeling was visualized by SDS/PAGE and in-gel fluorescence. (FIG. 21F) Nimbolide-alkyne labeling of endogenous RNF114 in 231MFP cells. 231MFP cells were treated with DMSO vehicle or nimbolide-alkyne (50 µM) for 1.5 h. Biotin-azide was appended to probe-labeled proteins by CuAAC, and these proteins were subsequently avidin-enriched. Resulting pulled down proteins were analyzed by SDS/PAGE and Western blotting for RNF114. Gels shown in FIGS. 21C-21F are representative gels from n=3 biologically independent samples/group.

(FIGS. 22A-22B) RNF114 ubiquitination assay with pure GST-Ube1, GST-UBE2D1, and RNF114 protein, Flag-Ubiquitin and ATP with or without addition of p21 and blotting against Flag-ubiquitin (FIG. 22A) or p21 (FIG. 22B). (FIG. 22C) RNF114 autoubiquitination assay with DMSO or nimbolide (100 µM) treatment with wild-type or C8A mutant RNF114. (FIG. 22D) In an in vitro incubation of pure RNF114 and p21 protein, Flag-RNF114 pulldown and p21 enrichment were inhibited by nimbolide (100 µM). (FIG. 22E) 231MFP cells were treated with nimbolide (100 µM). Shown are p21 levels in DMSO control or nimbolide-treated cells. (FIG. 22F) Tandem mass tag (TMT)-based quantitative proteomic profiling of 231MFP breast cancer cells treated with DMSO vehicle or nimbolide (100 nM) for 12 h. Shown in red are proteins that are significantly heightened in levels >2-fold. Data shown in (FIG. 22F) are for 6397 proteins quantified with 2 or more unique peptides in n=3 biologically independent samples/group. (FIG. 22G) RNF114 ubiquitination assay with pure GST-Ube1, GST-UBE2D1, and RNF114 protein, Flag-Ubiquitin and ATP with the addition of p21 (CDKN1A), PEG10, or CTGF and blotting against Flag-ubiquitin. DMSO or Nimbolide (100 µM) was pre-incubated with RNF114, before the addition of the E1 and E2 enzymes, Flag-ubiquitin and ATP to start the reaction. (FIG. 22H) p21 (CDKN1A) and p57 (CDKN1C) expression in siControl and siCDKN1A/siCDKN1C 231MFP cells, assessed by Western blotting, alongside actin as a loading control. (FIG. 22I) 231MFP cell proliferation in siControl or siCDKN1A/siCDKN1C cells treated with DMSO vehicle or nimbolide (6 µM) for 24 h. Gels shown in FIGS. 22A-22E and FIG. 22G are representative images from n=3 biologically independent samples/group. Quantification for blots shown in FIGS. 22A-22D are in FIGS. 23A-23D. All three biologically independent samples/group are shown in FIG. 22H. Data shown in FIG. 22I are average±sem, n=5 biologically independent samples/group. Statistical significance was calculated with unpaired two-tailed Student's t-tests in FIG. 22E and FIG. 22I. Significance is expressed as *p=000799, 0.0295, 0.00962, and 0.0135 for 1, 2, 4, and 8 h, respectively compared to vehicle-treated control groups for each time point in FIG. 22E, and p=5.65×10$^{-8}$ and 0.0173 compared to vehicle-treated siControl and siCDKN1A/siCDKN1C groups, respectively in FIG. 22I. Significance expressed as #p=6.70×10$^{-5}$ compared to nimbolide-treated siControl cells in FIG. 22I.

(FIG. 23A) Route for synthesizing XH2, a nimbolide-based degrader consisting of nimbolide as an RNF114 recruiter, a linker, and the BRD4 inhibitor JQ1. (FIG. 23B) Gel-based ABPP analysis of XH2 against RNF114. RNF114 was pre-incubated with DMSO vehicle or XH2 for 30 min prior to JNS27 labeling (50 µM) for 1 h followed by appending rhodamine-azide by CuAAC, SDS/PAGE, and analysis of in-gel fluorescence. (FIGS. 23C-23D) BRD4 expression in 231MFP breast cancer cells treated with XH2 (FIG. 23C) versus MZ1 (FIG. 23D) treatment for 12 h. (FIGS. 23E-23F) BRD4 expression in 231MFP breast cancer cells. Cells were pre-treated with DMSO vehicle or proteasome inhibitor bortezomib (BTZ) (1 µM) (FIG. 23E) or E1 ubiquitin activating enzyme inhibitor TAK-243 (10 µM) (FIG. 23F) 30 min prior to and also during treatment with MZ1 (1 µM) or XH2 (100 nM) treatment (100 nM) for 12 h. (FIG. 24G) RNF114 and loading control GAPDH expression in RNF114 wild-type (WT) and knockout (KO) HAP1 cells. (FIG. 23H) RNF114 and BRD4 expression in RNF114 wild-type (WT) or knock-out (KO) HAP1 cells treated with DMSO vehicle, MZ1 (1 µM), or XH2 (100 nM) for 12 h. (FIG. 23I) Tandem mass tag (TMT)-based quantitative proteomic profiling of 231MFP breast cancer cells treated with DMSO vehicle or XH2 (100 nM) for 12 h. Long and short BRD4 isoforms in FIGS. 23C-23H were visualized by SDS/PAGE and Western blotting, quantified by densitometry, and normalized to GAPDH loading controls. Gels shown in FIGS. 23B-23H are representative images from n=3 biologically independent samples/group and quantification for blots in FIGS. 23C-23F and FIG. 23H are shown in FIGS. 25C-25F and FIG. 25I. Data shown in FIG. 23I are for 5797 proteins quantified with 2 or more unique peptides in triplicate treatments. Statistical significance in FIG. 23I are described in the methods section.

DETAILED DESCRIPTION

I. Definitions

Figure 1A:
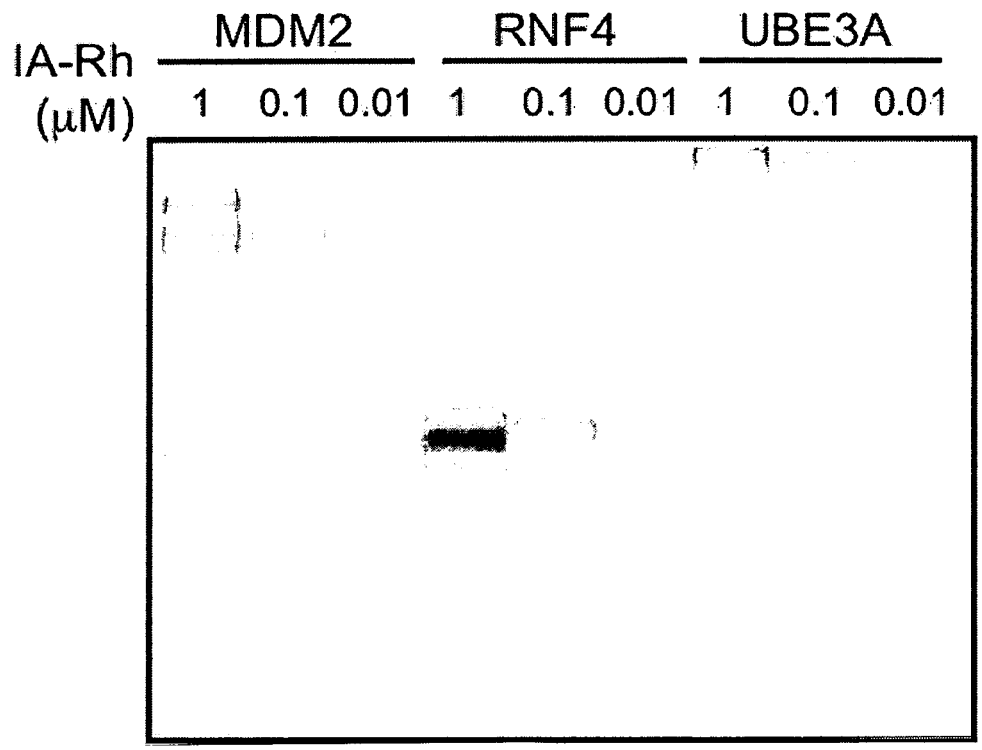
FIGS. 1A-1E. Covalent ligand screen against RNF4 using gel-based ABPP.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. An unsaturated alkyl group is one having one or more double bonds or triple bonds. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds. The term "alkylene," by itself or as part of another substituent, means, unless otherwise stated, a divalent radical derived from an alkyl. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$- and —$R'C(O)_2$—. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). In embodiments, the bridged or fused bicyclic cycloalkyl is attached to the parent molecular moiety through any carbon atom contained within the monocyclic cycloalkyl ring. In embodiments, the multicyclic cycloalkyl is attached to the parent molecular moiety through any carbon atom contained within the base ring.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). In embodiments, the bridged or fused bicyclic cycloalkenyl is attached to the parent molecular moiety through any carbon atom contained within the monocyclic cycloalkenyl ring. In embodiments, the multicyclic cycloalkenyl is attached to the parent molecular moiety through any carbon atom contained within the base ring.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. The heterocyclyl bicyclic heterocycle is connected to the parent molecular moiety through any carbon atom or any nitrogen atom contained within the monocyclic heterocycle portion of the bicyclic ring system. The multicyclic heterocyclyl is attached to the parent molecular moiety through any carbon atom or nitrogen atom contained within the base ring.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A heteroaryl group can be attached to the remainder of the molecule through a carbon or heteroatom. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⤳" denotes the point of attachment of a chemical moiety to the remainder of a molecule or chemical formula.

The term "oxo," as used herein, means an oxygen that is double bonded to a carbon atom.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR', —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR', —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, a "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure. The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —NH2, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc. (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g. phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex. The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a substance, compound, element, molecule, or composition detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86, 90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y $^{90}$Y. $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., L$^1$, L$^2$, or L$^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts. Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art. The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "RNF4" and "RING finger protein 4" refers to an E3 ligase protein (including homologs, isoforms, and functional fragments thereof). The term includes any recombinant or naturally-occurring form of RNF4 variants thereof that maintain RNF4 activity (e.g. within at least 30%, 40%, 50%, 60%, 70%, 80%, 90%, 95%, or 100% activity compared to wildtype RNF4). In embodiments, the RNF4 protein encoded by the RNF4 gene has the amino acid sequence set forth in or corresponding to Entrez 6047, UniProt P78317, RefSeq (protein) NP_002929, RefSeq (protein) NP_001171939, or RefSeq (protein) NP_001171938. In embodiments, the amino acid sequence or nucleic acid sequence is the sequence known at the time of filing of the present application. In embodiments, the RNF4 is a human RNF4, such as a human cancer causing RNF4. In embodiments, RNF4 has the sequence:

(SEQ ID NO: 1)
MSTRKRRGGAINSRQAQKRTREATSTPEISLEAEPIELVETAGDEIVDLT

CESLEPVVVDLTHNDSVVIVDERRRPRRNARRLPQDHADSCVVSSDDEEL

```
SRDRDVYVTTHTPRNARDEGATGLRPSGTVSCPICMDGYSEIVQNGRLIV

STECGHVFCSQCLRDSLKNANTCPTCRKKINHKRYHPIYI.
```

The terms "RNF114" and "RING finger protein 114" and "ZNF228" and "ZNF313" refers to an E3 ligase protein (including homologs, isoforms, and functional fragments thereof). The term includes any recombinant or naturally-occurring form of RNF4 variants thereof that maintain RNF114 activity (e.g. within at least 30%, 40%, 50%, 60%, 70%, 80%, 90%, 95%, or 100% activity compared to wildtype RNF114). In embodiments, the RNF114 protein encoded by the RNF4 gene has the amino acid sequence set forth in or corresponding to Entrez 55905, UniProt Q9Y508, or RefSeq (protein) NP_061153. In embodiments, the amino acid sequence or nucleic acid sequence is the sequence known at the time of filing of the present application. In embodiments, the RNF114 is a human RNF114, such as a human cancer causing RNF114. In embodiments, RNF114 has the sequence:

```
                                    (SEQ ID NO: 2)
MAAQQRDCGGAAQLAGPAAEADPLGRFTCPVCLEVYEKPVQVPCGHVFCS

ACLQECLKPKKPVCGVCRSALAPGVRAVELERQIESTETSCHGCRKNFFL

SKIRSHVATCSKYQNYIMEGVKATIKDASLQPRNVPNRYTFPCPYCPEKN

FDQEGLVEHCKLFHSTDTKSVVCPICASMPWGDPNYRSANFREHIQRRHR

FSYDTFVDYDVDEEDMMNQVLQRSIIDQ.
```

The terms "BRD4" and "bromodomain-containing protein 4" refer to a protein that associates with chromosomes during mitosis and plays a key role in transmission of epigenetic memory across cell divisions and transcription regulation. In embodiments, the BRD4 protein encoded by the BRD4 gene has the amino acid sequence set forth in or corresponding to Entrez 23476, UniProt 060885, RefSeq (protein) NP_001317313.1, RefSeq (protein) NP_055114.1, or RefSeq (protein) NP 490597.1. In embodiments, the amino acid sequence or nucleic acid sequence is the sequence known at the time of filing of the present application. In embodiments, BRD4 has the sequence:

```
                                    (SEQ ID NO: 3)
MSAESGPGTRLRNLPVMGDGLETSQMSTTQAQAQPQPANAASTNPPPPET

SNPNKPKRQTNQLQYLLRVVLKTLWKHQFAWPFQQPVDAVKLNLPDYYKI

IKTPMDMGTIKKRLENNYYWNAQECIQDFNTMFTNCYIYNKPGDDIVLMA

EALEKLFLQKINELPTEETEIMIVQAKGRGRGRKETGTAKPGVSTVPNTT

QASTPPQTQTPQPNPPPVQATPHPFPAVTPDLIVQTPVMTVVPPQPLQTP

PPVPPQPQPPPAPAPQPVQSHPPIIAATPQPVKTKKGVKRKADTTTPTTI

DPIHEPPSLPPEPKTTKLGQRRESSRPVKPPKKDVPDSQQHPAPEKSSKV

SEQLKCCSGILKEMFAKKHAAYAWPFYKPVDVEALGLHDYCDIIKHPMDM

STIKSKLEAREYRDAQEFGADVRLMFSNCYKYNPPDHEVVAMARKLQDVF

EMRFAKMPDEPEEPVVAVSSPAVPPPTKVVAPPSSSDSSSDSSSDSDSST

DDSEEERAQRLAELQEQLKAVHEQLAALSQPQQNKPKKKEKDKKEKKKEK

HKRKEEVEENKKSKAKEPPPKKTKKNNSSNSNVSKKEPAPMKSKPPPTYE

SEEEDKCKPMSYEEKRQLSLDINKLPGEKLGRVVHIIQSREPSLKNSNPD

EIEIDFETLKPSTLRELERYVTSCLRKKRKPQAEKVDVIAGSSKMKGFSS

SESESSSESSSSDSEDSETEMAPKSKKKGHPGREQKKHHHHHHQQMQQAP

APVPQQPPPPPQQPPPPPPPQQQQQPPPPPPPPSMPQQAAPAMKSSPPPF

IATQVPVLEPQLPGSVFDPIGHFTQPILHLPQPELPPHLPQPPEHSTPPH

LNQHAVVSPPALHNALPQQPSRPSNRAAALPPKPARPPAVSPALTQTPLL

PQPPMAQPPQVLLEDEEPPAPPLTSMQMQLYLQQLQKVQPPTPLLPSVKV

QSQPPPPLPPPPHPSVQQQLQQQPPPPPPPQPQPPPQQQHQPPPRPVHLQ

PMQFSTHIQQPPPPQGQQPPHPPPGQQPPPPQPAKPQQVIQHHHSPRHHK

SDPYSTGHLREAPSPLMIHSPQMSQFQSLTHQSPPQQNVQPKKQELRAAS

VVQPQPLVVVKEEKIHSPIIRSEPFSPSLRPEPPKHPESIKAPVHLPQRP

EMKPVDVGRPVIRPPEQNAPPPGAPDKDKQKQEPKTPVAPKKDLKIKNMG

SWASLVQKHPTTPSSTAKSSSDSFEQFRRAAREKEEREKALKAQAEHAEK

EKERLRQERMRSREDEDALEQARRAHEEARRRQEQQQQQRQEQQQQQQQQ

AAAVAAAATPQAQSSQPQSMLDQQRELARKREQERRRREAMAATIDMNFQ

SDLLSIFEENLF.
```

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator. The term "modulate" is used in accordance with its plain ordinary meaning and refers to the act of changing or varying one or more properties. "Modulation" refers to the process of changing or varying one or more properties.

The term "associated" or "associated with" in the context of a substance or substance activity or function associated with a disease means that the disease is caused by (in whole or in part), or a symptom of the disease is caused by (in whole or in part) the substance or substance activity or function.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components.

In this disclosure, "comprises," "comprising," "containing" and "having" and the like can have the meaning ascribed to them in U.S. Patent law and can mean "includes," "including," and the like. "Consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "disease" or "condition" refer to a state of being or health status of a patient or subject capable of being treated with the compounds or methods provided herein.

The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer."

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing. "Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things. "Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art. As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. A "stem cell" is a cell characterized by the ability of self-renewal through mitotic cell division and the potential to differentiate into a tissue or an organ. Among mammalian stem cells, embryonic stem cells (ES cells) and somatic stem cells (e.g., HSC) can be distinguished. Embryonic stem cells reside in the blastocyst and give rise to embryonic tissues, whereas somatic stem cells reside in adult tissues for the purpose of tissue regeneration and repair.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Anti-cancer agent" and "anticancer agent" are used in accordance with their plain ordinary meaning and refers to a composition, compound, drug, antagonist, inhibitor, modulator, peptide, protein, nucleic acid, or molecule having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxalaplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g., gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g., tomaymycin), carboplatin, CC-1065 and CC-1065 analogs including amino-CBIs, nitrogen mustards (such as chlorambucil and melphalan), dolastatin and dolastatin analogs (including auristatins: e.g., monomethyl auristatin E), anthracycline antibiotics (such as doxorubicin, daunorubicin, etc.), duocarmycins and duocarmycin analogs, enediynes (such as neocarzinostatin and calicheamicins), leptomycin derivatives, maytansinoids and maytansinoid analogs (e.g., mertansine), methotrexate, mitomycin C, taxoids, vinca alkaloids (such as vinblastine and vincristine), epothilones (e.g., epothilone B), camptothecin and its clinical analogs topotecan and irinotecan, or the like.

"Specific", "specifically", "specificity", or the like of a compound refers to the compound's ability to cause a particular action, such as inhibition, to a particular molecular target with minimal or no action to other proteins in the cell.

The term "electrophilic chemical moiety" or "electrophilic moiety" is used in accordance with its plain ordinary chemical meaning and refers to a chemical group (e.g., monovalent chemical group) that is electrophilic.

The term "irreversible covalent bond" is used in accordance with its plain ordinary meaning in the art and refers to the resulting association between atoms or molecules of (e.g., electrophilic chemical moiety and nucleophilic moiety) wherein the probability of dissociation is low. In embodiments, the irreversible covalent bond does not easily dissociate under normal biological conditions. In embodiments, the irreversible covalent bond is formed through a chemical reaction between two species (e.g., electrophilic chemical moiety and nucleophilic moiety).

The term "capable of binding" as used herein refers to a moiety (e.g. a compound as described herein) that is able to measurably bind to a target (e.g., an E3 Ubiquitin ligase binder is capable of forming a covalent bond with a cysteine of an E3 Ubiquitin ligase). In embodiments, where a moiety is capable of binding a target, the moiety is capable of binding with a Kd of less than about 10 µM, 5 µM, 1 µM, 500 nM, 250 nM, 100 nM, 75 nM, 50 nM, 25 nM, 15 nM, 10 nM, 5 nM, 1 nM, or about 0.1 nM.

The term "targeted protein degrader" as used herein refers to an agent (e.g., a compound or composition) that is capable of inducing protein degradation upon the target protein (e.g., the protein of interest). Typically, a targeted protein degrader is capable of recruiting E3 ligases to specific protein targets to ubiquitinate and degrade targets in a proteasome-dependent manner. As functional inhibition of the target is not necessary for degrader efficacy this strategy has the potential to target and degrade any protein in the proteome for which there exists a ligand (e.g., targeted protein binder or targeted protein degrader).

The term "targeted protein binder" refers to a moiety that is capable of binding to a protein (e.g., the targeted protein). In embodiments, the targeted protein binder is a molecule or substance that forms a complex with a protein (e.g., targeted protein). In embodiments, the targeted protein binder is a monovalent form of a molecule or substance that forms a complex with a protein (e.g., targeted protein).

The term "binder linker" refers to a covalent linker which binds a targeted protein binder and E3 Ubiquitin ligase binder.

The term "E3 Ubiquitin ligase binder" as used herein refers to a monovalent agent (e.g., a monovalent compound described herein) that is able to measurably bind to an E3 Ubiquitin ligase (E3 ligase) (e.g., a RNF4 or RNF114). For example, an E3 Ubiquitin ligase binder is a moiety or monovalent form of a compound having the formula:

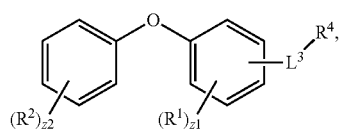

(I)

wherein $R^2$, z2, $R^1$, z1, $L^3$, and $R^4$ are as described herein;

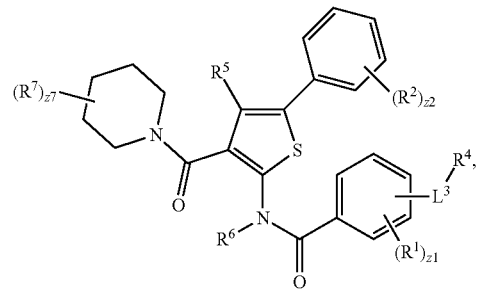

(II)

wherein $R^7$, z7, $R^5$, $R^2$, z2, $L^3$, $R^4$, $R^6$, $R^1$, and z1 are as described herein; or

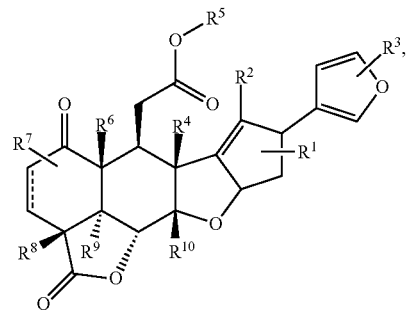

(III)

wherein $R^1$, $R^2$, $R^3$, $R^4$, $R^5$, $R^6$, $R^7$, $R^8$, $R^9$, and $R^{10}$ are described herein.

The term "covalent cysteine modifier moiety" as used herein refers to a monovalent electrophilic moiety that is able to measurably bind to a cysteine amino acid. In embodiments, the covalent cysteine modifier moiety binds via an irreversible covalent bond. In embodiments, the covalent cysteine modifier moiety is capable of binding with a Kd of less than about 10 µM, 5 µM, 1 µM, 500 nM, 250 nM, 100 nM, 75 nM, 50 nM, 25 nM, 15 nM, 10 nM, 5 nM, 1 nM, or about 0.1 nM.

II. Compounds

In an aspect is provided a targeted protein degrader including 1) a targeted protein binder and 2) an E3 Ubiquitin ligase binder, wherein the E3 Ubiquitin ligase is human RNF4 or human RNF114. In embodiments, the E3 Ubiquitin ligase is human RNF4. In embodiments, the E3 Ubiquitin ligase is human RNF114. In embodiments, the E3 Ubiquitin ligase binder is capable of forming a covalent bond with a cysteine of an E3 Ubiquitin ligase. In embodiments, the targeted protein binder and E3 Ubiquitin ligase binder are covalently bonded by a binder linker.

In embodiments, the E3 Ubiquitin ligase binder is a moiety of a compound having the formula:

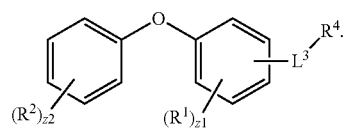

(I)

In embodiments, the E3 Ubiquitin ligase binder is a monovalent compound having the formula:

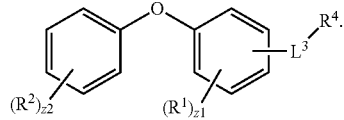
(I)

In embodiments, the E3 Ubiquitin ligase binder is a monovalent form of the formula:

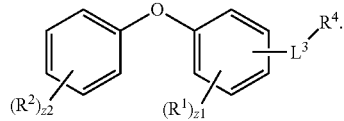
(I)

$R^1$ is independently halogen, $-CX^1_3$, $-CHX^1_2$, $-CH_2X^1$, $-CN$, $-OR^{1D}$, $-C(O)R^{1C}$, $-C(O)-OR^{1C}$, $-C(O)NR^{1A}R^{1B}$, $-N(O)_{m1}$, $-SO_{n1}R^{1D}$, $-SO_{v1}NR^{1A}R^{1B}$, $-NR^{1A}R^{1B}$, $-NHC(O)NR^{1A}R^{1B}$, $-NR^{1A}SO_2R^{1D}$, $-NR^{1A}C(O)R^{1C}$, $-NR^{1A}C(O)OR^{1C}$, $-NR^{1A}OR^{1C}$, $-OCX^1_3$, $-OCH_2X^1$, $-OCHX^1_2$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $R^2$ is independently halogen, $-CX^2_3$, $-CHX^2_2$, $-CH_2X^2$, $-CN$, $-OR^{2D}$, $-C(O)R^{2C}$, $-C(O)-OR^{2C}$, $-C(O)NR^{2A}R^{2B}$, $-N(O)_{m2}$, $-SO_{n2}R^{2D}$, $-SO_{v2}NR^{2A}R^{2B}$, $-NR^{2A}R^{2B}$, $-NHC(O)NR^{2A}R^{2B}$, $-NR^{2A}SO_2R^{2D}$, $-NR^{2A}C(O)R^{2C}$, $-NR^{2A}C(O)OR^{2C}$, $-NR^{2A}OR^{2C}$, $-OCX^2_3$, $-OCH_2X^2$, $-OCHX^2_2$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $L^3$ is a bond, $-N(R^3)-$, $-C(O)-$, $-C(O)N(R^3)-$, $-N(R^3)C(O)-$, $-N(H)-$, $-C(O)N(H)-$, $-N(H)C(O)-$, $-C(O)O-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^3$ is independently hydrogen, oxo, halogen, $-CX^3_3$, $-CHX^3_2$, $-CH_2X^3$, $-CN$, $-OR^{3D}$, $-C(O)R^{3C}$, $-C(O)-OR^{3C}$, $-C(O)NR^{3A}R^{3B}$, $-N(O)_{m3}$, $-SO_{n3}R^{3D}$, $-SO_{v3}NR^{3A}R^{3B}$, $-NR^{3A}R^{3B}$, $-NHC(O)NR^{3A}R^{3B}$, $-NR^{3A}SO_2R^{3D}$, $-NR^{3A}C(O)R^{3C}$, $-NR^{3A}C(O)OR^{3C}$, $-NR^{3A}OR^{3C}$, $-OCX^3_3$, $-OCH_2X^3$, $-OCHX^3_2$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or unsubstituted heteroaryl, or a bond to the binder linker. $R^4$ is independently hydrogen, oxo, halogen, $-CX^4_3$, $-CHX^4_2$, $-CH_2X^4$, $-CN$, $-OR^{4D}$, $-C(O)R^{4C}$, $-C(O)-OR^{4C}$, $-C(O)NR^{4A}R^{4B}$, $-N(O)_{m4}$, $-SO_{n4}R^{4D}$, $-SO_{v4}NR^{4A}R^{4B}$, $-NR^{4A}R^{4B}$, $-NHC(O)NR^{4A}R^{4B}$, $-NR^{4A}SO_2R^{4D}$, $-NR^{4A}C(O)R^{4C}$, $-NR^{4A}C(O)OR^{4C}$, $-NR^{4A}OR^{4C}$, $-OCX^4_3$, $-OCH_2X^4$, $-OCHX^4_2$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E. E is an electrophilic moiety. z1 is an integer from 0 to 4. z2 is an integer from 0 to 5. Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, and $R^{4D}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl. Each X, $X^1$, $X^2$, $X^3$, and $X^4$ is independently $-F$, $-Cl$, $-Br$, or $-I$. n1, n2, n3, and n4 are independently an integer from 0 to 4. m1, m2, m3, m4, v1, v2, v3, and v4 are independently 1 or 2. Only one $R^1$ or one $R^2$ or one $R^3$ is a bond to the binder linker. In embodiments, $R^1$ is a bond to the binder linker. In embodiments, $R^2$ is a bond to the binder linker. In embodiments, $R^3$ is a bond to the binder linker. In embodiments, one $R^1$ is independently a bond to the binder linker. In embodiments, one $R^2$ is independently a bond to the binder linker. In embodiments, one $R^3$ is independently a bond to the binder linker. One $R^1$ or one $R^2$ or one $R^3$ is a bond to the binder linker.

In embodiments, $R^3$ is independently hydrogen, halogen, $-CX^3_3$, $-CHX^3_2$, $-CH_2X^3$, $-CN$, $-OR^3D$, $-C(O)R^{3C}$, $-C(O)-OR^{3C}$, $-C(O)NR^{3A}R^{3B}$, $-N(O)_{m3}$, $-SO_{n3}R^{3D}$, $-SO_{v3}NR^{3A}R^{3B}$, $-NR^{3A}R^{3B}$, $-NHC(O)NR^{3A}R^{3B}$, $-NR^{3A}SO_2R^{3D}$, $-NR^{3A}C(O)R^{3C}$, $-NR^{3A}C(O)OR^{3C}$, $-NR^{3A}OR^{3C}$, $-OCX^3_3$, $-OCH_2X^3$, $-OCHX^3_2$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker. $R^{3A}$, $R^{3B}$, $R^{3C}$, $R^{3D}$, $X^3$, n3, m3, and v3 are as described herein, including in embodiments.

In embodiments, $R^4$ is independently hydrogen, halogen, $-CX^4_3$, $-CHX^4_2$, $-CH_2X^4$, $-CN$, $-OR^4D$, $-C(O)R^{4C}$, $-C(O)-OR^{4C}$, $-C(O)NR^{4A}R^{4B}$, $-N(O)_{m4}$, $-SO_{n4}R^{4D}$, $-SO_{v4}NR^{4A}R^{4B}$, $-NR^{4A}R^{4B}$, $-NHC(O)NR^{4A}R^{4B}$, $-NR^{4A}SO_2R^{4D}$, $-NR^{4A}C(O)R^{4C}$, $-NR^{4A}C(O)OR^{4C}$, $-NR^{4A}OR^{4C}$, $-OCX^4_3$, $-OCH_2X^4$, $-OCHX^4_2$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E. E is an electrophilic moiety. $R^{4A}$, $R^{4B}$, $R^{4C}$, $R^{4D}$, $X^4$, n4, m4, and v4 are as described herein, including in embodiments.

In embodiments, $R^1$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $R^2$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $R^3$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E. E is an electrophilic moiety. z1 is an integer from 0 to 4. z2 is an integer from 0 to 5. Only one $R^1$ or one $R^2$ is a bond to the binder linker. In embodiments, $R^1$ is a bond to the binder linker. In embodiments, $R^2$ is a bond to the binder linker.

In embodiments, the E3 Ubiquitin ligase binder is a moiety of a compound having the formula:

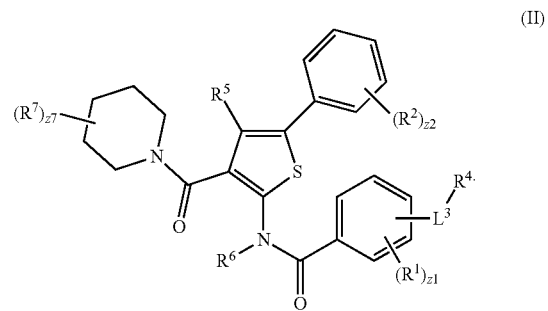

(II)

In embodiments, the E3 Ubiquitin ligase binder is a monovalent compound having the formula:

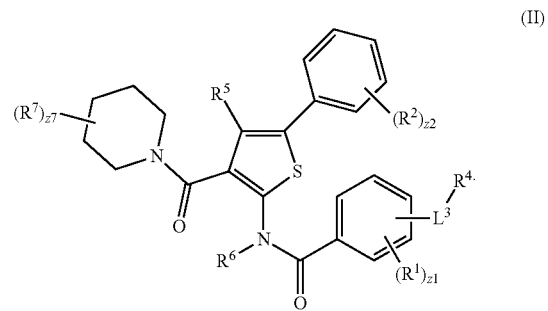

(II)

In embodiments, the E3 Ubiquitin ligase binder is a monovalent form of the formula:

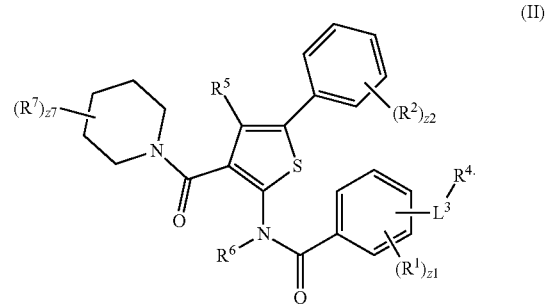

(II)

$R^1$, $R^2$, $L^3$, z1, z2, and $R^4$ are as described herein.

$R^5$ and $R^6$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker. R$^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two R$^7$ substituents may optionally be joined to form an substituted or unsubstituted cycloalkyl, substituted or unsubstituted heterocycloalkyl, substituted or unsubstituted aryl, or substituted or unsubstituted heteroaryl. The symbol z7 is an integer from 0 to 10. In embodiments, only one R$^1$, R$^2$, R$^5$, R$^6$, or R$^7$ is independently a bond to the binder linker. In embodiments, R$^1$ is independently a bond to the binder linker. In embodiments, R$^2$ is independently a bond to the binder linker. In embodiments, R$^3$ is independently a bond to the binder linker. In embodiments, R$^5$ is independently a bond to the binder linker. In embodiments, R$^6$ is independently a bond to the binder linker. In embodiments, R$^7$ is independently a bond to the binder linker.

In embodiments, the E3 Ubiquitin ligase binder is a moiety of a compound having the formula:

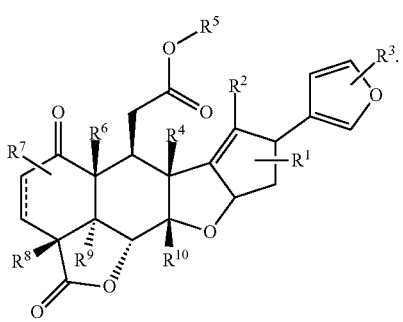

(III)

R$^1$, R$^2$, R$^3$, R$^4$, R$^5$, R$^6$, and R$^7$ are as described herein. R$^8$, R$^9$, and R$^{10}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a bond to the binder linker. Only one R$^1$, R$^2$, R$^3$, R$^4$, R$^5$, R$^6$, R$^7$, R$^8$, R$^9$, or R$^{10}$ is a bond to the binder linker; and

is a single bond or a double bond.

In embodiments, the E3 Ubiquitin ligase binder is a monovalent compound having the formula:

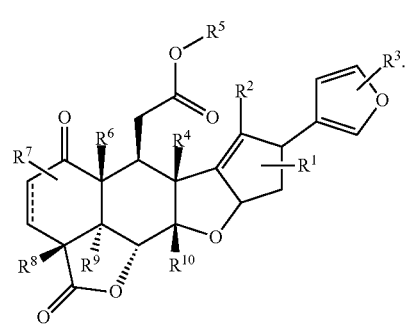

(III)

R$^1$, R$^2$, R$^3$, R$^4$, R$^5$, R$^6$, R$^7$, R$^8$, R$^9$, and R$^{10}$ are as described herein.

In embodiments, the E3 Ubiquitin ligase binder is a monovalent form of the formula:

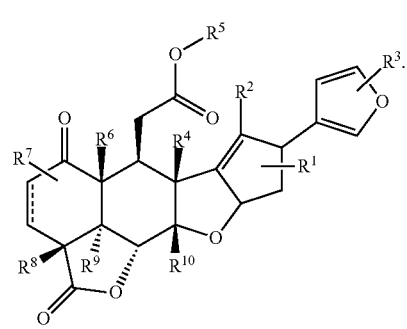

(III)

R$^1$, R$^2$, R$^3$, R$^4$, R$^5$, R$^6$, R$^7$, R$^8$, R$^9$, and R$^{10}$ are as described herein.

In embodiments, the E3 Ubiquitin ligase binder is a monovalent form of the formula:

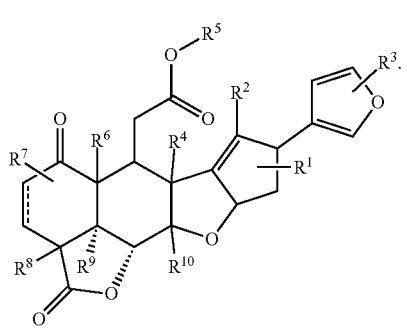

(IIIa)

$R^1$, $R^2$, $R^3$, $R^4$, $R^5$, $R^6$, $R^7$, $R^8$, $R^9$, and $R^{10}$ are as described herein.

In embodiments, the E3 Ubiquitin ligase binder is a monovalent form of the formula:

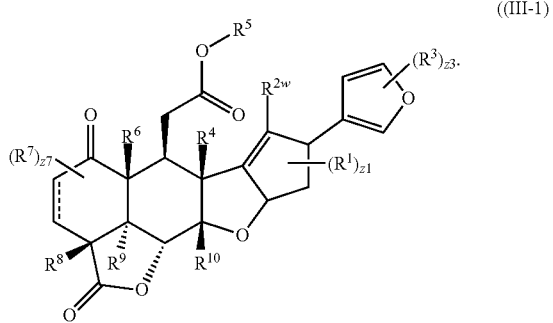

(III-1)

$R^1$, $R^2$, $R^3$, $R^4$, $R^5$, $R^6$, $R^7$, $R^8$, $R^9$, $R^{10}$, z1, and z7 are as described herein. $R^{2w}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered), or a bond to the binder linker. The symbol z3 is an integer from 0 to 3. Only one $R^1$, $R^{2w}$, $R^3$, $R^4$, $R^5$, $R^6$, $R^7$, $R^8$, $R^9$, or $R^{10}$ is a bond to the binder linker; and $$\vdots$$

is a single bond or a double bond.

In embodiments, the E3 Ubiquitin ligase binder is a monovalent form of the formula:

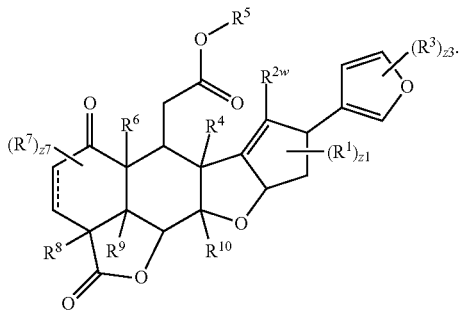

(IIIa-1)

$R^1$, $R^{2w}$, $R^3$, $R^4$, $R^5$, $R^6$, $R^7$, $R^8$, $R^9$, $R^{10}$, z1, z3, and z7 are as described herein.

In embodiments, $R^3$ is independently a bond to the binder linker. In embodiments, $R^8$ is independently a bond to the binder linker. In embodiments, $R^9$ is independently a bond to the binder linker. In embodiments, $R^{10}$ is independently a bond to the binder linker.

In embodiments, $R^{2w}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl (e.g., $C_6$-$C_{10}$ or phenyl), $R^{21}$-substituted or unsubstituted heteroaryl (e.g., 5 to 10 membered, 5 to 9 membered, or 5 to 6 membered), or a bond to the binder linker.

In embodiments, $R^{2w}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, substituted (e.g., substituted with at least one substituent group, size-limited substituent group, or lower substituent group) or unsubstituted heteroaryl, or a bond to the binder linker.

In embodiments, a substituted $R^{2w}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2w}$ is substituted with a plurality of groups selected from substituent groups, size-limited substituent groups, and lower substituent groups; each substituent group, size-limited substituent group, and/or lower substituent group may optionally be different. In embodiments, when $R^{2w}$ is substituted, it is substituted with at least one substituent group. In embodiments, when $R^{2w}$ is substituted, it is substituted with at least one size-limited substituent group. In embodiments, when $R^{2w}$ is substituted, it is substituted with at least one lower substituent group.

In embodiments, $R^{2w}$ is independently hydrogen or substituted or unsubstituted $C_1$-$C_4$ alkyl. In embodiments, $R^{2w}$ is independently hydrogen. In embodiments, $R^{2w}$ is independently substituted or unsubstituted $C_1$-$C_4$ alkyl. In embodiments, $R^{2w}$ is independently unsubstituted $C_1$-$C_4$ alkyl. In embodiments, $R^{2w}$ is independently unsubstituted methyl. In embodiments, $R^{2w}$ is independently unsubstituted ethyl. In embodiments, $R^{2w}$ is independently unsubstituted n-propyl. In embodiments, $R^{2w}$ is independently unsubstituted isopropyl. In embodiments, $R^{2w}$ is independently unsubstituted n-butyl. In embodiments, $R^{2w}$ is independently unsubstituted tert-butyl.

In embodiments, $R^3$ is independently substituted or unsubstituted $C_1$-$C_4$ alkyl. In embodiments, $R^3$ is independently unsubstituted $C_1$-$C_4$ alkyl. In embodiments, $R^3$ is independently unsubstituted methyl. In embodiments, $R^3$ is independently unsubstituted ethyl. In embodiments, $R^3$ is independently unsubstituted n-propyl. In embodiments, $R^3$ is independently unsubstituted isopropyl. In embodiments, $R^3$ is independently unsubstituted n-butyl. In embodiments, $R^3$ is independently unsubstituted tert-butyl.

In embodiments, z3 is 0. In embodiments, z3 is 1. In embodiments, z3 is 2. In embodiments, z3 is 3.

In embodiments, $R^7$ is independently substituted or unsubstituted $C_1$-$C_4$ alkyl. In embodiments, $R^7$ is independently unsubstituted $C_1$-$C_4$ alkyl. In embodiments, $R^7$ is independently unsubstituted methyl. In embodiments, $R^7$ is independently unsubstituted ethyl. In embodiments, $R^7$ is independently unsubstituted n-propyl. In embodiments, $R^7$ is independently unsubstituted isopropyl. In embodiments, $R^7$ is independently unsubstituted n-butyl. In embodiments, $R^7$ is independently unsubstituted tert-butyl.

In embodiments, $R^8$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered), or a bond to the binder linker.

In embodiments, $R^8$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, substituted (e.g., substituted with at least one substituent group, size-limited substituent group, or lower substituent group) or unsubstituted heteroaryl, or a bond to the binder linker.

In embodiments, a substituted $R^8$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^8$ is substituted with a plurality of groups selected from substituent groups, size-limited substituent groups, and lower substituent groups; each substituent group, size-limited substituent group, and/or lower substituent group may optionally be different. In embodiments, when $R^8$ is substituted, it is substituted with at least one substituent group. In embodiments, when $R^8$ is substituted, it is substituted with at least one size-limited substituent group. In embodiments, when $R^8$ is substituted, it is substituted with at least one lower substituent group.

In embodiments, $R^8$ is independently hydrogen or substituted or unsubstituted $C_1$-$C_4$ alkyl. In embodiments, $R^8$ is independently hydrogen. In embodiments, $R^8$ is independently substituted or unsubstituted $C_1$-$C_4$ alkyl. In embodiments, $R^8$ is independently unsubstituted $C_1$-$C_4$ alkyl. In embodiments, $R^8$ is independently unsubstituted methyl. In embodiments, $R^8$ is independently unsubstituted ethyl. In embodiments, $R^8$ is independently unsubstituted n-propyl. In embodiments, $R^8$ is independently unsubstituted isopropyl. In embodiments, $R^8$ is independently unsubstituted n-butyl. In embodiments, $R^8$ is independently unsubstituted tert-butyl.

In embodiments, $R^9$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered), or a bond to the binder linker.

In embodiments, $R^9$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, substituted (e.g., substituted with at least one substituent group, size-limited substituent group, or lower substituent group) or unsubstituted heteroaryl, or a bond to the binder linker.

In embodiments, a substituted $R^9$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^9$ is substituted with a plurality of groups selected from substituent groups, size-limited substituent groups, and lower substituent groups; each substituent group, size-limited substituent group, and/or lower substituent group may optionally be different. In embodiments, when $R^9$ is substituted, it is substituted with at least one substituent group. In embodiments, when $R^9$ is substituted, it is substituted with at least one size-limited substituent group. In embodiments, when $R^9$ is substituted, it is substituted with at least one lower substituent group.

In embodiments, $R^9$ is independently hydrogen or substituted or unsubstituted $C_1$-$C_4$ alkyl. In embodiments, $R^9$ is independently hydrogen. In embodiments, $R^9$ is independently substituted or unsubstituted $C_1$-$C_4$ alkyl. In embodiments, $R^9$ is independently unsubstituted $C_1$-$C_4$ alkyl. In embodiments, $R^9$ is independently unsubstituted methyl. In embodiments, $R^9$ is independently unsubstituted ethyl. In embodiments, $R^9$ is independently unsubstituted n-propyl. In embodiments, $R^9$ is independently unsubstituted isopropyl. In embodiments, $R^9$ is independently unsubstituted n-butyl. In embodiments, $R^9$ is independently unsubstituted tert-butyl.

In embodiments, $R^{10}$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered), or a bond to the binder linker.

In embodiments, $R^{10}$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, substituted (e.g., substituted with at least one substituent group, size-limited substituent group, or lower substituent group) or unsubstituted heteroaryl, or a bond to the binder linker.

In embodiments, a substituted $R^{10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group.

In embodiments, $R^{10}$ is independently hydrogen or substituted or unsubstituted $C_1$-$C_4$ alkyl. In embodiments, $R^{10}$ is independently hydrogen. In embodiments, $R^{10}$ is independently substituted or unsubstituted $C_1$-$C_4$ alkyl. In embodiments, $R^{10}$ is independently unsubstituted $C_1$-$C_4$ alkyl. In embodiments, $R^{10}$ is independently unsubstituted methyl. In embodiments, $R^{10}$ is independently unsubstituted ethyl. In embodiments, $R^{10}$ is independently unsubstituted n-propyl. In embodiments, $R^{10}$ is independently unsubstituted isopropyl. In embodiments, $R^{10}$ is independently unsubstituted n-butyl. In embodiments, $R^{10}$ is independently unsubstituted tert-butyl.

In embodiments, the E3 Ubiquitin ligase binder is a monovalent form of the formula:

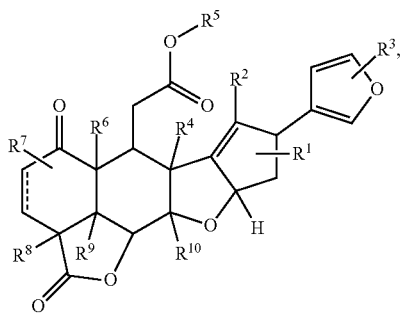

wherein $R^1$, $R^2$, $R^3$, $R^4$, $R^5$, $R^6$, $R^7$, $R^8$, $R^9$, and $R^{10}$ are as described herein. In embodiments, the E3 Ubiquitin ligase binder is a monovalent form of the formula:

In embodiments, the E3 Ubiquitin ligase binder is a monovalent form of the formula:

In embodiments, the E3 Ubiquitin ligase binder has the formula:

In embodiments, the E3 Ubiquitin ligase binder has the formula:

In embodiments, the E3 Ubiquitin ligase binder is a monovalent form of the formula:

wherein $R^1$, $R^{2w}$, $R^3$, $R^4$, $R^5$, $R^6$, $R^7$, $R^8$, $R^9$, $R^{10}$, z1, z3, and z7 are as described herein. In embodiments, the E3 Ubiquitin ligase binder is a monovalent form of the formula:

In embodiments, the E3 Ubiquitin ligase binder is a monovalent form of the formula:

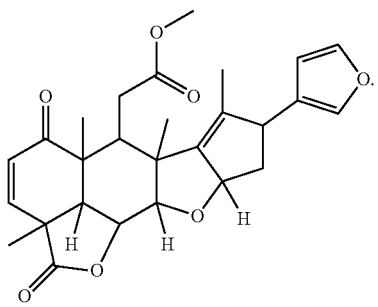

In embodiments, the E3 Ubiquitin ligase binder has the formula:

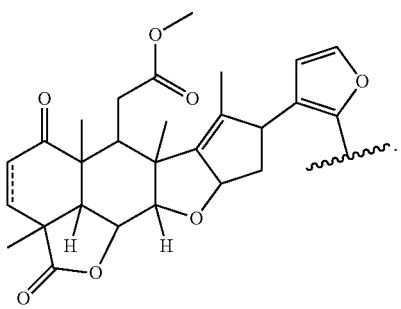

In embodiments, the E3 Ubiquitin ligase binder has the formula:

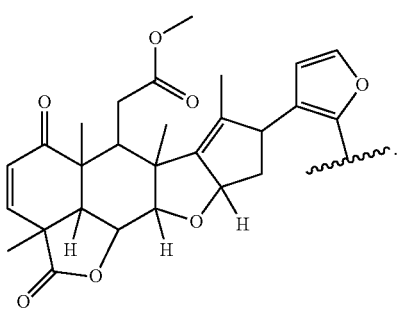

In embodiments, the E3 Ubiquitin ligase binder is a monovalent form of the formula:

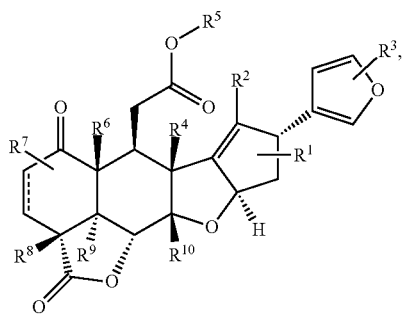

wherein $R^1$, $R^2$, $R^3$, $R^4$, $R^5$, $R^6$, $R^7$, $R^8$, $R^9$, and $R^{10}$ are as described herein. In embodiments, the E3 Ubiquitin ligase binder is a monovalent form of the formula:

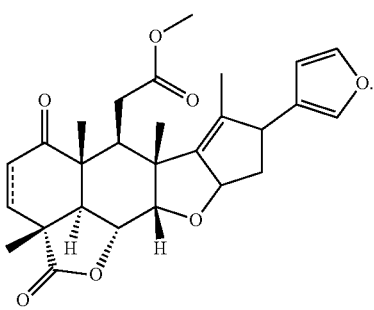

In embodiments, the E3 Ubiquitin ligase binder is a monovalent form of the formula:

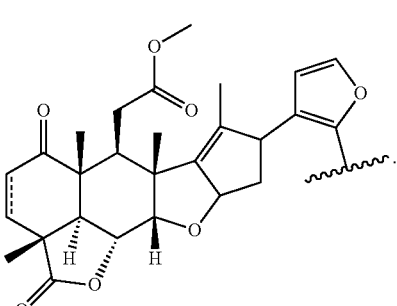

In embodiments, the E3 Ubiquitin ligase binder has the formula:

In embodiments, the E3 Ubiquitin ligase binder has the formula:

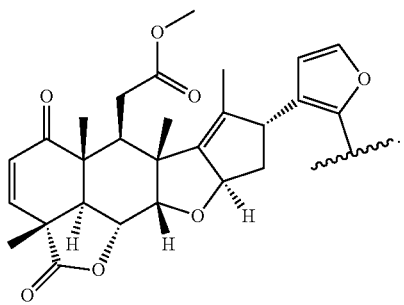

In embodiments, the E3 Ubiquitin ligase binder is a monovalent form of the formula:

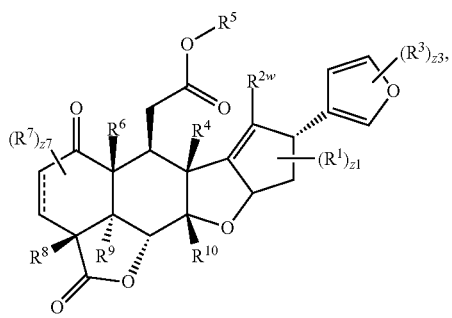

wherein $R^1$, $R^{2w}$, $R^3$, $R^4$, $R^5$, $R^6$, $R^7$, $R^8$, $R^9$, $R^{10}$, z1, z3, and z7 are as described herein. In embodiments, the E3 Ubiquitin ligase binder is a monovalent form of the formula:

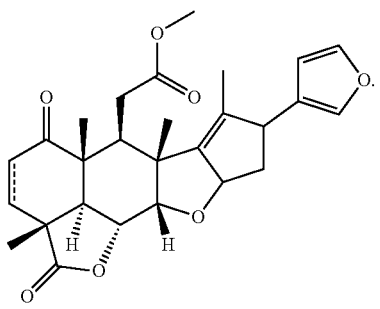

In embodiments, the E3 Ubiquitin ligase binder is a monovalent form of the formula:

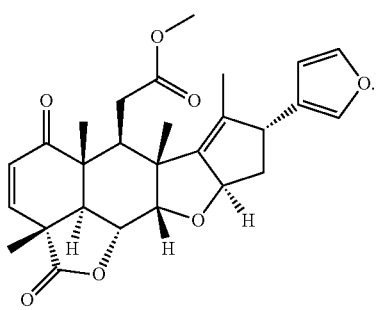

In embodiments, the E3 Ubiquitin ligase binder has the formula:

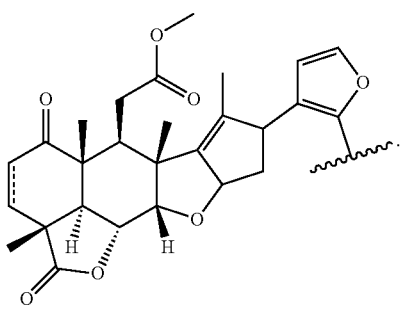

In embodiments, the E3 Ubiquitin ligase binder has the formula:

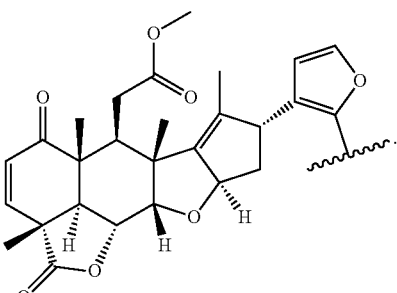

In embodiments, the E3 Ubiquitin ligase binder is a moiety of a compound having a monovalent form of the formula:

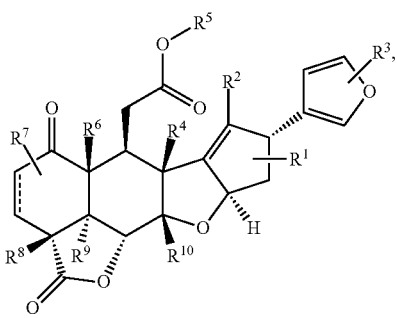

wherein $R^1$, $R^2$, $R^3$, $R^4$, $R^5$, $R^6$, $R^7$, $R^8$, $R^9$, and $R^{10}$ are as described herein. In embodiments, the E3 Ubiquitin ligase binder is a moiety of a compound having a monovalent form of the formula:

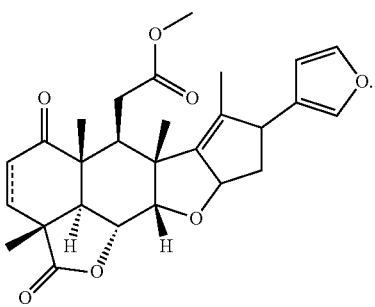

In embodiments, the E3 Ubiquitin ligase binder is a moiety of a compound having a monovalent form of the formula:

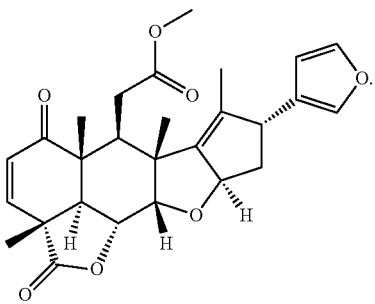

In embodiments, the E3 Ubiquitin ligase binder has the formula:

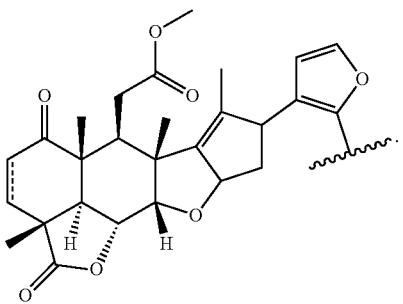

In embodiments, the E3 Ubiquitin ligase binder has the formula:

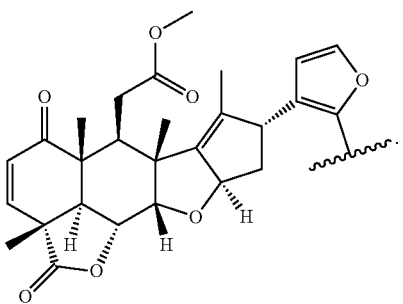

In embodiments, the E3 Ubiquitin ligase binder is a moiety of a compound having a monovalent form of the formula:

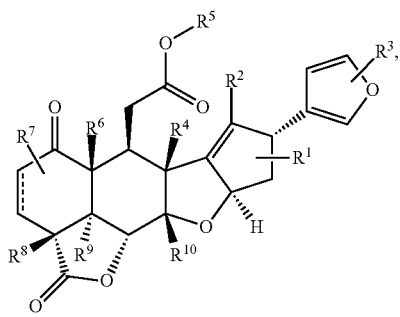

wherein $R^1$, $R^2$, $R^3$, $R^4$, $R^5$, $R^6$, $R^7$, $R^8$, $R^9$, and $R^{10}$ are as described herein. In embodiments, the E3 Ubiquitin ligase binder is a moiety of a compound having a monovalent form of the formula:

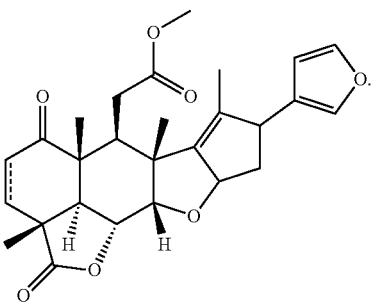

In embodiments, the E3 Ubiquitin ligase binder is a moiety of a compound having a monovalent form of the formula:

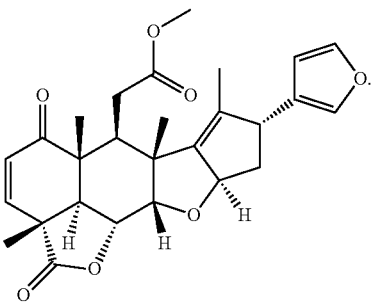

In embodiments, the E3 Ubiquitin ligase binder has the formula:

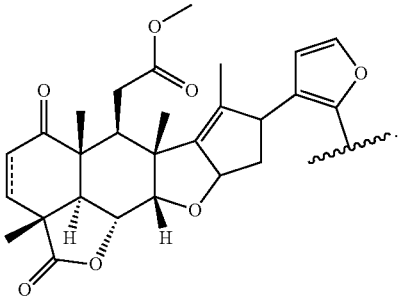

In embodiments, the E3 Ubiquitin ligase binder has the formula:

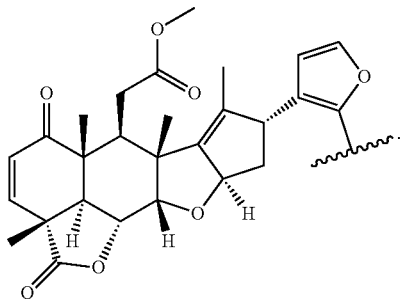

In embodiments, the E3 Ubiquitin ligase binder is a moiety of a compound having the formula:

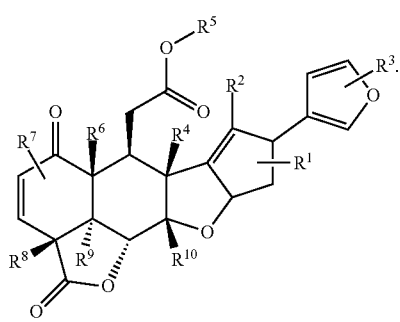

$R^1$, $R^2$, $R^3$, $R^4$, $R^5$, $R^6$, $R^7$, $R^8$, $R^9$, and $R^{10}$ are as described herein.

In embodiments, the E3 Ubiquitin ligase binder is a monovalent compound having the formula:

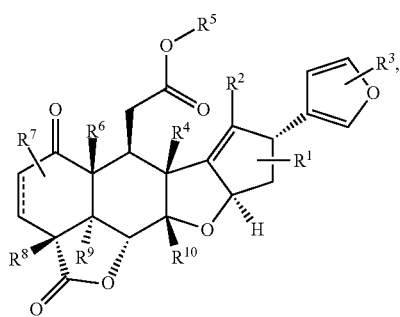

wherein $R^1$, $R^2$, $R^3$, $R^4$, $R^5$, $R^6$, $R^7$, $R^8$, $R^9$, and $R^{10}$ are as described herein. In embodiments, the E3 Ubiquitin ligase binder is a monovalent compound having the formula:

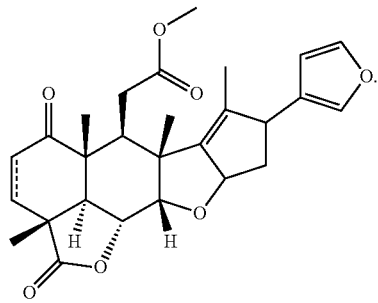

In embodiments, the E3 Ubiquitin ligase binder is a monovalent compound having the formula:

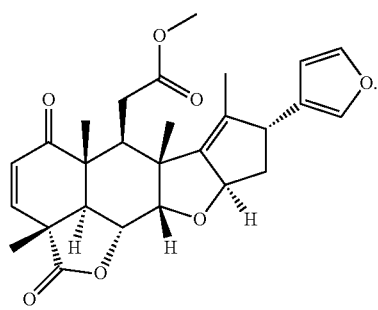

In embodiments, the E3 Ubiquitin ligase binder has the formula:

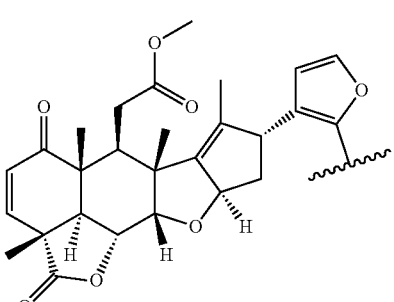

In embodiments, the E3 Ubiquitin ligase binder has the formula:

In embodiments, the E3 Ubiquitin ligase binder is a monovalent compound having the formula:

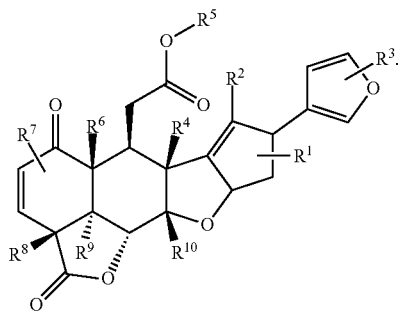

$R^1$, $R^2$, $R^3$, $R^4$, $R^5$, $R^6$, $R^7$, $R^8$, $R^9$, and $R^{10}$ are as described herein.

In embodiments, the E3 Ubiquitin ligase binder is a monovalent form of the formula:

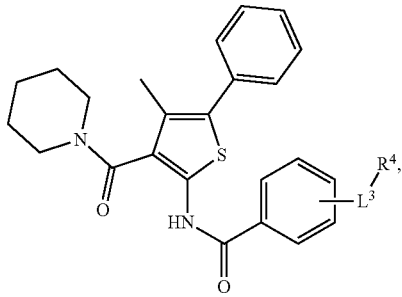

wherein $L^3$ and $R^4$ are as described herein.

In embodiments, the E3 Ubiquitin ligase binder is a moiety of a compound having the formula:

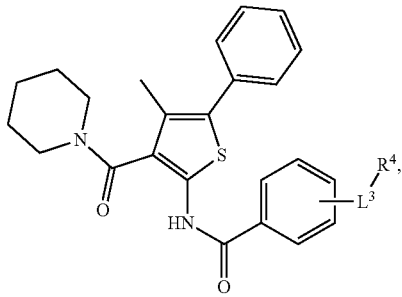

wherein $L^3$ and $R^4$ are as described herein.

In embodiments, the E3 Ubiquitin ligase binder is a monovalent compound having the formula:

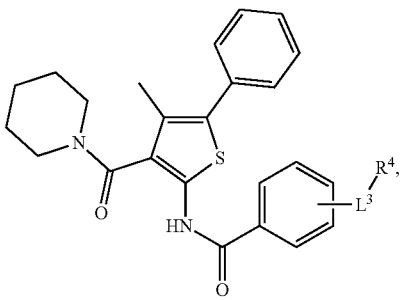

wherein $L^3$ and $R^4$ are as described herein.

In embodiments, the E3 Ubiquitin ligase binder is a monovalent form of the formula:

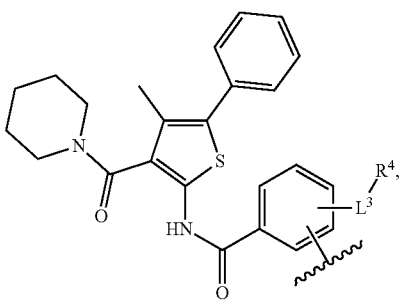

wherein $L^3$ and $R^4$ are as described herein.

In embodiments, the E3 Ubiquitin ligase binder has the formula:

wherein $L^3$ and $R^4$ are as described herein.

In embodiments, the E3 Ubiquitin ligase binder has the formula:

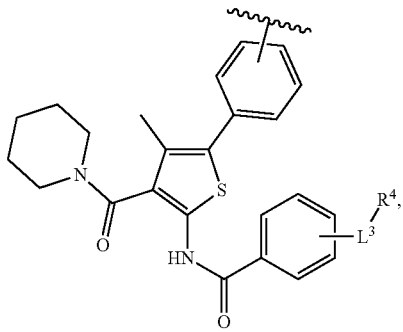

wherein $L^3$ and $R^4$ are as described herein.

In embodiments, the E3 Ubiquitin ligase binder has the formula:

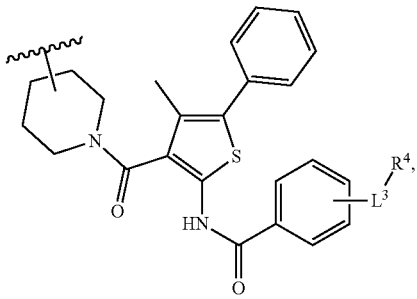

wherein $L^3$ and $R^4$ are as described herein.

In embodiments, the E3 Ubiquitin ligase binder has the formula:

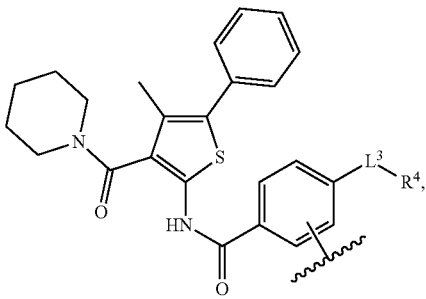

wherein $L^3$ and $R^4$ are as described herein.

In embodiments, the E3 Ubiquitin ligase binder has the formula:

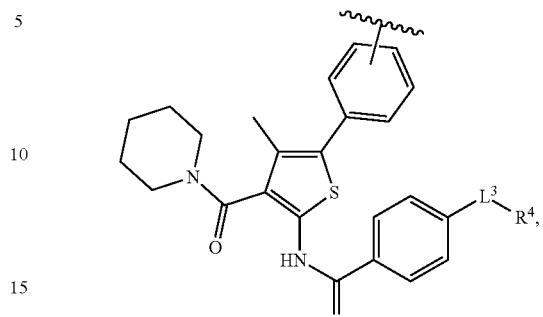

wherein $L^3$ and $R^4$ are as described herein.

In embodiments, the E3 Ubiquitin ligase binder has the formula:

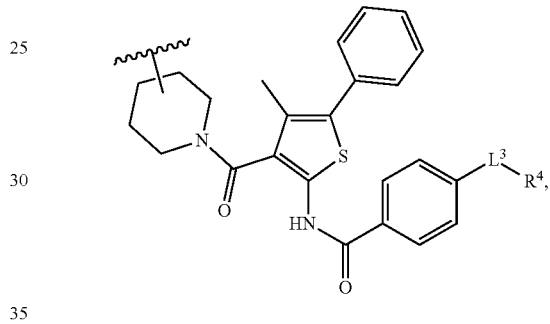

wherein $L^3$ and $R^4$ are as described herein.

In embodiments, $R^1$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, $R^1$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, $R^1$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^1$-substituted or unsubstituted alkyl (e.g., $C_1$-$C_9$, $C_1$-$C_6$, $C_1$-$C_4$, or $C_1$-$C_2$), $R^{11}$-substituted or unsubstituted heteroalkyl (e.g., 2 to 8 membered, 2 to 6 membered, 4 to 6 membered, 2 to 3 membered, or 4 to 5 membered), $R^1$-substituted or unsubstituted cycloalkyl (e.g., $C_3$-$C_8$, $C_3$-$C_6$, $C_4$-$C_6$, or $C_5$-$C_6$), $R^{11}$-substituted or unsubstituted heterocycloalkyl (e.g., 3 to 8 membered, 3 to 6 membered, 4 to 6 membered, 4 to 5 membered, or 5 to 6 membered), $R^{11}$-substituted or unsubstituted aryl (e.g., $C_6$-$C_{10}$ or phenyl), or $R^{11}$-substituted or unsubstituted heteroaryl (e.g., 5 to 10 membered, 5 to 9 membered, or 5 to 6 membered), or a bond to the binder linker; two $R^1$ substituents may optionally be joined to form an $R^{11}$-substituted or unsubstituted cycloalkyl (e.g., $C_3$-$C_8$, $C_3$-$C_6$, $C_4$-$C_6$, or $C_5$-$C_6$), $R^{11}$-substituted or unsubstituted heterocycloalkyl (e.g., 3 to 8 membered, 3 to 6 membered, 4 to 6 membered, 4 to 5 membered, or 5 to 6 membered), $R^{11}$-substituted or unsubstituted aryl (e.g., $C_6$-$C_{10}$ or phenyl), or $R^{11}$-substituted or unsubstituted heteroaryl (e.g., 5 to 10 membered, 5 to 9 membered, or 5 to 6 membered).

In embodiments, $R^1$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{11}$-substituted or unsubstituted $C_1$-$C_8$ alkyl, $R^{11}$-substituted or unsubstituted 2 to 8 membered heteroalkyl, $R^{11}$-substituted or unsubstituted $C_3$-$C_8$ cycloalkyl, $R^{11}$-substituted or unsubstituted 3 to 8 membered heterocycloalkyl, $R^{11}$-substituted or unsubstituted $C_6$-$C_{10}$ aryl, or $R^{11}$-substituted or unsubstituted 5 to 10 membered heteroaryl, or a bond to the binder linker; two $R^1$ substituents may optionally be joined to form an $R^{11}$-substituted or unsubstituted $C_3$-$C_8$ cycloalkyl, $R^{11}$-substituted or unsubstituted 3 to 8 membered heterocycloalkyl, $R^{11}$-substituted or unsubstituted $C_6$-$C_{10}$ aryl, or $R^{11}$-substituted or unsubstituted 5 to 10 membered heteroaryl.

In embodiments, $R^1$ is independently halogen. In embodiments, $R^1$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^1$ is independently halogen. In embodiments, $R^1$ is unsubstituted alkyl, unsubstituted heteroalkyl, unsubstituted cycloalkyl, unsubstituted heterocycloalkyl, unsubstituted aryl, or unsubstituted heteroaryl.

$R^{11}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

In embodiments, $R^{11}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{11}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^{11}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{11}$ is substituted with a plurality of groups selected from substituent groups, size-limited substituent groups, and lower substituent groups; each substituent group, size-limited substituent group, and/or lower substituent group may optionally be different. In embodiments, when $R^{11}$ is substituted, it is substituted with at least one substituent group. In embodiments, when $R^{11}$ is substituted, it is substituted with at least one size-limited substituent group. In embodiments, when $R^{11}$ is substituted, it is substituted with at least one lower substituent group.

In embodiments, $R^{11}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{12}$-substituted or unsubstituted alkyl (e.g., $C_1$-$C_8$, $C_1$-$C_6$, $C_1$-$C_4$, or $C_1$-$C_2$), $R^{12}$-substituted or unsubstituted heteroalkyl (e.g., 2 to 8 membered, 2 to 6 membered, 4 to 6 membered, 2 to 3 membered, or 4 to 5 membered), $R^{12}$-substituted or unsubstituted cycloalkyl (e.g., $C_3$-$C_8$, $C_3$-$C_6$, $C_4$-$C_6$, or $C_5$-$C_6$), $R^{12}$-substituted or unsubstituted heterocycloalkyl (e.g., 3 to 8 membered, 3 to 6 membered, 4 to 6 membered, 4 to 5 membered, or 5 to 6 membered), $R^{12}$-substituted or unsubstituted aryl (e.g., $C_6$-$C_{10}$ or phenyl), or $R^{12}$-substituted or unsubstituted heteroaryl (e.g., 5 to 10 membered, 5 to 9 membered, or 5 to 6 membered). In embodiments, $R^{11}$ is unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{11}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{12}$-substituted or unsubstituted $C_1$-$C_8$ alkyl, $R^{12}$-substituted or unsubstituted 2 to 8 membered heteroalkyl, $R^{12}$-substituted or unsubstituted $C_3$-$C_8$ cycloalkyl, $R^{12}$-substituted or unsubstituted 3 to 8 membered heterocycloalkyl, $R^{12}$-substituted or unsubstituted $C_6$-$C_{10}$ aryl, or $R^{12}$-substituted or unsubstituted 5 to 10 membered heteroaryl. In embodiments, $R^{11}$ is unsubstituted alkyl, unsubstituted heteroalkyl, unsubstituted cycloalkyl, unsubstituted heterocycloalkyl, unsubstituted aryl, or unsubstituted heteroaryl.

$R^{12}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{12}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_8$ alkyl, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{12}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

In embodiments, $R^2$ is independently halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, R$^2$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted R$^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^2$ is substituted with a plurality of groups selected from substituent groups, size-limited substituent groups, and lower substituent groups; each substituent group, size-limited substituent group, and/or lower substituent group may optionally be different. In embodiments, when R$^2$ is substituted, it is substituted with at least one substituent group. In embodiments, when R$^2$ is substituted, it is substituted with at least one size-limited substituent group. In embodiments, when R$^2$ is substituted, it is substituted with at least one lower substituent group.

In embodiments, R$^2$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{21}$-substituted or unsubstituted alkyl (e.g., C$_1$-C$_8$, C$_1$-C$_6$, C$_1$-C$_4$, or C$_1$-C$_2$), R$^{21}$-substituted or unsubstituted heteroalkyl (e.g., 2 to 8 membered, 2 to 6 membered, 4 to 6 membered, 2 to 3 membered, or 4 to 5 membered), R$^{21}$-substituted or unsubstituted cycloalkyl (e.g., C$_3$-C$_8$, C$_3$-C$_6$, C$_4$-C$_6$, or C$_5$-C$_6$), R$^{21}$-substituted or unsubstituted heterocycloalkyl (e.g., 3 to 8 membered, 3 to 6 membered, 4 to 6 membered, 4 to 5 membered, or 5 to 6 membered), R$^{21}$-substituted or unsubstituted aryl (e.g., C$_6$-C$_{10}$ or phenyl), or R$^{21}$-substituted or unsubstituted heteroaryl (e.g., 5 to 10 membered, 5 to 9 membered, or 5 to 6 membered); two R$^2$ substituents may optionally be joined to form an R$^{21}$-substituted or unsubstituted cycloalkyl (e.g., C$_3$-C$_8$, C$_3$-C$_6$, C$_4$-C$_6$, or C$_5$-C$_6$), R$^{21}$-substituted or unsubstituted heterocycloalkyl (e.g., 3 to 8 membered, 3 to 6 membered, 4 to 6 membered, 4 to 5 membered, or 5 to 6 membered), R$^{21}$-substituted or unsubstituted aryl (e.g., C$_6$-C$_{10}$ or phenyl), or R$^{21}$-substituted or unsubstituted heteroaryl (e.g., 5 to 10 membered, 5 to 9 membered, or 5 to 6 membered).

In embodiments, R$^2$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{21}$-substituted or unsubstituted C$_1$-C$_8$ alkyl, R$^{21}$-substituted or unsubstituted 2 to 8 membered heteroalkyl, R$^{21}$-substituted or unsubstituted C$_3$-C$_8$ cycloalkyl, R$^{21}$-substituted or unsubstituted 3 to 8 membered heterocycloalkyl, R$^{21}$-substituted or unsubstituted C$_6$-C$_{10}$ aryl, or R$^{21}$-substituted or unsubstituted 5 to 10 membered heteroaryl, or a bond to the binder linker; two R$^2$ substituents may optionally be joined to form an R$^{21}$-substituted or unsubstituted C$_3$-C$_8$ cycloalkyl, R$^{21}$-substituted or unsubstituted 3 to 8 membered heterocycloalkyl, R$^{21}$-substituted or unsubstituted C$_6$-C$_{10}$ aryl, or R$^{21}$-substituted or unsubstituted 5 to 10 membered heteroaryl.

In embodiments, R$^2$ is independently halogen, —CF$_3$, —NO$_2$, R$^{21}$-substituted or unsubstituted C$_1$-C$_3$ alkyl, unsubstituted 2 to 3 membered heteroalkyl, or a bond to the binder linker; two R$^2$ substituents may optionally be joined to form an unsubstituted phenyl.

In embodiments, R$^2$ is independently halogen, —CF$_3$, —NO$_2$, R$^{11}$-substituted or unsubstituted C$_1$-C$_3$ alkyl, unsubstituted 2 to 3 membered heteroalkyl, or a bond to the binder linker; two R$^2$ substituents may optionally be joined to form an unsubstituted phenyl; and R$^{21}$ is independently —OH.

In embodiments, R$^2$ is independently halogen. In embodiments, R$^2$ is independently —Cl. In embodiments, R$^2$ is independently —Br. In embodiments, R$^2$ is independently —I. In embodiments, R$^2$ is independently —F. In embodiments, R$^2$ is independently —CF$_3$. In embodiments, R$^2$ is independently —NO$_2$. In embodiments, R$^2$ is independently R$^{21}$-substituted C$_1$-C$_4$ alkyl. In embodiments, R$^2$ is independently R$^{21}$-substituted C$_1$-C$_4$ alkyl, wherein R$^{21}$ is independently —OH. In embodiments, R$^2$ is independently —CH$_2$OH. In embodiments, R$^2$ is independently unsubstituted C$_1$-C$_4$ alkyl. In embodiments, R$^2$ is independently unsubstituted methyl. In embodiments, R$^2$ is independently unsubstituted ethyl. In embodiments, R$^2$ is independently unsubstituted n-propyl. In embodiments, R$^2$ is independently unsubstituted isopropyl. In embodiments, R$^2$ is independently unsubstituted n-butyl. In embodiments, R$^2$ is independently unsubstituted tert-butyl. In embodiments, R$^2$ is independently unsubstituted 2 to 4 membered heteroalkyl. In embodiments, R$^2$ is independently —OCH$_3$. In embodiments, R$^2$ is independently —OCH$_2$CH$_3$. In embodiments, $R^2$ is independently a bond to the binder linker. In embodiments, two $R^2$ substituents may optionally be joined to form an unsubstituted phenyl.

$R^{21}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

In embodiments, $R^{21}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{21}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^{21}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{21}$ is substituted with a plurality of groups selected from substituent groups, size-limited substituent groups, and lower substituent groups; each substituent group, size-limited substituent group, and/or lower substituent group may optionally be different. In embodiments, when $R^{21}$ is substituted, it is substituted with at least one substituent group. In embodiments, when $R^{21}$ is substituted, it is substituted with at least one size-limited substituent group. In embodiments, when $R^{21}$ is substituted, it is substituted with at least one lower substituent group.

In embodiments, $R^{21}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 to 3 membered, or 4 to 5 membered), $R^{22}$-substituted or unsubstituted cycloalkyl (e.g., $C_3$-$C_8$, $C_3$-$C_6$, $C_4$-$C_6$, or $C_5$-$C_6$), $R^{22}$-substituted or unsubstituted heterocycloalkyl (e.g., 3 to 8 membered, 3 to 6 membered, 4 to 6 membered, 4 to 5 membered, or 5 to 6 membered), $R^{22}$-substituted or unsubstituted aryl (e.g., $C_6$-$C_{10}$ or phenyl), or $R^{22}$-substituted or unsubstituted heteroaryl (e.g., 5 to 10 membered, 5 to 9 membered, or 5 to 6 membered). In embodiments, $R^{21}$ is unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{21}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{22}$-substituted or unsubstituted $C_1$-$C_8$ alkyl, $R^{22}$-substituted or unsubstituted 2 to 8 membered heteroalkyl, $R^{22}$-substituted or unsubstituted $C_3$-$C_8$ cycloalkyl, $R^{22}$-substituted or unsubstituted 3 to 8 membered heterocycloalkyl, $R^{22}$-substituted or unsubstituted $C_6$-$C_{10}$ aryl, or $R^{22}$-substituted or unsubstituted 5 to 10 membered heteroaryl.

$R^{22}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{22}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{22}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_8$ alkyl, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{22}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

In embodiments, $L^3$ is a bond, —N(R³)—, —C(O)—, —C(O)N(R³)—, —N(R³)C(O)—, —N(H)—, —C(O)N(H)—, —N(H)C(O)—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^3$ is a bond, —N(R³)—, —C(O)—, —C(O)N(R³)—, —N(R³)C(O)—, —N(H)—, —C(O)N(H)—, —N(H)C(O)—, —C(O)O—, —OC(O)—, substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted (e.g., substituted with at least one substituent group, size-limited substituent group, or lower substituent group) or unsubstituted heteroarylene.

In embodiments, a substituted $L^3$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^3$ is substituted with a plurality of groups selected from substituent groups, size-limited substituent groups, and lower substituent groups; each substituent group, size-limited substituent group, and/or lower substituent group may optionally be different. In embodiments, when $L^3$ is substituted, it is substituted with at least one substituent group. In embodiments, when $L^3$ is substituted, it is substituted with at least one size-limited substituent group. In embodiments, when $L^3$ is substituted, it is substituted with at least one lower substituent group.

In embodiments, $L^3$ is a bond, —N(R³)—, —C(O)—, —C(O)N(R³)—, —N(R³)C(O)—, —N(H)—, —C(O)N(H)—, —N(H)C(O)—, —C(O)O—, R³-substituted or unsubstituted alkylene (e.g., $C_1$-$C_8$, $C_1$-$C_6$, $C_1$-$C_4$, or $C_1$-$C_2$), R³-substituted or unsubstituted heteroalkylene (e.g., 2 to 8 membered, 2 to 6 membered, 4 to 6 membered, 2 to 3 membered, or 4 to 5 membered), R³-substituted or unsubstituted cycloalkylene (e.g., $C_3$-$C_8$, $C_3$-$C_6$, $C_4$-$C_6$, or $C_5$-$C_6$), R³-substituted or unsubstituted heterocycloalkylene (e.g., 3 to 8 membered, 3 to 6 membered, 4 to 6 membered, 4 to 5 membered, or 5 to 6 membered), R³-substituted or unsubstituted arylene (e.g., $C_6$-$C_{10}$ or phenylene), or R³-substituted or unsubstituted heteroarylene (e.g., 5 to 10 membered, 5 to 9 membered, or 5 to 6 membered).

In embodiments, $L^3$ is a bond, —N(R³)—, —C(O)—, —C(O)N(R³)—, —N(R³)C(O)—, —N(H)—, —C(O)N(H)—, —N(H)C(O)—, —C(O)O—, R³-substituted or unsubstituted $C_1$-$C_8$ alkylene, R³-substituted or unsubstituted 2 to 8 membered heteroalkylene, R³-substituted or unsubstituted $C_3$-$C_8$ cycloalkylene, R³-substituted or unsubstituted 3 to 8 membered heterocycloalkylene, R³-substituted or unsubstituted $C_6$-$C_{10}$ arylene, or R³-substituted or unsubstituted 5 to 10 membered heteroarylene.

In embodiments, $L^3$ is —N(R³)—. In embodiments, $L^3$ is —N(R³)—; R³ is independently $R^{31}$-substituted methyl, unsubstituted phenyl, or unsubstituted 5 to 6 membered heteroaryl; and $R^{31}$ is independently unsubstituted phenyl, or unsubstituted 5 to 6 membered heteroaryl. In embodiments, $L^3$ is

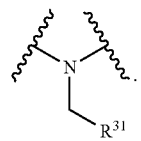

In embodiments, L³ is

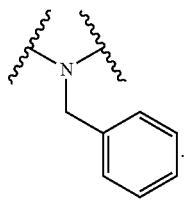 [SMILES: *N(*)Cc1ccccc1]

In embodiments, L³ is —CH₂NH—.

In embodiments, R³ is independently R³¹-substituted or unsubstituted C₁-C₄ alkyl. In embodiments, R³ is independently R³¹-substituted C₁-C₄ alkyl. In embodiments, R³ is independently R³¹-substituted methyl. In embodiments, R³ is independently R³¹-substituted ethyl. In embodiments, R³ is independently R³¹-substituted propyl. In embodiments, R³ is independently R³¹-substituted butyl. In embodiments, R³ is independently halogen. In embodiments, R³ is independently —F. In embodiments, R³ is independently —Cl. In embodiments, R³ is independently —Br. In embodiments, R³ is independently —I. In embodiments, R³ is independently R³¹-substituted or unsubstituted phenyl. In embodiments, R³ is independently R³¹-substituted phenyl. In embodiments, R³ is independently

In embodiments, R³¹ is independently —C(O)H, —COOH, or R³²-substituted or unsubstituted 2 to 6 membered heteroalkyl. In embodiments, R³¹ is independently —C(O)H. In embodiments, R³¹ is independently —COOH. In embodiments, R³¹ is independently R³²-substituted 2 to 6 membered heteroalkyl. In embodiments, R³¹ is independently unsubstituted 2 to 6 membered heteroalkyl. In embodiments, R³¹ is independently

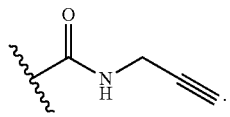

In embodiments, R³¹ is independently R³²-substituted or unsubstituted phenyl. In embodiments, R³¹ is independently unsubstituted phenyl. In embodiments, R³² is independently oxo.

In embodiments, R³ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R³ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl (e.g., C₁-C₈, C₁-C₆, C₁-C₄, or C₁-C₂), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C₃-C₈, C₃-C₆, C₄-C₆, or C₅-C₆), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C₆-C₁₀ or phenyl), or substituted or unsubstituted heteroaryl (e.g., 5 to 10 membered, 5 to 9 membered, or 5 to 6 membered).

In embodiments, R³ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted R³ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R³ is substituted with a plurality of groups selected from substituent groups, size-limited substituent groups, and lower substituent groups; each substituent group, size-limited substituent group, and/or lower substituent group may optionally be different. In embodiments, when R³ is substituted, it is substituted with at least one substituent group. In embodiments, when R³ is substituted, it is substituted with at least one size-limited substituent group. In embodiments, when R³ is substituted, it is substituted with at least one lower substituent group.

In embodiments, R³ is independently hydrogen, oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{31}$-substituted or unsubstituted alkyl (e.g., C$_1$-C$_8$, C$_1$-C$_6$, C$_1$-C$_4$, or C$_1$-C$_2$), R$^{31}$-substituted or unsubstituted heteroalkyl (e.g., 2 to 8 membered, 2 to 6 membered, 4 to 6 membered, 2 to 3 membered, or 4 to 5 membered), R$^{31}$-substituted or unsubstituted cycloalkyl (e.g., C$_3$-C$_8$, C$_3$-C$_6$, C$_4$-C$_6$, or C$_5$-C$_6$), R$^{31}$-substituted or unsubstituted heterocycloalkyl (e.g., 3 to 8 membered, 3 to 6 membered, 4 to 6 membered, 4 to 5 membered, or 5 to 6 membered), R$^{31}$-substituted or unsubstituted aryl (e.g., C$_6$-C$_{10}$ or phenyl), or R$^{31}$-substituted or unsubstituted heteroaryl (e.g., 5 to 10 membered, 5 to 9 membered, or 5 to 6 membered).

In embodiments, R$^3$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{31}$-substituted or unsubstituted C$_1$-C$_8$ alkyl, R$^{31}$-substituted or unsubstituted 2 to 8 membered heteroalkyl, R$^{31}$-substituted or unsubstituted C$_3$-C$_8$ cycloalkyl, R$^{31}$-substituted or unsubstituted 3 to 8 membered heterocycloalkyl, R$^{31}$-substituted or unsubstituted C$_6$-C$_{10}$ aryl, or R$^{31}$-substituted or unsubstituted 5 to 10 membered heteroaryl.

R$^{31}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

In embodiments, R$^{31}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, R$^{31}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted R$^{31}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{31}$ is substituted with a plurality of groups selected from substituent groups, size-limited substituent groups, and lower substituent groups; each substituent group, size-limited substituent group, and/or lower substituent group may optionally be different. In embodiments, when R$^{31}$ is substituted, it is substituted with at least one substituent group. In embodiments, when R$^{31}$ is substituted, it is substituted with at least one size-limited substituent group. In embodiments, when R$^{31}$ is substituted, it is substituted with at least one lower substituent group.

In embodiments, R$^{31}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{32}$-substituted or unsubstituted alkyl (e.g., C$_1$-C$_8$, C$_1$-C$_6$, C$_1$-C$_4$, or C$_1$-C$_2$), R$^{32}$-substituted or unsubstituted heteroalkyl (e.g., 2 to 8 membered, 2 to 6 membered, 4 to 6 membered, 2 to 3 membered, or 4 to 5 membered), R$^{32}$-substituted or unsubstituted cycloalkyl (e.g., C$_3$-C$_8$, C$_3$-C$_6$, C$_4$-C$_6$, or C$_5$-C$_6$), R$^{32}$-substituted or unsubstituted heterocycloalkyl (e.g., 3 to 8 membered, 3 to 6 membered, 4 to 6 membered, 4 to 5 membered, or 5 to 6 membered), R$^{32}$-substituted or unsubstituted aryl (e.g., C$_6$-C$_{10}$ or phenyl), or R$^{32}$-substituted or unsubstituted heteroaryl (e.g., 5 to 10 membered, 5 to 9 membered, or 5 to 6 membered).

In embodiments, R$^{31}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{32}$-substituted or unsubstituted C$_1$-C$_8$ alkyl, R$^{32}$-substituted or unsubstituted 2 to 8 membered heteroalkyl, $R^{32}$-substituted or unsubstituted $C_3$-$C_8$ cycloalkyl, $R^{32}$-substituted or unsubstituted 3 to 8 membered heterocycloalkyl, $R^{32}$-substituted or unsubstituted $C_6$-$C_{10}$ aryl, or $R^{32}$-substituted or unsubstituted 5 to 10 membered heteroaryl.

$R^{32}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{32}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{32}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{32}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

In embodiments, $R^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered), or a bond to the binder linker.

In embodiments, $R^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, substituted (e.g., substituted with at least one substituent group, size-limited substituent group, or lower substituent group) or unsubstituted heteroaryl, or a bond to the binder linker.

In embodiments, a substituted $R^4$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^4$ is independently hydrogen or substituted or unsubstituted $C_1$-$C_4$ alkyl. In embodiments, $R^4$ is independently hydrogen. In embodiments, $R^4$ is independently substituted or unsubstituted $C_1$-$C_4$ alkyl. In embodiments, $R^4$ is independently unsubstituted $C_1$-$C_4$ alkyl. In embodiments, $R^4$ is independently unsubstituted methyl. In embodiments, $R^4$ is independently unsubstituted ethyl. In embodiments, $R^4$ is independently unsubstituted n-propyl. In embodiments, $R^4$ is independently unsubstituted isopropyl. In embodiments, $R^4$ is independently unsubstituted n-butyl. In embodiments, $R^4$ is independently unsubstituted tert-butyl. In embodiments, $R^4$ is independently E, wherein E is as described herein, including in embodiments.

In embodiments, $R^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{41}$-substituted or unsubstituted alkyl (e.g., C$_1$-C$_8$, C$_1$-C$_6$, C$_1$-C$_4$, or C$_1$-C$_2$), $R^{41}$-substituted or unsubstituted heteroalkyl (e.g., 2 to 8 membered, 2 to 6 membered, 4 to 6 membered, 2 to 3 membered, or 4 to 5 membered), $R^{41}$-substituted or unsubstituted cycloalkyl (e.g., C$_3$-C$_8$, C$_3$-C$_6$, C$_4$-C$_6$, or C$_5$-C$_6$), $R^{41}$-substituted or unsubstituted heterocycloalkyl (e.g., 3 to 8 membered, 3 to 6 membered, 4 to 6 membered, 4 to 5 membered, or 5 to 6 membered), $R^{41}$-substituted or unsubstituted aryl (e.g., C$_6$-C$_{10}$ or phenyl), or $R^{41}$-substituted or unsubstituted heteroaryl (e.g., 5 to 10 membered, 5 to 9 membered, or 5 to 6 membered), or E.

In embodiments, $R^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{41}$-substituted or unsubstituted C$_1$-C$_8$ alkyl, $R^{41}$-substituted or unsubstituted 2 to 8 membered heteroalkyl, $R^{41}$-substituted or unsubstituted C$_3$-C$_8$ cycloalkyl, $R^{41}$-substituted or unsubstituted 3 to 8 membered heterocycloalkyl, $R^{41}$-substituted or unsubstituted C$_6$-C$_{10}$ aryl, or $R^{41}$-substituted or unsubstituted 5 to 10 membered heteroaryl, or E.

$R^{41}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

In embodiments, $R^{41}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, $R^{41}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^{41}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{41}$ is substituted with a plurality of groups selected from substituent groups, size-limited substituent groups, and lower substituent groups; each substituent group, size-limited substituent group, and/or lower substituent group may optionally be different. In embodiments, when $R^{41}$ is substituted, it is substituted with at least one substituent group. In embodiments, when $R^{41}$ is substituted, it is substituted with at least one size-limited substituent group. In embodiments, when $R^{41}$ is substituted, it is substituted with at least one lower substituent group.

In embodiments, $R^{41}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{42}$-substituted or unsubstituted alkyl (e.g., C$_1$-C$_8$, C$_1$-C$_6$, C$_1$-C$_4$, or C$_1$-C$_2$), $R^{42}$-substituted or unsubstituted heteroalkyl (e.g., 2 to 8 membered, 2 to 6 membered, 4 to 6 membered, 2 to 3 membered, or 4 to 5 membered), $R^{42}$-substituted or unsubstituted cycloalkyl (e.g., C$_3$-C$_8$, C$_3$-C$_6$, C$_4$-C$_6$, or C$_5$-C$_6$), $R^{42}$-substituted or unsubstituted heterocycloalkyl (e.g., 3 to 8 membered, 3 to 6 membered, 4 to 6 membered, 4 to 5 membered, or 5 to 6 membered), $R^{42}$-substituted or unsubstituted aryl (e.g., C$_6$-C$_{10}$ or phenyl), or $R^{42}$-substituted or unsubstituted heteroaryl (e.g., 5 to 10 membered, 5 to 9 membered, or 5 to 6 membered).

In embodiments, $R^{41}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{42}$-substituted or unsubstituted C$_1$-C$_8$ alkyl, R$^{42}$-substituted or unsubstituted 2 to 8 membered heteroalkyl, R$^{42}$-substituted or unsubstituted C$_3$-C$_8$ cycloalkyl, R$^{42}$-substituted or unsubstituted 3 to 8 membered heterocycloalkyl, R$^{42}$-substituted or unsubstituted C$_6$-C$_{10}$ aryl, or R$^{42}$-substituted or unsubstituted 5 to 10 membered heteroaryl.

R$^{42}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^{42}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, R$^{42}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl.

In embodiments, E is a covalent cysteine modifier moiety.
In embodiments, E is

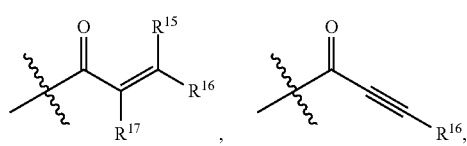

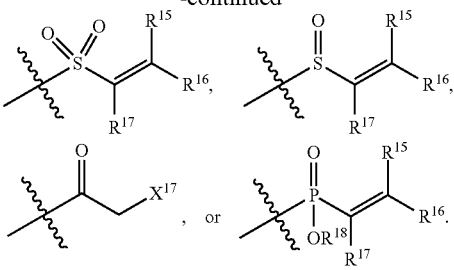

R$^{15}$, R$^{16}$, R$^{17}$, and R$^{18}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X$^{17}$ is halogen. In embodiments, X$^{17}$ is —F. In embodiments, X$^{17}$ is —Cl.

In embodiments, E is

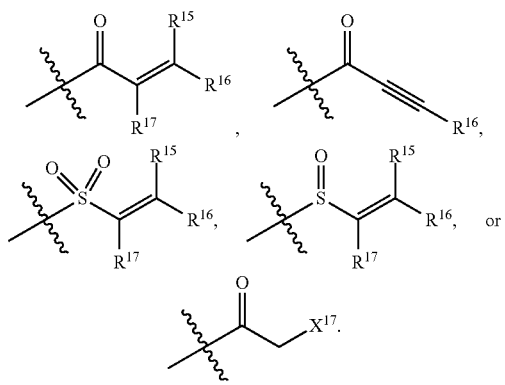

R$^{15}$, R$^{16}$, and R$^{17}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X$^{17}$ is halogen. In embodiments, X$^{17}$ is —F. In embodiments, X$^{17}$ is —Cl.

In embodiments, R$^{15}$, R$^{16}$, and R$^{17}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C4-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, R$^{18}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, R$^{15}$, R$^{16}$, R$^{17}$, and R$^{18}$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, R$^{15}$, R$^{16}$, and R$^{17}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, a substituted R$^{15}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{15}$ is substituted with a plurality of groups selected from substituent groups, size-limited substituent groups, and lower substituent groups; each substituent group, size-limited substituent group, and/or lower substituent group may optionally be different. In embodiments, when R$^{15}$ is substituted, it is substituted with at least one substituent group. In embodiments, when R$^{15}$ is substituted, it is substituted with at least one size-limited substituent group. In embodiments, when R$^{15}$ is substituted, it is substituted with at least one lower substituent group.

In embodiments, a substituted R$^{16}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{16}$ is substituted with a plurality of groups selected from substituent groups, size-limited substituent groups, and lower substituent groups; each substituent group, size-limited substituent group, and/or lower substituent group may optionally be different. In embodiments, when R$^{16}$ is substituted, it is substituted with at least one substituent group. In embodiments, when R$^{16}$ is substituted, it is substituted with at least one size-limited substituent group. In embodiments, when R$^{16}$ is substituted, it is substituted with at least one lower substituent group.

In embodiments, a substituted R$^{17}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{17}$ is substituted with a plurality of groups selected from substituent groups, size-limited substituent groups, and lower substituent groups; each substituent group, size-limited substituent group, and/or lower substituent group may optionally be different. In embodiments, when R$^{17}$ is substituted, it is substituted with at least one substituent group. In embodiments, when R$^{17}$ is substituted, it is substituted with at least one size-limited substituent group. In embodiments, when R$^{17}$ is substituted, it is substituted with at least one lower substituent group.

In embodiments, a substituted R$^{18}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{18}$ is substituted with a plurality of groups selected from substituent groups, size-limited substituent groups, and lower substituent groups; each substituent group, size-limited substituent group, and/or lower substituent group may optionally be different. In embodiments, when $R^{18}$ is substituted, it is substituted with at least one substituent group. In embodiments, when $R^{18}$ is substituted, it is substituted with at least one size-limited substituent group. In embodiments, when $R^{18}$ is substituted, it is substituted with at least one lower substituent group.

In embodiments, $R^{15}$, $R^{16}$, $R^{17}$, and $R^{18}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, C3-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{15}$, $R^{16}$, and $R^{17}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl, unsubstituted heteroalkyl, unsubstituted cycloalkyl, unsubstituted heterocycloalkyl, unsubstituted aryl, or unsubstituted heteroaryl.

In embodiments, E is

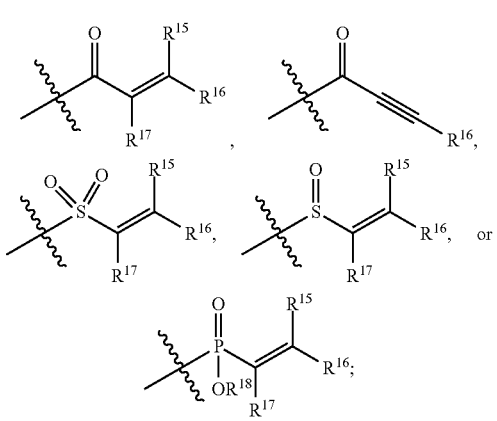

and $R^{15}$, $R^{16}$, $R^{17}$, and $R^{18}$ are independently hydrogen.

In embodiments, E is

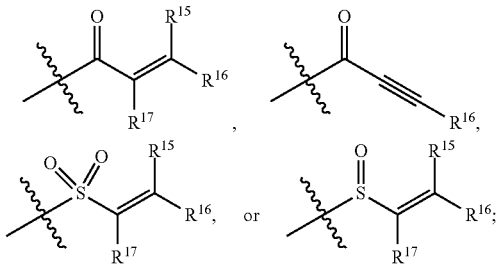

and $R^{15}$, $R^{16}$, and $R^{17}$ are independently hydrogen. In embodiments, E is

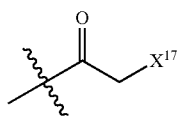

and $R^{17}$ is independently —Cl.

In embodiments, -$L^3$-$R^4$ is:

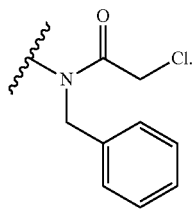 [SMILES: *N(Cc1ccccc1)C(=O)CCl]

In embodiments, -$L^3$-$R^4$ is:

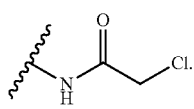 [SMILES: *NC(=O)CCl]

In embodiments, -$L^3$-$R^4$ is:

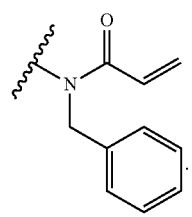 [SMILES: *N(Cc1ccccc1)C(=O)C=C]

In embodiments, -$L^3$-$R^4$ is:

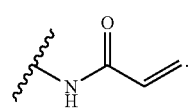 [SMILES: *NC(=O)C=C]

In embodiments, z1 is an integer from 0 to 2. In embodiments, z2 is an integer from 0 to 2. In embodiments, z1 is 0. In embodiments, z1 is 1. In embodiments, z1 is 2. In embodiments, z1 is 3. In embodiments, z1 is 4. In embodiments, z2 is 0. In embodiments, z2 is 1. In embodiments, z2 is 2. In embodiments, z2 is 3. In embodiments, z2 is 4. In embodiments, z2 is 5.

In embodiments, z2 is 1 and $R^2$ is a bond to the binder linker.

In embodiments, $R^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered), or a bond to the binder linker.

In embodiments, $R^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, substituted (e.g., substituted with at least one substituent group, size-limited substituent group, or lower substituent group) or unsubstituted heteroaryl, or a bond to the binder linker.

In embodiments, a substituted $R^7$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^7$ is substituted with a plurality of groups selected from substituent groups, size-limited substituent groups, and lower substituent groups; each substituent group, size-limited substituent group, and/or lower substituent group may optionally be different. In embodiments, when $R^7$ is substituted, it is substituted with at least one substituent group. In embodiments, when $R^7$ is substituted, it is substituted with at least one size-limited substituent group. In embodiments, when $R^7$ is substituted, it is substituted with at least one lower substituent group.

In embodiments, $R^1$, $R^2$, and $R^7$ are independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{51}$-substituted or unsubstituted $C_1$-$C_8$ alkyl, $R^{51}$-substituted or unsubstituted 2 to 8 membered heteroalkyl, $R^{51}$-substituted or unsubstituted $C_3$-$C_8$ cycloalkyl, $R^{51}$-substituted or unsubstituted 3 to 8 membered heterocycloalkyl, $R^{51}$-substituted or unsubstituted $C_6$-$C_{10}$ aryl, or $R^{51}$-substituted or unsubstituted 5 to 10 membered heteroaryl, or a bond to the binder linker; two $R^1$ substituents or two $R^2$ substituents or two $R^7$ substituents may optionally be joined to form an $R^{51}$-substituted or unsubstituted $C_3$-$C_8$ cycloalkyl, $R^{51}$-substituted or unsubstituted 3 to 8 membered heterocycloalkyl, $R^{51}$-substituted or unsubstituted $C_6$-$C_{10}$ aryl, or $R^{51}$-substituted or unsubstituted 5 to 10 membered heteroaryl.

In embodiments, $R^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{51}$-substituted or unsubstituted alkyl (e.g., $C_1$-$C_8$, $C_1$-$C_6$, $C_1$-$C_4$, or $C_1$-$C_2$), $R^{51}$-substituted or unsubstituted heteroalkyl (e.g., 2 to 8 membered, 2 to 6 membered, 4 to 6 membered, 2 to 3 membered, or 4 to 5 membered), $R^{51}$-substituted or unsubstituted cycloalkyl (e.g., $C_3$-$C_8$, $C_3$-$C_6$, $C_4$-$C_6$, or $C_5$-$C_6$), $R^{51}$-substituted or unsubstituted heterocycloalkyl (e.g., 3 to 8 membered, 3 to 6 membered, 4 to 6 membered, 4 to 5 membered, or 5 to 6 membered), $R^{51}$-substituted or unsubstituted aryl (e.g., $C_6$-$C_{10}$ or phenyl), or $R^{51}$-substituted or unsubstituted heteroaryl (e.g., 5 to 10 membered, 5 to 9 membered, or 5 to 6 membered), or a bond to the binder linker; two $R^7$ substituents may optionally be joined to form an $R^{51}$-substituted or unsubstituted cycloalkyl (e.g., $C_3$-$C_8$, $C_3$-$C_6$, $C_4$-$C_6$, or $C_5$-$C_6$), $R^{51}$-substituted or unsubstituted heterocycloalkyl (e.g., 3 to 8 membered, 3 to 6 membered, 4 to 6 membered, 4 to 5 membered, or 5 to 6 membered), $R^{51}$-substituted or unsubstituted aryl (e.g., $C_6$-$C_{10}$ or phenyl), or $R^{51}$-substituted or unsubstituted heteroaryl (e.g., 5 to 10 membered, 5 to 9 membered, or 5 to 6 membered).

In embodiments, $R^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{51}$-substituted or unsubstituted $C_1$-$C_8$ alkyl, $R^{51}$-substituted or unsubstituted 2 to 8 membered heteroalkyl, $R^{51}$-substituted or unsubstituted $C_3$-$C_8$ cycloalkyl, $R^{51}$-substituted or unsubstituted 3 to 8 membered heterocycloalkyl, $R^{51}$-substituted or unsubstituted $C_6$-$C_{10}$ aryl, or $R^{51}$- substituted or unsubstituted 5 to 10 membered heteroaryl, or a bond to the binder linker; two $R^7$ substituents may optionally be joined to form an $R^{51}$-substituted or unsubstituted $C_3$-$C_8$ cycloalkyl, $R^{51}$-substituted or unsubstituted 3 to 8 membered heterocycloalkyl, $R^{51}$-substituted or unsubstituted $C_6$-$C_{10}$ aryl, or $R^{51}$-substituted or unsubstituted 5 to 10 membered heteroaryl.

In embodiments, $R^5$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered), or a bond to the binder linker.

In embodiments, $R^5$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, substituted (e.g., substituted with at least one substituent group, size-limited substituent group, or lower substituent group) or unsubstituted heteroaryl, or a bond to the binder linker.

In embodiments, a substituted $R^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, $R^5$ is independently hydrogen or substituted or unsubstituted $C_1$-$C_4$ alkyl. In embodiments, $R^5$ is independently hydrogen. In embodiments, $R^5$ is independently substituted or unsubstituted $C_1$-$C_4$ alkyl. In embodiments, $R^5$ is independently unsubstituted $C_1$-$C_4$ alkyl. In embodiments, $R^5$ is independently unsubstituted methyl. In embodiments, $R^5$ is independently unsubstituted ethyl. In embodiments, $R^5$ is independently unsubstituted n-propyl. In embodiments, $R^5$ is independently unsubstituted isopropyl. In embodiments, $R^5$ is independently unsubstituted n-butyl. In embodiments, $R^5$ is independently unsubstituted tert-butyl.

In embodiments, $R^6$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered), or a bond to the binder linker.

In embodiments, $R^6$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, substituted (e.g., substituted with at least one substituent group, size-limited substituent group, or lower substituent group) or unsubstituted heteroaryl, or a bond to the binder linker.

In embodiments, a substituted $R^6$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, $R^6$ is independently hydrogen or substituted or unsubstituted $C_1$-$C_4$ alkyl. In embodiments, $R^6$ is independently hydrogen. In embodiments, $R^6$ is independently substituted or unsubstituted $C_1$-$C_4$ alkyl. In embodiments, $R^6$ is independently unsubstituted $C_1$-$C_4$ alkyl. In embodiments, $R^6$ is independently unsubstituted methyl. In embodiments, $R^6$ is independently unsubstituted ethyl. In embodiments, $R^6$ is independently unsubstituted n-propyl. In embodiments, $R^6$ is independently unsubstituted isopropyl. In embodiments, $R^6$ is independently unsubstituted n-butyl. In embodiments, $R^6$ is independently unsubstituted tert-butyl.

In embodiments, $R^5$ and $R^6$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{51}$-substituted or unsubstituted alkyl (e.g., $C_1$-$C_8$, $C_1$-$C_6$, $C_1$-$C_4$, or $C_1$-$C_2$), $R^{51}$-substituted or unsubstituted heteroalkyl (e.g., 2 to 8 membered, 2 to 6 membered, 4 to 6 membered, 2 to 3 membered, or 4 to 5 membered), $R^{51}$-substituted or unsubstituted cycloalkyl (e.g., $C_3$-$C_8$, $C_3$-$C_6$, $C_4$-$C_6$, or C5-$C_6$), $R^{51}$-substituted or unsubstituted heterocycloalkyl (e.g., 3 to 8 membered, 3 to 6 membered, 4 to 6 membered, 4 to 5 membered, or 5 to 6 membered), $R^{51}$-substituted or unsubstituted aryl (e.g., $C_6$-$C_{10}$ or phenyl), or $R^{51}$-substituted or unsubstituted heteroaryl (e.g., 5 to 10 membered, 5 to 9 membered, or 5 to 6 membered), or a bond to the binder linker.

In embodiments, $R^5$ and $R^6$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{51}$-substituted or unsubstituted $C_1$-$C_8$ alkyl, $R^{51}$-substituted or unsubstituted 2 to 8 membered heteroalkyl, $R^{51}$-substituted or unsubstituted $C_3$-$C_8$ cycloalkyl, $R^{51}$-substituted or unsubstituted 3 to 8 membered heterocycloalkyl, $R^{51}$-substituted or unsubstituted $C_6$-$C_{10}$ aryl, or $R^{51}$-substituted or unsubstituted 5 to 10 membered heteroaryl, or a bond to the binder linker.

$R^{51}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{51}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{51}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

In embodiments, $R^1$, $R^2$, $R^3$, $R^4$, $R^5$, $R^6$, $R^7$, $R^8$, $R^9$, and $R^{10}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{51}$-substituted or unsubstituted $C_1$-$C_8$ alkyl, $R^{51}$-substituted or unsubstituted alkyl (e.g., $C_1$-$C_8$, $C_1$-$C_6$, $C_1$-$C_4$, or $C_1$-$C_2$), $R^{51}$-substituted or unsubstituted heteroalkyl (e.g., 2 to 8 membered, 2 to 6 membered, 4 to 6 membered, 2 to 3 membered, or 4 to 5 membered), $R^{51}$-substituted or unsubstituted cycloalkyl (e.g., $C_3$-$C_8$, $C_3$-$C_6$, $C_4$-$C_6$, or $C_5$-$C_6$), $R^{51}$-substituted or unsubstituted heterocycloalkyl (e.g., 3 to 8 membered, 3 to 6 membered, 4 to 6 membered, 4 to 5 membered, or 5 to 6 membered), $R^{51}$-substituted or unsubstituted aryl (e.g., $C_6$-$C_{10}$ or phenyl), or $R^{51}$-substituted or unsubstituted heteroaryl (e.g., 5 to 10 membered, 5 to 9 membered, or 5 to 6 membered); or a bond to the binder linker; wherein only one $R^1$, $R^2$, $R^3$, $R^4$, $R^5$, $R^6$, $R^7$, $R^8$, $R^9$, or $R^{10}$ is a bond to the binder linker; and $R^{51}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, R$^1$, R$^2$, R$^3$, R$^4$, R$^5$, R$^6$, R$^7$, R$^8$, R$^9$, and R$^{10}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{51}$-substituted or unsubstituted C$_1$-C$_8$ alkyl, R$^{51}$-substituted or unsubstituted 2 to 8 membered heteroalkyl, R$^{51}$-substituted or unsubstituted C$_3$-C$_8$ cycloalkyl, R$^{51}$-substituted or unsubstituted 3 to 8 membered heterocycloalkyl, R$^{51}$-substituted or unsubstituted C$_6$-C$_{10}$ aryl, or R$^{51}$-substituted or unsubstituted 5 to 10 membered heteroaryl; or a bond to the binder linker; wherein only one R$^1$, R$^2$, R$^3$, R$^4$, R$^5$, R$^6$, R$^7$, R$^8$, R$^9$, or R$^{10}$ is a bond to the binder linker; and R$^{51}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl.

In embodiments, the binder linker is L$^{11}$-L$^{12}$-L$^{13}$-L$^{14}$. L$^{11}$ is connected directly to the E3 Ubiquitin ligase binder.

L$^{11}$ is a bond, —N(R$^{61}$)—, —C(O)—, —C(O)N(R$^{61}$)—, —N(R$^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

L$^{12}$, L$^{13}$, and L$^{14}$ are independently a bond, —N(R$^{61}$)—, —C(O)—, —C(O)N(R$^{61}$)—, —N(R$^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

In embodiments, L$^{11}$ is a bond, —N(R$^{61}$)—, —C(O)—, —C(O)N(R$^{61}$)—, —N(R$^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., C$_3$-C$_8$, C$_3$-C$_6$, C$_4$-C$_6$, or C$_5$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., C$_6$-C$_{10}$ or phenylene), or substituted or unsubstituted heteroarylene (e.g., 5 to 10 membered, 5 to 9 membered, or 5 to 6 membered), or a bioconjugate linker.

In embodiments, L$^{11}$ is —N(R$^{61}$)—, —C(O)—, —C(O)N(R$^{61}$)—, —N(R$^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

In embodiments, L$^{11}$ is —N(R$^{61}$)—, —C(O)—, —C(O)N(R$^{61}$)—, —N(R$^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., C$_3$-C$_8$, C$_3$-C$_6$, C$_4$-C$_6$, or C$_5$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., C$_6$-C$_{10}$ or phenylene), or substituted or unsubstituted heteroarylene (e.g., 5 to 10 membered, 5 to 9 membered, or 5 to 6 membered), or a bioconjugate linker.

In embodiments, L$^{11}$ is —N(R$^{61}$)—, —C(O)—, —C(O)N(R$^{61}$)—, —N(R$^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, R$^{61}$-substituted or unsubstituted alkylene (e.g., C$_1$-C$_8$, C$_1$-C$_6$, C$_1$-C$_4$, or C$_1$-C$_2$), R$^{61}$-substituted or unsubstituted heteroalkylene (e.g., 2 to 8 membered, 2 to 6 membered, 4 to 6 membered, 2 to 3 membered, or 4 to 5 membered), R$^{61}$-substituted or unsubstituted cycloalkylene (e.g., C$_3$-C$_8$, C$_3$-C$_6$, C$_4$-C$_6$, or C$_5$-C$_6$), R$^{61}$-substituted or unsubstituted heterocycloalkylene (e.g., 3 to 8 membered, 3 to 6 membered, 4 to 6 membered, 4 to 5 membered, or 5 to 6 membered), R$^{61}$-substituted or unsubstituted arylene (e.g., C$_6$-C$_{10}$ or phenylene), or R$^{61}$-substituted or unsubstituted heteroarylene (e.g., 5 to 10 membered, 5 to 9 membered, or 5 to 6 membered), or a bioconjugate linker. In embodiments, L$^{11}$ is —N(R$^{61}$)—, —C(O)—, —C(O)N(R$^{61}$)—, —N(R$^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, unsubstituted alkylene (e.g., C$_1$-C$_8$, C$_1$-C$_6$, C$_1$-C$_4$, or C$_1$-C$_2$), unsubstituted heteroalkylene (e.g., 2 to 8 membered, 2 to 6 membered, 4 to 6 membered, 2 to 3 membered, or 4 to 5 membered), unsubstituted cycloalkylene (e.g., C$_3$-C$_8$, C$_3$-C$_6$, C$_4$-C$_6$, or C$_5$-C$_6$), unsubstituted heterocycloalkylene (e.g., 3 to 8 membered, 3 to 6 membered, 4 to 6 membered, 4 to 5 membered, or 5 to 6 membered), unsubstituted arylene (e.g., C$_6$-C$_{10}$ or phenylene), or unsubstituted heteroarylene (e.g., 5 to 10 membered, 5 to 9 membered, or 5 to 6 membered), or a bioconjugate linker.

In embodiments, L$^{11}$ is —N(R$^{61}$)—, —C(O)—, —C(O)N(R$^{61}$)—, —N(R$^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, $R^{61}$-substituted or unsubstituted $C_1$-$C_{20}$ alkylene, $R^{61}$-substituted or unsubstituted 2 to 20 membered heteroalkylene, $R^{61}$-substituted or unsubstituted $C_3$-$C_8$ cycloalkylene, $R^{61}$-substituted or unsubstituted 3 to 8 membered heterocycloalkylene, $R^{61}$-substituted or unsubstituted $C_6$-$C_{10}$ arylene, $R^{61}$-substituted or unsubstituted 5 to 10 membered heteroarylene, or a bioconjugate linker. In embodiments, $L^{11}$ is —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, unsubstituted alkylene, unsubstituted heteroalkylene, unsubstituted cycloalkylene, unsubstituted heterocycloalkylene, unsubstituted arylene, unsubstituted heteroarylene, or a bioconjugate linker.

In embodiments, $L^{11}$ is —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted (e.g., substituted with at least one substituent group, size-limited substituent group, or lower substituent group) or unsubstituted heteroarylene, or a bioconjugate linker.

In embodiments, a substituted $L^{11}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{11}$ is substituted with a plurality of groups selected from substituent groups, size-limited substituent groups, and lower substituent groups; each substituent group, size-limited substituent group, and/or lower substituent group may optionally be different. In embodiments, when $L^{11}$ is substituted, it is substituted with at least one substituent group. In embodiments, when $L^{11}$ is substituted, it is substituted with at least one size-limited substituent group. In embodiments, when $L^{11}$ is substituted, it is substituted with at least one lower substituent group.

In embodiments, $L^{12}$, $L^{13}$, and $L^{14}$ are independently a bond, —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, $R^{61}$-substituted or unsubstituted alkylene (e.g., $C_1$-$C_8$, $C_1$-$C_6$, $C_1$-$C_4$, or $C_1$-$C_2$), $R^{61}$-substituted or unsubstituted heteroalkylene (e.g., 2 to 8 membered, 2 to 6 membered, 4 to 6 membered, 2 to 3 membered, or 4 to 5 membered), $R^{61}$-substituted or unsubstituted cycloalkylene (e.g., $C_3$-$C_8$, $C_3$-$C_6$, $C_4$-$C_6$, or $C_5$-$C_6$), $R^{61}$-substituted or unsubstituted heterocycloalkylene (e.g., 3 to 8 membered, 3 to 6 membered, 4 to 6 membered, 4 to 5 membered, or 5 to 6 membered), $R^{61}$-substituted or unsubstituted arylene (e.g., $C_6$-$C_{10}$ or phenylene), or $R^{61}$-substituted or unsubstituted heteroarylene (e.g., 5 to 10 membered, 5 to 9 membered, or 5 to 6 membered), or a bioconjugate linker.

In embodiments, $L^{12}$, $L^{13}$, and $L^{14}$ are independently a bond, —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, $R^{61}$-substituted or unsubstituted $C_1$-$C_{20}$ alkylene, $R^{61}$-substituted or unsubstituted 2 to 20 membered heteroalkylene, $R^{61}$-substituted or unsubstituted $C_3$-$C_8$ cycloalkylene, $R^{61}$-substituted or unsubstituted 3 to 8 membered heterocycloalkylene, $R^{61}$-substituted or unsubstituted $C_6$-$C_{10}$ arylene, $R^{61}$-substituted or unsubstituted 5 to 10 membered heteroarylene, or a bioconjugate linker. In embodiments, $L^{12}$, $L^{13}$, and $L^{14}$ are independently a bond, —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, unsubstituted alkylene, unsubstituted heteroalkylene, unsubstituted cycloalkylene, unsubstituted heterocycloalkylene, unsubstituted arylene, unsubstituted heteroarylene, or a bioconjugate linker.

In embodiments, $L^{12}$ is independently a bond, —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted or unsubstituted heteroarylene, or a bioconjugate linker.

In embodiments, a substituted $L^{12}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{12}$ is substituted with a plurality of groups selected from substituent groups, size-limited substituent groups, and lower substituent groups; each substituent group, size-limited substituent group, and/or lower substituent group may optionally be different. In embodiments, when $L^{12}$ is substituted, it is substituted with at least one substituent group. In embodiments, when $L^{12}$ is substituted, it is substituted with at least one size-limited substituent group. In embodiments, when $L^{12}$ is substituted, it is substituted with at least one lower substituent group.

In embodiments, $L^{13}$ is independently a bond, —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted or unsubstituted heteroarylene, or a bioconjugate linker.

In embodiments, a substituted $L^{13}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{13}$ is substituted with a plurality of groups selected from substituent groups, size-limited substituent groups, and lower substituent groups; each substituent group, size-limited substituent group, and/or lower substituent group may optionally be different. In embodiments, when $L^{13}$ is substituted, it is substituted with at least one substituent group. In embodiments, when $L^{13}$ is substituted, it is substituted with at least one size-limited substituent group. In embodiments, when $L^{13}$ is substituted, it is substituted with at least one lower substituent group.

In embodiments, $L^{14}$ is independently a bond, —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted or unsubstituted heteroarylene, or a bioconjugate linker.

In embodiments, a substituted $L^{14}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{14}$ is substituted with a plurality of groups selected from substituent groups, size-limited substituent groups, and lower substituent groups; each substituent group, size-limited substituent group, and/or lower substituent group may optionally be different. In embodiments, when $L^{14}$ is substituted, it is substituted with at least one substituent group. In embodiments, when $L^{14}$ is substituted, it is substituted with at least one size-limited substituent group. In embodiments, when $L^{14}$ is substituted, it is substituted with at least one lower substituent group.

$R^{61}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{61}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, $R^{61}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl.

In embodiments, the binder linker has the formula:

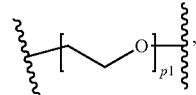

wherein p1 is an integer from 1 to 6. In embodiments, the binder linker has the formula:

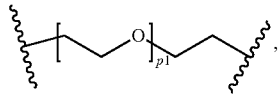

wherein p1 is an integer from 1 to 6. In embodiments, p1 is 3. In embodiments, the binder linker has the formula:

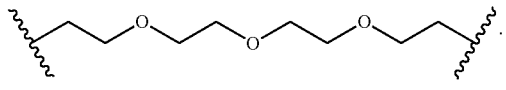 [SMILES: *CCOCCOCCOCC*]

In embodiments, the binder linker has the formula:

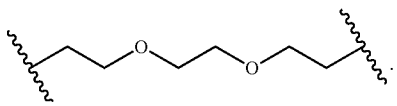 [SMILES: *CCOCCOCC*]

In embodiments, the binder linker is an unsubstituted $C_1$-$C_{12}$ alkylene. In embodiments, the binder linker is an unsubstituted $C_1$-$C_{10}$ alkylene. In embodiments, the binder linker is an unsubstituted $C_1$-$C_8$ alkylene. In embodiments, the binder linker is an unsubstituted $C_2$-$C_{10}$ alkylene. In embodiments, the binder linker is an unsubstituted $C_2$-$C_6$ alkylene. In embodiments, the binder linker is an unsubstituted $C_1$-$C_4$ alkylene. In embodiments, the binder linker is an unsubstituted $C_1$ alkylene. In embodiments, the binder linker is an unsubstituted $C_2$ alkylene. In embodiments, the binder linker is an unsubstituted $C_3$ alkylene. In embodiments, the binder linker is an unsubstituted $C_4$ alkylene.

In embodiments, the binder linker has the formula:

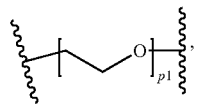

wherein p1 is an integer from 1 to 6. In embodiments, p1 is 3. In embodiments, the binder linker has the formula:

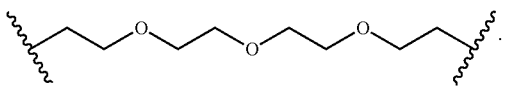 [SMILES: *CCOCCOCCOCC*]

In embodiments, the binder linker has the formula:

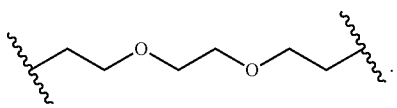 [SMILES: *CCOCCOCC*]

In embodiments, the binder linker is an unsubstituted $C_1$-$C_{12}$ alkylene. In embodiments, the binder linker is an unsubstituted $C_1$-$C_{10}$ alkylene. In embodiments, the binder linker is an unsubstituted $C_1$-$C_8$ alkylene. In embodiments, the binder linker is an unsubstituted $C_2$-$C_{10}$ alkylene. In embodiments, the binder linker is an unsubstituted $C_2$-$C_6$ alkylene. In embodiments, the binder linker is an unsubstituted $C_1$-$C_4$ alkylene. In embodiments, the binder linker is an unsubstituted $C_1$ alkylene. In embodiments, the binder linker is an unsubstituted $C_2$ alkylene. In embodiments, the binder linker is an unsubstituted $C_3$ alkylene. In embodiments, the binder linker is an unsubstituted $C_4$ alkylene.

In embodiments, z7 is an integer from 0 to 2. In embodiments, z7 is 0. In embodiments, z7 is 1. In embodiments, z7 is 2. In embodiments, z7 is 3. In embodiments, z7 is 4. In embodiments, z7 is 5. In embodiments, z7 is 6. In embodiments, z7 is 7. In embodiments, z7 is 8. In embodiments, z7 is 9. In embodiments, z7 is 10.

In embodiments, the targeted protein binder is capable of binding a targeted protein associated with a disease. In embodiments, the targeted protein binder is

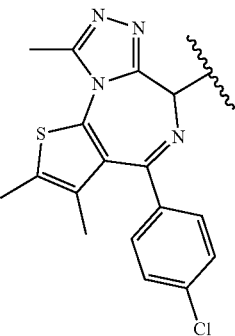 [SMILES: *C1N=C(c2ccc(Cl)cc2)c2c(sc(C)c2C)-n2c(C)nnc21]

and the targeted protein binder binds BRD4.

In an aspect is provided a compound having the formula:

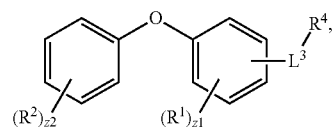

wherein $R^1$, $R^2$, z1, z2, $L^3$, and $R^4$ are as described herein.

In an aspect is provided a compound having the formula:

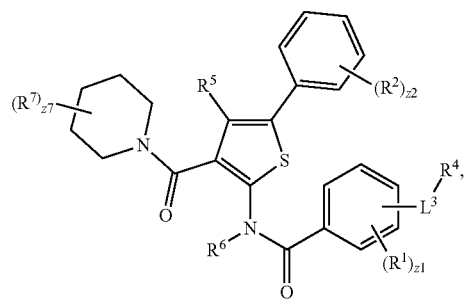

wherein $R^1$, $R^2$, $R^5$, $R^6$, $R^7$, $L^3$, z1, z2, z7, and $R^4$ are as described herein.

In an aspect is provided a compound having the formula:

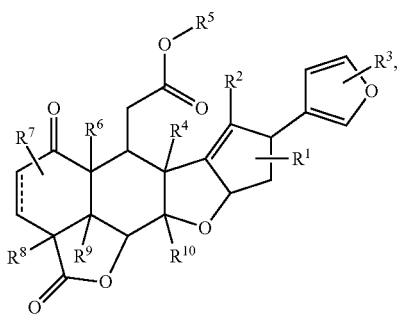

wherein $R^1$, $R^2$, $R^3$, $R^4$, $R^5$, $R^6$, $R^7$, $R^8$, $R^9$, and $R^{10}$ are as described herein.

In an aspect is provided a compound having the formula:

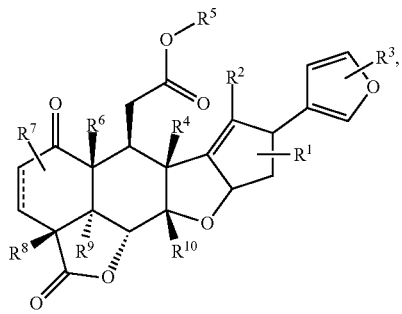

wherein $R^1$, $R^2$, $R^3$, $R^4$, $R^5$, $R^6$, $R^7$, $R^8$, $R^9$, and $R^{10}$ are as described herein.

In an aspect is provided a compound having the formula:

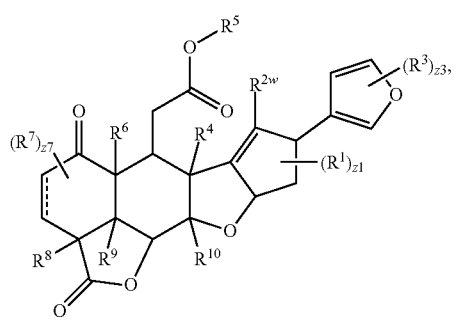

wherein $R^1$, $R^{2w}$, $R^3$, $R^4$, $R^5$, $R^6$, $R^8$, $R^9$, $R^{10}$, z1, z3, and z7 are as described herein.

In an aspect is provided a compound having the formula:

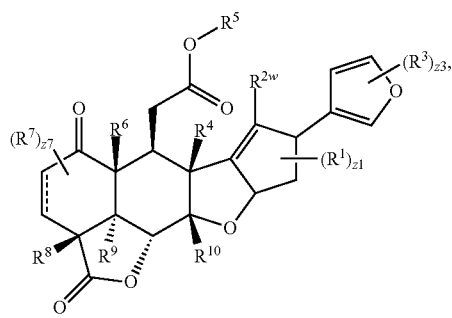

wherein $R^1$, $R^{2w}$, $R^3$, $R^4$, $R^5$, $R^6$, $R^7$, $R^8$, $R^9$, $R^{10}$, z1, z3, and z7 are as described herein.

In embodiments, the E3 Ubiquitin ligase binder is a monovalent form of the formula:

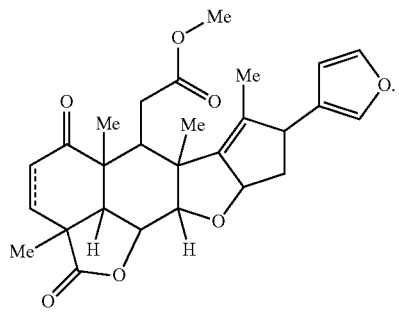

In embodiments, the E3 Ubiquitin ligase binder is a monovalent form of the formula:

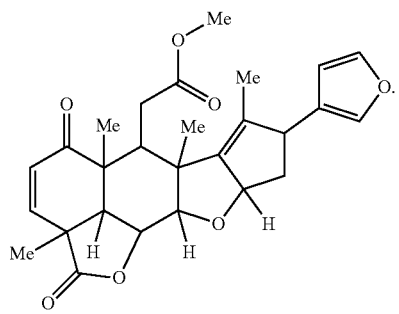

In embodiments, the E3 Ubiquitin ligase binder is a monovalent form of the formula:

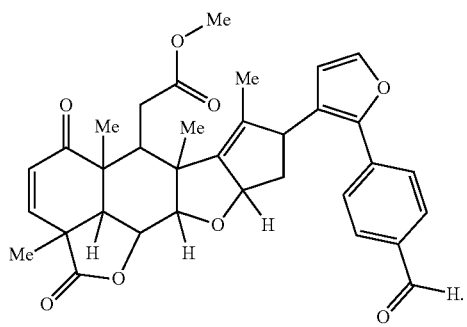

In embodiments, the E3 Ubiquitin ligase binder is a monovalent form of the formula:

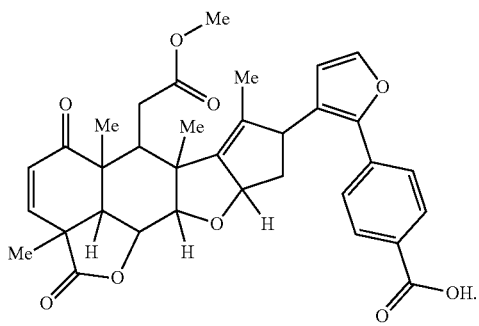

In embodiments, the E3 Ubiquitin ligase binder is a monovalent form of the formula:

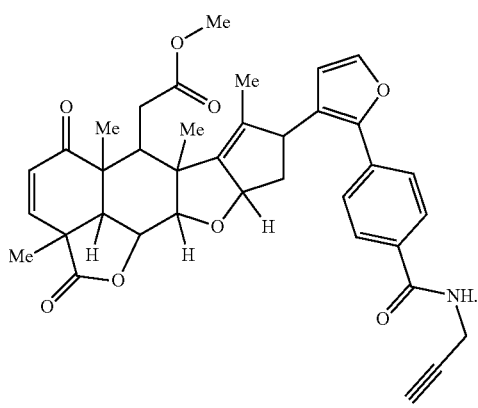

In embodiments, the E3 Ubiquitin ligase binder is a monovalent form of the formula:

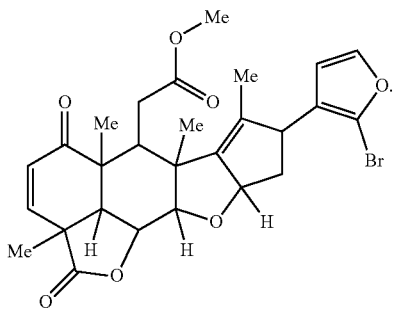

In embodiments, the E3 Ubiquitin ligase binder is a monovalent form of the formula:

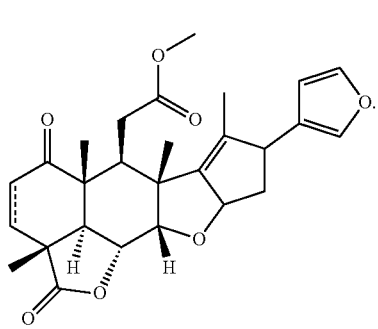

In embodiments, the E3 Ubiquitin ligase binder is a monovalent form of the formula:

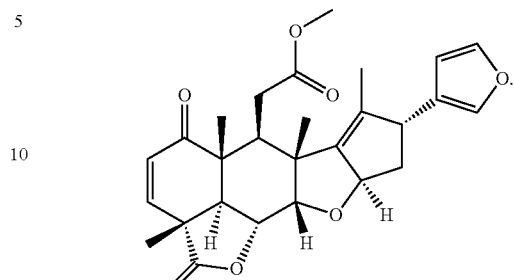

In embodiments, the E3 Ubiquitin ligase binder is a monovalent form of the formula:

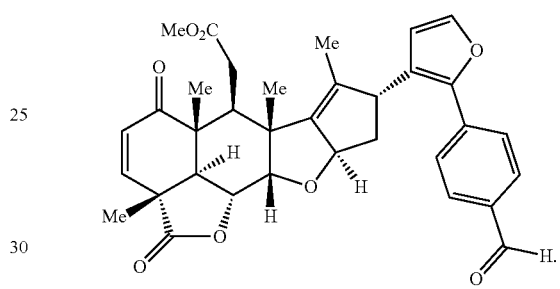

In embodiments, the E3 Ubiquitin ligase binder is a monovalent form of the formula:

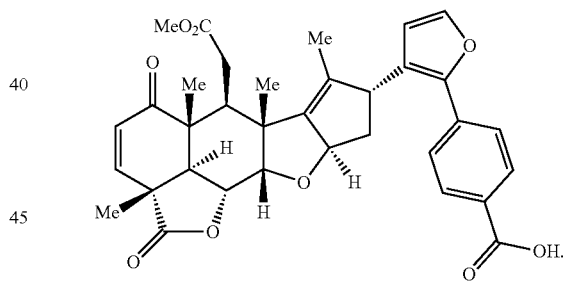

In embodiments, the E3 Ubiquitin ligase binder is a monovalent form of the formula:

In embodiments, the E3 Ubiquitin ligase binder is a monovalent form of the formula:

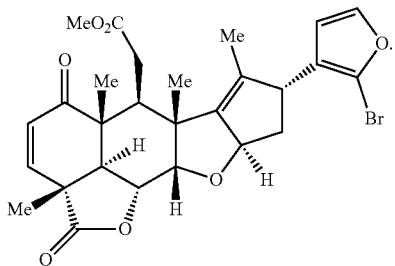

In embodiments, the E3 Ubiquitin ligase binder is a monovalent form of the formula:

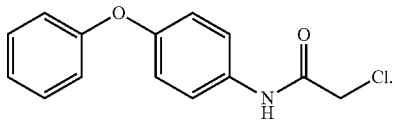 [SMILES: O=C(CCl)Nc1ccc(Oc2ccccc2)cc1]

In embodiments, the E3 Ubiquitin ligase binder is a monovalent form of the formula:

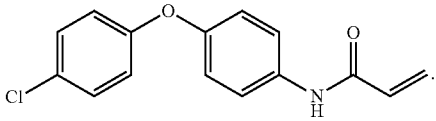 [SMILES: C=CC(=O)Nc1ccc(Oc2ccc(Cl)cc2)cc1]

In embodiments, the E3 Ubiquitin ligase binder is a monovalent form of the formula:

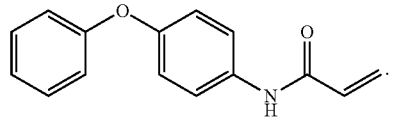 [SMILES: C=CC(=O)Nc1ccc(Oc2ccccc2)cc1]

In embodiments, the E3 Ubiquitin ligase binder is a monovalent form of the formula:

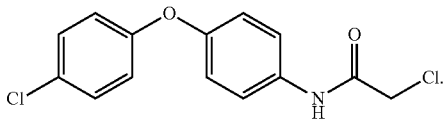 [SMILES: O=C(CCl)Nc1ccc(Oc2ccc(Cl)cc2)cc1]

In embodiments, the E3 Ubiquitin ligase binder is a monovalent form of the formula:

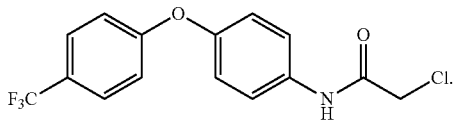

In embodiments, the E3 Ubiquitin ligase binder is a monovalent form of the formula:

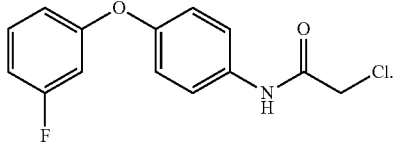 [SMILES: O=C(CCl)Nc1ccc(Oc2cccc(F)c2)cc1]

In embodiments, the E3 Ubiquitin ligase binder is a monovalent form of the formula:

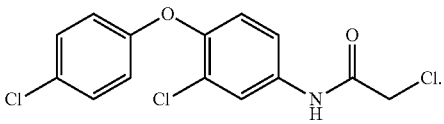 [SMILES: O=C(CCl)Nc1ccc(Oc2ccc(Cl)cc2)c(Cl)c1]

In embodiments, the E3 Ubiquitin ligase binder is a monovalent form of the formula:

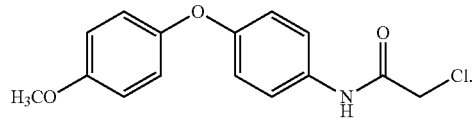 [SMILES: COc1ccc(Oc2ccc(NC(=O)CCl)cc2)cc1]

In embodiments, the E3 Ubiquitin ligase binder is a monovalent form of the formula:

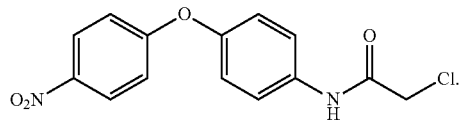 [SMILES: O=C(CCl)Nc1ccc(Oc2ccc([N+](=O)[O-])cc2)cc1]

In embodiments, the E3 Ubiquitin ligase binder is a monovalent form of the formula:

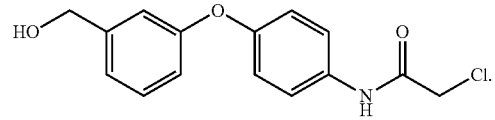 [SMILES: O=C(CCl)Nc1ccc(Oc2cccc(CO)c2)cc1]

In embodiments, the E3 Ubiquitin ligase binder is a monovalent form of the formula:

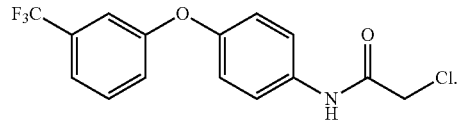 [SMILES: O=C(CCl)Nc1ccc(Oc2cccc(C(F)(F)F)c2)cc1]

In embodiments, the E3 Ubiquitin ligase binder is a monovalent form of the formula:

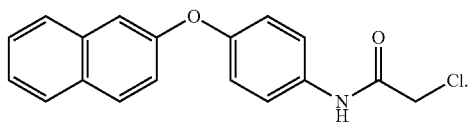 [SMILES: O=C(CCl)Nc1ccc(Oc2ccc3ccccc3c2)cc1]

In embodiments, the E3 Ubiquitin ligase binder is a monovalent form of the formula:

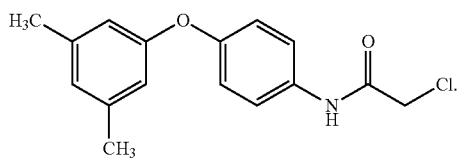 [SMILES: Cc1cc(C)cc(Oc2ccc(NC(=O)CCl)cc2)c1]

In embodiments, the E3 Ubiquitin ligase binder is a monovalent form of the formula:

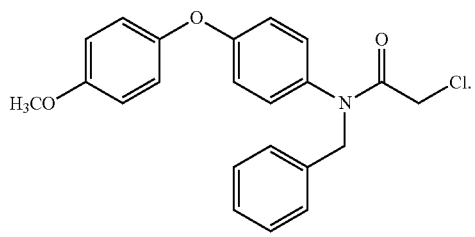

In embodiments, the E3 Ubiquitin ligase binder has the formula:

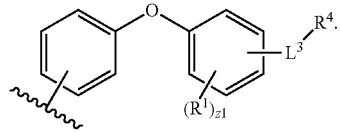

In embodiments, $R^4$ is independently E, wherein E is as described herein, including in embodiments.

In embodiments, the E3 Ubiquitin ligase binder has the formula:

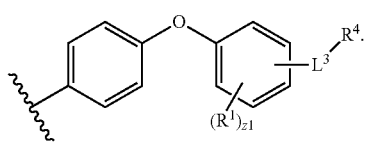

In embodiments, $R^4$ is independently E, wherein E is as described herein, including in embodiments.

In embodiments, the E3 Ubiquitin ligase binder has the formula:

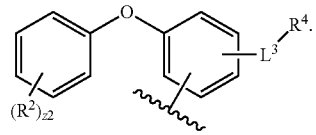

In embodiments, $R^4$ is independently E, wherein E is as described herein, including in embodiments.

In embodiments, the E3 Ubiquitin ligase binder has the formula:

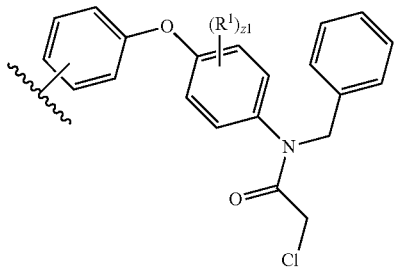

In embodiments, the E3 Ubiquitin ligase binder has the formula:

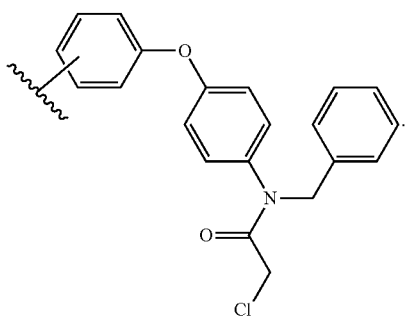

In embodiments, the E3 Ubiquitin ligase binder has the formula:

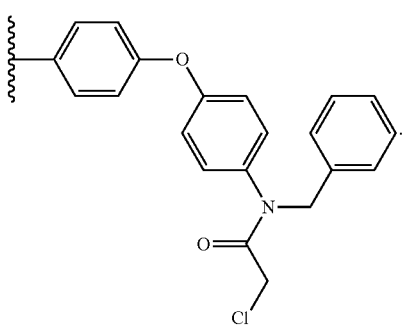 [SMILES: *c1ccc(Oc2ccc(N(Cc3ccccc3)C(=O)CCl)cc2)cc1]

In embodiments, the E3 Ubiquitin ligase binder has the formula:
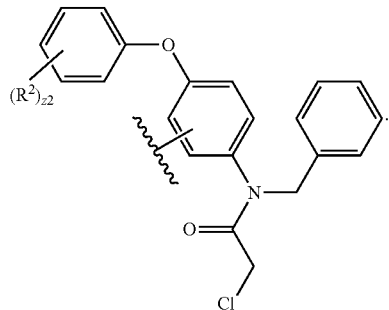
In embodiments, the E3 Ubiquitin ligase binder is a monovalent form of the formula:
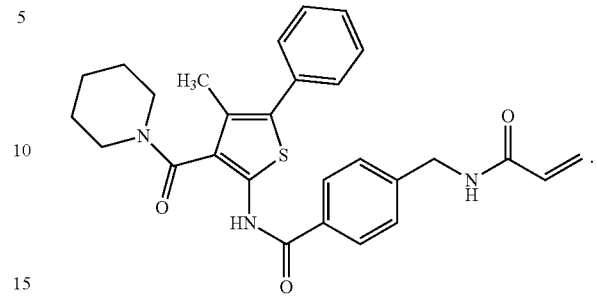
In embodiments, the targeted protein degrader has the formula:
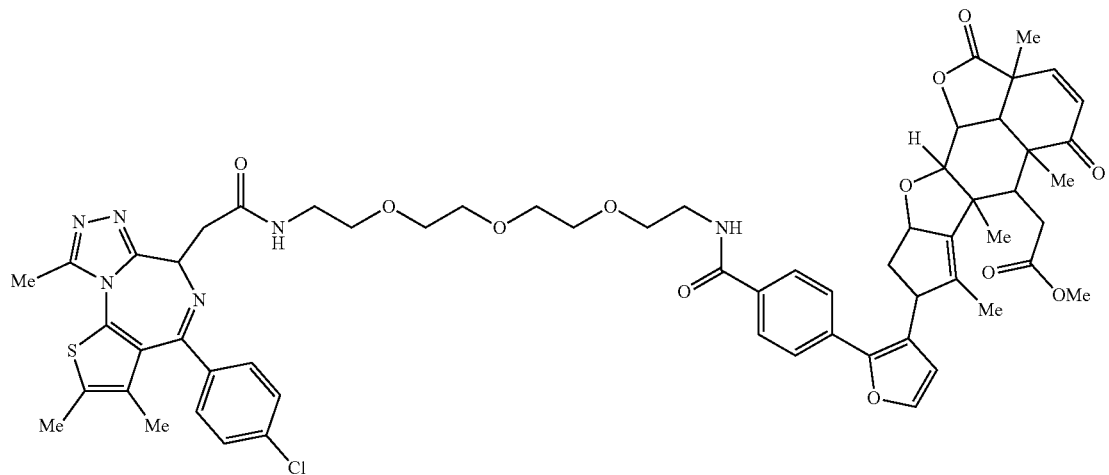 [SMILES: COC(=O)CC1C2(C)C3=C(C)C(c4ccoc4-c4ccc(C(=O)NCCOCCOCCOCCNC(=O)CC5N=C(c6ccc(Cl)cc6)c6c(sc(C)c6C)-n6c(C)nnc65)cc4)CC3OC2C2OC(=O)C3(C)C=CC(=O)C1(C)C23]
In embodiments, the targeted protein degrader has the formula:
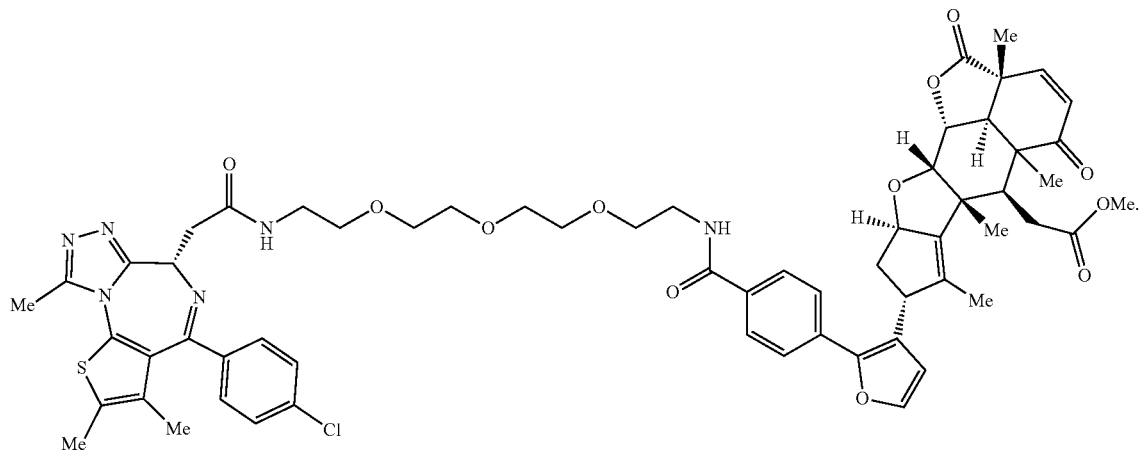

In embodiments, the targeted protein degrader has the formula:
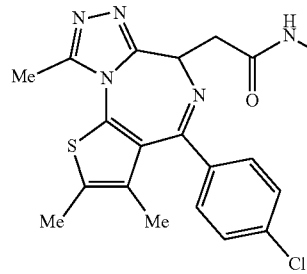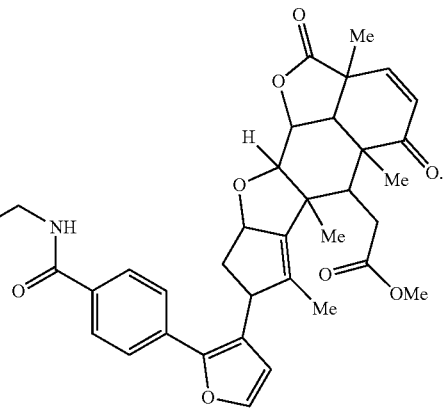
In embodiments, the targeted protein degrader has the formula:
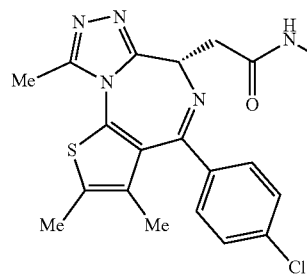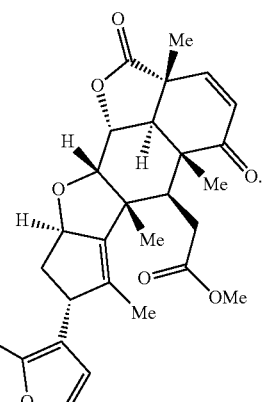
In embodiments, the targeted protein degrader has the formula:
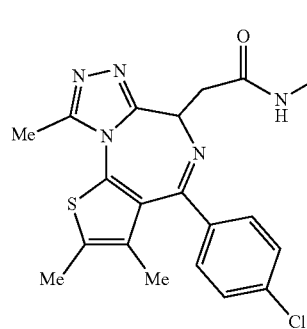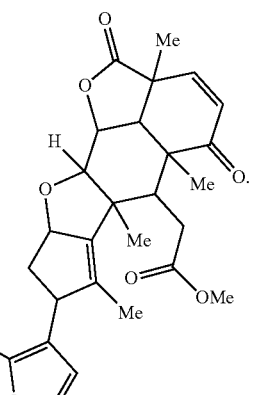

In embodiments, the targeted protein degrader has the formula:
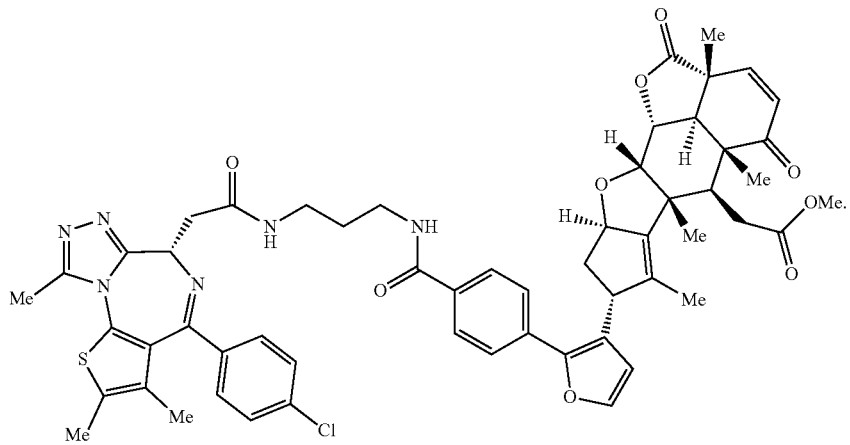
In embodiments, the targeted protein degrader has the formula:
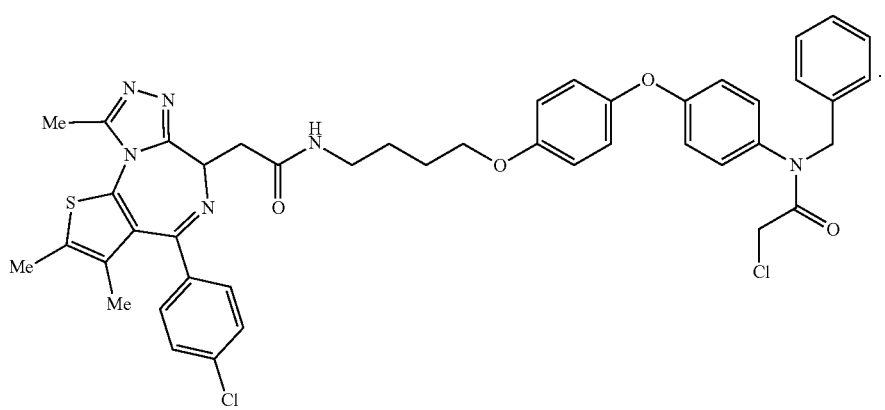 [SMILES: Cc1sc2c(c1C)C(c1ccc(Cl)cc1)=NC(CC(=O)NCCCCOc1ccc(Oc3ccc(N(Cc4ccccc4)C(=O)CCl)cc3)cc1)c1nnc(C)n1-2]
In embodiments, the targeted protein degrader has the formula:
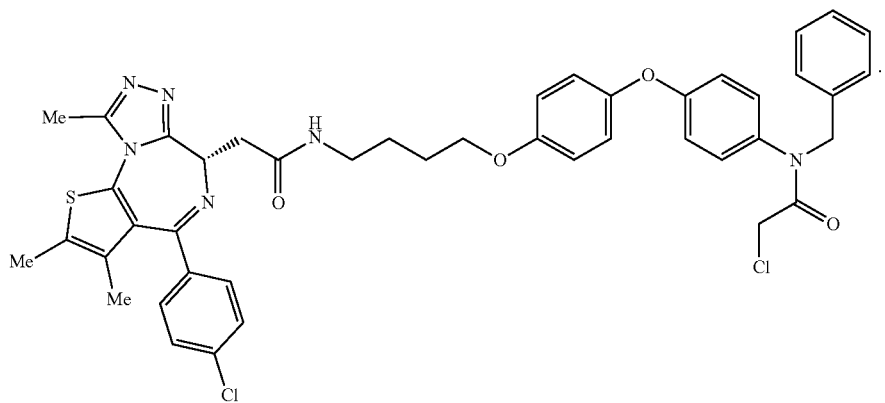 [SMILES: Cc1sc2c(c1C)C(c1ccc(Cl)cc1)=N[C@@H](CC(=O)NCCCCOc1ccc(Oc3ccc(N(Cc4ccccc4)C(=O)CCl)cc3)cc1)c1nnc(C)n1-2]

In embodiments, the targeted protein degrader has the formula:
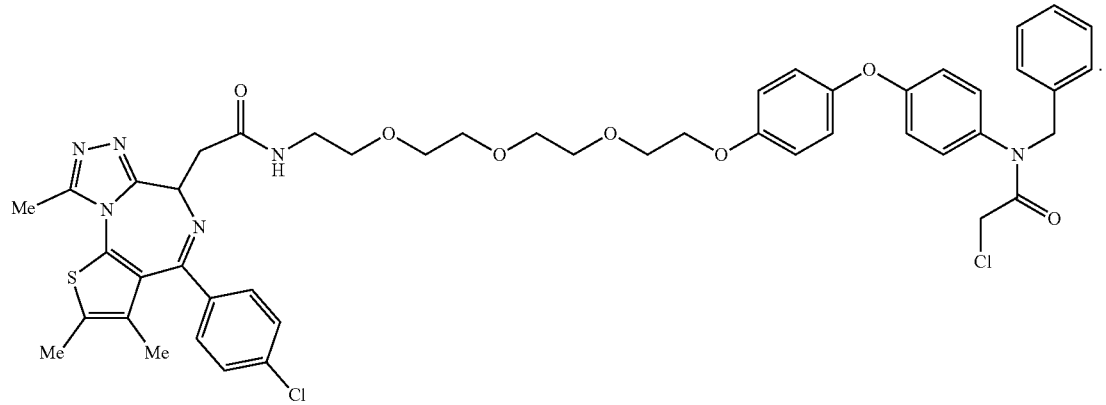 [SMILES: Cc1sc2c(c1C)C(c1ccc(Cl)cc1)=NC(CC(=O)NCCOCCOCCOCCOc1ccc(Oc3ccc(N(Cc4ccccc4)C(=O)CCl)cc3)cc1)c1nnc(C)n1-2]
In embodiments, the targeted protein degrader has the formula:
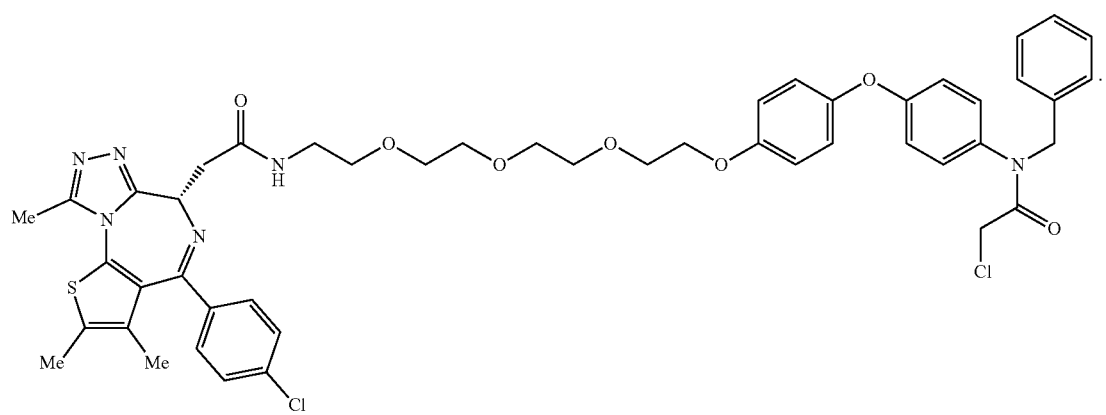 [SMILES: Cc1sc2c(c1C)C(c1ccc(Cl)cc1)=N[C@@H](CC(=O)NCCOCCOCCOCCOc1ccc(Oc3ccc(N(Cc4ccccc4)C(=O)CCl)cc3)cc1)c1nnc(C)n1-2]
In embodiments, the targeted protein degrader has the formula:
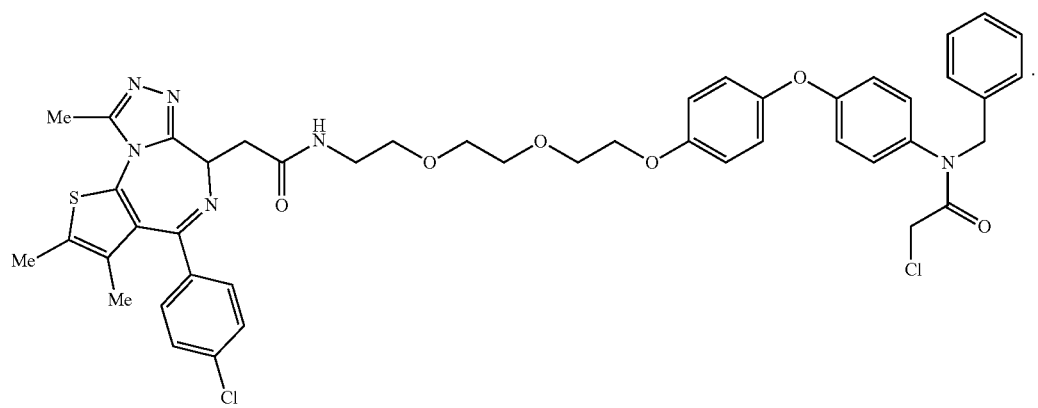 [SMILES: Cc1sc2c(c1C)C(c1ccc(Cl)cc1)=NC(CC(=O)NCCOCCOCCOc1ccc(Oc3ccc(N(Cc4ccccc4)C(=O)CCl)cc3)cc1)c1nnc(C)n1-2]

In embodiments, the targeted protein degrader has the formula:

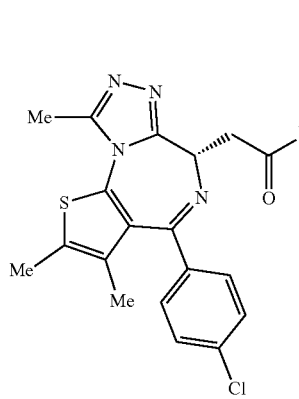 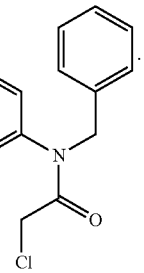

In embodiments, the targeted protein degrader is a compound described herein (e.g., in an aspect, embodiment, example, table, figure, or claim). In embodiments, the compound is a compound described herein (e.g., in an aspect, embodiment, example, table, figure, or claim). In embodiments, the compound is a targeted protein degrader described herein (e.g., in an aspect, embodiment, example, table, figure, or claim). In embodiments, the E3 ubiquitin ligase binder is a monovalent form of a compound described herein (e.g., in an aspect, embodiment, example, table, figure, or claim). In embodiments, the targeted protein binder is a monovalent form of a compound described herein (e.g., in an aspect, embodiment, example, table, figure, or claim).

III. Pharmaceutical Compositions

In an aspect is provided a pharmaceutical composition including a compound as described herein (e.g., a targeted protein degrader as described herein), including embodiments, and a pharmaceutically acceptable excipient. In embodiments, the compound as described herein is included in a therapeutically effective amount.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g., therapeutic agent). In embodiments of the pharmaceutical compositions, the pharmaceutical composition includes a second agent (e.g., therapeutic agent) in a therapeutically effective amount. In embodiments of the pharmaceutical compositions, the second agent is an agent for treating cancer. In embodiments, the second agent is an anti-cancer agent. In embodiments, the second agent is a chemotherapeutic. In embodiments, the second agent is an anti-inflammatory agent. In embodiments, the administering does not include administration of any active agent other than the recited active agent (e.g., a compound described herein).

The pharmaceutical compositions may include optical isomers, diastereomers, or pharmaceutically acceptable salts of the modulators disclosed herein. The compound included in the pharmaceutical composition may be covalently attached to a carrier moiety. Alternatively, the compound included in the pharmaceutical composition is not covalently linked to a carrier moiety.

In an aspect is provided a pharmaceutical composition including a targeted protein degrader (e.g., as described herein or a compound described herein) and a pharmaceutically acceptable excipient.

In embodiments, the pharmaceutical composition includes an effective amount of the targeted protein degrader. In embodiments, the pharmaceutical composition includes a therapeutically effective amount of the targeted protein degrader. In embodiments, the pharmaceutical composition includes a second agent. In embodiments of the pharmaceutical compositions, the pharmaceutical composition includes a second agent in a therapeutically effective amount.

IV. Methods of Use

In an aspect is provided a method of reducing (e.g., reducing relative to a control) the level of a cellular protein, said method including contacting the cellular protein with a targeted protein degrader. In embodiments, the targeted protein degrader is a compound described herein.

In an aspect is provided a method of reducing (e.g., reducing relative to a control) the level of a cellular protein, said method including contacting the cellular protein with a targeted protein degrader (e.g., a compound described herein or an E3 Ubiquitin ligase binder described herein). In embodiments, the targeted protein degrader is a compound described herein.

In embodiments, the method further includes the steps of: (A) Allowing the cellular protein contacting the targeted protein degrader to be ubiquitinated and thereby form a ubiquitinated cellular protein; and (B) Allowing the ubiquitinated cellular protein to contact the proteasome and thereby form a ubiquitinated cellular protein-proteasome complex; and proteolyzing the cellular protein by the proteasome.

In an aspect is provided a method of treating cancer, the method including contacting a cellular protein associated with cancer with a targeted protein degrader (e.g., a compound described herein).

In an aspect is provided a method of treating cancer, the method including contacting a cellular protein associated with cancer with a targeted protein degrader (e.g., a compound described herein or an E3 Ubiquitin ligase binder described herein).

In an aspect is provided a method of treating cancer, the method including administering to a subject in need thereof a therapeutically effective amount of a targeted protein binder as described herein, including embodiments.

In embodiments, the cancer is breast cancer. In embodiments, the cancer is triple-negative breast cancer. In embodiments, the cancer is renal cell carcinoma. In embodiments, the cancer is follicular lymphoma. In embodiments, the cancer is glioblastoma. In embodiments, the cancer is colorectal cancer. In embodiments, the cancer is endometrial cancer. In embodiments, the cancer is lung cancer. In embodiments, the cancer is pancreatic cancer. In embodiments, the cancer is melanoma. In embodiments, the cancer is acute myeloid leukemia. In embodiments, the cancer is endometrial cancer. In embodiments, the cancer is non-Hodgkin lymphoma. In embodiments, the cancer is mantle cell lymphoma. In embodiments, the method includes immunomodulation. In embodiments, the method includes cancer immunotherapy (e.g., immunostimulant, immunotoxin, or radioimmunotherapy).

In an aspect is provided a method of reducing the level of a cellular protein, the method including contacting the cellular protein with a targeted protein degrader and thereby forming a targeted protein degrader-cellular protein complex; wherein the targeted protein degrader includes: (i) an E3 Ubiquitin ligase binder; (ii) a targeted protein binder; and (iii) a binder linker directly bonded to the E3 Ubiquitin ligase binder and the targeted protein binder. In embodiments, the method further includes, prior to the contacting, the targeted protein degrader is synthesized by covalently reacting an E3 Ubiquitin ligase binder, a binder linker, and a targeted protein binder to produce the targeted protein degrader. In embodiments, the method further includes prior to the synthesizing, the E3 Ubiquitin ligase binder is identified from a candidate E3 Ubiquitin ligase binder.

In an aspect is provided a method of reducing the level of a cellular protein, the method including contacting the cellular protein with a targeted protein degrader and thereby form a targeted protein degrader-cellular protein complex; wherein the targeted protein degrader includes: (i) a monovalent E3 Ubiquitin ligase binder; (ii) a monovalent targeted protein binder; and (iii) a binder linker directly bonded to the monovalent E3 Ubiquitin ligase binder and the monovalent targeted protein binder. In embodiments, the method further includes, prior to the contacting, the targeted protein degrader is synthesized by covalently reacting an E3 Ubiquitin ligase binder, a binder linker, and a targeted protein binder to produce the targeted protein degrader. In embodiments, the method further includes prior to the synthesizing, the E3 Ubiquitin ligase binder is identified from a candidate E3 Ubiquitin ligase binder.

In an aspect is provided a method of reducing the level of a cellular protein, the method including contacting the cellular protein with a targeted protein degrader and thereby forming a targeted protein degrader-cellular protein complex; wherein the targeted protein degrader includes: (i) an E3 Ubiquitin ligase binder (e.g., a compound described herein or an E3 Ubiquitin ligase binder described herein); (ii) a targeted protein binder; and (iii) a binder linker directly bonded to the E3 Ubiquitin ligase binder and the targeted protein binder. In embodiments, the method further includes, prior to the contacting, the targeted protein degrader is synthesized by covalently reacting an E3 Ubiquitin ligase binder, a binder linker, and a targeted protein binder to produce the targeted protein degrader. In embodiments, the method further includes prior to the synthesizing, the E3 Ubiquitin ligase binder is identified from a candidate E3 Ubiquitin ligase binder.

In an aspect is provided a method of reducing the level of a cellular protein, the method including contacting the cellular protein with a targeted protein degrader and thereby form a targeted protein degrader-cellular protein complex; wherein the targeted protein degrader includes: (i) a monovalent E3 Ubiquitin ligase binder (e.g., a compound described herein or an E3 Ubiquitin ligase binder described herein); (ii) a monovalent targeted protein binder; and (iii) a binder linker directly bonded to the monovalent E3 Ubiquitin ligase binder and the monovalent targeted protein binder. In embodiments, the method further includes, prior to the contacting, the targeted protein degrader is synthesized by covalently reacting an E3 Ubiquitin ligase binder, a binder linker, and a targeted protein binder to produce the targeted protein degrader. In embodiments, the method further includes prior to the synthesizing, the E3 Ubiquitin ligase binder is identified from a candidate E3 Ubiquitin ligase binder.

In an aspect is provided a method of reducing the level of a cellular protein, the method including contacting the cellular protein with a targeted protein degrader and thereby forming a cellular protein-targeted protein binder complex; wherein the targeted protein degrader includes: (i) an E3 Ubiquitin ligase binder; (ii) a targeted protein binder; and (iii) a binder linker directly bonded to the E3 Ubiquitin ligase binder and the targeted protein binder. In embodiments, the method further includes, prior to the contacting, the targeted protein degrader is synthesized by covalently reacting an E3 Ubiquitin ligase binder, a binder linker, and a targeted protein binder to produce the targeted protein degrader. In embodiments, the method further includes prior to the synthesizing, the E3 Ubiquitin ligase binder is identified from a candidate E3 Ubiquitin ligase binder.

In an aspect is provided a method of reducing the level of a cellular protein, the method including contacting the cellular protein with a targeted protein degrader and thereby form a cellular protein-targeted protein binder complex; wherein the targeted protein degrader includes: (i) a monovalent E3 Ubiquitin ligase binder; (ii) a monovalent targeted protein binder; and (iii) a binder linker directly bonded to the monovalent E3 Ubiquitin ligase binder and the monovalent targeted protein binder. In embodiments, the method further includes, prior to the contacting, the targeted protein degrader is synthesized by covalently reacting an E3 Ubiquitin ligase binder, a binder linker, and a targeted protein binder to produce the targeted protein degrader. In embodiments, the method further includes prior to the synthesizing, the E3 Ubiquitin ligase binder is identified from a candidate E3 Ubiquitin ligase binder.

In an aspect is provided a method of reducing the level of a cellular protein, the method including contacting the cellular protein with a targeted protein degrader and thereby form a cellular protein-targeted protein binder complex; wherein the targeted protein degrader includes: (i) an E3 Ubiquitin ligase binder (e.g., a compound described herein or an E3 Ubiquitin ligase binder described herein); (ii) a targeted protein binder; and (iii) a binder linker directly bonded to the E3 Ubiquitin ligase binder and the targeted protein binder. In embodiments, the method further includes, prior to the contacting, the targeted protein degrader is synthesized by covalently reacting an E3 Ubiquitin ligase binder, a binder linker, and a targeted protein binder to produce the targeted protein degrader. In embodiments, the method further includes prior to the synthesizing, the E3 Ubiquitin ligase binder is identified from a candidate E3 Ubiquitin ligase binder.

In an aspect is provided a method of reducing the level of a cellular protein, the method including contacting the cellular protein with a targeted protein degrader and thereby form a cellular protein-targeted protein binder complex; wherein the targeted protein degrader includes: (i) a monovalent E3 Ubiquitin ligase binder (e.g., a compound described herein or an E3 Ubiquitin ligase binder described herein); (ii) a monovalent targeted protein binder; and (iii) a binder linker directly bonded to the monovalent E3 Ubiquitin ligase binder and the monovalent targeted protein binder. In embodiments, the method further includes, prior to the contacting, the targeted protein degrader is synthesized by covalently reacting an E3 Ubiquitin ligase binder, a binder linker, and a targeted protein binder to produce the targeted protein degrader. In embodiments, the method further includes prior to the synthesizing, the E3 Ubiquitin ligase binder is identified from a candidate E3 Ubiquitin ligase binder.

In embodiments, the method further includes the E3 Ubiquitin ligase binder is identified by a method including the steps: (i) contacting an E3 Ubiquitin ligase protein with a mixture of candidate E3 Ubiquitin ligase binders and thereby forming an E3 Ubiquitin ligase protein-E3 Ubiquitin ligase binder complex; and identifying the candidate E3 Ubiquitin ligase binders from an E3 Ubiquitin ligase protein-E3 Ubiquitin ligase binder complex as E3 Ubiquitin ligase binders.

In embodiments, the method further includes the E3 Ubiquitin ligase binder is identified by a method including the steps: (i) contacting an E3 Ubiquitin ligase protein with a mixture of compounds including candidate E3 Ubiquitin ligase binders and thereby forming an E3 Ubiquitin ligase protein-E3 Ubiquitin ligase binder complex; and identifying the compounds including candidate E3 Ubiquitin ligase binders from an E3 Ubiquitin ligase protein-E3 Ubiquitin ligase binder complex as compounds including E3 Ubiquitin ligase binders.

In embodiments, the method further includes the steps: (i) contacting an E3 Ubiquitin ligase protein with a plurality of E3 Ubiquitin ligase binders and thereby forming an E3 Ubiquitin ligase protein-E3 Ubiquitin ligase binder complex; and identifying the E3 Ubiquitin ligase binders from an E3 Ubiquitin ligase protein-E3 Ubiquitin ligase binder complex as E3 Ubiquitin ligase binders.

In embodiments, the method further includes the steps: (i) contacting an E3 Ubiquitin ligase protein with a plurality of candidate E3 Ubiquitin ligase binders and thereby forming an E3 Ubiquitin ligase protein-E3 Ubiquitin ligase binder complex; and identifying the candidate E3 Ubiquitin ligase binders from an E3 Ubiquitin ligase protein-E3 Ubiquitin ligase binder complex as E3 Ubiquitin ligase binders.

In embodiments, the candidate E3 Ubiquitin ligase binders include a covalent cysteine modifier moiety and a candidate E3 Ubiquitin ligase binder is identified as an E3 Ubiquitin ligase binder by detection of covalent binding of the E3 Ubiquitin ligase binder to the E3 Ubiquitin ligase protein to form an E3 Ubiquitin ligase protein-E3 Ubiquitin ligase binder complex.

In embodiments, the detection of an E3 Ubiquitin ligase protein-E3 Ubiquitin ligase binder complex comprises use of a detectable label or mass spectroscopy. In embodiments, prior to the synthesizing, the targeted protein binder is identified.

In embodiments, the targeted protein binder is identified by a method including the steps: (i) mixing a cellular protein with a library of candidate targeted protein binders and thereby forming a cellular protein-targeted protein binder complex; and (ii) identifying the targeted protein binder that forms a cellular protein-targeted protein binder complex. In embodiments, the candidate targeted protein binder forming a cellular protein-targeted protein binder complex is identified as a targeted protein binder by detection of the cellular protein-targeted protein binder complex. In embodiments, the detection of cellular protein-targeted protein binder complex includes use of a detectable label or mass spectroscopy. In embodiments, prior to the synthesizing, the E3 Ubiquitin ligase binder is modified (e.g., the E3 Ubiquitin ligase binder undergoes a chemical reaction to remove a covalent cysteine modifier moiety) to remove a covalent cysteine modifier moiety.

In embodiments, the targeted protein binder is identified by a method including the steps: (i) mixing a cellular protein with a library of compounds including candidate targeted protein binders and thereby forming a cellular protein-targeted protein binder complex; and (ii) identifying the compounds including the targeted protein binder that forms a cellular protein-targeted protein binder complex. In embodiments, the compound including the candidate targeted protein binder forming a cellular protein-targeted protein binder complex is identified as a compound including a targeted protein binder by detection of the cellular protein-targeted protein binder complex. In embodiments, the detection of cellular protein-targeted protein binder complex includes use of a detectable label or mass spectroscopy. In embodiments, prior to the synthesizing, the E3 Ubiquitin ligase binder is modified (e.g., the E3 Ubiquitin ligase binder undergoes a chemical reaction to remove a covalent cysteine modifier moiety) to remove a covalent cysteine modifier moiety.

In embodiments, the cellular protein is BRD4. In embodiments, the level of BRD4 is reduced by greater than 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, or greater than 10,000 fold compared to the absence of a targeted protein degrader. In embodiments, the level of BRD4 is reduced by about 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, or about 10,000 fold compared to the absence of a targeted protein degrader. In embodiments, the level of BRD4 is reduced by 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, or 10,000 fold compared to the absence of a targeted protein degrader.

In an aspect is provided a method of identifying a cellular protein contacted by a targeted protein binder including: (A) contacting a first sample of a cell proteome or cell with the targeted protein binder thereby forming a cellular protein-targeted protein binder complex; (B) contacting both the resulting first sample of a cell proteome or cell of step A and a second sample of the cell proteome or cell that has not been contacted with the targeted protein binder, with a compound having the formula:

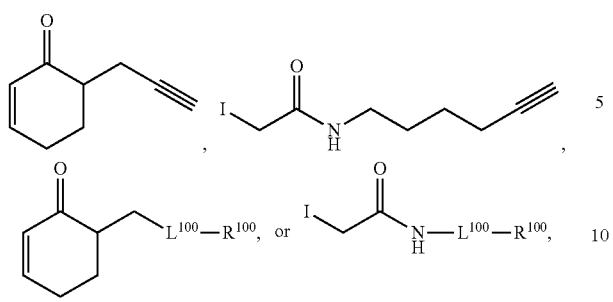

wherein $L^{100}$ is a covalent linker (e.g., a bond, —S(O)$_2$—, —NH—, —O—, —S—, —C(O)—, —C(O)NH—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene) and $R^{100}$ is a detectable moiety; (C) contacting the resulting first sample of step B with a first detectable agent and the resulting second sample of step B with a second detectable agent; (D) measuring the level of the first detectable agent and second detectable agent bound to selected proteins; and (E) identifying the cellular protein in a cellular protein-targeted protein binder complex by measuring a difference between the level of the first detectable agent and second detectable agent bound to the cellular protein capable of forming the cellular protein-targeted protein binder complex. In embodiments, the method further includes (A) One of the first or second detectable agents includes a light isotope of an atom and a second of the first or second detectable agents includes a heavy isotope of the atom; (B) the level of the first detectable agent and second detectable agent of selected proteins is measured by liquid chromatography mass spectrometry; and (C) the cellular protein capable of binding the targeted protein binder is identified by a difference between the level of the cellular protein bound to the first detectable agent and the level of the cellular protein bound to the second detectable agent.

In embodiments, the cell is a mammalian cell. In embodiments, the cell is a human cell. In embodiments, the cell is a disease cell. In embodiments, the cell is a cancer cell. In embodiments, the cell is a breast cancer cell. In embodiments, the cell is a triple negative breast cancer cell. In embodiments, the cell is a 231MFP cell. In embodiments, the cell is a HCC38 cell.

In embodiments, the compound is:

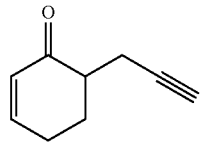

In embodiments, the compound is:

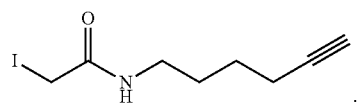

In embodiments, the compound is:

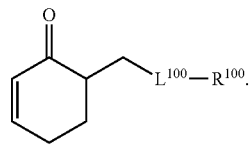

In embodiments, the compound is:

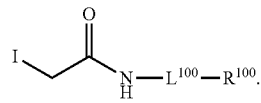

In embodiments, $L^{100}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $R^{100}$ is rhodamine moiety. In embodiments, the compound is:

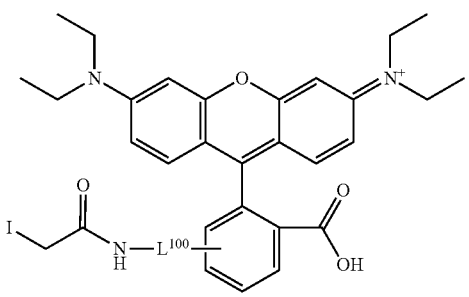

wherein $L^{100}$ is as described herein. In embodiments, $L^{100}$ is a bond or substituted or unsubstituted $C_1$-$C_4$ alkylene. In embodiments, the compound is:

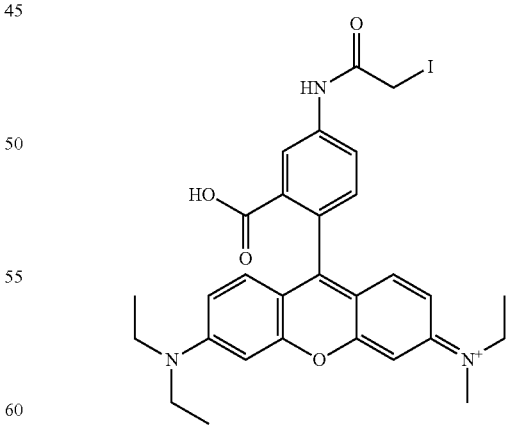

In embodiments, $L^{100}$ is a bond, —S(O)$_2$—, —NH—, —O—, —S—, —C(O)—, —C(O)NH—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^{100}$ is a bond, —S(O)$_2$—, —NH—, —O—, —S—, —C(O)—, —C(O)NH—, —NHC(O)NH—, —C(O)O—, —OC(O)—, substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted (e.g., substituted with at least one substituent group, size-limited substituent group, or lower substituent group) or unsubstituted heteroarylene.

In embodiments, $L^{100}$ is substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered). In embodiments, $L^{100}$ is substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene. In embodiments, $L^{100}$ is unsubstituted alkylene, unsubstituted heteroalkylene, unsubstituted cycloalkylene, unsubstituted heterocycloalkylene, unsubstituted arylene, or unsubstituted heteroarylene. In embodiments, $L^{100}$ is a bond.

In embodiments, $L^{100}$ is a substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted (e.g., substituted with at least one substituent group, size-limited substituent group, or lower substituent group) or unsubstituted heteroarylene.

In embodiments, a substituted $L^{100}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{100}$ is substituted with a plurality of groups selected from substituent groups, size-limited substituent groups, and lower substituent groups; each substituent group, size-limited substituent group, and/or lower substituent group may optionally be different. In embodiments, when $L^{100}$ is substituted, it is substituted with at least one substituent group. In embodiments, when $L^{100}$ is substituted, it is substituted with at least one size-limited substituent group. In embodiments, when $L^{100}$ is substituted, it is substituted with at least one lower substituent group.

In embodiments, the E3 Ubiquitin ligase binder contacts an E3 Ubiquitin ligase cysteine residue (e.g., a cysteine amino acid in human RNF4 or a cysteine amino acid in human RF 114). In embodiments, the E3 Ubiquitin ligase binder contacts an E3 Ubiquitin ligase cysteine residue (e.g., a cysteine amino acid in human RNF4 or a cysteine amino acid in human RF114). In embodiments, the E3 Ubiquitin ligase is human RNF4. In embodiments, the cysteine residue is C132 of human RNF4. In embodiments, the cysteine residue is C135 of human RNF4. In embodiments, the E3 Ubiquitin ligase is human RNF114. In embodiments, the cysteine residue is C8 of human RNF114.

In an aspect is a method of making an E3 Ubiquitin ligase-targeted protein degrader-cellular protein complex including: (A) contacting the E3 Ubiquitin ligase with a targeted protein degrader and thereby forming an E3 Ubiquitin ligase-targeted protein degrader complex; and (B) contacting the E3 Ubiquitin ligase-targeted protein degrader complex with the cellular protein and thereby forming an E3 Ubiquitin ligase-targeted protein degrader-cellular protein complex.

In an aspect is a method of making an E3 Ubiquitin ligase-targeted protein degrader-cellular protein complex including: (A) contacting the E3 Ubiquitin ligase with a targeted protein degrader (e.g., a compound described herein or a targeted protein degrader described herein) and thereby forming an E3 Ubiquitin ligase-targeted protein degrader complex; and (B) contacting the E3 Ubiquitin ligase-targeted protein degrader complex with the cellular protein and thereby forming an E3 Ubiquitin ligase-targeted protein degrader-cellular protein complex.

In an aspect is provided a method of making a cellular protein-targeted protein degrader-E3 Ubiquitin ligase complex including: (A) contacting the cellular protein with a targeted protein degrader and thereby forming a cellular protein-targeted protein degrader complex; and (B) contacting the cellular protein-targeted protein degrader complex with the E3 Ubiquitin ligase and thereby forming a cellular protein-targeted protein degrader-E3 Ubiquitin ligase complex.

In an aspect is provided a method of making a cellular protein-targeted protein degrader-E3 Ubiquitin ligase complex including: (A) contacting the cellular protein with an targeted protein degrader (e.g., a compound described herein or a targeted protein degrader described herein) and thereby forming a cellular protein-targeted protein degrader complex; and (B) contacting the cellular protein-targeted protein degrader complex with the E3 Ubiquitin ligase and thereby forming a cellular protein-targeted protein degrader-E3 Ubiquitin ligase complex.

In an aspect is a method of making an E3 Ubiquitin ligase-E3 Ubiquitin ligase binder-cellular protein complex including: (A) contacting the E3 Ubiquitin ligase with an E3 Ubiquitin ligase binder and thereby forming an E3 Ubiquitin ligase-E3 Ubiquitin ligase binder complex; and (B) contacting the E3 Ubiquitin ligase-E3 Ubiquitin ligase binder complex with the cellular protein and thereby forming an E3 Ubiquitin ligase-E3 Ubiquitin ligase binder-cellular protein complex.

In an aspect is a method of making an E3 Ubiquitin ligase-E3 Ubiquitin ligase binder-cellular protein complex including: (A) contacting the E3 Ubiquitin ligase with an E3 Ubiquitin ligase binder (e.g., a compound described herein or an E3 Ubiquitin ligase binder described herein) and thereby forming an E3 Ubiquitin ligase-E3 Ubiquitin ligase binder complex; and (B) contacting the E3 Ubiquitin ligase-E3 Ubiquitin ligase binder complex with the cellular protein and thereby forming an E3 Ubiquitin ligase-E3 Ubiquitin ligase binder-cellular protein complex.

In an aspect is provided a method of making a cellular protein-E3 Ubiquitin ligase binder-E3 Ubiquitin ligase complex including: (A) contacting the cellular protein with an E3 Ubiquitin ligase binder and thereby forming a cellular protein-E3 Ubiquitin ligase binder complex; and (B) contacting the cellular protein-E3 Ubiquitin ligase binder complex with the E3 Ubiquitin ligase and thereby forming a cellular protein-E3 Ubiquitin ligase binder-E3 Ubiquitin ligase complex.

In an aspect is provided a method of making a cellular protein-E3 Ubiquitin ligase binder-E3 Ubiquitin ligase complex including: (A) contacting the cellular protein with an E3 Ubiquitin ligase binder (e.g., a compound described herein or an E3 Ubiquitin ligase binder described herein) and thereby forming a cellular protein-E3 Ubiquitin ligase binder complex; and (B) contacting the cellular protein-E3 Ubiquitin ligase binder complex with the E3 Ubiquitin ligase and thereby forming a cellular protein-E3 Ubiquitin ligase binder-E3 Ubiquitin ligase complex.

In an aspect is provided a method of inhibiting the formation of a cellular protein-E3 Ubiquitin ligase complex including contacting the E3 Ubiquitin ligase with an E3 Ubiquitin ligase binder and thereby inhibiting the formation of a cellular protein-E3 Ubiquitin ligase complex.

In an aspect is provided a method of inhibiting the formation of a cellular protein-E3 Ubiquitin ligase complex including contacting the E3 Ubiquitin ligase with an E3 Ubiquitin ligase binder (e.g., a compound described herein or an E3 Ubiquitin ligase binder described herein) and thereby inhibiting the formation of a cellular protein-E3 Ubiquitin ligase complex.

In embodiments, the E3 Ubiquitin ligase binder covalently bonds a cysteine of the E3 Ubiquitin ligase. In embodiments, the E3 Ubiquitin ligase binder contacts the E3 Ubiquitin ligase at amino acids of the E3 Ubiquitin ligase that are capable of contacting the cellular protein to form the cellular protein-E3 Ubiquitin ligase complex in the absence of the E3 Ubiquitin ligase binder. In embodiments, the E3 Ubiquitin ligase is human RNF4. In embodiments, the E3 Ubiquitin ligase is RNF4 and the cysteine is C132 of human RNF4. In embodiments, the E3 Ubiquitin ligase is RNF4 and the cysteine is C135 of human RNF4.

In embodiments, the E3 Ubiquitin ligase binder has a monovalent form of the formula:

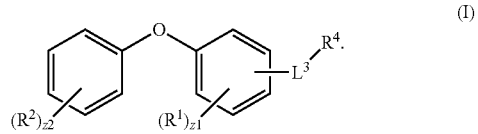

$R^1$, $R^2$, $L^3$, $R^4$, z1, and z2 are as described herein, including in embodiments.

In embodiments, the E3 Ubiquitin ligase binder is a monovalent form of the formula:

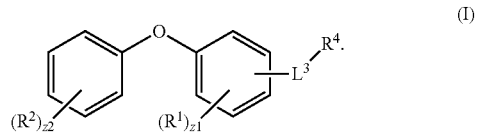

$R^1$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $R^2$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^3$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E. E is an electrophilic moiety. z1 is an integer from 0 to 4. z2 is an integer from 0 to 5. Only one R$^1$ or one R$^2$ is a bond to the binder linker.

In embodiments, the E3 Ubiquitin ligase binder has having the formula

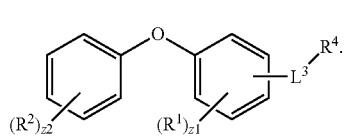

(I)

R$^1$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two R$^1$ substituents may optionally be joined to form a substituted or unsubstituted cycloalkyl, substituted or unsubstituted heterocycloalkyl, substituted or unsubstituted aryl, or substituted or unsubstituted heteroaryl. R$^2$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two R$^2$ substituents may optionally be joined to form a substituted or unsubstituted cycloalkyl, substituted or unsubstituted heterocycloalkyl, substituted or unsubstituted aryl, or substituted or unsubstituted heteroaryl. L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R$^3$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E. E is an electrophilic moiety. z1 is an integer from 0 to 4. z2 is an integer from 0 to 5. Only one R$^1$ or one R$^2$ is a bond to the binder linker.

In embodiments, the E3 Ubiquitin ligase is human RNF114. In embodiments, the E3 Ubiquitin ligase is human RNF114 and the cysteine is C8 of human RNF114. In embodiments, the cellular protein is p21.

In embodiments, the E3 Ubiquitin ligase binder is a monovalent form of the formula:

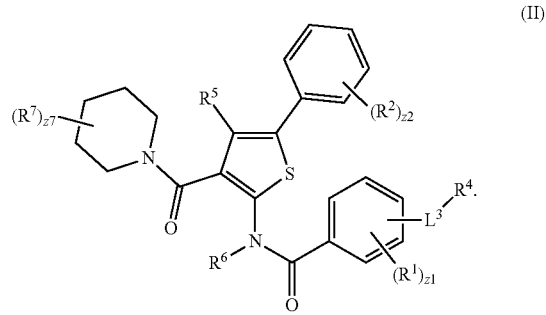

(II)

R$^1$, R$^2$, L$^3$, R$^4$, R$^5$, R$^6$, R$^7$, z1, z2, and z7 are as described herein, including in embodiments.

In embodiments, the E3 Ubiquitin ligase binder is a monovalent form of the formula:

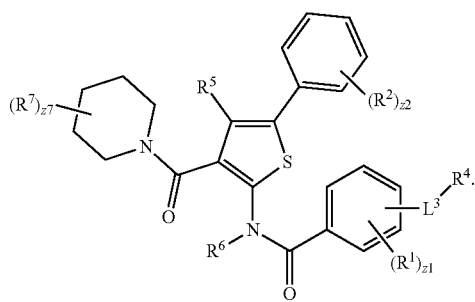

R¹, R², and R⁷ are independently halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two R¹ substituents or two R² substituents or two R⁴ substituents may optionally be joined to form an substituted or unsubstituted cycloalkyl, substituted or unsubstituted heterocycloalkyl, substituted or unsubstituted aryl, or substituted or unsubstituted heteroaryl. R⁵ and R⁶ are independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker. L³ is a bond, —N(R³)—, —C(O)—, —C(O)N(R³)—, —N(R³)C(O)—, —N(H)—, —C(O)N(H)—, —N(H)C(O)—, —C(O)O—, substituted or unsubstituted alkylene, or unsubstituted heteroalkylene, substituted or unsubstituted cycloalkylene, substituted or unsubstituted heterocycloalkylene, substituted or unsubstituted arylene, or substituted or unsubstituted heteroarylene. R³ is independently hydrogen, oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E. E is an electrophilic moiety. z1 is an integer from 0 to 4. z2 is an integer from 0 to 5. z7 is an integer from 0 to 10. Only one R¹, R², R⁵, R⁶, or R⁷ is independently a bond to the binder linker.

In embodiments, the E3 Ubiquitin ligase binder has the formula:

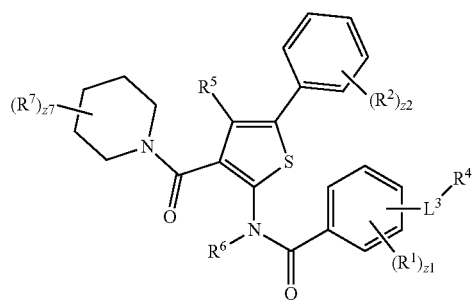

R¹, R², and R⁷ are independently halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two R¹ substituents or two R² substituents or two R⁴ substituents may optionally be joined to form an substituted or unsubstituted cycloalkyl, substituted or unsubstituted heterocycloalkyl, substituted or unsubstituted aryl, or substituted or unsubstituted heteroaryl. R⁵ and R⁶ are independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker. $L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^3$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E. E is an electrophilic moiety. z1 is an integer from 0 to 4. z2 is an integer from 0 to 5. z7 is an integer from 0 to 10. Only one $R^1$, $R^2$, $R^5$, $R^6$, or $R^7$ is independently a bond to the binder linker.

In embodiments, the E3 Ubiquitin ligase binder is a monovalent form of the formula:

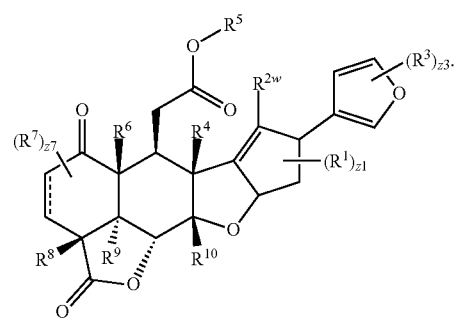

(IIIa-1)

$R^1$, $R^{2w}$, $R^3$, $R^4$, $R^5$, $R^6$, $R^7$, $R^8$, $R^9$, $R^{10}$, z1, z3, and z7 are as described herein.

In embodiments, the E3 Ubiquitin ligase binder is a monovalent form of the formula:

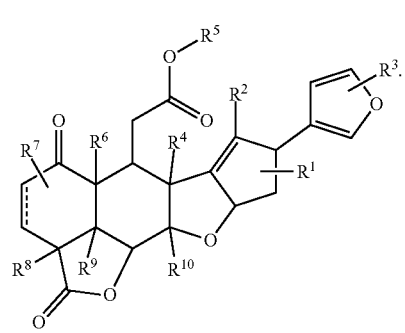

(III)

$R^1$, $R^2$, $R^3$, $R^4$, $R^5$, $R^6$, $R^7$, $R^8$, $R^9$, and $R^{10}$ are as described herein, including in embodiments.

In embodiments, the E3 Ubiquitin ligase binder is a monovalent form of the formula:

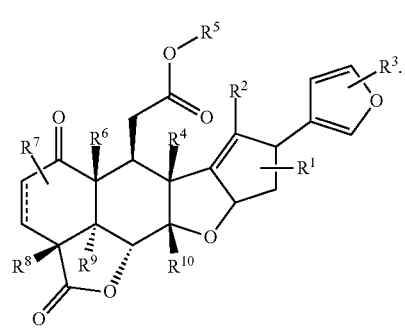

(III)

$R^1$, $R^2$, $R^3$, $R^4$, $R^5$, $R^6$, $R^7$, $R^8$, $R^9$, and $R^{10}$ are as described herein, including in embodiments.

In embodiments, the E3 Ubiquitin ligase binder is a monovalent form of the formula:

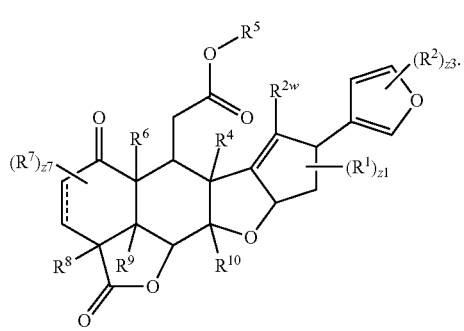

$R^1$, $R^{2w}$, $R^3$, $R^4$, $R^5$, $R^6$, $R^7$, $R^8$, $R^9$, $R^{10}$, z1, z3, and z7 are as described herein.

In embodiments, the E3 Ubiquitin ligase binder is a monovalent form of the formula:

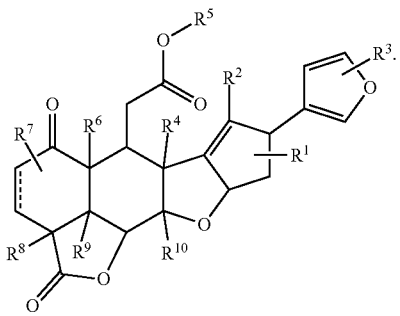

(III)

$R^1$, $R^2$, $R^3$, $R^4$, $R^5$, $R^6$, $R^7$, $R^8$, $R^9$, and $R^{10}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a bond to the binder linker. Only one $R^1$, $R^2$, $R^3$, $R^4$, $R^5$, $R^6$, $R^7$, $R^8$, $R^9$, or $R^{10}$ is a bond to the binder linker.

$$\vdots$$

is a single bond or a double bond.

In embodiments, the E3 Ubiquitin ligase binder is a monovalent form of the formula:

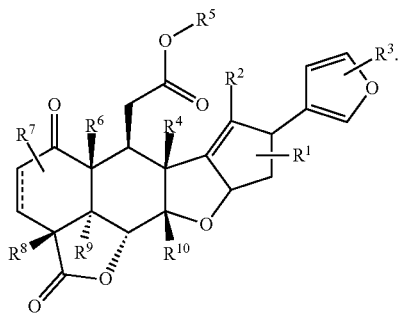

(III)

$R^1$, $R^2$, $R^3$, $R^4$, $R^5$, $R^6$, $R^7$, $R^8$, $R^9$, and $R^{10}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a bond to the binder linker. Only one $R^1$, $R^2$, $R^3$, $R^4$, $R^5$, $R^6$, $R^7$, $R^8$, $R^9$, or $R^{10}$ is a bond to the binder linker.

$$\vdots$$

is a single bond or a double bond.

In embodiments, the E3 Ubiquitin ligase binder has the formula:

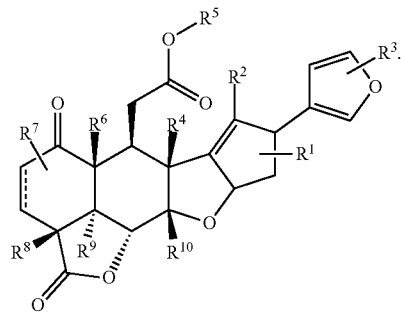

(III)

$R^1$, $R^2$, $R^3$, $R^4$, $R^5$, $R^6$, $R^7$, $R^8$, $R^9$, and $R^{10}$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a bond to the binder linker. Only one $R^1$, $R^2$, $R^3$, $R^4$, $R^5$, $R^6$, $R^7$, $R^8$, $R^9$, or $R^{10}$ is a bond to the binder linker.

$$\vdots$$

is a single bond or a double bond.

In embodiments, the E3 Ubiquitin ligase binder contacts amino acids of the E3 Ubiquitin ligase lacking stable secondary or tertiary conformational structure in the absence of the E3 Ubiquitin ligase binder. In embodiments, the amino acids contacting the E3 Ubiquitin ligase binder adopt a stable secondary or tertiary conformational structure upon contacting the E3 Ubiquitin ligase binder.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A targeted protein degrader comprising 1) a monovalent targeted protein binder and 2) a monovalent E3 Ubiquitin ligase binder, wherein the E3 Ubiquitin ligase is human RNF4 or human RNF114.

Embodiment P2. The targeted protein degrader of embodiment P1 wherein the E3 Ubiquitin ligase binder is capable of forming a covalent bond with a cysteine of an E3 Ubiquitin ligase.

Embodiment P3. The targeted protein degrader of one of embodiments P1 to P2, wherein the targeted protein binder and E3 Ubiquitin ligase binder are covalently bonded by a binder linker.

Embodiment P4. The targeted protein degrader of one of embodiments P1 to P3, wherein the E3 Ubiquitin ligase is human RNF4.

Embodiment P5. The targeted protein degrader of one of embodiments P1 to P4, wherein the E3 Ubiquitin ligase binder is a monovalent compound having the formula:

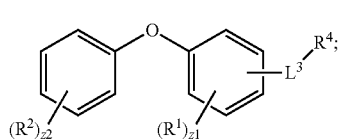

(I)

wherein

R$^1$ is independently halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two R$^1$ substituents may optionally be joined to form a substituted or unsubstituted cycloalkyl, substituted or unsubstituted heterocycloalkyl, substituted or unsubstituted aryl, or substituted or unsubstituted heteroaryl;

R$^2$ is independently halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two R$^2$ substituents may optionally be joined to form a substituted or unsubstituted cycloalkyl, substituted or unsubstituted heterocycloalkyl, substituted or unsubstituted aryl, or substituted or unsubstituted heteroaryl;

L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^3$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E;

E is an electrophilic moiety;

z1 is an integer from 0 to 4;

z2 is an integer from 0 to 5; and wherein only one R$^1$ or one R$^2$ is a bond to the binder linker.

Embodiment P6. The targeted protein degrader of one of embodiments P1 to P5, wherein R$^1$ is independently halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{11}$-substituted or unsubstituted C$_1$-C$_8$ alkyl, R$^{11}$-substituted or unsubstituted 2 to 8 membered heteroalkyl, R$^{11}$-substituted or unsubstituted C$_3$-C$_8$ cycloalkyl, R$^{11}$-substituted or unsubstituted 3 to 8 membered heterocycloalkyl, R$^{11}$-substituted or unsubstituted C$_6$-C$_{10}$ aryl, or R$^{11}$-substituted or unsubstituted 5 to 10 membered heteroaryl, or a bond to the binder linker; two R$^1$ substituents may optionally be joined to form an R$^{11}$-substituted or unsubstituted C$_3$-C$_8$ cycloalkyl, R$^{11}$-substituted or unsubstituted 3 to 8 membered heterocycloalkyl, R$^{11}$-substituted or unsubstituted $C_6$-$C_{10}$ aryl, or $R^1$-substituted or unsubstituted 5 to 10 membered heteroaryl;

$R^{11}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{12}$-substituted or unsubstituted $C_1$-$C_8$ alkyl, $R^2$-substituted or unsubstituted 2 to 8 membered heteroalkyl, $R^{12}$-substituted or unsubstituted $C_3$-$C_8$ cycloalkyl, $R^{12}$-substituted or unsubstituted 3 to 8 membered heterocycloalkyl, $R^2$-substituted or unsubstituted $C_6$-$C_{10}$ aryl, or $R^{12}$-substituted or unsubstituted 5 to 10 membered heteroaryl;

$R^{12}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl;

$R^2$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{21}$-substituted or unsubstituted $C_1$-$C_8$ alkyl, $R^{21}$-substituted or unsubstituted 2 to 8 membered heteroalkyl, $R^{21}$-substituted or unsubstituted $C_3$-$C_8$ cycloalkyl, $R^{21}$-substituted or unsubstituted 3 to 8 membered heterocycloalkyl, $R^{21}$-substituted or unsubstituted $C_6$-$C_{10}$ aryl, or $R^{21}$-substituted or unsubstituted 5 to 10 membered heteroaryl, or a bond to the binder linker; two $R^2$ substituents may optionally be joined to form an $R^{21}$-substituted or unsubstituted $C_3$-$C_8$ cycloalkyl, $R^{21}$-substituted or unsubstituted 3 to 8 membered heterocycloalkyl, $R^{21}$-substituted or unsubstituted $C_6$-$C_{10}$ aryl, or $R^{21}$-substituted or unsubstituted 5 to 10 membered heteroaryl;

$R^{21}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{22}$-substituted or unsubstituted $C_1$-$C_8$ alkyl, $R^{22}$-substituted or unsubstituted 2 to 8 membered heteroalkyl, $R^{22}$-substituted or unsubstituted $C_3$-$C_8$ cycloalkyl, $R^{22}$-substituted or unsubstituted 3 to 8 membered heterocycloalkyl, $R^{22}$-substituted or unsubstituted $C_6$-$C_{10}$ aryl, or $R^{22}$-substituted or unsubstituted 5 to 10 membered heteroaryl;

$R^{22}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl;

$L^3$ is a bond, —$N(R^3)$—, —C(O)—, —$C(O)N(R^3)$—, —$N(R^3)C(O)$—, —N(H)—, —C(O)N(H)—, —N(H)C(O)—, —C(O)O—, $R^3$-substituted or unsubstituted $C_1$-$C_8$ alkylene, $R^3$-substituted or unsubstituted 2 to 8 membered heteroalkylene, $R^3$-substituted or unsubstituted $C_3$-$C_8$ cycloalkylene, $R^3$-substituted or unsubstituted 3 to 8 membered heterocycloalkylene, $R^3$-substituted or unsubstituted $C_6$-$C_{10}$ arylene, or $R^3$-substituted or unsubstituted 5 to 10 membered heteroarylene;

$R^3$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{31}$-substituted or unsubstituted $C_1$-$C_8$ alkyl, $R^{31}$-substituted or unsubstituted 2 to 8 membered heteroalkyl, $R^{31}$-substituted or unsubstituted $C_3$-$C_8$ cycloalkyl, $R^{31}$-substituted or unsubstituted 3 to 8 membered heterocycloalkyl, $R^{31}$-substituted or unsubstituted $C_6$-$C_{10}$ aryl, or $R^{31}$-substituted or unsubstituted 5 to 10 membered heteroaryl;

$R^{31}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{32}$-substituted or unsubstituted $C_1$-$C_8$ alkyl, $R^{32}$-substituted or unsubstituted 2 to 8 membered heteroalkyl, $R^{32}$-substituted or unsubstituted $C_3$-$C_8$ cycloalkyl, $R^{32}$-substituted or unsubstituted 3 to 8 membered heterocycloalkyl, $R^{32}$-substituted or unsubstituted $C_6$-$C_{10}$ aryl, or $R^{32}$-substituted or unsubstituted 5 to 10 membered heteroaryl;

$R^{32}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

R$^4$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{41}$-substituted or unsubstituted C$_1$-C$_8$ alkyl, R$^{41}$-substituted or unsubstituted 2 to 8 membered heteroalkyl, R$^{41}$-substituted or unsubstituted C$_3$-C$_8$ cycloalkyl, R$^{41}$-substituted or unsubstituted 3 to 8 membered heterocycloalkyl, R$^{41}$-substituted or unsubstituted C$_6$-C$_{10}$ aryl, or R$^{41}$-substituted or unsubstituted 5 to 10 membered heteroaryl, or E;

R$^{41}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{42}$-substituted or unsubstituted C$_1$-C$_8$ alkyl, R$^{42}$-substituted or unsubstituted 2 to 8 membered heteroalkyl, R$^{42}$-substituted or unsubstituted C$_3$-C$_8$ cycloalkyl, R$^{42}$-substituted or unsubstituted 3 to 8 membered heterocycloalkyl, R$^{42}$-substituted or unsubstituted C$_6$-C$_{10}$ aryl, or R$^{42}$-substituted or unsubstituted 5 to 10 membered heteroaryl;

R$^{42}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl.

Embodiment P7. The targeted protein degrader of embodiment P6, wherein R$^2$ is independently halogen, —CF$_3$, —NO$_2$, R$^{21}$-substituted or unsubstituted C$_1$-C$_3$ alkyl, unsubstituted 2 to 3 membered heteroalkyl, or a bond to the binder linker; two R$^2$ substituents may optionally be joined to form an unsubstituted phenyl; and R$^{21}$ is independently —OH.

Embodiment P8. The targeted protein degrader of one of embodiments P6 to P7, wherein z2 is 1 and R$^2$ is a bond to the binder linker.

Embodiment P9. The targeted protein degrader of one of embodiments P6 to P8, wherein R$^1$ is independently halogen.

Embodiment P10. The targeted protein degrader of one of embodiments P6 to P9, wherein z1 is 0.

Embodiment P11. The targeted protein degrader of one of embodiments P6 to P10, wherein L$^3$ is —N(R$^3$)—;

R$^3$ is independently R$^{31}$-substituted methyl, unsubstituted phenyl, or unsubstituted 5 to 6 membered heteroaryl; and R$^{31}$ is independently unsubstituted phenyl, or unsubstituted 5 to 6 membered heteroaryl.

Embodiment P12. The targeted protein degrader of one of embodiments P6 to P11, wherein E is

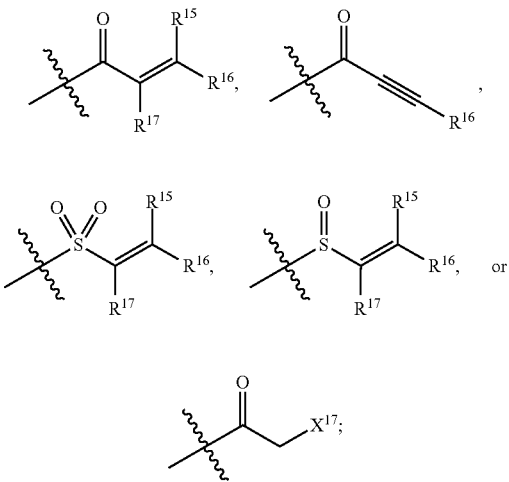

R$^{15}$, R$^{16}$, and R$^{17}$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

and X$^{17}$ is halogen.

Embodiment P13. The targeted protein degrader of one of embodiments P6 to P12, wherein E is

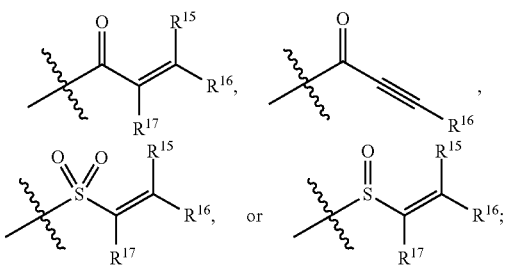

R$^{15}$, R$^{16}$, and R$^{17}$ are independently hydrogen.

Embodiment P14. The targeted protein degrader of one of embodiments P6 to P12, wherein E is

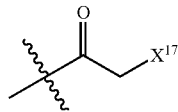

and $X^{17}$ is independently —Cl.

Embodiment P15. The targeted protein degrader of one of embodiments P1 to P3, wherein the E3 Ubiquitin ligase is human RNF114.

Embodiment P16. The targeted protein degrader of one of embodiments P1 to P3, and P15, wherein the E3 Ubiquitin ligase binder is a monovalent compound having the formula:

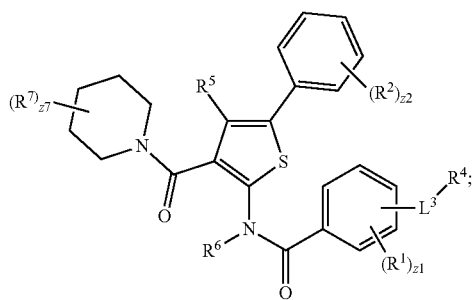

wherein $R^1$ and $R^2$ are independently halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two $R^1$ substituents or two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^5$ and $R^6$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker;

$R^7$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two $R^7$ substituents may optionally be joined to form a substituted or unsubstituted cycloalkyl, substituted or unsubstituted heterocycloalkyl, substituted or unsubstituted aryl, or substituted or unsubstituted heteroaryl;

$L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E;

E is an electrophilic moiety;

z1 is an integer from 0 to 4;

z2 is an integer from 0 to 5;

z7 is an integer from 0 to 10; and wherein only one $R^1$, $R^2$, $R^5$, $R^6$, or $R^7$ is independently a bond to the binder linker.

Embodiment P17. The targeted protein degrader of embodiment P16, wherein $R^1$, $R^2$, and $R^7$ are independently halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{51}$-substituted or unsubstituted C$_1$-C$_8$ alkyl, R$^{51}$-substituted or unsubstituted 2 to 8 membered heteroalkyl, R$^{51}$-substituted or unsubstituted C$_3$-C$_8$ cycloalkyl, R$^{51}$-substituted or unsubstituted 3 to 8 membered heterocycloalkyl, R$^{51}$-substituted or unsubstituted C$_6$-C$_{10}$ aryl, or R$^{51}$-substituted or unsubstituted 5 to 10 membered heteroaryl, or a bond to the binder linker; two R$^1$ substituents or two R$^2$ substituents may optionally be joined to form an R$^{51}$-substituted or unsubstituted C$_3$-C$_8$ cycloalkyl, R$^{51}$-substituted or unsubstituted 3 to 8 membered heterocycloalkyl, R$^{51}$-substituted or unsubstituted C$_6$-C$_{10}$ aryl, or R$^{51}$-substituted or unsubstituted 5 to 10 membered heteroaryl;

R$^5$ and R$^6$ are independently hydrogen, halogen, —CCl$_3$, —CBr$_3$, —CF$_3$, —C$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{51}$-substituted or unsubstituted C$_1$-C$_8$ alkyl, R$^{51}$-substituted or unsubstituted 2 to 8 membered heteroalkyl, R$^{51}$-substituted or unsubstituted C$_3$-C$_8$ cycloalkyl, R$^5$-substituted or unsubstituted 3 to 8 membered heterocycloalkyl, R$^{51}$-substituted or unsubstituted C$_6$-C$_{10}$ aryl, or R$^{51}$-substituted or unsubstituted 5 to 10 membered heteroaryl, or a bond to the binder linker;

R$^7$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{51}$-substituted or unsubstituted C$_1$-C$_8$ alkyl, R$^{11}$-substituted or unsubstituted 2 to 8 membered heteroalkyl, R$^{51}$-substituted or unsubstituted C$_3$-C$_8$ cycloalkyl, R$^5$-substituted or unsubstituted 3 to 8 membered heterocycloalkyl, R$^{51}$-substituted or unsubstituted C$_6$-C$_{10}$ aryl, or R$^{51}$-substituted or unsubstituted 5 to 10 membered heteroaryl, or a bond to the binder linker; two R$^7$ substituents may optionally be joined to form an R$^{51}$-substituted or unsubstituted C$_3$-C$_8$ cycloalkyl, R$^{51}$-substituted or unsubstituted 3 to 8 membered heterocycloalkyl, R$^{51}$-substituted or unsubstituted C$_6$-C$_{10}$ aryl, or R$^{51}$-substituted or unsubstituted 5 to 10 membered heteroaryl R$^{51}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C6-C$_{10}$ aryl, or unsubstituted 5 to 10 membered heteroaryl.

L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, R$^3$-substituted or unsubstituted C$_1$-C$_8$ alkylene, R$^3$-substituted or unsubstituted 2 to 8 membered heteroalkylene, R$^3$-substituted or unsubstituted C$_3$-C$_8$ cycloalkylene, R$^3$-substituted or unsubstituted 3 to 8 membered heterocycloalkylene, R$^3$-substituted or unsubstituted C$_6$-C$_{10}$ arylene, or R$^3$-substituted or unsubstituted 5 to 10 membered heteroarylene; R$^3$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{31}$-substituted or unsubstituted C$_1$-C$_8$ alkyl, R$^{31}$-substituted or unsubstituted 2 to 8 membered heteroalkyl, R$^{31}$-substituted or unsubstituted C$_3$-C$_8$ cycloalkyl, R$^{31}$-substituted or unsubstituted 3 to 8 membered heterocycloalkyl, R$^{31}$-substituted or unsubstituted C$_6$-C$_{10}$ aryl, or R$^{31}$-substituted or unsubstituted 5 to 10 membered heteroaryl;

R$^{31}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{32}$-substituted or unsubstituted C1-C$_8$ alkyl, R$^{32}$-substituted or unsubstituted 2 to 8 membered heteroalkyl, R$^{32}$-substituted or unsubstituted C$_3$-C$_8$ cycloalkyl, R$^{32}$-substituted or unsubstituted 3 to 8 membered heterocycloalkyl, R$^{32}$-substituted or unsubstituted C$_6$-C$_{10}$ aryl, or R$^{32}$-substituted or unsubstituted 5 to 10 membered heteroaryl;

R$^{32}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

R$^4$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{41}$-substituted or unsubstituted $C_1$-$C_8$ alkyl, $R^{41}$-substituted or unsubstituted 2 to 8 membered heteroalkyl, $R^{41}$-substituted or unsubstituted $C_3$-$C_8$ cycloalkyl, $R^{41}$-substituted or unsubstituted 3 to 8 membered heterocycloalkyl, $R^{41}$-substituted or unsubstituted $C_6$-$C_{10}$ aryl, or $R^{41}$-substituted or unsubstituted 5 to 10 membered heteroaryl, or E;

$R^{41}$ is independently oxo, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{42}$-substituted or unsubstituted C1-$C_8$ alkyl, $R^{42}$-substituted or unsubstituted 2 to 8 membered heteroalkyl, $R^{42}$-substituted or unsubstituted $C_3$-$C_8$ cycloalkyl, $R^{42}$-substituted or unsubstituted 3 to 8 membered heterocycloalkyl, $R^{42}$-substituted or unsubstituted $C_6$-$C_{10}$ aryl, or $R^{42}$-substituted or unsubstituted 5 to 10 membered heteroaryl;

$R^{42}$ is independently oxo, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

Embodiment P18. The targeted protein degrader of embodiment P17, wherein the E3 Ubiquitin ligase binder is a monovalent compound having the formula:

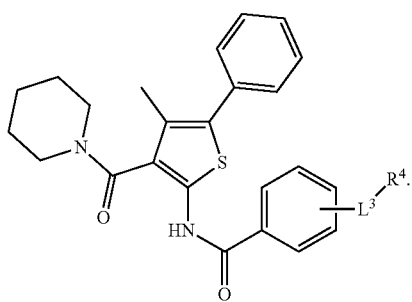

Embodiment P19. The targeted protein degrader of one of embodiments P17 to P18, wherein $L^3$ is —CH₂NH—.

Embodiment P20. The targeted protein degrader of one of embodiments P17 to P19, wherein E is

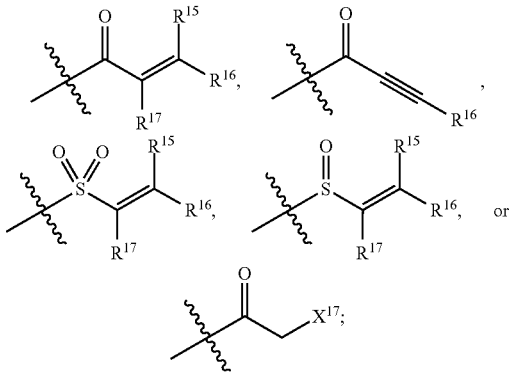

$R^{15}$, $R^{16}$, and $R^{17}$ are independently hydrogen, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

and $X^{17}$ is halogen.

Embodiment P21. The targeted protein degrader of one of embodiments P17 to P20, wherein E is

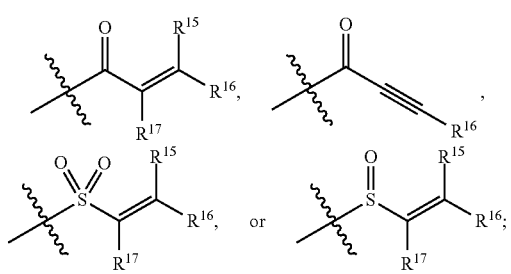

$R^{15}$, $R^{16}$, and $R^{17}$ are independently hydrogen.

Embodiment P22. The targeted protein degrader of one of embodiments P17 to P21, wherein E is

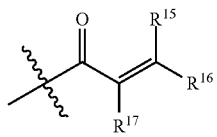

and $R^{15}$, $R^{16}$, and $R^7$ are independently hydrogen.

Embodiment P23. The targeted protein degrader of one of embodiments P1 to P3, and P15, wherein the E3 Ubiquitin ligase binder is a monovalent compound having the formula:

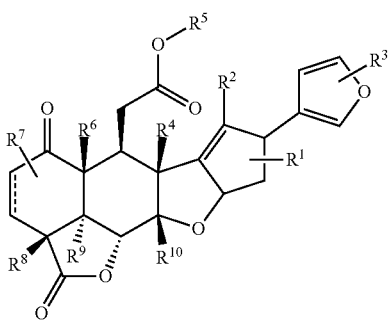

$R^1$, $R^2$, $R^3$, $R^4$, $R^5$, $R^6$, $R^7$, $R^8$, $R^9$, and $R^{10}$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a bond to the binder linker;

wherein only one $R^1$, $R^2$, $R^3$, $R^4$, $R^5$, $R^6$, $R^7$, $R^8$, $R^9$, or $R^{10}$ is a bond to the binder linker; and is a single bond or a double bond.

Embodiment P24. The targeted protein degrader of embodiment P23, wherein $R^1$, $R^2$, $R^3$, $R^4$, $R^5$, $R^6$, $R^7$, $R^8$, $R^9$, and $R^{10}$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{51}$-substituted or unsubstituted C$_1$-C$_8$ alkyl, $R^{51}$-substituted or unsubstituted 2 to 8 membered heteroalkyl, $R^{51}$-substituted or unsubstituted C$_3$-C$_8$ cycloalkyl, $R^{51}$-substituted or unsubstituted 3 to 8 membered heterocycloalkyl, $R^{51}$-substituted or unsubstituted C$_6$-C$_{10}$ aryl, or $R^{51}$-substituted or unsubstituted 5 to 10 membered heteroaryl; or a bond to the binder linker;

wherein only one $R^1$, $R^2$, $R^3$, $R^4$, $R^5$, $R^6$, $R^7$, $R^8$, $R^9$, or $R^{10}$ is a bond to the binder linker;

$R^{51}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl.

Embodiment P25. The targeted protein degrader of embodiment P23, wherein the E3 Ubiquitin ligase binder is a monovalent compound having the formula:

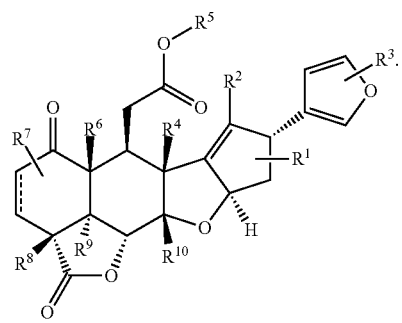

Embodiment P26. The targeted protein degrader of embodiment P24, wherein the E3 Ubiquitin ligase binder is a monovalent compound having the formula:

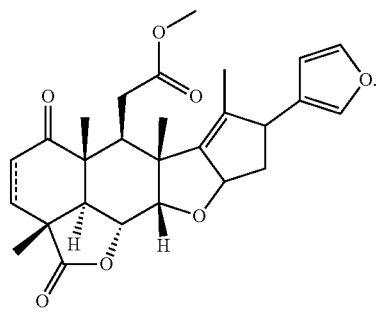

Embodiment P27. The targeted protein degrader of embodiment P24, wherein the E3 Ubiquitin ligase binder is a monovalent compound having the formula:

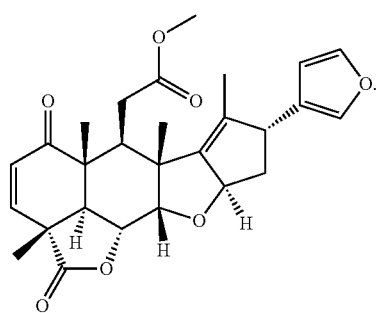

Embodiment P28. The targeted protein degrader of embodiment P24, wherein the E3 Ubiquitin ligase binder has the formula:

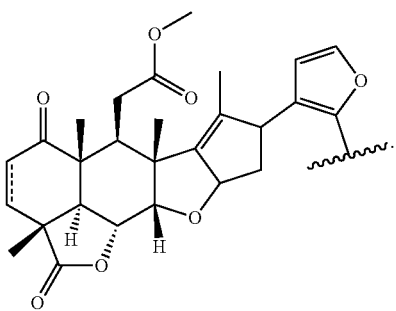

Embodiment P29. The targeted protein degrader of embodiment P24, wherein the E3 Ubiquitin ligase binder has the formula:

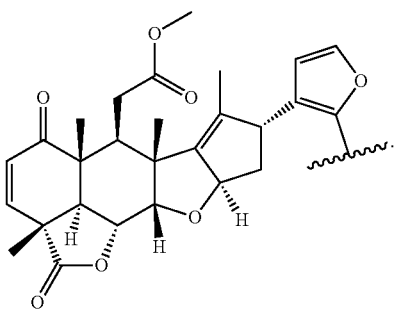

Embodiment P30. The targeted protein degrader of one of embodiments P3 to P29, wherein the binder linker is $L^{11}$-$L^{12}$-$L^{13}$-$L^{14}$;

$L^{11}$ is connected directly to the E3 Ubiquitin ligase binder;

$L^{11}$ is —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker; and $L^{12}$, $L^{13}$, and $L^{14}$ are independently a bond, —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

Embodiment P31. The targeted protein degrader of embodiment P30, wherein $L^{11}$ is —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, $R^{61}$-substituted or unsubstituted $C_1$-$C_{20}$ alkylene, $R^{61}$-substituted or unsubstituted 2 to 20 membered heteroalkylene, $R^{61}$-substituted or unsubstituted $C_3$-$C_8$ cycloalkylene, $R^{61}$-substituted or unsubstituted 3 to 8 membered heterocycloalkylene, $R^{61}$-substituted or unsubstituted $C_6$-$C_{10}$ arylene, $R^{61}$-substituted or unsubstituted 5 to 10 membered heteroarylene, or a bioconjugate linker;

$L^{12}$, $L^{13}$, and $L^{14}$ are independently a bond, —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, $R^{61}$-substituted or unsubstituted $C_1$-$C_{20}$ alkylene, $R^{61}$-substituted or unsubstituted 2 to 20 membered heteroalkylene, $R^{61}$-substituted or unsubstituted $C_3$-$C_8$ cycloalkylene, $R^{61}$-substituted or unsubstituted 3 to 8 membered heterocycloalkylene, $R^{61}$-substituted or unsubstituted $C_6$-$C_{10}$ arylene, $R^{61}$-substituted or unsubstituted 5 to 10 membered heteroarylene, or a bioconjugate linker;

$R^{61}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted 2 to 8 membered heteroalkyl, unsubstituted C3-$C_8$ cycloalkyl, unsubstituted 3 to 8 membered heterocycloalkyl, unsubstituted $C_6$-$C_{10}$ aryl, or unsubstituted 5 to 10 membered heteroaryl.

Embodiment P32. The targeted protein degrader of one of embodiments P1 to P31, wherein the targeted protein binder is capable of binding a targeted protein associated with a disease.

Embodiment P33. The targeted protein degrader of one of embodiments P1 to P32, wherein the targeted protein binder is

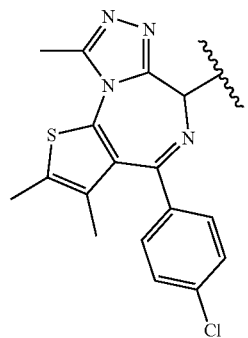 [SMILES: *C1N=C(c2ccc(Cl)cc2)c2c(sc(C)c2C)-n2c(C)nnc21]

and the targeted protein binder binds BRD4.

Embodiment P34. A pharmaceutical composition comprising a targeted protein degrader of one of embodiments P1 to P33 and a pharmaceutically acceptable excipient.

Embodiment P35. A method of reducing the level of a cellular protein, said method comprising contacting the cellular protein with a targeted protein degrader.

Embodiment P36. A method of reducing the level of a cellular protein, said method comprising contacting the cellular protein with a targeted protein degrader of one of embodiments 1 to P33.

Embodiment P37. The method of one of embodiments P35 to P36, further comprising the steps of:
A) Allowing the cellular protein contacting the targeted protein degrader to be ubiquitinated and thereby form a ubiquitinated cellular protein;
B) Allowing the ubiquitinated cellular protein to contact the proteasome and thereby form a ubiquitinated cellular protein-proteasome complex; and
C) proteolyzing the cellular protein by the proteasome.

Embodiment P38. A method of treating cancer, said method comprising contacting a cellular protein associated with cancer with a targeted protein degrader.

Embodiment P39. A method of treating cancer, said method comprising administering to a subject in need thereof a therapeutically effective amount of a targeted protein degrader of one of embodiments P1 to P33.

Embodiment P40. A method of reducing the level of a cellular protein, said method comprising contacting the cellular protein with a targeted protein degrader and thereby forming a targeted protein degrader-cellular protein complex; wherein the targeted protein degrader comprises:
i) a monovalent E3 Ubiquitin ligase binder;
ii) a monovalent targeted protein binder; and
iii) a binder linker directly bonded to the monovalent E3 Ubiquitin ligase binder and the monovalent targeted protein binder.

Embodiment P41. The method of embodiment P40, wherein prior to the contacting, the targeted protein degrader is synthesized by covalently reacting a E3 Ubiquitin ligase binder, a binder linker, and a targeted protein binder to produce the targeted protein degrader.

Embodiment P42. The method of embodiment P41, wherein prior to the synthesizing, the E3 Ubiquitin ligase binder is identified from a candidate E3 Ubiquitin ligase binder.

Embodiment P43. The method of embodiment P42, wherein the E3 Ubiquitin ligase binder is identified by a method comprising the steps:
i) contacting an E3 Ubiquitin ligase protein with a mixture of candidate E3 Ubiquitin ligase binders and thereby forming an E3 Ubiquitin ligase protein-E3 Ubiquitin ligase binder complex; and
ii) identifying the candidate E3 Ubiquitin ligase binders from an E3 Ubiquitin ligase protein-E3 Ubiquitin ligase binder complex as E3 Ubiquitin ligase binders.

Embodiment P44. The method of embodiment P43, wherein the candidate E3 Ubiquitin ligase binders comprise a covalent cysteine modifier moiety and a candidate E3 Ubiquitin ligase binder is identified as an E3 Ubiquitin ligase binder by detection of covalent binding of the E3 Ubiquitin ligase binder to the E3 Ubiquitin ligase protein to form an E3 Ubiquitin ligase protein-E3 Ubiquitin ligase binder complex.

Embodiment P45. The method of embodiment P44, wherein the detection of an E3 Ubiquitin ligase protein-E3 Ubiquitin ligase binder complex comprises use of a detectable label or mass spectroscopy.

Embodiment P46. The method of embodiment P40, wherein prior to the synthesizing, the targeted protein binder is identified.

Embodiment P47. The method of embodiment P46, wherein the targeted protein binder is identified by a method comprising the steps:
i) contacting a cellular protein with a mixture of candidate targeted protein binders and thereby forming a cellular protein-targeted protein binder complex; and
ii) identifying the targeted protein binder that forms a cellular protein-targeted protein binder complex.

Embodiment P48. The method of embodiment P47, wherein the candidate targeted protein binder forming a cellular protein-targeted protein binder complex is identified as a targeted protein binder by detection of the cellular protein-targeted protein binder complex.

Embodiment P49. The method of embodiment P48, wherein the detection of cellular protein-targeted protein binder complex comprises use of a detectable label or mass spectroscopy.

Embodiment P50. The method of embodiment P40, wherein prior to the synthesizing, the E3 Ubiquitin ligase binder is modified to remove a covalent cysteine modifier moiety.

Embodiment P51. A method of identifying a cellular protein contacted by a targeted protein binder comprising:
A) contacting a first sample of a cell proteome or cell with the targeted protein binder thereby forming a cellular protein-targeted protein binder complex;
B) contacting both the resulting first sample of a cell proteome or cell of step A and a second sample of the cell proteome or cell that has not been contacted with the targeted protein binder, with a compound having the formula:

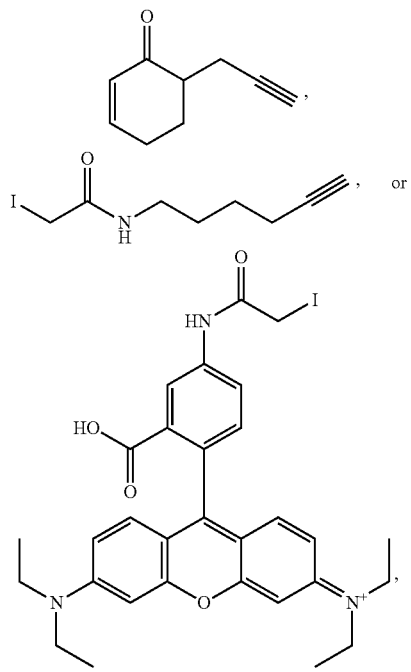

C) contacting the resulting first sample of step B with a first detectable agent and the resulting second sample of step B with a second detectable agent;
D) measuring the level of the first detectable agent and second detectable agent bound to selected proteins; and
E) identifying the cellular protein in a cellular protein-targeted protein binder complex by measuring a difference between the level of the first detectable agent and second detectable agent bound to the cellular protein capable of forming the cellular protein-targeted protein binder complex.

Embodiment P52. The method of embodiment P51, wherein
A) One of the first or second detectable agents comprises a light isotope of an atom and a second of the first or second detectable agents comprises a heavy isotope of the atom;

B) the level of the first detectable agent and second detectable agent of selected proteins is measured by liquid chromatography mass spectrometry; and
C) the cellular protein capable of binding the targeted protein binder is identified by a difference between the level of the cellular protein bound to the first detectable agent and the level of the cellular protein bound to the second detectable agent.

Embodiment P53. The method of one of embodiment P35 to P52, wherein the E3 Ubiquitin ligase binder contacts an E3 Ubiquitin ligase cysteine residue.

Embodiment P54. The method of embodiment P53, wherein the E3 Ubiquitin ligase binder covalently binds an E3 Ubiquitin ligase cysteine residue.

Embodiment P55. The method of one of embodiments P53 to P54 wherein the E3 Ubiquitin ligase is human RNF4.

Embodiment P56. The method of embodiment P55, wherein the cysteine residue is C132 of human RNF4.

Embodiment P57. The method of embodiment P55, wherein the cysteine residue is C135 of human RNF4.

Embodiment P58. The method of one of embodiments P53 to P54 wherein the E3 Ubiquitin ligase is human RNF114.

Embodiment P59. The method of embodiment P58, wherein the cysteine residue is C8 of human RNF114.

Embodiment P60. A method of making an E3 Ubiquitin ligase-E3 Ubiquitin ligase binder-cellular protein complex comprising:
A) contacting the E3 Ubiquitin ligase with an E3 Ubiquitin ligase binder and thereby forming an E3 Ubiquitin ligase-E3 Ubiquitin ligase binder complex; and
B) contacting the E3 Ubiquitin ligase-E3 Ubiquitin ligase binder complex with the cellular protein and thereby forming an E3 Ubiquitin ligase-E3 Ubiquitin ligase binder-cellular protein complex.

Embodiment P61. A method of making a cellular protein-E3 Ubiquitin ligase binder-E3 Ubiquitin ligase complex comprising:
A) contacting the cellular protein with an E3 Ubiquitin ligase binder and thereby forming a cellular protein-E3 Ubiquitin ligase binder complex; and
B) contacting the cellular protein-E3 Ubiquitin ligase binder complex with the E3 Ubiquitin ligase and thereby forming a cellular protein-E3 Ubiquitin ligase binder-E3 Ubiquitin ligase complex.

Embodiment P62. A method of inhibiting the formation of a cellular protein-E3 Ubiquitin ligase complex comprising contacting the E3 Ubiquitin ligase with an E3 Ubiquitin ligase binder and thereby inhibiting the formation of a cellular protein-E3 Ubiquitin ligase complex.

Embodiment P63. The method of one of one of embodiments P60 to P62, wherein the E3 Ubiquitin ligase binder covalently bonds a cysteine of the E3 Ubiquitin ligase.

Embodiment P64. The method of one of embodiments P62 to P63, wherein the E3 Ubiquitin ligase binder contacts the E3 Ubiquitin ligase at amino acids of the E3 Ubiquitin ligase that are capable of contacting the cellular protein to form the cellular protein-E3 Ubiquitin ligase complex in the absence of the E3 Ubiquitin ligase binder.

Embodiment P65. The method of one of embodiments P60 to P64, wherein the E3 Ubiquitin ligase is human RNF4.

Embodiment P66. The method of one of embodiments P63 to P64, wherein the E3 Ubiquitin ligase is RNF4 and the cysteine is C132 of human RNF4.

Embodiment P67. The method of one of embodiments P63 to P64, wherein the E3 Ubiquitin ligase is RNF4 and the cysteine is C135 of human RNF4.

Embodiment P68. The method of one of embodiments P65 to P67, wherein the E3 Ubiquitin ligase binder has having the formula:

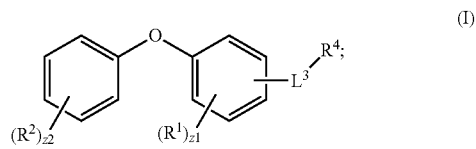

wherein
$R^1$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E;

E is an electrophilic moiety;

z1 is an integer from 0 to 4; and z2 is an integer from 0 to 5.

Embodiment P69. The method of one of embodiments P60 to P64, wherein the E3 Ubiquitin ligase is human RNF114.

Embodiment P70. The method of one of embodiments P63 to P64, wherein the E3 Ubiquitin ligase is human RNF114 and the cysteine is C8 of human RNF114.

Embodiment P71. The method of one of embodiments P69 to P70, wherein the cellular protein is p21.

Embodiment P72. The method of one of embodiments P69 to P71, wherein the E3 Ubiquitin ligase binder has the formula:

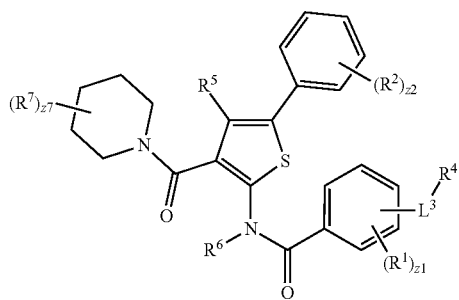

$R^1$ and $R^2$ are independently halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^1$ substituents or two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^5$ and $R^6$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^7$ substituents may optionally be joined to form an substituted or unsubstituted cycloalkyl, substituted or unsubstituted heterocycloalkyl, substituted or unsubstituted aryl, or substituted or unsubstituted heteroaryl;

$L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E;

E is an electrophilic moiety;

z1 is an integer from 0 to 4;

z2 is an integer from 0 to 5; and z7 is an integer from 0 to 10.

Embodiment P73. The method of one of embodiments P69 to P71, wherein the E3 Ubiquitin ligase binder has the formula:

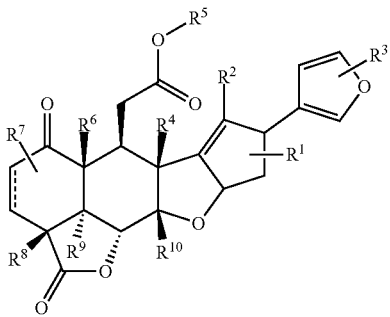

$R^1$, $R^2$, $R^3$, $R^4$, $R^5$, $R^6$, $R^7$, $R^8$, $R^9$, and $R^{10}$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and

⋮ is a single bond or a double bond.

Embodiment P74. The method of one of embodiments P35 to P73, wherein the E3 Ubiquitin ligase binder contacts amino acids of the E3 Ubiquitin ligase lacking stable secondary or tertiary conformational structure in the absence of the E3 Ubiquitin ligase binder.

Embodiment P75. The method of embodiment P74, wherein the amino acids contacting the E3 Ubiquitin ligase binder adopt a stable secondary or tertiary conformational structure upon contacting the E3 Ubiquitin ligase binder.

VI. Additional Embodiments

Embodiment 1. A targeted protein degrader comprising 1) a targeted protein binder and 2) an E3 Ubiquitin ligase binder, wherein the E3 Ubiquitin ligase is human RNF4 or human RNF114.

Embodiment 2. The targeted protein degrader of embodiment 1, wherein the E3 Ubiquitin ligase binder is capable of forming a covalent bond with a cysteine of an E3 Ubiquitin ligase.

Embodiment 3. The targeted protein degrader of one of embodiments 1 to 2, wherein the targeted protein binder and E3 Ubiquitin ligase binder are covalently bonded by a binder linker.

Embodiment 4. The targeted protein degrader of one of embodiments 1 to 3, wherein the E3 Ubiquitin ligase is human RNF4.

Embodiment 5. The targeted protein degrader of one of embodiments 1 to 4, wherein the E3 Ubiquitin ligase binder is a monovalent form of the formula:

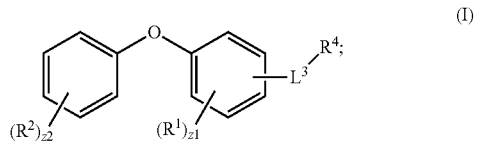

(I)

wherein $R^1$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$11, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E;

E is an electrophilic moiety;

z1 is an integer from 0 to 4;

z2 is an integer from 0 to 5; and wherein only one $R^1$ or one $R^2$ is a bond to the binder linker.

Embodiment 6. The targeted protein degrader of one of embodiments 1 to 5, wherein $R^1$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{11}$-substituted or unsubstituted C$_1$-C$_8$ alkyl, $R^{11}$-substituted or unsubstituted 2 to 8 membered heteroalkyl, $R^{11}$-substituted or unsubstituted C$_3$-C$_8$ cycloalkyl, $R^{11}$-substituted or unsubstituted 3 to 8 membered heterocycloalkyl, $R^{11}$-substituted or unsubstituted C$_6$-C$_{10}$ aryl, or $R^{11}$-substituted or unsubstituted 5 to 10 membered heteroaryl, or a bond to the binder linker; two $R^1$ substituents may optionally be joined to form an $R^{11}$-substituted or unsubstituted C$_3$-C$_8$ cycloalkyl, $R^{11}$-substituted or unsubstituted 3 to 8 membered heterocycloalkyl, $R^{11}$-substituted or unsubstituted C$_6$-C$_{10}$ aryl, or $R^{11}$-substituted or unsubstituted 5 to 10 membered heteroaryl;

$R^{11}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{12}$-substituted or unsubstituted C$_1$-C$_8$ alkyl, $R^{12}$-substituted or unsubstituted 2 to 8 membered heteroalkyl, $R^{12}$-substituted or unsubstituted C$_3$-C$_8$ cycloalkyl, $R^{12}$-substituted or unsubstituted 3 to 8 membered heterocycloalkyl, $R^{12}$-substituted or unsubstituted C$_6$-C$_{10}$ aryl, or $R^{12}$-substituted or unsubstituted 5 to 10 membered heteroaryl;

$R^{12}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

$R^2$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{21}$-substituted or unsubstituted C$_1$-C$_8$ alkyl, $R^{21}$-substituted or unsubstituted 2 to 8 membered heteroalkyl, $R^{21}$-substituted or unsubstituted C$_3$-C$_8$ cycloalkyl, $R^{21}$-substituted or unsubstituted 3 to 8 membered heterocycloalkyl, $R^{21}$-substituted or unsubstituted C$_6$-C$_{10}$ aryl, or $R^{21}$-substituted or unsubstituted 5 to 10 membered heteroaryl, or a bond to the binder linker; two $R^2$ substituents may optionally be joined to form an $R^{21}$-substituted or unsubstituted C$_3$-C$_8$ cycloalkyl, $R^{21}$-substituted or unsubstituted 3 to 8 membered heterocycloalkyl, $R^{21}$-substituted or unsubstituted C$_6$-C$_{10}$ aryl, or $R^{21}$-substituted or unsubstituted 5 to 10 membered heteroaryl;

$R^{21}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{22}$-substituted or unsubstituted C$_1$-C$_8$ alkyl, $R^{22}$-substituted or unsubstituted 2 to 8 membered heteroalkyl, $R^{22}$-substituted or unsubstituted C$_3$-C$_8$ cycloalkyl, $R^{22}$-substituted or unsubstituted 3 to 8 membered heterocycloalkyl, $R^{22}$-substituted or unsubstituted C$_6$-C$_{10}$ aryl, or $R^{22}$-substituted or unsubstituted 5 to 10 membered heteroaryl;

$R^{22}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

L$^3$ is a bond, —N(R$^3$)—, —C(O)—, —C(O)N(R$^3$)—, —N(R$^3$)C(O)—, —N(H)—, —C(O)N(H)—, —N(H)C(O)—, —C(O)O—, R$^3$-substituted or unsubstituted C$_1$-C$_8$ alkylene, R$^3$-substituted or unsubstituted 2 to 8 membered heteroalkylene, R$^3$-substituted or unsubstituted C$_3$-C$_8$ cycloalkylene, R$^3$-substituted or unsubstituted 3 to 8 membered heterocycloalkylene, R$^3$-substituted or unsubstituted C$_6$-C$_{10}$ arylene, or R$^3$-substituted or unsubstituted 5 to 10 membered heteroarylene;

R$^3$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{31}$-substituted or unsubstituted C$_1$-C$_8$ alkyl, R$^{31}$-substituted or unsubstituted 2 to 8 membered heteroalkyl, R$^{31}$-substituted or unsubstituted C$_3$-C$_8$ cycloalkyl, R$^{31}$-substituted or unsubstituted 3 to 8 membered heterocycloalkyl, R$^{31}$-substituted or unsubstituted C$_6$-C$_{10}$ aryl, or R$^{31}$-substituted or unsubstituted 5 to 10 membered heteroaryl;

R$^{31}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{32}$-substituted or unsubstituted C$_1$-C$_8$ alkyl, R$^{32}$-substituted or unsubstituted 2 to 8 membered heteroalkyl, R$^{32}$-substituted or unsubstituted C$_3$-C$_8$ cycloalkyl, R$^{32}$-substituted or unsubstituted 3 to 8 membered heterocycloalkyl, R$^{12}$-substituted or unsubstituted C$_6$-C$_{10}$ aryl, or R$^{32}$-substituted or unsubstituted 5 to 10 membered heteroaryl;

R$^{32}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl;

R$^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{41}$-substituted or unsubstituted C$_1$-C$_8$ alkyl, R$^{41}$-substituted or unsubstituted 2 to 8 membered heteroalkyl, R$^{41}$-substituted or unsubstituted C$_3$-C$_8$ cycloalkyl, R$^{41}$-substituted or unsubstituted 3 to 8 membered heterocycloalkyl, R$^{41}$-substituted or unsubstituted C$_6$-C$_{10}$ aryl, or R$^{41}$-substituted or unsubstituted 5 to 10 membered heteroaryl, or E;

R$^{41}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{42}$-substituted or unsubstituted C$_1$-C$_8$ alkyl, R$^{42}$-substituted or unsubstituted 2 to 8 membered heteroalkyl, R$^{42}$-substituted or unsubstituted C$_3$-C$_8$ cycloalkyl, R$^{42}$-substituted or unsubstituted 3 to 8 membered heterocycloalkyl, R$^{42}$-substituted or unsubstituted C$_6$-C$_{10}$ aryl, or R$^{42}$-substituted or unsubstituted 5 to 10 membered heteroaryl;

R$^{42}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl.

Embodiment 7. The targeted protein degrader of embodiment 6, wherein R$^2$ is independently halogen, —CF$_3$, —NO$_2$, R$^{21}$-substituted or unsubstituted C$_1$-C$_3$ alkyl, unsubstituted 2 to 3 membered heteroalkyl, or a bond to the binder linker; two R$^2$ substituents may optionally be joined to form an unsubstituted phenyl; and R$^{21}$ is independently —OH.

Embodiment 8. The targeted protein degrader of one of embodiments 6 to 7, wherein z2 is 1 and R$^2$ is a bond to the binder linker.

Embodiment 9. The targeted protein degrader of one of embodiments 6 to 8, wherein R$^1$ is independently halogen.

Embodiment 10. The targeted protein degrader of one of embodiments 6 to 9, wherein z1 is 0.

Embodiment 11. The targeted protein degrader of one of embodiments 6 to 10, wherein L$^3$ is —N(R$^3$)—;

R$^3$ is independently R$^{31}$-substituted methyl, unsubstituted phenyl, or unsubstituted 5 to 6 membered heteroaryl; and R$^{31}$ is independently unsubstituted phenyl, or unsubstituted 5 to 6 membered heteroaryl.

Embodiment 12. The targeted protein degrader of one of embodiments 6 to 11, wherein E is

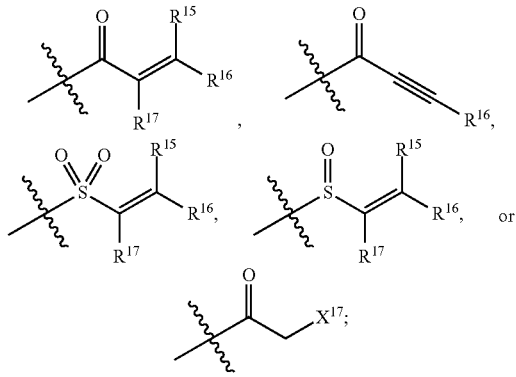

R$^{15}$, R$^{16}$, and R$^{17}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

and X$^{17}$ is halogen.

Embodiment 13. The targeted protein degrader of one of embodiments 6 to 12, wherein E is

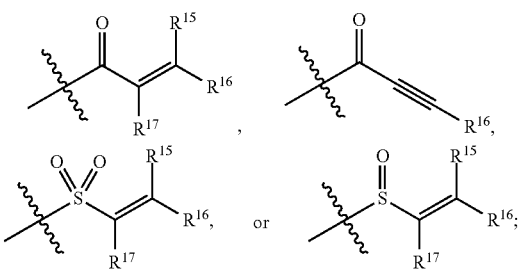

R$^{15}$, R$^{16}$, and R$^{17}$ are independently hydrogen.

Embodiment 14. The targeted protein degrader of one of embodiments 6 to 12, wherein E is

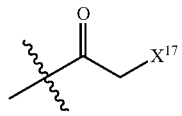

and X$^7$ is independently —Cl.

Embodiment 15. The targeted protein degrader of one of embodiments 1 to 3, wherein the E3 Ubiquitin ligase is human RNF114.

Embodiment 16. The targeted protein degrader of one of embodiments 1 to 3, and 15, wherein the E3 Ubiquitin ligase binder is a monovalent form of the formula:

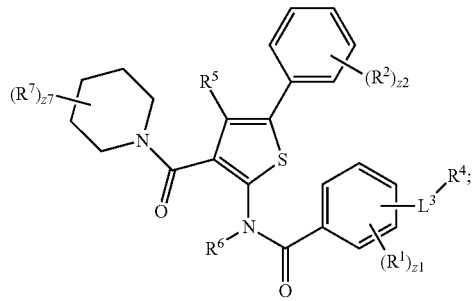

(II)

wherein

R$^1$ and R$^2$ are independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two R$^1$ substituents or two R$^2$ substituents may optionally be joined to form a substituted or unsubstituted cycloalkyl, substituted or unsubstituted heterocycloalkyl, substituted or unsubstituted aryl, or substituted or unsubstituted heteroaryl;

R$^5$ and R$^6$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker;

R$^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a bond to the binder linker; two R$^7$ substituents may optionally be joined to form a substituted or unsubstituted cycloalkyl, substituted or unsubstituted heterocycloalkyl, substituted or unsubstituted aryl, or substituted or unsubstituted heteroaryl;

$L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E;

E is an electrophilic moiety;

z1 is an integer from 0 to 4;

z2 is an integer from 0 to 5;

z7 is an integer from 0 to 10; and wherein only one $R^1$, $R^2$, $R^5$, $R^6$, or $R^7$ is independently a bond to the binder linker.

Embodiment 17. The targeted protein degrader of embodiment 16, wherein $R^1$, $R^2$, and $R^7$ are independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{51}$-substituted or unsubstituted $C_1$-$C_8$ alkyl, $R^{51}$-substituted or unsubstituted 2 to 8 membered heteroalkyl, $R^{51}$-substituted or unsubstituted $C_3$-$C_8$ cycloalkyl, $R^{51}$-substituted or unsubstituted 3 to 8 membered heterocycloalkyl, $R^{51}$-substituted or unsubstituted $C_6$-$C_{10}$ aryl, or $R^{51}$-substituted or unsubstituted 5 to 10 membered heteroaryl, or a bond to the binder linker; two $R^1$ substituents or two $R^2$ substituents may optionally be joined to form an $R^{51}$-substituted or unsubstituted $C_3$-$C_8$ cycloalkyl, $R^{51}$-substituted or unsubstituted 3 to 8 membered hetero-cycloalkyl, $R^{51}$-substituted or unsubstituted $C_6$-$C_{10}$ aryl, or $R^{51}$-substituted or unsubstituted 5 to 10 membered heteroaryl;

$R^5$ and $R^6$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{51}$-substituted or unsubstituted $C_1$-$C_8$ alkyl, $R^{51}$-substituted or unsubstituted 2 to 8 membered heteroalkyl, $R^{51}$-substituted or unsubstituted $C_3$-$C_8$ cycloalkyl, $R^{51}$-substituted or unsubstituted 3 to 8 membered heterocycloalkyl, $R^{51}$-substituted or unsubstituted $C_6$-$C_{10}$ aryl, or $R^{51}$-substituted or unsubstituted 5 to 10 membered heteroaryl, or a bond to the binder linker;

$R^7$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{51}$-substituted or unsubstituted $C_1$-$C_8$ alkyl, $R^{51}$-substituted or unsubstituted 2 to 8 membered heteroalkyl, $R^{51}$-substituted or unsubstituted $C_3$-$C_8$ cycloalkyl, $R^{51}$-substituted or unsubstituted 3 to 8 membered heterocycloalkyl, $R^{51}$-substituted or unsubstituted $C_6$-$C_{10}$ aryl, or $R^{51}$-substituted or unsubstituted 5 to 10 membered heteroaryl, or a bond to the binder linker; two $R^7$ substituents may optionally be joined to form an $R^{51}$-substituted or unsubstituted $C_3$-$C_8$ cycloalkyl, $R^{51}$-substituted or unsubstituted 3 to 8 membered heterocycloalkyl, $R^{51}$-substituted or unsubstituted $C_6$-$C_{10}$ aryl, or $R^{51}$-substituted or unsubstituted 5 to 10 membered heteroaryl $R^{51}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

$L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, $R^3$-substituted or unsubstituted $C_1$-$C_8$ alkylene, $R^3$-substituted or unsubstituted 2 to 8 membered heteroalkylene, $R^3$-substituted or unsubstituted $C_3$-$C_8$ cycloalkylene, $R^3$-substituted or unsubstituted 3 to 8 membered heterocycloalkylene, $R^3$-substituted or unsubstituted $C_6$-$C_{10}$ arylene, or $R^3$-substituted or unsubstituted 5 to 10 membered heteroarylene;

$R^3$ is independently oxo, halogen, —$CCl_3$, —$CBr_3$, —$CF_3$, —$CI_3$, —$CHCl_2$, —$CHBr_2$, —$CHF_2$, —$CHI_2$, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{31}$-substituted or unsubstituted $C_1$-$C_8$ alkyl, $R^{31}$-substituted or unsubstituted 2 to 8 membered heteroalkyl, $R^{31}$-substituted or unsubstituted $C_3$-$C_8$ cycloalkyl, $R^{31}$-substituted or unsubstituted 3 to 8 membered heterocycloalkyl, $R^{31}$-substituted or unsubstituted $C_6$-$C_{10}$ aryl, or $R^{31}$-substituted or unsubstituted 5 to 10 membered heteroaryl;

$R^{31}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{32}$-substituted or unsubstituted $C_1$-$C_8$ alkyl, $R^{32}$-substituted or unsubstituted 2 to 8 membered heteroalkyl, $R^{32}$-substituted or unsubstituted $C_3$-$C_8$ cycloalkyl, $R^{32}$-substituted or unsubstituted 3 to 8 membered heterocycloalkyl, $R^{32}$-substituted or unsubstituted $C_6$-$C_{10}$ aryl, or $R^{32}$-substituted or unsubstituted 5 to 10 membered heteroaryl;

$R^{32}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl;

$R^4$ is independently hydrogen, oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{41}$-substituted or unsubstituted $C_1$-$C_8$ alkyl, $R^{41}$-substituted or unsubstituted 2 to 8 membered heteroalkyl, $R^{41}$-substituted or unsubstituted $C_3$-$C_8$ cycloalkyl, $R^{41}$-substituted or unsubstituted 3 to 8 membered heterocycloalkyl, $R^{41}$-substituted or unsubstituted $C_6$-$C_{10}$ aryl, or $R^{41}$-substituted or unsubstituted 5 to 10 membered heteroaryl, or E;

$R^{41}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, $R^{42}$-substituted or unsubstituted $C_1$-$C_8$ alkyl, $R^{42}$-substituted or unsubstituted 2 to 8 membered heteroalkyl, $R^{42}$-substituted or unsubstituted $C_3$-$C_8$ cycloalkyl, $R^{42}$-substituted or unsubstituted 3 to 8 membered heterocycloalkyl, $R^{42}$-substituted or unsubstituted $C_6$-$C_{10}$ aryl, or $R^{42}$-substituted or unsubstituted 5 to 10 membered heteroaryl;

$R^{42}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

Embodiment 18. The targeted protein degrader of embodiment 17, wherein the E3 Ubiquitin ligase binder is a monovalent form of the formula:

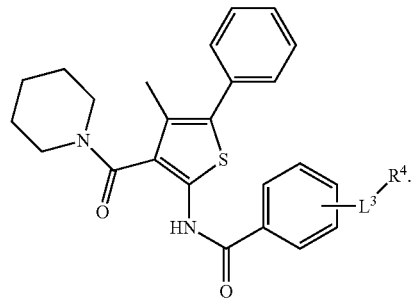

Embodiment 19. The targeted protein degrader of one of embodiments 17 to 18, wherein $L^3$ is —CH₂NH—.

Embodiment 20. The targeted protein degrader of one of embodiments 17 to 19, wherein E is

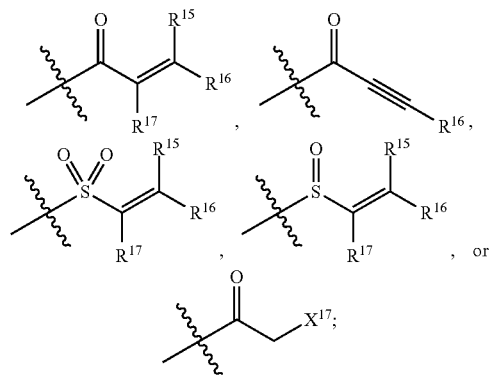

$R^{15}$, $R^{16}$, and $R^{17}$ are independently hydrogen, —CCl₃, —CBr₃, —CF₃, —CI₃, —CHCl₂, —CHBr₂, —CHF₂, —CHI₂, —CH₂Cl, —CH₂Br, —CH₂F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

and X$^7$ is halogen.

Embodiment 21. The targeted protein degrader of one of embodiments 17 to 20, wherein E is

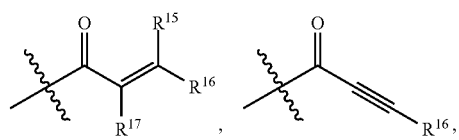

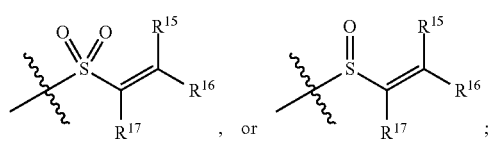

$R^{15}$, $R^{16}$, and $R^{17}$ are independently hydrogen.

Embodiment 22. The targeted protein degrader of one of embodiments 17 to 21, wherein E is

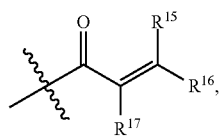

and $R^{15}$, $R^{16}$, and $R^{17}$ are independently hydrogen.

Embodiment 23. The targeted protein degrader of one of embodiments 1 to 3, and 15, wherein the E3 Ubiquitin ligase binder is a monovalent form of the formula:

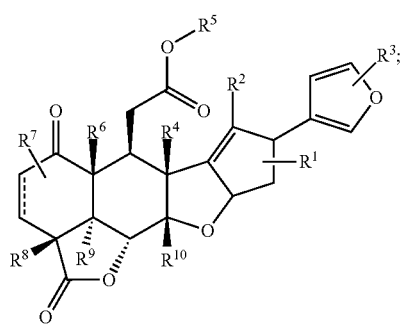

$R^1$, $R^2$, $R^3$, $R^4$, $R^5$, $R^6$, $R^7$, $R^8$, $R^9$, and $R^{10}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a bond to the binder linker;

wherein only one $R^1$, $R^2$, $R^3$, $R^4$, $R^5$, $R^6$, $R^7$, $R^8$, $R^9$, or $R^{10}$ is a bond to the binder linker; and

is a single bond or a double bond.

Embodiment 24. The targeted protein degrader of embodiment 23, wherein $R^1$, $R^2$, $R^3$, $R^4$, $R^5$, $R^6$, $R^7$, $R^8$, $R^9$, and $R^{10}$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, $R^{51}$-substituted or unsubstituted $C_1$-$C_8$ alkyl, $R^{51}$-substituted or unsubstituted 2 to 8 membered heteroalkyl, $R^{51}$-substituted or unsubstituted $C_3$-$C_8$ cycloalkyl, $R^{51}$-substituted or unsubstituted 3 to 8 membered heterocycloalkyl, $R^{51}$-substituted or unsubstituted $C_6$-$C_{10}$ aryl, or $R^{51}$-substituted or unsubstituted 5 to 10 membered heteroaryl; or a bond to the binder linker;

wherein only one $R^1$, $R^2$, $R^3$, $R^4$, $R^5$, $R^6$, $R^7$, $R^8$, $R^9$, or $R^{10}$ is a bond to the binder linker;

$R^{51}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

Embodiment 25. The targeted protein degrader of embodiment 23, wherein the E3 Ubiquitin ligase binder is a monovalent form of the formula:

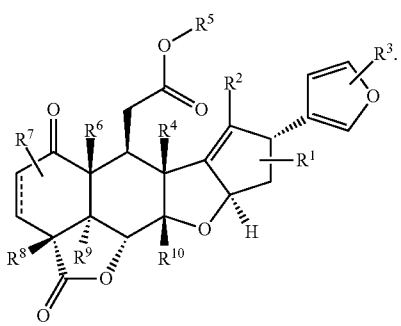

Embodiment 26. The targeted protein degrader of embodiment 24, wherein the E3 Ubiquitin ligase binder is a monovalent form of the formula:

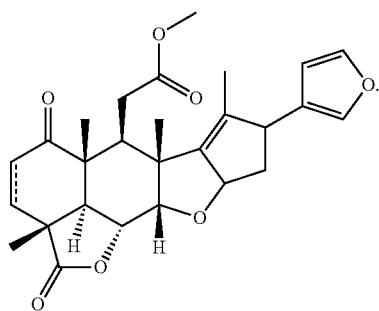

Embodiment 27. The targeted protein degrader of embodiment 24, wherein the E3 Ubiquitin ligase binder is a monovalent form of the formula:

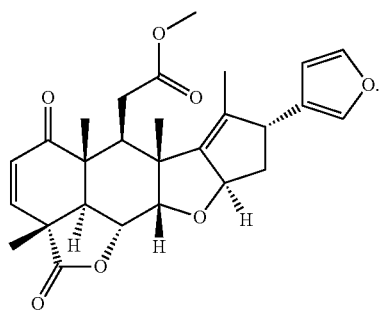

Embodiment 28. The targeted protein degrader of embodiment 24, wherein the E3 Ubiquitin ligase binder has the formula:

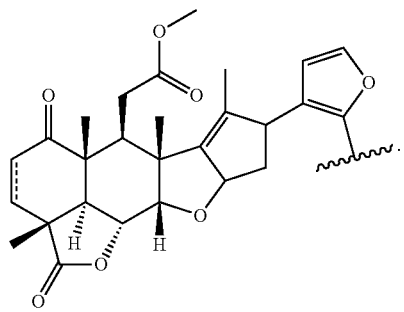

Embodiment 29. The targeted protein degrader of embodiment 24, wherein the E3 Ubiquitin ligase binder has the formula:

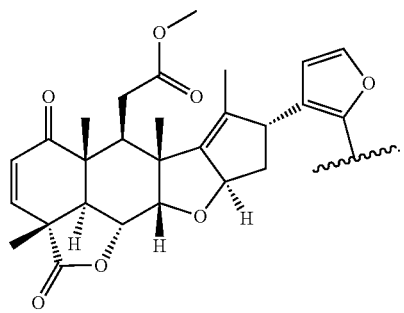

Embodiment 30. The targeted protein degrader of one of embodiments 3 to 29, wherein the binder linker is $L^{11}$-$L^{12}$-$L^{13}$-$L^{14}$;

$L^{11}$ is connected directly to the E3 Ubiquitin ligase binder; $L^{11}$ is —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker; and $L^{12}$, $L^{13}$, and $L^{14}$ are independently a bond, —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

Embodiment 31. The targeted protein degrader of embodiment 30, wherein $L^{11}$ is —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, $R^{61}$-substituted or unsubstituted $C_1$-$C_{20}$ alkylene, $R^{61}$-substituted or unsubstituted 2 to 20 membered heteroalkylene, $R^{61}$-substituted or unsubstituted $C_3$-$C_8$ cycloalkylene, $R^{61}$-substituted or unsubstituted 3 to 8 membered heterocycloalkylene, $R^{61}$-substituted or unsubstituted $C_6$-$C_{10}$ arylene, $R^{61}$-substituted or unsubstituted 5 to 10 membered heteroarylene, or a bioconjugate linker;

$L^{12}$, $L^{13}$, and $L^{14}$ are independently a bond, —N($R^{61}$)—, —C(O)—, —C(O)N($R^{61}$)—, —N($R^{61}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, $R^{61}$-substituted or unsubstituted $C_1$-$C_{20}$ alkylene, $R^{61}$-substituted or unsubstituted 2 to 20 membered heteroalkylene, $R^{61}$-substituted or unsubstituted $C_3$-$C_8$ cycloalkylene, $R^{61}$-substituted or unsubstituted 3 to 8 membered heterocycloalkylene, $R^{61}$-substituted or unsubstituted $C_6$-$C_{10}$ arylene, $R^{61}$-substituted or unsubstituted 5 to 10 membered heteroarylene, or a bioconjugate linker;

$R^{61}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

Embodiment 32. The targeted protein degrader of one of embodiments 1 to 31, wherein the targeted protein binder is capable of binding a targeted protein associated with a disease.

Embodiment 33. The targeted protein degrader of one of embodiments 1 to 32, wherein the targeted protein binder is

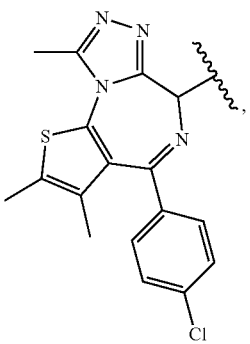 [SMILES: *C1N=C(c2ccc(Cl)cc2)c2c(sc(C)c2C)-n2c(C)nnc21]

and the targeted protein binder binds BRD4.

Embodiment 34. A pharmaceutical composition comprising a targeted protein degrader of one of embodiments 1 to 33 and a pharmaceutically acceptable excipient.

Embodiment 35. A method of reducing the level of a cellular protein, said method comprising contacting the cellular protein with a targeted protein degrader.

Embodiment 36. A method of reducing the level of a cellular protein, said method comprising contacting the cellular protein with a targeted protein degrader of one of embodiments 1 to 33.

Embodiment 37. The method of one of embodiments 35 to 36, further comprising the steps of:

A) allowing the cellular protein contacting the targeted protein degrader to be ubiquitinated and thereby form a ubiquitinated cellular protein;

B) allowing the ubiquitinated cellular protein to contact the proteasome and thereby form a ubiquitinated cellular protein-proteasome complex; and C) proteolyzing the cellular protein by the proteasome.

Embodiment 38. A method of treating cancer, said method comprising contacting a cellular protein associated with cancer with a targeted protein degrader.

Embodiment 39. A method of treating cancer, said method comprising administering to a subject in need thereof a therapeutically effective amount of a targeted protein degrader of one of embodiments 1 to 33.

Embodiment 40. A method of reducing the level of a cellular protein, said method comprising contacting the cellular protein with a targeted protein degrader and thereby forming a targeted protein degrader-cellular protein complex; wherein the targeted protein degrader comprises:

i) an E3 Ubiquitin ligase binder;

ii) a targeted protein binder; and iii) a binder linker directly bonded to the E3 Ubiquitin ligase binder and the targeted protein binder.

Embodiment 41. The method of embodiment 40, wherein prior to the contacting, the targeted protein degrader is synthesized by covalently reacting an E3 Ubiquitin ligase binder, a binder linker, and a targeted protein binder to produce the targeted protein degrader.

Embodiment 42. The method of embodiment 41, wherein prior to the synthesizing, the E3 Ubiquitin ligase binder is identified from a candidate E3 Ubiquitin ligase binder.

Embodiment 43. The method of embodiment 42, wherein the E3 Ubiquitin ligase binder is identified by a method comprising the steps:

i) contacting an E3 Ubiquitin ligase protein with a mixture of candidate E3 Ubiquitin ligase binders and thereby forming an E3 Ubiquitin ligase protein-E3 Ubiquitin ligase binder complex; and ii) identifying the candidate E3 Ubiquitin ligase binders from an E3 Ubiquitin ligase protein-E3 Ubiquitin ligase binder complex as E3 Ubiquitin ligase binders.

Embodiment 44. The method of embodiment 43, wherein the candidate E3 Ubiquitin ligase binders comprise a covalent cysteine modifier moiety and a candidate E3 Ubiquitin ligase binder is identified as an E3 Ubiquitin ligase binder by detection of covalent binding of the E3 Ubiquitin ligase binder to the E3 Ubiquitin ligase protein to form an E3 Ubiquitin ligase protein-E3 Ubiquitin ligase binder complex.

Embodiment 45. The method of embodiment 44, wherein the detection of an E3 Ubiquitin ligase protein-E3 Ubiquitin ligase binder complex comprises use of a detectable label or mass spectroscopy.

Embodiment 46. The method of embodiment 40, wherein prior to the synthesizing, the targeted protein binder is identified.

Embodiment 47. The method of embodiment 46, wherein the targeted protein binder is identified by a method comprising the steps:

i) contacting a cellular protein with a mixture of candidate targeted protein binders and thereby forming a cellular protein-targeted protein binder complex; and ii) identifying the targeted protein binder that forms a cellular protein-targeted protein binder complex.

Embodiment 48. The method of embodiment 47, wherein the candidate targeted protein binder forming a cellular protein-targeted protein binder complex is identified as a targeted protein binder by detection of the cellular protein-targeted protein binder complex.

Embodiment 49. The method of embodiment 48, wherein the detection of cellular protein-targeted protein binder complex comprises use of a detectable label or mass spectroscopy.

Embodiment 50. The method of embodiment 40, wherein prior to the synthesizing, the E3 Ubiquitin ligase binder is modified to remove a covalent cysteine modifier moiety.

Embodiment 51. A method of identifying a cellular protein contacted by a targeted protein binder comprising:
A) contacting a first sample of a cell proteome or cell with the targeted protein binder thereby forming a cellular protein-targeted protein binder complex;
B) contacting both the resulting first sample of a cell proteome or cell of step A and a second sample of the cell proteome or cell that has not been contacted with the targeted protein binder, with a compound having the formula:

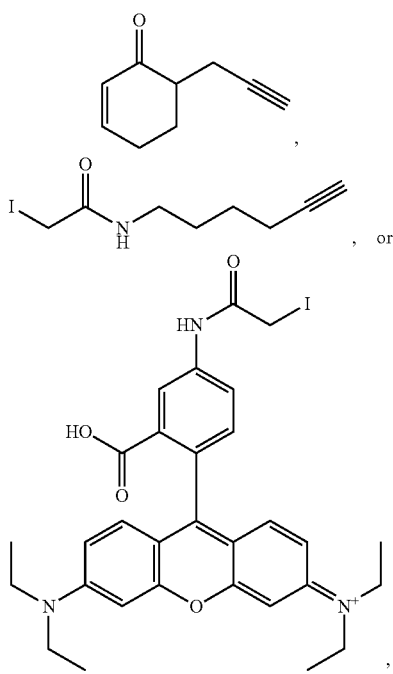

C) contacting the resulting first sample of step B with a first detectable agent and the resulting second sample of step B with a second detectable agent;
D) measuring the level of the first detectable agent and second detectable agent bound to selected proteins; and
E) identifying the cellular protein in a cellular protein-targeted protein binder complex by measuring a difference between the level of the first detectable agent and second detectable agent bound to the cellular protein capable of forming the cellular protein-targeted protein binder complex.

Embodiment 52. The method of embodiment 51, wherein
A) one of the first or second detectable agents comprises a light isotope of an atom and a second of the first or second detectable agents comprises a heavy isotope of the atom;
B) the level of the first detectable agent and second detectable agent of selected proteins is measured by liquid chromatography mass spectrometry; and
C) the cellular protein capable of binding the targeted protein binder is identified by a difference between the level of the cellular protein bound to the first detectable agent and the level of the cellular protein bound to the second detectable agent.

Embodiment 53. The method of one of embodiments 35 to 52, wherein the E3 Ubiquitin ligase binder contacts an E3 Ubiquitin ligase cysteine residue.

Embodiment 54. The method of embodiment 53, wherein the E3 Ubiquitin ligase binder covalently binds an E3 Ubiquitin ligase cysteine residue.

Embodiment 55. The method of one of embodiments 53 to 54, wherein the E3 Ubiquitin ligase is human RNF4.

Embodiment 56. The method of embodiment 55, wherein the cysteine residue is $CI_{32}$ of human RNF4.

Embodiment 57. The method of embodiment 55, wherein the cysteine residue is $CI_{35}$ of human RNF4.

Embodiment 58. The method of one of embodiments 53 to 54, wherein the E3 Ubiquitin ligase is human RNF114.

Embodiment 59. The method of embodiment 58, wherein the cysteine residue is C8 of human RNF114.

Embodiment 60. A method of making an E3 Ubiquitin ligase-E3 Ubiquitin ligase binder-cellular protein complex comprising:
A) contacting the E3 Ubiquitin ligase with an E3 Ubiquitin ligase binder and thereby forming an E3 Ubiquitin ligase-E3 Ubiquitin ligase binder complex; and
B) contacting the E3 Ubiquitin ligase-E3 Ubiquitin ligase binder complex with the cellular protein and thereby forming an E3 Ubiquitin ligase-E3 Ubiquitin ligase binder-cellular protein complex.

Embodiment 61. A method of making a cellular protein-E3 Ubiquitin ligase binder-E3 Ubiquitin ligase complex comprising:
A) contacting the cellular protein with an E3 Ubiquitin ligase binder and thereby forming a cellular protein-E3 Ubiquitin ligase binder complex; and
B) contacting the cellular protein-E3 Ubiquitin ligase binder complex with the E3 Ubiquitin ligase and thereby forming a cellular protein-E3 Ubiquitin ligase binder-E3 Ubiquitin ligase complex.

Embodiment 62. A method of inhibiting the formation of a cellular protein-E3 Ubiquitin ligase complex comprising contacting the E3 Ubiquitin ligase with an E3 Ubiquitin ligase binder and thereby inhibiting the formation of a cellular protein-E3 Ubiquitin ligase complex.

Embodiment 63. The method of one of embodiments 60 to 62, wherein the E3 Ubiquitin ligase binder covalently bonds a cysteine of the E3 Ubiquitin ligase.

Embodiment 64. The method of one of embodiments 62 to 63, wherein the E3 Ubiquitin ligase binder contacts the E3 Ubiquitin ligase at amino acids of the E3 Ubiquitin ligase that are capable of contacting the cellular protein to form the cellular protein-E3 Ubiquitin ligase complex in the absence of the E3 Ubiquitin ligase binder.

Embodiment 65. The method of one of embodiments 60 to 64, wherein the E3 Ubiquitin ligase is human RNF4.

Embodiment 66. The method of one of embodiments 63 to 64, wherein the E3 Ubiquitin ligase is RNF4 and the cysteine is $CI_{32}$ of human RNF4.

Embodiment 67. The method of one of embodiments 63 to 64, wherein the E3 Ubiquitin ligase is RNF4 and the cysteine is $CI_{35}$ of human RNF4.

Embodiment 68. The method of one of embodiments 65 to 67, wherein the E3 Ubiquitin ligase binder is a monovalent form of the formula:

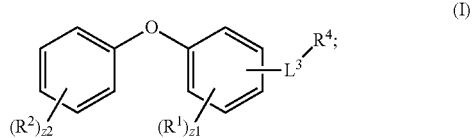

(I)

wherein $R^1$ is independently halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E;

E is an electrophilic moiety;

z1 is an integer from 0 to 4; and z2 is an integer from 0 to 5.

Embodiment 69. The method of one of embodiments 60 to 64, wherein the E3 Ubiquitin ligase is human RNF114.

Embodiment 70. The method of one of embodiments 63 to 64, wherein the E3 Ubiquitin ligase is human RNF114 and the cysteine is C8 of human RNF114.

Embodiment 71. The method of one of embodiments 69 to 70, wherein the cellular protein is p21.

Embodiment 72. The method of one of embodiments 69 to 71, wherein the E3 Ubiquitin ligase binder is a monovalent form of the formula:

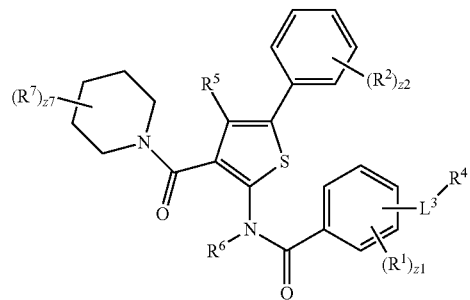

$R^1$ and $R^2$ are independently halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^1$ substituents or two $R^2$ substituents may optionally be joined to form an substituted or unsubstituted cycloalkyl, substituted or unsubstituted heterocycloalkyl, substituted or unsubstituted aryl, or substituted or unsubstituted heteroaryl;

$R^5$ and $R^6$ are independently hydrogen, halogen, —CCl₃, —CBr₃, —CF₃, —C₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^7$ substituents may optionally be joined to form an substituted or unsubstituted cycloalkyl, substituted or unsubstituted heterocycloalkyl, substituted or unsubstituted aryl, or substituted or unsubstituted heteroaryl;

$L^3$ is a bond, —N($R^3$)—, —C(O)—, —C(O)N($R^3$)—, —N($R^3$)C(O)—, —N(H)—, —C(O)N(H)—, —N(H)C(O)—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or E;

E is an electrophilic moiety;

z1 is an integer from 0 to 4;
z2 is an integer from 0 to 5; and
z7 is an integer from 0 to 10.

Embodiment 73. The method of one of embodiments 69 to 71, wherein the E3 Ubiquitin ligase binder is a monovalent form of the formula:

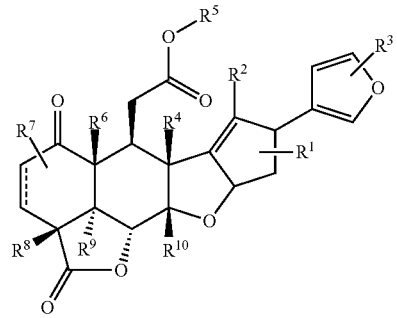

$R^1$, $R^2$, $R^3$, $R^4$, $R^5$, $R^6$, $R^7$, $R^8$, $R^9$, and $R^{10}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and

is a single bond or a double bond.

Embodiment 74. The method of one of embodiments 35 to 73, wherein the E3 Ubiquitin ligase binder contacts amino acids of the E3 Ubiquitin ligase lacking stable secondary or tertiary conformational structure in the absence of the E3 Ubiquitin ligase binder.

Embodiment 75. The method of embodiment 74, wherein the amino acids contacting the E3 Ubiquitin ligase binder adopt a stable secondary or tertiary conformational structure upon contacting the E3 Ubiquitin ligase binder.

EXAMPLES

Example 1: Covalent Ligand Screening Uncovers a RNF4 E3 Ligase Recruiter for Targeted Protein Degradation Application Targeted protein degradation has arisen as a powerful strategy for drug discovery allowing the targeting of undruggable proteins for proteasomal degradation. This approach employs bifunctional degraders consisting of a protein targeting ligand linked to an E3 ligase recruiter which brings the E3 ligase to particular protein substrates to ubiquitinate and degrade these substrates in a proteasome-dependent manner. One challenge with this approach, however, is the relatively few E3 ligase recruiters that currently exist for targeted protein degradation applications, despite the hundreds of known E3 ligases in the human genome. Here, we have used activity-based protein profiling (ABPP)-based covalent ligand screening approaches to identify cysteine-reactive small-molecules that react with the E3 ubiquitin ligase RNF4. The lead covalent ligand from this screen reacts with one of two zinc-coordinating cysteines in the RING domain, $CI_{32}$ and $CI_{35}$, with no effect on RNF4 activity. We further optimized the potency of this lead and incorporated this potential RNF4 recruiter into a bifunctional degrader linked to the BRD4 inhibitor JQ1: CCW 28-3. We demonstrate that CCW 28-3 is capable of degrading BRD4 in a proteasome-dependent manner and that this degradation is attenuated in RNF4 knockout cells. We demonstrate the feasibility of using chemoproteomics-enabled covalent ligand screening platforms to expand the scope of E3 ligase recruiters that can be exploited for targeted protein degradation applications.

Targeted protein degradation is a groundbreaking drug discovery platform for tackling the undruggable proteome by exploiting cellular protein degradation machinery to selectively eliminate target proteins[1,2]. This technology involves the utilization of bifunctional molecules called "degraders" consisting of a protein-targeting ligand linked to an E3 ligase recruiter. These degraders are capable of recruiting E3 ligases to specific protein targets to ubiquitinate and degrade targets in a proteasome-dependent manner. As functional inhibition of the target is not necessary for degrader efficacy this strategy has the potential to target and degrade any protein in the proteome for which there exists a ligand. However, a major challenge in the application of this technology is relatively small number of E3 ligase recruiters. While there are ~600 different E3 ligases, there are only a few E3 ligase recruiters, including small-molecule recruiters for cereblon, VHL, MDM2, and cIAP[2,3]. Identifying facile strategies for discovering ligands that bind to E3 ligases remains crucial for expanding the set of E3 ligase recruiters that can be utilized for targeted protein degradation applications.

Activity-based protein profiling (ABPP) has arisen as a powerful platform for ligand discovery against undruggable proteins[4-10]. ABPP utilizes reactivity-based chemical probes to map proteome-wide reactive and ligandable hotspots directly in complex biological systems[11,12]. When used in a competitive manner, covalently-acting small-molecules can be competed against the binding of reactivity-based probes to facilitate covalent ligand discovery against proteins of interest[4-7,9,13-15]. Towards discovering covalent ligands that may react with E3 ubiquitin ligases, we first investigated whether representative commercially available E3 ligases could be labeled by the cysteine-reactive iodoacetamide-rhodamine (IA-rhodamine) reactivity-based probe. IA-rhodamine was capable of labeling MDM2, RNF4, and UBE3A in a dose-responsive manner (FIG. 1A). While previous studies have already uncovered MDM2 and UBE3A small-molecule modulators[16-18], no chemical tools exist for the E3 ubiquitin ligase RNF4, which recognizes SUMOylated proteins and ubiquitinates these proteins for subsequent proteasomal degradation[19,20]. We thus focused our efforts on developing a potential E3 ligase recruiter for RNF4.

Figure 1B:
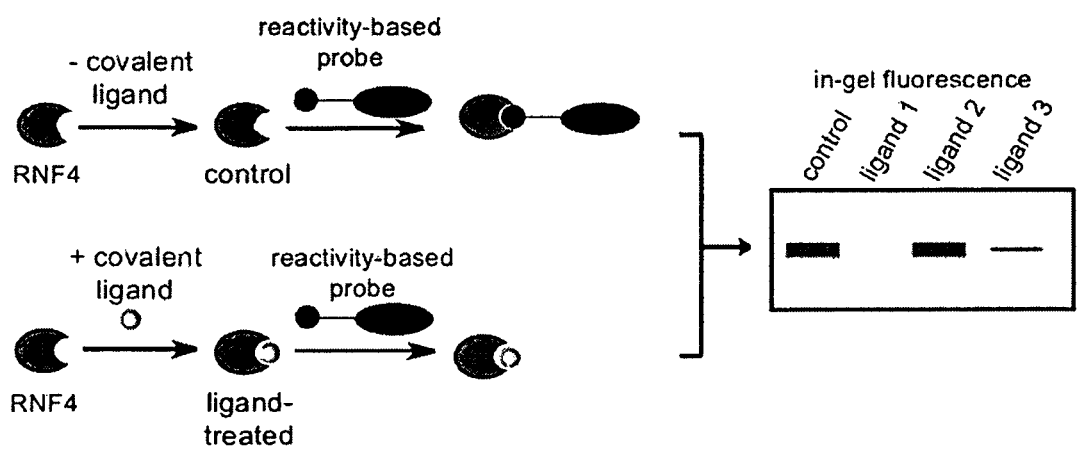
Figure 1C:
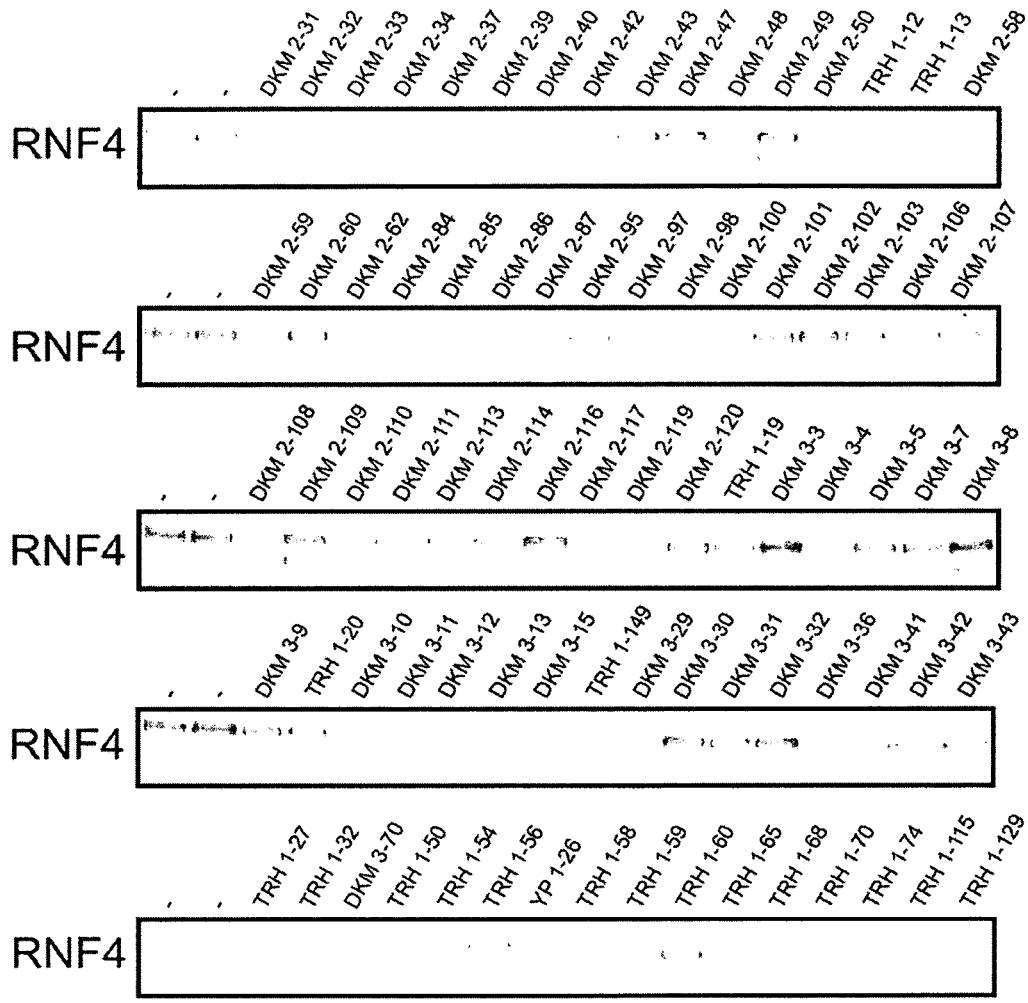
Figure 1D:
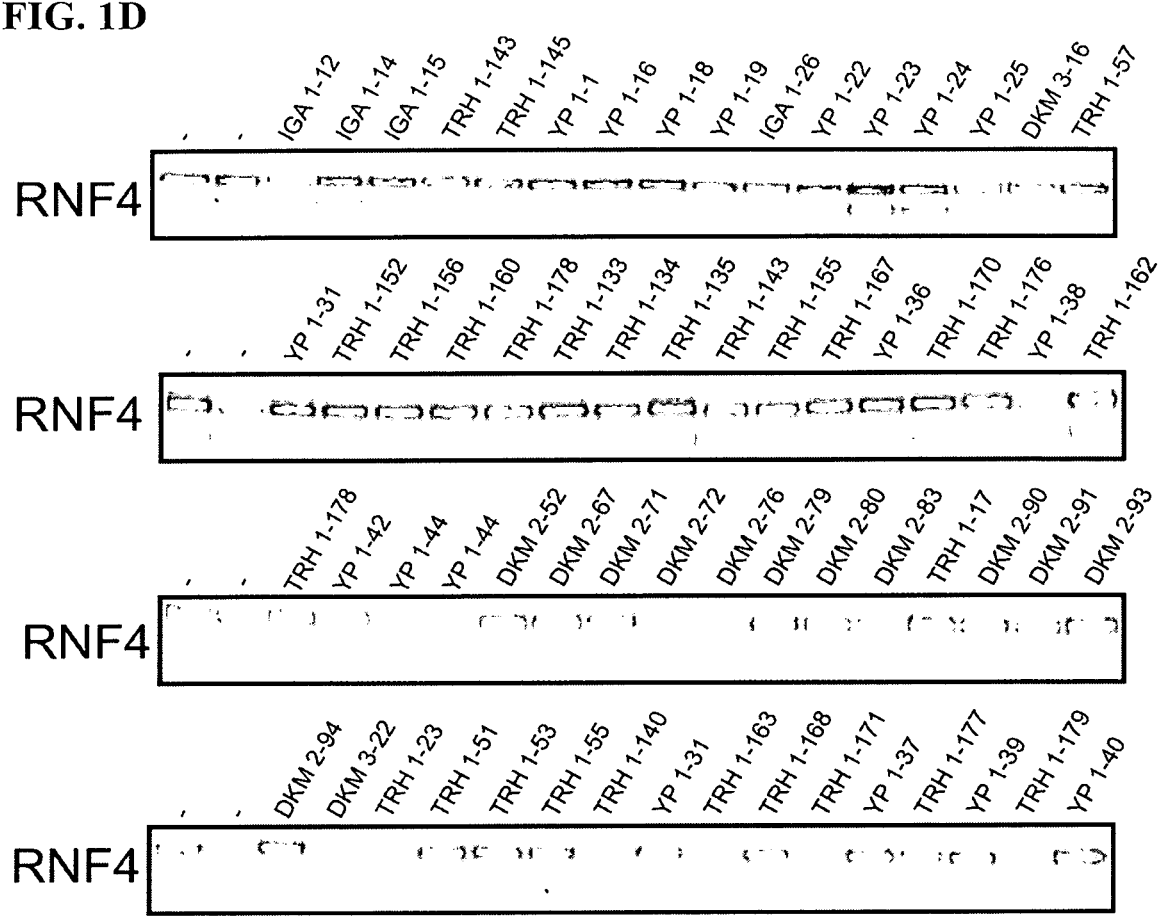
Figure 1E:
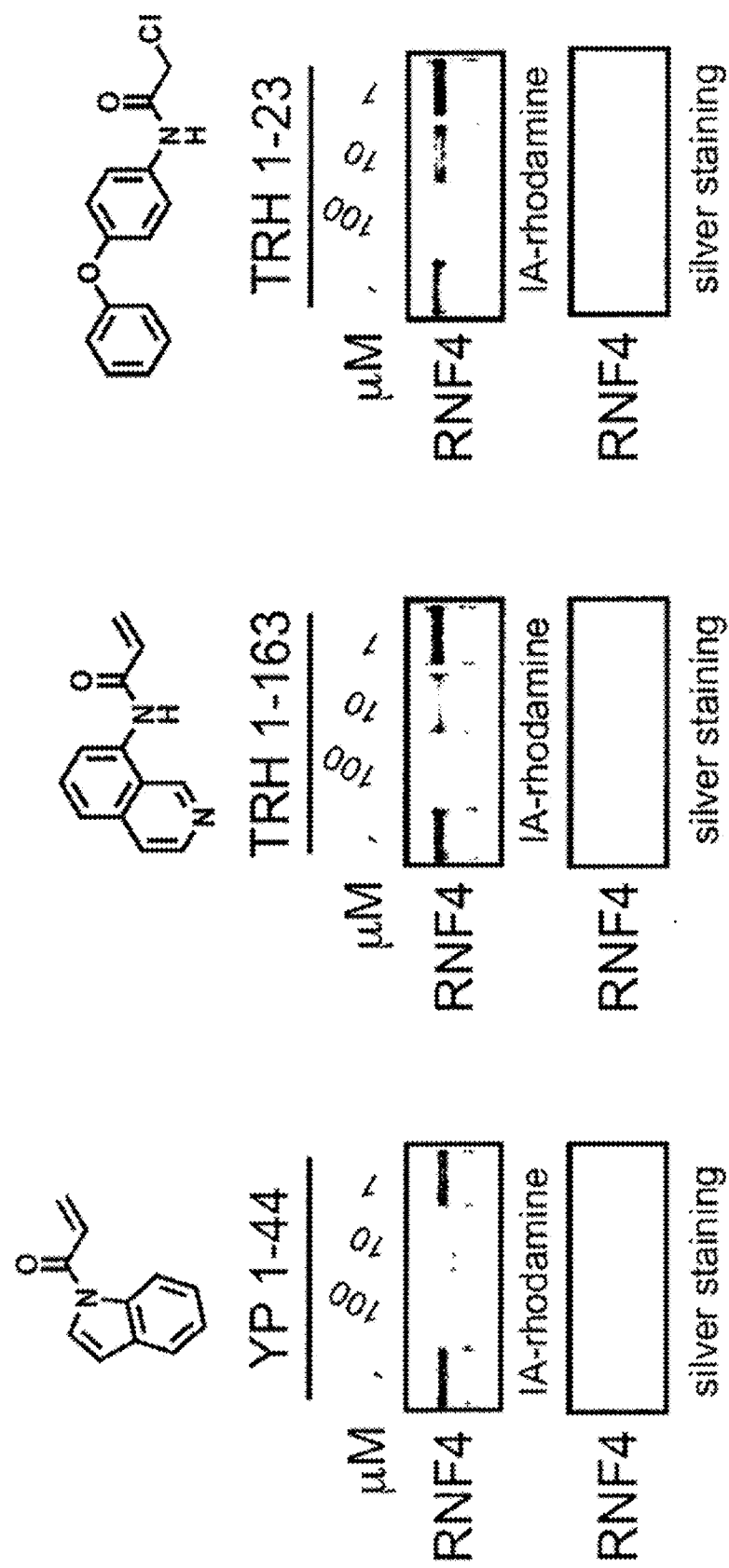
Figure 5:
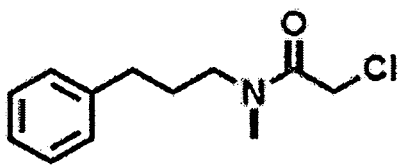
FIG. 5. Additional hits against RNF4 and general assessment of proteome-wide selectivity of RNF4 hits by gel-based ABPP. Gel-based ABPP analysis of DKM 2-76 and TRH 1-74 against IA-rhodamine labeling of RNF4. Covalent ligands were pre-incubated with pure RNF4 protein for 30 min prior to IA-rhodamine labeling (250 nM) for 1 h. Proteins were subjected to SDS/PAGE and visualized by in-gel fluorescence. Gel-based ABPP screen of RNF4 hits YP 1-44 and TRH 1-23 against IA-rhodamine labeling in 231MFP breast cancer cell proteomes. YP 1-44 and TRH 1-23 were pre-incubated with proteome for 30 min prior to IA-rhodamine labeling (250 nM) for 1 h. Proteins were subjected to SDS/PAGE and visualized by in-gel fluorescence.
Figure 5:
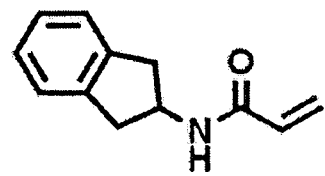
Figure 5:
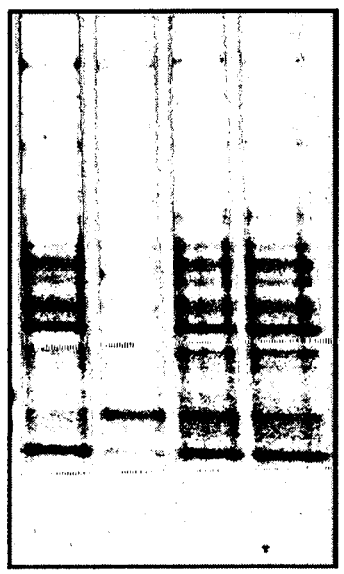
Figure 5:
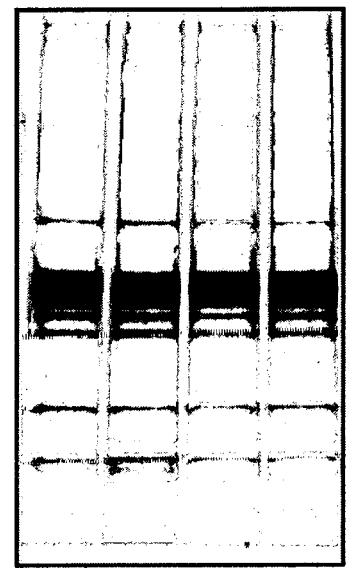

In search of RNF4 covalent ligands, we screened our cysteine-reactive covalent ligand library against IA-rhodamine labeling of pure human RNF4 using gel-based ABPP (FIG. 1B; Table 1). We identified several potential hits from this screen, including TRH 1-74, YP 1-44, DKM 2-76, TRH 1-23, and TRH 1-163. From these, YP 1-44, TRH 1-163, and TRH 1-23 showed reproducible and dose-responsive inhibition of IA-rhodamine labeling of RNF4 (FIG. 1D, FIG. 5). Based on corresponding silver staining of RNF4 in these experiments, we found that TRH 1-163 may be causing protein precipitation. Based on gel-based ABPP analysis of general cysteine-reactivity in 231MFP lysates, YP 1-44 was much less selective compared to TRH 1-23 (FIG. 5). Thus, TRH 1-23 appeared to be the most promising RNF4 hit (FIG. 1D).

Figure 2A:
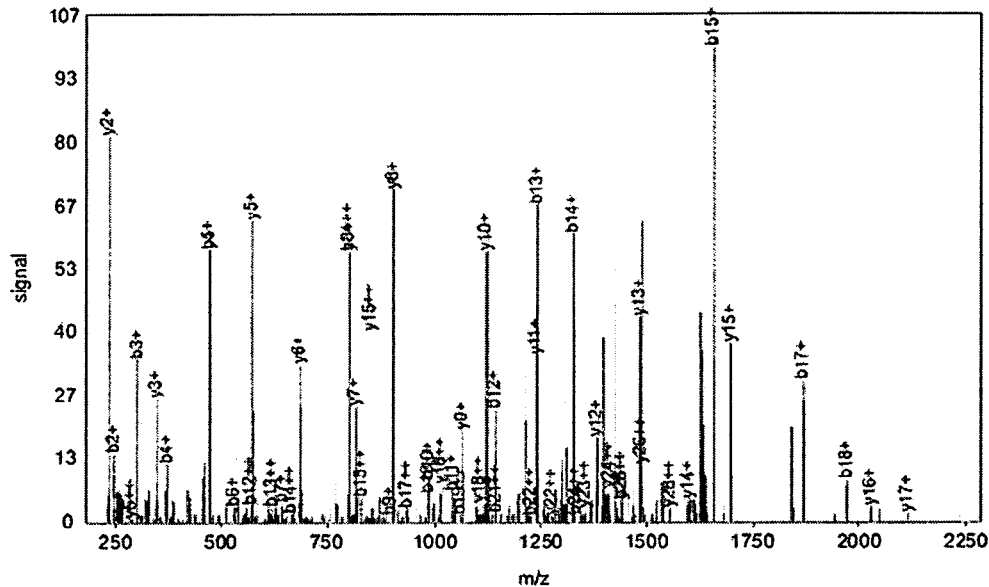
FIGS. 2A-2C. TRH 1-23 reacts non-functionally with zinc-coordinating cysteines in RNF4.
Figure 2A:
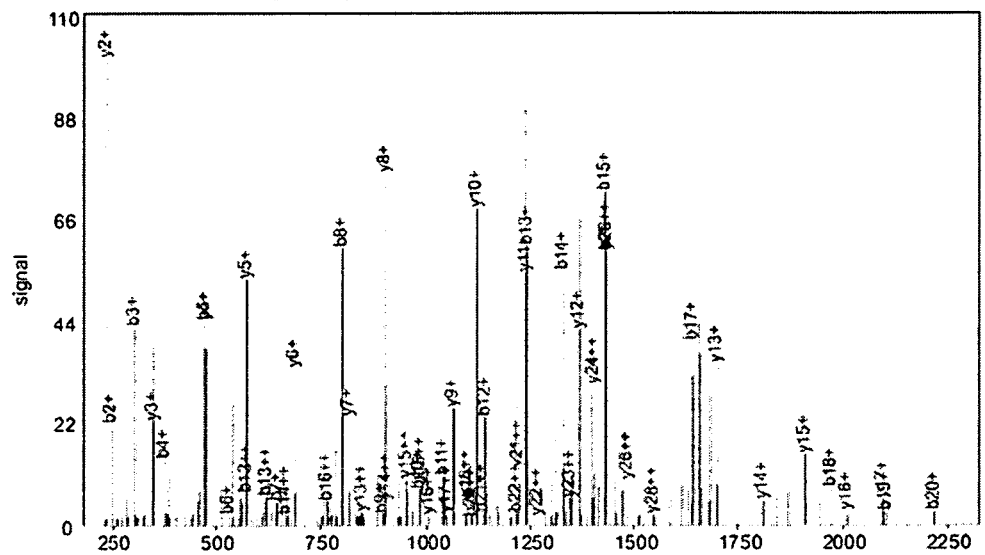
Figure 2B:
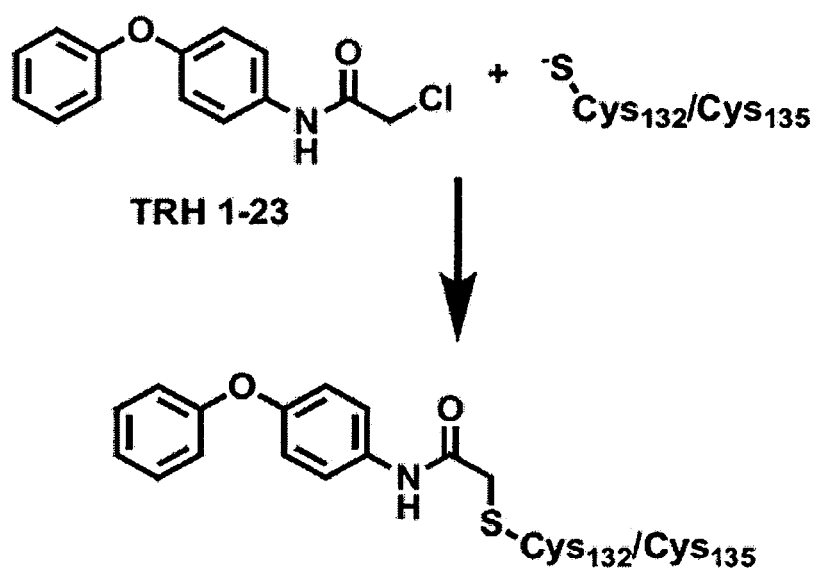
Figure 2C:
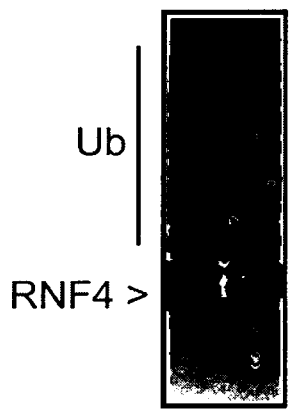

We next sought to identify the site-of-modification of TRH 1-23 within RNF4. We performed liquid chromatography-tandem mass spectrometry (LC-MS/MS) analysis of tryptic digests from TRH 1-23-treated RNF4 pure protein and found that TRH 1-23 covalently modified either, but not both, of the two zinc-coordinating cysteines $CI_{32}$ and $CI_{35}$ in the RING domain of RNF4 (FIGS. 2A, 2B). In support of its utility as a functional RNF4 recruiter, we wanted to see if TRH 1-23 had any effect upon RNF4 autoubiquitination activity, since previous studies had shown that mutation of these cysteines to serines inhibits RNF4 function[21-23]. Surprisingly, TRH 1-23 treatment does not inhibit RNF4 autoubiquitination activity in an in vitro reconstituted assay (FIG. 2C). While we do not yet understand the underlying mechanism explaining the lack of RNF4 inhibition with TRH 1-23 treatment, we postulate that perhaps zinc may still bind in the coordination site, as three cysteines are unmodified by TRH 1-23, or that TRH 1-23 may fill the space usually occupied by zinc to maintain RNF4 activity. Nonetheless, this lack of RNF4 inhibition was ideal for its potential application as an E3 ligase recruiter.

Figure 3A:
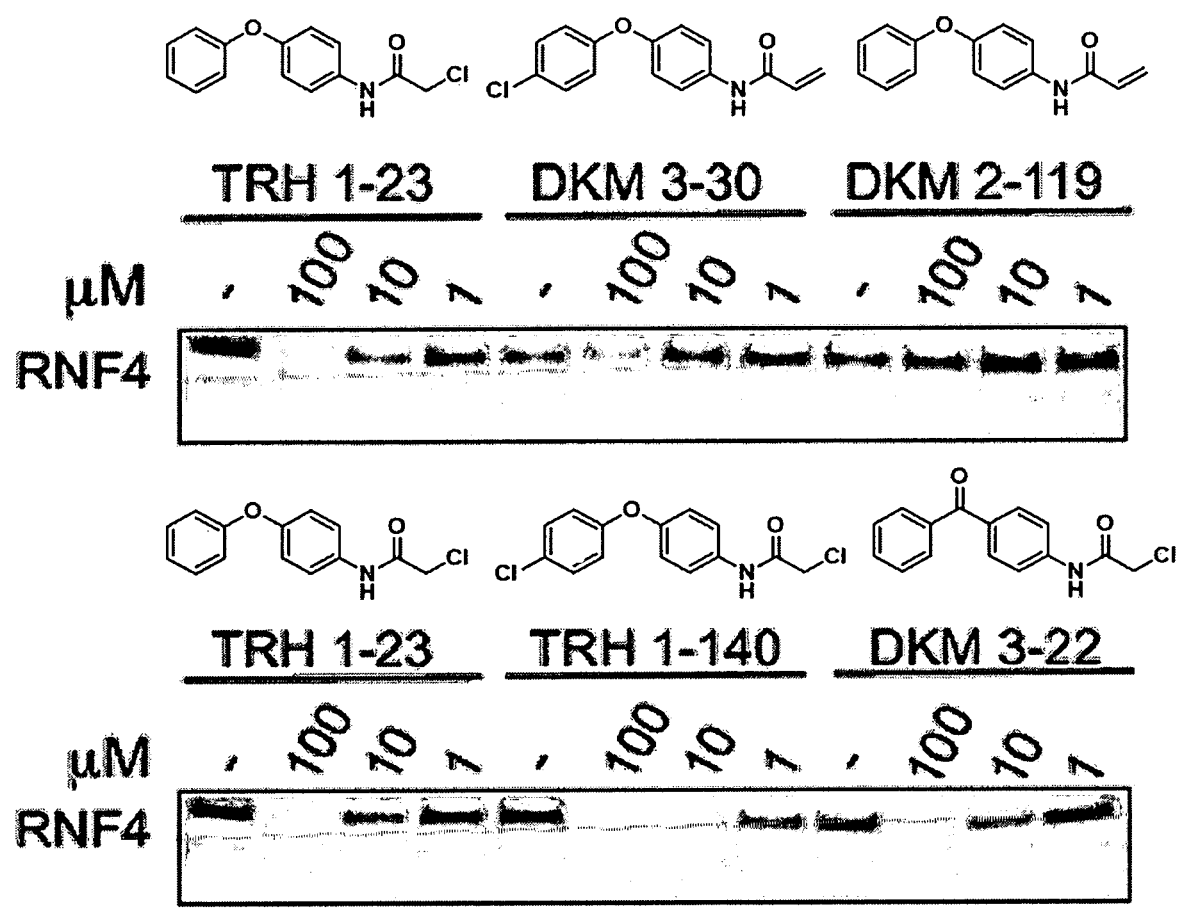
FIGS. 3A-3C. Optimizing RNF4 covalent ligands using gel-based ABPP.
Figure 3B:
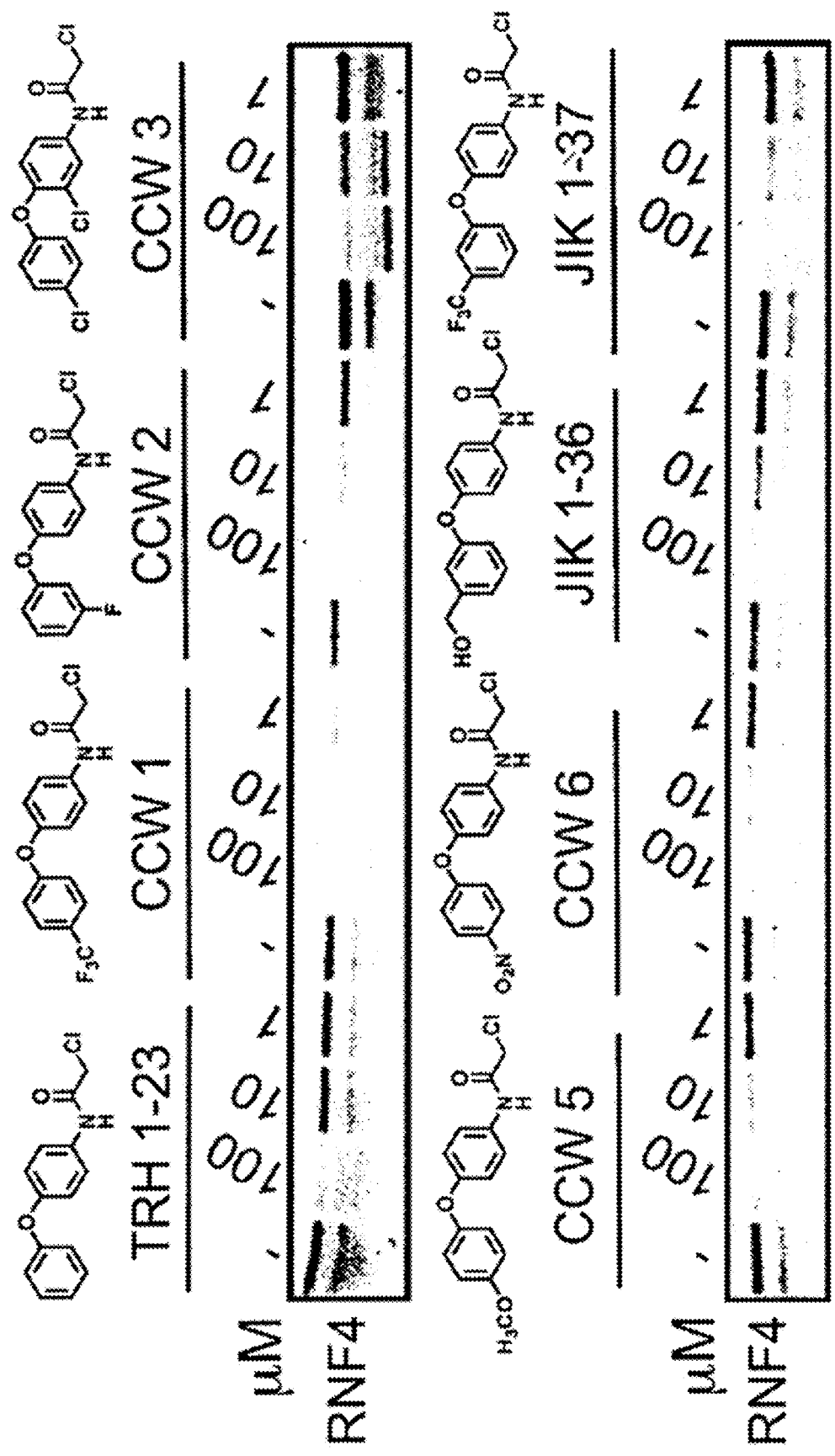
Figure 3B:
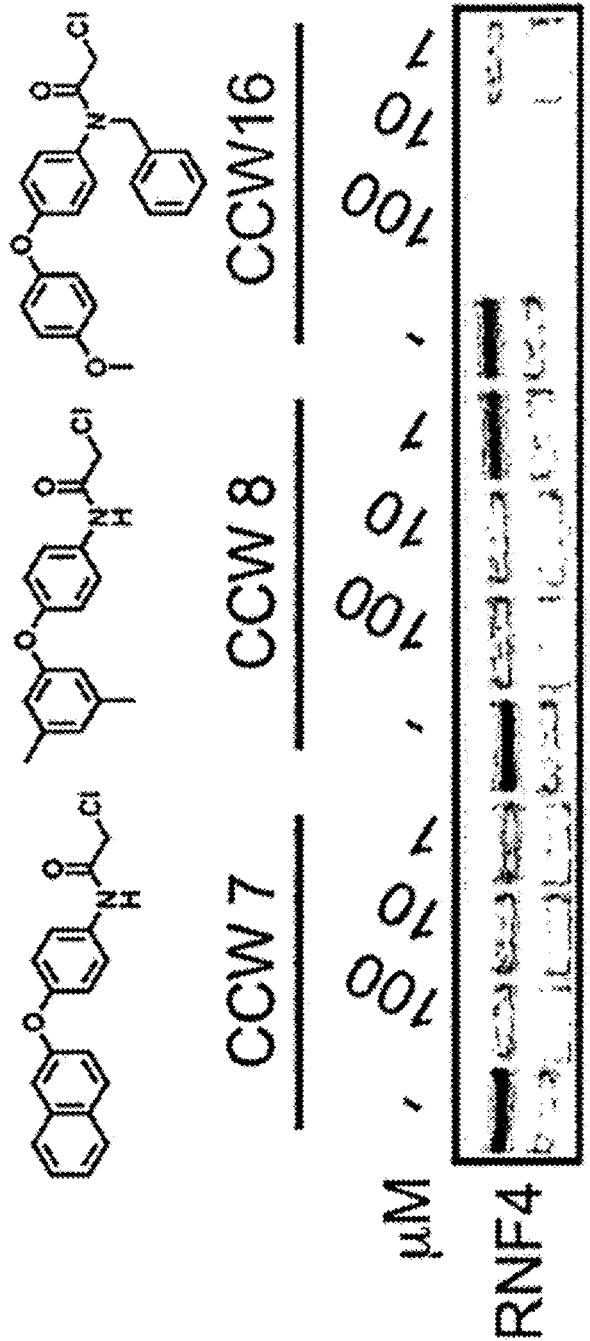
Figure 3C:
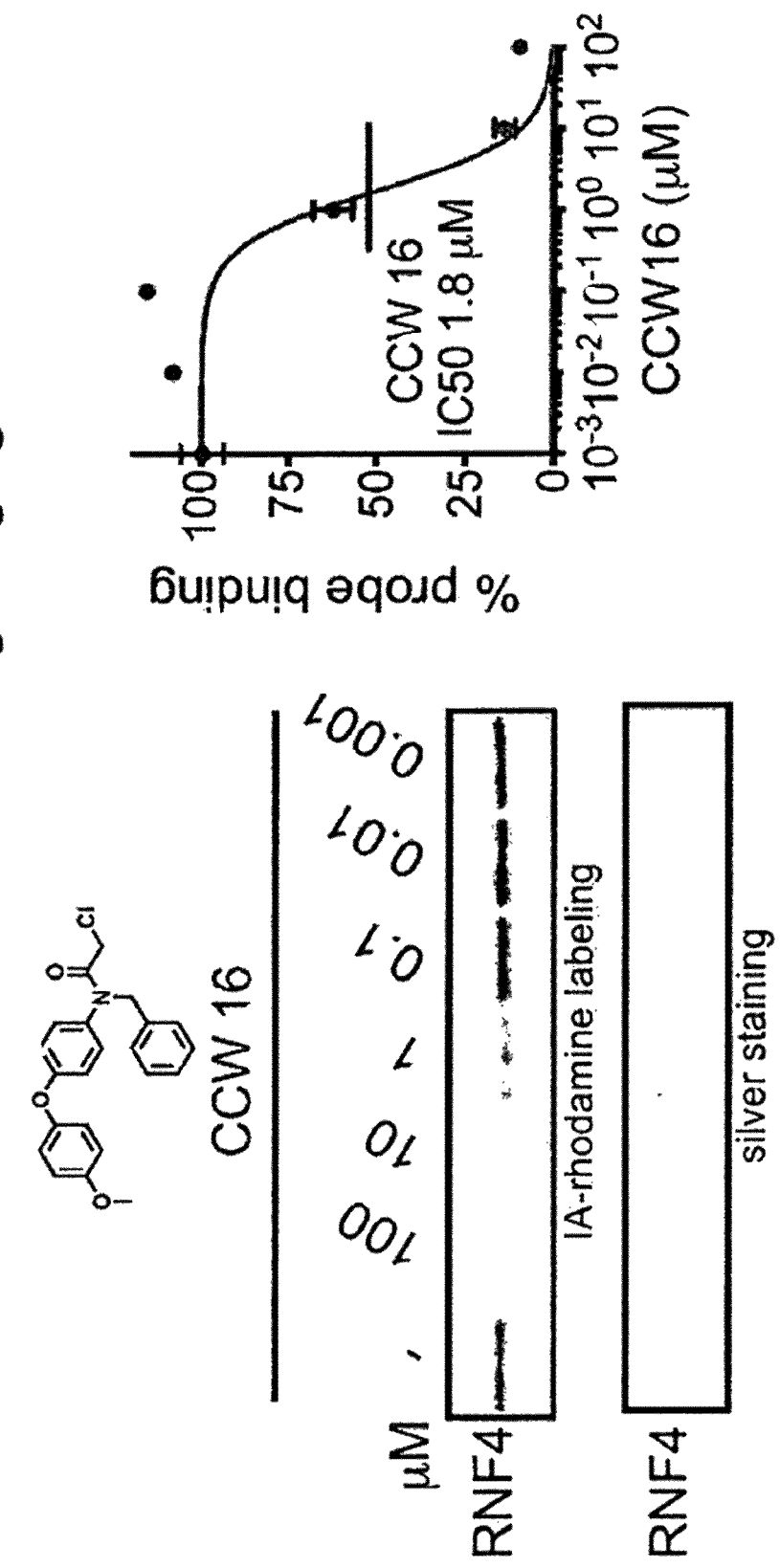

While a promising non-functional ligand against RNF4, TRH 1-23 did not show sufficient potency to be useful as an RNF4 recruiter. We thus synthesized several TRH 1-23 analogs and used gel-based ABPP to test their potency and structure-activity relationships against RNF4 (FIGS. 3A-3B). Among these analogs, we found CCW16, with an N-benzyl and 4-methoxyphenoxyphenyl substitution on the chloroacetamide scaffold, to be among the most potent of the analogs with reduced IA-rhodamine labeling of RNF4 observed down to 1 µM. Further confirmatory studies revealed a CCW16 50% inhibitory concentration (IC50) of 1.8 µM (FIG. 3C). Based on the structure-activity relationships observed with TRH 1-23 analogs, we thought that the 4-methoxy group on CCW16 would be an ideal position for extending a linker to make an RNF4-based degrader.

Figure 4A:
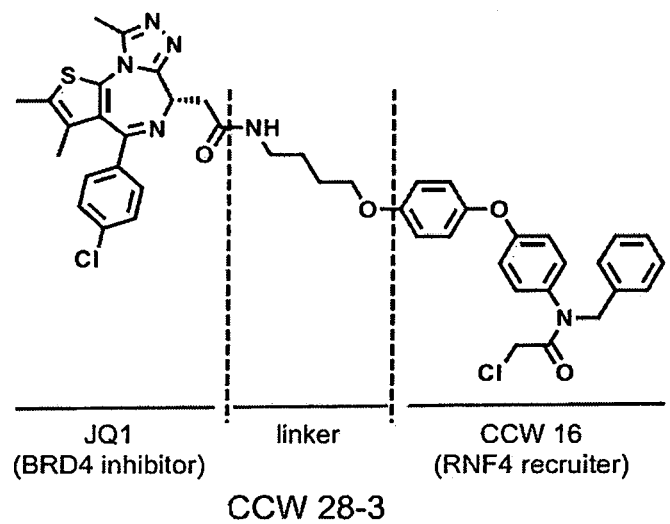
FIGS. 4A-4F. RNF4 recruiter-based BRD4 degrader.
Figure 4B:
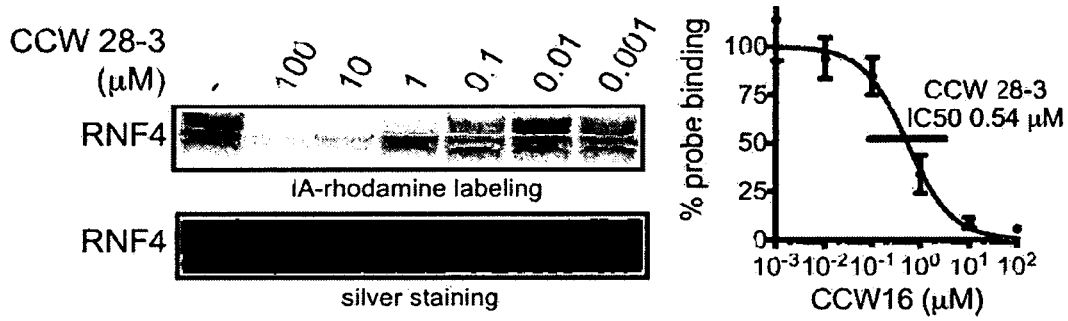
Figure 4C:
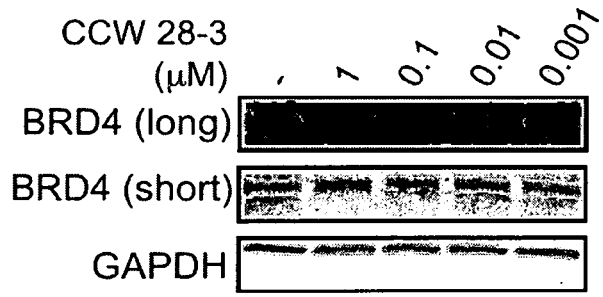
Figure 4D:
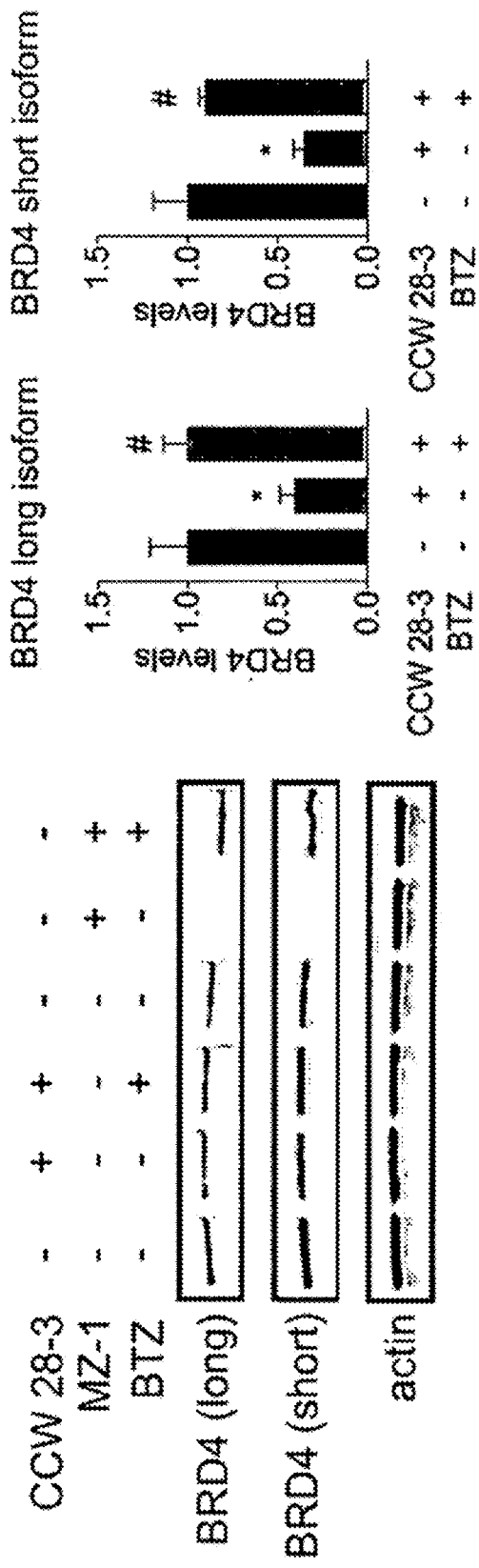
Figure 4E:
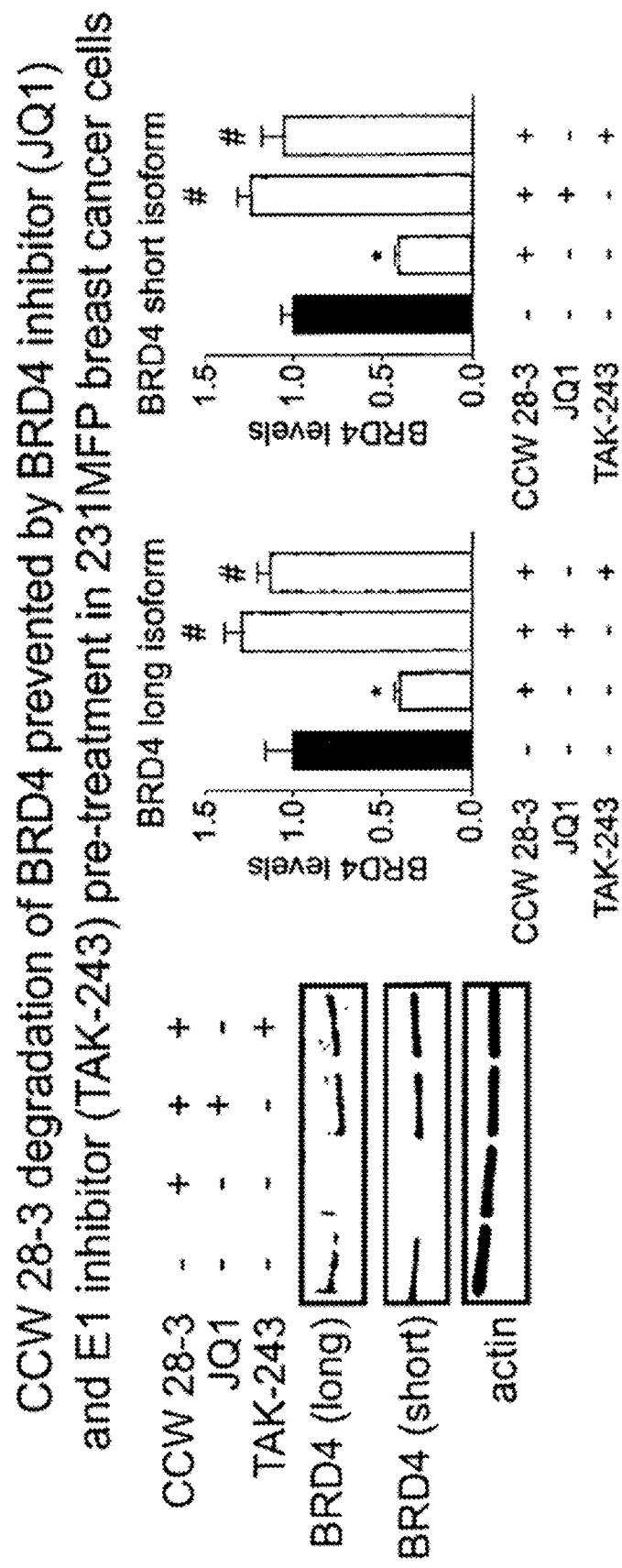

To demonstrate that we could use CCW16 as a potential RNF4 recruiter for targeted protein degradation applications, we synthesized CCW-28-3, a bifunctional degrader linking CCW16 to the BRD4 inhibitor JQ1 (FIG. 4A). CCW-28-3 showed higher potency for RNF4 than CCW16 with an IC50 of 0.54 µM (FIG. 4B). Compellingly, treatment with CCW 28-3 degrades BRD4 in a dose-responsive manner in 231MFP breast cancer cells (FIG. 4C) and this degradation is prevented by pre-treatment of cells with the proteasome inhibitor bortezomib (BTZ), the BRD4 inhibitor JQ1, as well as the E1 ubiquitin activating enzyme inhibitor TAK-243 (FIGS. 4D-4E).

Figure 6:
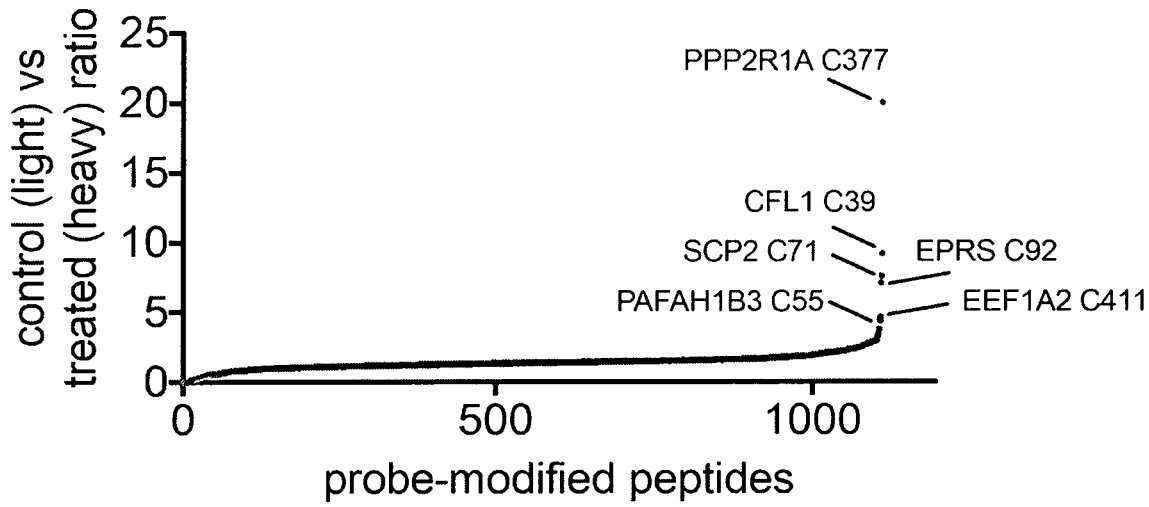
FIG. 6. isoTOP-ABPP analysis of CCW 28-3 in 231MFP breast cancer cells in situ. 231MFP cells were treated with DMSO vehicle or CCW 28-3 (10 μM) in situ for 1 h prior to labeling of proteomes in vitro with IA-alkyne (100 μM) for 1h. Isotopically light (for DMSO-treated) or heavy (for compound-treated) TEV protease-cleavable biotin-azide tag were appended by CuAAC for isoTOP-ABPP analysis. Data is for three biological replicates.

We next used isotopic tandem orthogonal proteolysis-enabled ABPP (isoTOP-ABPP) platforms to assess the proteome-wide selectivity of CCW 28-3[4,6,7,12] (FIG. 6). We treated 231MFP cells with vehicle or CCW 28-3 and labeled the resulting proteomes with the cysteine-reactive iodoacetamide-alkyne (IA-alkyne) probe, followed by appendage of isotopically light or heavy TEV protease-cleavable biotin-azide tags onto probe-labeled proteins in vehicle and CCW-28-3-treated groups, respectively. Probe-modified peptides were enriched and eluted and analyzed using previously described methods for isoTOP-ABPP[4,6,7,12]. While we were not able to observe the probe-modified peptide for RNF4 in this experiment likely due to its low abundance compared to other IA-alkyne labeled proteins, we demonstrated that there are only 7 targets with isotopically light to heavy ratios greater than 4 out of 1114 total quantified probe-modified peptides identified Most notably, none of these off-targets of CCW 28-3 are part of the ubiquitin-proteasome system (FIG. 6).

Figure 4F:
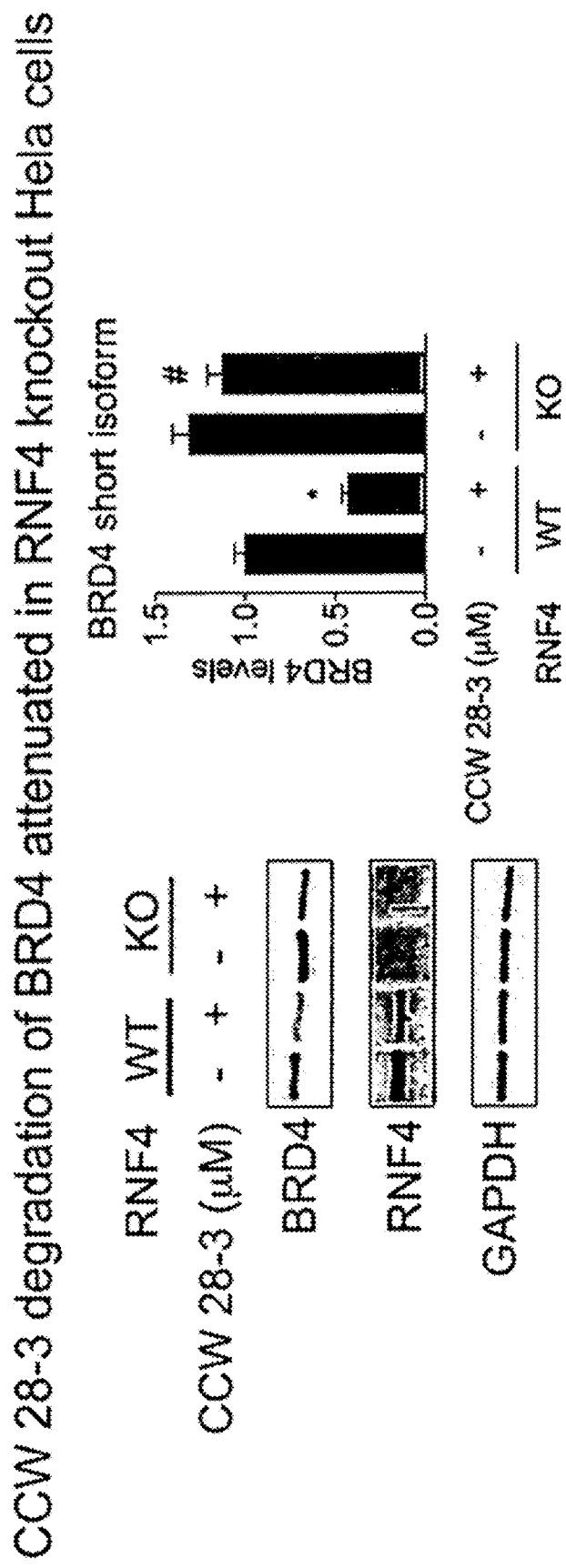
Figure 7:
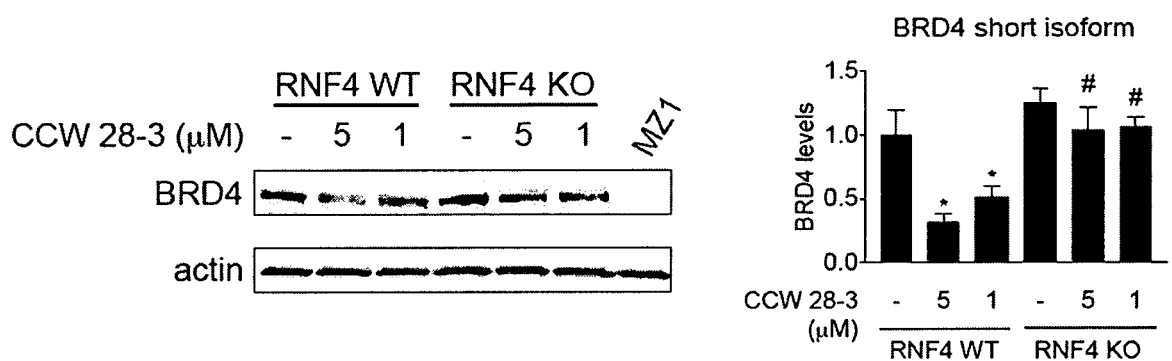
FIG. 7. CCW 28-3 tested at lower concentrations in RNF4 wild-type and knockout Hela cells. RNF4 wild-type and knockout Hela cells were treated with DMSO vehicle or CCW 28-3 (5 or 1 μM) for 5 h and subjected to SDS/PAGE and Western blotting for BRD4 and GAPDH. Blots were quantified by densitometry. Data in are from representative gels from n=3. Bar graphs are average±sem, n=3/group. Significance is expressed as *p<0.05 compared to vehicle-treated controls and #p<0.05 compared to CCW 28-3 treated wild-type cells.

Because CCW-28-3 was not completely selective and we were targeting conserved zinc-coordinating cysteines across the RING family of E3 ligases, we wanted to confirm the contributions of RNF4 to CCW-28-3-mediated degradation of BRD4. Therefore, we compared CCW 28-3-mediated BRD4 degradation in control and RNF4 knockout HeLa cells. Convincingly, CCW 28-3-mediated degradation of BRD4 observed in HeLa control cells was not evident in RNF4 knockout cells (FIG. 4F; FIG. 7). These data further indicate that CCW 28-3 degrades BRD4 through RNF4 recruitment.

Our study demonstrates the feasibility of using ABPP-based covalent ligand screening approaches to rapidly discover entry points into targeting E3 ligases and that these covalent ligand hits can be identified, optimized, and incorporated into degraders for targeted protein degradation applications. While CCW16 and CCW-28-3 are not yet completely selective for RNF4 in cells, we demonstrate that we can still degrade BRD4 in an RNF4-dependent manner. We note that CCW 28-3 does not degrade BRD4 as well as other previously reported BRD4 degraders such as MZ1 that utilizes a VHL-recruiter linked to JQ1[24]. Future medicinal chemistry efforts can be employed to optimize the potency and selectivity of CCW16 for RNF4 and to optimize linker positioning and composition of CCW 28-3 to promote better degradation of protein substrates. Nonetheless, CCW16 represents a novel, small-molecule E3 ligase recruiter for RNF4, beyond the four other E3 ligase recruiters that have been reported previously, targeting cereblon, VHL, MDM2, and cIAP[2]. We believe that the approaches described here can be utilized for future applications in expanding the scope of E3 ligase recruiters or modulators.

Example 2: Methods and Assays Pertaining to Covalent Ligand Screening and Synthesis Covalent Ligand Library used in Initial Screen. The synthesis and characterization of many of the covalent ligands screened against RNF4 have been previously reported[4-6,13].

Gel-Based ABPP. Gel-based ABPP methods were performed as previously described[5,6,25,26]. Pure recombinant human RNF4 was purchased from Boston Biochem (K-220). RNF4 (0.25 µg) was diluted into 50 µL of PBS and 1p L of either DMSO (vehicle) or covalently acting small molecule to achieve the desired concentration. After 30 minutes at room temperature, the samples were treated with 250 nM IA-Rhodamine (Setareh Biotech, 6222, prepared in anhydrous DMSO) for 1 h at room temperature. Samples were then diluted with 20 µL of 4× reducing Laemmli SDS sample loading buffer (Alfa Aesar) and heated at 90° C. for 5 min. The samples were separated on precast 4-20% Criterion TGX gels (Bio-Rad Laboratories, Inc.). Fluorescent imaging was performed on a ChemiDoc MP (Bio-Rad Laboratories, Inc) inhibition of target labeling was assessed by densitometry using ImageJ.

LC-MS/MS analysis of RNF4. Purified RNF4 (10 µg) was diluted into 80 µL of PBS and treated for 30 min with DMSO or compound (50 µM). The DMSO control was then treated with light iodoacetamide (IA) while the compound treated sample was incubated with heavy IA for 1 h each at room temperature (100 µM, Sigma-Aldrich, 721328). The samples were precipitated by additional of 20 µL of 100% (w/v) TCA and combined pairwise before cooling to −80 C for one hour. The combined sample was then spun for at max speed for 20 min at 4° C., supernatant is carefully removed and the sample is washed with ice cold 0.01 M HCl/90% acetone solution. The sample was then resuspended in 2.4 M urea containing 0.1% Protease Max (Promega Corp. V2071) in 100 mM ammonium bicarbonate buffer. The samples were reduced with 10 mM TCEP at 60° C. for 30 min. The samples were then diluted 50% with PBS before sequencing grade trypsin (1 ug per sample, Promega Corp, V5111) was added for an overnight incubation at 37° C. The next day the sample was centrifuged at 13200 rpm for 30 min. The supernatant was transferred to a new tube and acidified to a final concentration of 5% formic acid and stored at −80° C. until MS analysis.

RNF4 ubiquitination assay. For in vitro auto-ubiquitination assay, 200 nM RNF4 in 15 µL ubiquitination assay buffer (50 mM Tris, 150 mM NaCl, 5 mM $MgCl_2$, 5 mM DTT, pH 7.4) was pre-incubated with DMSO vehicle or the covalently-acting compound for 30 min at room temperature. Subsequently, UBE1 (50 nM, Boston Biochem, E-305), UBE2D1 (400 nM Boston Bichem, E2-615), Flag-ubiquitin (4000 nM, Boston Biochem, U-120) and ATP (200 µM) were added in ubiquitination assay buffer bring the total volume to 30 µL. The mixture was incubated at RT for 30 min before quenching with 10 µL of 4× Laemmli's buffer. Ubiquitination activity was measured by separation on an SDS-PAGE gel and western blotting as previously described.

Cell Culture. The 231MFP cells were obtained from Prof. Benjamin Cravatt and were generated from explanted tumor xenografts of MDA-MB-231 cells as previously described[27]. RNF4 knockout HeLa cells were purchased from EdiGene USA (CL0033025003A). RNF4 wild-type HeLa cells were provided by EdiGene USA or the UC Berkeley Cell Culture Facility. 231MFP cells were cultured in L-15 media (Corning) containing 10% (v/v) fetal bovine serum (FBS) and maintained at 37° C. with 0% $CO_2$. HeLa cells were cultured in DMEM media (Corning) containing 10% (v/v) fetal bovine serum (FBS) and maintained at 37° C. with 5% $CO_2$.

Cell based degrader assays. For assaying degrader activity, cells were seeded (500,000 for 231MFP cells, 300,000 for HeLa cells) into a 6 cm tissue culture dish (Corning) in 2.0-2.5 mL of media and allowed to adhere overnight. The following morning, media was replaced with complete media containing the desired concentration of compound diluted from a 1000× stock in DMSO. At the specified timepoint, cells were washed once with PBS on ice, before 150 uL of lysis buffer was added to the plate (10 mM sodium phosphate, 150 mM NaCl, 0.1% SDS, 0.5% sodium deoxycholate, 1% Triton X100). The cells were incubated in lysis buffer for 5 min before scraping and transfer to microcentrifuge tubes. The lysates were then frozen at −80 C or immediately processed for western blotting. To prepare for western blotting, the lysates were cleared with 20,000 g spin for 10 min and the resulting supernatants quantified via BCA assay. The lysates were normalized by dilution with PBS to match the lowest concentration lysate and appropriate amount of 4× Laemmli's reducing buffer added.

Western blotting. Antibodies to RNF4 (Proteintech, 17810-1-AP, 1:1000), GAPDH (Proteintech, 60004-1-IG, 1:5000), BRD4 (Abcam, Ab128874, 1:1000), and beta-actin (Proteintech Group Inc., 6609-1-IG, 1:7000) were obtained from the specified commercial sources and dilutions were prepared in 5% BSA/TBST at the specified dilutions. Proteins were resolved by SDS/PAGE and transferred to nitrocellulose membranes using the iBlot system (Invitrogen). Blots were blocked with 5% BSA in Tris-buffered saline containing Tween 20 (TBST) solution for 1 h at room temperature, washed in TBST, and probed with primary antibody diluted in recommended diluent per manufacturer overnight at 4° C. Following washes with TBST, the blots were incubated in the dark with secondary antibodies purchased from Ly-Cor and used at 1:10,000 dilution in 5% BSA in TBST at room temperature. Blots were visualized using an Odyssey Li-Cor scanner after additional washes. If additional primary antibody incubations were required the membrane was stripped using ReBlot Plus Strong Antibody Stripping Solution (EMD Millipore, 2504), washed and blocked again before being re-incubated with primary antibody.

IsoTOP-ABPP chemoproteomic studies. IsoTOP-ABPP studies were done as previously reported[4,6,7,12]. Briefly, cells were lysed by probe sonication in PBS and protein concentrations were measured by BCA assay[28]. For in situ experiments, cells were treated for 90 min with either DMSO vehicle or covalently-acting small molecule (from 1000×DMSO stock) before cell collection and lysis. For in vitro experiments, proteome samples diluted in PBS (4 mg of proteome per biological replicate) were treated with a DMSO vehicle or covalently-acting small molecule for 30 min at room temperature. Proteomes were subsequently treated with IA-alkyne (100 µM, Chess GmbH, 3187) for 1 h at RT. CuAAC was performed by sequential addition of tris(2-carboxyethyl)phosphine (TCEP) (1 mM, Sigma), tris [(1-benzyl-1H-1,2,3-triazol-4-yl)methyl]amine (TBTA) (34 µM, Sigma), copper (II) sulfate (1 mM, Sigma), and biotin-linker-azide—the linker functionalized with a TEV protease recognition sequence as well as an isotopically light or heavy valine for treatment of control or treated proteome, respectively. After CuAAC, proteomes were precipitated by centrifugation at 6500×g, washed in ice-cold methanol, combined in a 1:1 control/treated ratio, washed again, then denatured and resolubilized by heating in 1.2% SDS/PBS to 80° C. for 5 minutes. Insoluble components were precipitated by centrifugation at 6500×g and soluble proteome was diluted in 5 ml 0.2% SDS/PBS. Labeled proteins were bound to avidin-agarose beads (170 µl resuspended beads/sample, Thermo Pierce) while rotating overnight at 4° C. Bead-linked proteins were enriched by washing three times each in PBS and water, then resuspended in 6 M urea/PBS (Sigma) and reduced in TCEP (1 mM, Sigma), alkylated with iodoacetamide (IA) (18 mM, Sigma), then washed and resuspended in 2 M urea and trypsinized overnight with 2 ug/sample sequencing grade trypsin (Promega). Tryptic peptides were eluted off. Beads were washed three times each in PBS and water, washed in TEV buffer solution (water, TEV buffer, 100 µM dithiothreitol) and resuspended in buffer with Ac-TEV protease (Invitrogen) and incubated overnight. Peptides were diluted in water and acidified with formic acid (1.2 M, Spectrum) and prepared for analysis.

Mass Spectrometry Analysis. Peptides from all proteomic experiments were pressure-loaded onto a 250 µm inner diameter fused silica capillary tubing packed with 4 cm of Aqua C18 reverse-phase resin (Phenomenex #04A-4299) which was previously equilibrated on an Agilent 600 series HPLC using gradient from 100% buffer A to 100% buffer B over 10 min, followed by a 5 min wash with 100% buffer B and a 5 min wash with 100% buffer A. The samples were then attached using a MicroTee PEEK 360 µm fitting (Thermo Fisher Scientific #p-888) to a 13 cm laser pulled column packed with 10 cm Aqua C18 reverse-phase resin and 3 cm of strong-cation exchange resin for isoTOP-ABPP studies. Samples were analyzed using an Q Exactive Plus mass spectrometer (Thermo Fisher Scientific) using a 5-step Multidimensional Protein Identification Technology (MudPIT) program, using 0%, 25%, 50%, 80%, and 100% salt bumps of 500 mM aqueous ammonium acetate and using a gradient of 5-55% buffer B in buffer A (buffer A: 95:5 water:acetonitrile, 0.1% formic acid; buffer B 80:20 acetonitrile:water, 0.1% formic acid). Data was collected in data-dependent acquisition mode with dynamic exclusion enabled (60 s). One full MS (MS1) scan (400-1800 m/z) was followed by 15 MS2 scans (ITMS) of the nth most abundant ions. Heated capillary temperature was set to 200° C. and the nanospray voltage was set to 2.75 kV.

Data was extracted in the form of MS1 and MS2 files using Raw Extractor 1.9.9.2 (Scripps Research Institute) and searched against the Uniprot human database using ProLu-CID search methodology in IP2 v.3 (Integrated Proteomics Applications, Inc)[29]. Cysteine residues were searched with a static modification for carboxyaminomethylation (+57.02146) and up to three differential modifications for methionine oxidation and either the light or heavy TEV tags (+464.28596 or +470.29977, respectively). Peptides were required to have at least one tryptic end and to contain the TEV modification. ProLUCID data was filtered through DTASelect to achieve a peptide false-positive rate below 5%. Only those probe-modified peptides that were evident across all two out of three biological replicates were interpreted for their isotopic light to heavy ratios. Those probe-modified peptides that showed ratios >3 were further analyzed as potential targets of the covalently-acting small-molecule. For modified peptides with ratios >3, we filtered these hits for peptides were present in all three biological replicates. For those probe-modified peptide ratios >3, only those peptides with 3 ratios >3 were interpreted, and otherwise replaced with the lowest ratio. For those probe-modified peptide ratios >4, only those peptides with 3 ratios >4 were interpreted, and otherwise replaced with the lowest ratio. MS1 peak shapes of any resulting probe-modified peptides with ratios >3 were then manually confirmed to be of good quality for interpreted peptides across all biological replicates.

Example 3. Synthesis and Characterization of Covalent Ligands Screened Against RNF4

General Procedure A. The amine (1 eq.) was dissolved in DCM (5 mL/mmol) and cooled to 0° C. To the solution was added acryloyl chloride (1.2 eq.) followed by triethylamine (1.2 eq.). The solution was allowed to warm to room temperature and stirred overnight. The solution was then washed with brine and the crude product was purified by silica gel chromatography (and recrystallization if necessary) to afford the corresponding acrylamide.

General Procedure B. The amine (1 eq.) was dissolved in DCM (5 mL/mmol) and cooled to 0° C. To the solution was added chloroacetyl chloride (1.2 eq.) followed by triethylamine (1.2 eq.). The solution was allowed to warm to room temperature and stirred overnight. The solution was then washed with brine and the crude product was purified by silica gel chromatography (and recrystallization if necessary) to afford the corresponding acrylamide.

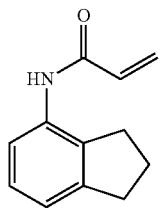

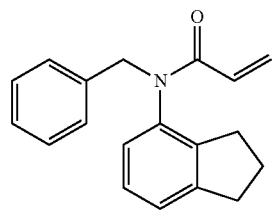

N-(2,3-dihydro-1H-inden-4-yl)acrylamide (DKM 2-84). A solution of 4-aminoindan (402 mg, 3.0 mmol) in DCM (10 mL) was cooled to 0° C. To the solution was added acryloyl chloride (379 mg, 4.2 mmol) followed by triethylamine (379 mg, 3.7 mmol). The solution was allowed to warm to room temperature and stirred overnight. The solution was washed with brine and the crude product was purified via silica gel chromatography (30% ethyl acetate in hexanes) to afford the product in 59% yield as a white solid (332 mg). $^1$H NMR (400 MHz, CDCl$_3$): δ 7.72 (d, J=7.5 Hz, 1H), 7.54 (s, 1H), 7.10 (t, J=7.7 Hz, 1H), 7.01 (d, J=7.2 Hz, 1H), 6.40-6.26 (m, 2H), 5.69 (dd, J=1.9, 9.7 Hz, 1H), 2.91 (t, J=7.4 Hz, 2H), 2.78 (t, J=7.4 Hz, 2H), 2.05 (quint, J=7.4 Hz, 2H). $^{13}$C NMR (100 MHz, CDCl$_3$): 163.5, 145.3, 134.4, 133.6, 131.2, 127.5, 127.2, 12.0, 19.2, 33.2, 30.1, 24.8. HRMS (+ESI): Calculated: 188.1070 (C$_{12}$H$_{14}$NO). Observed: 188.1069

N-benzyl-N-(2,3-dihydro-1H-inden-4-yl)acrylamide (IGA 1-14). A solution of sodium hydride (96 mg, 4.0 mmol) in tetrahydrofuran (8 mL) was put under nitrogen atmosphere. To the solution was added N-(2,3-dihydro-1H-inden-4-yl)acrylamide (187 mg, 1.0 mmol) in tetrahydrofuran (2 mL). The solution was cooled to 0° C. and stirred. Benzyl bromide (476 mg, 4.0 mmol) was added after 30 minutes, after which the solution was allowed to warm to room temperature and was stirred overnight. The solution was quenched with water and extracted with ethyl acetate. The crude product was purified via silica gel chromatography (20% ethyl acetate in hexanes) to afford the product in 63% yield as an orange oil (173 mg). $^1$H NMR (400 MHz, CDCl$_3$): δ 7.10-7.35 (m, 7H), 6.74-6.85 (dd, J=7.8, 1.1 Hz, 1H), 6.40-6.55 (dd, J=16.8, 2.1 Hz, 1H), 5.93-6.08 (dd, J=16.8, 10.3 Hz, 1H), 5.49-5.62 (dd, J=10.3, 2.1 Hz, 1H), 4.78-5.10 (m, 2H), 2.85-3.02 (m, 2H), 2.52-2.67 (m, 1H), 2.22-2.37 (m, 1H), 1.83-2.01 (m, 2H). $^{13}$C NMR (100 MHz, CDCl$_3$): δ 146.4, 142.9, 137.7, 137.3, 129.3, 128.4, 128.3, 128.0, 127.5, 127.5, 126.0, 124.3, 52.3, 33.2, 30.6, 25.1. HRMS (+ESI): Calculated: 278.15 (C$_{19}$H$_{19}$NO). Observed: 278.1538.

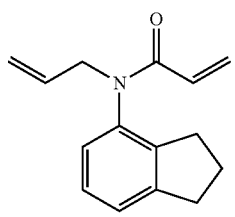 [SMILES: C=CCN(C(=O)C=C)c1cccc2c1CCC2]

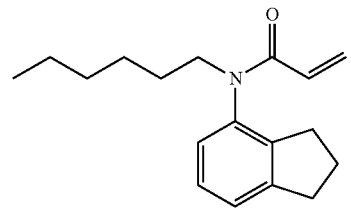 [SMILES: C=CC(=O)N(CCCCCC)c1cccc2c1CCC2]

N-allyl-N-(2,3-dihydro-1H-inden-4-yl)acrylamide (IGA 1-12). A solution of sodium hydride (96 mg, 4.0 mmol) in tetrahydrofuran (8 mL) was put under nitrogen atmosphere. To the solution was added N-(2,3-dihydro-1H-inden-4-yl) acrylamide (187 mg, 1.0 mmol) in tetrahydrofuran (2 mL). The solution was cooled to 0° C. and stirred. 3-bromoprop-1-ene (484 mg, 4.0 mmol) was added after 30 minutes, after which the solution was allowed to warm to room temperature and was stirred overnight. The solution was quenched with water and extracted with ethyl acetate. The crude product was purified via silica gel chromatography (20% ethyl acetate in hexanes) to afford the product in 67% yield as a yellow crystalline solid (151 mg). $^1$H NMR (400 MHz, CDCl$_3$): δ 7.06-7.18 (m, 2H), 6.80-6.88 (m, 1H), 6.26-6.37 (dd, J=16.8, 2.0 Hz, 1H), 5.76-5.96 (m, 2H), 5.38-5.48 (dd, J=10.3, 2.1 Hz, 1H), 4.98-5.08 (m, 2H), 4.40-4.52 (ddt, J=14.5, 6.3, 1.3 Hz, 1H), 4.00-4.11 (ddt, J=14.5, 6.8, 1.2 Hz, 1H), 2.82-2.98 (m, 2H), 2.59-2.79 (m, 2H), 1.92-2.07 (m, 2H). $^{13}$C NMR (100 MHz, CDCl$_3$): δ 165.1, 146.5, 142.4, 137.9, 133.0, 128.4, 127.8, 127.48, 126.1, 124.3, 118.1, 51.6, 33.3, 30.9, 25.0. HRMS (+ESI): Calculated: 228.13 (C$_{15}$H$_{17}$NO). Observed: 228.1381.

N-allyl-N-(2,3-dihydro-1H-inden-4-yl)acrylamide (IGA 1-15). A solution of sodium hydride (96 mg, 4.0 mmol) in tetrahydrofuran (8 mL) was put under nitrogen atmosphere. To the solution was added N-(2,3-dihydro-1H-inden-4-yl) acrylamide (187 mg, 1.0 mmol) in tetrahydrofuran (2 mL). The solution was cooled to 0° C. and stirred. 1-bromohexane (660 mg, 4.0 mmol) was added after 30 minutes, after which the solution was allowed to warm to room temperature and was stirred overnight. The solution was quenched with water and extracted with ethyl acetate. The crude product was purified via silica gel chromatography (20% ethyl acetate in hexanes) to afford the product in 34% yield as a yellow oil (92 mg). $^1$H NMR (400 MHz, CDCl$_3$): δ 7.11-7.25 (m, 2H), 6.86-6.96 (dd, J=7.5, 1.2 Hz, 1H), 6.30-6.40 (dd, J=16.8, 2.1 Hz, 1H), 5.86-6.00 (m, 1H), 5.41-5.51 (dd, J=10.3, 2.1 Hz, 1H), 3.82-3.96 (m, 1H), 3.42-3.56 (m, 1H), 2.90-3.04 (m, 2H), 2.65-2.85 (m, 2H), 1.98-2.16 (m, 2H), 1.47-1.63 (m, 2H), 1.20-1.36 (m, 6H), 0.80-0.90 (m, 3H). $^{13}$C NMR (100 MHz, CDCl$_3$): δ 165.16, 146.54, 142.38, 138.21, 128.59, 127.51, 127.35, 126.09, 124.13, 48.67, 33.26, 31.62, 30.85, 27.85, 26.72, 25.01, 22.59, 14.05. HRMS (+ESI): Calculated: 272.19 (C$_{18}$H$_{25}$NO). Observed: 272.2007.

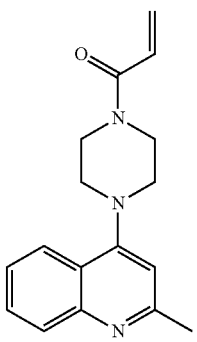 [SMILES: C=CC(=O)N1CCN(c2cc(C)nc3ccccc23)CC1]

1-(4-(2-methylquinolin-4-yl)piperazin-1-yl)prop-2-en-1-one (IGA 1-26). A solution of 2-methyl-4-(piperazin-1-yl)quinolone (455 mg, 2.0 mmol) in DCM (20 mL) was cooled to 0° C. To the solution was added acryloyl chloride (217 mg, 2.4 mmol) followed by triethylamine (243 mg, 2.4 mmol). The solution was allowed to warm to room temperature and stirred overnight. The solution was washed with brine and the crude product was purified via basic alumina chromatography (100% ethyl acetate) to afford the product in 26% yield as a yellow oil (145 mg). $^1$H NMR (400 MHz, CDCl$_3$): δ 7.90-8.05 (m, 2H), 7.58-7.70 (ddd, J=8.4, 6.8, 1.5 Hz, 1H), 7.40-7.50 (ddd, J=8.2, 6.8, 1.3 Hz, 1H), 6.68-6.76 (s, 1H), 6.56-6.67 (dd, J=16.8, 10.5 Hz, 1H), 6.30-6.40 (dd, J=16.8, 2.0 Hz, 1H), 5.70-5.80 (dd, J=10.5, 2.0 Hz, 1H), 3.70-4.06 (d, J=54.7 Hz, 4H), 3.10-3.30 (t, J=5.0 Hz, 4H), 2.62-2.72 (s, 3H). $^{13}$C NMR (100 MHz, CDCl$_3$): δ 165.5, 159.4, 156.2, 149.2, 129.26, 129.24, 128.3, 127.3, 124.9, 123.0, 121.6, 109.8, 52.3, 51.9, 45.8, 42.0, 25.6. HRMS (+ESI): Calculated: 282.17 ($C_{17}H_{19}N_3O$). Observed: 282.1597.

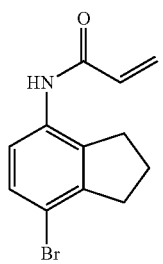

N-(7-bromo-2,3-dihydro-1H-inden-4-yl)acrylamide (TRH 1-65). To a solution of N-(2,3-dihydro-1H-inden-4-yl)acrylamide (DKM 2-84, 469 mg, 2.5 mmol) in acetic acid (10 mL) was added ammonium bromide (305 mg, 3.1 mmol) followed by dropwise addition of hydrogen peroxide solution (50% in water, 1.90 mL). The reaction was stirred overnight, after which it was carefully neutralized with a solution of saturated sodium bicarbonate and extracted with ethyl acetate (3×20 mL). The combined organics were then evaporated and the resulting crude was purified via silica gel chromatography (20% ethyl acetate in hexanes) to give 621 mg of the product as a white solid (93%). $^1$H NMR (400 MHz, MeOD): δ 7.36 (d, J=8.5 Hz, 1H), 7.27 (d, J=8.5 Hz, 1H), 6.49 (dd, J=10.2, 17.0 Hz, 1H), 6.35 (dd, J=1.8, 17.0 Hz, 1H), 5.77 (dd, J=1.8, 10.2 Hz, 1H), 2.95 (q, J=8.0 Hz, 4H), 2.08 (quint, J=7.5 Hz, 2H). $^{13}$C NMR (100 MHz, MeOD): δ 146.5, 140.2, 134.2, 132.0, 130.8, 128.1, 124.3, 116.9, 101.4, 35.8, 32.9, 24.9.

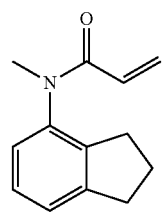

N-methyl-N-(2,3-dihydro-1H-inden-4-yl)acrylamide (TRH 1-115). To a solution of sodium hydride (60% dispersion in mineral oil, 167 mg, 4.0 mmol) in tetrahydrofuran (8 mL) under nitrogen atmosphere at 0° C. was added a solution N-(2,3-dihydro-1H-inden-4-yl)acrylamide (DKM-2-84, 188 mg, 1.0 mmol) in tetrahydrofuran (2 mL). After stirring for 30 minutes, methyl iodide (0.25 mL, 4.0 mmol) was added. The solution was allowed to warm to room temperature and stirred overnight. The solution was quenched with water and extracted with three times with ethyl acetate. The combined organics were washed with brine, dried with magnesium sulfate, filtered, and evaporated, and the resulting crude product was purified via silica gel chromatography (20% ethyl acetate in hexanes) to afford the product in 35% yield as a clear oil (71 mg). $^1$H NMR (400 MHz, CDCl$_3$): δ 7.19-7.13 (m, 2H), 6.90 (d, J=7.4 Hz, 1H), 6.32 (dd, J=2.0, 16.8 Hz, 1H), 5.96 (dd, J=10.3, 16.8 Hz, 1H), 5.43 (dd, J=2.0, 10.3 Hz, 1H), 3.24 (s, 3H), 2.93 (t, J=7.5 Hz, 2H), 2.81-2.66 (m, 2H), 2.08-2.00 (m, 2H). $^{13}$C NMR (100 MHz, CDCl$_3$): δ 165.6, 146.6, 141.7, 139.3, 128.2, 127.7, 127.4, 125.1, 124.2, 36.0, 33.2, 30.5, 24.9. HRMS (+ESI): Calculated: 202.1226 ($C_{13}H_{16}NO$). Observed: 202.1224.

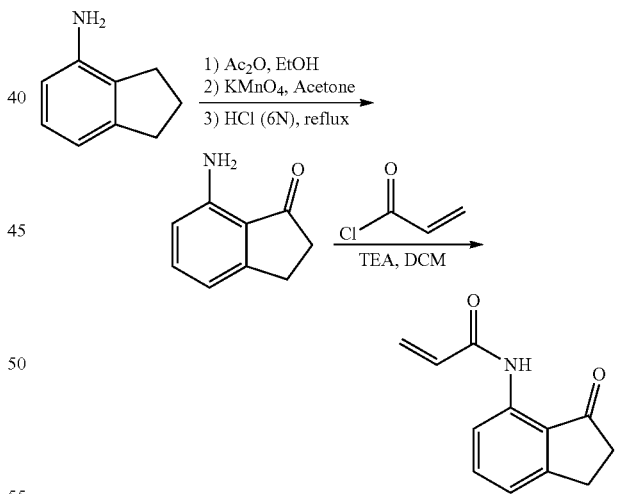

N-(3-oxo-2,3-dihydro-1H-inden-4-yl)acrylamide (TRH 1-129). To a solution of 4-aminoindan (1.0 g, 7.5 mmol) in ethanol (20 mL) at 0° C. was added acetic anhydride (1.4 mL, 15.0 mmol). The solution was raised to room temperature and stirred overnight, after which the solvent was evaporated. The residue was then dissolved in acetone (50 mL) to which was added 15% aqueous magnesium sulfate (1.2 g in 6.75 mL of water) followed by potassium permanganate (3.4 g, 17.0 mmol), and the resulting solution was stirred for 24 hours. The reaction filtered through a pad of celite, eluting with chloroform and then water. The eluent was separated, and the aqueous layer was extracted several times with additional chloroform. The combined organics were dried over magnesium sulfate, filtered and evaporated. The residue was then dissolved in a 6N HCl solution (20 mL) and heated to 90° C. After stirring for 5 hours, the solution was cooled, neutralized with small portions of potassium carbonate, and extracted with ethyl acetate. The combined organics were dried with magnesium sulfate, filtered, and evaporated to give 610 mg (55% over 3 steps) of crude 7-aminoindan-1-one which was used without further purification. To a solution of 7-aminoindan-1-one in dichloromethane (15 mL) was added acryloyl chloride (0.39 mL, 4.8 mmol) followed by triethylamine (0.67 mL, 4.8 mmol) at 0° C. under $N_2$ atmosphere. The reaction mixture was allowed to warm to room temperature and was stirred overnight. The solution was washed 1M HCl solution (2×) and brine, and the resulting crude was purified by silica gel chromatography (10% to 20% ethyl acetate in hexanes) to yield 390 mg of white solid (47% yield, 26% combined over 4 steps). $^1$H NMR (400 MHz, CDCl$_3$): δ 10.64 (s, 1H), 8.45 (d, J=8.2 Hz, 1H), 7.55 (t, J=7.9 Hz, 1H), 7.12 (d, J=7.6 Hz, 1H), 6.45 (dd, J=1.0, 17.0 Hz, 1H), 6.33 (dd, J=10.1, 17.0 Hz, 1H), 5.82 (dd, J=1.0, 10.1 Hz, 1H), 3.11 (t, J=11.5 Hz, 2H), 2.74-2.71 (m, 2H). $^{13}$C NMR (100 MHz, CDCl$_3$): δ 209.3, 164.4, 155.9, 138.7, 137.0, 131.7, 128.0, 123.1, 120.8, 116.9, 36.5, 25.5. HRMS (+ESI): Calculated: 202.0863 ($C_{12}H_{12}NO_2$). Observed: 202.0860.

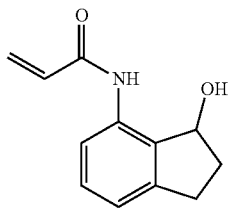

N-(3-hydroxy-2,3-dihydro-1H-inden-4-yl)acrylamide (TRH 1-133). To a solution of N-(3-oxo-2,3-dihydro-1H-inden-4-yl)acrylamide (TRH-1-129, 201 mg, 1.0 mmol) in anhydrous methanol (7 mL) under nitrogen atmosphere was added sodium borohydride (46.1 mg, 1.2 mmol). After 30 minutes of stirring, the reaction was quenched with saturated sodium bicarbonate solution and extracted three times with DCM. The combined organics were dried with magnesium sulfate, filtered, and concentrated. Crude was purified by silica gel chromatography (30 to 50% ethyl acetate in hexanes) to give 190 mg of the product as a white solid (94% yield). $^1$H NMR (400 MHz, CDCl$_3$): δ 8.93 (s, 1H), 7.98 (d, J=7.8 Hz, 1H), 7.19 (t, J=7.9 Hz, 1H), 6.95 (d, J=7.4 Hz, 1H), 6.29 (d, J=16.8 Hz, 1H), 6.15 (dd, J=10.2, 16.9 Hz, 1H), 5.66 (d, J=10.2 Hz, 1H), 5.32 (q, J=6.9 Hz, 1H), 3.60 (d, J=6.7 Hz, 11H), 2.96 (ddd, J=2.4, 9.0, 15.7 Hz), 2.73 (quint, J=8.1 Hz, 1H), 2.56-2.48 (m, 1H), 1.96-1.86 (m, 1H). $^{13}$C NMR (100 MHz, CDCl$_3$): δ 164.1, 143.7, 135.6, 132.8, 131.6, 129.5, 127.3, 121.0, 118.5, 76.2, 36.0, 29.8. HRMS (-ESI): Calculated: 202.0874 ($C_{12}H_{12}NO_2$). Observed: 202.0874.

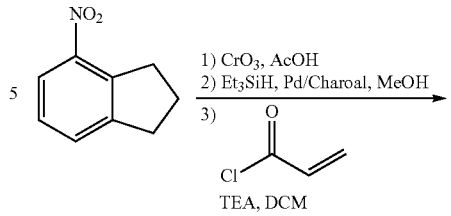

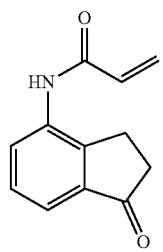

N-(1-oxo-2,3-dihydro-1H-inden-4-yl)acrylamide (TRH 1-134). To a solution of 4-nitroindan (5.38 g, 33 mmol) in acetic acid (250 mL) was slowly added chromium trioxide (8.95 g, 90 mmol). After stirring for 24 hours, the reaction was neutralized with 2M NaOH and extracted five times with ethyl acetate. The combined organics were washed with a saturated sodium bicarbonate solution and brine, then dried over magnesium sulfate, filtered, and concentrated. The crude material was purified by silica gel chromatography (10-20% ethyl acetate in hexanes) to give 1.26 g (ca. 7.1 mmol) of 4-nitroindanone as a white solid. This intermediate was combined with palladium on activated charcoal (125 mg, 10 wt %) dissolved in anhydrous methanol (21 mL) under the atmosphere of a nitrogen balloon. Triethylsilane (11.3 mL, 71 mmol) was slowly added by addition funnel over the course of 10 minutes while the reaction was stirred under the cooling of a room temperature water bath. After an additional 20 minutes of stirring, the reaction mixture was filtered through a pad of celite and subsequently concentrated to give crude 4-aminoindanone which was used without further purification. This final intermediate was then dissolved in DCM (21 mL) under $N_2$ atmosphere and cooled to 0° C., after which acryloyl chloride (0.77 mL, 9.5 mmol) and triethylamine (1.19 mL, 8.5 mmol) were slowly added. The reaction was allowed to warm to room temperature while stirring overnight, at which point the reaction was washed twice with brine, dried with magnesium sulfate, filtered, and concentrated. The crude was purified by silica gel chromatography (30-50% ethyl acetate in hexanes) to give 989 mg of a white solid (15% yield over 3 steps). $^1$H NMR (400 MHz, CDCl$_3$): δ 8.20 (d, J=5.8 Hz, 1H), 7.63 (s, 1H), 7.56 (d, J=7.5 Hz, 1H), 7.39 (t, J=7.7 Hz, 1H), 6.48 (d, J=16.7 Hz, 1H), 6.37 (dd, J=10.0 Hz, 16.8 Hz, 1H), 5.83 (d, J=10.1 Hz, 1H), 3.04 (t, J=5.6 Hz, 2H), 2.70 (t, J=5.7 Hz, 2H). $^{13}$C NMR (100 MHz, CDCl$_3$): δ 206.3, 163.9, 146.0, 138.0, 135.4, 130.7, 128.8, 128.7, 127.6, 120.4, 36.1, 23.4. HRMS (-ESI): Calculated: 200.0717 ($C_{12}H_{10}NO_2$). Observed: 200.0715.

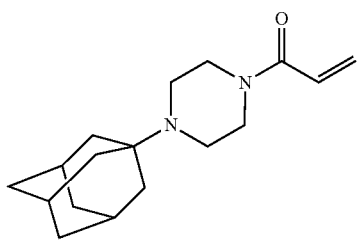 [SMILES: C=CC(=O)N1CCN(C23CC4CC(CC(C4)C2)C3)CC1]

1-(4-((3s,5s,7s)-adamantan-1-yl)piperazin-1-yl)prop-2-en-1-one (TRH 1-143). To a solution 1-(1-adamantyl)piperazine (441 mg, 2.0 mmol) in dichloromethane (10 mL) was added acryloyl chloride (0.20 mL, 2.4 mmol) followed by triethylamine (0.34 mL, 2.4 mmol) at 0° C. under $N_2$ atmosphere. After stirring for 20 minutes, the reaction mixture was allowed to warm to room temperature and was stirred for 24 hours. The solution was washed twice with brine, dried with magnesium sulfate, and the resulting crude was purified by silica gel chromatography (0% to 5% methanol in DCM) to yield 131 mg of brown solid (24% yield). $^1$H NMR (400 MHz, $CDCl_3$): δ 6.59 (dd, J=10.5, 16.8 Hz, 1H), 6.31 (dd, J=1.8, 16.8 Hz, 1H), 5.77 (dd, J=5.77 Hz, 1H), 4.12 (s, 4H), 3.17 (s, 4H), 2.25 (s, 3H), 2.06 (s, 6H), 1.71 (q, J=8.6 Hz, 6H). $^{13}$C NMR (100 MHz, $CDCl_3$): δ 165.0, 129.0, 126.4, 63.3, 44.6, 44.1, 42.9, 39.0, 36.4, 35.5, 29.3. HRMS (+ESI): Calculated: 275.2118 ($C_{17}H_{27}N_2O$). Observed: 275.2113.

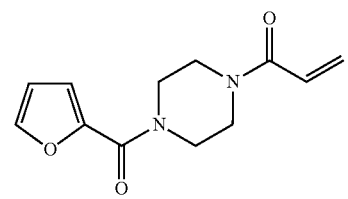 [SMILES: C=CC(=O)N1CCN(C(=O)c2ccco2)CC1]

1-(4-(furan-2-carbonyl)piperazin-1-yl)prop-2-en-1-one (TRH 1-145). To a solution 1-(2-furoyl)piperazine (362 mg, 2.0 mmol) in dichloromethane (10 mL) was added acryloyl chloride (0.20 mL, 2.4 mmol) followed by triethylamine (0.34 mL, 2.4 mmol) at 0° C. under $N_2$ atmosphere. After stirring for 20 minutes, the reaction mixture was allowed to warm to room temperature and was stirred for 24 hours. The solution was washed twice with brine, dried with magnesium sulfate, and the resulting crude was purified by silica gel chromatography (70% to 100% ethyl acetate in hexanes) to yield 446 mg of yellow solid (95% yield). $^1$H NMR (400 MHz, $CDCl_3$): δ 7.53 (m, 1H), 7.06 (dd, J=0.7, 3.5 Hz, 1H), 6.61 (dd, J=10.5, 16.8 Hz, 1H), 6.52 (dd, J=1.8, 3.5 Hz, 1H), 6.33 (dd, J=1.9, 16.8 Hz, 1H), 5.75 (dd, J=1.9, 10.5 Hz, 1H), 3.84-3.67 (m, 8H). $^{13}$C NMR (100 MHz, $CDCl_3$): δ 165.5, 159.1, 147.5, 144.0, 128.5, 127.1, 117.0, 111.5, 45.6, 41.9. HRMS (+ESI): Calculated: 235.1077 ($C_{12}H_{15}N_2O_3$). Observed: 235.1075.

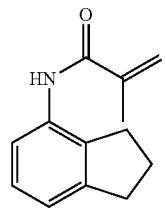

N-(2,3-dihydro-1H-inden-4-yl)methacrylamide (TRH 1-149). To a solution 4-aminoindan (0.24 mL, 2.0 mmol) in dichloromethane (10 mL) was added methacryloyl chloride (0.23 mL, 2.4 mmol) followed by triethylamine (0.34 mL, 2.4 mmol) at 0° C. under $N_2$ atmosphere. After stirring for 20 minutes, the reaction mixture was allowed to warm to room temperature and was stirred for 3.5 hours. The solution was washed twice with brine, dried with magnesium sulfate, and the resulting crude was purified by silica gel chromatography (35% to 40% ethyl acetate in hexanes) to yield 378 mg of off-white solid (94% yield). $^1$H NMR (400 MHz, $CDCl_3$): δ 7.72 (d, J=8.0 Hz, 1H), 7.55 (s, 1H), 7.12 (t, J=7.7 Hz, 1H), 7.01 (d, J=7.4 Hz, 1H), 5.79 (s, 1H), 5.42 (s, 11H), 2.93 (t, J=7.5 Hz, 2H), 2.79 (t, J=7.4 Hz, 2H), 7.12-2.06 (m, 2H), 2.04 (s, 3H). $^{13}$C NMR (100 MHz, $CDCl_3$): δ 166.3, 145.1, 140.6, 134.5, 133.7, 127.0, 120.7, 119.8, 118.9, 33.1, 29.9, 24.7, 18.6. HRMS (+ESI): Calculated: 202.1226 ($C_{13}H_{16}NO$). Observed: 202.1224.

N-(3-oxoisoindolin-4-yl)acrylamide (TRH 1-152). To a solution of 7-aminoisoindolin-1-one (99 mg, 0.67 mmol) in dichloromethane (4 mL) was added acryloyl chloride (0.07 mL, 0.8 mmol) followed by triethylamine (0.11 mL, 0.8 mmol) at 0° C. under $N_2$ atmosphere. After stirring for 20 minutes, the reaction mixture was allowed to warm to room temperature and was stirred overnight. The solution was washed twice with brine, dried with magnesium sulfate, and the resulting crude was purified by silica gel chromatography (50 to 60% ethyl acetate in hexanes) to yield 58 mg of a white solid (43% yield). $^1$H NMR (400 MHz, $CDCl_3$): δ 10.50 (s, 1H), 8.58 (d, J=8.2 Hz, 1H), 7.55 (t, J=7.9 Hz, 1H), 7.15 (d, J=7.5 Hz, 1H), 6.82 (s, 1H), 6.46 (dd, J=1.3, 17.0 Hz, 1H), 6.36 (dd, J=10.0, 17.0 Hz, 1H), 5.81 (dd, J=1.3, 10.0 Hz, 1H), 4.46 (s, 2H). $^{13}$C NMR (100 MHz, $CDCl_3$): δ 172.9, 164.2, 143.9, 138.2, 133.8, 131.8, 127.8, 118.0, 117.7, 117.6, 45.6. HRMS (+ESI): Calculated: 203.0815 ($C_{11}H_{11}N_2O_2$). Observed: 203.0814.

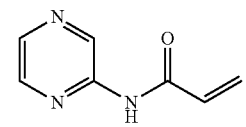

N-(Pyrazin-2-yl)acrylamide (TRH 1-156). To a solution of aminopyrazine (192 mg, 2.0 mmol) in dichloromethane (10 mL) was added acryloyl chloride (0.20 mL, 2.4 mmol) followed by triethylamine (0.34 mL, 2.4 mmol) at 0° C. under $N_2$ atmosphere. After stirring for 20 minutes, the reaction mixture was allowed to warm to room temperature and was stirred overnight. The solution was washed twice with brine, dried with magnesium sulfate, and the resulting crude was purified by silica gel chromatography (50% to 70% ethyl acetate in hexanes) to yield 22 mg of white solid (7% yield). $^1$H NMR (600 MHz, $CDCl_3$): δ 9.65 (d, J=1.3 Hz, 1H), 8.38 (d, J=2.5 Hz, 1H), 8.27 (dd, J=1.6, 2.5 Hz, 1H), 8.19 (s, 1H), 6.54 (dd, J=0.8, 16.9 Hz, 1H), 6.33 (dd, J=10.3, 16.9 Hz, 1H), 5.90 (dd, J=0.8, 10.3 Hz, 1H). $^{13}$C NMR (150 MHz, $CDCl_3$): δ 163.5, 148.2, 142.2, 140.6, 137.4, 130.2, 129.8. HRMS (+ESI): Calculated: 150.0662 ($C_7H_8N_3O$). Observed: 150.0660.

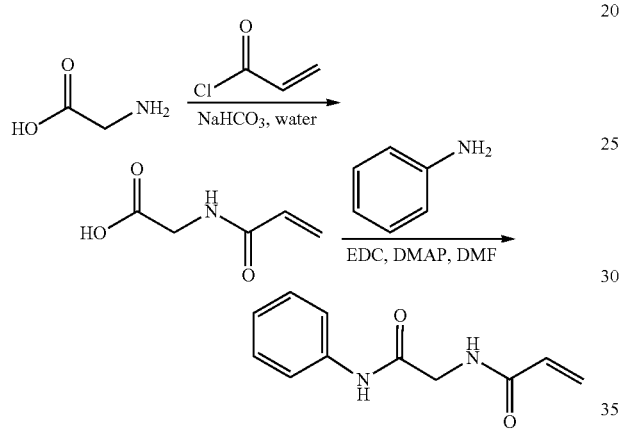

N-(2-oxo-2-(phenylamino)ethyl)acrylamide (TRH 1-160). To a solution of glycine (1.50 g, 20.0 mmol) and sodium bicarbonate (1.70 g, 20.2 mmol) in water (30 mL) at 0° C. was slowly added acryloyl chloride (2.45 mL, 30.2 mmol). After stirring for 3.5 hours, the reaction was extracted 3 times with ethyl acetate. The combined organics were dried over magnesium sulfate, filtered, and concentrated to give an oil. The oil was treated with hexanes causing a white solid to crash out which was collected by gravity filtration to give 124 mg of crude acryloylglycine of which 58 mg (47% of the crude material) was used immediately without further purification. This solid (ca. 0.45 mmol) was dissolved in DMF (2.5 mL) and a solution of N-(3-dimethylaminopropyl)-N'-ethylcarbodiimide hydrochloride (104 mg, 0.54 mmol) and 4-dimethylaminopyridine (68 mg, 0.56 mmol) in DMF (2.5 mL) was added followed by aniline (0.050 mL, 0.54 mmol). The solution was stirred overnight, diluted with ethyl acetate, and washed with both a saturated solution of sodium bicarbonate and brine. The organics were then dried over magnesium sulfate, filtered, and concentrated, and the resulting crude was purified by silica gel chromatography (30-60% ethyl acetate in hexanes) to give 19 mg of the title compound as a white solid (1% yield over two steps). $^1$H NMR (400 MHz, MeOD): δ 7.56-7.53 (m, 2H), 7.30 (t, J=8.0 Hz, 2H), 7.08 (t, J=7.4 Hz, 1H), 6.35 (dd, J=9.9, 17.1 Hz, 1H), 6.26 (dd, J=2.0, 17.1 Hz, 1H), 5.71 (dd, J=2.0, 9.9 Hz, 1H), 4.08 (s, 2H). $^{13}$C NMR (100 MHz, MeOD): δ 169.4, 168.6, 139.5, 131.7, 129.8, 127.2, 125.3, 121.2, 44.0. HRMS (−ESI): Calculated: 203.0826 ($C_{11}H_{11}N_2O_2$). Observed: 203.0825.

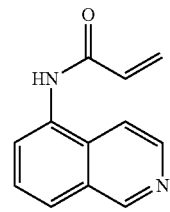

N-(isoquinolin-5-yl)acrylamide (TRH 1-162). To a solution of 5-aminoisoquinoline (287 mg, 2.0 mmol) in dichloromethane (10 mL) was added acryloyl chloride (0.20 mL, 2.4 mmol) followed by triethylamine (0.34 mL, 2.4 mmol) at 0° C. under $N_2$ atmosphere. After stirring for 20 minutes, the reaction mixture was allowed to warm to room temperature and was stirred overnight. The solution was washed with brine, and the resulting aqueous layer was extracted with a 2:1 chloroform:methanol solution. The resulting crude was purified by chromatography on basic alumina (50% ethyl acetate in hexanes to 4% ethanol in ethyl acetate) to yield 43 mg of a yellow solid (11% yield). $^1$H NMR (400 MHz, MeOD): δ 9.23 (s, 1H), 8.45 (d, J=6.1 Hz, 1H), 8.03 (d, J=7.5 Hz, 1H), 7.97 (d, J=8.2 Hz, 1H), 7.88 (d, J=6.1 Hz, 1H), 7.68 (t, J=7.9 Hz, 1H), 6.66 (dd, J=10.2, 17.0 Hz, 1H), 6.47 (dd, J=1.5, 17.0 Hz, 1H), 5.88 (dd, J=1.7, 10.2 Hz, 1H). $^{13}$C NMR (100 MHz, MeOD): δ 167.1, 153.5, 143.0, 133.6, 132.4, 131.9, 130.6, 128.7, 127.9, 127.1, 117.2. HRMS (+ESI): Calculated: 199.0866 ($C_{12}H_{11}N_2O$). Observed: 199.0863.

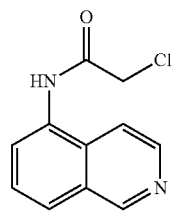 [SMILES: O=C(CCl)Nc1cccc2cnccc12]

2-Chloro-N-(isoquinolin-5-yl)acetamide (TRH 1-163). To a solution 5-aminoisoquinoline (289 mg, 2.0 mmol) in dichloromethane (10 mL) was added chloroacetyl chloride (0.19 mL, 2.4 mmol) followed by triethylamine (0.34 mL, 2.4 mmol) at 0° C. under $N_2$ atmosphere. After stirring for 20 minutes, the reaction mixture was allowed to warm to room temperature and was stirred overnight. The solution was washed with saturated sodium bicarbonate solution and brine, dried with magnesium sulfate, and the resulting crude was purified by chromatography on basic alumina (30% ethyl acetate in hexanes to 4% ethanol in ethyl acetate) to yield 157 mg of yellow solid (36% yield). $^1$H NMR (600 MHz, MeOD): δ 9.26 (s, 1H), 8.48 (d, J=6.1 Hz, 1H), 8.03 (d, J=8.2 Hz, 1H), 7.98 (d, J=7.4 Hz, 1H), 7.91 (d, J=6.1 Hz, 1H), 7.71 (t, J=7.9 Hz, 1H), 4.39, (s, 2H). $^{13}$C NMR (150 MHz, MeOD): δ 167.4, 152.1, 141.7, 131.8, 131.2, 129.2, 127.3, 127.0, 126.1, 115.7, 42.3. HRMS (+ESI): Calculated: 221.0476 ($C_{11}H_{10}N_2O$). Observed: 221.0473.

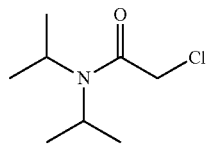

2-Chloro-N,N-diisopropylacetamide (TRH 1-168). To a solution diisopropylamine (0.42 mL, 3.0 mmol) in dichloromethane (10 mL) was added chloroacetyl chloride (0.29 mL, 3.6 mmol) followed by triethylamine (0.50 mL, 3.6 mmol) at 0° C. under $N_2$ atmosphere. After stirring for 20 minutes, the reaction mixture was allowed to warm to room temperature and was stirred overnight. The solution was washed with saturated sodium bicarbonate solution and brine, dried with magnesium sulfate, and the resulting crude was purified by silica gel chromatography (0 to 20% ethyl acetate in hexanes) to yield 376 mg of white solid (70% yield). $^1$H NMR (400 MHz, CDCl$_3$): δ 3.93 (s, 2H), 3.88-3.82 (m, 1H), 3.38-3.31 (m, 1H), 1.29 (d, J=6.5 Hz, 6H), 1.14 (d, J=6.4 Hz, 6H). $^{13}$C NMR (100 MHz, CDCl$_3$): δ 165.0, 49.7, 46.1, 43.2, 20.7, 20.0. HRMS (+ESI): Calculated: 200.0813 (C$_8$H$_{16}$NOClNa). Observed: 200.0811.

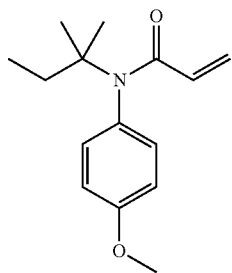 [SMILES: C=CC(=O)N(c1ccc(OC)cc1)C(C)(C)CC]

N-(4-methoxyphenyl)-N-(tert-pentyl)acrylamide (TRH 1-170). To a solution of 4-methoxy-N-(tert-pentyl)aniline (94 mg, 0.49 mmol) in dichloromethane (5 mL) was added acryloyl chloride (0.05 mL, 0.6 mmol) followed by triethylamine (0.09 mL, 0.6 mmol) at 0° C. under $N_2$ atmosphere. After stirring for 15 minutes, the reaction mixture was allowed to warm to room temperature and was stirred for 18 hours. The solution was washed with a saturated solution of sodium bicarbonate followed by brine, dried with magnesium sulfate, and the resulting crude was purified by silica gel chromatography (0% to 20% ethyl acetate in hexanes) to yield 82 mg of a pale-yellow oil (68% yield). $^1$H NMR (400 MHz, CDCl$_3$): δ 6.99 (d, J=8.7 Hz, 2H), 6.85 (d, J=8.7 Hz, 2H), 6.17 (dd, J=1.9, 16.7 Hz, 1H), 5.76 (dd, J=10.3, 16.7 Hz, 1H), 5.28 (dd, J=1.9, 10.3 Hz, 1H), 3.81 (s, 3H), 2.11 (q, J=7.5 Hz, 2H), 1.20 (s, 6H), 0.91 (t, J=7.5 Hz, 3H). $^{13}$C NMR (100 MHz, CDCl$_3$): δ 166.3, 159.0, 134.3, 131.49, 131.45, 125.6, 114.1, 61.7, 55.5, 32.0, 27.4, 9.4. HRMS (+EI): Calculated: 247.1572 (C$_{15}$H$_{21}$NO$_2$). Observed: 247.1577.

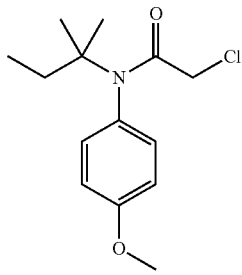 [SMILES: CCC(C)(C)N(C(=O)CCl)c1ccc(OC)cc1]

2-Chloro-N-(4-methoxyphenyl)-N-(tert-pentyl)acetamide (TRH 1-171). To a solution 4-methoxy-N-(tert-pentyl)aniline (95 mg, 0.5 mmol) in dichloromethane (5 mL) was added chloroacetyl chloride (0.05 mL, 0.6 mmol) followed by triethylamine (0.085 mL, 0.6 mmol) at 0° C. under $N_2$ atmosphere. After stirring for 15 minutes, the reaction mixture was allowed to warm to room temperature and was stirred overnight. The solution was washed with saturated sodium bicarbonate solution and brine, dried with magnesium sulfate, and the resulting crude was purified by silica gel chromatography (0 to 10% ethyl acetate in hexanes) to yield 99 mg of a yellow oil (74% yield). $^1$H NMR (400 MHz, CDCl$_3$): δ 7.04 (d, J=8.6 Hz, 2H), 6.87 (d, J=8.6 Hz, 2H), 3.80 (s, 3H), 3.63 (s, 2H), 2.05 (q, J=7.4 Hz, 2H), 1.16 (s, 6H), 0.90 (t, J=7.4 Hz, 3H). $^{13}$C NMR (100 MHz, CDCl$_3$): δ 166.0, 159.5, 133.2, 131.0, 114.5, 62.5, 55.5, 44.8, 31.8, 27.1, 9.3. HRMS (+ESI): Calculated: 270.1255 (C$_{14}$H$_{21}$NO$_2$Cl). Observed: 270.1254.

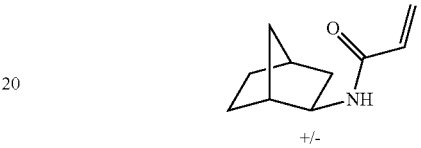

+/−

N-(exo-norborn-2-yl)acrylamide (TRH 1-176). To a solution of exo-2-aminonorbornane (0.24 mL, 2 mmol) in dichloromethane (10 mL) was added acryloyl chloride (0.20 mL, 2.4 mmol) followed by triethylamine (0.33 mL, 2.4 mmol) at 0° C. under $N_2$ atmosphere. After stirring for 20 minutes, the reaction mixture was allowed to warm to room temperature and was stirred for 18 hours. The solution was washed with a saturated solution of sodium bicarbonate followed by brine, dried with magnesium sulfate, and the resulting crude was purified by silica gel chromatography (30% ethyl acetate in hexanes) to yield 271 mg of a white solid (82% yield). $^1$H NMR (400 MHz, CDCl$_3$): δ 6.42 (s, 1H), 6.25 (dd, J=2.3, 17.0 Hz, 1H), 6.18 (dd, J=9.5, 17.0 Hz, 1H), 5.58 (dd, J=2.3, 9.5 Hz, 1H), 3.8-3.77 (m, 1H), 2.27-2.24 (m, 2H), 1.78 (ddd, J=2.1, 8.1, 13.0 Hz, 1H), 1.55-1.38 (m, 3H), 1.30-1.10 (m, 4H). $^{13}$C NMR (100 MHz, CDCl$_3$): δ 165.0, 131.4, 125.8, 52.9, 42.4, 40.0, 35.7, 35.6, 28.2, 26.6. HRMS (+EI): Calculated: 165.1154 (C$_{10}$H$_{15}$NO). Observed: 165.1155.

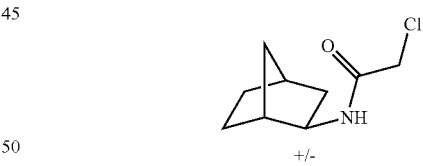

+/−

2-Chloro-N-(exo-norborn-2-yl)acetamide (TRH 1-177). To a solution of exo-2-aminonorbornane (0.24 mL, 2 mmol) in dichloromethane (10 mL) was added chloroacetyl chloride (0.19 mL, 2.4 mmol) followed by triethylamine (0.33 mL, 2.4 mmol) at 0° C. under $N_2$ atmosphere. After stirring for 20 minutes, the reaction mixture was allowed to warm to room temperature and was stirred overnight. The solution was washed with saturated sodium bicarbonate solution and brine, dried with magnesium sulfate, and the resulting crude was purified by silica gel chromatography (20 to 40% ethyl acetate in hexanes) to yield 345 mg of a white solid (91% yield). $^1$H NMR (400 MHz, CDCl$_3$): δ 6.48 (s, 1H), 3.93 (s, 2H), 3.67-3.63 (m, 1H), 2.24-2.22 (m, 1H), 2.16-2.15 (m, 1H), 1.74 (ddd, J=1.9, 8.1, 13.0 Hz, 1H), 1.50-1.36 (m, 2H), 1.30-1.26 (m, 1H), 1.21-1.14 (m, 3H), 1.09-1.03 (m, 1H).

<sup>13</sup>C NMR (100 MHz, CDCl₃): δ 165.0, 53.1, 42.6, 42.2, 40.0, 35.6, 35.5, 28.0, 26.3. HRMS (+ESI): Calculated: 187.0764 ($C_9H_{14}NOCl$). Observed: 187.0765.

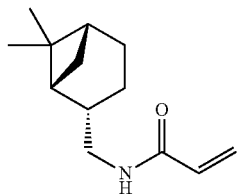

N-(((1R,2S,5R)-6,6-dimethylbicyclo[3.1.1]heptan-2-yl)methyl)acrylamide (TRH 1-178). To a solution of (−)-cis-myrtanylamine (0.34 mL, 2 mmol) in dichloromethane (10 mL) was added acryloyl chloride (0.20 mL, 2.4 mmol) followed by triethylamine (0.33 mL, 2.4 mmol) at 0° C. under N₂ atmosphere. After stirring for 20 minutes, the reaction mixture was allowed to warm to room temperature and was stirred for 21 hours. The solution was washed with a saturated solution of sodium bicarbonate followed by brine, dried with magnesium sulfate, and the resulting crude was purified by silica gel chromatography (20 to 30% ethyl acetate in hexanes) to yield 369 mg of a white solid (89% yield). ¹H NMR (600 MHz, CDCl₃): δ 6.26 (dd, J=1.5, 17.0 Hz, 1H), 6.11 (dd, J=10.3, 17.0 Hz, 1H) 5.85 (s, 1H), 5.61 (dd, J=1.5, 10.3 Hz, 1H), 3.39-3.29 (m, 2H), 2.38-2.34 (m, 1H), 2.26-2.21 (m, 1H), 1.98-1.90 (m, 4H), 1.88-1.83 (m, 1H), 1.53-1.47 (m, 1H), 1.19 (s, 3H), 1.04 (s, 3H), 0.89 (d, J=9.6 Hz, 1H). ¹³C NMR (150 MHz, CDCl₃): δ 165.7, 131.2, 126.2, 45.3, 43.9, 41.5, 38.8, 33.3, 28.1, 26.1, 23.3, 19.9. HRMS (−ESI): Calculated: 206.1550 ($C_{13}H_{20}NO$). Observed: 206.1551.

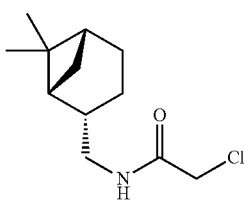

2-Chloro-N-(((1R,2S,5R)-6,6-dimethylbicyclo[3.1.1]heptan-2-yl)methyl)acetamide (TRH 1-179). To a solution of (−)-cis-myrtanylamine (0.34 mL, 2 mmol) in dichloromethane (10 mL) was added chloroacetyl chloride (0.19 mL, 2.4 mmol) followed by triethylamine (0.33 mL, 2.4 mmol) at 0° C. under N₂ atmosphere. After stirring for 20 minutes, the reaction mixture was allowed to warm to room temperature and was stirred overnight. The solution was washed with saturated sodium bicarbonate solution and brine, dried with magnesium sulfate, and the resulting crude was purified by silica gel chromatography (0 to 20% ethyl acetate in hexanes) to yield 405 mg of an off-white solid (88% yield). ¹H NMR (600 MHz, CDCl₃): δ 6.61 (s, 1H), 4.05 (s, 2H), 3.33-3.30 (m, 2H), 2.40-2.36 (m, 1H), 2.27-2.21 (m, 1H), 1.99-1.83 (m, 5H), 1.53-1.46 (m, 1H), 1.20 (s, 3H), 1.05 (s, 3H), 0.90 (d, J=9.7 Hz, 1H). ¹³C NMR (150 MHz, CDCl₃): δ 165.8, 45.5, 43.8, 42.9, 41.4, 41.2, 38.8, 33.3, 28.0, 26.0, 23.3, 19.8. HRMS (−ESI): Calculated: 228.1161 ($C_{12}H19NOCl$). Observed: 228.1162.

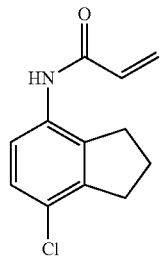

N-(7-chloro-2,3-dihydro-1H-inden-4-yl)acrylamide (YP 1-1). A solution of N-(2,3-dihydro-1H-inden-4-yl)acrylamide (187 mg, 1.0 mmol) in PEG 400 (5.2 mL) was cooled to 0° C. To the solution was added N-chlorosuccinimide (140 mg, 1.0 mmol). The solution was allowed to warm to room temperature after 30 min and stirred overnight. The solution was diluted with ethyl acetate and washed two times with brine and dried with magnesium sulfate. The crude product was purified via silica gel chromatography (30% ethyl acetate in hexanes). The obtained mixture of isomers was separated by recrystallization to afford the product in 22% yield as a white solid (47 mg). ¹H NMR (400 MHz, CDCl₃): δ 7.78 (d, J=8.8 Hz, 1H), 7.15-7.11 (m, 2H), 6.42 (dd, J=1.4, 16.8 Hz, 1H), 6.26 (dd, J=10.2, 16.8 Hz, 1H), 5.77 (dd, J=1.4, 10.2 Hz, 1H), 2.98 (t, J=7.6 Hz, 2H), 2.87 (t, J=7.5 Hz, 2H), 2.12 (quint, J=7.5 Hz, 2H). ¹³C NMR (100 MHz, CDCl₃): δ 163.4, 143.1, 136.1, 132.2, 131.0, 128.0, 127.2, 126.7, 120.9, 32.7, 31.1, 24.0. HRMS (+ESI): Calculated: 220.0535 ($C_{12}H_{11}ClNO$). Observed: 220.0533.

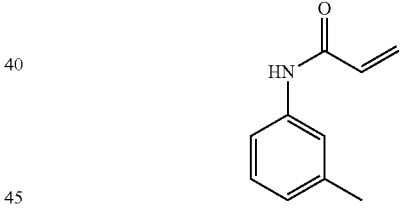

N-(m-tolyl)acrylamide (YP 1-16). A solution of o-toluidine (107 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 40 min and stirred overnight. The solution was washed two times with brine and dried with magnesium sulfate. The crude product was purified via silica gel chromatography (20% to 40% ethyl acetate in hexanes) to afford the product in 86% yield as a white solid (139 mg). ¹H NMR (400 MHz, CDCl₃): δ 7.82 (d, J=7.9 Hz, 1H), 7.32 (s, 1H), 7.21-7.17 (m, 2H), 7.10-7.06 (m, 1H), 6.43-6.38 (m, 1H), 6.29 (dd, J=10.2, 17.1 Hz, 1H), 5.75-5.72 (m, 1H), 2.25 (s, 1H). ¹³C NMR (100 MHz, CDCl₃): δ 135.5, 131.2, 130.5, 127.5, 126.8, 125.5, 123.4, 17.8. HRMS (+ESI): Calculated: 162.0913 ($C_{10}H_{12}NO$). Observed: 162.0912.

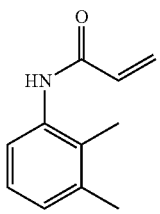

N-(2,3-dimethylphenyl)acrylamide (YP 1-18). A solution of 2,3-dimethylaniline (121 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 29 min and stirred overnight. The solution was washed two times with brine and dried with magnesium sulfate. The crude product was purified via silica gel chromatography (30% to 40% ethyl acetate in hexanes) to afford the product in 88% yield as a white solid (154 mg). $^1$H NMR (400 MHz, CDCl$_3$): δ 7.49 (d, J=7.9 Hz, 1H), 7.29 (s, 1H), 7.11-7.07 (m, 1H), 7.01 (d, J=7.7, 1H) 6.40 (d, J=17.1, 1H), 6.30 (dd, J=7.3, 17.1 Hz, 1H), 5.74 (d, J=10.1 Hz, 11H), 2.29 (s, 1H), 2.13 (s, 1H). $^{13}$C NMR (100 MHz, CDCl$_3$): δ 135.1, 131.2, 127.6, 127.3, 125.9, 122.3, 20.6, 13.9. HRMS (+ESI): Calculated: 176.1070 (C$_{11}$H$_{14}$NO). Observed: 176.1068.

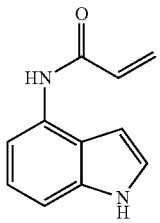

N-(1H-indol-4-yl)acrylamide (YP 1-19). A solution of 4-aminoindole (132 mg, 1 mmol) in DCM (5 mL) and DMF (5 mL) was cooled to 0° C. To the solution was added acryloyl chloride (109 mg, 1.2 mmol) followed by triethylamine (121 mg, 1.2 mmol). The solution was allowed to warm to room temperature after 26 min and stirred overnight. The solution was washed two times with brine and dried with magnesium sulfate. The crude product was purified via basic alumina chromatography (60% to 75% ethyl acetate in hexanes) to afford the product in 30% yield as a white-grey solid (56 mg). $^1$H NMR (600 MHz, MeOD): δ 7.51 (d, J=7.6 Hz, 1H), 7.24-7.22 (m, 2H), 7.08 (t, J=7.6 Hz, 1H), 6.64 (dd, J=10.1, 16.7 Hz, 2H), 6.38 (dd, J=1.7, 16.9 Hz, 1H), 5.78 (dd, J=1.7, 10.3 Hz, 1H), 4.6 (s, 1H). $^{13}$C NMR (150 MHz, MeOD): δ 165.0, 137.2, 131.1, 129.2, 126.0, 123.8, 121.5, 120.9, 112.2, 108.4, 98.5. HRMS (+ESI): Calculated: 187.0866 (C$_{11}$H$_{11}$N$_2$O). Observed: 187.0865.

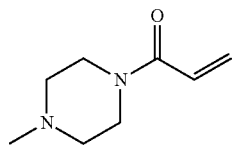

1-(4-Methylpiperazin-1-yl)prop-2-en-1-one (YP 1-22). A solution of 1-methylpiperazine (100 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 30 min and stirred overnight. The solution was washed two times with brine and dried with magnesium sulfate. The crude product was purified via silica gel chromatography (85% to 100% ethyl acetate in hexanes) to afford the product in 29% yield as a yellow gel (44 mg). $^1$H NMR (400 MHz, CDCl$_3$): δ 6.56 (dd, J=10.6, 16.9 Hz, 1H), 6.29 (dd, J=2.0, 16.8 Hz, 1H), 5.69 (dd, J=2.0, 10.6 Hz, 1H), 3.71 (s, 2H), 3.58 (s, 2H), 2.42 (t, J=5.1 Hz, 4H), 2.32 (s, 3H). $^{13}$C NMR (100 MHz, CDCl$_3$): δ 165.4, 127.8, 127.5, 55.2, 54.6, 46.0, 45.7, 41.9. HRMS (+ESI): Calculated: 155.1179 (C$_8$H$_{15}$N$_2$O). Observed: 155.1178.

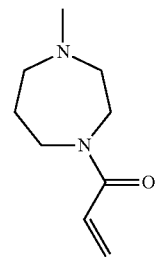

1-(4-methyl-1,4-diazepan-1-yl)prop-2-en-1-one (YP 1-23). A solution of 1-methylhomopiperazine (114 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 32 minutes and stirred overnight. The solution was washed two times with brine and dried with magnesium sulfate. The crude product was purified via silica gel chromatography (1% to 10% methanol in DCM) to afford the product in 51% yield as a yellow oil (58 mg). $^1$H NMR (400 MHz, CDCl$_3$): δ 6.61-6.53 (m, 1H), 6.35-6.29 (m, 1H), 5.70-5.66 (m, 1H), 3.74-3.72 (m, 1H), 3.69 (t, J=6.4 Hz, 1H), 3.65-3.61 (m, 2H), 2.66-2.63 (m, 2H), 2.59-2.54 (m, 2H), 2.37 (s, 3H), 1.94 (quint, J=6.2 Hz, 2H). $^{13}$C NMR (100 MHz, CDCl$_3$): δ 166.4, 166.3, 128.0, 127.9, 127.8, 127.6, 59.1, 58.0, 57.1, 56.8, 47.4, 47.1, 46.7, 46.6, 45.3, 44.8, 28.1, 26.9. HRMS (+ESI): Calculated: 169.1335 (C$_9$H$_{17}$N$_2$O). Observed: 169.1333.

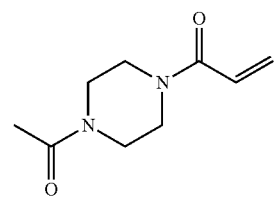

1-(4-acetylpiperazin-1-yl)prop-2-en-1-one (YP 1-24). A solution of 1-acetylpiperazine (128 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 23 minutes and stirred for two hours. The solution was washed two times with brine and dried with magnesium sulfate. The crude product was purified via silica gel chromatography (0% to 10% methanol in DCM) to afford the product in 18% yield as a yellow oil (40 mg). $^1$H NMR (400 MHz, CDCl$_3$): δ 6.57 (dd, J=10.5, 16.8 Hz, 1H), 6.33 (dd, J=1.8, 16.8 Hz, 1H), 5.75 (dd, J=1.9, 10.5 Hz, 1H), 3.72 (s, 1H), 3.66-3.64 (m, 3H), 3.57 (s, 1H), 3.51-3.49 (m, 2H), 2.13 (s, 3H). $^{13}$C NMR (100 MHz, CDCl$_3$): δ 165.6, 128.7, 127.0, 41.9, 41.4, 21.4. HRMS (+ESI): Calculated: 183.1128 (C$_9$H$_{15}$N$_2$O$_2$). Observed: 183.1126.

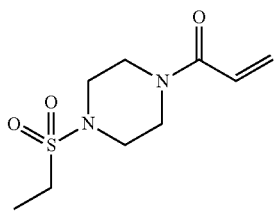

1-(4-(Ethylsulfonyl)piperazin-1-yl)prop-2-en-1-one (YP 1-25). A solution of 1-(ethanesulfonyl)piperazine (178 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 27 min and stirred for two hours. The solution was washed two times with brine and dried with magnesium sulfate. The crude product was purified via silica gel chromatography (1% to 10% methanol in DCM) to afford the product in 70% yield as a white-yellow solid (163 mg). $^1$H NMR (400 MHz, CDCl$_3$): δ 6.57 (dd, J=10.5, 16.8 Hz, 1H), 6.32 (dd, J=1.9, 16.8 Hz, 1H), 5.76 (dd, J=1.8, 10.5 Hz, 1H), 3.77 (s, 2H), 3.67 (s, 2H), 3.32 (t, J=5.2 Hz, 4H), 2.98 (q, J=7.5 Hz, 2H), 1.37 (t, J=7.4, 3H). $^{13}$C NMR (100 MHz, CDCl$_3$): δ 165.5, 128.8, 127.0, 77.4, 45.9, 45.6, 44.2, 41.9, 7.8. HRMS (+ESI): Calculated: 233.0954 (C$_9$H$_7$N$_2$O$_3$S$_1$). Observed: 233.0953.

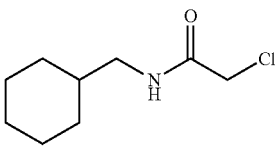 [SMILES: O=C(CCl)NCC1CCCCC1]

2-chloro-N-(cyclohexylmethyl)acetamide (YP 1-31). Following General Procedure B starting from cyclohexanemethylamine (113 mg, 1.0 mmol), product was obtained after silica gel chromatography (100% dichloromethane to 3% methanol in dichloromethane) in 60% yield as a white solid (112 mg). $^1$H NMR (400 MHz, CDCl$_3$): δ 6.70 (s, 1H), 4.06 (s, 2H), 3.15 (t, J=6.47 Hz, 2H), 1.77-1.65 (m, 5H), 1.56-1.46 (m, 1H), 1.30-1.10 (m, 3H), 1.00-0.90 (m, 2H). $^{13}$C NMR (100 MHz, CDCl$_3$): δ 165.8, 58.1, 46.0, 42.8, 37.7, 30.7, 26.3, 25.7, 18.2. HRMS (+ESI): Calculated: 190.0993 (C$_9$H$_{17}$ONCl). Observed: 190.0992.

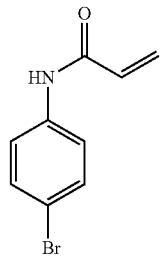

N-(4-bromophenyl)acrylamide (YP 1-36). Following General Procedure A starting from 4-bromoaniline (688 mg, 4.0 mmol), product was obtained after silica gel chromatography (30% to 60% ethyl acetate in hexanes) in 28% yield as a white solid (250 mg). $^1$H NMR (400 MHz, CD$_3$OD): δ 7.90 (s, 1H), 7.60-7.56 (m, 2H), 7.47-7.44 (m, 2H), 6.45-6.33 (m, 2H), 5.78 (dd, J=2.8, 9.1 Hz, 1H). $^{13}$C NMR (100 MHz, CD$_3$OD): δ 164.7, 137.7, 131.4, 130.9, 126.7, 121.5, 116.3, 101.1, 78.1. HRMS (+ESI): Calculated: 223.9716 (C$_9$H$_7$NOBr). Observed: 223.9719.

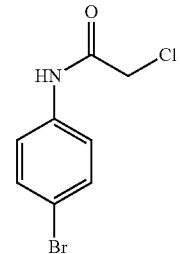 [SMILES: O=C(CCl)Nc1ccc(Br)cc1]

N-(4-bromophenyl)-2-chloroacetamide (YP 1-37). Following General Procedure B starting from 4-bromoaniline (688 mg, 4.0 mmol), product was obtained after silica gel chromatography (30% to 60% ethyl acetate in hexanes) in 49% yield as a white solid (491 mg). $^1$H NMR (400 MHz, CD$_3$OD): δ 7.9 (s, 1H), 7.57-7.53 (m, 2H), 7.50-7.47 (m, 2H), 4.17 (s, 2H). $^{13}$C NMR (100 MHz, CD$_3$OD): δ 166.0, 137.2, 131.5, 121.6, 116.7, 99.3, 78.1, 42.6. HRMS (+ESI): Calculated: 245.9327 (C$_8$H$_6$NOBrCl). Observed: 245.9329.

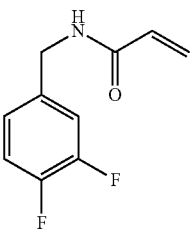

N-(3,4-difluorobenzyl)acrylamide (YP 1-38). Following General Procedure A starting from 3,4-difluorobenzylamine (286 mg, 2.0 mmol), product was obtained after silica gel chromatography (40% to 80% ethyl acetate in hexanes) in 61% yield as a white solid (239 mg). $^1$H NMR (400 MHz, CDCl$_3$): δ 7.56 (t, J=6.2, 1H), 7.07-7.00 (m, 2H), 6.95-6.91 (m, 1H), 6.21-6.20 (m, 2H), 5.62-5.59 (m, 1H), 4.35 (d, J=6.1, 2H). $^{13}$C NMR (100 MHz, CDCl$_3$): δ 166.1, 151.4 (d), 150.7 (d), 148.9 (d), 148.2 (d), 135.5-135.4 (m), 130.5, 126.8, 123.5-123.4 (m), 117.2 (d), 116.3 (d), 42.4. HRMS (+ESI): Calculated: 196.0579 (C$_{10}$H$_8$NOF$_2$). Observed: 196.0582.

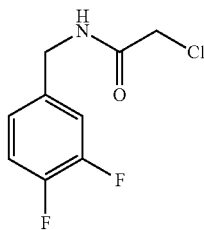 [SMILES: O=C(CCl)NCc1ccc(F)c(F)c1]

2-chloro-N-(3,4-difluorobenzyl)acetamide (YP 1-39). Following General Procedure B starting from 3,4-difluorobenzylamine (286 mg, 2.0 mmol), product was obtained after silica gel chromatography (40% to 50% ethyl acetate in hexanes) in 82% yield as a white solid (359 mg). $^1$H NMR (400 MHz, CDCl$_3$): δ 7.23 (s, 1H), 7.15-7.08 (m, 2H), 7.03-7.6.99 (m, 1H), 4.42 (d, J=6.1 Hz, 2H), 4.08 (s, 2H). $^{13}$C NMR (100 MHz, CDCl$_3$): δ 166.3, 151.5 (d), 151.0 (d), 149.1 (d), 148.5 (d), 134.7-134.6 (m), 123.7-123.6 (m), 117.5 (d), 116.6 (d), 42.6 (d). HRMS (+ESI): Calculated: 218.0190 (C$_9$H$_7$NOClF$_2$). Observed: 218.0192

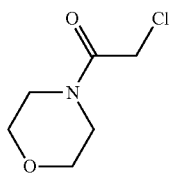

2-chloro-1-morpholinoethan-1-one (YP 1-40). Following General Procedure B starting from morpholine (174 mg, 2.0 mmol), product was obtained after silica gel chromatography (85% ethyl acetate in hexanes) in 61% yield as a white solid (200 mg). $^1$H NMR (400 MHz, CDCl$_3$): δ 4.01 (s, 2H), 3.65-3.59 (m, 4H), 3.55-3.52 (m, 2H), 3.45 (t, J=4.8 Hz, 2H). $^{13}$C NMR (100 MHz, CDCl$_3$): δ 165.1, 66.5 (d), 46.6, 42.4, 40.7. HRMS (+ESI): Calculated: 186.0292 (C$_6$H$_{10}$O$_2$NClNa). Observed: 186.0292.

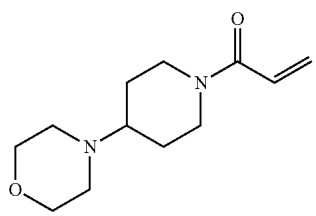 [SMILES: C=CC(=O)N1CCC(N2CCOCC2)CC1]

1-(4-morpholinopiperidin-1-yl)prop-2-en-1-one (YP 1-42). Following General Procedure A starting from 4-morpholinopiperidine (336 mg, 2.0 mmol), product was obtained after silica gel chromatography (1% methanol and 80% ethyl acetate in hexanes) in 58% yield as a colorless oil (259 mg). $^1$H NMR (400 MHz, CDCl$_3$): δ 6.42 (dd, J=10.6, 16.8 Hz, 1H), 6.06 (dd, J=2.0, 16.8 Hz, 1H), 5.49 (dd, J=2.0, 10.6 Hz, 1H), 4.45 (d, J=12.8 Hz, 11H), 3.86 (d, J=12.8 Hz, 1H), 3.52 (t, J=4.7 Hz, 4H), 2.90 (t, J=12.8 Hz, 1H), 2.55-2.48 (m, 1H), 2.37-2.35 (m, 4H), 2.26 (tt, J=3.7, 11.0 Hz, 1H), 1.72 (d, J=12.8 Hz, 2H), 1.30-1.20 (m, 2H). $^{13}$C NMR (100 MHz, CDCl$_3$): δ 165.0, 127.7, 127.3, 67.1, 61.6, 49.6, 44.9, 41.1, 28.9, 27.8. HRMS (+ESI): Calculated: 225.1598 (C$_{12}$H$_{21}$N$_2$O$_2$). Observed: 225.1595.

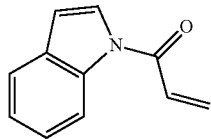

1-(1H-indol-1-yl)prop-2-en-1-one (YP 1-44). A solution of indole (117 mg, 1.0 mmol) in 2-methyltetrahydrofuran (10 mL) was cooled to 0° C. To the solution was added sodium hydride (60 mg, 2.5 mmol). The resultant intermediate was subjected to General Procedure A and product was obtained after alumina gel chromatography (10% to 40% ethyl acetate in hexanes) in 8% yield as a white solid (14 mg). $^1$H NMR (400 MHz, CD$_3$OD): δ 8.48-8.46 (m, 1H), 7.82 (d, J=3.9 Hz, 1H), 7.61-7.59 (m, 1H), 7.36-7.32 (m, 1H), 7.31-7.21 (m, 2H), 6.73 (dd, J=0.8, 3.8 Hz, 1H), 6.64 (dd, J=1.7, 16.7 Hz, 1H), 6.09 (dd, J=1.7, 10.5 Hz, 1H). $^{13}$C NMR (100 MHz, CD$_3$OD): δ 164.3, 135.7, 131.0, 130.9, 128.0, 125.0, 124.4, 123.6, 120.5, 116.2, 108.9. HRMS (+ESI): Calculated: 172.0757 (C$_{11}$H$_{10}$NO). Observed: 172.0756.

Synthesis and characterization of TRH 1-23 Analogs and CCW 28-3 Degrader.

General synthetic methods. Chemicals and reagents were purchased from major commercial suppliers and used without further purification. Reactions were performed under a nitrogen atmosphere unless otherwise noted. Silica gel flash column chromatography was performed using EMD or Sigma Aldrich silica gel 60 (230-400 mesh). Proton and carbon nuclear magnetic resonance ($^1$H NMR and $^{13}$C NMR) data was acquired on a Bruker AVB 400, AVQ 400, or AV 600 spectrometer at the University of California, Berkeley. High resolution mass spectrum were obtained from the QB3 mass spectrometry facility using positive or negative electrospray ionization (+ESI or −ESI). Yields are reported as a single run.

General method for chloroacetamide synthesis. The amine (1 eq.) was dissolved in anhydrous DCM (2-10 mL) in a 20 mL scintillation vial. To the solution was added 2-chloroacetyl chloride (Sigma, 1.2 eq.) followed by triethylamine (Sigma, 1.2 eq.). The solution was stirred overnight under nitrogen. The reaction was monitored by TLC with ninhydrin staining. Upon reaction completion, the solvent was removed with rotary evaporation and the crude applied directly to a silica gel column for flash chromatography which gave the corresponding chloroacetamide.

2-chloro-N-(4-(4-(trifluoromethyl)phenoxy)phenyl)acetamide (CCW 1). To a solution of 4-(4-(trifluoromethyl)phenoxy)aniline (AK Scientific, 63 mg, 0.25 mmol) in DCM 2-chloroacetyl chloride (Sigma, 34 mg, 0.30 mmol) and triethylamine (Sigma, 30.4 mg, 0.30 mmol) were added and the reaction stirred overnight. Upon reaction completion the crude was purified by silica gel chromatography (10-40% EtOAc/hexanes) to yield 65 mg (78%). $^1$H NMR (400 MHz, CDCl$_3$): δ 8.25 (s, 1H), 7.63-7.51 (m, 4H), 7.12-6.99 (m, 4H), 4.22 (s, 2H). HRMS: (−ESI): calcd. for: C$_{15}$H$_{10}$O$_2$NF$_3$Cl=328.0358, found: 327.0356.

2-chloro-N-(4-(3-fluorophenoxy)phenyl)acetamide (CCW 2). To a solution of 4-(3-fluorophenoxy)aniline (AK Scientific, 63 mg, 0.31 mmol) in DCM 2-chloroacetyl chloride (Sigma, 42 mg, 0.37 mmol) and triethylamine (Sigma, 38 mg, 0.37 mmol) were added and the reaction stirred overnight. Upon reaction completion the crude was purified by silica gel chromatography (10-40% EtOAc/hexanes) to yield 53 mg (61%). $^1$H NMR (400 MHz, CDCl$_3$): δ 8.24 (s, 1H), 7.55 (dq, J=10.0, 3.5, 2.4 Hz, 2H), 7.33-7.23 (m, 1H), 7.05 (dq, J=10.1, 3.5, 2.6 Hz, 2H), 6.85-6.74 (m, 2H), 6.69 (dq, J=10.2, 2.3 Hz, 1H), 4.21 (s, 2H). $^{13}$C NMR (151 MHz, CDCl$_3$): δ 164.29, 163.75, 162.66, 158.85, 158.78, 153.31, 132.67, 130.51, 130.45, 121.95, 120.13, 113.71, 113.69, 109.98, 109.84, 105.92, 105.75, 77.19, 76.97, 76.76, 42.79. HRMS: (−ESI): calcd. for: $C_{14}H_{10}O_2NFCl$=278.0390, found: 278.0389.

2-chloro-N-(3-chloro-4-(4-chlorophenoxy)phenyl)acetamide (CCW 3). To a solution of 3-chloro-4-(4-chlorophenoxy)aniline (Sigma, 64 mg, 0.25 mmol) in DCM 2-chloroacetyl chloride (Sigma, 34 mg, 0.30 mmol) and triethylamine (Sigma, 30.4 mg, 0.30 mmol) were added and the reaction stirred overnight. Upon reaction completion the crude was purified by silica gel chromatography (10-40% EtOAc/hexanes) to yield 69 mg (83%). $^1$H NMR (400 MHz, CDCl$_3$): δ 8.28 (s, 1H), 7.83 (d, J=2.6 Hz, 1H), 7.44 (dd, J=8.8, 2.6 Hz, 1H), 7.36-7.28 (m, 3H), 7.05 (d, J=8.8 Hz, 1H), 6.95-6.89 (m, 2H), 4.25 (s, 2H). $^{13}$C NMR (151 MHz, CDCl$_3$): δ 163.85, 155.67, 148.97, 133.57, 129.72, 128.30, 126.60, 122.59, 121.48, 119.87, 118.65, 77.20, 76.98, 76.77, 42.73. HRMS: (−ESI): calcd. for: $C_{14}H_9O_2NCl$=327.9704, found: 327.9702.

2-chloro-N-(4-(4-methoxyphenoxy)phenyl)acetamide (CCW 5). To a solution of 4-(4-methoxyphenoxy)aniline HCl (Astatech, 63 mg, 0.25 mmol) in DCM 2-chloroacetyl chloride (Sigma, 34 mg, 0.30 mmol) and triethylamine (Sigma, 60.8 mg, 0.60 mmol) were added and the reaction stirred overnight. Upon reaction completion the crude was purified by silica gel chromatography (10-40% EtOAc/hexanes) to yield 69 mg (95%). $^1$H NMR (400 MHz, CDCl$_3$): δ 8.18 (s, 1H), 7.49-7.42 (m, 2H), 7.00-6.84 (m, 6H), 4.19 (s, 2H), 3.80 (s, 3H). $^{13}$C NMR (151 MHz, CDCl$_3$): δ 163.67, 155.92, 155.72, 150.11, 131.22, 121.95, 120.57, 118.14, 114.87, 77.18, 76.97, 76.76, 55.63, 42.79. HRMS: (−ESI): calcd. for: $C_{15}H_{13}O_3NCl$=290.0589, found: 290.0587.

2-chloro-N-(4-(4-nitrophenoxy)phenyl)acetamide (CCW 6). To a solution of 4-(4-nitrophenoxy)aniline (Sigma, 50 mg, 0.22 mmol) in DCM 2-chloroacetyl chloride (Sigma, 29 mg, 0.26 mmol) and triethylamine (Sigma, 26 mg, 0.26 mmol) were added and the reaction stirred overnight. Upon reaction completion the crude was purified by silica gel chromatography (10-40% EtOAc/hexanes) to yield 62.5 mg (93%). $^1$H NMR (400 MHz, CDCl$_3$): δ 8.29 (s, 1H), 8.25-8.16 (m, 2H), 7.67-7.59 (m, 2H), 7.14-7.07 (m, 2H), 7.05-6.96 (m, 2H), 4.22 (s, 2H). $^{13}$C NMR (101 MHz, CDCl$_3$): δ 163.93, 163.27, 151.63, 142.77, 133.98, 126.01, 122.18, 121.26, 117.01, 77.36, 77.04, 76.73, 42.85. HRMS: (+ESI): calcd. for: $C_{14}H_{10}O_4N_2Cl$=305.0335, found: 305.0332.

2-chloro-N-(4-(naphthalen-2-yloxy)phenyl)acetamide (CCW 7). To a solution of 2-(4-Aminophenoxy)naphthalene (TCI, 118 mg, 0.50 mmol) in DCM 2-chloroacetyl chloride (Sigma, 67.8 mg, 0.60 mmol) and triethylamine (Sigma, 60.8 mg, 0.60 mmol) were added and the reaction stirred overnight. Upon reaction completion the crude was purified by silica gel chromatography (10-40% EtOAc/hexanes) to yield 111 mg (71%). $^1$H NMR (400 MHz, CDCl$_3$): δ 8.25 (s, 1H), 7.83 (dt, J=7.8, 3.3 Hz, 2H), 7.69 (d, J=8.1 Hz, 1H), 7.57-7.50 (m, 2H), 7.49-7.37 (m, 2H), 7.31-7.22 (m, 2H), 7.12-7.03 (m, 2H), 4.21 (s, 2H). $^{13}$C NMR (101 MHz, CDCl$_3$): δ 163.86, 155.13, 154.31, 134.30, 132.22, 130.19, 129.93, 127.77, 127.14, 126.63, 124.80, 122.10, 119.84, 119.76, 113.84, 77.39, 77.07, 76.75, 42.89. HRMS: (+ESI): calcd. for: $C_8H_{15}O_2NCl$=312.0786, found: 312.0785.

2-chloro-N-(4-(3,5-dimethylphenoxy)phenyl)acetamide (CCW 8). To a solution of 4-(3,5-dimethylphenoxy)aniline (Enamine, 107 mg, 0.50 mmol) in DCM 2-chloroacetyl chloride (Sigma, 67.8 mg, 0.60 mmol) and triethylamine (Sigma, 60.8 mg, 0.60 mmol) were added and the reaction stirred overnight. Upon reaction completion the crude was purified by silica gel chromatography (10-40% EtOAc/hexanes) to yield 60 mg (41%). $^1$H NMR (400 MHz, CDCl$_3$): δ 8.22 (s, 1H), 7.53-7.46 (m, 2H), 7.03-6.96 (m, 2H), 6.74 (s, 1H), 6.61 (s, 2H), 4.20 (s, 2H), 2.28 (s, 6H). $^{13}$C NMR (101 MHz, CDCl$_3$): δ 163.80, 157.21, 154.61, 139.67, 131.79, 125.09, 121.98, 119.55, 116.36, 77.37, 77.06, 76.74, 42.87, 21.33. HRMS: (+ESI): calcd. for: $C_{18\backslash 6}H_{17}O_2NCl$=290.0942, found: 290.0941.

N-benzyl-4-(4-methoxyphenoxy)aniline (CCW 14). 4-(4-methoxyphenoxy)aniline (Astatech, 108 mg, 0.50 mmol) was dissolved in anhydrous DCM (5 mL) in a 20 mL scintillation vial. Benzaldehyde (Alfa Aesar, 53 mg, 0.50 mmol) was added and the solution stirred for 2 h under nitrogen. Sodium triacetoxyborohydride (Sigma, 159 mg, 0.75 mmol) was added in small aliquots and the reaction stirred overnight. TLC (20% EtOAc/hexanes) showed full conversion of starting materials. The solution was washed with saturated sodium bicarbonate and, followed by brine. The aqueous fractions were combined, extracted with 3×5 mL EtOAc and all organic fractions combined, concentrated and purified on a silica gel column (10-40% EtOAc/hexanes) to give 89.7 mg (58.8%). 1H NMR (400 MHz, CDCl$_3$): δ 7.42-7.33 (m, 4H), 7.32-7.27 (m, 1H), 6.94-6.81 (m, 6H), 6.64-6.59 (m, 2H), 4.31 (s, 2H), 3.79 (s, 3H). HRMS: (+ESI): calcd. for: $C_{20}H_{20}O_2N_1$=306.1489, found: 307.1481.

N-benzyl-2-chloro-N-(4-(4-methoxyphenoxy)phenyl)acetamide (CCW 16). To a solution of N-benzyl-4-(4-methoxyphenoxy)aniline (CCW 14) (25 mg, 0.081 mmol) in DCM 2-chloroacetyl chloride (Sigma, 11 mg, 0.097 mmol) and triethylamine (Sigma, 9.8 mg, 0.097 mmol) were added and the reaction stirred overnight. Upon reaction completion the crude was purified by silica gel chromatography (10-40% EtOAc/hexanes) to yield 26 mg (84%). $^1$H NMR (400 MHz, CDCl$_3$): δ 7.26 (s, 3H), 7.20 (dd, J=7.3, 2.3 Hz, 2H), 7.01-6.96 (m, 2H), 6.93-6.82 (m, 6H), 4.86 (s, 2H), 3.87 (s, 2H), 3.81 (s, 3H). $^{13}$C NMR (101 MHz, CDCl$_3$): δ 166.45, 158.95, 156.54, 148.89, 136.63, 134.71, 129.54, 129.03, 128.51, 127.71, 121.47, 117.82, 115.07, 77.36, 77.25, 77.05, 76.73, 55.69, 53.85, 42.09. HRMS: (+ESI): calcd. for: $C_{22}H_{21}O_3NCl$=382.1204, found: 307.1199.

2-chloro-N-(4-(4-(hydroxymethyl)phenoxy)phenyl)acetamide (JIK 1-36). To a solution of (4-(4-aminophenoxy)phenyl)methanol (Sigma, 54.8 mg, 0.25 mmol) in DCM 2-choloracetyl chloride (Sigma, 34 mg, 0.30 mmol) and triethylamine (Sigma, 30.4 mg, 0.30 mmol) were added and the reaction stirred overnight. Upon reaction completion the crude was purified by silica gel chromatography (10-40% EtOAc/hexanes) to yield 55 mg (74%). $^1$H NMR (400 MHz, CDCl$_3$): δ 8.21 (s, 1H), 7.55-7.48 (m, 2H), 7.34 (d, J=8.4 Hz, 2H), 7.05-6.96 (m, 4H), 4.67 (s, 2H), 4.20 (s, 2H). $^{13}$C NMR (151 MHz, CDCl$_3$) δ 163.70, 156.77, 154.32, 135.82, 132.01, 128.68, 121.93, 119.46, 118.71, 64.85, 42.79. HRMS: (−ESI): calc'd for $C_{15}H_{10}ClF_3NO_2$=328.0352; found 328.0358.

2-chloro-N-(4-(3-(trifluoromethyl)phenoxy)phenyl)acetamide (JIK 1-37). To a solution of (4-(3-trifluoromethyl)phenyl)aniline (Sigma, 64.5 mg, 0.25 mmol) in DCM 2-choloracetyl chloride (Sigma, 34 mg, 0.30 mmol) and triethylamine (Sigma, 30.4 mg, 0.30 mmol) were added and the reaction stirred overnight. Upon reaction completion the crude was purified by silica gel chromatography (10-40% EtOAc/hexanes) to yield 80 mg (95%). $^1$H NMR (400 MHz, CDCl$_3$): δ 8.26 (s, 1H), 7.56 (d, J=8.8 Hz, 2H), 7.44 (t, J=7.9 Hz, 1H), 7.34 (d, J=7.7 Hz, 1H), 7.22 (s, 1H), 7.15 (d, J=8.1 Hz, 1H), 7.04 (d, J=8.8 Hz, 2H), 4.21 (s, 2H). $^{13}$C NMR (151 MHz, CDCl$_3$) δ 163.76, 157.81, 153.12, 132.85, 130.30, 124.51, 122.71, 122.04, 121.31, 120.10, 119.69, 115.02, 42.78. HRMS: (−ESI): calc'd for C$_{15}$H$_{13}$ClNO$_3$=290.0585; found 290.0589.
CCW-16+JQ1 bifunctional degrader synthesis scheme (CCW 28-3):
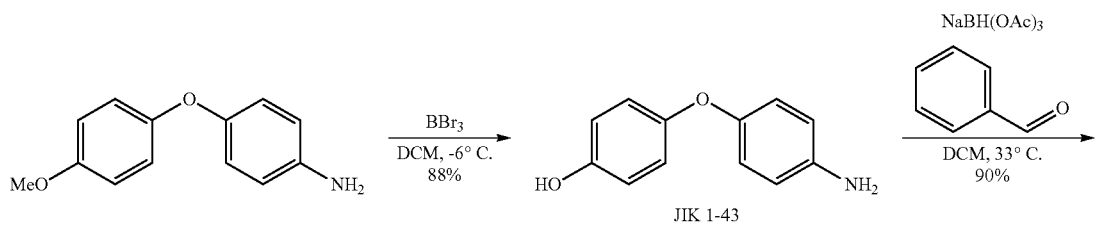
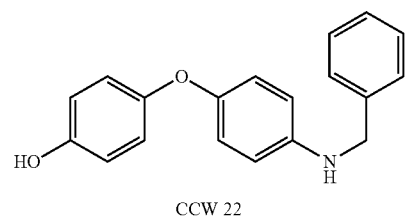
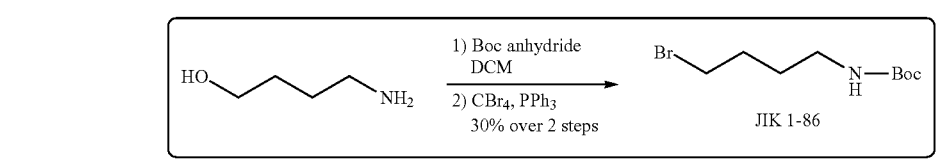
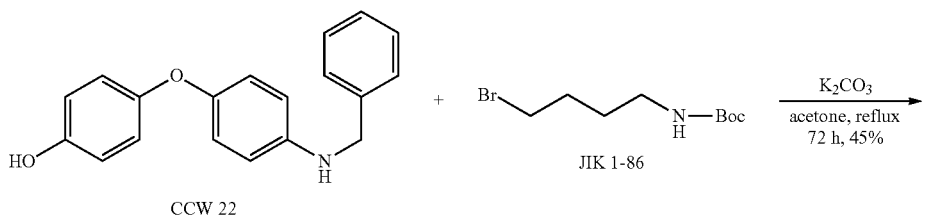
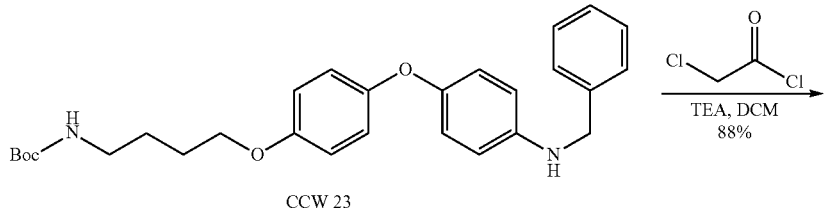
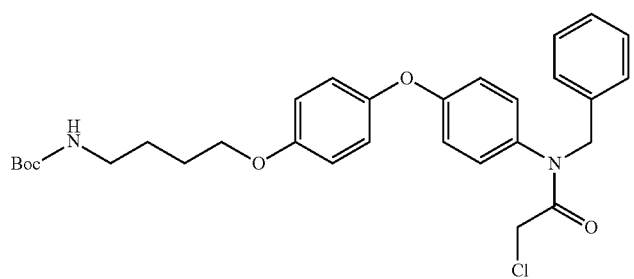

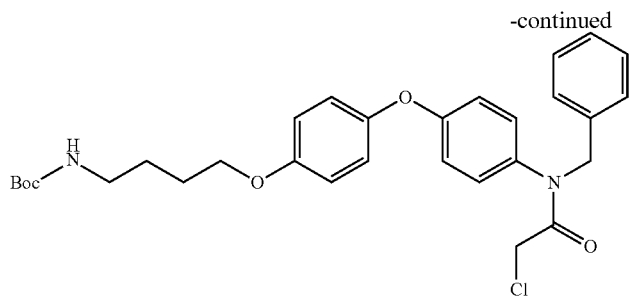

CCW 24

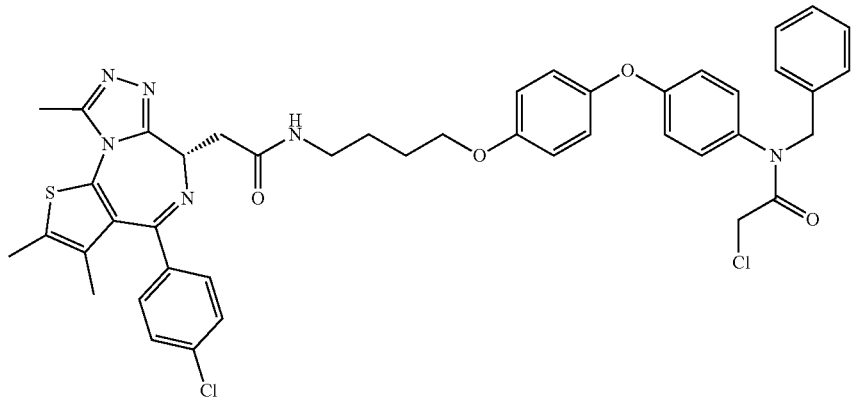

CCW 28-3 tert-butyl (4-bromobutyl)carbamate (JIK 1-86). 4-amino-1-butanol (TCI; 5.0 g, 56.0 mmol) was dissolved in dry DCM (22 mL). To the solution di-tert-butyl dicarbonate (Chem-Impex Int'l Inc.; 17.3 g, 79.4 mmol) was added. The reaction was stirred at room temperature for 3 hours and was monitored by TLC (developed in 100% EtOAc, visualized by ninhydrin). Upon completion, the solvent was removed by rotary evaporation. The crude was partially purified by silica gel chromatography (55 to 100% EtOAc in hexanes) to remove baseline impurity; eluent from column was carried forward to next reaction. DCM (22 mL, dry) was added to column eluent and the solution was cooled to 0° C. To the solution carbon tetrabromide (Aldrich; 23.9 g, 72.0 mmol) was added and dissolved, followed by triphenylphosphine (Sigma Aldrich; 22.3 g, 84.9 mmol). Reaction was stirred for 1 hr, then allowed to warm to room temperature and run overnight. After 24 hours, solvent was removed by rotary evaporation. The crude was purified by silica gel chromatography (2-15% EtOAc in hexanes) to afford 4.1 g of product as a pale yellow oil (29.6% yield over two reactions). $^1$H NMR (400 MHz, CDCl$_3$): δ 4.55 (s, 1H), 3.42 (t, J=6.7 Hz, 2H), 3.15 (q, J=6.8 Hz, 2H), 1.93-1.83 (m, 2H), 1.63 (m, 1H), 1.43 (s, 10H).

4-(4-aminophenoxy)phenol (JIK 1-43). 4-(4-methoxyphenoxy)aniline (AstaTech; 2.5 g, 11.6 mmol) was dissolved in DCM (40 mL) at −6° C. Boron tribromide (Acros; 34.8 mL, 1M in DCM, 34.8 mmol) was added dropwise over the course of 3 hours, monitored by TLC (40% EtOAc/Hex, KMnO$_4$). Upon completion, solution was quenched with 1 volume of sodium bicarbonate. Biphasic mixture was refrigerated overnight and product crystallized out and was removed by filtration. The aqueous layer was neutralized with NaOH, and back extracted with 3×25 mL EtOAc. The combined organic layers were dried with MgSO$_4$ and condensed. Yielded 2.33 g (88%) product as a tan solid which required no further purification. $^1$H NMR (400 MHz, Methanol-d$_4$): δ 5.22-5.09 (m, 8H), 1.73 (p, J=1.6 Hz, 3H). HRMS: (+ESI): calc'd for C$_{12}$H$_{12}$NO$_2$=202.0863; found 202.0860.

4-(4-(benzylamino)phenoxy)phenol (CCW 22). 4-(4-aminophenoxy)phenol (JIK 1-43) (604 mg, 3.0 mmol) was dissolved in anhydrous DCM (50 mL) at 33 C to aid solubility, benzaldehyde (Alfa Aesar, 240 mg, 3.0 mmol) was added and the reaction stirred for two hours under nitrogen. Sodium triacetoxyborohydride (Sigma, 952 mg, 4.5 mmol) was added and the reaction stirred overnight. The mixture was concentrated and applied directly to a silica column for flash chromatography, yielding 787 mg (90%). $^1$H NMR (400 MHz, CDCl$_3$): δ 7.41-7.24 (m, 5H), 6.89-6.80 (m, 4H), 6.78-6.71 (m, 2H), 6.65-6.58 (m, 2H), 4.31 (s, 2H).

tert-butyl (4-(4-(4-(benzylamino)phenoxy)phenoxy)butyl)carbamate (CCW 23). 4-(4-(benzylamino)phenoxy)phenol (CCW 22) (450 mg, 1.55 mmol) and tert-butyl (4-bromobutyl)carbamate (JIK 1-86) (585 mg, 2.32 mmol) were dissolved in acetone (20 mL). Potassium carbonate (642 mg, 4.65 mmol) was added and the solution brought to reflux and stirred for 72 h. The mixture was concentrated and applied directly to a silica column for flash chromatography (10-30% EtOAc/hexanes), yielding 325 mg (45.3%). $^1$H NMR (400 MHz, CDCl$_3$): δ 7.41-7.27 (m, 5H), 6.91-6.77 (m, 6H), 6.60 (d, J=8.8 Hz, 2H), 4.62 (s, 1H), 4.30 (s, 2H), 3.93 (t, J=6.2 Hz, 2H), 3.19 (q, J=6.4 Hz, 2H), 1.83-1.74 (m, 2H), 1.66 (p, J=7.1 Hz, 2H), 1.44 (s, 9H). HRMS: (+ESI): calc'd for C$_{28}$H$_{35}$O$_4$N$_2$=463.2591; found 462.2583.

tert-butyl (4-(4-(4-(N-benzyl-2-chloroacetamido)phenoxy)phenoxy)butyl)carbamate (CCW 24). To a solution of CCW 23 (200 mg, 0.43 mmol) in DCM (10 mL). 2-choloracetyl chloride (Sigma, 59 mg, 0.52 mmol) and triethylamine (Sigma, 53 mg, 0.52 mmol) were added and the reaction stirred overnight. Upon reaction completion the crude was purified by silica gel chromatography (20-60%

EtOAc/hexanes) to yield 232 mg (87.6%). ¹H NMR (400 MHz, CDCl₃): δ 7.29 (d, J=4.8 Hz, 2H), 7.20 (dd, J=7.2, 2.2 Hz, 3H), 6.97 (d, J=9.0 Hz, 2H), 6.93-6.83 (m, 6H), 4.86 (s, 2H), 4.61 (s, 1H), 3.96 (t, J=6.2 Hz, 2H), 3.87 (s, 2H), 3.20 (q, J=6.4 Hz, 2H), 1.87-1.77 (m, 2H), 1.68 (p, J=7.1 Hz, 2H), 1.45 (s, 9H).

(S)-2-(4-(4-chlorophenyl)-2,3,9-trimethyl-6H-thieno[3,2-f][1,2,4]triazolo[4,3-a][1,4]diazepin-6-yl)acetic acid (JQ1-acid). tert-butyl (S)-2-(4-(4-chlorophenyl)-2,3,9-trimethyl-6H-thieno[3,2-f][1,2,4]triazolo[4,3-a][1,4]diazepin-6-yl) acetate (JQ1) was prepared based on previous procedures[1]. JQ1 (eNovation Chemicals, 204 mg, 0.446 mmol) was dissolved in formic acid (3 mL) and stirred at 45° C. overnight. The mixture was diluted with DCM and solvent removed in vacuo. The resulting yellow oil was redissolved in 3 mL DCL and evaporated to dryness repeated until the process gave a fine yellow-brown solid: 178 mg (99.8%). No further purification was necessary. 1H NMR (400 MHz, CDCl₃): δ 7.46-7.40 (m, 2H), 7.34 (d, J=8.7 Hz, 2H), 4.59 (t, J=6.8 Hz, 1H), 3.75-3.55 (m, 2H), 2.68 (s, 3H), 2.41 (s, 3H), 1.74-1.65 (m, 3H). HRMS: (−ESI): calcd. for C₁₉H₁₆O₂N₄ClS=399.0688; found 399.0683.

(S)—N-benzyl-2-chloro-N-(4-(4-(4-(2-(4-(4-chlorophenyl)-2,3,9-trimethyl-6H-thieno[3,2-f][1,2,4]triazolo[4,3-a][1,4]diazepin-6-yl)acetamido)butoxy)phenoxy)phenyl)acetamide (CCW-28-3). CCW 24 (175 mg, 0.325 mmol) was deprotected in 1:1 DCM/TFA (5 mL) by adding trifluoroacetic acid (Sigma-Aldrich) slowly over 20 min followed by stirring for an additional 20 min. TLC showed full conversion to amine and the solvent was removed in vacuo, and chases three times with 3 mL DCM to remove excess TFA. The deprotected crude was used without further purification for amide coupling. The resulting TFA salt was dissolved in 8 mL DCM, JQ1-acid (180 mg, 0.390 mmol), 1-[Bis(dimethylamino)methylene]-1H-1,2,3-triazolo[4,5-b]pyridinium 3-oxid hexafluorophosphate (HATU) (Small Molecules Inc., 201.5 mg, 0.530 mmol), and N,N-Diisopropylethylamine (DIPEA) (Sigma-Aldrich, 168 mg, 1.30 mmol). Stirred overnight and monitored by TLC (5% MeOH in DCM, 100% EtOAc). Crude concentrated and applied direct to a silica column for flash chromatography (1-5% MeOH/DCM). The eluted fractions were insufficiently pure and those containing product were combined, concentrated and purified again by flash silica chromatography (100-0% EtOAc/DCM followed by 0-5% MeOH/DCM) to afford 91.4 mg (34.2%). ¹H NMR (600 MHz, CDCl₃): δ 7.36 (dd, J=50.3, 8.3 Hz, 4H), 7.26 (s, 2H), 7.22-7.18 (m, 2H), 6.99-6.95 (m, 2H), 6.92-6.83 (m, 6H), 6.59 (d, J=6.1 Hz, 1H), 4.86 (s, 2H), 4.62 (dd, J=7.9, 6.1 Hz, 1H), 3.96 (t, J=6.2 Hz, 2H), 3.87 (s, 2H), 3.57 (dd, J=14.1, 7.9 Hz, 1H), 3.42 (dq, J=13.3, 6.7 Hz, 1H), 3.32 (ddd, J=13.2, 11.4, 6.2 Hz, 2H), 2.67 (s, 3H), 2.40 (s, 3H), 1.82 (td, J=13.8, 13.2, 6.9 Hz, 2H), 1.74 (p, J=6.8 Hz, 2H), 1.67 (s, 3H). ¹³C NMR (151 MHz, CDCl₃): δ 170.46, 166.38, 163.87, 158.90, 155.84, 155.63, 149.84, 148.82, 136.79, 136.58, 136.56, 134.65, 132.10, 130.87, 130.82, 130.42, 129.76, 129.46, 128.97, 128.69, 128.44, 127.63, 121.39, 117.78, 115.64, 67.84, 54.53, 53.78, 42.01, 39.60, 39.20, 29.65, 26.59, 26.26, 14.32, 13.04, 11.78. HRMS: (+ESI): calcd. for C₄₄H₄₃Cl₂N₆O₄S=821.2438; found 821.2426.

Table 1. Structures of covalent ligands screened against RNF4.

TABLE 1

STRUCTURES OF COVALENT LIGANDS SCREENED AGAINST RNF114

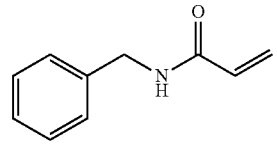

DKM 2-31

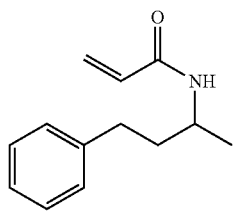

DKM 2-32

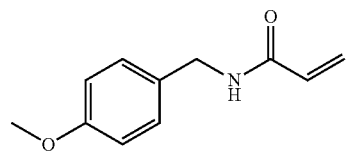

DKM 2-33

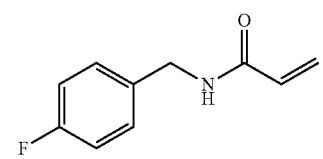

DKM 2-34

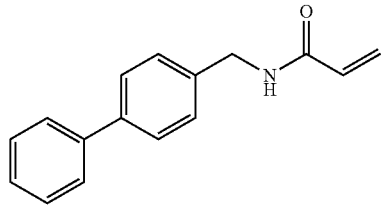 [SMILES: C=CC(=O)NCc1ccc(-c2ccccc2)cc1]

DKM 2-37

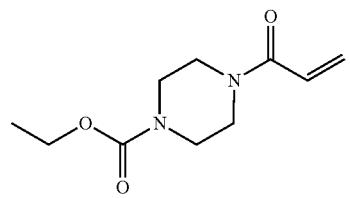

DKM 2-39

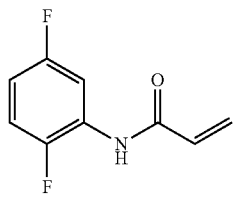

DKM 2-40

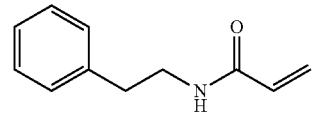

DKM 2-42

TABLE 1-continued
STRUCTURES OF COVALENT LIGANDS SCREENED AGAINST RNF114
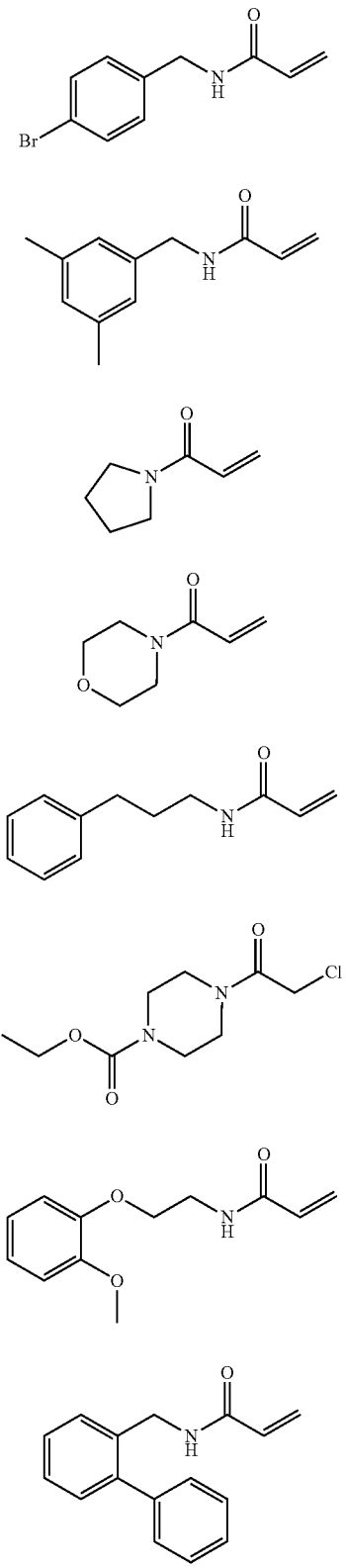
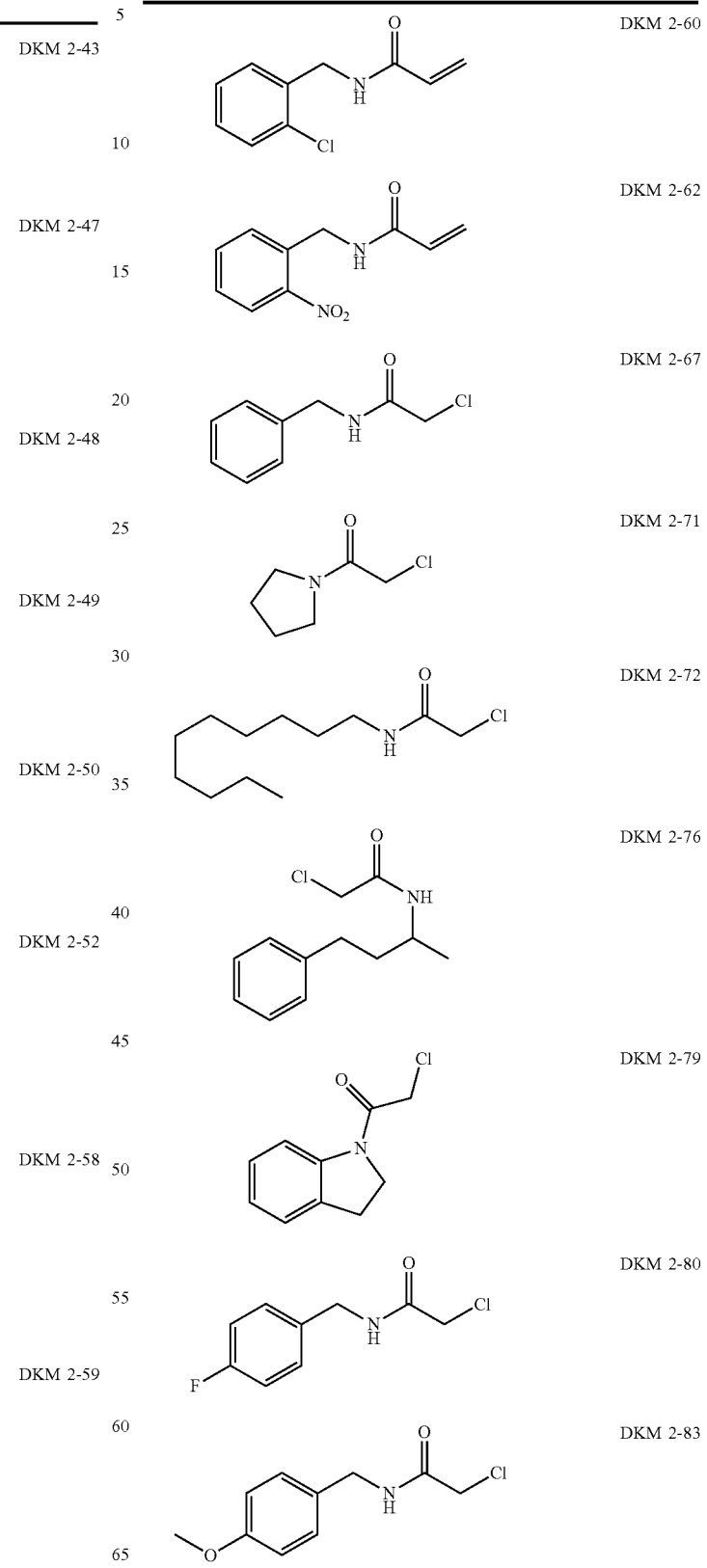

TABLE 1-continued
STRUCTURES OF COVALENT LIGANDS SCREENED AGAINST RNF114
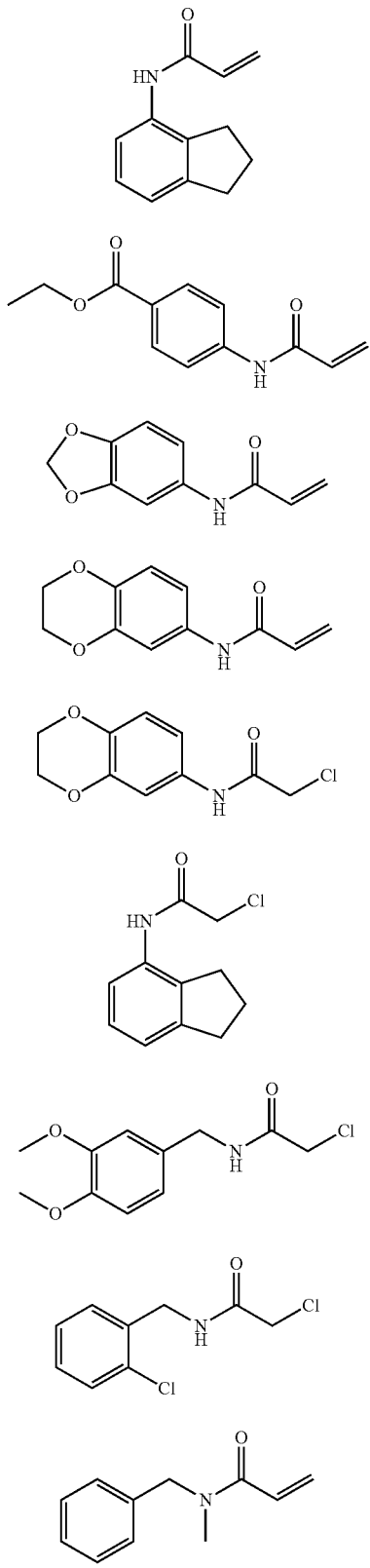
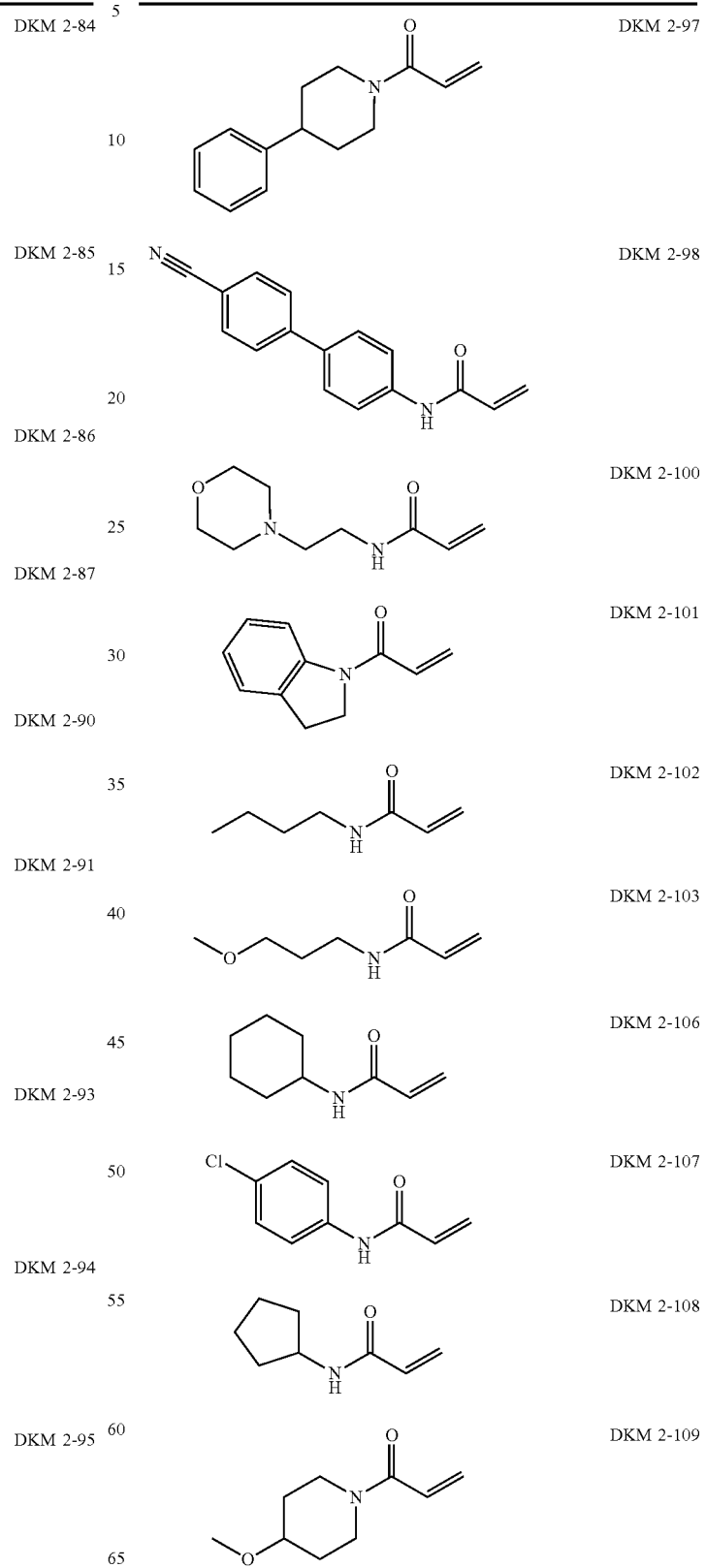

TABLE 1-continued
STRUCTURES OF COVALENT LIGANDS SCREENED AGAINST RNF114
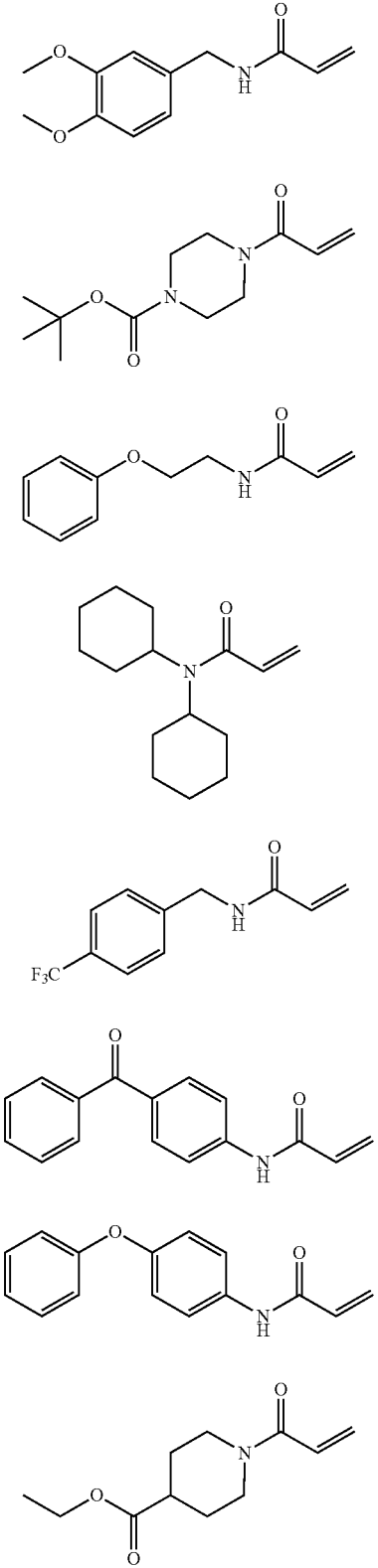
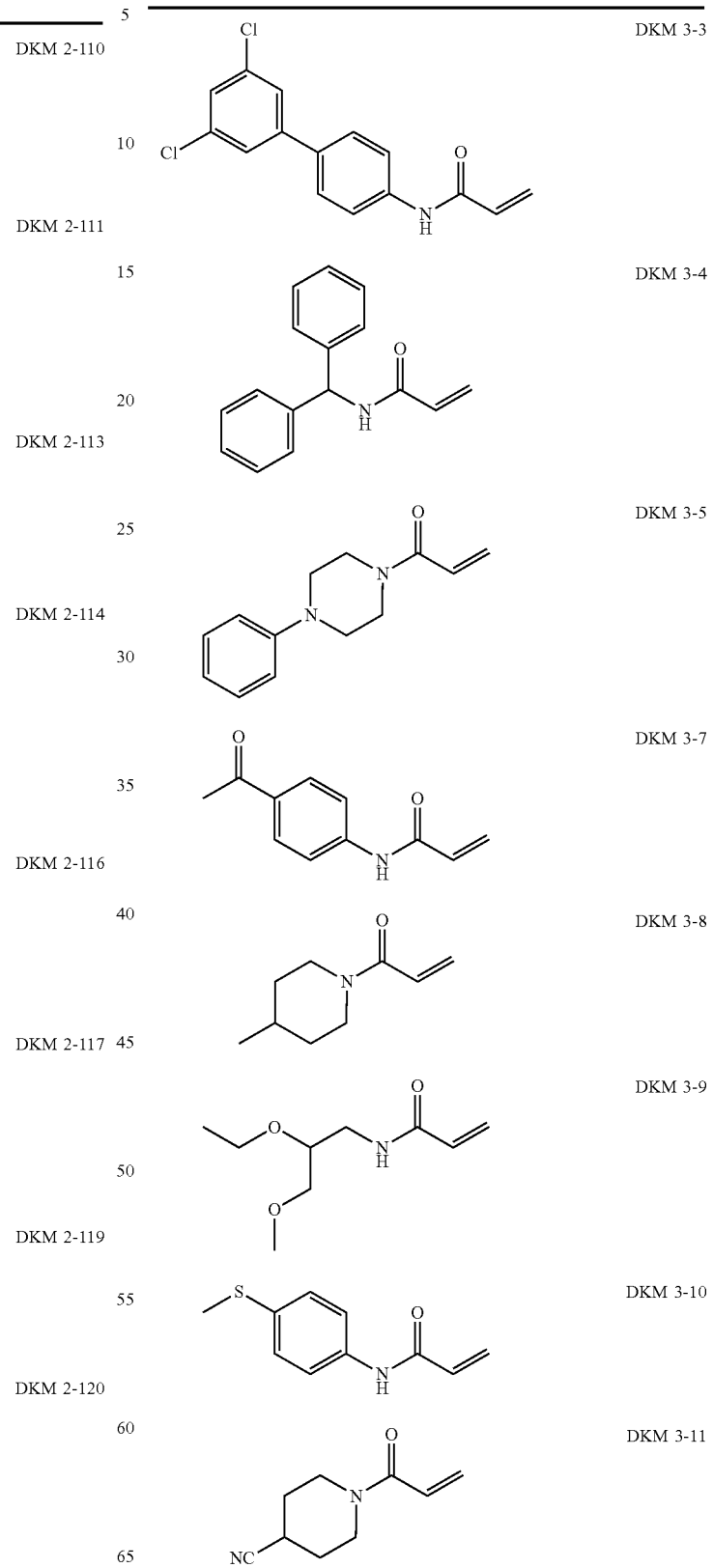

TABLE 1-continued

STRUCTURES OF COVALENT LIGANDS
SCREENED AGAINST RNF114

| ID |
|---|
| DKM 3-12 |
| DKM 3-13 |
| DKM 3-15 |
| DKM 3-16 |
| DKM 3-22 |
| DKM 3-29 |
| DKM 3-30 |
| DKM 3-31 |
| DKM 3-32 |
| DKM 3-36 |
| DKM 3-41 |
| DKM 3-42 |
| DKM 3-43 |
| DKM 3-70 |
| TRH 1-12 |
| TRH 1-13 |
| TRH 1-17 |

TABLE 1-continued
STRUCTURES OF COVALENT LIGANDS
SCREENED AGAINST RNF114
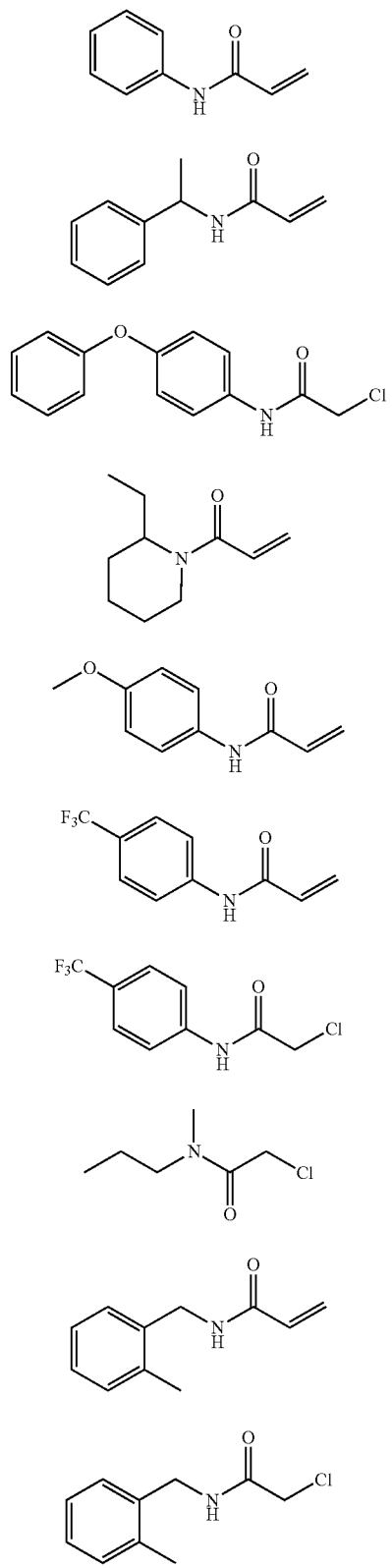
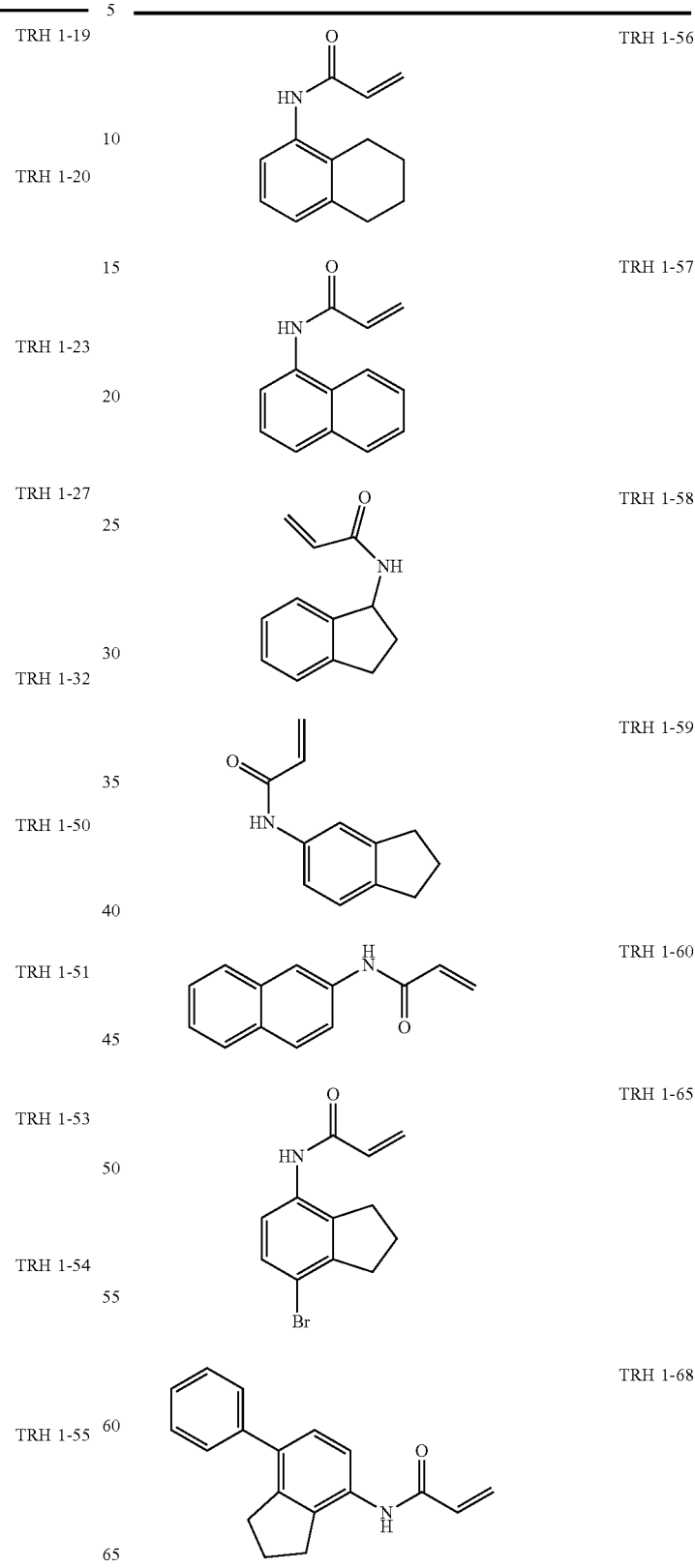

TABLE 1-continued
STRUCTURES OF COVALENT LIGANDS SCREENED AGAINST RNF114
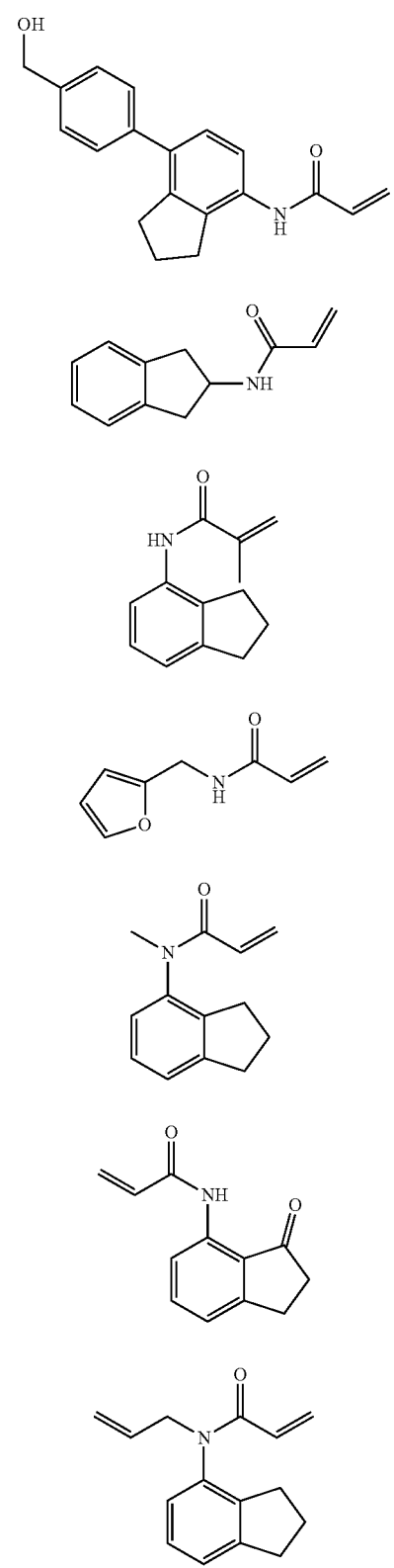
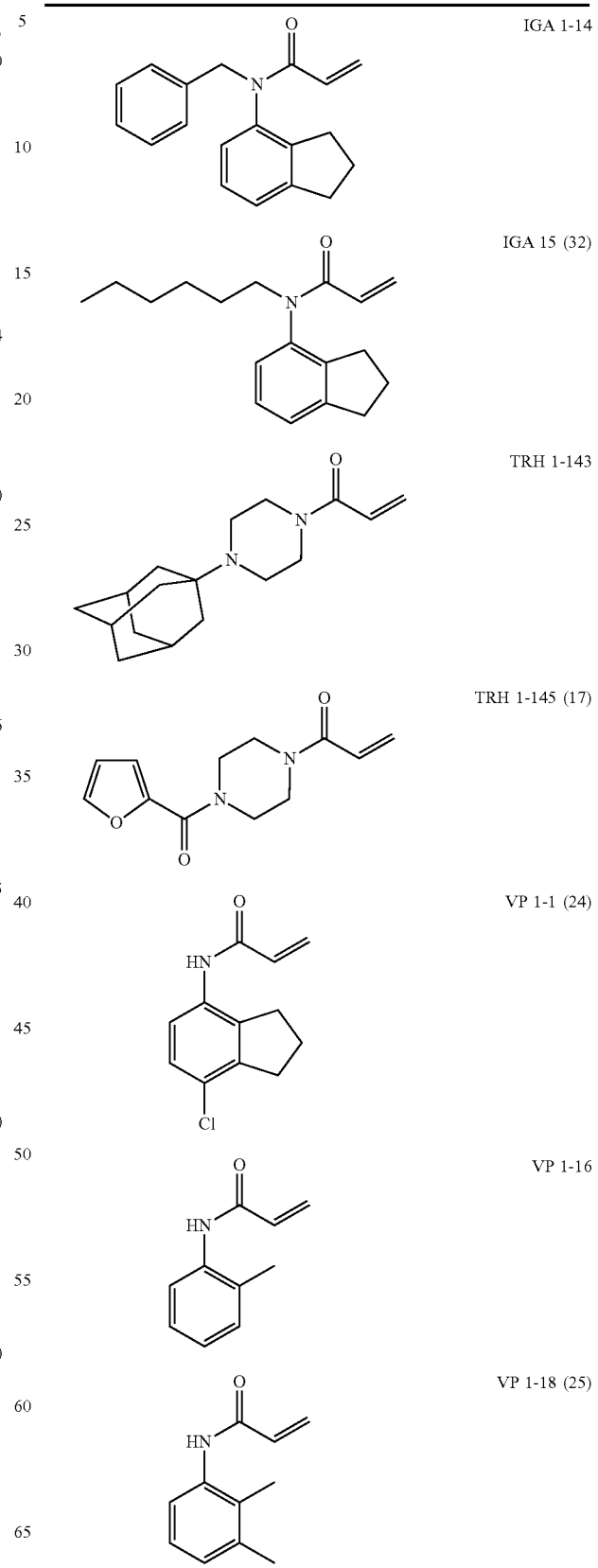

TABLE 1-continued
STRUCTURES OF COVALENT LIGANDS SCREENED AGAINST RNF114
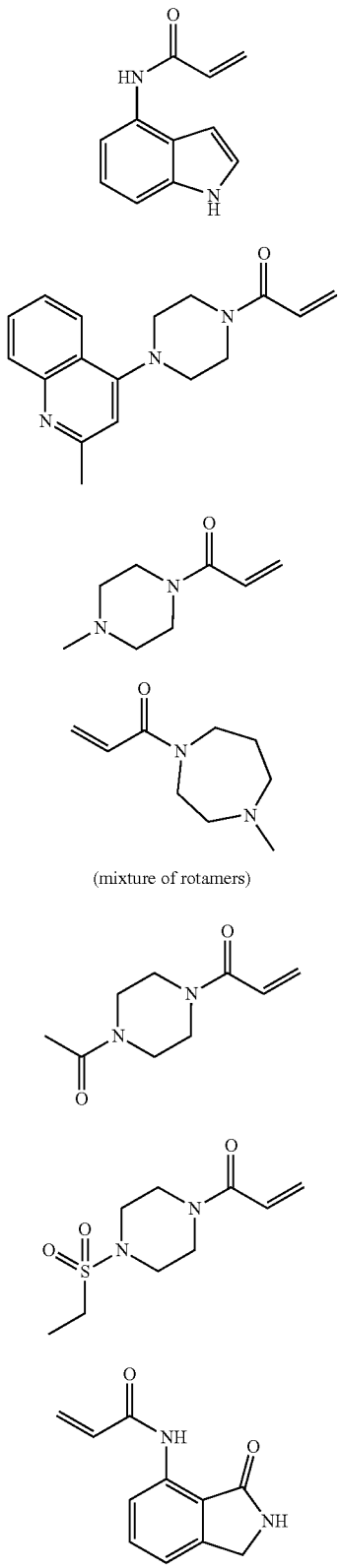
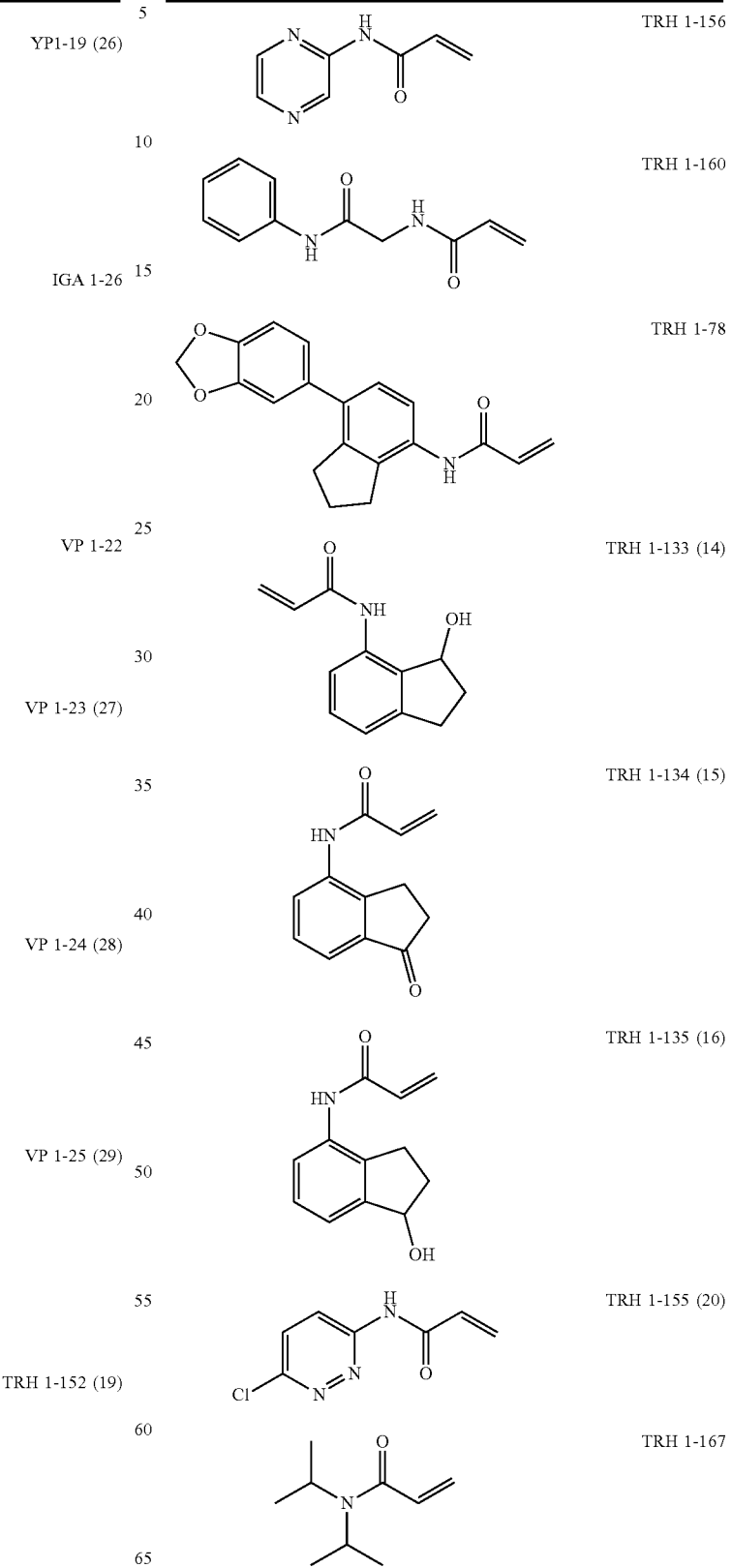

TABLE 1-continued
STRUCTURES OF COVALENT LIGANDS
SCREENED AGAINST RNF114
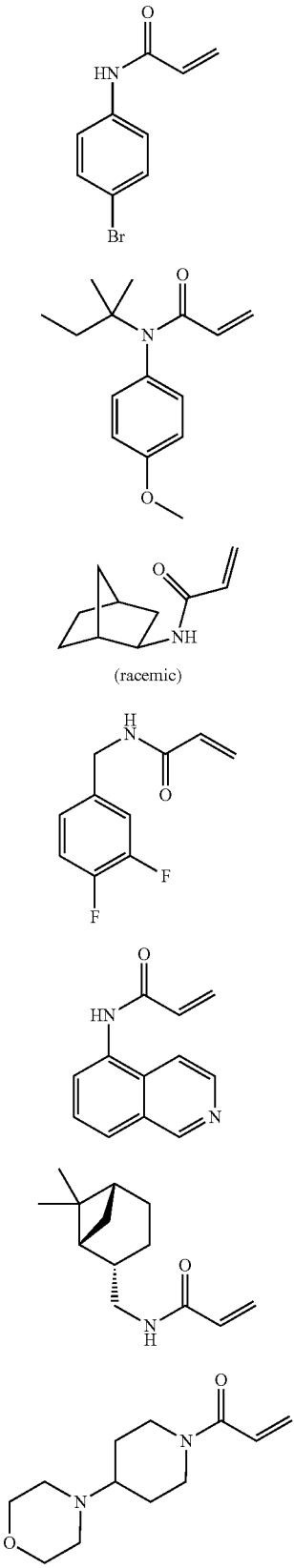
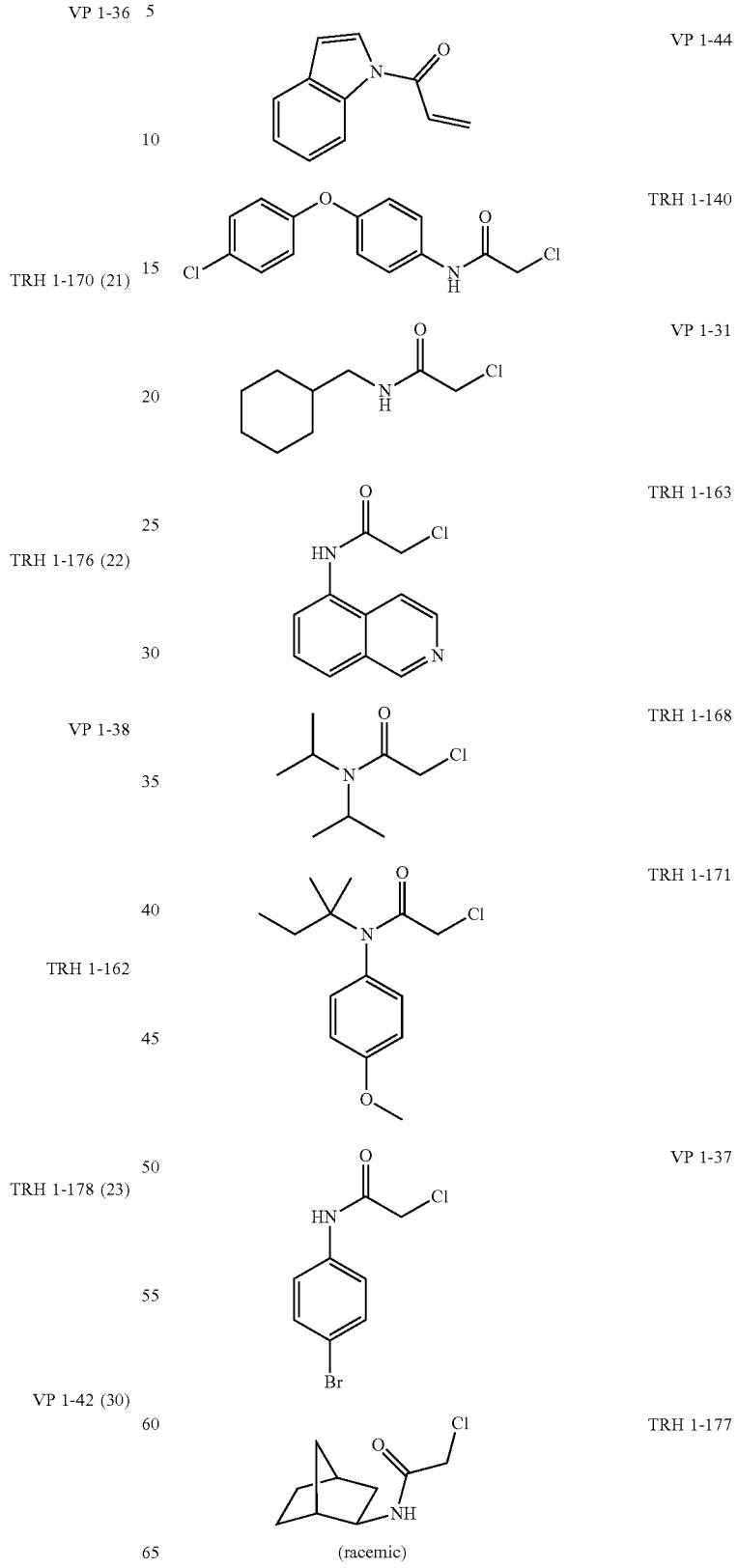

TABLE 1-continued

STRUCTURES OF COVALENT LIGANDS
SCREENED AGAINST RNF114

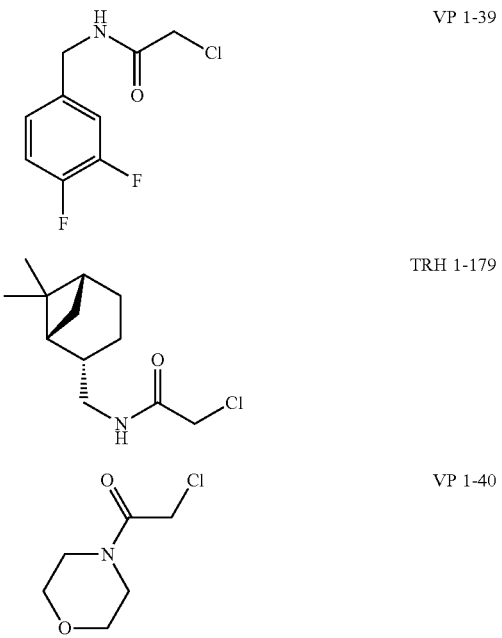

Note:
Numbers in parentheses correspond to compound numbers in Example 9.

231MFP cells were treated with DMSO vehicle or CCW 28-3 (10 μM) in situ for 1 h prior to labeling of proteomes in vitro with IA-alkyne (100 μM) for 1 h. Isotopically light (for DMSO-treated) or heavy (for compound-treated) TEV protease-cleavable biotin-azide tag were appended by CuAAC for isoTOP-ABPP analysis. Only probe-modified peptides that were present in two out of three biological replicates were interpreted. For those ratios >3, we only interpreted those peptides that were present in all biological replicates where all replicate ratios were >3. For those ratios >4, we only interpreted those peptides that were present in all biological replicates where all replicate ratios were >4. MS1 peak shape qualities were manually curated to confirm good peak quality for all replicates.

References Pertaining to Examples 1-3

(1) Burslem, G. M.; Crews, C. M. Small-Molecule Modulation of Protein Homeostasis. *Chem. Rev.* 2017, 117 (17), 11269-11301. (2) Lai, A. C.; Crews, C. M. Induced Protein Degradation: An Emerging Drug Discovery Paradigm. *Nat. Rev. Drug Discov.* 2017, 16 (2), 101-114. (3) Rape, M. Ubiquitylation at the Crossroads of Development and Disease. *Nat. Rev. Mol. Cell Biol.* 2018, 19 (1), 59-70. (4) Grossman, E. A.; Ward, C. C.; Spradlin, J. N.; Bateman, L. A.; Huffman, T. R.; Miyamoto, D. K.; Kleinman, J. I.; Nomura, D. K. Covalent Ligand Discovery against Druggable Hotspots Targeted by Anti-Cancer Natural Products. *Cell Chem. Biol.* 2017, 24 (11), 1368-1376.e4. (5) Counihan, J. L.; Wiggenhorn, A. L.; Anderson, K. E.; Nomura, D. K. Chemoproteomics-Enabled Covalent Ligand Screening Reveals ALDH3A1 as a Lung Cancer Therapy Target. *ACS Chem. Biol.* 2018. (6) Bateman, L. A.; Nguyen, T. B.; Roberts, A. M.; Miyamoto, D. K.; Ku, W.-M.; Huffman, T. R.; Petri, Y.; Heslin, M. J.; Contreras, C. M.; Skibola, C. F.; et al. Chemoproteomics-Enabled Covalent Ligand Screen Reveals a Cysteine Hotspot in Reticulon 4 That Impairs ER Morphology and Cancer Pathogenicity. *Chem. Commun. Camb. Engl.* 2017, 53 (53), 7234-7237. (7) Backus, K. M.; Correia, B. E.; Lum, K. M.; Forli, S.; Homing, B. D.; González-Páez, G. E.; Chatterjee, S.; Lanning, B. R.; Teijaro, J. R.; Olson, A. J.; et al. Proteome-Wide Covalent Ligand Discovery in Native Biological Systems. *Nature* 2016, 534 (7608), 570-574. (8) Wang, C.; Weerapana, E.; Blewett, M. M.; Cravatt, B. F. A Chemoproteomic Platform to Quantitatively Map Targets of Lipid-Derived Electrophiles. *Nat. Methods* 2014, 11 (1), 79-85. (9) Hacker, S. M.; Backus, K. M.; Lazear, M. R.; Forli, S.; Correia, B. E.; Cravatt, B. F. Global Profiling of Lysine Reactivity and Ligandability in the Human Proteome. *Nat. Chem.* 2017, 9 (12), 1181-1190. (10) Backus, K. M. Applications of Reactive Cysteine Profiling. *Curr. Top. Microbiol. Immunol.* 2018. (11) Liu, Y.; Patricelli, M. P.; Cravatt, B. F. Activity-Based Protein Profiling: The Serine Hydrolases. *Proc. Natl. Acad. Sci. U.S.A.* 1999, 96 (26), 14694-14699. (12) Weerapana, E.; Wang, C.; Simon, G. M.; Richter, F.; Khare, S.; Dillon, M. B. D.; Bachovchin, D. A.; Mowen, K.; Baker, D.; Cravatt, B. F. Quantitative Reactivity Profiling Predicts Functional Cysteines in Proteomes. *Nature* 2010, 468 (7325), 790-795. (13) Roberts, A. M.; Miyamoto, D. K.; Huffman, T. R.; Bateman, L. A.; Ives, A. N.; Akopian, D.; Heslin, M. J.; Contreras, C. M.; Rape, M.; Skibola, C. F.; et al. Chemoproteomic Screening of Covalent Ligands Reveals UBA5 As a Novel Pancreatic Cancer Target. *ACS Chem. Biol.* 2017, 12 (4), 899-904. (14) Wang, C.; Weerapana, E.; Blewett, M. M.; Cravatt, B. F. A Chemoproteomic Platform to Quantitatively Map Targets of Lipid-Derived Electrophiles. *Nat. Methods* 2014, 11 (1), 79-85. (15) Anderson, K. E.; To, M.; Olzmann, J. A.; Nomura, D. K. Chemoproteomics-Enabled Covalent Ligand Screening Reveals a Thioredoxin-Caspase 3 Interaction Disruptor That Impairs Breast Cancer Pathogenicity. *ACS Chem. Biol.* 2017, 12 (10), 2522-2528. (16) Vassilev, L. T.; Vu, B. T.; Graves, B.; Carvajal, D.; Podlaski, F.; Filipovic, Z.; Kong, N.; Kammlott, U.; Lukacs, C.; Klein, C.; et al. In Vivo Activation of the P53 Pathway by Small-Molecule Antagonists of MDM2. *Science* 2004, 303 (5659), 844-848. (17) Schneekloth, A. R.; Pucheault, M.; Tae, H. S.; Crews, C. M. Targeted Intracellular Protein Degradation Induced by a Small Molecule: En Route to Chemical Proteomics. *Bioorg. Med. Chem. Lett.* 2008, 18 (22), 5904-5908. (18) Malecka, K. A.; Fera, D.; Schultz, D. C.; Hodawadekar, S.; Reichman, M.; Donover, P. S.; Murphy, M. E.; Marmorstein, R. Identification and Characterization of Small Molecule Human Papillomavirus E6 Inhibitors. *ACS Chem. Biol.* 2014, 9 (7), 1603-1612. (19) Staudinger, J. L. The Molecular Interface Between the SUMO and Ubiquitin Systems. *Adv. Exp. Med. Biol.* 2017, 963, 99-110. (20) Sriramachandran, A. M.; Dohmen, R. J. SUMO-Targeted Ubiquitin Ligases. *Biochim. Biophys. Acta* 2014, 1843 (1), 75-85. (21) Tan, B.; Mu, R.; Chang, Y.; Wang, Y.-B.; Wu, M.; Tu, H.-Q.; Zhang, Y.-C.; Guo, S.-S.; Qin, X.-H.; Li, T.; et al. RNF4 Negatively Regulates NF-KB Signaling by down-Regulating TAB2. *FEBS Lett.* 2015, 589 (19 Pt B), 2850-2858. (22) Fryrear, K. A.; Guo, X.; Kerscher, O.; Semmes, O. J. The Sumo-Targeted Ubiquitin Ligase RNF4 Regulates the Localization and Function of the HTLV-1 Oncoprotein Tax. *Blood* 2012, 119 (5), 1173-1181. (23) Bilodeau, S.; Caron, V.; Gagnon, J.; Kuftedjian, A.; Tremblay, A. A CK2-RNF4 Interplay Coordinates Non-Canonical SUMOylation and Degradation of Nuclear Receptor FXR. *J. Mol. Cell Biol.* 2017, 9 (3), 195-208. (24) Zengerle, M.; Chan, K.-H.; Ciulli, A. Selective Small Molecule Induced Degradation of the BET Bromodomain Protein BRD4. *ACS Chem. Biol.* 2015, 10 (8), 1770-1777. (25) Louie, S. M.; Grossman, E. A.; Crawford, L. A.; Ding, L.; Camarda, R.; Huffman, T. R.; Miyamoto, D. K.; Goga, A.; Weerapana, E.; Nomura, D. K. GSTP1 Is a Driver of Triple-Negative Breast Cancer Cell Metabolism and Pathogenicity. *Cell Chem. Biol.* 2016, 23 (5), 567-578. (26) Medina-Cleghom, D.; Bateman, L. A.; Ford, B.; Heslin, A.; Fisher, K. J.; Dalvie, E. D.; Nomura, D. K. Mapping Proteome-Wide Targets of Environmental Chemicals Using Reactivity-Based Chemoproteomic Platforms. *Chem. Biol.* 2015, 22 (10), 1394-1405. (27) Jessani, N.; Humphrey, M.; McDonald, W. H.; Niessen, S.; Masuda, K.; Gangadharan, B.; Yates, J. R.; Mueller, B. M.; Cravatt, B. F. Carcinoma and Stromal Enzyme Activity Profiles Associated with Breast Tumor Growth in Vivo. *Proc. Natl. Acad. Sci. U.S.A.* 2004, 101 (38), 13756-13761. (28) Smith, P. K.; Krohn, R. I.; Hermanson, G. T.; Mallia, A. K.; Gartner, F. H.; Provenzano, M. D.; Fujimoto, E. K.; Goeke, N. M.; Olson, B. J.; Klenk, D. C. Measurement of Protein Using Bicinchoninic Acid. *Anal. Biochem.* 1985, 150 (1), 76-85. (29) Xu, T.; Park, S. K.; Venable, J. D.; Wohlschlegel, J. A.; Diedrich, J. K.; Cociorva, D.; Lu, B.; Liao, L.; Hewel, J.; Han, X.; et al. ProLuCID: An Improved SEQUEST-like Algorithm with Enhanced Sensitivity and Specificity. *J. Proteomics* 2015, 129, 16-24. Example 3 (1) Zengerle, M.; Chan, K.-H.; Ciulli, A. Selective Small Molecule Induced Degradation of the BET Bromodomain Protein BRD4. ACS Chem. Biol. 2015, 10 (8), 1770-1777.

Example 4. Harnessing the Anti-Cancer Natural Product Nimbolide for Targeted Protein Degradation Nimbolide, a terpenoid natural product derived from the Neem tree, impairs cancer pathogenicity across many types of human cancers; however, the direct targets and anti-cancer mechanisms of nimbolide are poorly understood. Here, we used activity-based protein profiling (ABPP) chemoproteomic platforms to discover that nimbolide reacts with a novel functional cysteine crucial for substrate recognition in the E3 ubiquitin ligase RNF114. Nimbolide impairs breast cancer cell proliferation through disrupting RNF114 substrate recognition, leading to inhibition of ubiquitination and degradation of the tumor-suppressor p21, resulting in its rapid stabilization. We further demonstrate the ability to exploit this reactive node in RNF114 for E3 ligase recruitment in targeted protein degradation applications and show that synthetically simpler scaffolds are also capable of accessing this unique reactive site.

Natural products from organisms such as plants and microbes are a rich source of therapeutic lead compounds[1-5]. The characterization of their biological activities have resulted in myriad medications for disparate pathologies such as cancer, bacterial and fungal infections, inflammation, and diabetes[1-5]. Among natural products is a subset of covalently acting molecules that bear electrophilic moieties capable of undergoing largely irreversible reactions with nucleophilic amino acid hotspots within proteins to exert their therapeutic activity. Examples of these natural products include penicillin, which irreversibly inhibits serine transpeptidases inducing anti-bacterial activity, or wortmannin, which covalently modifies a functional lysine on PI3-kinase to inhibit its activity[5-7]. Discovering druggable hotspots targeted by anti-cancer and covalently-acting natural products can not only yield new cancer drugs and therapeutic targets but can also reveal unique insights into druggable modalities accessed by natural products in protein targets that are often considered undruggable or difficult to tackle with standard drug discovery efforts. One example of a druggable modality that would be difficult to predict a priori is FK506 or Tacrolimus that inhibits peptidylprolyl isomerase activity by binding to and creating a new FKBP12-FK506 complex to modulate T cell signaling[8]. Gaining insights into nature's strategies for engaging protein targets can thus provide access to new and unexpected rules governing druggability.

Figure 8A:
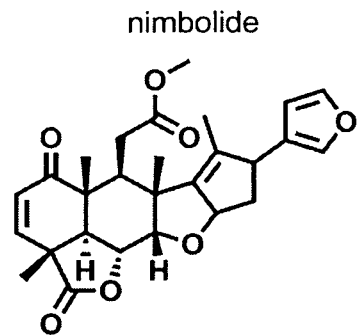
FIGS. 8A-8C. Nimbolide impairs breast cancer cell proliferation or survival.

In this example, we characterized an anti-cancer mechanism of action of the natural product nimbolide, a limonoid natural product derived from the Neem tree (Azadirachta indica) (FIG. 8A)[9]. Nimbolide has been shown to exert multiple therapeutic effects and possesses a cyclic enone capable of reacting with cysteines[10-12] In the context of cancer, nimbolide has been shown to inhibit tumorigenesis and metastasis without causing any toxicity or unwanted side effects across a wide range of cancers[10,11,13-17]. While previous studies suggest that nimbolide impairs cancer pathogenicity through modulating signaling pathways and transcription factors linked to survival, growth, invasion, angiogenesis, and inflammation, and through affecting oxidative stress, the direct targets of nimbolide still remain poorly characterized[10,15,18-22].

Identifying direct protein targets of complex natural products remains challenging and oftentimes requires synthesizing analogs of these compounds bearing photoaffinity and enrichment handles, a task which is often synthetically challenging and may alter the activity of the molecule[23-25]. Even with the generation of such probes, identifying the specific amino acid site targeted by natural products is challenging. In this study, we utilized activity-based protein profiling (ABPP) chemoproteomic approaches to map the proteome-wide targets of nimbolide in breast cancer cell proteomes. Using ABPP platforms, we reveal that one of the primary targets of nimbolide in breast cancer cells is C8 of the E3 ubiquitin ligase RNF114. Covalent modification of RNF114 by nimbolide leads to impaired recognition, ubiquitination, and degradation of its substrate—the tumor suppressor p21—leading to its rapid stabilization. Intriguingly, because nimbolide binds at a substrate recognition site within RNF114, we demonstrate that nimbolide can be used to recruit RNF114 to other protein substrates for targeted protein degradation applications. Using chemoproteomics-enabled covalent ligand screening platforms, we also identify more synthetically tractable compounds that can similarly react with C8 of RNF114 and phenocopy nimbolide action.

Figure 8B:
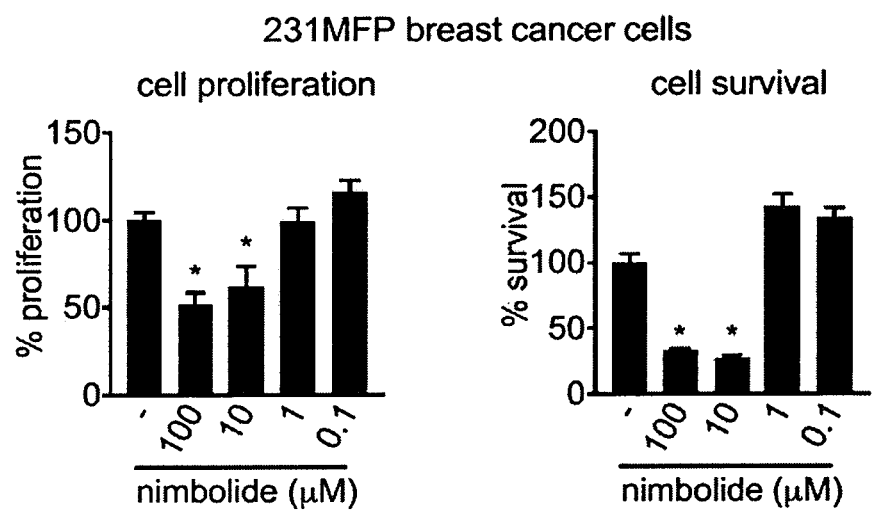
Figure 8C:
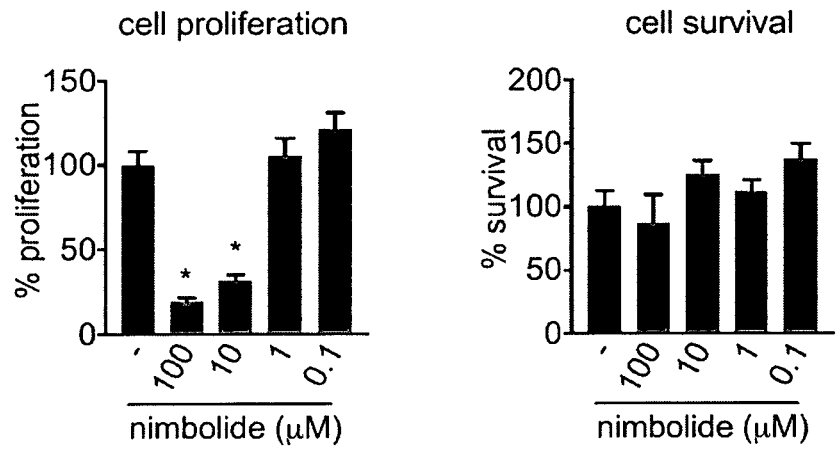

Effects of nimbolide on breast cancer cell survival and proliferation. While nimbolide has been shown to impair cancer pathogenicity across many different types of human cancers, we chose to focus on elucidating the role of nimbolide in triple-negative breast cancers (TNBCs). TNBCs are devoid of estrogen, progesterone, and HER2 receptors and are amongst the most aggressive cancers with the worst prognosis[26,27]. Very few targeted therapies currently exist for TNBC patients. Uncovering new therapeutic modalities in TNBCs would thus potentially contribute significantly to reducing breast cancer-associated mortalities. Consistent with previous reports showing anti-cancer activity in breast cancer cells, nimbolide impaired cell proliferation or serum-free cell survival in 231MFP and HCC38 TNBC cells (FIG. 8B)[14,15,17].

Figure 9A:
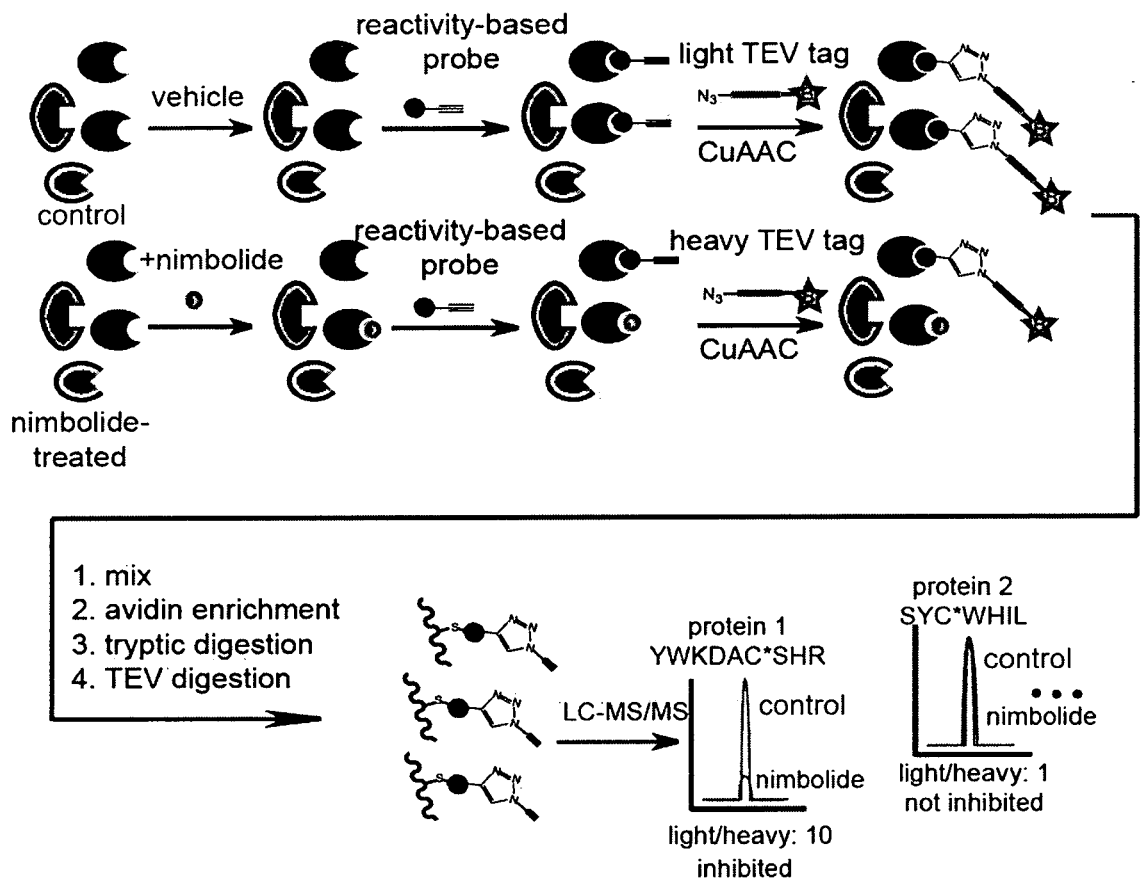
FIGS. 9A-9E. isoTOP-ABPP analysis of nimbolide in 231MFP breast cancer cell proteomes reveal RNF114 as a target.
Figure 9B:
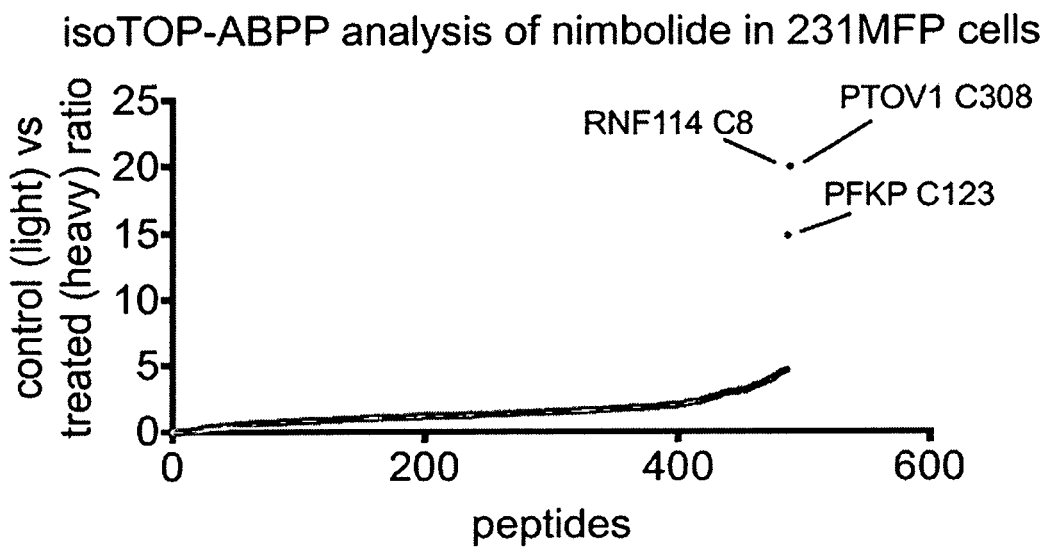
Figure 9C:
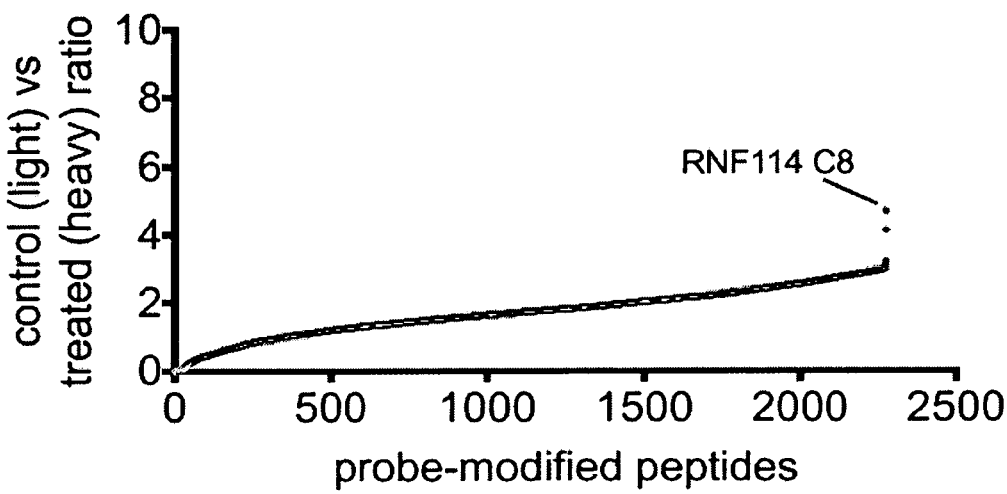
Figure 9D:
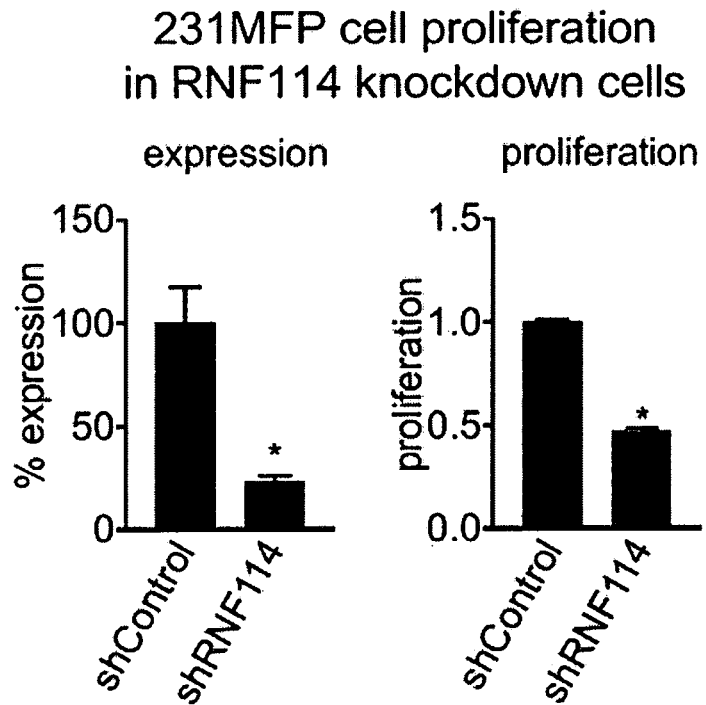
Figure 9E:
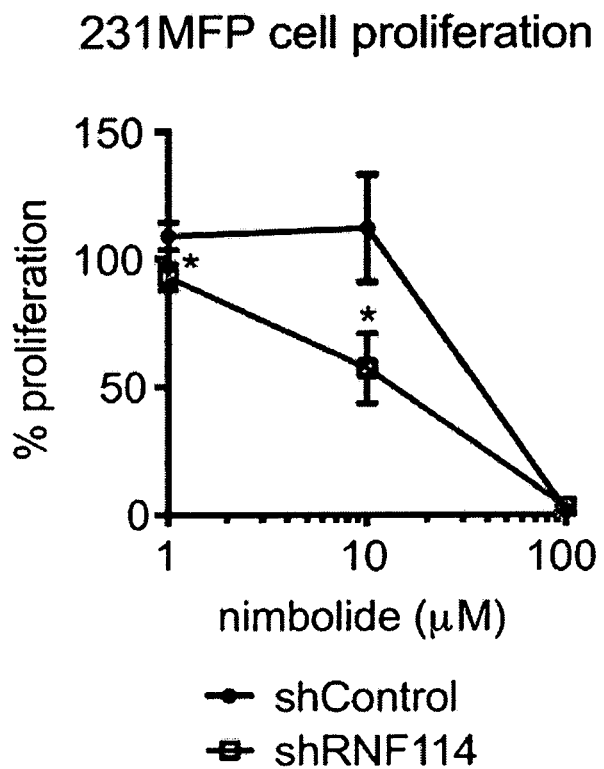

Using ABPP platforms to map druggable hotspots targeted by nimbolide in breast cancer cells. To better understand how nimbolide impairs breast cancer pathogenicity, we applied a chemoproteomic platform termed isotopic tandem orthogonal proteolysis-enabled activity-based protein profiling (isoTOP-ABPP) to map druggable hotspots targeted by nimbolide. Pioneered by Cravatt and Weerapana, isoTOP-ABPP uses reactivity-based chemical probes to map reactive, functional, and druggable hotspots directly in complex proteomes[28-31]. When used in a competitive manner, covalently-acting small-molecules can be competed against reactivity-based probe binding to facilitate target identification[31-38] (FIG. 9A). In this study, we treated breast cancer cell proteomes in vitro or breast cancer cells in situ with vehicle or nimbolide followed by competitive labeling of proteomes with a cysteine-reactive alkyne-functionalized iodoacetamide probe (IA-alkyne), after which isotopically light or heavy cleavable enrichment handles were appended to probe-labeled proteins for isoTOP-ABPP analysis. Probe-modified tryptic peptides were analyzed by liquid chromatography-mass spectrometry (LC-MS/MS) and light to heavy tryptic probe-modified peptide ratios, representing control versus treated IA-alkyne labeled sites, were quantified. IsoTOP-ABPP analysis of ligandable hotspots targeted by nimbolide in 231MFP TNBC proteomes showed three primary in vitro targets—PTOV1 C308, RNF114 C8, and PFKP C123—and one primary in situ target RNF114 C8 (FIG. 9B, 2C; Table Si). Knockdown of each of these targets using RNA interference revealed that RNF114 knockdown most closely resembled the anti-proliferative effects of nimbolide in 231MFP cells (FIG. 9D, Figure SI). Further demonstrating that RNF114 was the target responsible for nimbolide action, RNF114 knockdown exhibited significantly heightened sensitivity to nimbolide-mediated anti-proliferative effects (FIG. 9E).

Figure 10A:
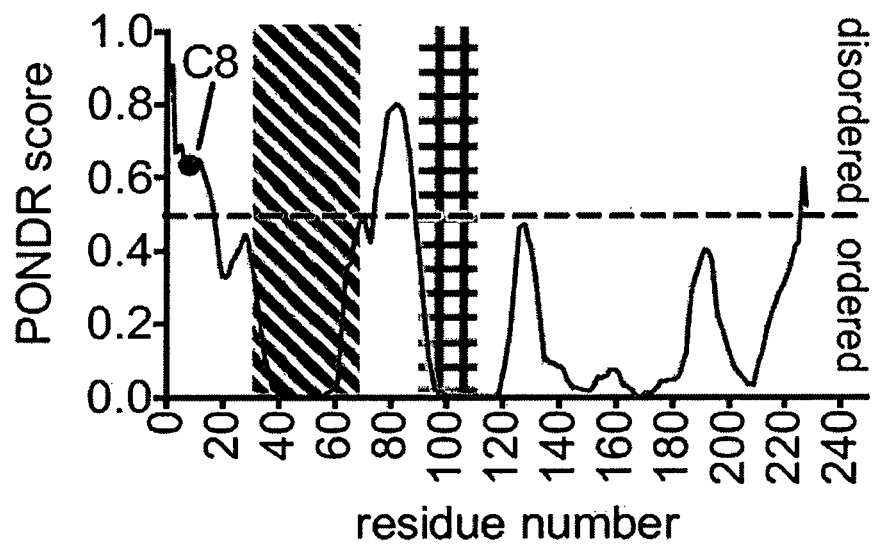
FIGS. 10A-10E. Nimbolide reacts covalently with C8 of RNF114.

Biochemical characterization of nimbolide interactions with RNF114. RNF114 is an E3 ubiquitin ligase of the RING family[39,40]. The site on RNF114 identified by isoTOP-ABPP as the target of nimbolide, C8, falls within the N-terminal region of the protein, predicted to be intrinsically disordered, and resides outside of the two annotated zinc finger domains (FIG. 10A). Intrigued by the apparent selective targeting of an intrinsically disordered region of a protein by a natural product, we sought to further confirm and characterize this interaction between nimbolide and RNF114.

Figure 10B:
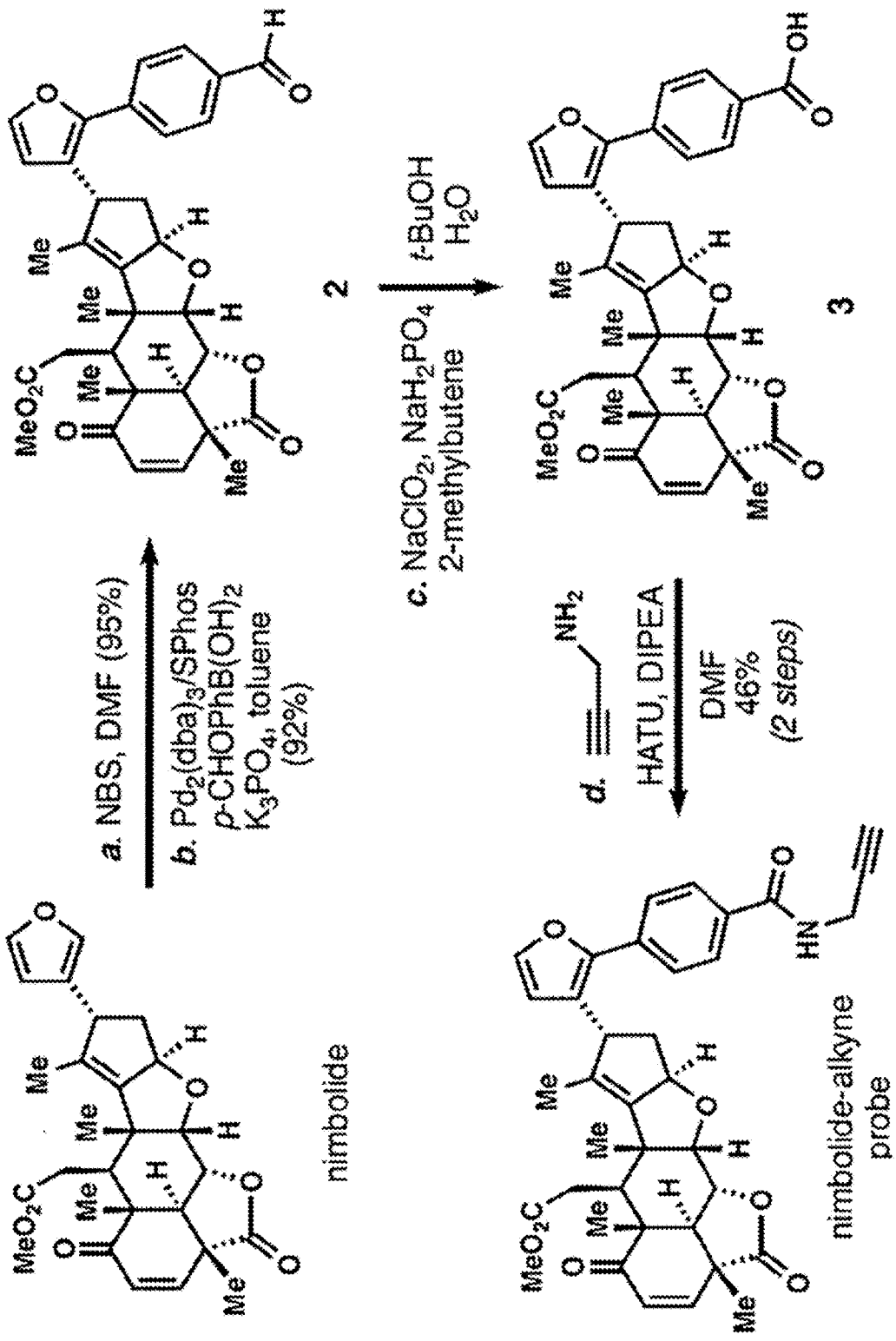
Figure 10C:
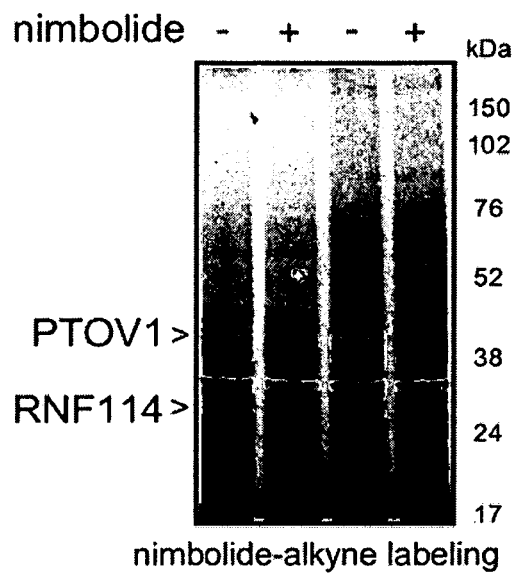
Figure 10D:
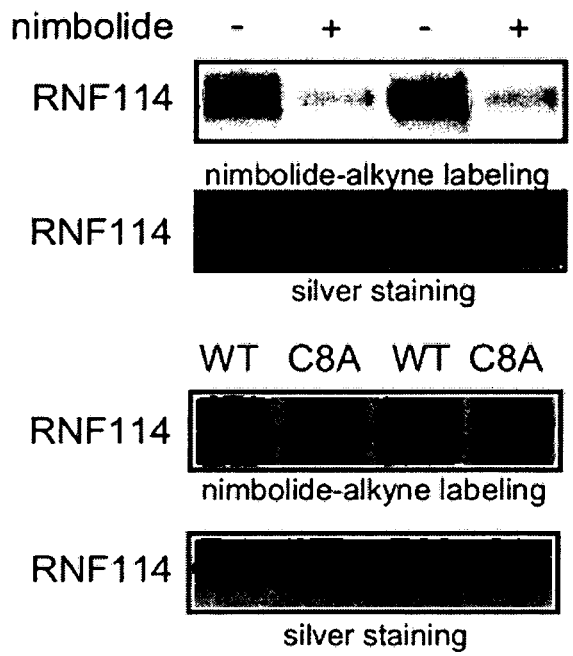
Figure 10E:
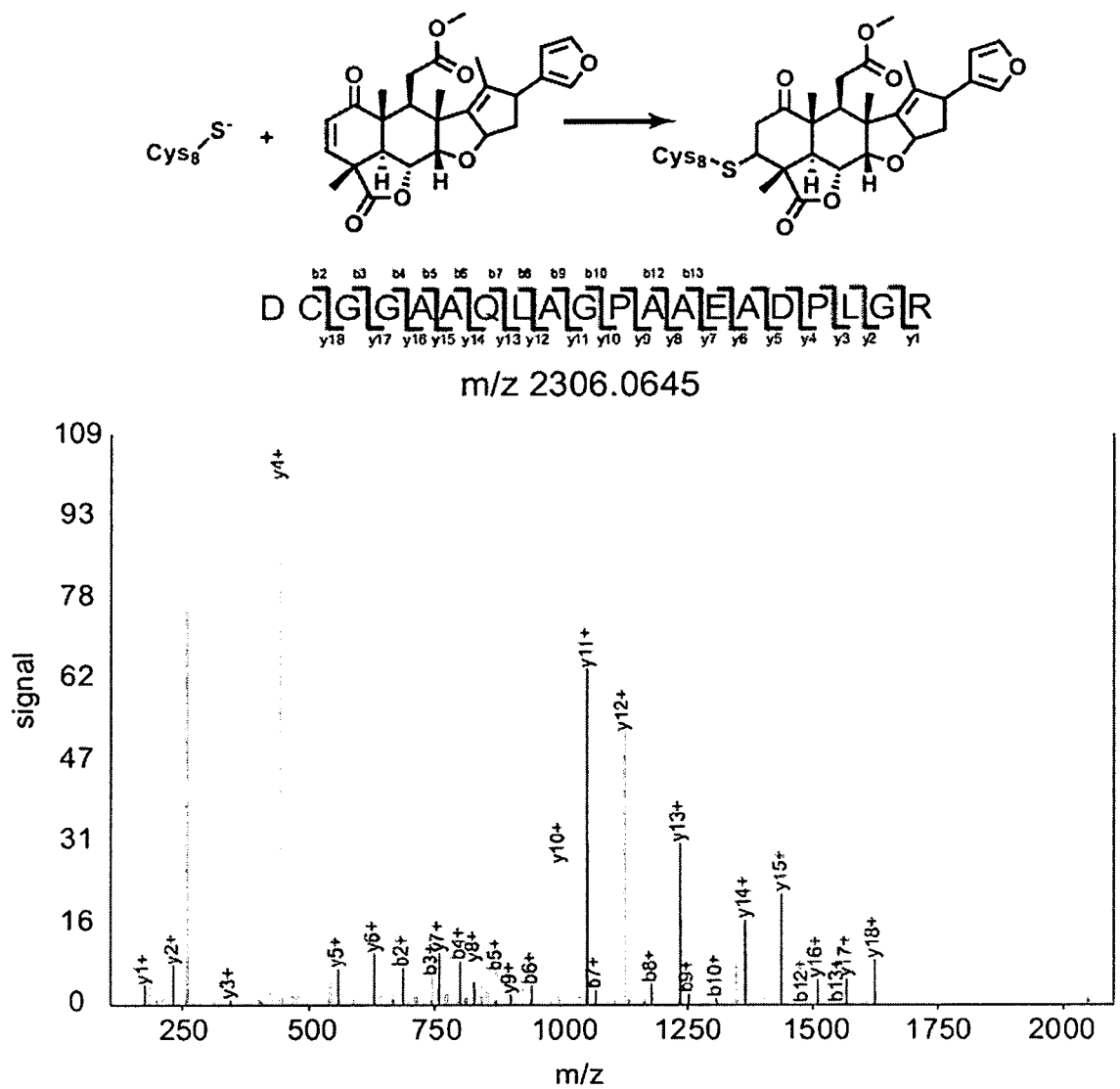

Because isoTOP-ABPP is a competitive assay between the covalently-acting molecule and a broader reactive probe, it is an indirect read-out of potential nimbolide-targeting hotspots. To confirm that nimbolide directly targeted RNF114, we synthesized the alkyne-functionalized probe shown in three steps from nimbolide (FIG. 10B). Selective bromination of the furan moiety and Suzuki coupling with 4-Formylphenylboronic acid afforded aldehyde 2, which was converted to its corresponding carboxylic acid (3) via Pinnick oxidation. Finally, coupling of 3 and propargyl amine (HATU, DIPEA) afforded the target probe. While the probe labeled multiple proteins in 231MFP breast cancer cell proteomes, only two of these proteins were competed by nimbolide itself. The molecular weight of these competed proteins was consistent with the molecular weights of PTOV1 and RNF114 (FIG. 10C). We further demonstrated that this nimbolide probe reacts with pure human RNF114 and was also competed by nimbolide and that this labeling was abrogated in the C8A RNF114 mutant (FIG. 10D). Furthermore, a direct mass adduct of nimbolide on C8 of RNF114 was observed by LC-MS/MS after incubation of pure protein with the natural product (FIG. 10E). Taken together, these findings provide convincing evidence that nimbolide covalently modifies an intrinsically disordered region of RNF114 at C8.

Figure 11A:
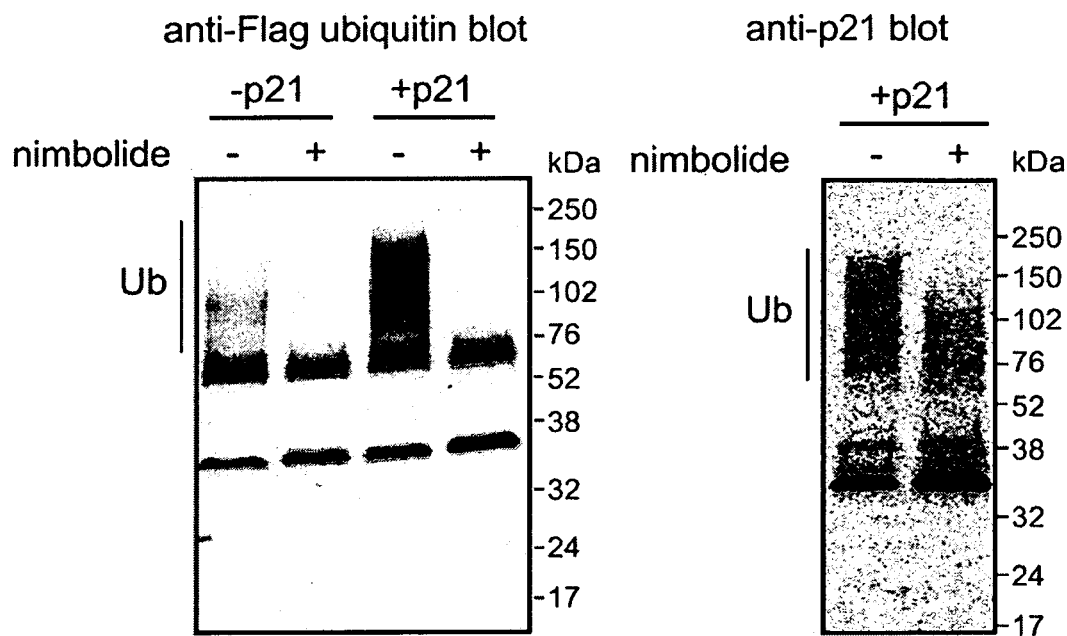
FIGS. 11A-11D. Nimbolide inhibits RNF114 activity through disrupting substrate recognition.
Figure 11B:
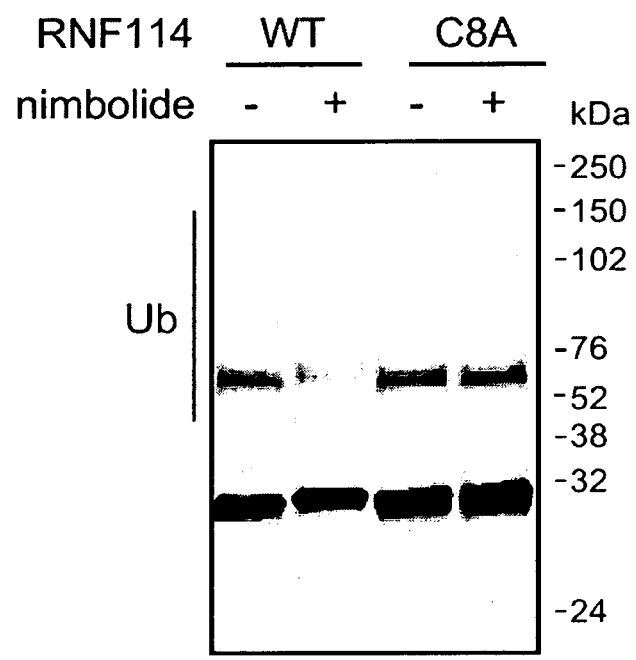
Figure 11C:
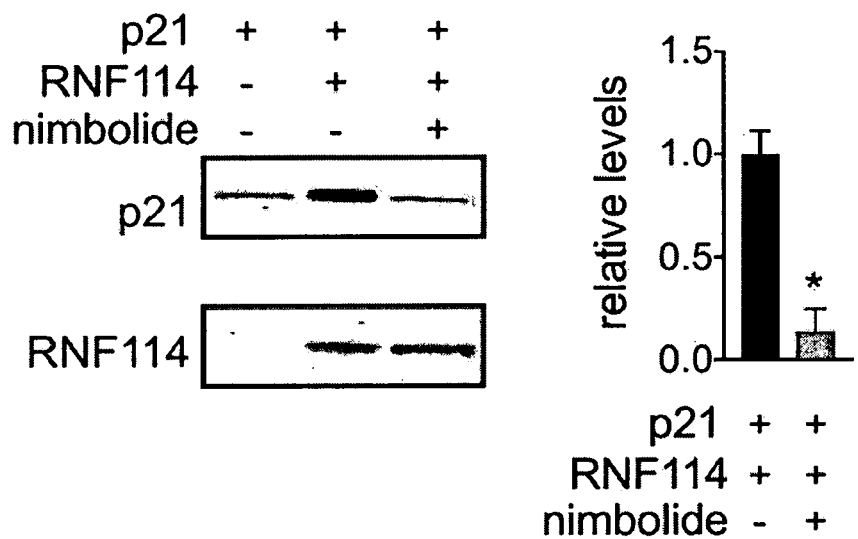
Figure 11D:
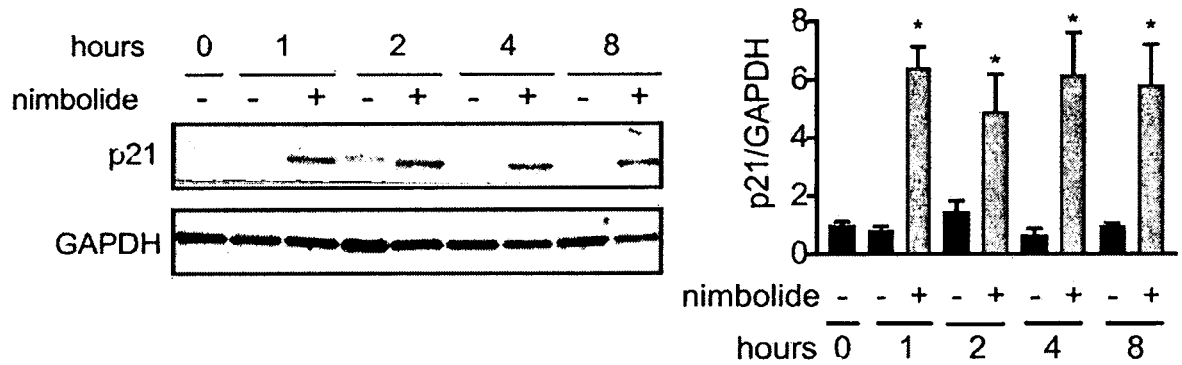

Effects of nimbolide on RNF114 activity and substrate binding in vitro and in situ. RNF114 has been previously shown to ubiquitinate and degrade the tumor suppressor p21, among other substrates[39,41,42]. In an in vitro reconstituted system, nimbolide inhibited both RNF114 autoubiquitination and p21 ubiquitination activity (FIG. 11A). The RNF114 C8A mutation did not affect basal RNF114 autoubiquitination activity, but attenuated the inhibition observed with nimbolide treatment (FIG. 11B). Previous characterization of RNF114 suggested that the N-terminus may be involved in substrate recognition[39]. Consistent with this premise, we found that RNF114 pulldown of p21 was inhibited by nimbolide, suggesting that the apparent inhibition of RNF114 may be due to impaired substrate recognition, rather than direct inhibition of activity (FIG. 11C). We further demonstrated that nimbolide treatment in 231MFP cells stabilized p21 protein expression within 1 hour, with no significant changes to p53 levels (FIG. 11D, Figure S2). Collectively, this data suggests that nimbolide reacts with an intrinsically disordered C8 of RNF114 to disrupt RNF114-p21 substrate recognition, leading to inhibition of p21 ubiquitination, rapid p21 stabilization, and impaired cell proliferation in breast cancer cells.

Figure 12A:
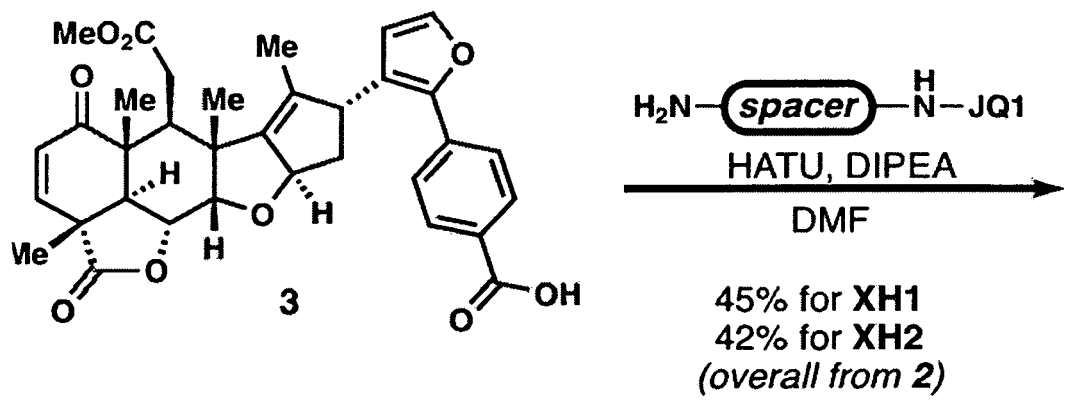
FIGS. 12A-12G. Nimbolide can be used to recruit RNF114 for targeted protein degradation of BRD4.
Figure 12A:
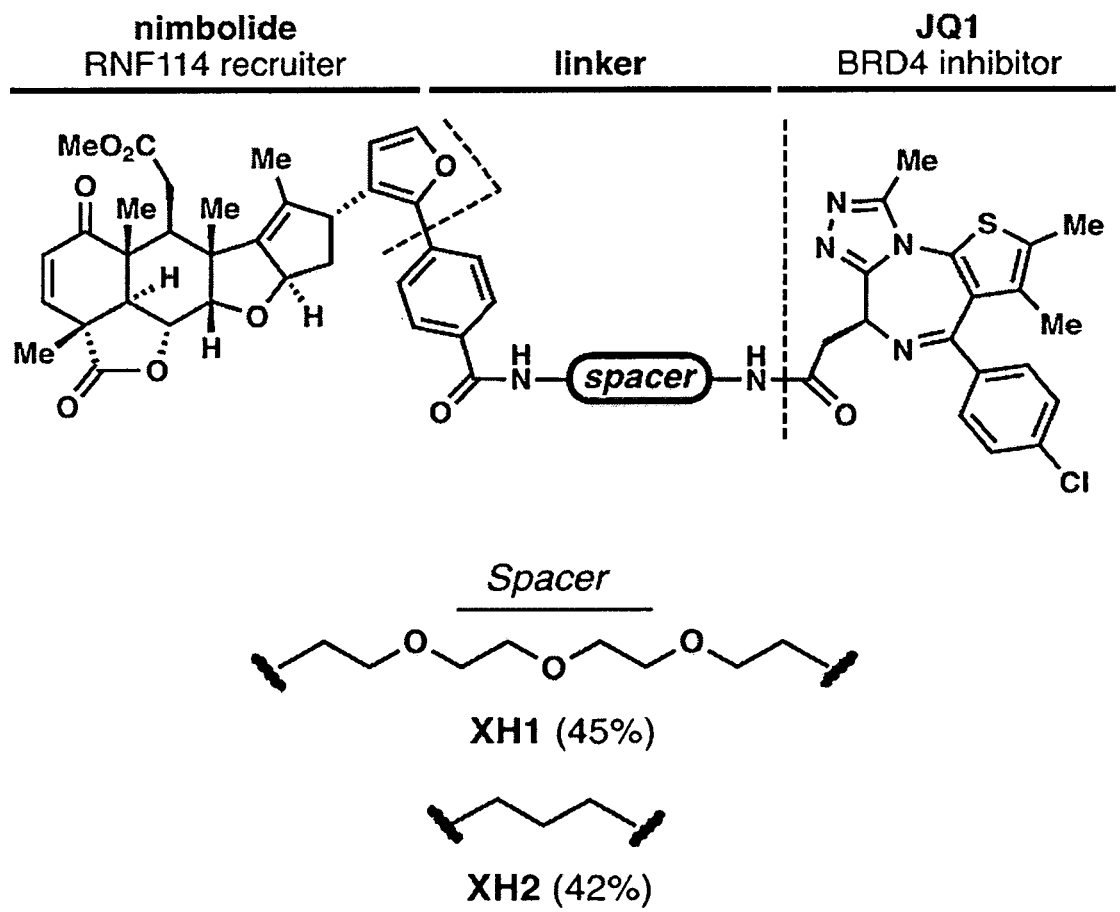
Figure 12B:
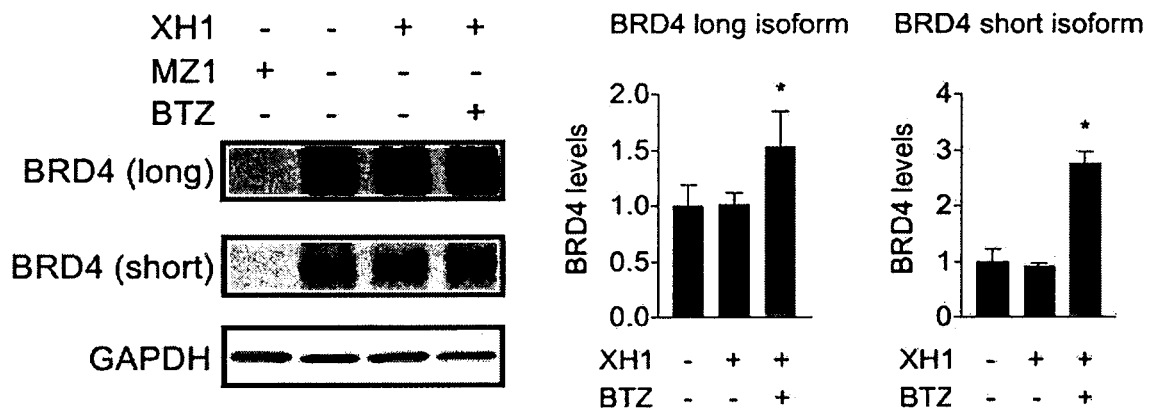
Figure 12C:
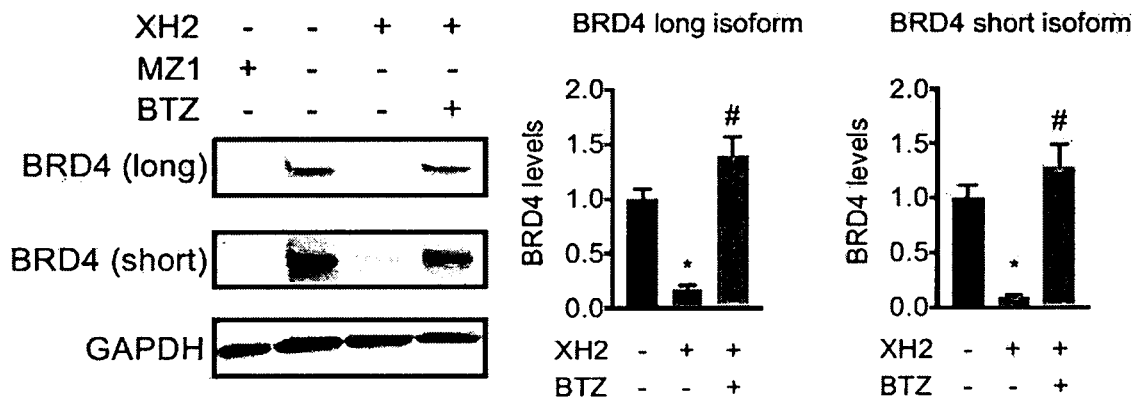
Figure 12D:
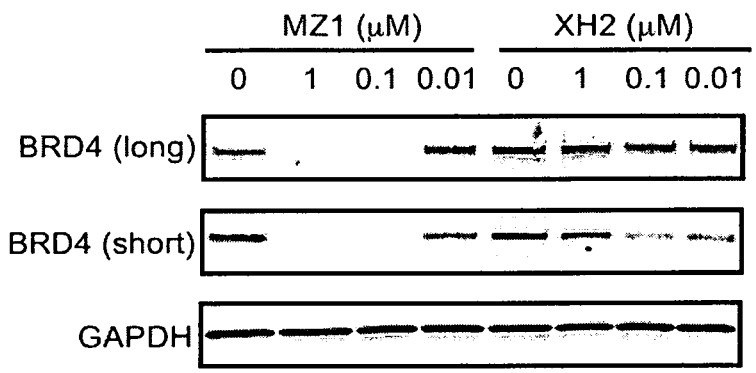
Figure 12E:
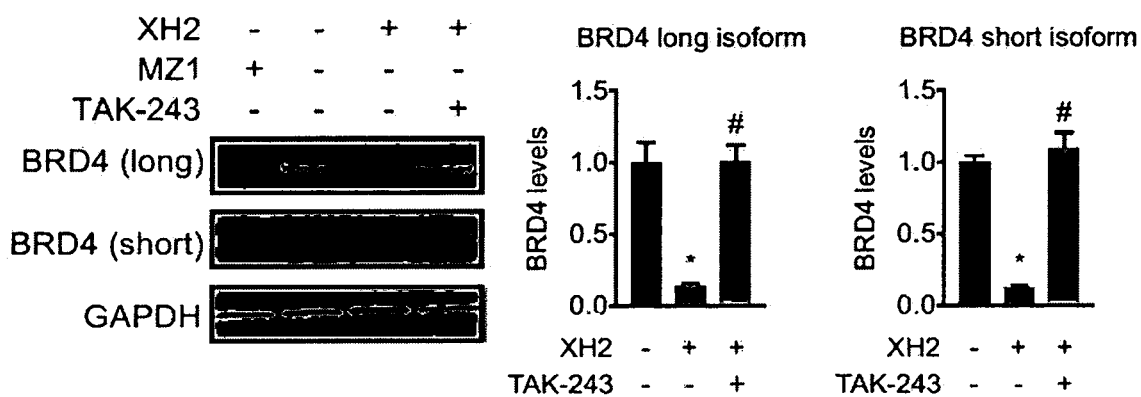
Figure 12F:
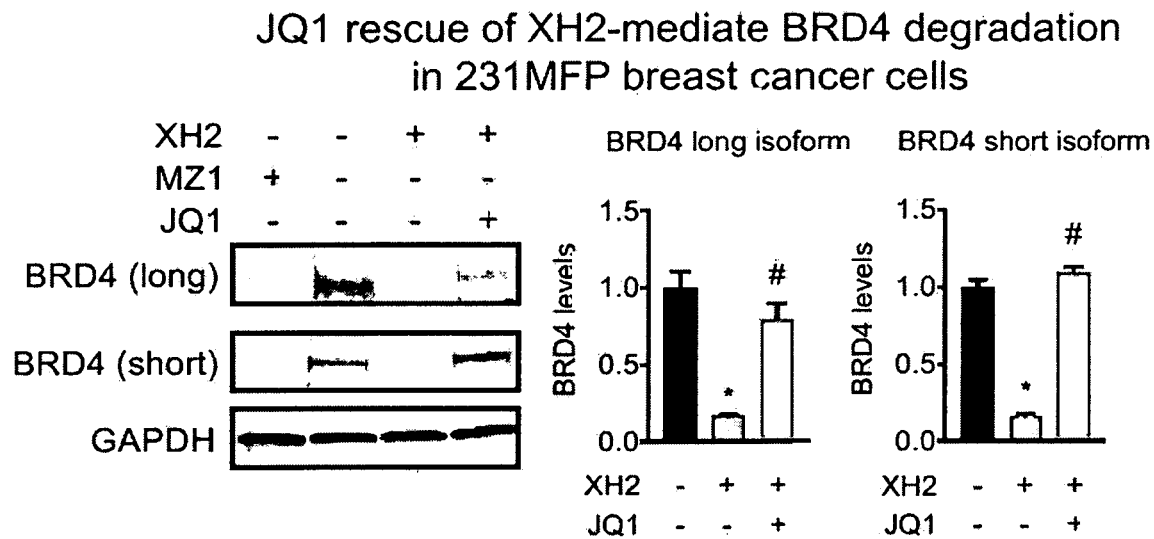
Figure 12G:
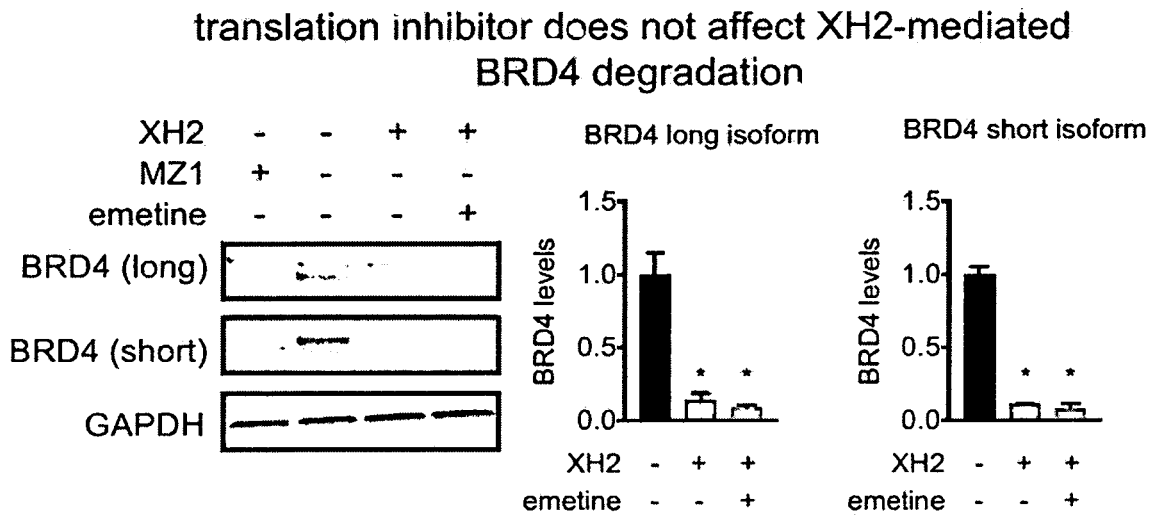

Using nimbolide as an RNF114-recruiter for targeted protein degradation. Targeted protein degradation is a powerful drug discovery platform that has arisen to tackle the undruggable proteome, through the utilization of bifunctional molecules called "degraders" that consist of a protein-targeting ligand, a linker, and an E3 ligase recruiter to bring an E3 ligase to a protein of interest to ubiquitinate and degrade the target in a proteasome-dependent manner[43-51]. Because nimbolide targets a potential substrate recognition site, we conjectured that nimbolide could be used to recruit RNF114 to other protein substrates for proteasomal degradation through the development of bifunctional degraders using nimbolide as an RNF114 recruiter. To demonstrate feasibility, two degraders formed by linking nimbolide to the BRD4 inhibitor JQ1 were synthesized (FIG. 12A). Prior studies have demonstrated efficient proteasome-dependent BRD4 degradation with JQ1-based degraders linked to either a cereblon-recruiter thalidomide or a VHL recruiter[44,47,51]. Previously prepared acid 3 was coupled to JQ1-functionalized amines containing both longer (PEG-based) and shorter (alkyl-based) spacer units, arriving at degraders XH1 and XH2. While XH1 did not show appreciable BRD4 degradation, XH2 treatment (100 nM) in 231MFP cells led to BRD4 degradation within 12 h and this degradation was attenuated by treatment with the proteasome inhibitor bortezomib (BTZ) (FIG. 12C). We compared the dose-response of BRD4 degradation with XH2 to that of previously reported BRD4 degrader MZ1, which utilizes a VHL ligand linked to JQ1 (FIG. 12D). MZ1 showed better BRD4 degradation at 1 and 0.1 µM, and equivalent degradation to XH2 at 10 nM. Interestingly, XH2 showed less degradation at 1 µM compared to 0.1 and 0.01 µM, which we attribute to the "hook effect" previously reported with degraders including MZ1[43,44]. XH2-mediated BRD4 degradation was also attenuated by treatment with an E1 ubiquitin-activating enzyme inhibitor (TAK-243) or pre-competing with the BRD4 ligand itself (JQ1) (FIG. 12E-12F). However, treatment with a translation inhibitor (emetine) had no effect of the observed degradation of BRD4 (FIG. 12G). These results strongly suggest that nimbolide reactivity with C8 of RNF114 can be exploited to recruit this E3 ligase to other protein substrates, such as BRD4, to ubiquitinate and degrade them.

Figure 13A:
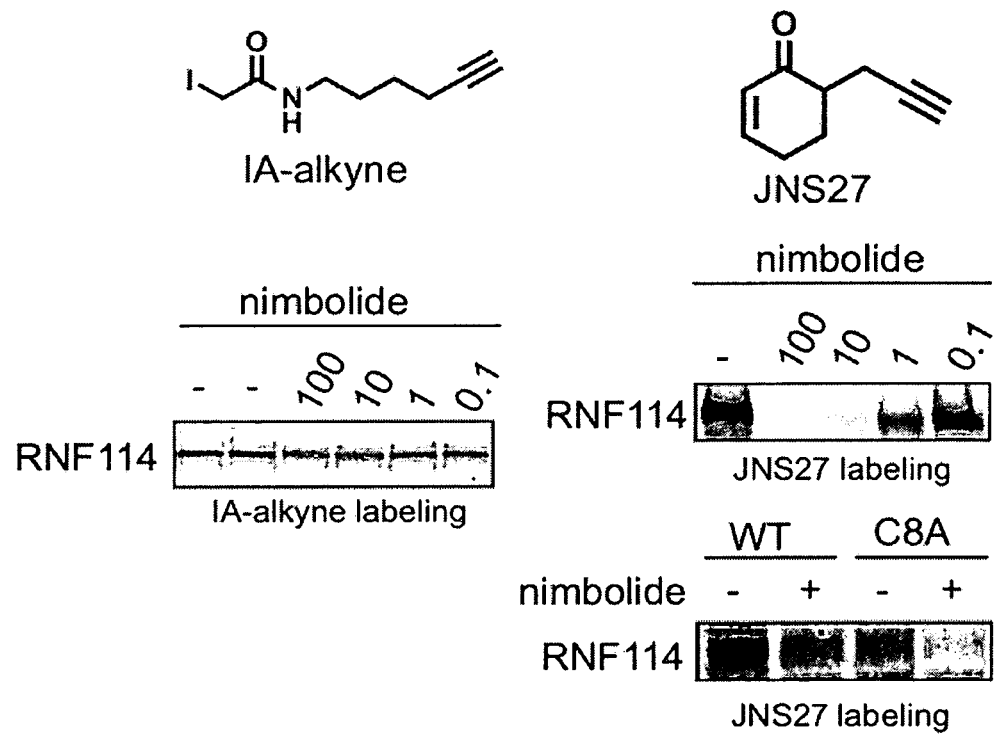
FIGS. 13A-13F. Chemoproteomics-enabled covalent ligand screening to identify more synthetically tractable covalent ligands against RNF114.
Figure 13B:
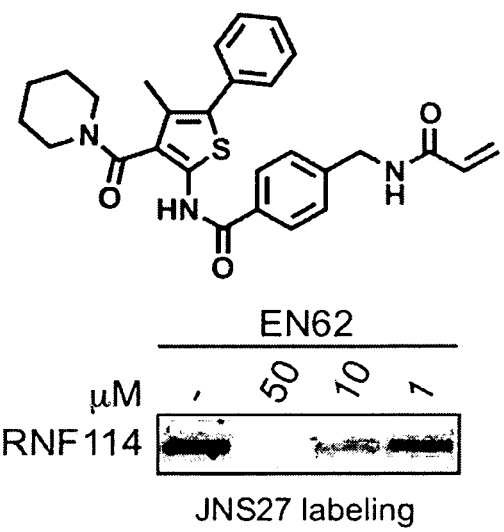
Figure 13C:
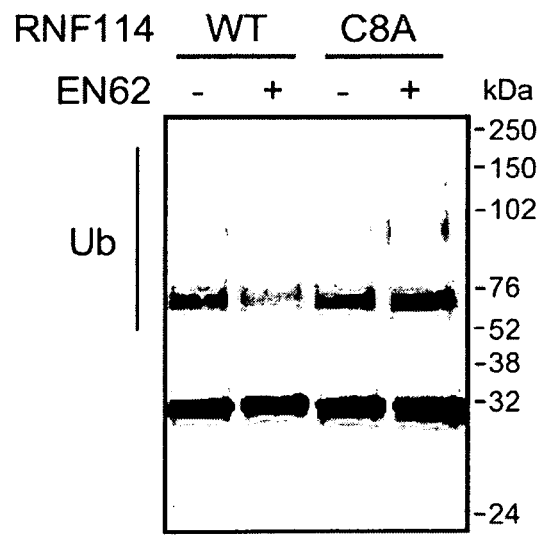
Figure 13D:
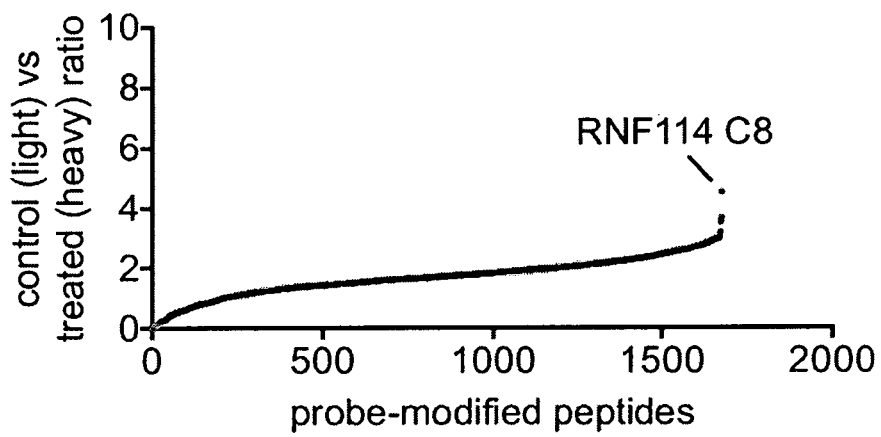
Figure 13E:
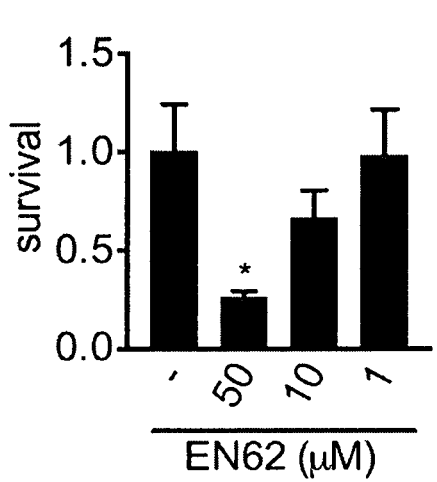
Figure 13F:
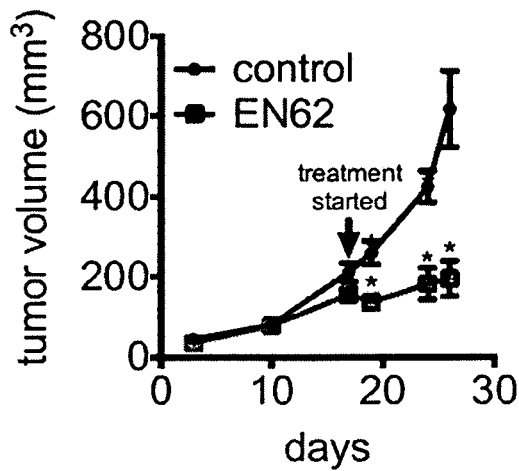
Figure 14:
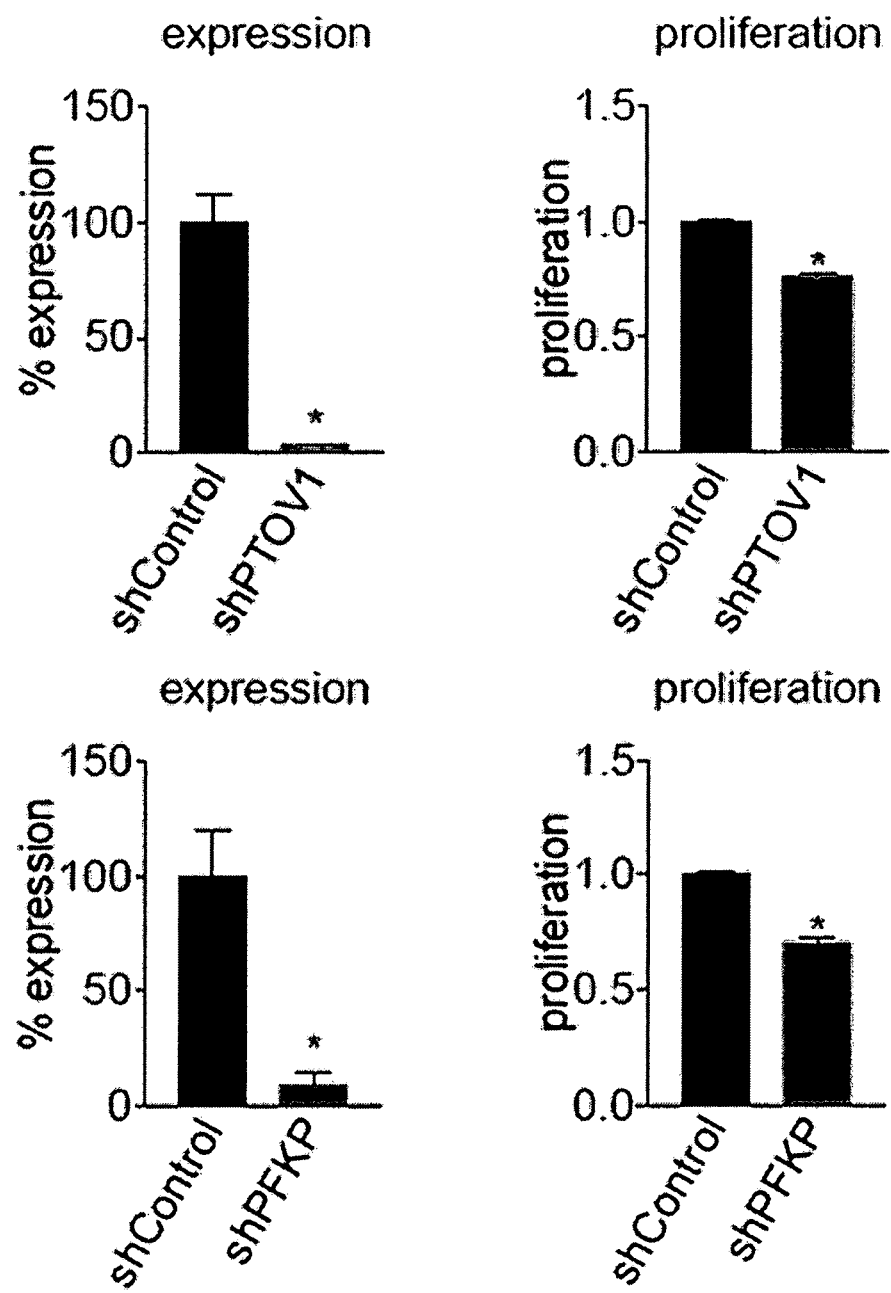
FIG. 14. PTOV1 and PFKP knockdown in 231MFP breast cancer cells. PTOV1 and PFKP were stably knocked down with shRNA oligonucleotides and expression was confirmed by qPCR. 231MFP shControl cells used shRNA oligonucleotides targeting GFP. 231MFP shControl, shPFKP, and shPTOV1 cell proliferation were assessed after 48 h by Hoechst stain. Data shown are average±sem, n=6/group. Significance is expressed as *p<0.05 compared to shControl cells.
Figure 15:
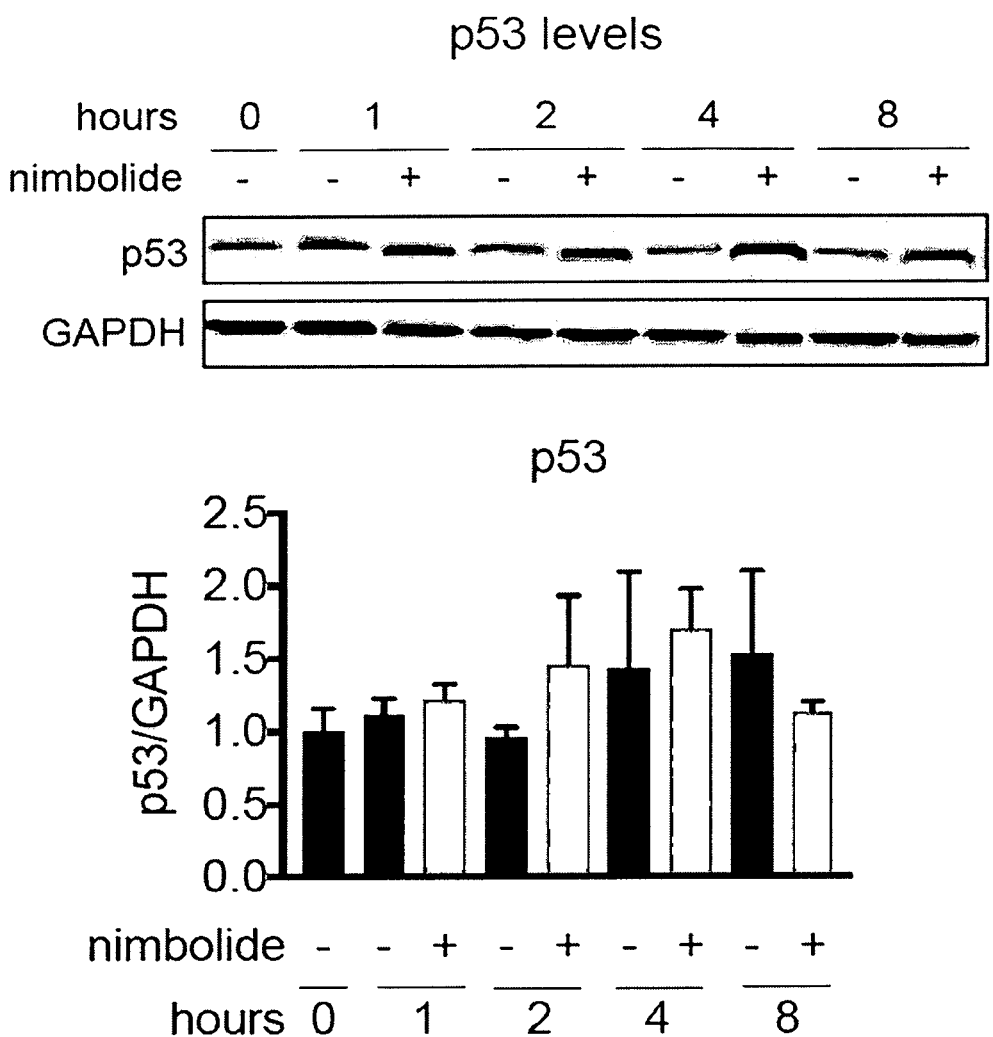
FIG. 15. Levels of p53 in nimbolide-treated 231MFP breast cancer cells. p53 levels in 231MFP breast cancer cells treated with DMSO vehicle or nimbolide (100 µM) assessed by Western blotting alongside GAPDH levels as a loading control. Gels are representative of an n=3/group. Blots were quantified by densitometry and normalizing to loading control. Data shown in bar graph are average±sem.
Figure 16A:
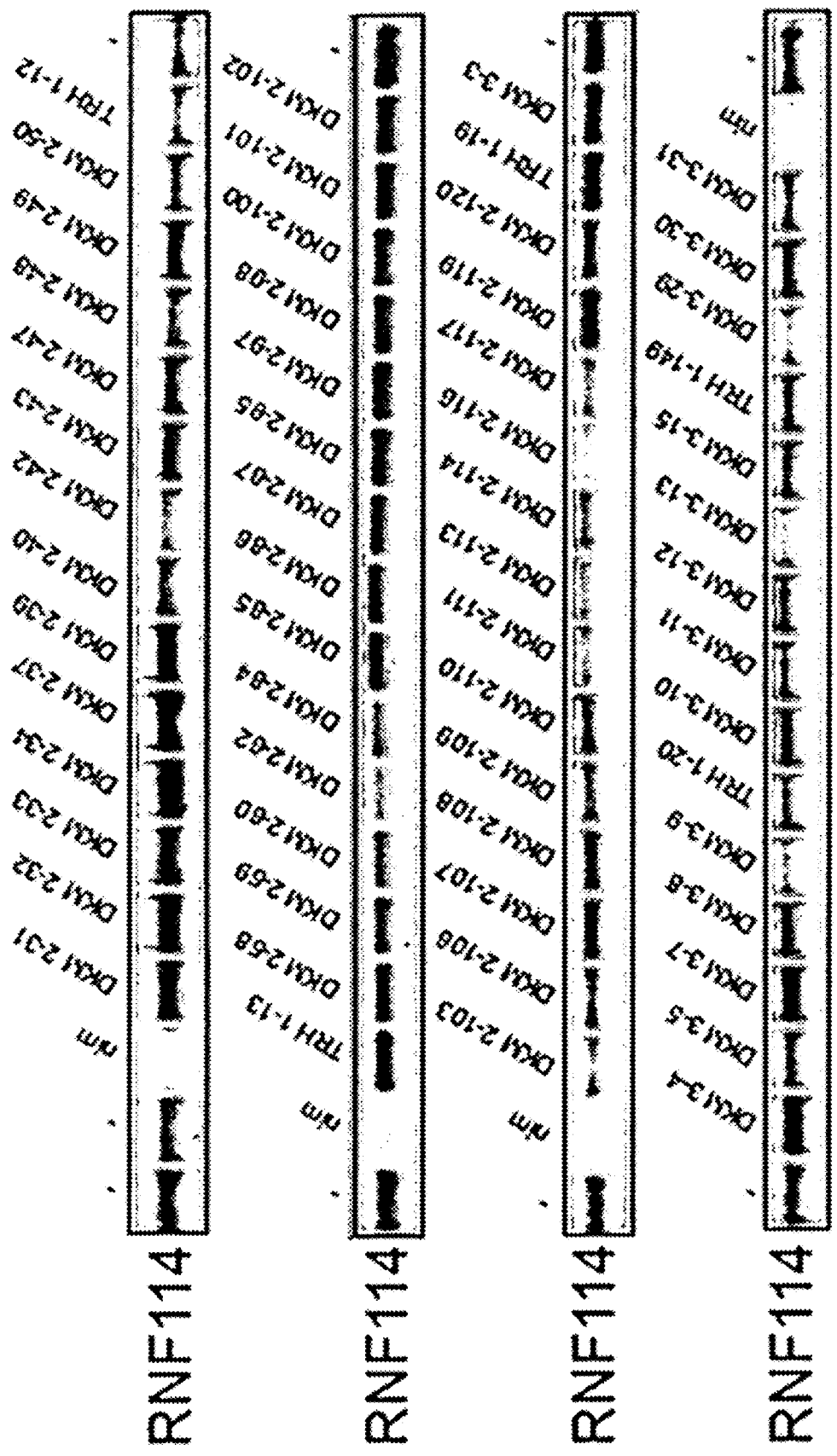
FIGS. 16A-16C. Gel-based ABPP screen of cysteine-reactive ligands against RNF114. Cysteine-reactive covalent ligands were screened against JNS27 labeling of pure human RNF114 protein. Covalent ligands (50 µM) were pre-incubated with RNF114 for 30 min prior to labeling with JNS27 for 1 h. Rhodamine-azide was then appended to probe-labeled proteins by CuAAC. Proteins were separated by SDS/PAGE and visualized by in-gel fluorescence. Those proteins that showed inhibition of probe-labeling were re-tested in dose-response studies below to identify hits that reproducibly inhibited JNS27 labeling of RNF114.
Figure 16B:
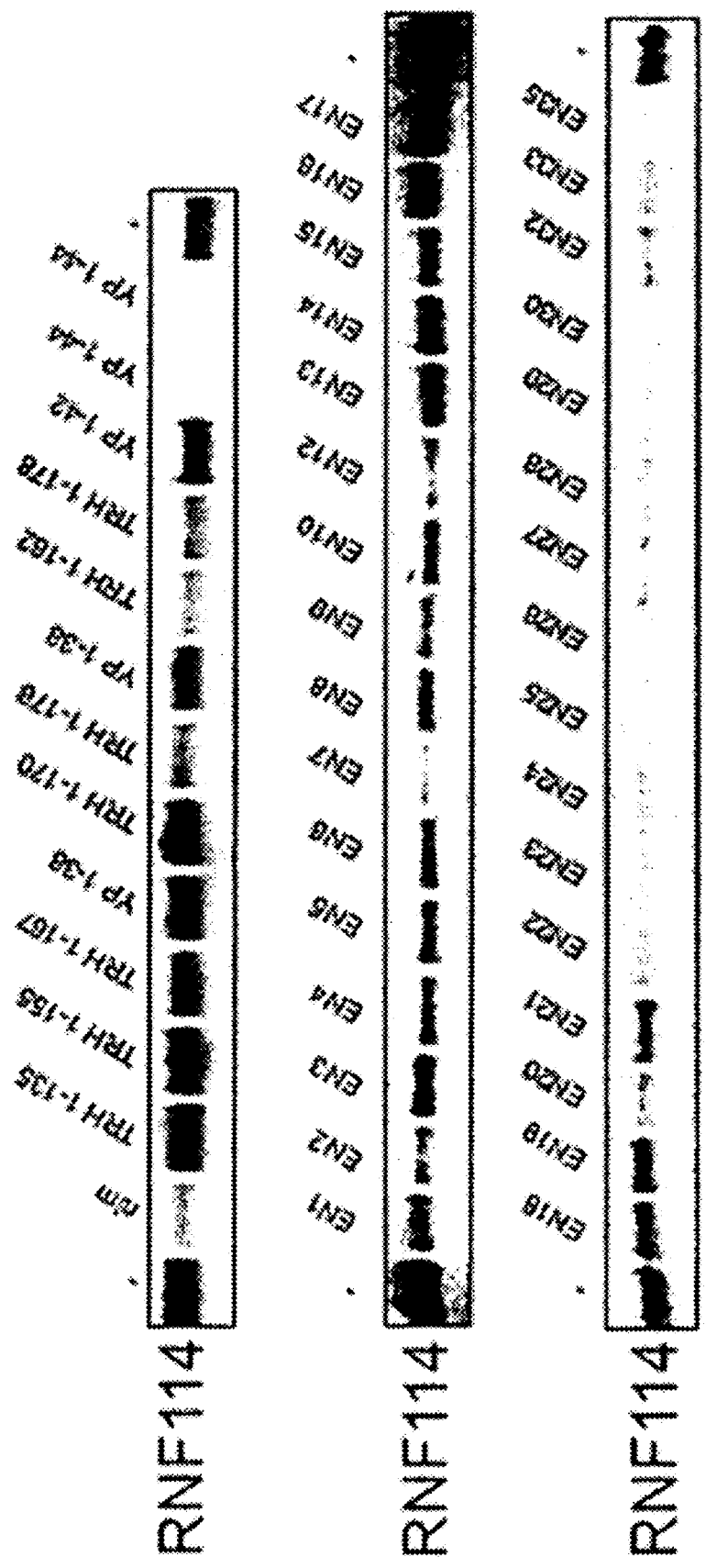
Figure 16B:
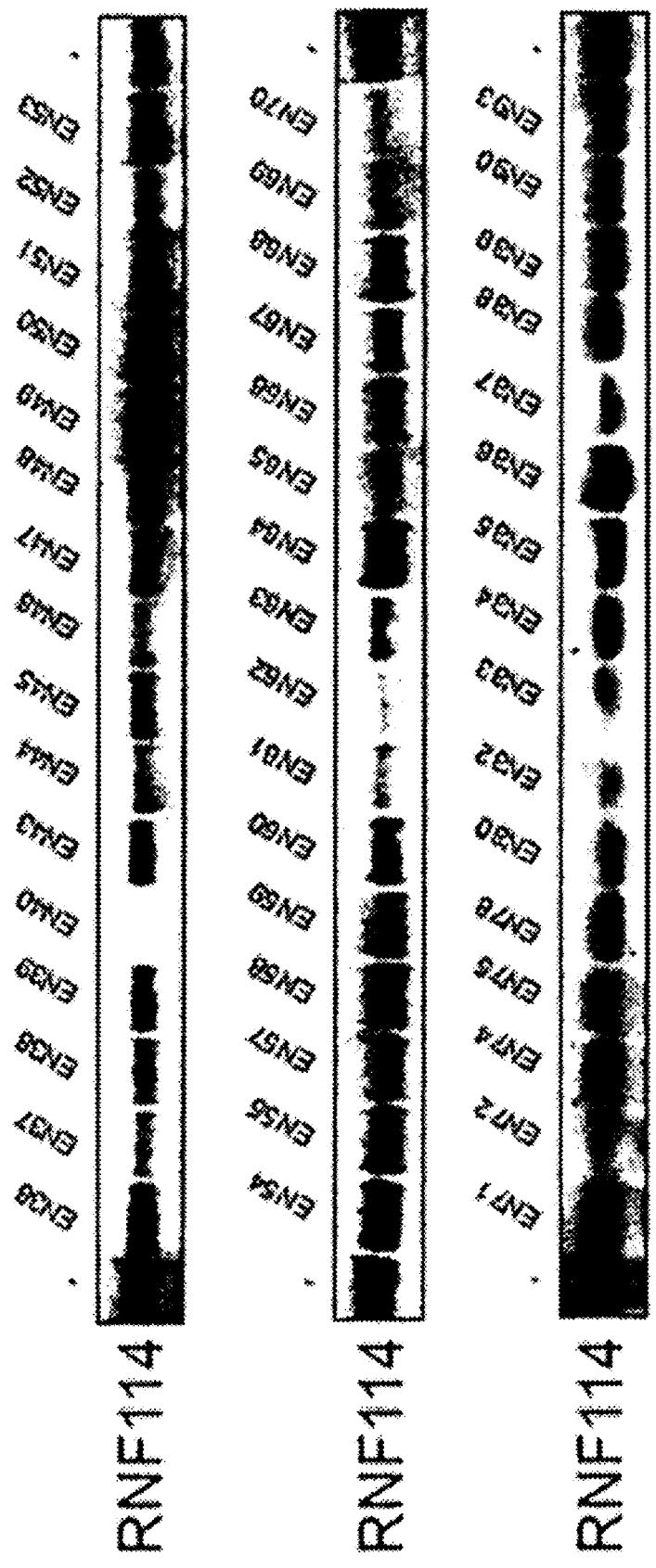
Figure 16C:
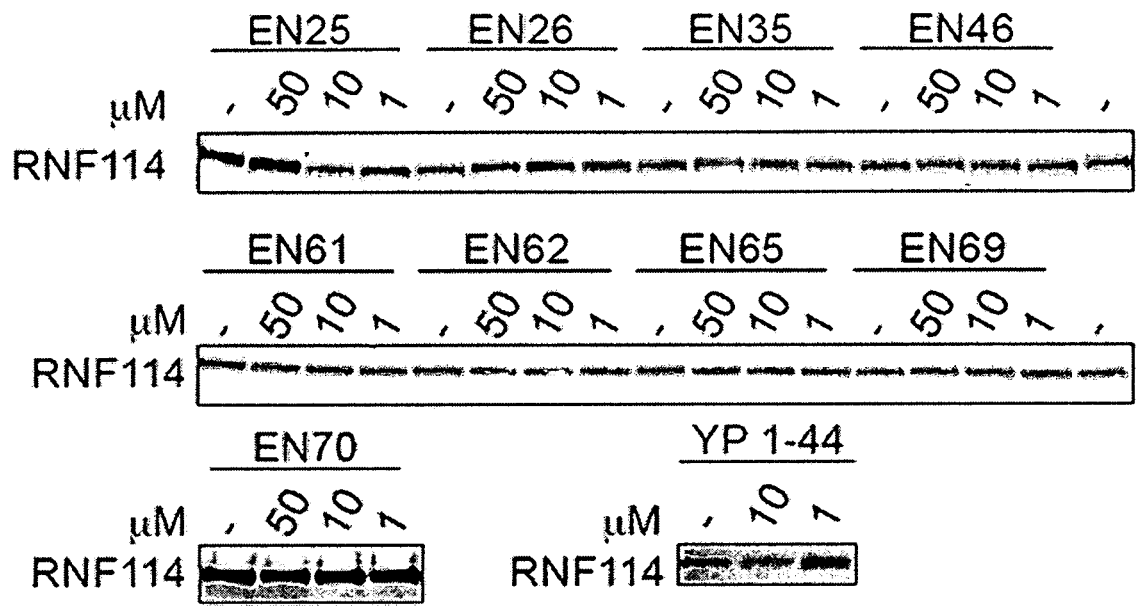
Figure 17A:
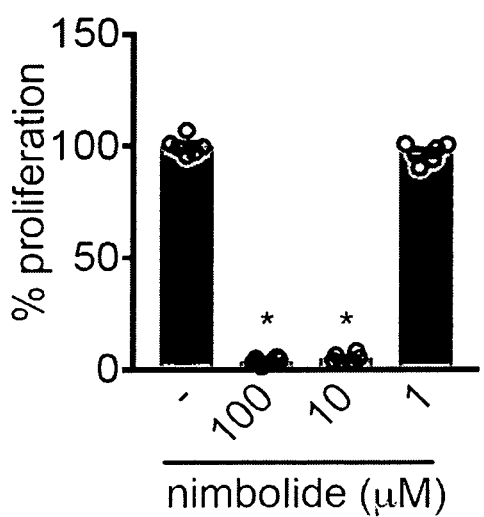
FIGS. 17A-17C. Nimbolide impairs breast cancer cell proliferation or survival.
Figure 17B:
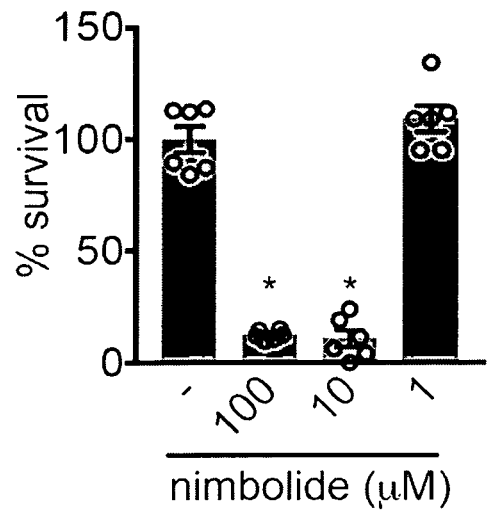
Figure 17C:
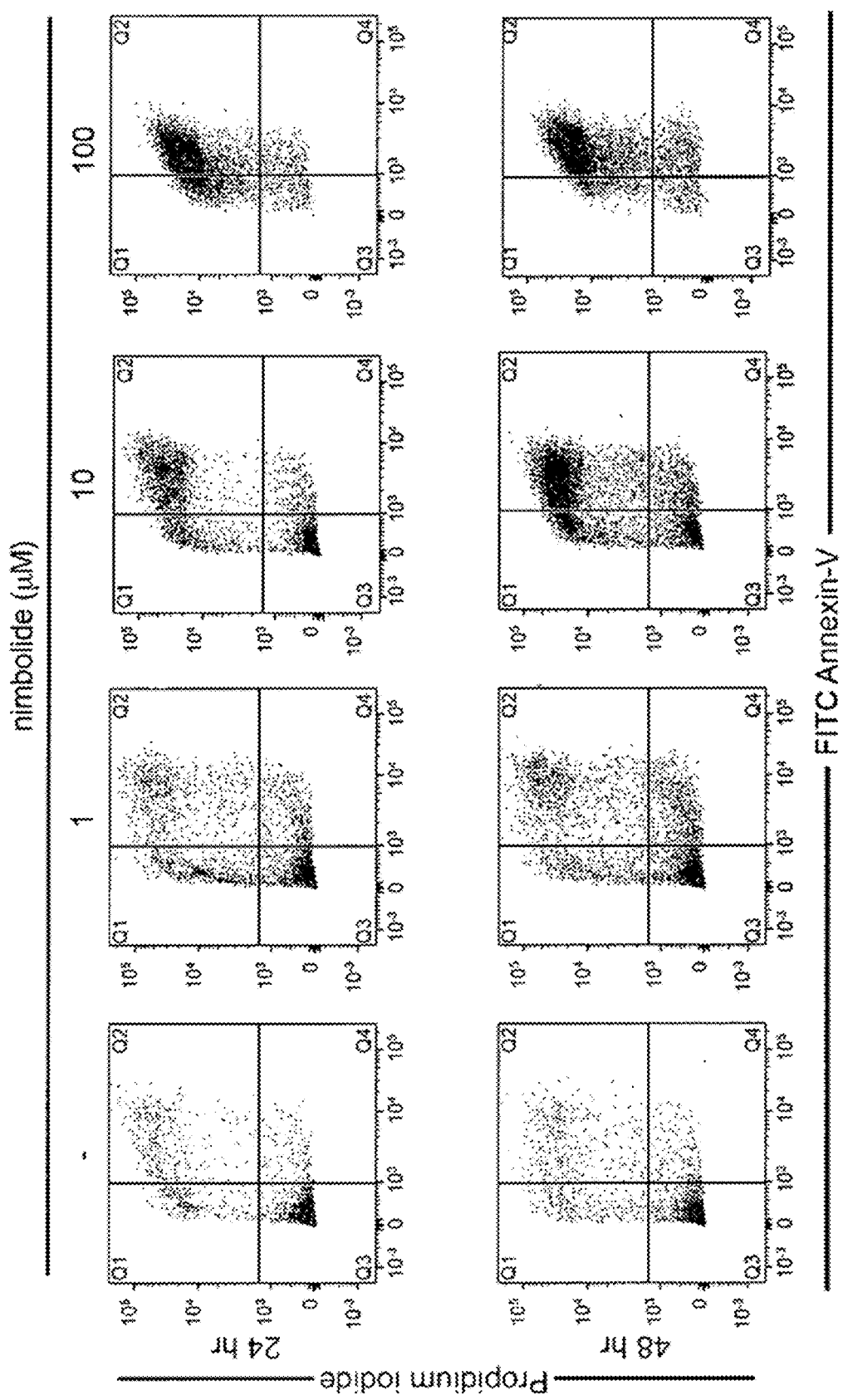
Figure 18A:
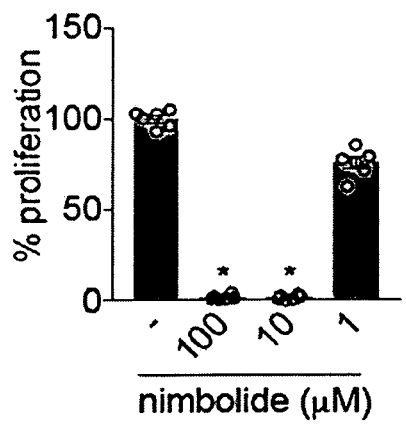
FIGS. 18A-18E. Nimbolide impairs breast cancer cell proliferation and survival and induces apoptosis.
Figure 18B:
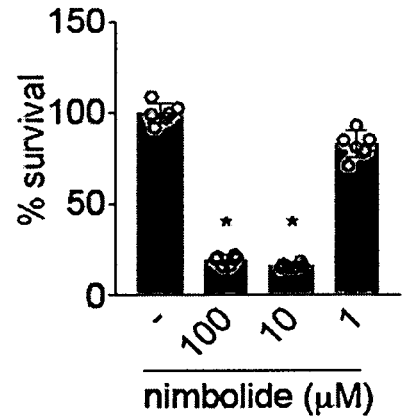
Figure 18C:
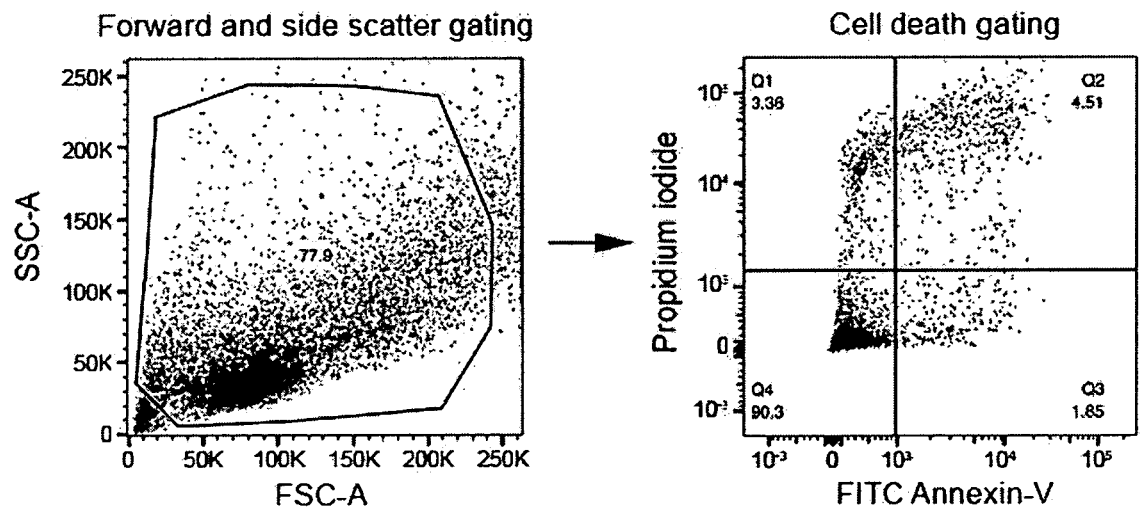
Figure 18D:
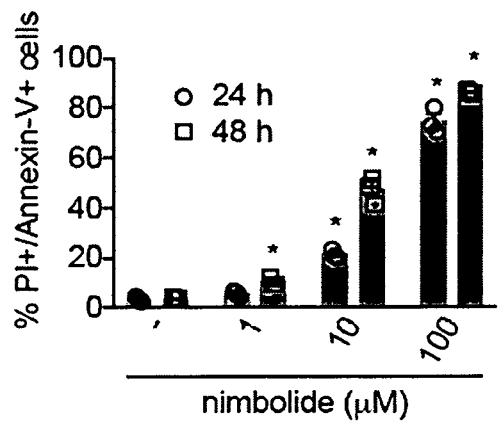
Figure 18E:
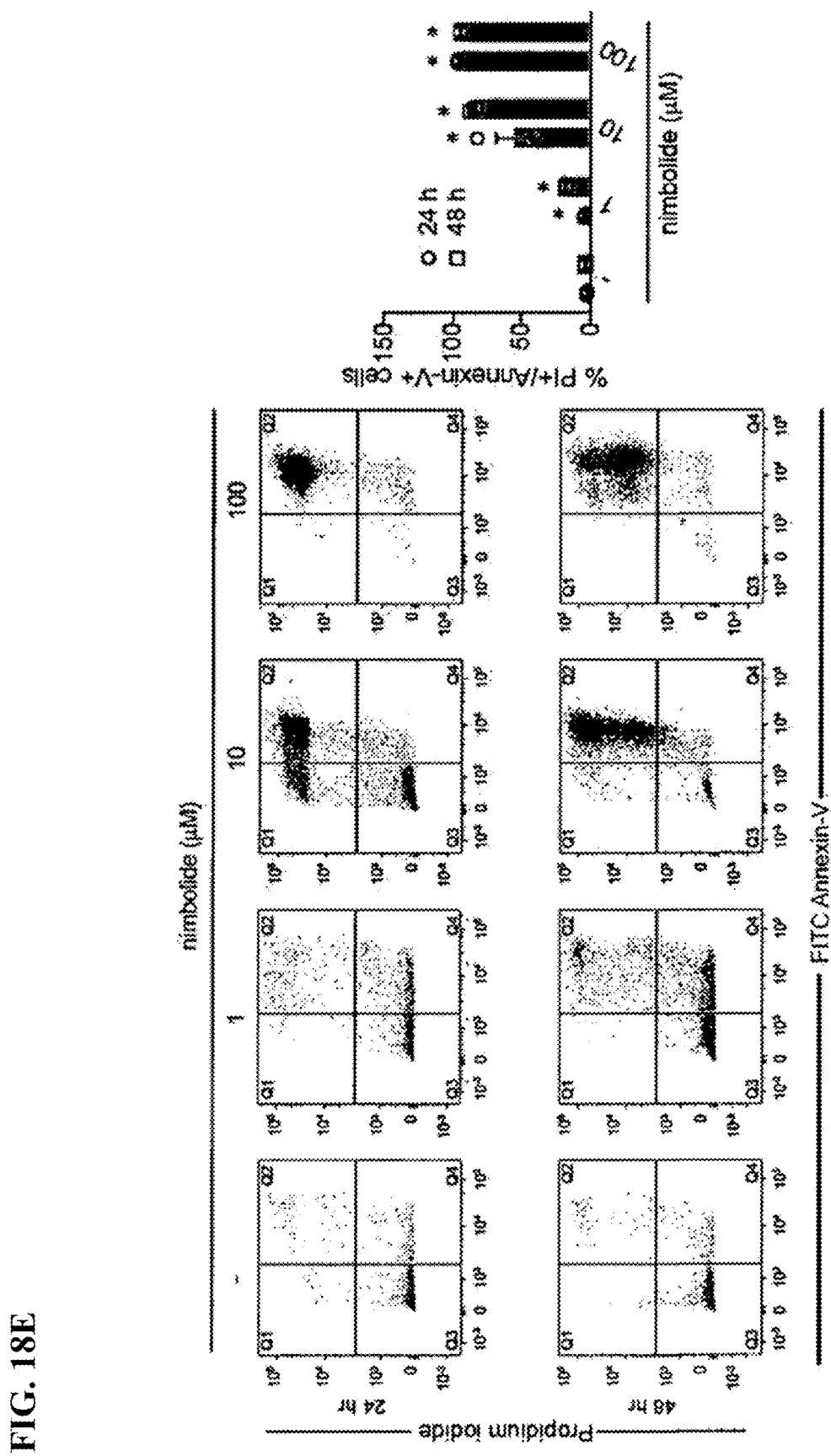

Chemoproteomics-enabled covalent ligand screening to identifying covalent ligands against RNF114. With the insight gained that C8 of RNF114 is a unique druggable modality that can be exploited for cancer therapy and targeted protein degradation applications, we searched for more synthetically tractable covalent ligands that similarly target RNF114. To achieve this goal, we screened a library of cysteine-reactive covalent ligands against RNF114 using a moderate-throughput gel-based ABPP approach, in which covalent ligands are competed against IA-alkyne labeling of RNF114, followed by appending a rhodamine-azide and analysis by SDS/PAGE and in-gel fluorescence. Initial studies competing nimbolide against IA-alkyne labeling of RNF114 did not show full inhibition of labeling, likely due to alkylation of multiple cysteines by IA-alkyne beyond C8. Thus, we synthesized a more tailored alkyne-functionalized cyclic enone probe JNS27, which showed selective labeling of C8 on RNF114 as evidenced by lack of labeling of C8A RNF114 mutant protein and the observed full competition with nimbolide (FIG. 13A). Of the approximately ~200 cysteine-reactive covalent ligands screened against RNF114, the acrylamide EN62 emerged as a promising hit (FIG. 13B; FIGS. 16A-16C). EN62 inhibited RNF114 autoubiquitination activity in a C8-dependent manner and also exhibited proteome-wide selectivity in 231MFP breast cancer cell proteomes (FIG. 13C-13D). EN62 also impaired 231MFP breast cancer cell survival and attenuated in vivo 231MFP tumor xenograft growth in immune-deficient mice (FIGS. 13E-13F). While EN62 requires further improvements to potency, this covalent ligand represents a more synthetically tractable starting point for future cancer therapy and protein degradation applications.

We show compelling evidence that nimbolide impairs breast cancer pathogenicity in-part through targeting a substrate recognition domain at C8 within RNF114 to inhibit p21 ubiquitination and degradation, leading to its stabilization. We demonstrate that nimbolide targeting of C8 on RNF114 can be used to recruit RNF114 for targeted protein degradation applications and demonstrate degradation of BRD4 with a nimbolide-JQ1 degrader XH2. Additionally, using chemoproteomics-enabled covalent ligand screening approaches, we show proof-of-concept that more synthetically tractable covalent ligands, such as EN62, can be rapidly identified to target druggable modalities employed by complex natural products, such as C8 of RNF114.

We report here that nimbolide disrupts RNF114 interactions with p21 and we also show that p21 levels are rapidly stabilized in breast cancer cells in a p53-independent manner. Several other E3 ligases have also been reported to degrade p21, including $SCF^{Skp2}$, $CRL4^{Cdt2}$, and CHIP under varying conditions during cell cycle or exogenous stress[52-54]. Previous studies have shown that RNF114 expression is elevated at late G1 phase to regulate p21 levels and is crucial for G1-to-S phase transition 39. Other RNF114 substrates that have been reported include TAB1 involved in maternal-to-zygotic transition and A20 involved in NF-κB activity and T cell activation[55,56] In cancer contexts or other cell and tissue types, nimbolide may thus have additional activities through regulating the levels of other RNF114 protein substrates. Furthermore, while we show that RNF114 is one of the primary functional targets of nimbolide, there may be additional reversible or irreversible protein targets that may not have been readily identified using this method. Nonetheless, we demonstrate that RNF114 is an important and functional nimbolide target in breast cancer cell proliferation, since knockdown of RNF114 hypersensitized cells to nimbolide.

Our results also demonstrate that nimbolide functionally targets an intrinsically disordered region within RNF114. Solving the structure of RNF114 with nimbolide has thus far proven challenging, but future studies investigating whether nimbolide induces order in the N-terminus would provide insights into the ligandability of intrinsically disordered and undruggable protein targets and strategies for potentially targeting other E3 ligases.

Targeted protein degradation has emerged as a formidable and effective drug discovery paradigm for targeting proteins for elimination through the proteasome[43,45]. One of the challenges, however, is that there are only a small number of E3 ligase recruiters that have been developed among the approximately 600 E3 ligases in the human genome[57]. These E3 ligase recruiters include the thalidomide-type immunomodulatory drugs (IMiD) that recruit cereblon, ligands that recruit VHL, nutlin that recruits MDM2, and ligands that recruit cIAP[43,45]. Here, we report that nimbolide can potentially be used as a novel RNF114 recruiter for targeted protein degradation applications. It should be possible to greatly optimize the performance of this degrader class via further linker modifications, an area of the molecule that has already been shown to be important. It may also be possible to utilize more synthetically tractable covalent ligands capable of targeting C8 of RNF114, such as EN62, as RNF114 recruiters. Since nimbolide targets a substrate recognition domain within RNF114, it will also be of future interest to determine whether nimbolide may act as a molecular glue to recruit and degrade neo-substrates, as has been reported for the IMiDs[58-60].

Overall, this demonstrates the utility of using ABPP-based chemoproteomic platforms to identify unique druggable modalities exploited by natural products. Intriguingly, we show that a natural product can functionally access an E3 ligase protein-protein interaction site for potential cancer therapy and targeted protein degradation applications and remarkably does so in an intrinsically disordered region of the protein. Our study also showcases how covalent ligand screening approaches can be utilized to identify more synthetically tractable small-molecules that act similarly to more complex natural products and that covalent ligands may be able to access other E3 ligases to expand the scope of E3 ligase recruiters.

Example 5. Methods and Assays

Cell Culture. The 231MFP cells were generated from explanted tumor xenografts of MDA-MB-231 cells as previously described[61]. HCC38 and HEK293T cells were obtained from the American Type Culture Collection. HEK293T cells were cultured in DMEM containing 10% (v/v) fetal bovine serum (FBS) and maintained at 37° C. with 5% $CO_2$. 231MFP were cultured in L15 medium containing 10% FBS and maintained at 37° C. with 0% $CO_2$. HCC38 cells were cultured in RPMI medium containing 10% FBS and maintained at 37° C. with 5% $CO_2$.

Survival and Proliferation Assays. Cell survival and proliferation assays were performed as previously described using Hoechst 33342 dye (Invitrogen) according to manufacturer's protocol and as previously described[62]. 231MFP cells were seeded into 96-well plates (40,000 for survival and 20,000 for proliferation) in a volume of 150 μl and allowed to adhere overnight. Cells were treated with an additional 50 μL of media containing 1:250 dilution of 1000× compound stock in DMSO. After the appropriate incubation period, media was removed from each well and 100 μl of staining solution containing 10% formalin and Hoechst 33342 dye was added to each well and incubated for 15 min in the dark at room temperature. After incubation, staining solution was removed, and wells were washed with PBS before imaging. Studies with HCC38 cells were also performed as above but were seeded with 20,000 cells for survival and 10,000 cells for proliferation.

IsoTOP-ABPP chemoproteomic studies. IsoTOP-ABPP studies were done as previously reported[28,31,35,63]. Cells were lysed by probe sonication in PBS and protein concentrations were measured by BCA assay[64]. For in situ experiments, cells were treated for 90 min with either DMSO vehicle or covalently-acting small molecule (from 1000× DMSO stock) before cell collection and lysis. For in vitro experiments, proteome samples diluted in PBS (4 mg of proteome per biological replicate) were treated with a DMSO vehicle or covalently-acting small-molecule for 30 min at room temperature. Proteomes were subsequently labeled with IA-alkyne labeling (100 μM) for 1 h at room temperature. CuAAC was used by sequential addition of tris(2-carboxyethyl)phosphine (1 mM, Sigma), tris[(1-benzyl-1H-1,2,3-triazol-4-yl)methyl]amine (34 μM, Sigma), copper (II) sulfate (1 mM, Sigma), and biotin-linker-azide—the linker functionalized with a TEV protease recognition sequence as well as an isotopically light or heavy valine for treatment of control or treated proteome, respectively. After CuAAC, proteomes were precipitated by centrifugation at 6500×g, washed in ice-cold methanol, combined in a 1:1 control/treated ratio, washed again, then denatured and resolubilized by heating in 1.2% SDS/PBS to 80° C. for 5 minutes. Insoluble components were precipitated by centrifugation at 6500×g and soluble proteome was diluted in 5 ml 0.2% SDS/PBS. Labeled proteins were bound to avidin-agarose beads (170 μl resuspended beads/sample, Thermo Pierce) while rotating overnight at 4° C. Bead-linked proteins were enriched by washing three times each in PBS and water, then resuspended in 6 M urea/PBS (Sigma) and reduced in TCEP (1 mM, Sigma), alkylated with iodoacetamide (IA) (18 mM, Sigma), then washed and resuspended in 2 M urea and trypsinized overnight with 0.5 μg/μl sequencing grade trypsin (Promega). Tryptic peptides were eluted off. Beads were washed three times each in PBS and water, washed in TEV buffer solution (water, TEV buffer, 100 μM dithiothreitol) and resuspended in buffer with Ac-TEV protease and incubated overnight. Peptides were diluted in water and acidified with formic acid (1.2 M, Spectrum) and prepared for analysis.

Mass Spectrometry Analysis. Peptides from all proteomic experiments were pressure-loaded onto a 250 μm inner diameter fused silica capillary tubing packed with 4 cm of Aqua C18 reverse-phase resin (Phenomenex #04A-4299) which was previously equilibrated on an Agilent 600 series HPLC using gradient from 100% buffer A to 100% buffer B over 10 min, followed by a 5 min wash with 100% buffer B and a 5 min wash with 100% buffer A. The samples were then attached using a MicroTee PEEK 360 μm fitting (Thermo Fisher Scientific #p-888) to a 13 cm laser pulled column packed with 10 cm Aqua C18 reverse-phase resin and 3 cm of strong-cation exchange resin for isoTOP-ABPP studies. Samples were analyzed using an Q Exactive Plus mass spectrometer (Thermo Fisher Scientific) using a 5-step Multidimensional Protein Identification Technology (MudPIT) program, using 0%, 25%, 50%, 80%, and 100% salt bumps of 500 mM aqueous ammonium acetate and using a gradient of 5-55% buffer B in buffer A (buffer A: 95:5 water:acetonitrile, 0.1% formic acid; buffer B 80:20 acetonitrile:water, 0.1% formic acid). Data was collected in data-dependent acquisition mode with dynamic exclusion enabled (60 s). One full MS (MS1) scan (400-1800 m/z) was followed by 15 MS2 scans (ITMS) of the nth most abundant ions. Heated capillary temperature was set to 200° C. and the nanospray voltage was set to 2.75 kV.

Data was extracted in the form of MS1 and MS2 files using Raw Extractor 1.9.9.2 (Scripps Research Institute) and searched against the Uniprot human database using ProLuCID search methodology in IP2 v.3 (Integrated Proteomics Applications, Inc)[65]. Cysteine residues were searched with a static modification for carboxyaminomethylation (+57.02146) and up to two differential modifications for methionine oxidation and either the light or heavy TEV tags (+464.28596 or +470.29977, respectively). Peptides were required to have at least one tryptic end and to contain the TEV modification. ProLUCID data was filtered through DTASelect to achieve a peptide false-positive rate below 5%. Only those probe-modified peptides that were evident across all two out of three biological replicates were interpreted for their isotopic light to heavy ratios. Those probe-modified peptides that showed ratios >3 were further analyzed as potential targets of the covalently-acting small-molecule. For modified peptides with ratios >3, we filtered these hits for peptides were present in all three biological replicates. For those probe-modified peptide ratios >3, only those peptides with 3 ratios >3 were interpreted, and otherwise replaced with the lowest ratio. For those probe-modified peptide ratios >4, only those peptides with 3 ratios >4 were interpreted, and otherwise replaced with the lowest ratio. MS1 peak shapes of any resulting probe-modified peptides with ratios >3 were then manually confirmed to be of good quality for interpreted peptides across all biological replicates.

Constructing knockdown lines. We used short-hairpin oligonucleotides to knock down the expression of RNF114 in 231MFP cells using previously described methods[66]. For generation of stable shRNA lines, lentiviral plasmids in the pLKO.1 backbone containing shRNA (Sigma) against human RNF114 were transfected into HEK293T cells using Lipofectamine (Invitrogen). Lentivirus was collected from filtered cultured medium and used to infect the target cancer cell line with Polybrene. Target cells were selected over 3 days with 1 μg/ml puromycin. The short-hairpin sequence used for generation of the RNF114 knockdown lines was:

(SEQ ID NO: 4)
CCGGCCATGGCTGCCGTAAGAATTTCTCGAGAAATTCTTACGGCAGCCAT

GGTTTTTG (Sigma RNF114 MISSION shRNA Bacterial Glycerol Stock, TRCN0000314877).

The control shRNA was targeted against GFP with the target sequence GCAAGCTGACCCTGAAGTTCAT (SEQ ID NO:5)

Knockdown was confirmed by qPCR.

Gene Expression by qPCR. Gene expression was confirmed by qPCR using the manufacturer's protocol for Fisher Maxima SYBR Green. Primer sequences for Fisher Maxima SYBR Green were derived from Primer Bank. Sequences of primers are as follows:

RNF114 Forward:

(SEQ ID NO: 6)
AAT GTT CCA AAC CG

```
RNF114 Reverse:
                                    (SEQ ID NO: 7)
TTG CAG TGT TCC AC Cyclophilin Forward:
                                    (SEQ ID NO: 8)
CCC ACC GTG TTC TTC GAC ATT Cyclophilin Reverse:
                                    (SEQ ID NO: 9)
GGA CCC GTA TGC TTT AGG ATG A
```

Gel-Based ABPP. Gel-based ABPP methods were performed as previously described[34,62,63,67]. Recombinant pure human proteins were purchased from Origene. Pure proteins (0.1 µg) were pre-treated with DMSO vehicle or covalently-acting small molecules for 30 min at room temperature in an incubation volume of 50 µL PBS, and were subsequently treated with JNS-1-27 (50 µM final concentration) for 1 h at room temperature. CuAAC was performed to append rhodamine-azide (1 µM final concentration) onto alkyne probe-labeled proteins. Samples were then diluted with 20 µL of 4× reducing Laemmli SDS sample loading buffer (Alfa Aesar) and heated at 90° C. for 5 min. The samples were separated on precast 4-20% TGX gels (Bio-Rad Laboratories, Inc.). Prior to scanning by ChemiDoc MP (Bio-Rad Laboratories, Inc), gels were fixed in a solution of 10% acetic acid, 30% ethanol for 2 hrs. Inhibition of target labeling was assessed by densitometry using ImageJ.

Covalent Ligand Library. The synthesis and characterization of most of the covalent ligands screened against RNF114 have been previously reported[31,32,34,63]. Compounds starting with "EN" were purchased from Enamine LLC. The synthesis and characterization of other covalent ligands not previously reported are described in Example 6.

Western blotting. Antibodies to RNF114 (Millipore Sigma, HPA021184), p21 (Cell Signaling Technology, 12D1), GAPDH (Proteintech Group Inc., 60004-1-Ig), BRD4 (Abcam plc, Ab128874), DYKDDDDK Tag (Cell Signaling Technology, D6W5B) and beta-actin (Proteintech Group Inc., 6609-1-Ig) were obtained from various commercial sources and dilutions were prepared per recommended manufacturers' procedures. Proteins were resolved by SDS/PAGE and transferred to nitrocellulose membranes using the iBlot system (Invitrogen). Blots were blocked with 5% BSA in Tris-buffered saline containing Tween 20 (TBST) solution for 1 h at room temperature, washed in TBST, and probed with primary antibody diluted in recommended diluent per manufacturer overnight at 4° C. Following washes with TBST, the blots were incubated in the dark with secondary antibodies purchased from Ly-Cor and used at 1:10,000 dilution in 5% BSA in TBST at room temperature. Blots were visualized using an Odyssey Li-Cor scanner after additional washes. If additional primary antibody incubations were required the membrane was stripped using ReBlot Plus Strong Antibody Stripping Solution (EMD Millipore, 2504), washed and blocked again before being reincubated with primary antibody.

Expression and purification of wild-type and C8A RNF114. RNF114 was expressed and purified using several methods. In each case, RNF114 activity and sensitivity to nimbolide was confirmed. For the first method, we purchased wild-type mammalian expression plasmids with C-terminal FLAG tag were purchased from Origene (Origene Technologies Inc., RC209752). The RNF114 C8A mutant was generated with Q5 site-directed mutagenesis kit according to manufacturer's instructions (New England Biolabs, E0554S). Expression and purification conditions were optimized as reported previously[68]. HEK293T cells were grown to 60% confluency in DMEM (Corning) supplemented with 10% FBS (Corning) and 2 mM L-glutamine (Life Technologies) and maintained at 37° C. with 5% $CO_2$. Immediately prior to transfection, media was replaced with DMEM containing 5% FBS. Each plate was transfected with 20 µg of overexpression plasmid with 100 µg PEI (Sigma). After 48 h cells were collected in TBS, lysed by sonication, and batch bound with anti-DYKDDDDK resin (GenScript, L00432) for 90 min. Lysate and resin was loaded onto a gravity flow column and washed, followed by elution with 250 ng/µL 3×FLAG peptide (ApexBio, A6001). Purity and concentration were verified by PAGE, UV/Spectroscopy, and BCA assay.

For the second method, DNA encoding the complete human isoform of RNF114 (Uniprot id: Q9Y508) was codon optimized for expression in E. coli and synthesized by Integrated DNA Technologies. Desired constructs were amplified from the complete RNF114 sequence with primers that contained 20 base pairs of homology to a pET24a plasmid (Novagen) that had been modified to contain a $His_8$-MBP-TEV sequence between the Nde1 and BamH1 restriction sites. PCR products were analyzed using precast 1% agarose gels (Invitrogen), and those of the correct length were purified using a QIAquick Gel Extraction kit (Qiagen). The purified PCR product was assembled into the linearized vector using Gibson Assembly (NEB Gibson Assembly 2× Master Mix), and transformed into E. coli 10G chemically competent cells (Lucigen, Middleton, WI). Colonies resistant to kanamycin (Kan) were grown in LB medium, and the plasmid was isolated via Miniprep (Qiagen) prior to being sequence verified using forward and reverse primers.

100 ng of pET24a $His_8$-MBP plasmid containing the desired RNF114 construct was transformed into E. coli BL21(DE3) chemically competent cells (NEB product #C2530H). The following day, a single transformed colony was used to inoculate 50 mL of nutrient rich LB medium containing kanamycin (50 µg/mL) and was incubated overnight at 37° C., with agitation at 250 rpm. The following morning, 1 L of Terrific Broth (TB) supplemented with 50 mM 3-(N-morpholino)propanesulfonic acid (MOPS) pH 7.5, 1 mM zinc chloride, and kanamycin (50 µg/mL) was inoculated with the overnight starter culture to a starting optical density at 600 nm ($OD_{600}$) of 0.1. Cells were grown at 37° C. with agitation at 250 rpm until an $OD_{600}$ of 0.8 was achieved. At this stage, expression of the RNF114 fusion protein was induced with 1 mM isopropyl β-D-1-thiogalactopyranoside (IPTG), and the temperature of the incubator was reduced to 18° C. Cells were left growing at 18° C. for 18 hours and were subsequently harvested by centrifugation, washed with 1× phosphate buffered saline (PBS) buffer and stored at −20° C.

10 g of E. coli cells containing the overexpressed RNF114 fusion protein were re-suspended in 80 mL of lysis buffer (50 mM Tris, pH 7.5, 150 mM NaCl, 2 Roche protease inhibitor tablets [without EDTA], 200 mM $ZnCl_2$, 1 mM DTT) and sonicated on ice, with a cycling time of 60 seconds on, 60 seconds off, over a total sonication time of three minutes. The cell lysate was centrifuged at 18,000 rpm for 20 minutes and the soluble protein was incubated with agitation for four hours at 4° C. with 2 mL of Ni-NTA resin, which had been pre-equilibrated with wash buffer (50 mM Tris, pH 7.5, 150 mM NaCl, 200 mM $ZnCl_2$, 1 mM DTT, 25 mM imidazole). The cell lysate/Ni-NTA resin mixture was placed into a disposable column and all non-tagged soluble protein, which do not bind to the resin, was collected for a second round of purification. The resin was washed with 25 mL of wash buffer before the His-MBP-RNF114 protein was eluted from the Ni-NTA resin with 25 mL of elution buffer (50 mM tris, pH 7.5, 500 mM imidazole, 200 mM $ZnCl_2$, 150 mM NaCl, 1 mM DTT). This process was repeated incubating the collected flow thorough with an additional 2 mL of pre-equilibrated Ni-NTA resin.

His-MBP-RNF114 protein was simultaneously digested at 4° C. with TEV protease (100 units/mg MBP-RNF114), and dialyzed overnight against dialysis buffer (50 mM tris, pH 7.5, 150 mM NaCl, 200 mM $ZnCl_2$, 1 mM DTT). The following morning two 5 mL His Trap Excel columns assembled in tandem were placed on an Äkta Avant and equilibrated with five column volumes of wash buffer. The TEV cleaved sample was loaded onto the column at a rate of 2 mL/min and the resin was washed with an additional five column volumes of wash buffer. All fractions identified to contain cleaved RNF114 were concentrated to a volume of 5 mL and loaded onto a HiLoad 16/60 Superdex 75 gel filtration column (GE Healthcare) that had been pre-equilibrated with either crystallography buffer, (25 mM Tris, pH 7.5, 137 mM NaCl) or NMR buffer, (20 mM Sodium Phosphate pH 6.8, 150 mM NaCl,). The gel filtration column was run using a flow rate of 0.25 mL/min and 2 mL fractions were collected. Fractions corresponding to peaks eluting from the gel filtration column were analyzed using SDS-PAGE and all fractions containing RNF114 were concentrated to a final concentration of 10 mg/mL, flash frozen in liquid nitrogen and stored at −80° C. until needed.

LC-MS/MS analysis of RNF114. Purified RNF114 (10 µg) in 50 µL PBS were incubated 30 min at room temperature either with DMSO vehicle or covalently acting compound (100 µM). The DMSO control was then treated with light IA while the compound treated sample was incubated with heavy IA for 1 h each at room temperature (200 µM final concentration, Sigma-Aldrich, 721328). The samples were precipitated by additional of 12.5 µL of 100% (w/v) TCA and the treated and control groups were combined pairwise, before cooling to −80° C. for 1 h. The combined sample was then spun for at max speed for 10 min at 4° C., supernatant is carefully removed and the sample is washed with ice cold 0.01 M HCl/90% acetone solution. The pellet was resuspended in 4 M urea containing 0.1% Protease Max (Promega Corp. V2071) and diluted in 40 mM ammonium bicarbonate buffer. The samples were reduced with 10 mM TCEP at 60° C. for 30 min. The sample was then diluted 50% with PBS before sequencing grade trypsin (1 µg per sample, Promega Corp, V5111) was added for an overnight incubation at 37° C. The next day the sample was centrifuged at 13200 rpm for 30 min. The supernatant was transferred to a new tube and acidified to a final concentration of 5% formic acid and stored at −80° C. until MS analysis.

RNF114 ubiquitination assay. Recombinant Myc-Flag-RNF114 proteins were either purified from HEK292T cells as described above or purchased from Origene (Origene Technologies Inc., TP309752). For in vitro auto-ubiquitination assay, 0.2 µg of RNF114 in 25 µL of TBS was pre-incubated with DMSO vehicle or the covalently-acting compound for 30 min at room temperature. Subsequently, 0.1 µg of UBE1 (Boston Biochem. Inc, E-305), 0.1 µg UBE2D1 (Boston Bichem. Inc, e2-615), 5 µg of Flag-ubiquitin (Boston Bichem. Inc, u-120) in a total volume of 25 µL Tris buffer containing 2 mM ATP were added to achieve a final volume of 50 µL. The mixture was incubated at 37° C. with agitation for 1.5 h. 20 µL of Laemmli's buffer was added to quench the reaction and proteins were analyzed by western blot assay.

RNF114/p21 pulldown. Recombinant Flag-tagged RNF114 was used as bait to precipitate pure recombinant p21 (Origene Technologies Inc., TP309752 and TP720567) using Anti-Flag agarose beads (GenScript Biotech Corp., L00432). One microgram of Flag-RNF114 was added to 50 µL of TBS, followed by the addition of nimbolide (100 µM final concentration, Cayman Chemical Co., 19230) or equivalent volume of DMSO. Samples were incubated at room temperature for 30 min. One microgram of pure p21 was added to each sample, and samples were incubated at room temperature 30 min with agitation. Ten microliters of Flag agarose beads were added to each sample, and samples were agitated at room temperature for 30 min. Washes (3 times, 1 mL TBS) were performed before proteins were eluted using 50 µL of TBS supplemented with 250 ng/µL 3×FLAG peptide (ApexBio A6001). Supernatant (30 µL) were collected and after the addition of Laemmli's reducing agent (10 µL), samples were boiled at 95° C. for 5 min and allowed to cool. Samples were analyzed by Western blotting as described above.

Tumor xenograft studies. Human tumor xenografts were established by transplanting cancer cells ectopically into the flank of female C.B17 severe combined immunodeficiency (SCID) mice (Taconic Farms) as previously described[66,69] In brief, cells were washed with PBS, trypsinized, and harvested in serum-containing medium. Harvested cells were washed in serum-free media and resuspended in serum-free media at a concentration of $2.0 \times 10^4$ cells/µl, and 100 µl was injected subcutaneously into the flank of each mouse. Tumors were measured with calipers. Animal experiments were conducted in accordance with the guidelines of the Institutional Animal Care and Use Committees of the University of California, Berkeley.

Example 6. Additional Synthesis and Characterization Data

Synthesis and characterization of the nimbolide-alkyne probe (SI-2) and degraders XH1 and XH2

General Procedures. Unless otherwise stated, all reactions were performed in oven-dried or flame-dried Fisherbrand® borosilicate glass tubes (Fisher Scientific, 1495925A, 13×100 mm) with a black phenolic screw cap (13-425) under an atmosphere of dry nitrogen. Dry N,N-dimethylformamide (DMF), toluene, and acetonitrile were obtained by passing these previously degassed solvents through activated alumina columns. Nimbolide was purchased from Sigma-Aldrich or Cayman Chemical, and used directly without further purification. Propargylamine and N-methylpropargylamine were purchased from Fisher Scientific and used directly without further purification. Reactions were monitored by thin layer chromatography (TLC) on TLC silica gel 60 $F_{254}$ glass plates (EMD Millipore) and visualized by UV irradiation and staining with p-anisaldehyde, phosphomolybdic acid, or potassium permanganate. Volatile solvents were removed under reduced pressure using a rotary evaporator. Flash column chromatography was performed using Silicycle F60 silica gel (60Å, 230-400 mesh, 40-63 μm). Ethyl acetate and hexanes were purchased from Fisher Chemical and used for chromatography without further purification. Proton nuclear magnetic resonance ($^1$H NMR) and carbon nuclear magnetic resonance ($^{13}$C NMR) spectra were recorded on Bruker AV-600 and AV-700 spectrometers operating at 600 and 700 MHz for $^1$H, and 150 and 175 MHz for $^{13}$C. Chemical shifts are reported in parts per million (ppm) with respect to the residual solvent signal CDCl$_3$ ($^1$H NMR: δ=7.26; $^{13}$C NMR: δ=77.16), CD$_2$Cl$_2$ ($^1$H NMR: δ=5.32; $^{13}$C NMR: δ=53.84). Peak multiplicities are reported as follows: s=singlet, d=doublet, t=triplet, dd=doublet of doublets, tt=triplet of triplets, m=multiplet, br=broad signal, app=apparent. IR spectra were recorded on a Nicolet 380 FT-IR spectrometer. High-resolution mass spectra (HRMS) were obtained by the QB3/chemistry mass spectrometry facility at the University of California, Berkeley. Optical rotations were measured on a Perkin-Elmer 241 polarimeter.

Scheme S1. Synthesis of the nimbolide-alkyne probe (SI-2).

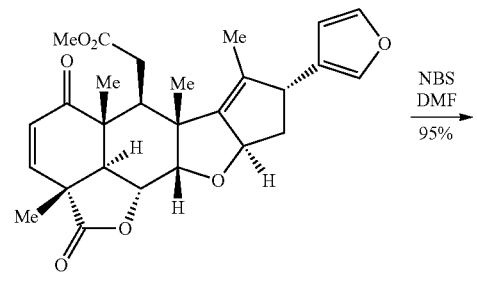

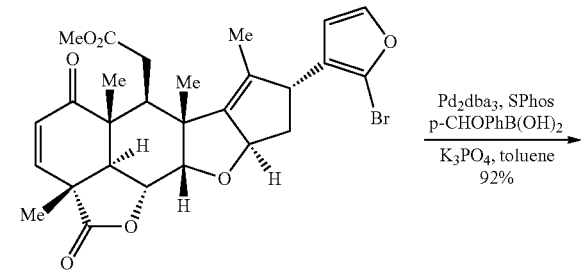

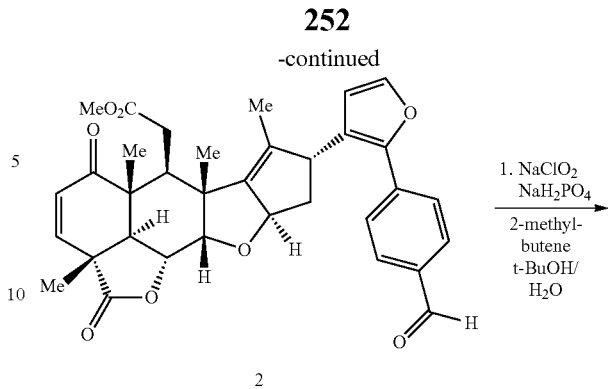

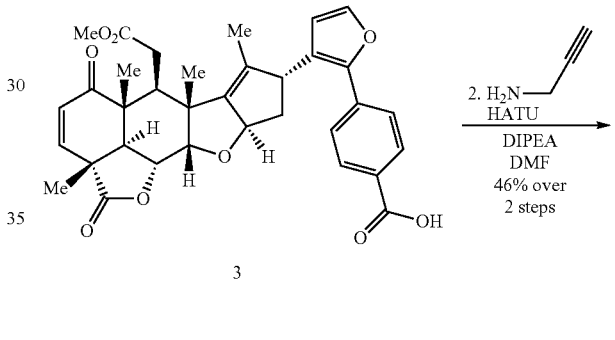

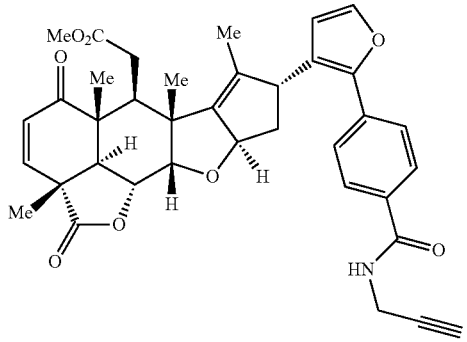

Scheme S2. Synthesis of nimbolide-derived bifunctional degraders XH1 and XH2.

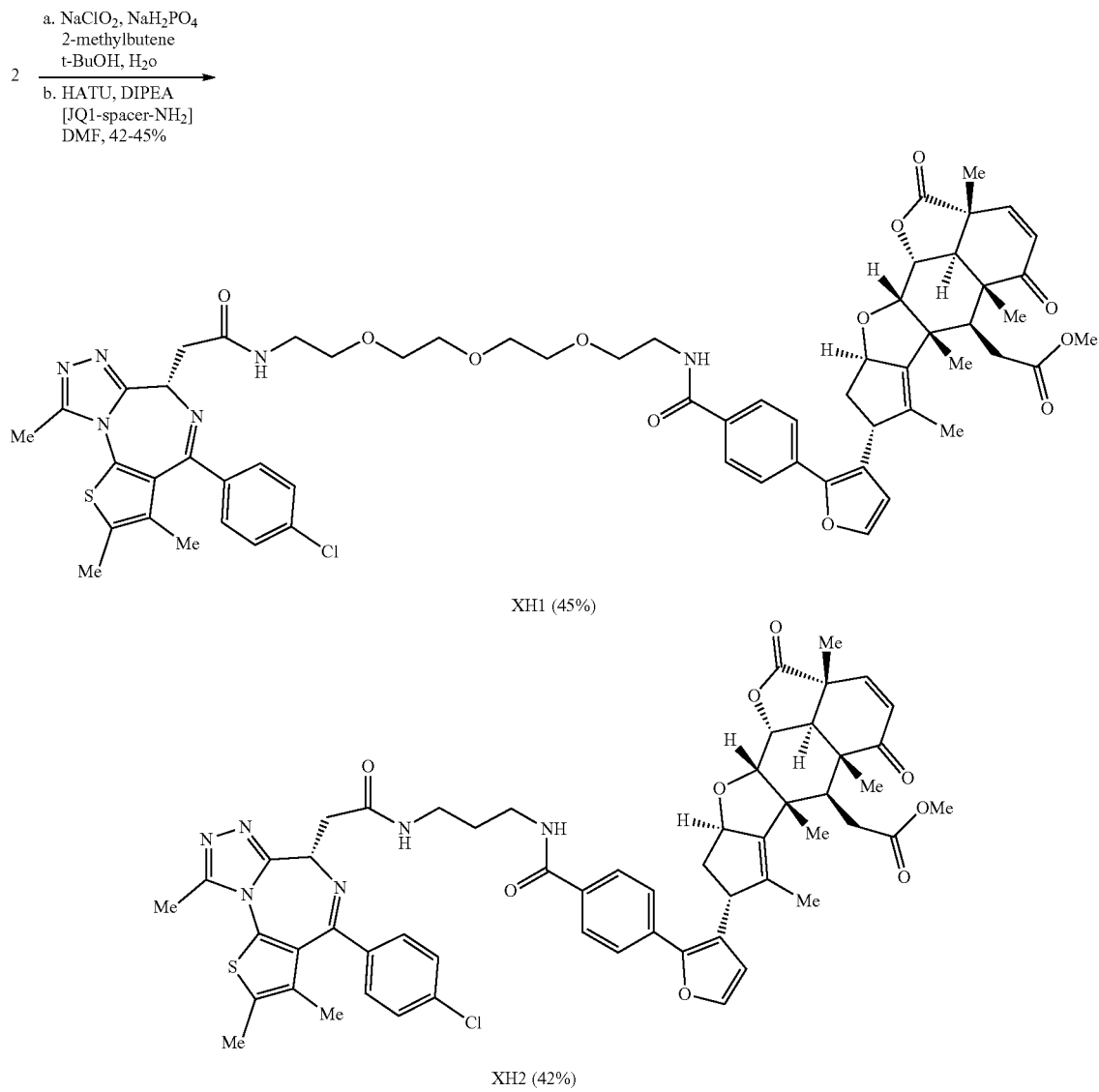

XH1 (45%)

XH2 (42%)

Scheme S2. Synthesis of nimbolide-derived bifunctional degraders XH1 and XH2.

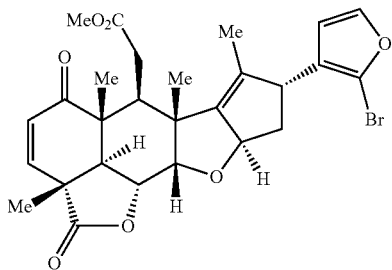

Bromofuran SI-1: Nimbolide (100 mg, 0.214 mmol) was divided evenly into four reaction tubes (Fisher Scientific, 13×100 mm), each charged with a stir bar. The tubes were evacuated and back-filled with nitrogen, dry DMF (0.25 mL each) was added, and the resulting solutions were cooled to 0° C. in an ice bath. Recrystallized N-bromosuccinimide (40.0 mg, 0.225 mmol) was dissolved in dry DMF (4 mL), and the solution was slowly added to each reaction tube (1 mL each). The reaction mixture was stirred at 0° C. for 1 hour and then quenched by the addition of saturated aq. $Na_2S_2O_3$ (5 mL each). The resulting mixtures were combined and extracted with EtOAc (3×20 mL). The combined organic layer was washed with $H_2O$ (50 mL) and brine (50 mL), dried over $MgSO_4$, and concentrated in vacuo. The crude mixture was purified by column chromatography (EtOAc:hexane=1:3 to 1:1), affording SI-1 (111 mg, 95%) as a white foam: $[\alpha]_D^{20}$=+190.3° (c 0.010 g/ml, $CHCl_3$); $^1$H NMR (700 MHz, $CDCl_3$) δ 7.34 (d, J=2.1 Hz, 1H), 7.28 (d, J=9.7 Hz, 1H), 6.29 (d, J=2.1 Hz, 1H), 5.92 (d, J=9.7 Hz, 1H), 5.56 (app. tt, J=7.4, 1.8 Hz, 1H), 4.62 (dd, J=12.5, 3.7 Hz, 1H), 4.27 (d, J=3.7 Hz, 11H), 3.67 (brd, J=7.0 Hz, 1H), 3.56 (s, 3H), 3.24 (dd, J=16.3, 5.5 Hz, 1H), 3.18 (d, J=12.5 Hz, 1H), 2.75 (dd, J=5.5, 5.5 Hz, 11H), 2.36 (dd, J=16.3, 5.5

Hz, 1H), 2.18-2.13 (m, 2H), 1.66 (d, J=1.4 Hz, 3H), 1.47 (s, 3H), 1.36 (s, 3H), 1.22 (s, 3H); $^{13}$C NMR (175 MHz, CDCl$_3$) δ 200.9, 175.0, 173.2, 149.8, 145.4, 144.2, 136.1, 131.2, 125.2, 120.3, 112.1, 88.5, 83.1, 73.5, 52.0, 50.5, 50.0, 47.9, 45.4, 43.8, 41.2, 40.4, 32.2, 18.7, 17.3, 15.3, 13.0; IR (thin film, cm$^{-1}$) 2974, 2929, 2875, 1783, 1734, 1678, 1594, 1438, 1394, 1373; HRMS (ESI) calcd. for [C$_{27}$H$_{29}$O$_7$BrNa]$^+$ (M+Na)$^+$: m/z 567.0989, found 567.0990.

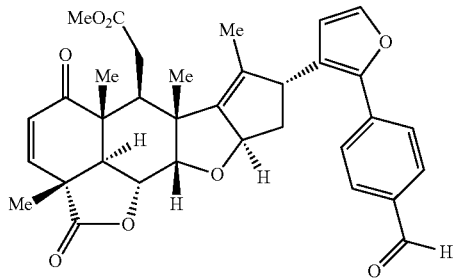

Aldehyde 2: A reaction tube (Fisher Scientific, 13×100 mm) was charged with a stir bar, SI-1 (12 mg, 0.022 mmol, 1 equiv), Pd$_2$(dba)$_3$ (10 mg, 0.011 mmol, 0.5 equiv), SPhos (10 mg, 0.024 mmol, 1 equiv), anhydrous K$_3$PO$_4$ (35 mg, 0.17 mmol, 7.5 equiv) and 4-formylphenylboronic acid (16 mg, 0.11 mmol, 5 equiv). The tube was evacuated and back-filled with nitrogen and dry toluene (0.5 mL) added. The resulting mixture was heated at 60° C. for 48 h, cooled to room temperature, and passed through a plug of Celite®. The filtrate was concentrated in vacuo and purified by column chromatography (EtOAc:hexane=1:3 to 1:1) to afforded aldehyde 2 (11.5 mg, 92%) as a light yellow oil: [α]$_D^{20}$=+4.8° (c 0.005 g/mL, CHCl$_3$); $^1$H NMR (600 MHz, CDCl$_3$) δ 10.01 (s, 1H), 7.92 (d, J=8.3 Hz, 2H), 7.71 (d, J=8.3 Hz, 2H), 7.42 (d, J=1.9 Hz, 1H), 7.29 (d, J=9.7 Hz, 1H), 6.39 (d, J=1.9 Hz, 1H), 5.93 (d, J=9.7 Hz, 1H), 5.60 (app. tt, J=7.3, 1.7 Hz, 1H), 4.64 (dd, J=12.5, 3.6 Hz, 1H), 4.32 (d, J=3.6 Hz, 1H), 4.17-4.13 (m, 1H), 3.69 (s, 3H), 3.23 (dd, J=16.4, 5.5 Hz, 1H), 3.20 (d, J=12.5 Hz, 1H), 2.78 (dd, J=5.5, 5.5 Hz, 1H), 2.41 (dd, J=16.4, 5.5 Hz, 1H), 2.31-2.27 (m, 2H), 1.69 (d, J=1.7 Hz, 3H), 1.49 (s, 3H), 1.38 (s, 3H), 1.25 (s, 3H); $^{13}$C NMR (150 MHz, CDCl$_3$) δ 200.8, 191.7, 175.0, 173.2, 149.8, 147.9, 146.3, 143.1, 137.0, 136.1, 134.8, 131.1, 130.3, 126.1, 126.0, 112.6, 88.4, 83.3, 73.4, 52.1, 50.8, 50.0, 47.9, 45.5, 43.8, 41.3, 32.5, 18.8, 17.5, 15.3, 13.4; IR (thin film, cm$^{-1}$) 2977, 2935, 2873, 1782, 1733, 1702, 1677, 1608, 1438, 1393, 1372; HRMS (ESI) calcd. for [C$_{34}$H$_{34}$O$_8$Na]$^+$ (M+Na)$^+$: m/z 593.2146, found 593.2154.

Nimbolide Alkyne Probe SI-2: i. A reaction tube (Fisher Scientific, 13×100 mm) was charged with a stir bar, aldehyde 2 (7.0 mg, 0.012 mmol, 1 equiv), and a mixture of t-BuOH and 2-methyl-2-butene (0.6 mL, 3:5 v/v). A solution of NaClO$_2$ (3.3 mg, 3 equiv) and NaH$_2$PO$_4$ (13.2 mg, 9 equiv) in H$_2$O (0.2 mL) was added in one portion and the resulting mixture was stirred at room temperature for 6 hours. After the reaction was complete as judged by TLC (EtOAc:hexane=2:1), the mixture was diluted with EtOAc (10 mL) and saturated aq. NH$_4$Cl (10 mL), and the aqueous phase was extracted by EtOAc (10 mL×2). The combined organic layer was washed with brine (20 mL), dried over MgSO$_4$, and concentrated in vacuo. The resulting crude material was used directly without further purification.

ii. A reaction tube (Fisher Scientific, 13×100 mm) charged with a stir bar, crude 3 (0.012 mmol assumed), and HATU (13.7 mg, 0.036 mmol, 3 equiv) was added a solution of DIPEA (6.4 µL, 0.036 mmol, 3 equiv) in DMF (0.1 mL). The resulting mixture was cooled to 0° C. and stirred for 10 minutes. A solution of propargylamine (1.6 µL, 0.024 mmol, 2 equiv) in DMF (0.2 mL) was then added and the reaction mixture was further stirred at 0-4° C. for 12 hours. After the reaction was complete, as judged by TLC (EtOAc:hexane=2:1), the mixture was diluted with EtOAc (10 mL) and saturated aq. NH$_4$Cl (10 mL), and the aqueous phase was extracted by EtOAc (10 mL×2). The combined organic layer was washed with H$_2$O (20 mL), brine (20 mL), dried over MgSO$_4$, and concentrated in vacuo. The resulting crude was purified by preparative TLC (EtOAc:hexane=2:1), affording SI-3 (3.5 mg, 46% over 2 steps) as a white solid: [α]$_D^{20}$=+21.5° (c 0.002 g/mL, CHCl$_3$); $^1$H NMR (600 MHz, CDCl$_3$) δ 7.83 (d, J=8.2 Hz, 2H), 7.61 (d, J=8.2 Hz, 2H), 7.39 (d, J=1.8 Hz, 1H), 7.29 (d, J=9.7 Hz, 1H), 6.36 (d, J=1.8 Hz, 11H), 6.27 (t, J=5.2 Hz, 11H), 5.93 (d, J=9.7 Hz, 11H), 5.60 (app. t, J=7.6 Hz, 1H), 4.64 (dd, J=12.6, 3.7 Hz, 1H), 4.31 (d, J=3.7 Hz, 1H), 4.28 (dd, J=5.2, 2.6 Hz, 2H), 4.11 (brd, J=7.6 Hz, 1H), 3.68 (s, 3H), 3.25-3.18 (m, 2H), 2.78 (dd, J=5.5, 5.5 Hz, 1H), 2.40 (dd, J=16.4, 5.5 Hz, 1H), 2.32-2.24 (m, 3H), 1.67 (brs, 3H), 1.49 (s, 3H), 1.38 (s, 3H), 1.24 (s, 3H); $^{13}$C NMR (150 MHz, CDCl$_3$) δ 200.8, 175.0, 173.2, 166.6, 149.8, 148.2, 146.1, 142.5, 136.3, 134.7, 132.1, 131.2, 127.6, 126.1, 124.8, 112.3, 88.5, 83.2, 79.6, 73.5, 72.2, 52.1, 50.8, 50.0, 48.0, 45.5, 43.8, 41.3, 41.3, 32.5, 30.0, 18.8, 17.5, 15.3, 13.4; IR (thin film, cm$^{-1}$) 3337, 2954, 2921, 2852, 1781, 1734, 1663, 1609; HRMS (ESI) calcd. for [C$_{37}$H$_{37}$NO$_8$Na]$^+$ (M+Na)$^+$: m/z 646.2417, found 646.2417.

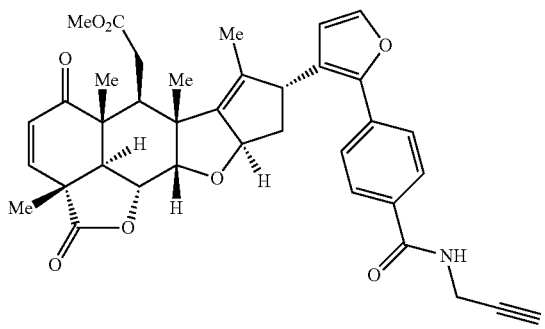

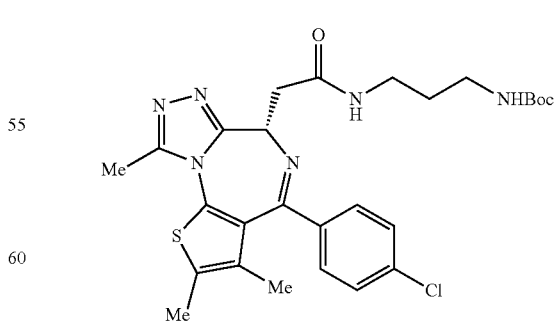

This compound was prepared according to conditions reported by Waring and coworkers (*J. Med. Chem.*, 2016, 59, 7801).

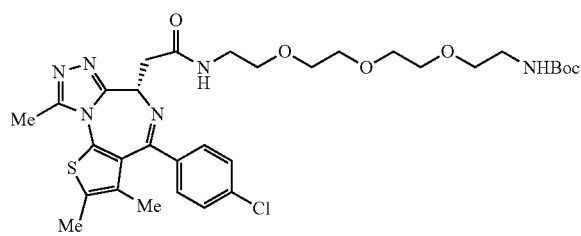 [SMILES: Cc1sc2c(c1C)C(c1ccc(Cl)cc1)=N[C@@H](CC(=O)NCCOCCOCCOCCNC(=O)OC(C)(C)C)c1nnc(C)n1-2]

This compound was prepared according to the conditions reported by Bradner and co-workers (PCT Int. Appl. 2017, WO 2017091673 A2).

General procedure for the synthesis of bifunctional degraders XH1 and XH2:

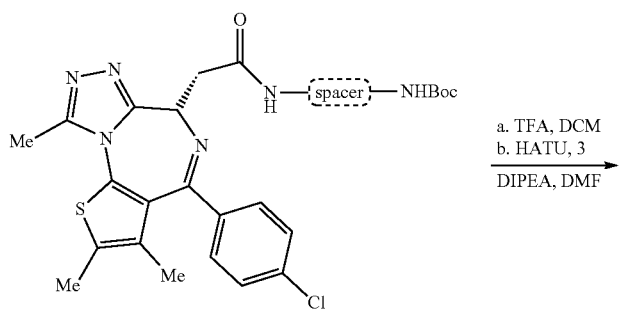

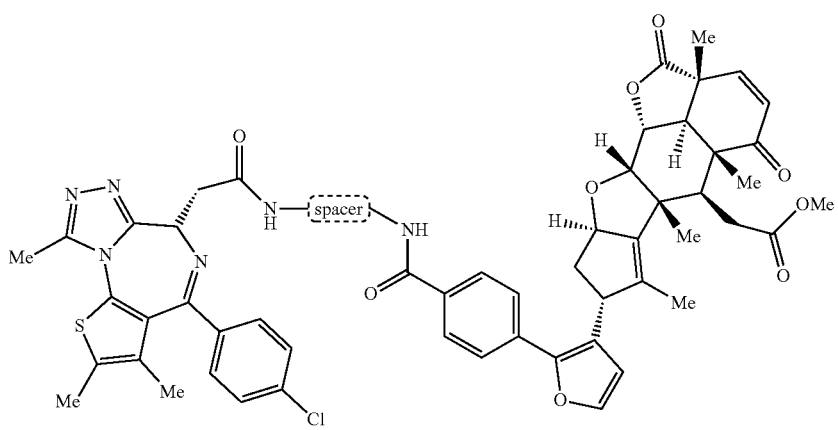

i. A reaction tube (Fisher Scientific, 13×100 mm) was charged with a stir bar, the Boc-protected amine (0.04 mmol), triethylsilane (12 μL, 0.075 mmol), and DCM (0.4 mL). The resulting mixture was cooled to 0° C., followed by the dropwise addition of TFA (0.12 mL). The reaction mixture was allowed to warm to room temperature and further stirred for 2 hours. After the reaction was complete as judged by TLC (MeOH:DCM=1:10), the mixture was diluted with toluene (2 mL), and concentrated in vacuo. The resulting crude was dried under high vacuum for 30 minutes, and directly used in the next step without further purification. Acid 3 was prepared from aldehyde 2 according to the aforementioned procedure, and used without further purification.

ii. A reaction tube (Fisher Scientific, 13×100 mm) was charged with a stir bar, the crude amine (0.04 mmol assumed), unpurified 3 (0.02 mmol assumed), and DMF (0.6 mL). The resulting mixture was cooled to 0° C. in an ice bath, followed by the addition of HATU (23.0 mg, 0.06 mmol) and DIPEA (11 μL, 0.06 mmol). The reaction mixture was stirred at 4° C. for 16 hours. After the reaction was complete as judged by TLC (MeOH:DCM=1:10), the mixture was diluted with EtOAc (10 mL) and saturated aq. NH$_4$Cl (10 mL), and the aqueous phase extracted with EtOAc (2×10 mL). The combined organic layer was washed with H$_2$O (20 mL), brine (20 mL), dried over MgSO$_4$, and concentrated in vacuo. The resulting crude material was purified by preparative TLC (MeOH:DCM=1:15, developed twice), affording the bifunctional degraders XH1 or XH2.

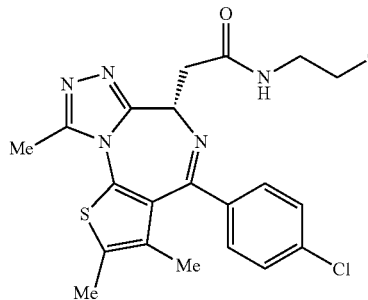
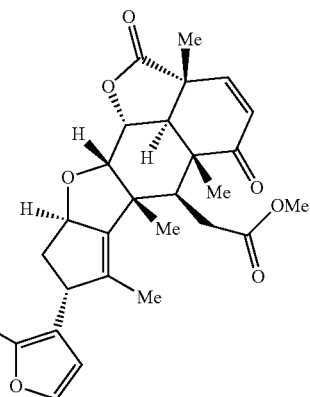

XH1 (45% yield from SI-2), a white foam: $[\alpha]_D^{20}=+48.7°$ (c 0.0052 g/mL, CHCl$_3$); $^1$H NMR (600 MHz, CDCl$_3$) δ 7.87 (d, J=8.5 Hz, 2H), 7.53 (d, J=8.5 Hz, 2H), 7.40 (d, J=8.2 Hz, 1H), 7.36 (d, J=1.9 Hz, 1H), 7.34-7.29 (m, 2H), 7.28 (d, J=9.7 Hz, 1H), 6.33 (d, J=1.9 Hz, 1H), 5.93 (d, J=9.7 Hz, 1H), 5.61-5.55 (m, 1H), 4.73 (app. t, J=7.1 Hz, 1H), 4.64 (dd, J=12.5, 3.7 Hz, 1H), 4.30 (d, J=3.6 Hz, 1H), 4.12-4.08 (m, 1H), 3.75-3.64 (m, 15H), 3.64-3.53 (m, 3H), 3.51-3.40 (m, 3H), 3.25-3.16 (m, 2H), 2.77 (app. t, J=5.5 Hz, 1H), 2.70 (s, 3H), 2.42-2.36 (m, 4H), 2.26-2.20 (m, 2H), 1.68-1.65 (m, 3H), 1.65 (d, J=1.8 Hz, 3H), 1.48 (s, 3H), 1.37 (s, 3H), 1.24 (s, 3H); $^{13}$C NMR (150 MHz, CDCl$_3$) δ 200.6, 174.8, 173.0, 170.1, 167.0, 164.4, 155.3, 149.9, 149.6, 148.3, 146.1, 145.6, 142.1, 137.2, 136.3, 135.8, 133.8, 133.0, 131.6, 131.2, 131.0, 130.6, 130.0, 130.0, 128.7, 128.7, 127.6, 127.6, 125.7, 125.7, 124.1, 112.0, 88.3, 83.0, 73.3, 70.5, 70.5, 70.3, 70.2, 69.7, 69.6, 54.1, 51.9, 50.5, 49.7, 47.8, 45.3, 43.6, 41.1, 41.1, 39.7, 39.4, 38.5, 32.3, 18.6, 17.3, 15.1, 14.4, 13.1, 13.1, 11.6; IR (thin film, cm$^{-1}$) 3339, 2923, 2866, 1781, 1734, 1659, 1540, 1487, 1437, 1419, 1300; HRMS (ESI) calcd. for [C$_{61}$H$_{67}$N$_6$O$_{12}$Cl$_1$S$_1$Na]$^+$ (M+Na)$^+$: m/z 1165.4118, found 1165.4142.

XH2 (42% yield from SI-2), a white foam: $[\alpha]_D^{20}=+18.60$ (c 0.004 g/mL, CHCl$_3$); $^1$H NMR (600 MHz, CD$_2$Cl$_2$) δ 7.90 (d, J=8.3 Hz, 2H), 7.65-7.57 (m, 3H), 7.44-7.39 (m, 3H), 7.33 (d, J=8.5 Hz, 2H), 7.25 (d, J=9.7 Hz, 1H), 7.07 (t, J=6.5 Hz, 1H), 6.36 (d, J=1.9 Hz, 1H), 5.89 (d, J=9.7 Hz, 1H), 5.52 (app. t, J=7.6 Hz, 1H), 4.66-4.59 (m, 2H), 4.26 (d, J=3.6 Hz, 1H), 4.12 (brd, J=7.6 Hz, 1H), 3.63 (s, 3H), 3.52-3.45 (m, 2H), 3.44-3.34 (m, 4H), 3.20 (dd, J=16.4, 5.5 Hz, 1H), 3.15 (d, J=12.5 Hz, 1H), 2.74 (app. t, J=5.5 Hz, 1H), 2.63 (s, 3H), 2.45-2.37 (m, 4H), 2.25-2.21 (m, 2H), 1.75-1.70 (m, 2H), 1.65 (s, 6H), 1.46 (s, 3H), 1.36 (s, 3H), 1.22 (s, 3H); $^{13}$C NMR (150 MHz, CD$_2$Cl$_2$) δ 201.2, 175.6, 173.5, 171.9, 166.7, 164.5, 156.1, 150.5, 149.9, 148.8, 146.3, 142.5, 137.1, 137.0, 136.6, 134.2, 133.7, 132.7, 131.6, 131.3, 131.2, 130.8, 130.3, 130.3, 129.0, 129.0, 127.8, 127.8, 126.2, 126.2, 124.8, 112.6, 88.6, 83.4, 73.9, 54.9, 52.1, 51.0, 50.2, 48.2, 45.8, 44.1, 41.6, 41.5, 39.7, 36.5, 36.2, 32.7, 29.9, 18.8, 17.5, 15.4, 14.6, 13.4, 13.3, 12.0; IR (thin film, cm$^{-1}$) 3308, 3023, 2930, 2867, 1782, 1734, 1654, 1540, 1488, 1437, 1301; HRMS (ESI) calcd. for [C$_{56}$H$_{57}$ClN$_6$O$_9$S]$^+$ (M+H)$^+$: m/z 1025.3669, found 1025.3669.

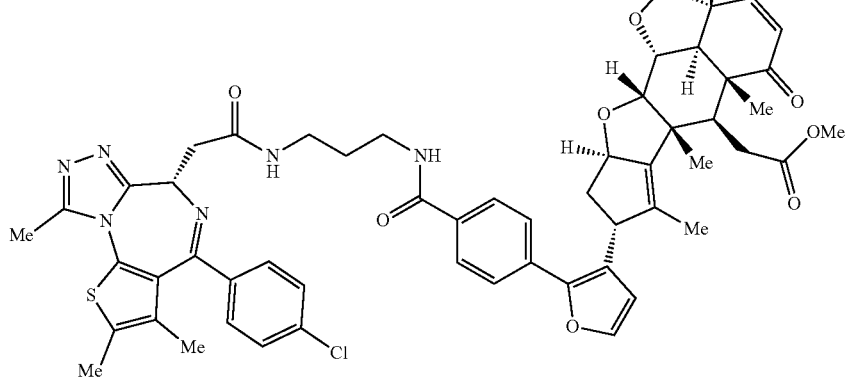

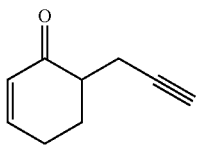

Synthesis and characterization of JNS27. JNS27. To a stirring solution of lithium diisopropylamide (6 mL, 1.2 equiv) at −78° C. under nitrogen atmosphere, a solution of cyclohexenone (0.48 mL, 1 equiv) in 5 mL THF was added drop wise. After 45 min a solution of 3-bromo-1-(trimethylsilyl)-propyne (0.85 mL, 2.4 equiv) in 5 mL THF was gradually added, before allowing the reaction to come to room temperature overnight. The reaction was quenched with saturated NH$_4$Cl (20 mL). The mixture was extracted with EtOAc (20 mL×3). The combined organic layers were washed with brine, dried with Na$_2$SO$_4$, and concentrated. Flash chromatography of the residue on silica gel (10-20% EtOAc in hexanes) gave TMS-alkyne in 25.4% yield (261 mg). To a solution of TMS-alkyne (261 mg, 1 equiv) in 5 mL THF under N$_2$ was added TBAF (0.44 mL, 1 equiv). After 4 hours of stirring at room temperature the reaction was quenched by addition of saturated NH4Cl (15 mL). The mixture was extracted with EtOAc (15 mL×3). The combined organic layers were washed with brine, dried with Na$_2$SO$_4$, and concentrated. Flash chromatography of the residue on silica gel (0-20% EtOAc in hexanes) gave JNS-27 as a pale yellow wax in 81% yield (168 mg, 20.6% over 2 steps). $^1$H NMR (400 MHz, CDCl$_3$) δ 6.99 (m, 1H), 6.03 (dt, J=10.02, 1.97 Hz, 1H), 2.78 (m, 1H), 2.48 (m, 3H), 2.33 (m, 2H), 1.98 (t, J=2.68, 1H), 1.88 (m, 1H); $^{13}$C NMR (400 MHz, CDCl$_3$) δ 150.30, 129.34, 45.74, 27.68, 25.78, 20.27; HRMS (ESI) calcd. for [C$_9$H$_{10}$ONa]$^+$ (M+Na)$^+$: m/z 134.0732, found 134.0728.

General synthetic methods. Chemicals and reagents were purchased from major commercial suppliers and used without further purification. Reactions were performed under a nitrogen atmosphere unless otherwise noted. Silica gel flash column chromatography was performed using EMD or Sigma Aldrich silica gel 60 (230-400 mesh). Proton and carbon nuclear magnetic resonance ($^1$H NMR and $^{13}$C NMR) data was acquired on a Bruker AVB 400, AVQ 400, or AV 600 spectrometer at the University of California, Berkeley. High resolution mass spectrum were obtained from the QB3 mass spectrometry facility at the University of California, Berkeley using positive or negative electrospray ionization (+ESI or −ESI). Yields are reported as a single run.

General Procedure A. The amine (1 eq.) was dissolved in DCM (5 mL/mmol) and cooled to 0° C. To the solution was added acryloyl chloride (1.2 eq.) followed by triethylamine (1.2 eq.). The solution was warmed to room temperature and stirred overnight. The solution was then washed with brine and the crude product was purified by silica gel chromatography (and recrystallization if necessary) to afford the corresponding acrylamide.

General Procedure B. The amine (1 eq.) was dissolved in DCM (5 mL/mmol) and cooled to 0° C. To the solution was added chloroacetyl chloride (1.2 eq.) followed by triethylamine (1.2 eq.). The solution was warmed to room temperature and stirred overnight. The solution was then washed with brine and the crude product was purified by silica gel chromatography (and recrystallization if necessary) to afford the corresponding chloroacetamide.

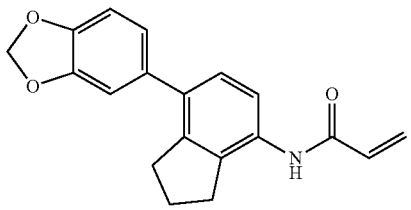 [SMILES: C=CC(=O)Nc1ccc(-c2ccc3c(c2)OCO3)c2c1CCC2]

N-(7-(benzo[d][1,3]dioxol-5-yl)-2,3-dihydro-1H-inden-4-yl)acrylamide (TRH 1-78). To a solution of N-(7-bromo-2,3-dihydro-1H-inden-4-yl)acrylamide (TRH 1-65, 55 mg, 0.2 mmol) in a mixture of dioxane and water (4:1 dioxane:water, 2.1 mL) under nitrogen atmosphere was added sequentially 3,4-(methylenedioxy)phenylboronic acid (70 mg, 0.4 mmol), potassium carbonate (74 mg, 0.5 mmol), and tetrakis(triphenylphosphine)palladium(0) (24 mg, 10 mol %). The reaction mixture was heated to a reflux and stirred overnight. The reaction was diluted with water (20 mL) and extracted with DCM (3×20 mL). The combined organics were dried with magnesium sulfate, filtered, and evaporated, and the resulting crude was purified by silica gel chromatography (0% to 25% ethyl acetate in hexanes) to give 7 mg of white solid (11% yield). $^1$H NMR (600 MHz, CDCl$_3$): δ 7.93 (d, J=7.0 Hz, 1H), 7.18 (d, J=8.2 Hz, 1H), 7.10 (s, 1H), 6.90 (s, 1H), 6.86 (t, J=8.1 Hz, 2H), 6.45 (d, J=16.8 Hz, 1H), 6.30 (dd, J=10.3, 16.8 Hz, 1H), 5.79 (d, J=10.2 Hz, 1H), 3.00 (t, J=7.3 Hz, 2H), 2.88 (t, J=7.3 Hz, 2H), 2.10 (quint, 7.3 Hz, 2H). $^{13}$C NMR (150 MHz, CDCl$_3$): δ 147.7, 146.7, 142.84, 142.81, 135.2, 134.9, 132.8, 131.3, 127.9, 127.8, 122.1, 119.8, 109.2, 108.3, 101.2, 36.8, 33.5, 30.5, 25.4. HRMS (−ESI): Calculated: 306.1136 (C$_{19}$H$_{16}$NO$_3$). Observed: 306.1130.

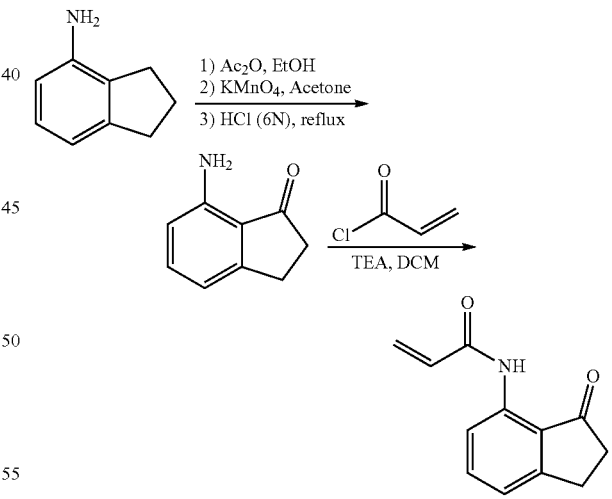

N-(3-oxo-2,3-dihydro-1H-inden-4-yl)acrylamide (TRH 1-129). To a solution of 4-aminoindan (1.0 g, 7.5 mmol) in ethanol (20 mL) at 0° C. was added acetic anhydride (1.4 mL, 15.0 mmol). The solution was raised to room temperature and stirred overnight, after which the solvent was evaporated. The residue was then dissolved in acetone (50 mL) to which was added 15% aqueous magnesium sulfate (1.2 g in 6.75 mL of water) followed by potassium permanganate (3.4 g, 17.0 mmol), and the resulting solution was stirred for 24 hours. The reaction filtered through a pad of celite, eluting with chloroform and then water. The eluent was separated, and the aqueous layer was extracted several times with additional chloroform. The combined organics were dried over magnesium sulfate, filtered and evaporated. The residue was then dissolved in a 6N HCl solution (20 mL) and heated to 90° C. After stirring for 5 hours, the solution was cooled, neutralized with small portions of potassium carbonate, and extracted with ethyl acetate. The combined organics were dried with magnesium sulfate, filtered, and evaporated to give 610 mg (55% over 3 steps) of crude 7-aminoindan-1-one which was used without further purification.

To a solution of 7-aminoindan-1-one in dichloromethane (15 mL) was added acryloyl chloride (0.39 mL, 4.8 mmol) followed by triethylamine (0.67 mL, 4.8 mmol) at 0° C. under $N_2$ atmosphere. The reaction mixture was allowed to warm to room temperature and was stirred overnight. The solution was washed 1M HCl solution (2×) and brine, and the resulting crude was purified by silica gel chromatography (10% to 20% ethyl acetate in hexanes) to yield 390 mg of white solid (47% yield, 26% combined over 4 steps). $^1$H NMR (400 MHz, CDCl$_3$): δ 10.64 (s, 1H), 8.45 (d, J=8.2 Hz, 1H), 7.55 (t, J=7.9 Hz, 1H), 7.12 (d, J=7.6 Hz, 1H), 6.45 (dd, J=1.0, 17.0 Hz, 11H), 6.33 (dd, J=10.1, 17.0 Hz, 1H), 5.82 (dd, J=1.0, 10.1 Hz, 1H), 3.11 (t, J=11.5 Hz, 2H), 2.74-2.71 (m, 2H). $^{13}$C NMR (100 MHz, CDCl$_3$): δ 209.3, 164.4, 155.9, 138.7, 137.0, 131.7, 128.0, 123.1, 120.8, 116.9, 36.5, 25.5. HRMS (+ESI): Calculated: 202.0863 ($C_{12}H_{12}NO_2$). Observed: 202.0860.

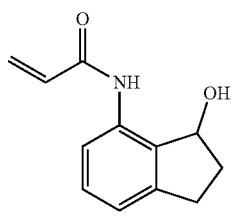

N-(3-hydroxy-2,3-dihydro-1H-inden-4-yl)acrylamide (TRH 1-133). To a solution of N-(3-oxo-2,3-dihydro-1H-inden-4-yl)acrylamide (TRH 1-129, 201 mg, 1.0 mmol) in anhydrous methanol (7 mL) under nitrogen atmosphere was added sodium borohydride (46.1 mg, 1.2 mmol). After 30 minutes of stirring, the reaction was quenched with saturated sodium bicarbonate solution and extracted three times with DCM. The combined organics were dried with magnesium sulfate, filtered, and concentrated. Crude was purified by silica gel chromatography (30 to 50% ethyl acetate in hexanes) to give 190 mg of the product as a white solid (94% yield). $^1$H NMR (400 MHz, CDCl$_3$): δ 8.93 (s, 1H), 7.98 (d, J=7.8 Hz, 1H), 7.19 (t, J=7.9 Hz, 1H), 6.95 (d, J=7.4 Hz, 1H), 6.29 (d, J=16.8 Hz, 1H), 6.15 (dd, J=10.2, 16.9 Hz, 1H), 5.66 (d, J=10.2 Hz, 1H), 5.32 (q, J=6.9 Hz, 1H), 3.60 (d, J=6.7 Hz, 1H), 2.96 (ddd, J=2.4, 9.0, 15.7 Hz), 2.73 (quint, J=8.1 Hz, 1H), 2.56-2.48 (m, 1H), 1.96-1.86 (m, 1H). $^{13}$C NMR (100 MHz, CDCl$_3$): δ 164.1, 143.7, 135.6, 132.8, 131.6, 129.5, 127.3, 121.0, 118.5, 76.2, 36.0, 29.8. HRMS (−ESI): Calculated: 202.0874 ($C_{12}H_{12}NO_2$). Observed: 202.0874.

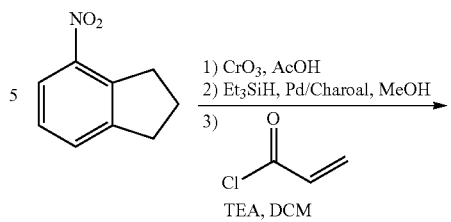

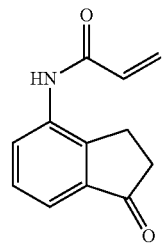

N-(1-oxo-2,3-dihydro-1H-inden-4-yl)acrylamide (TRH 1-134). To a solution of 4-nitroindan (5.38 g, 33 mmol) in acetic acid (250 mL) was slowly added chromium trioxide (8.95 g, 90 mmol). After stirring for 24 hours, the reaction was neutralized with 2M NaOH and extracted five times with ethyl acetate. The combined organics were washed with a saturated sodium bicarbonate solution and brine, then dried over magnesium sulfate, filtered, and concentrated. The crude material was purified by silica gel chromatography (10-20% ethyl acetate in hexanes) to give 1.26 g (ca. 7.1 mmol) of 4-nitroindanone as a white solid.

This intermediate was combined with palladium on activated charcoal (125 mg, 10 wt %) dissolved in anhydrous methanol (21 mL) under the atmosphere of a nitrogen balloon. Triethylsilane (11.3 mL, 71 mmol) was slowly added by addition funnel over the course of 10 minutes while the reaction was stirred under the cooling of a room temperature water bath. After an additional 20 minutes of stirring, the reaction mixture was filtered through a pad of celite and subsequently concentrated to give crude 4-aminoindanone which was used without further purification.

This final intermediate was then dissolved in DCM (21 mL) under $N_2$ atmosphere and cooled to 0° C., after which acryloyl chloride (0.77 mL, 9.5 mmol) and triethylamine (1.19 mL, 8.5 mmol) were slowly added. The reaction was allowed to warm to room temperature while stirring overnight, at which point the reaction was washed twice with brine, dried with magnesium sulfate, filtered, and concentrated. The crude was purified by silica gel chromatography (30-50% ethyl acetate in hexanes) to give 989 mg of a white solid (15% yield over 3 steps). $^1$H NMR (400 MHz, CDCl$_3$): δ 8.20 (d, J=5.8 Hz, 1H), 7.63 (s, 1H), 7.56 (d, J=7.5 Hz, 1H), 7.39 (t, J=7.7 Hz, 11H), 6.48 (d, J=16.7 Hz, 1H), 6.37 (dd, J=10.0 Hz, 16.8 Hz, 1H), 5.83 (d, J=10.1 Hz, 1H), 3.04 (t, J=5.6 Hz, 2H), 2.70 (t, J=5.7 Hz, 2H). $^{13}$C NMR (100 MHz, CDCl$_3$): δ 206.3, 163.9, 146.0, 138.0, 135.4, 130.7, 128.8, 128.7, 127.6, 120.4, 36.1, 23.4. HRMS (−ESI): Calculated: 200.0717 ($C_{12}H_{10}NO_2$). Observed: 200.0715.

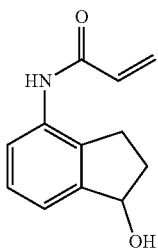

N-(1-hydroxy-2,3-dihydro-1H-inden-4-yl)acrylamide (TRH 1-135). To a solution of N-(1-oxo-2,3-dihydro-1H-inden-4-yl)acrylamide (TRH 1-134, 1.26 g, 6.25 mmol) in anhydrous methanol (50 mL) under nitrogen atmosphere was added sodium borohydride (292.7 mg, 7.7 mmol). After 30 minutes of stirring, the reaction was quenched with water and the methanol was removed in vacuo. The residue was saturated with NaCl and extracted five times with a 2:1 chloroform:methanol solution. The combined organics were dried over 3 angstrom molecular sieves, filtered, and concentrated. The crude material was purified by silica gel chromatography (40 to 70% ethyl acetate in hexanes) to give 1.05 g of the product as a white solid (83% yield). $^1$H NMR (400 MHz, MeOD): δ 7.50 (dd, J=2.3, 6.3 Hz, 1H), 7.25-7.20 (m, 2H), 6.51 (dd, J=10.2, 17.0 Hz, 1H), 6.35 (dd, J=1.7, 17.0 Hz, 1H), 5.77 (dd, J=1.7, 10.2 Hz, 1H), 5.17 (t, J=6.3 Hz, 1H), 2.97 (ddd, J=4.5, 8.6, 16.2, 1 H), 2.74 (quint, J=7.8 Hz, 1H), 2.47-2.39 (m, 1H), 1.95-1.86 (m, 1H). $^{13}$C NMR (100 MHz, MeOD): δ 166.3, 148.0, 137.8, 134.8, 132.1, 128.3, 127.9, 124.0, 122.7, 76.9, 36.1, 28.6. HRMS (−ESI): Calculated: 202.0874 (C$_{12}$H$_{12}$NO$_2$). Observed: 202.0872.

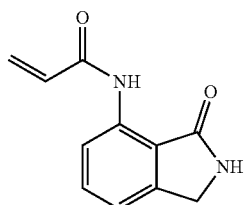

1-(4-(furan-2-carbonyl)piperazin-1-yl)prop-2-en-1-one (TRH 1-145). To a solution 1-(2-furoyl)piperazine (362 mg, 2.0 mmol) in dichloromethane (10 mL) was added acryloyl chloride (0.20 mL, 2.4 mmol) followed by triethylamine (0.34 mL, 2.4 mmol) at 0° C. under N$_2$ atmosphere. After stirring for 20 minutes, the reaction mixture was allowed to warm to room temperature and was stirred for 24 hours. The solution was washed twice with brine, dried with magnesium sulfate, and the resulting crude was purified by silica gel chromatography (70% to 100% ethyl acetate in hexanes) to yield 446 mg of yellow solid (95% yield). $^1$H NMR (400 MHz, CDCl$_3$): δ 7.53 (m, 1H), 7.06 (dd, J=0.7, 3.5 Hz, 1H), 6.61 (dd, J=10.5, 16.8 Hz, 1H), 6.52 (dd, J=1.8, 3.5 Hz, 1H), 6.33 (dd, J=1.9, 16.8 Hz, 1H), 5.75 (dd, J=1.9, 10.5 Hz, 1H), 3.84-3.67 (m, 8H). $^{13}$C NMR (100 MHz, CDCl$_3$): δ 165.5, 159.1, 147.5, 144.0, 128.5, 127.1, 117.0, 111.5, 45.6, 41.9. HRMS (+ESI): Calculated: 235.1077 (C$_{12}$H$_{15}$N$_2$O$_3$). Observed: 235.1075.

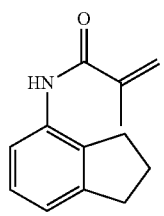

N-(2,3-dihydro-1H-inden-4-yl)methacrylamide (TRH 1-149). To a solution 4-aminoindan (0.24 mL, 2.0 mmol) in dichloromethane (10 mL) was added methacryloyl chloride (0.23 mL, 2.4 mmol) followed by triethylamine (0.34 mL, 2.4 mmol) at 0° C. under N$_2$ atmosphere. After stirring for 20 minutes, the reaction mixture was allowed to warm to room temperature and was stirred for 3.5 hours. The solution was washed twice with brine, dried with magnesium sulfate, and the resulting crude was purified by silica gel chromatography (35% to 40% ethyl acetate in hexanes) to yield 378 mg of off-white solid (94% yield). $^1$H NMR (400 MHz, CDCl$_3$): δ 7.72 (d, J=8.0 Hz, 1H), 7.55 (s, 1H), 7.12 (t, J=7.7 Hz, 1H), 7.01 (d, J=7.4 Hz, 1H), 5.79 (s, 1H), 5.42 (s, 1H), 2.93 (t, J=7.5 Hz, 2H), 2.79 (t, J=7.4 Hz, 2H), 7.12-2.06 (m, 2H), 2.04 (s, 3H). $^{13}$C NMR (100 MHz, CDCl$_3$): δ 166.3, 145.1, 140.6, 134.5, 133.7, 127.0, 120.7, 119.8, 118.9, 33.1, 29.9, 24.7, 18.6. HRMS (+ESI): Calculated: 202.1226 (C$_{13}$H$_{16}$NO). Observed: 202.1224.

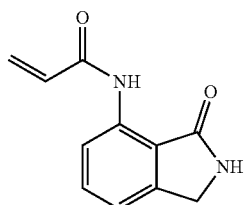

N-(3-oxoisoindolin-4-yl)acrylamide (TRH 1-152). To a solution of 7-aminoisoindolin-1-one (99 mg, 0.67 mmol) in dichloromethane (4 mL) was added acryloyl chloride (0.07 mL, 0.8 mmol) followed by triethylamine (0.11 mL, 0.8 mmol) at 0° C. under N$_2$ atmosphere. After stirring for 20 minutes, the reaction mixture was allowed to warm to room temperature and was stirred overnight. The solution was washed twice with brine, dried with magnesium sulfate, and the resulting crude was purified by silica gel chromatography (50 to 60% ethyl acetate in hexanes) to yield 58 mg of a white solid (43% yield). $^1$H NMR (400 MHz, CDCl$_3$): δ 10.50 (s, 1H), 8.58 (d, J=8.2 Hz, 1H), 7.55 (t, J=7.9 Hz, 1H), 7.15 (d, J=7.5 Hz, 1H), 6.82 (s, 1H), 6.46 (dd, J=1.3, 17.0 Hz, 1H), 6.36 (dd, J=10.0, 17.0 Hz, 1H), 5.81 (dd, J=1.3, 10.0 Hz, 1H), 4.46 (s, 2H). $^{13}$C NMR (100 MHz, CDCl$_3$): δ 172.9, 164.2, 143.9, 138.2, 133.8, 131.8, 127.8, 118.0, 117.7, 117.6, 45.6. HRMS (+ESI): Calculated: 203.0815 (C$_{11}$H$_{11}$N$_2$O$_2$). Observed: 203.0814.

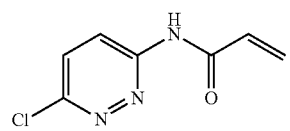

N-(6-chloropyridazin-3-yl)acrylamide (TRH 1-155). To a solution 3-amino-6-chloropyridazine (261 mg, 2.0 mmol) in dichloromethane (10 mL) was added acryloyl chloride (0.20 mL, 2.4 mmol) followed by triethylamine (0.34 mL, 2.4 mmol) at 0° C. under $N_2$ atmosphere. After stirring for 20 minutes, the reaction mixture was allowed to warm to room temperature and was stirred overnight. The solution was washed twice with brine, dried with magnesium sulfate, and the resulting crude was purified by silica gel chromatography (40% to 50% ethyl acetate in hexanes) to yield 23 mg of a pale-yellow solid (6% yield). $^1$H NMR (400 MHz, $CDCl_3$): δ 10.06 (s, 1H), 8.70 (d, J=9.4 Hz, 1H), 7.57 (d, J=9.4 Hz, 1H), 6.73 (dd, J=10.2, 16.8 Hz, 1H) 6.56 (dd, J=1.2, 16.8, 1H), 5.94 (dd, J=1.2, 10.2 Hz, 1H). $^{13}$C NMR (100 MHz, $CDCl_3$): δ 164.8, 155.2, 152.3, 130.7, 130.4, 130.3, 122.0. HRMS (+ESI): Calculated: 182.0127 ($C_7H_5N_3OCl$). Observed: 182.0126.

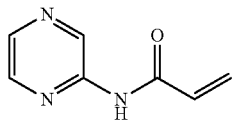

N-(Pyrazin-2-yl)acrylamide (TRH 1-156). To a solution of aminopyrazine (192 mg, 2.0 mmol) in dichloromethane (10 mL) was added acryloyl chloride (0.20 mL, 2.4 mmol) followed by triethylamine (0.34 mL, 2.4 mmol) at 0° C. under $N_2$ atmosphere. After stirring for 20 minutes, the reaction mixture was allowed to warm to room temperature and was stirred overnight. The solution was washed twice with brine, dried with magnesium sulfate, and the resulting crude was purified by silica gel chromatography (50% to 70% ethyl acetate in hexanes) to yield 22 mg of white solid (7% yield). $^1$H NMR (600 MHz, $CDCl_3$): δ 9.65 (d, J=1.3 Hz, 1H), 8.38 (d, J=2.5 Hz, 1H), 8.27 (dd, J=1.6, 2.5 Hz, 1H), 8.19 (s, 1H), 6.54 (dd, J=0.8, 16.9 Hz, 11H), 6.33 (dd, J=10.3, 16.9 Hz, 1H), 5.90 (dd, J=0.8, 10.3 Hz, 1H). $^{13}$C NMR (150 MHz, $CDCl_3$): δ 163.5, 148.2, 142.2, 140.6, 137.4, 130.2, 129.8. HRMS (+ESI): Calculated: 150.0662 ($C_7H_8N_3O$). Observed: 150.0660.

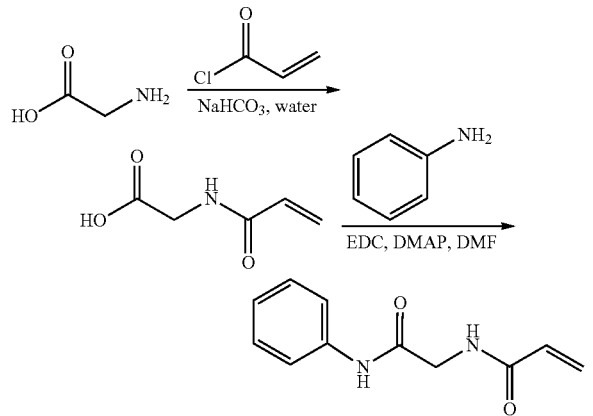

N-(2-oxo-2-(phenylamino)ethyl)acrylamide (TRH 1-160). To a solution of glycine (1.50 g, 20.0 mmol) and sodium bicarbonate (1.70 g, 20.2 mmol) in water (30 mL) at 0° C. was slowly added acryloyl chloride (2.45 mL, 30.2 mmol). After stirring for 3.5 hours, the reaction was extracted 3 times with ethyl acetate. The combined organics were dried over magnesium sulfate, filtered, and concentrated to give an oil. The oil was treated with hexanes causing a white solid to crash out which was collected by gravity filtration to give 124 mg of crude acryloylglycine of which 58 mg (47% of the crude material) was used immediately without further purification. This solid (ca. 0.45 mmol) was dissolved in DMF (2.5 mL) and a solution of N-(3-dimethylaminopropyl)-N'-ethylcarbodiimide hydrochloride (104 mg, 0.54 mmol) and 4-dimethylaminopyridine (68 mg, 0.56 mmol) in DMF (2.5 mL) was added followed by aniline (0.050 mL, 0.54 mmol). The solution was stirred overnight, diluted with ethyl acetate, and washed with both a saturated solution of sodium bicarbonate and brine. The organics were then dried over magnesium sulfate, filtered, and concentrated, and the resulting crude was purified by silica gel chromatography (30-60% ethyl acetate in hexanes) to give 19 mg of the title compound as a white solid (1% yield over two steps). $^1$H NMR (400 MHz, MeOD): δ 7.56-7.53 (m, 2H), 7.30 (t, J=8.0 Hz, 2H), 7.08 (t, J=7.4 Hz, 1H), 6.35 (dd, J=9.9, 17.1 Hz, 1H), 6.26 (dd, J=2.0, 17.1 Hz, 1H), 5.71 (dd, J=2.0, 9.9 Hz, 1H), 4.08 (s, 2H). $^{13}$C NMR (100 MHz, MeOD): δ 169.4, 168.6, 139.5, 131.7, 129.8, 127.2, 125.3, 121.2, 44.0. HRMS (−ESI): Calculated: 203.0826 ($C_{11}H_{11}N_2O_2$). Observed: 203.0825.

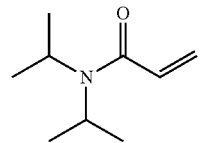

N,N-diisopropylacrylamide (TRH 1-167). To a solution of diisopropylamine (0.42 mL, 3.0 mmol) in dichloromethane (10 mL) was added acryloyl chloride (0.29 mL, 3.6 mmol) followed by triethylamine (0.50 mL, 3.6 mmol) at 0° C. under $N_2$ atmosphere. After stirring for 20 minutes, the reaction mixture was allowed to warm to room temperature and was stirred for 19 hours. The solution was washed with a saturated solution of sodium bicarbonate followed by brine, dried with magnesium sulfate, and the resulting crude was purified by silica gel chromatography (0% to 30% ethyl acetate in hexanes) to yield 392 mg of a pale-yellow oil (84% yield). $^1$H NMR (400 MHz, $CDCl_3$): δ 6.35 (dd, J=10.6, 16.8 Hz, 1H), 5.98 (dd, J=1.7, 16.8 Hz, 1H), 5.36 (dd, J=1.7, 10.6 Hz, 1H), 3.85 (s, 1H), 3.56 (s, 1H), 1.18 (s, 6H), 1.06 (s, 6H). $^{13}$C NMR (100 MHz, $CDCl_3$): δ 165.9, 130.5, 125.3, 47.9, 45.4, 21.1, 20.3. HRMS (+ESI): Calculated: 178.1202 ($C_9H_{17}NONa$). Observed: 178.1201.

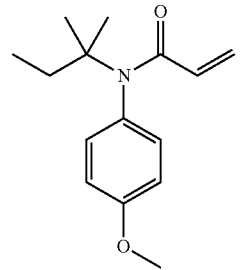 [SMILES: C=CC(=O)N(c1ccc(OC)cc1)C(C)(C)CC]

N-(4-methoxyphenyl)-N-(tert-pentyl)acrylamide (TRH 1-170). To a solution of 4-methoxy-N-(tert-pentyl)aniline (94 mg, 0.49 mmol) in dichloromethane (5 mL) was added acryloyl chloride (0.05 mL, 0.6 mmol) followed by triethylamine (0.09 mL, 0.6 mmol) at 0° C. under N$_2$ atmosphere. After stirring for 15 minutes, the reaction mixture was allowed to warm to room temperature and was stirred for 18 hours. The solution was washed with a saturated solution of sodium bicarbonate followed by brine, dried with magnesium sulfate, and the resulting crude was purified by silica gel chromatography (0% to 20% ethyl acetate in hexanes) to yield 82 mg of a pale-yellow oil (68% yield). $^1$H NMR (400 MHz, CDCl$_3$): δ 6.99 (d, J=8.7 Hz, 2H), 6.85 (d, J=8.7 Hz, 2H), 6.17 (dd, J=1.9, 16.7 Hz, 1H), 5.76 (dd, J=10.3, 16.7 Hz, 1H), 5.28 (dd, J=1.9, 10.3 Hz, 1H), 3.81 (s, 3H), 2.11 (q, J=7.5 Hz, 2H), 1.20 (s, 6H), 0.91 (t, J=7.5 Hz, 3H). $^{13}$C NMR (100 MHz, CDCl$_3$): δ 166.3, 159.0, 134.3, 131.49, 131.45, 125.6, 114.1, 61.7, 55.5, 32.0, 27.4, 9.4. HRMS (+ESI): Calculated: 247.1572 (C$_{15}$H$_{21}$NO$_2$). Observed: 247.1577.

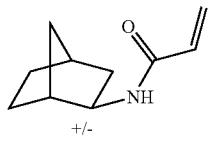

N-(exo-norborn-2-yl)acrylamide (TRH 1-176). To a solution of exo-2-aminonorbornane (0.24 mL, 2 mmol) in dichloromethane (10 mL) was added acryloyl chloride (0.20 mL, 2.4 mmol) followed by triethylamine (0.33 mL, 2.4 mmol) at 0° C. under N$_2$ atmosphere. After stirring for 20 minutes, the reaction mixture was allowed to warm to room temperature and was stirred for 18 hours. The solution was washed with a saturated solution of sodium bicarbonate followed by brine, dried with magnesium sulfate, and the resulting crude was purified by silica gel chromatography (30% ethyl acetate in hexanes) to yield 271 mg of a white solid (82% yield). $^1$H NMR (400 MHz, CDCl$_3$): δ 6.42 (s, 1H), 6.25 (dd, J=2.3, 17.0 Hz, 1H), 6.18 (dd, J=9.5, 17.0 Hz, 1H), 5.58 (dd, J=2.3, 9.5 Hz, 1H), 3.8-3.77 (m, 1H), 2.27-2.24 (m, 2H), 1.78 (ddd, J=2.1, 8.1, 13.0 Hz, 1H), 1.55-1.38 (m, 3H), 1.30-1.10 (m, 4H). $^{13}$C NMR (100 MHz, CDCl$_3$): δ 165.0, 131.4, 125.8, 52.9, 42.4, 40.0, 35.7, 35.6, 28.2, 26.6. HRMS (+EI): Calculated: 165.1154 (C$_{10}$H$_{15}$NO). Observed: 165.1155.

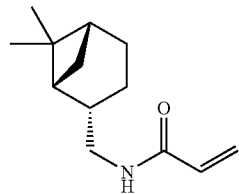

N-(((1R,2S,5R)-6,6-dimethylbicyclo[3.1.1]heptan-2-yl)methyl)acrylamide (TRH 1-178). To a solution of (−)-cis-myrtanylamine (0.34 mL, 2 mmol) in dichloromethane (10 mL) was added acryloyl chloride (0.20 mL, 2.4 mmol) followed by triethylamine (0.33 mL, 2.4 mmol) at 0° C. under N$_2$ atmosphere. After stirring for 20 minutes, the reaction mixture was allowed to warm to room temperature and was stirred for 21 hours. The solution was washed with a saturated solution of sodium bicarbonate followed by brine, dried with magnesium sulfate, and the resulting crude was purified by silica gel chromatography (20 to 30% ethyl acetate in hexanes) to yield 369 mg of a white solid (89% yield). $^1$H NMR (600 MHz, CDCl$_3$): δ 6.26 (dd, J=1.5, 17.0 Hz, 1H), 6.11 (dd, J=10.3, 17.0 Hz, 1H) 5.85 (s, 1H), 5.61 (dd, J=1.5, 10.3 Hz, 1H), 3.39-3.29 (m, 2H), 2.38-2.34 (m, 1H), 2.26-2.21 (m, 1H), 1.98-1.90 (m, 4H), 1.88-1.83 (m, 1H), 1.53-1.47 (m, 1H), 1.19 (s, 3H), 1.04 (s, 3H), 0.89 (d, J=9.6 Hz, 1H). $^{13}$C NMR (150 MHz, CDCl$_3$): δ 165.7, 131.2, 126.2, 45.3, 43.9, 41.5, 38.8, 33.3, 28.1, 26.1, 23.3, 19.9. HRMS (−ESI): Calculated: 206.1550 (C$_{13}$H$_{20}$NO). Observed: 206.1551.

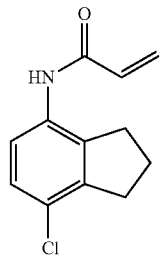

N-(7-chloro-2,3-dihydro-1H-inden-4-yl)acrylamide (YP 1-1). A solution of N-(2,3-dihydro-1H-inden-4-yl)acrylamide (187 mg, 1.0 mmol) in PEG 400 (5.2 mL) was cooled to 0° C. To the solution was added N-chlorosuccinimide (140 mg, 1.0 mmol). The solution was allowed to warm to room temperature after 30 min and stirred overnight. The solution was diluted with ethyl acetate and washed two times with brine and dried with magnesium sulfate. The crude product was purified via silica gel chromatography (30% ethyl acetate in hexanes). The obtained mixture of isomers was separated by recrystallization to afford the product in 22% yield as a white solid (47 mg). $^1$H NMR (400 MHz, CDCl$_3$): δ 7.78 (d, J=8.8 Hz, 1H), 7.15-7.11 (m, 2H), 6.42 (dd, J=1.4, 16.8 Hz, 1H), 6.26 (dd, J=10.2, 16.8 Hz, 1H), 5.77 (dd, J=1.4, 10.2 Hz, 1H), 2.98 (t, J=7.6 Hz, 2H), 2.87 (t, J=7.5 Hz, 2H), 2.12 (quint, J=7.5 Hz, 2H). $^{13}$C NMR (100 MHz, CDCl$_3$): δ 163.4, 143.1, 136.1, 132.2, 131.0, 128.0, 127.2, 126.7, 120.9, 32.7, 31.1, 24.0. HRMS (+ESI): Calculated: 220.0535 (C$_{12}$H$_{11}$ClNO). Observed: 220.0533.

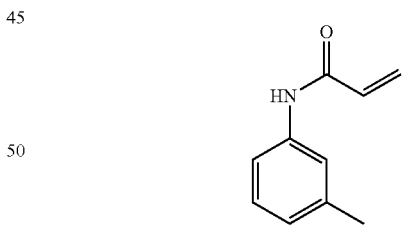

N-(m-tolyl)acrylamide (YP 1-16). A solution of o-toluidine (107 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 40 min and stirred overnight. The solution was washed two times with brine and dried with magnesium sulfate. The crude product was purified via silica gel chromatography (20% to 40% ethyl acetate in hexanes) to afford the product in 86% yield as a white solid (139 mg). $^1$H NMR (400 MHz, CDCl$_3$): δ 7.82 (d, J=7.9 Hz, 1H), 7.32 (s, 1H), 7.21-7.17 (m, 2H), 7.10-7.06 (m, 1H), 6.43-6.38 (m, 1H), 6.29 (dd, J=10.2, 17.1 Hz, 1H), 5.75-5.72 (m, 1H), 2.25 (s, 1H). $^{13}$C NMR (100 MHz, CDCl$_3$): δ 135.5, 131.2, 130.5, 127.5, 126.8, 125.5, 123.4, 17.8. HRMS (+ESI): Calculated: 162.0913 (C$_{10}$H$_{12}$NO). Observed: 162.0912.

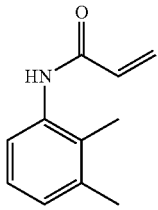

N-(2,3-dimethylphenyl)acrylamide (YP 1-18). A solution of 2,3-dimethylaniline (121 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 29 min and stirred overnight. The solution was washed two times with brine and dried with magnesium sulfate. The crude product was purified via silica gel chromatography (30% to 40% ethyl acetate in hexanes) to afford the product in 88% yield as a white solid (154 mg). $^1$H NMR (400 MHz, CDCl$_3$): δ 7.49 (d, J=7.9 Hz, 1H), 7.29 (s, 1H), 7.11-7.07 (m, 1H), 7.01 (d, J=7.7, 1H) 6.40 (d, J=17.1, 1H), 6.30 (dd, J=7.3, 17.1 Hz, 1H), 5.74 (d, J=10.1 Hz, 1H), 2.29 (s, 1H), 2.13 (s, 1H). $^{13}$C NMR (100 MHz, CDCl$_3$): δ 135.1, 131.2, 127.6, 127.3, 125.9, 122.3, 20.6, 13.9. HRMS (+ESI): Calculated: 176.1070 (C$_{11}$H$_{14}$NO). Observed: 176.1068.

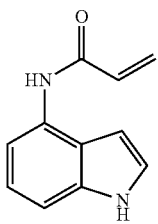

N-(1H-indol-4-yl)acrylamide (YP 1-19). A solution of 4-aminoindole (132 mg, 1 mmol) in DCM (5 mL) and DMF (5 mL) was cooled to 0° C. To the solution was added acryloyl chloride (109 mg, 1.2 mmol) followed by triethylamine (121 mg, 1.2 mmol). The solution was allowed to warm to room temperature after 26 min and stirred overnight. The solution was washed two times with brine and dried with magnesium sulfate. The crude product was purified via basic alumina chromatography (60% to 75% ethyl acetate in hexanes) to afford the product in 30% yield as a white-grey solid (56 mg). $^1$H NMR (600 MHz, MeOD): δ 7.51 (d, J=7.6 Hz, 1H), 7.24-7.22 (m, 2H), 7.08 (t, J=7.6 Hz, 1H), 6.64 (dd, J=10.1, 16.7 Hz, 2H), 6.38 (dd, J=1.7, 16.9 Hz, 1H), 5.78 (dd, J=1.7, 10.3 Hz, 1H), 4.6 (s, 1H). $^{13}$C NMR (150 MHz, MeOD): δ 165.0, 137.2, 131.1, 129.2, 126.0, 123.8, 121.5, 120.9, 112.2, 108.4, 98.5. HRMS (+ESI): Calculated: 187.0866 (C$_{11}$H$_{11}$N$_2$O). Observed: 187.0865.

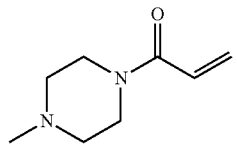

1-(4-Methylpiperazin-1-yl)prop-2-en-1-one (YP 1-22). A solution of 1-methylpiperazine (100 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 30 min and stirred overnight. The solution was washed two times with brine and dried with magnesium sulfate. The crude product was purified via silica gel chromatography (85% to 100% ethyl acetate in hexanes) to afford the product in 29% yield as a yellow gel (44 mg). $^1$H NMR (400 MHz, CDCl$_3$): δ 6.56 (dd, J=10.6, 16.9 Hz, 1H), 6.29 (dd, J=2.0, 16.8 Hz, 1H), 5.69 (dd, J=2.0, 10.6 Hz, 1H), 3.71 (s, 2H), 3.58 (s, 2H), 2.42 (t, J=5.1 Hz, 4H), 2.32 (s, 3H). $^{13}$C NMR (100 MHz, CDCl$_3$): δ 165.4, 127.8, 127.5, 55.2, 54.6, 46.0, 45.7, 41.9. HRMS (+ESI): Calculated: 155.1179 (C$_8$H$_{15}$N$_2$O). Observed: 155.1178.

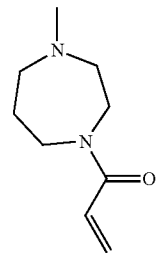

1-(4-methyl-1,4-diazepan-1-yl)prop-2-en-1-one (YP 1-23). A solution of 1-methylhomopiperazine (114 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 32 minutes and stirred overnight. The solution was washed two times with brine and dried with magnesium sulfate. The crude product was purified via silica gel chromatography (1% to 10% methanol in DCM) to afford the product in 51% yield as a yellow oil (58 mg). $^1$H NMR (400 MHz, CDCl$_3$): δ 6.61-6.53 (m, 1H), 6.35-6.29 (m, 1H), 5.70-5.66 (m, 1H), 3.74-3.72 (m, 1H), 3.69 (t, J=6.4 Hz, 1H), 3.65-3.61 (m, 2H), 2.66-2.63 (m, 2H), 2.59-2.54 (m, 2H), 2.37 (s, 3H), 1.94 (quint, J=6.2 Hz, 2H). $^{13}$C NMR (100 MHz, CDCl$_3$): δ 166.4, 166.3, 128.0, 127.9, 127.8, 127.6, 59.1, 58.0, 57.1, 56.8, 47.4, 47.1, 46.7, 46.6, 45.3, 44.8, 28.1, 26.9. HRMS (+ESI): Calculated: 169.1335 (C$_9$H$_{17}$N$_2$O). Observed: 169.1333.

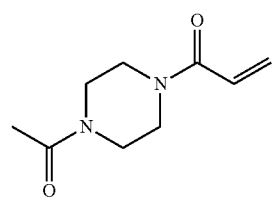

1-(4-acetylpiperazin-1-yl)prop-2-en-1-one (YP 1-24). A solution of 1-acetylpiperazine (128 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 23 minutes and stirred for two hours. The solution was washed two times with brine and dried with magnesium sulfate. The crude product was purified via silica gel chromatography (0% to 10% methanol in DCM) to afford the product in 18% yield as a yellow oil (40 mg). $^1$H NMR (400 MHz, CDCl$_3$): δ 6.57 (dd, J=10.5, 16.8 Hz, 1H), 6.33 (dd, J=1.8, 16.8 Hz, 1H), 5.75 (dd, J=1.9, 10.5 Hz, 1H), 3.72 (s, 1H), 3.66-3.64 (m, 3H), 3.57 (s, 1H), 3.51-3.49 (m, 2H), 2.13 (s, 3H). 13C NMR (100 MHz, CDCl$_3$): δ 165.6, 128.7, 127.0, 41.9, 41.4, 21.4. HRMS (+ESI): Calculated: 183.1128 (C$_9$H$_{15}$N$_2$O$_2$). Observed: 183.1126.

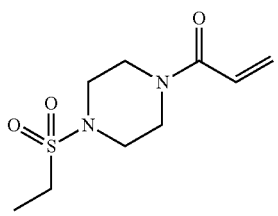

1-(4-(Ethylsulfonyl)piperazin-1-yl)prop-2-en-1-one (YP 1-25). A solution of 1-(ethanesulfonyl)piperazine (178 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 27 min and stirred for two hours. The solution was washed two times with brine and dried with magnesium sulfate. The crude product was purified via silica gel chromatography (1% to 10% methanol in DCM) to afford the product in 70% yield as a white-yellow solid (163 mg). $^1$H NMR (400 MHz, CDCl$_3$): δ 6.57 (dd, J=10.5, 16.8 Hz, 1H), 6.32 (dd, J=1.9, 16.8 Hz, 1H), 5.76 (dd, J=1.8, 10.5 Hz, 1H), 3.77 (s, 2H), 3.67 (s, 2H), 3.32 (t, J=5.2 Hz, 4H), 2.98 (q, J=7.5 Hz, 2H), 1.37 (t, J=7.4, 3H). $^{13}$C NMR (100 MHz, CDCl$_3$): δ 165.5, 128.8, 127.0, 77.4, 45.9, 45.6, 44.2, 41.9, 7.8. HRMS (+ESI): Calculated: 233.0954 (C$_9$H$_{17}$N$_2$O$_3$S$_1$). Observed: 233.0953.

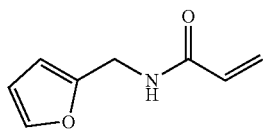

N-(Furan-2-ylmethyl)acrylamide (YP 1-26). A solution of furfurylamine (97 mg, 1.0 mmol) in DCM (10 mL) was cooled to 0° C. To the solution was added acryloyl chloride (109 mg, 1.2 mmol) followed by triethylamine (121 mg, 1.2 mmol). The solution was allowed to warm to room temperature after 17 min and stirred for two and a half hours. The solution was washed two times with brine and dried with magnesium sulfate. The crude product was purified via silica gel chromatography (35% to 70% ethyl acetate in hexanes) to afford the product in 86% yield as a white solid (132 mg). $^1$H NMR (400 MHz, CDCl$_3$): δ 7.33 (s, 1H), 6.60 (s, 1H), 6.31-6.22 (m, 3H), 6.15 (dd, J=10.1, 16.9 Hz, 1H), 5.63 (dd, J=1.6, 10.1 Hz, 1H), 4.48 (d, J=5.6 Hz, 2H). $^{13}$C NMR (100 MHz, CDCl$_3$): δ 165.5, 151.2, 142.2, 130.6, 126.8, 110.5, 107.5, 36.5. HRMS (+ESI): Calculated: 152.0706 (C$_8$H$_{10}$O$_2$Ni). Observed: 152.0706.

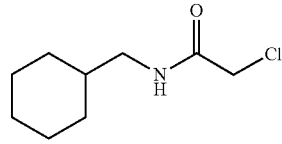 [SMILES: O=C(CCl)NCC1CCCCC1]

2-chloro-N-(cyclohexylmethyl)acetamide (YP 1-31). Following General Procedure B starting from cyclohexanemethylamine (113 mg, 1.0 mmol), product was obtained after silica gel chromatography (100% dichloromethane to 3% methanol in dichloromethane) in 60% yield as a white solid (112 mg). $^1$H NMR (400 MHz, CDCl$_3$): δ 6.70 (s, 1H), 4.06 (s, 2H), 3.15 (t, J=6.47 Hz, 2H), 1.77-1.65 (m, 5H), 1.56-1.46 (m, 1H), 1.30-1.10 (m, 3H), 1.00-0.90 (m, 2H). $^{13}$C NMR (100 MHz, CDCl$_3$): δ 165.8, 58.1, 46.0, 42.8, 37.7, 30.7, 26.3, 25.7, 18.2. HRMS (+ESI): Calculated: 190.0993 (C$_9$H$_{17}$ONCl). Observed: 190.0992.

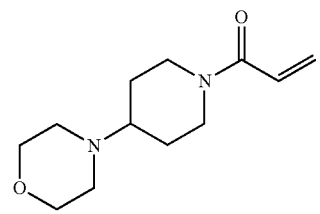 [SMILES: C=CC(=O)N1CCC(N2CCOCC2)CC1]

1-(4-morpholinopiperidin-1-yl)prop-2-en-1-one (YP 1-42). Following General Procedure A starting from 4-morpholinopiperidine (336 mg, 2.0 mmol), product was obtained after silica gel chromatography (1% methanol and 80% ethyl acetate in hexanes) in 58% yield as a colorless oil (259 mg). $^1$H NMR (400 MHz, CDCl$_3$): δ 6.42 (dd, J=10.6, 16.8 Hz, 1H), 6.06 (dd, J=2.0, 16.8 Hz, 1H), 5.49 (dd, J=2.0, 10.6 Hz, 1H), 4.45 (d, J=12.8 Hz, 1H), 3.86 (d, J=12.8 Hz, 1H), 3.52 (t, J=4.7 Hz, 4H), 2.90 (t, J=12.8 Hz, 1H), 2.55-2.48 (m, 1H), 2.37-2.35 (m, 4H), 2.26 (tt, J=3.7, 11.0 Hz, 1H), 1.72 (d, J=12.8 Hz, 2H), 1.30-1.20 (m, 2H). $^{13}$C NMR (100 MHz, CDCl$_3$): δ 165.0, 127.7, 127.3, 67.1, 61.6, 49.6, 44.9, 41.1, 28.9, 27.8. HRMS (+ESI): Calculated: 225.1598 (C$_{12}$H$_{21}$N$_2$O$_2$). Observed: 225.1595.

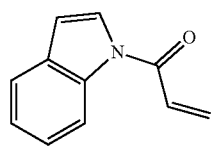

1-(1H-indol-1-yl)prop-2-en-1-one (YP 1-44). A solution of indole (117 mg, 1.0 mmol) in 2-methyltetrahydrofuran (10 mL) was cooled to 0° C. To the solution was added sodium hydride (60 mg, 2.5 mmol). The resultant intermediate was subjected to General Procedure A and product was obtained after alumina gel chromatography (10% to 40% ethyl acetate in hexanes) in 8% yield as a white solid (14 mg). $^1$H NMR (400 MHz, CD$_3$OD): δ 8.48-8.46 (m, 1H), 7.82 (d, J=3.9 Hz, 1H), 7.61-7.59 (m, 1H), 7.36-7.32 (m, 1H), 7.31-7.21 (m, 2H), 6.73 (dd, J=0.8, 3.8 Hz, 1H), 6.64 (dd, J=1.7, 16.7 Hz, 1H), 6.09 (dd, J=1.7, 10.5 Hz, 1H). $^{13}$C NMR (100 MHz, CD$_3$OD): δ 164.3, 135.7, 131.0, 130.9, 128.0, 125.0, 124.4, 123.6, 120.5, 116.2, 108.9. HRMS (+ESI): Calculated: 172.0757 (C$_{11}$H$_{10}$NO). Observed: 172.0756.

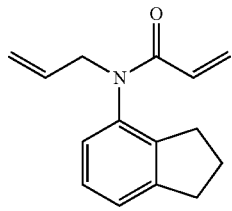 [SMILES: C=CCN(C(=O)C=C)c1cccc2c1CCC2]

N-allyl-N-(2,3-dihydro-1H-inden-4-yl)acrylamide (IGA 1-12). A solution of sodium hydride (96 mg, 4.0 mmol) in tetrahydrofuran (8 mL) was put under nitrogen atmosphere. To the solution was added N-(2,3-dihydro-1H-inden-4-yl)acrylamide (187 mg, 1.0 mmol) in tetrahydrofuran (2 mL). The solution was cooled to 0° C. and stirred. 3-bromoprop-1-ene (484 mg, 4.0 mmol) was added after 30 minutes, after which the solution was allowed to warm to room temperature and was stirred overnight. The solution was quenched with water and extracted with ethyl acetate. The crude product was purified via silica gel chromatography (20% ethyl acetate in hexanes) to afford the product in 67% yield as a yellow crystalline solid (151 mg). $^1$H NMR (400 MHz, CDCl$_3$): δ 7.06-7.18 (m, 2H), 6.80-6.88 (m, 1H), 6.26-6.37 (dd, J=16.8, 2.0 Hz, 11H), 5.76-5.96 (m, 2H), 5.38-5.48 (dd, J=10.3, 2.1 Hz, 1H), 4.98-5.08 (m, 2H), 4.40-4.52 (ddt, J=14.5, 6.3, 1.3 Hz, 1H), 4.00-4.11 (ddt, J=14.5, 6.8, 1.2 Hz, 1H), 2.82-2.98 (m, 2H), 2.59-2.79 (m, 2H), 1.92-2.07 (m, 2H). $^{13}$C NMR (100 MHz, CDCl$_3$): δ 165.1, 146.5, 142.4, 137.9, 133.0, 128.4, 127.8, 127.48, 126.1, 124.3, 118.1, 51.6, 33.3, 30.9, 25.0. HRMS (+ESI): Calculated: 228.13 (C$_{15}$H$_{17}$NO). Observed: 228.1381.

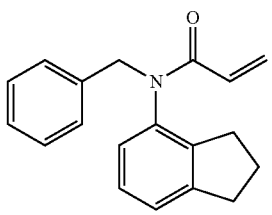 [SMILES: C=CC(=O)N(Cc1ccccc1)c1cccc2c1CCC2]

N-benzyl-N-(2,3-dihydro-1H-inden-4-yl)acrylamide (IGA 1-14). A solution of sodium hydride (96 mg, 4.0 mmol) in tetrahydrofuran (8 mL) was put under nitrogen atmosphere. To the solution was added N-(2,3-dihydro-1H-inden-4-yl)acrylamide (187 mg, 1.0 mmol) in tetrahydrofuran (2 mL). The solution was cooled to 0° C. and stirred. Benzyl bromide (476 mg, 4.0 mmol) was added after 30 minutes, after which the solution was allowed to warm to room temperature and was stirred overnight. The solution was quenched with water and extracted with ethyl acetate. The crude product was purified via silica gel chromatography (20% ethyl acetate in hexanes) to afford the product in 63% yield as an orange oil (173 mg). $^1$H NMR (400 MHz, CDCl$_3$): δ 7.10-7.35 (m, 7H), 6.74-6.85 (dd, J=7.8, 1.1 Hz, 1H), 6.40-6.55 (dd, J=16.8, 2.1 Hz, 11H), 5.93-6.08 (dd, J=16.8, 10.3 Hz, 1H), 5.49-5.62 (dd, J=10.3, 2.1 Hz, 1H), 4.78-5.10 (m, 2H), 2.85-3.02 (m, 2H), 2.52-2.67 (m, 1H), 2.22-2.37 (m, 1H), 1.83-2.01 (m, 2H). $^{13}$C NMR (100 MHz, CDCl$_3$): δ 146.4, 142.9, 137.7, 137.3, 129.3, 128.4, 128.3, 128.0, 127.5, 127.5, 126.0, 124.3, 52.3, 33.2, 30.6, 25.1. HRMS (+ESI): Calculated: 278.15 (C$_{19}$H$_{19}$NO). Observed: 278.1538.

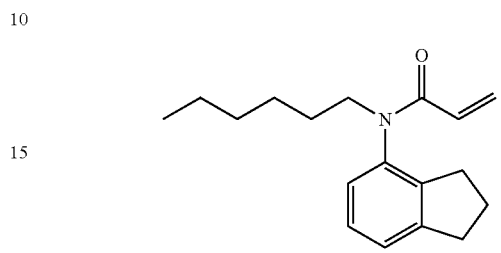

N-allyl-N-(2,3-dihydro-1H-inden-4-yl)acrylamide (IGA 1-15). A solution of sodium hydride (96 mg, 4.0 mmol) in tetrahydrofuran (8 mL) was put under nitrogen atmosphere. To the solution was added N-(2,3-dihydro-1H-inden-4-yl)acrylamide (187 mg, 1.0 mmol) in tetrahydrofuran (2 mL). The solution was cooled to 0° C. and stirred. 1-bromohexane (660 mg, 4.0 mmol) was added after 30 minutes, after which the solution was allowed to warm to room temperature and was stirred overnight. The solution was quenched with water and extracted with ethyl acetate. The crude product was purified via silica gel chromatography (20% ethyl acetate in hexanes) to afford the product in 34% yield as a yellow oil (92 mg). $^1$H NMR (400 MHz, CDCl$_3$): δ 7.11-7.25 (m, 2H), 6.86-6.96 (dd, J=7.5, 1.2 Hz, 1H), 6.30-6.40 (dd, J=16.8, 2.1 Hz, 1H), 5.86-6.00 (m, 11H), 5.41-5.51 (dd, J=10.3, 2.1 Hz, 11H), 3.82-3.96 (m, 1H), 3.42-3.56 (m, 1H), 2.90-3.04 (m, 2H), 2.65-2.85 (m, 2H), 1.98-2.16 (m, 2H), 1.47-1.63 (m, 2H), 1.20-1.36 (m, 6H), 0.80-0.90 (m, 3H). $^{13}$C NMR (100 MHz, CDCl$_3$): δ 165.16, 146.54, 142.38, 138.21, 128.59, 127.51, 127.35, 126.09, 124.13, 48.67, 33.26, 31.62, 30.85, 27.85, 26.72, 25.01, 22.59, 14.05. HRMS (+ESI): Calculated: 272.19 (C$_{18}$H$_{25}$NO). Observed: 272.2007.

For in vitro experiments, DMSO vehicle, nimbolide, or EN62 were treated in 231MFP breast cancer cell proteomes for 30 min prior to labeling of proteomes with IA-alkyne (100 μM) for 1h. Isotopically light (for DMSO-treated) or heavy (for compound-treated) TEV protease-cleavable biotin-azide tag were appended by CuAAC for isoTOP-ABPP analysis. For in situ experiments, DMSO vehicle or nimbolide were treated in 231MFP breast cancer cells in situ for 1 h prior to labeling of proteomes in vitro with IA-alkyne (100 μM) for 1h. Isotopically light (for DMSO-treated) or heavy (for compound-treated) TEV protease-cleavable biotin-azide tag were appended by CuAAC for isoTOP-ABPP analysis. Only probe-modified peptides that were present in two out of three biological replicates were interpreted. For those ratios >3, we only interpreted those peptides that were present in all biological replicates where all replicate ratios were >3. For those ratios >4, we only interpreted those peptides that were present in all biological replicates where all replicate ratios were >4. MS1 peak shape qualities were manually curated to confirm good peak quality for all replicates.

Table 2. Structures of covalent ligands screened against RNF114.
TABLE 2
STRUCTURES OF COVALENT LIGANDS SCREENED AGAINST RNF114
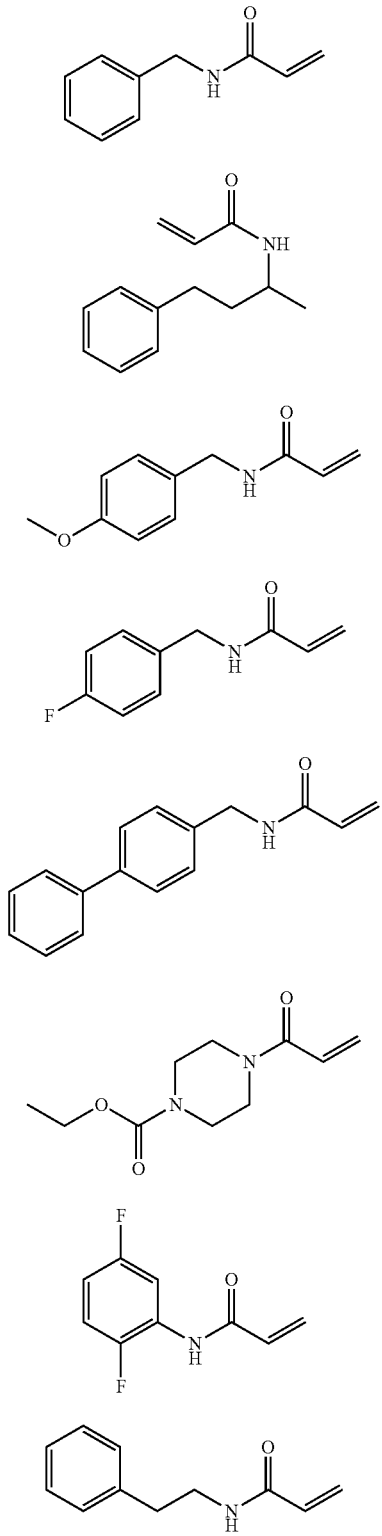
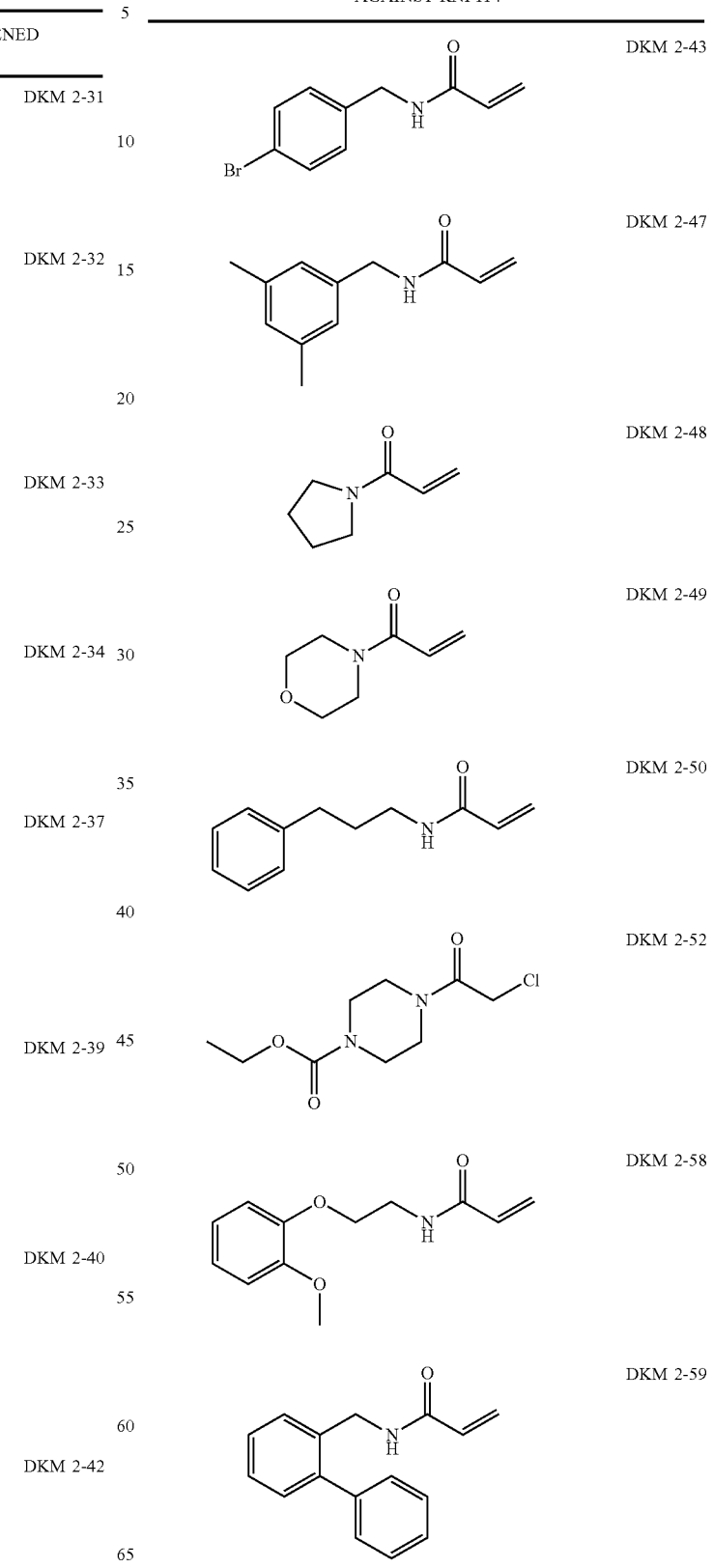

TABLE 2-continued
STRUCTURES OF COVALENT LIGANDS SCREENED AGAINST RNF114
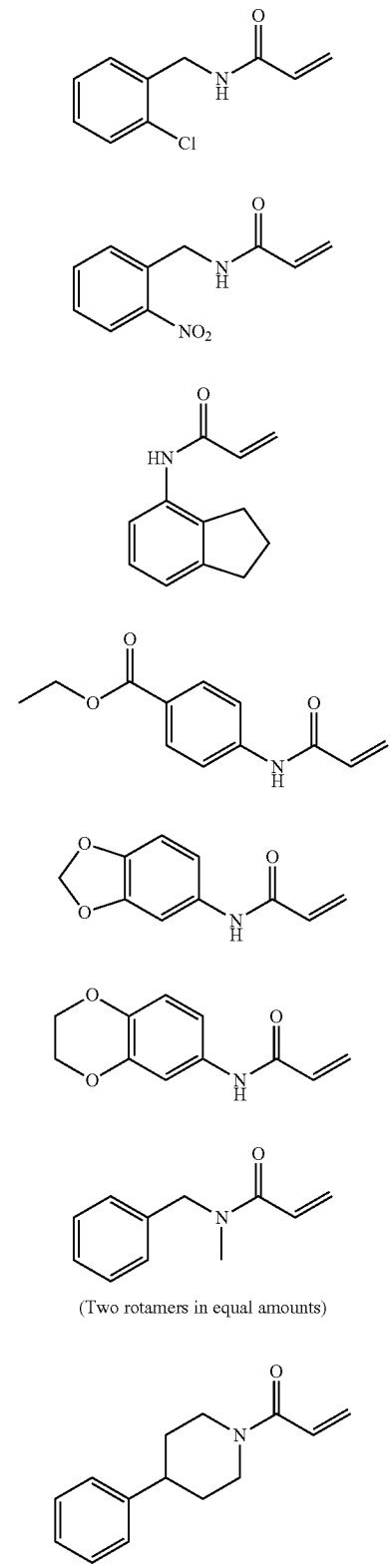
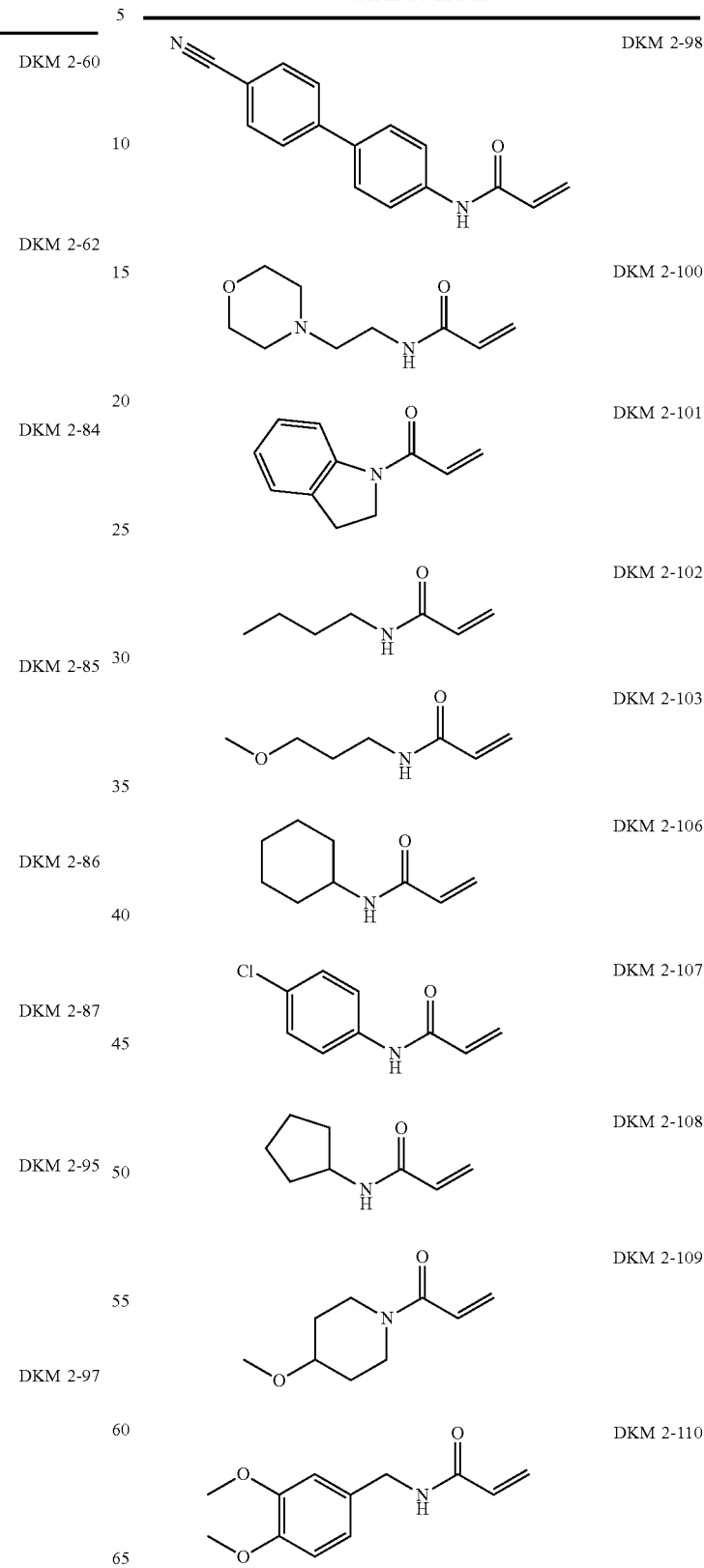

TABLE 2-continued
STRUCTURES OF COVALENT LIGANDS SCREENED AGAINST RNF114
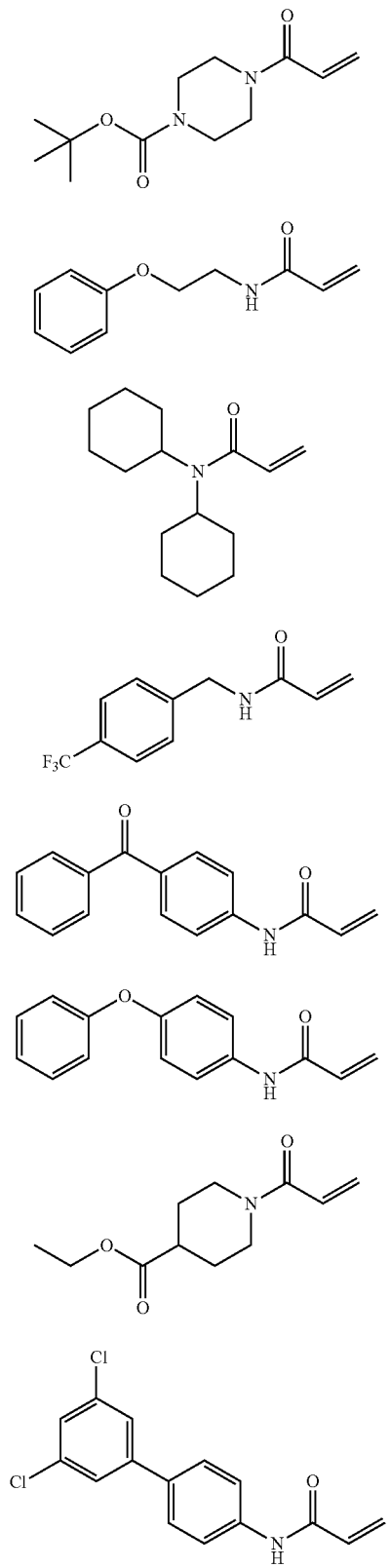
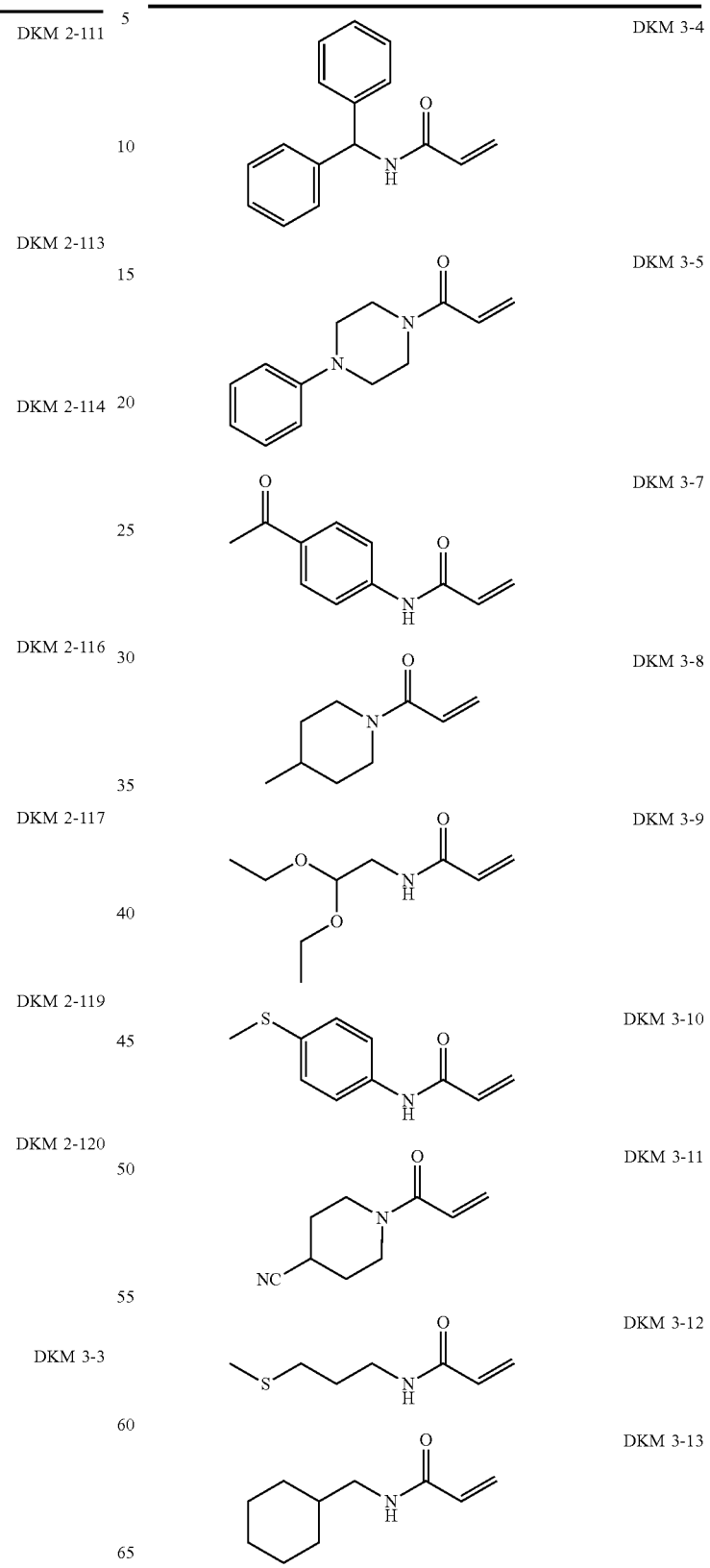

TABLE 2-continued
STRUCTURES OF COVALENT LIGANDS SCREENED AGAINST RNF114
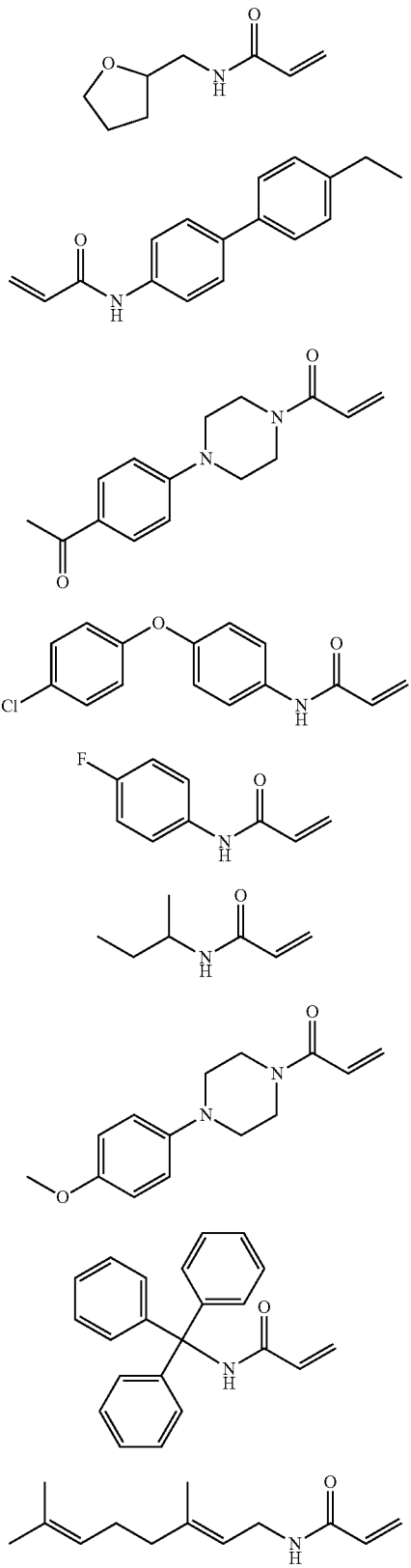
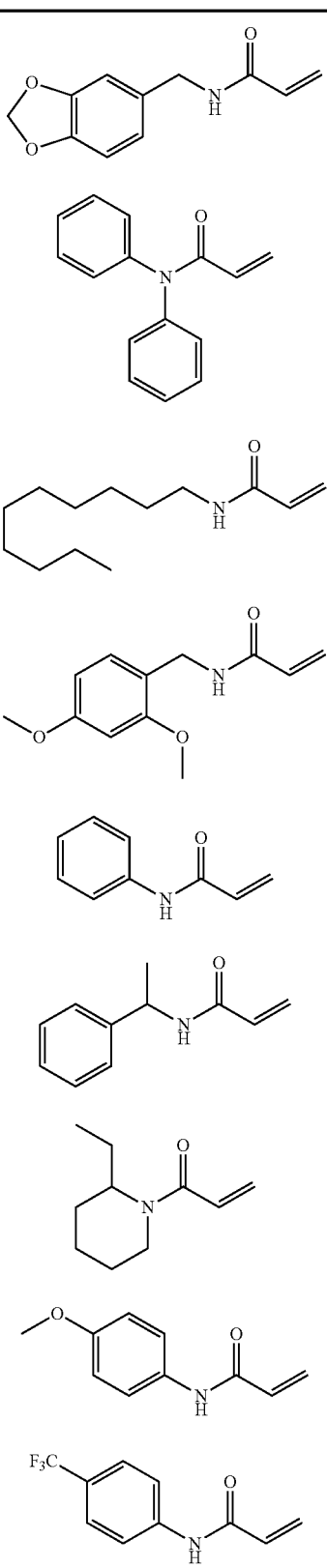

TABLE 2-continued
STRUCTURES OF COVALENT LIGANDS SCREENED AGAINST RNF114
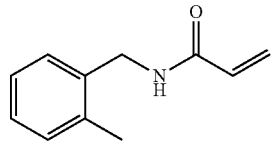
TRH 1-54
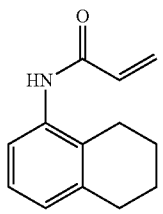
TRH 1-56
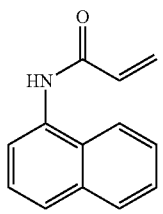
TRH 1-57
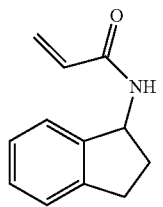
TRH 1-58
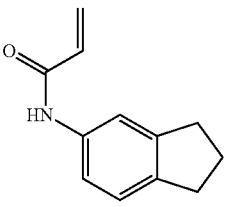
TRH 1-59
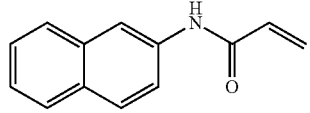
TRH 1-60
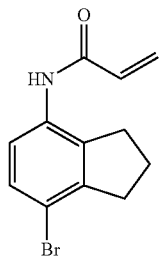
TRH 1-65
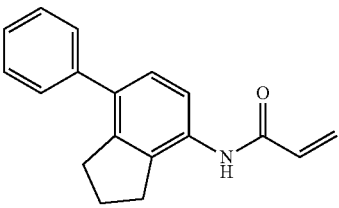 [SMILES: C=CC(=O)Nc1ccc(-c2ccccc2)c2c1CCC2]
TRH 1-68
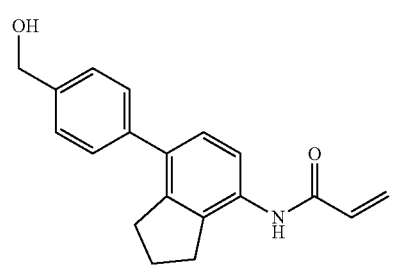 [SMILES: C=CC(=O)Nc1ccc(-c2ccc(CO)cc2)c2c1CCC2]
TRH 1-70
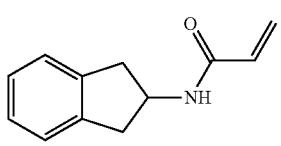
TRH 1-74
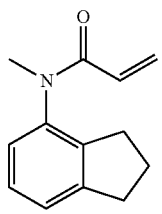
TRH 1-115
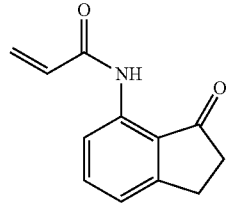
TRH 1-129
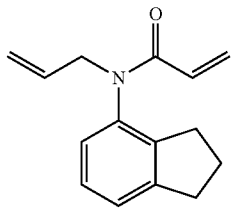 [SMILES: C=CCN(C(=O)C=C)c1cccc2c1CCC2]
IGA 1-12
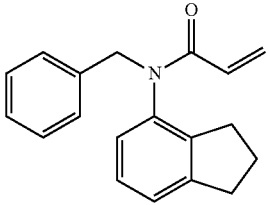 [SMILES: C=CC(=O)N(Cc1ccccc1)c1cccc2c1CCC2]
IGA 1-14

TABLE 2-continued
STRUCTURES OF COVALENT LIGANDS SCREENED AGAINST RNF114
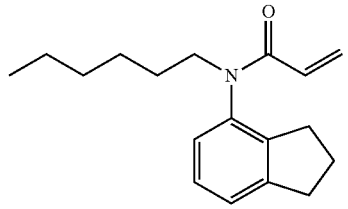 [SMILES: C=CC(=O)N(CCCCCC)c1cccc2c1CCC2]
IGA 1-15
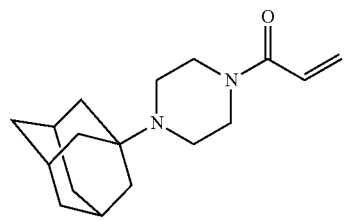 [SMILES: C=CC(=O)N1CCN(C23CC4CC(CC(C4)C2)C3)CC1]
TRH 1-143
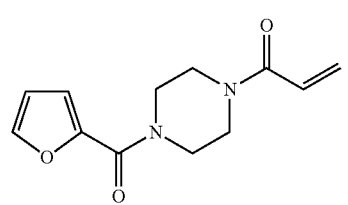 [SMILES: C=CC(=O)N1CCN(C(=O)c2ccco2)CC1]
TRH 1-145
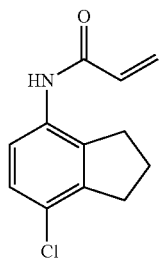
YP 1-1
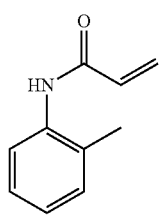
YP 1-16
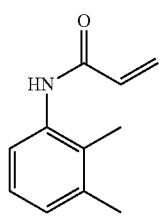
YP 1-18
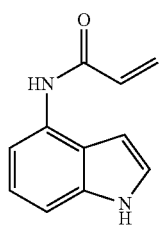
YP 1-19
TABLE 2-continued
STRUCTURES OF COVALENT LIGANDS SCREENED AGAINST RNF114
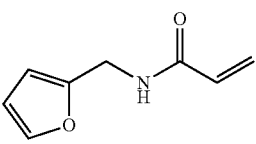
YP 1-26
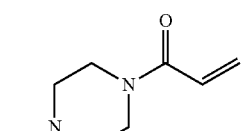
YP 1-22
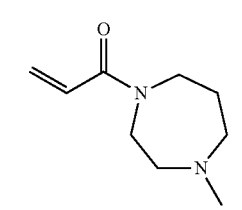
YP 1-23
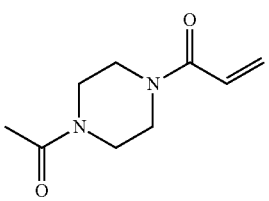
YP 1-24
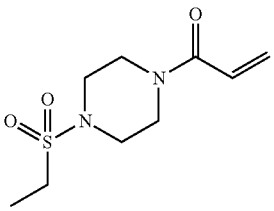
YP 1-25
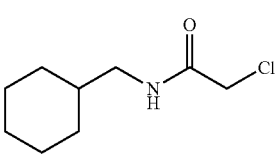 [SMILES: O=C(CCl)NCC1CCCCC1]
YP 1-31
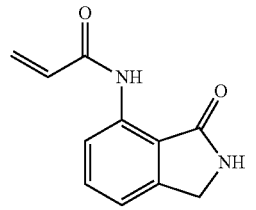
TRH 1-152
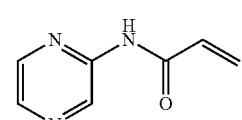
TRH 1-156

TABLE 2-continued
STRUCTURES OF COVALENT LIGANDS SCREENED AGAINST RNF114
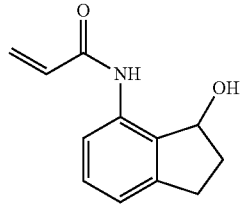
TRH 1-133
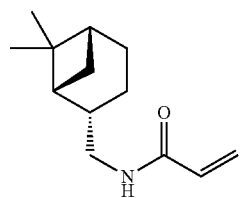
TRH 1-133
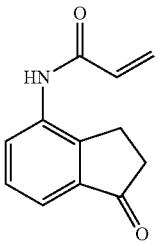
TRH 1-134
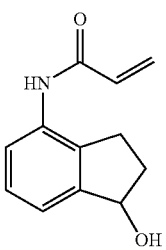
TRH 1-135
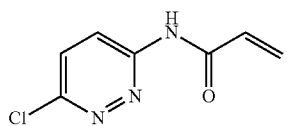
TRH 1-155
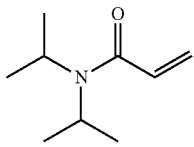
TRH 1-167
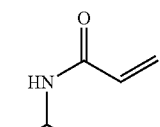
YP 1-36
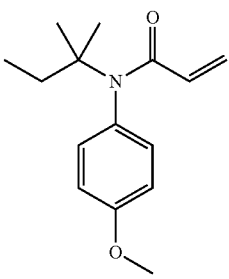 [SMILES: C=CC(=O)N(c1ccc(OC)cc1)C(C)(C)CC]
TRH 1-170
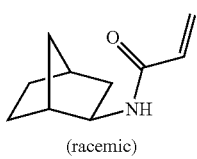
TRH 1-176
(racemic)
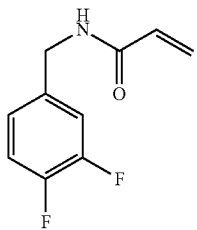
YP 1-38
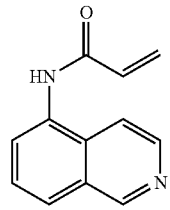
TRH 1-162
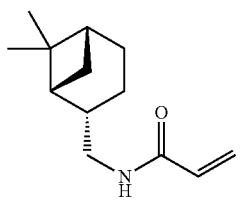
TRH 1-178
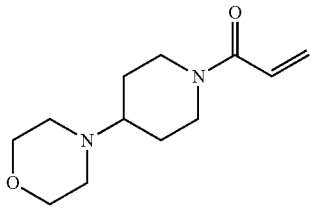 [SMILES: C=CC(=O)N1CCC(N2CCOCC2)CC1]
YP 1-42
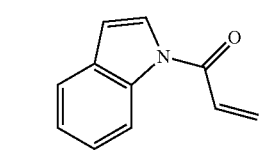
YP 1-44

TABLE 2-continued
STRUCTURES OF COVALENT LIGANDS SCREENED AGAINST RNF114
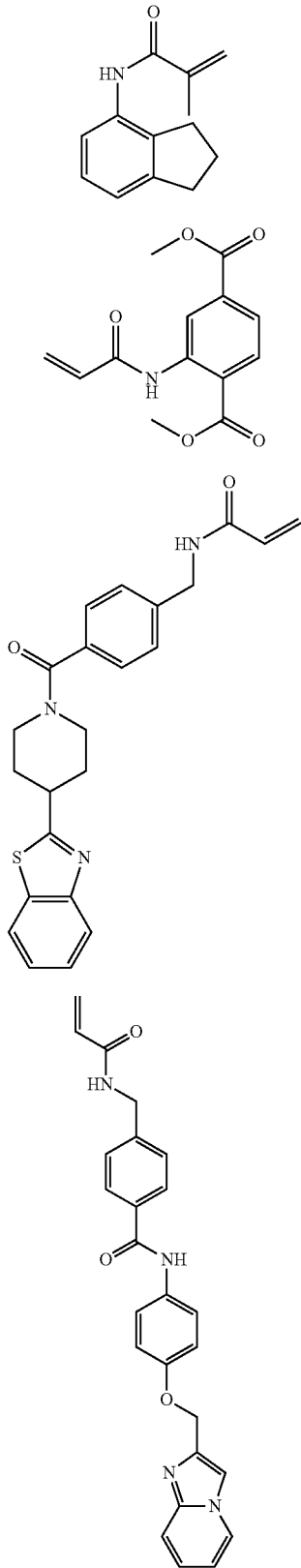
TRH 1-149
EN1
EN2
EN3
TABLE 2-continued
STRUCTURES OF COVALENT LIGANDS SCREENED AGAINST RNF114
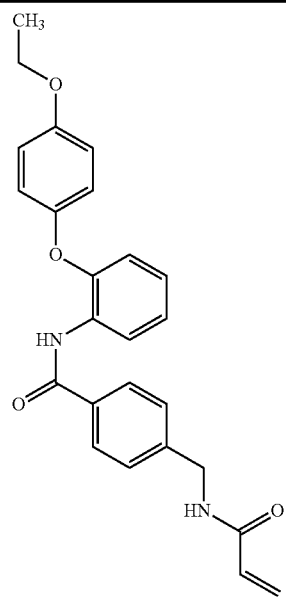
EN4
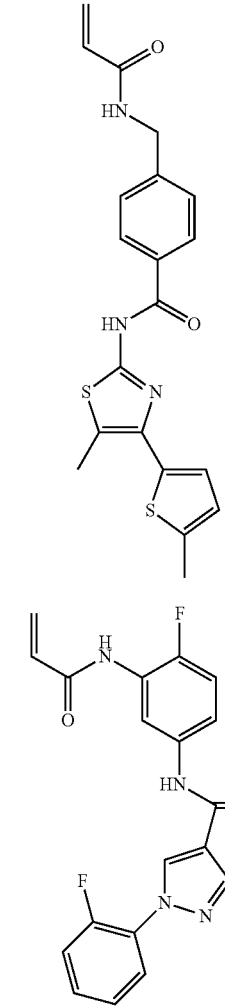
EN5
EN6

TABLE 2-continued
STRUCTURES OF COVALENT LIGANDS SCREENED AGAINST RNF114
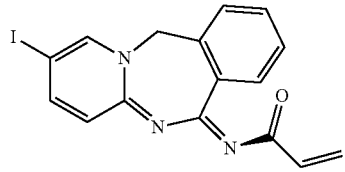
EN7
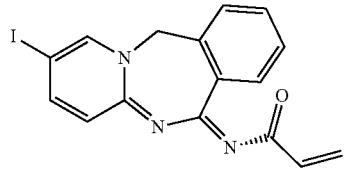
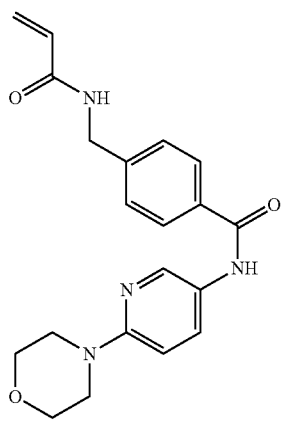 [SMILES: C=CC(=O)NCc1ccc(C(=O)Nc2ccc(N3CCOCC3)nc2)cc1]
EN8
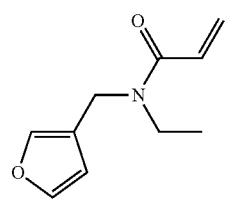
EN9
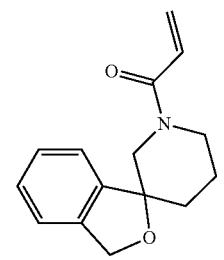 [SMILES: C=CC(=O)N1CCCC2(C1)OCc1ccccc12]
EN10
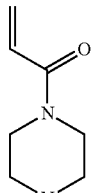
EN12
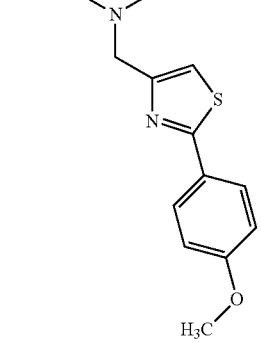
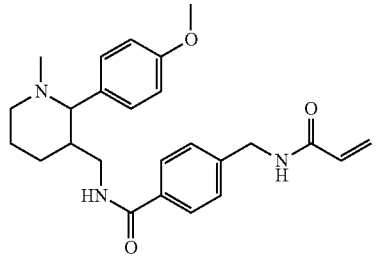 [SMILES: C=CC(=O)NCc1ccc(C(=O)NCC2CCCN(C)C2c2ccc(OC)cc2)cc1]
EN13
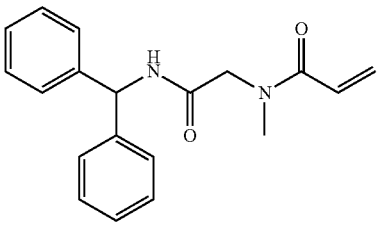 [SMILES: C=CC(=O)N(C)CC(=O)NC(c1ccccc1)c1ccccc1]
EN14
EN15

TABLE 2-continued
STRUCTURES OF COVALENT LIGANDS SCREENED AGAINST RNF114
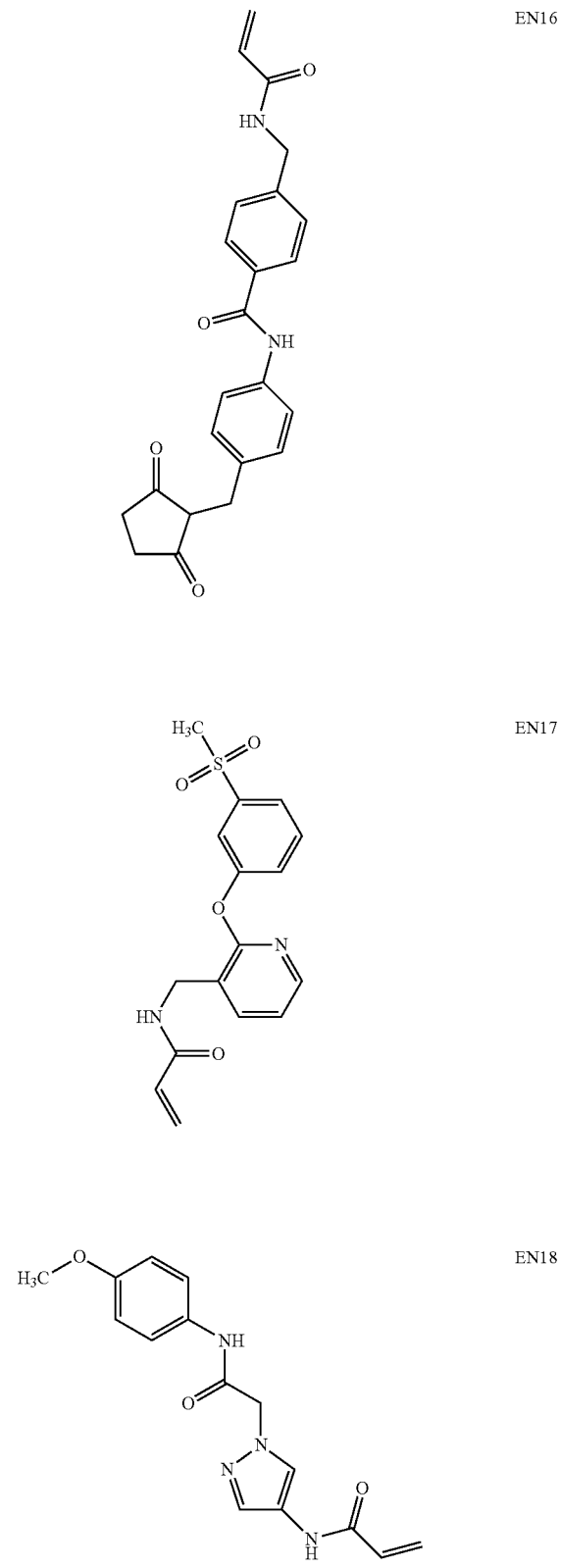
EN16
EN17
EN18
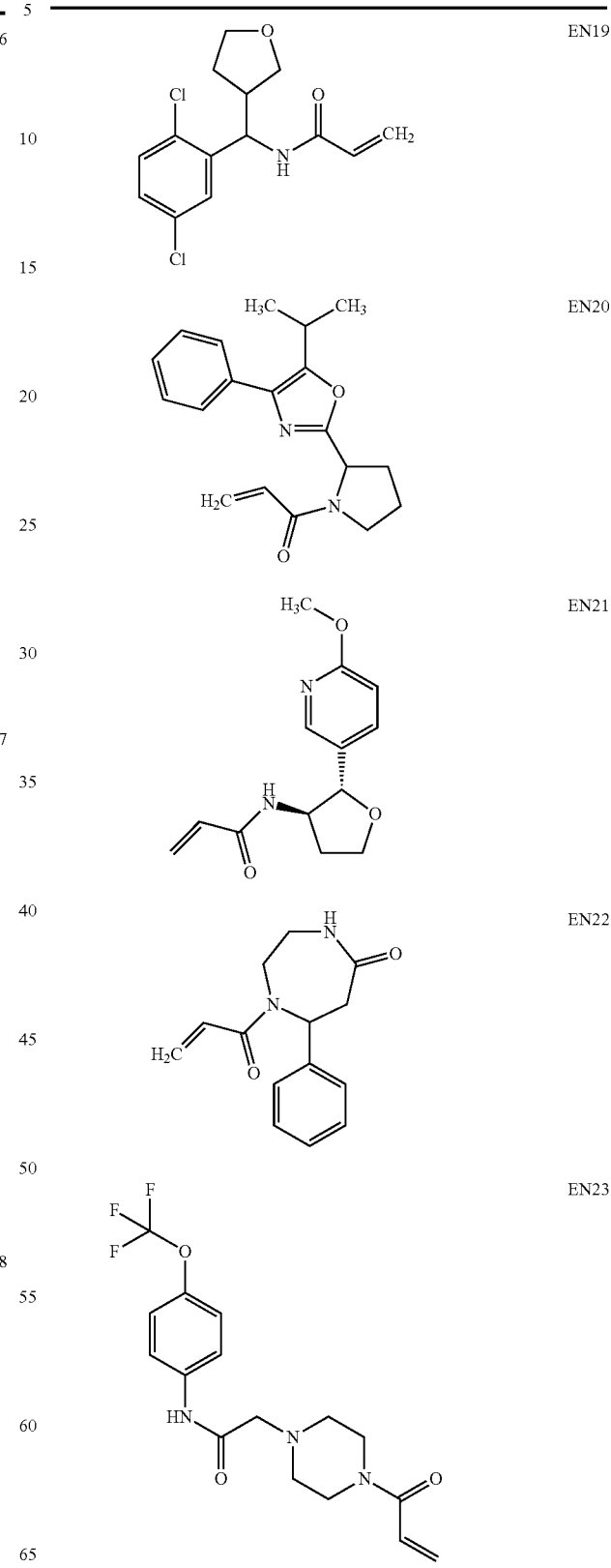
EN19
EN20
EN21
EN22
EN23

TABLE 2-continued
STRUCTURES OF COVALENT LIGANDS SCREENED AGAINST RNF114
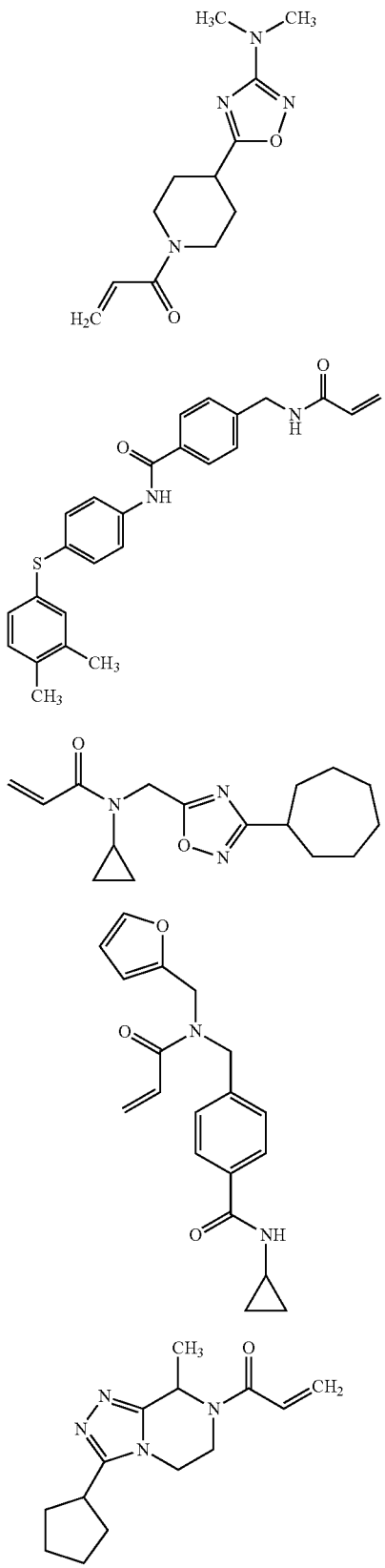
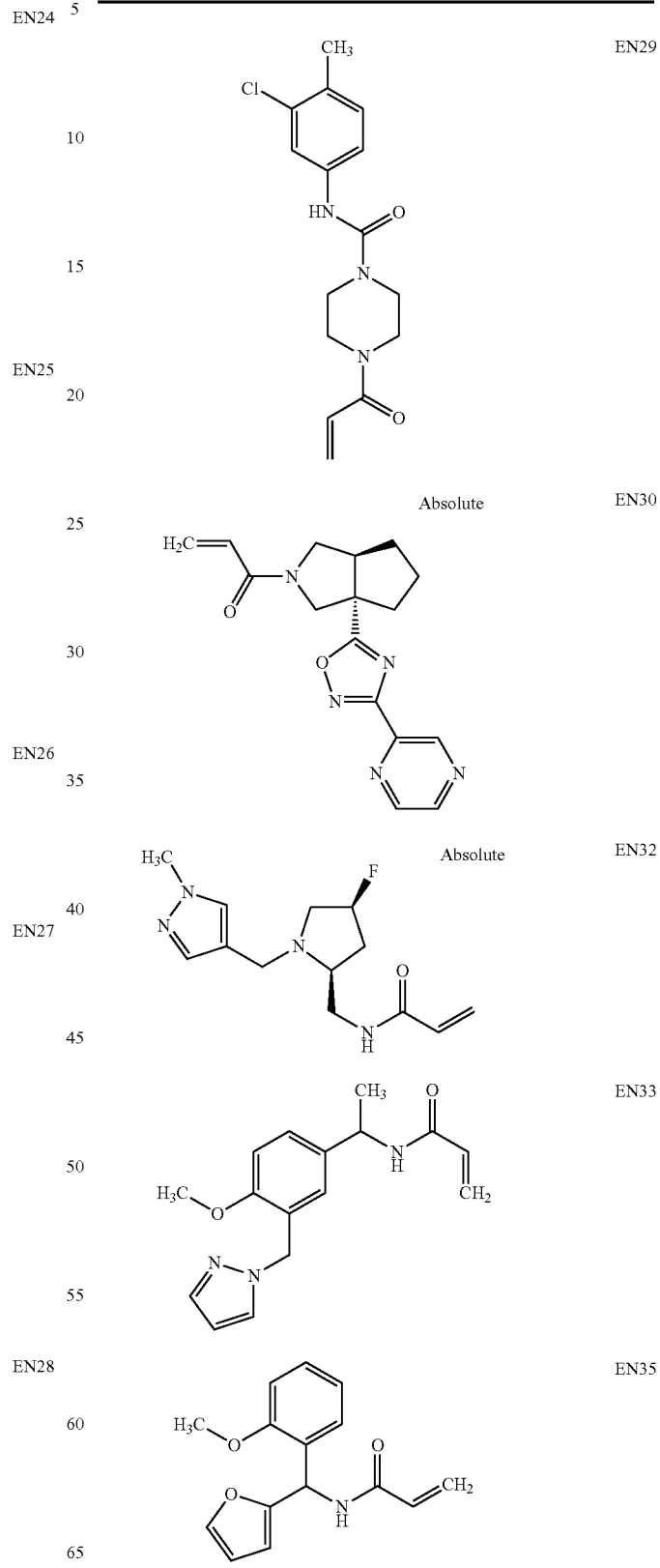

TABLE 2-continued
STRUCTURES OF COVALENT LIGANDS SCREENED AGAINST RNF114
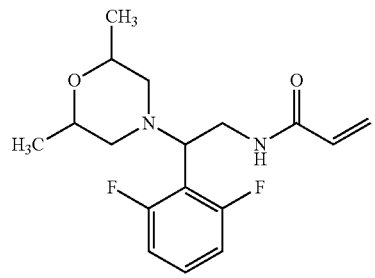 [SMILES: C=CC(=O)NCC(c1c(F)cccc1F)N1CC(C)OC(C)C1]
EN36
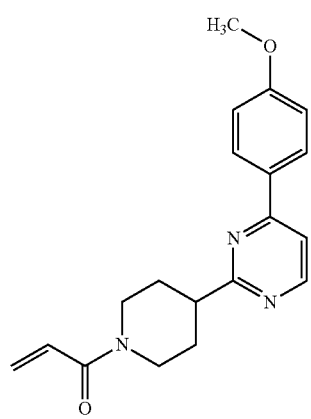 [SMILES: C=CC(=O)N1CCC(c2nccc(-c3ccc(OC)cc3)n2)CC1]
EN37
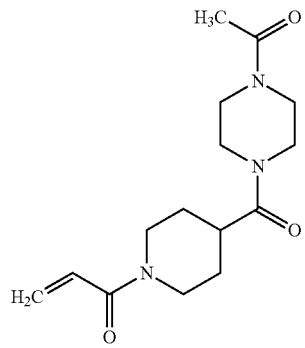 [SMILES: C=CC(=O)N1CCC(C(=O)N2CCN(C(C)=O)CC2)CC1]
EN38
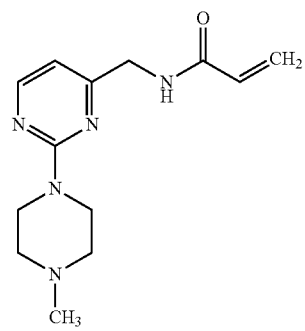 [SMILES: C=CC(=O)NCc1ccnc(N2CCN(C)CC2)n1]
EN39
TABLE 2-continued
STRUCTURES OF COVALENT LIGANDS SCREENED AGAINST RNF114
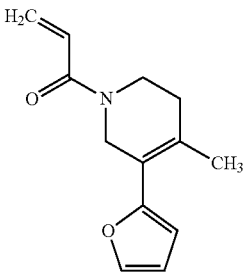 [SMILES: C=CC(=O)N1CCC(C)=C(c2ccco2)C1]
EN40
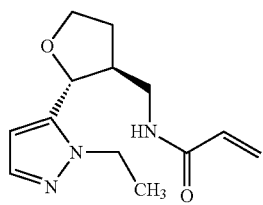 [SMILES: C=CC(=O)NC[C@@H]1CCO[C@H]1c1ccnn1CC]
EN43
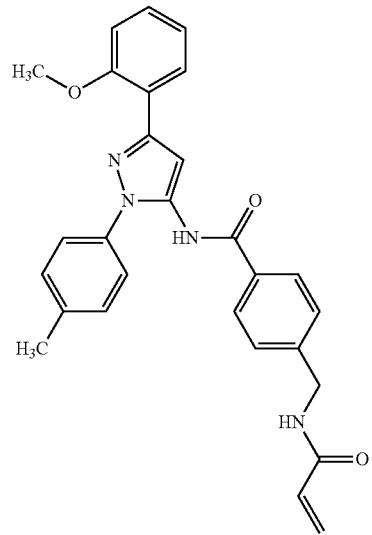 [SMILES: C=CC(=O)NCc1ccc(C(=O)Nc2cc(-c3ccccc3OC)nn2-c2ccc(C)cc2)cc1]
EN44

TABLE 2-continued
STRUCTURES OF COVALENT LIGANDS SCREENED AGAINST RNF114
EN45
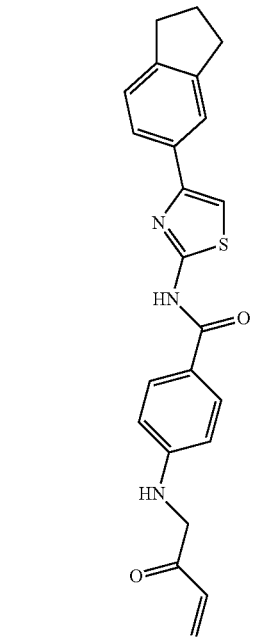 [SMILES: C=CC(=O)CNc1ccc(C(=O)Nc2nc(-c3ccc4c(c3)CCC4)cs2)cc1]
EN46
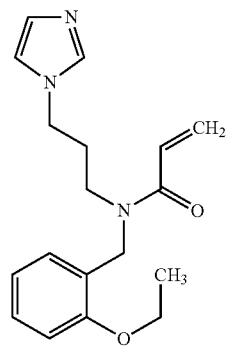 [SMILES: C=CC(=O)N(CCCn1ccnc1)Cc1ccccc1OCC]
EN47
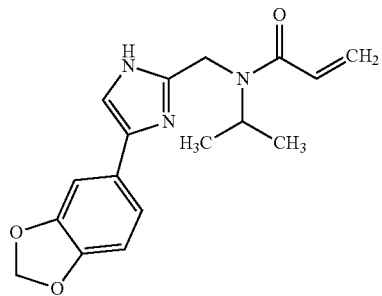 [SMILES: C=CC(=O)N(Cc1nc(-c2ccc3c(c2)OCO3)c[nH]1)C(C)C]
EN48
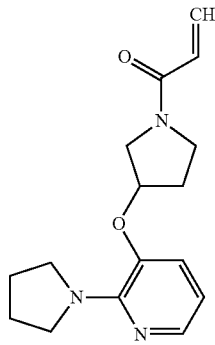
EN49
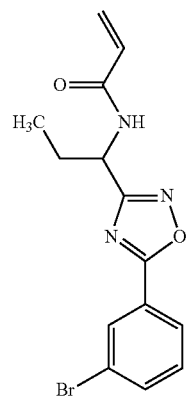
EN50
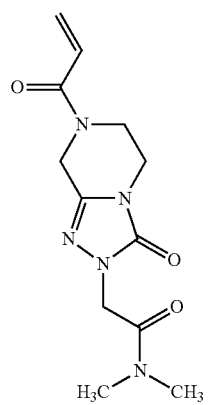 [SMILES: C=CC(=O)N1CCn2c(nn(CC(=O)N(C)C)c2=O)C1]
EN51
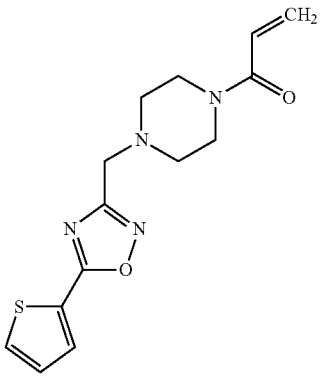 [SMILES: C=CC(=O)N1CCN(Cc2noc(-c3cccs3)n2)CC1]

TABLE 2-continued
STRUCTURES OF COVALENT LIGANDS SCREENED AGAINST RNF114
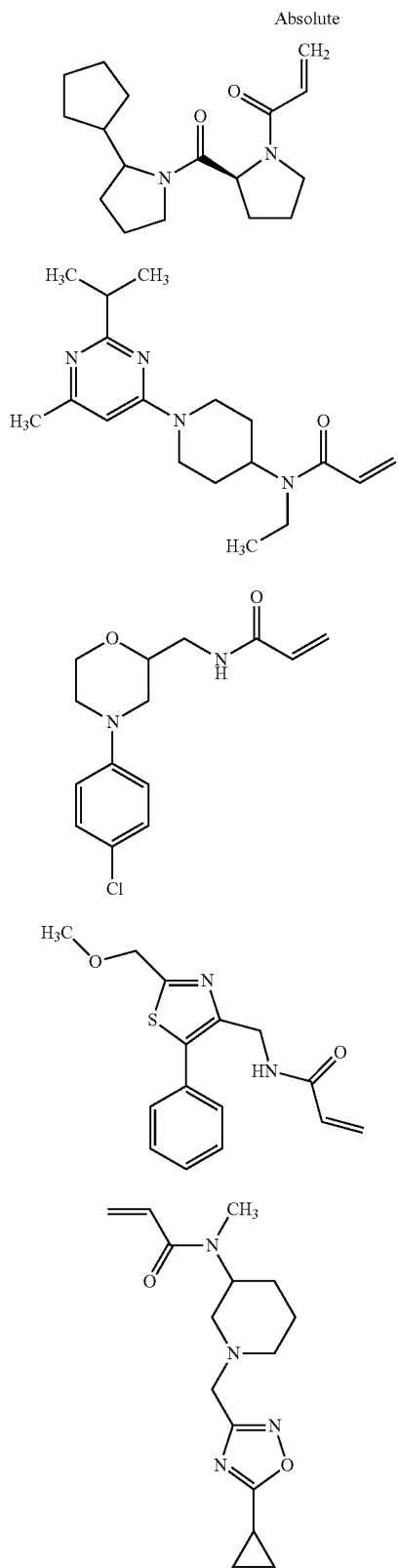
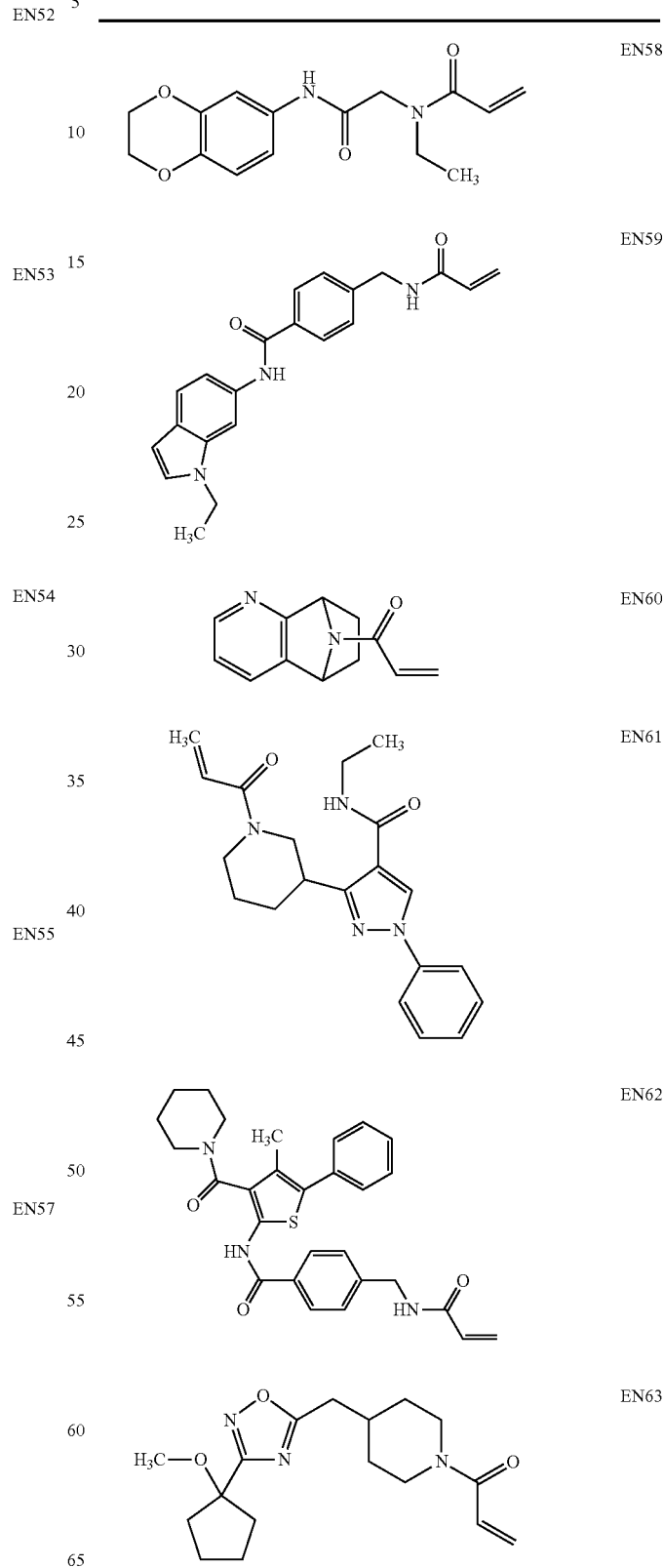

TABLE 2-continued
STRUCTURES OF COVALENT LIGANDS SCREENED AGAINST RNF114
EN64
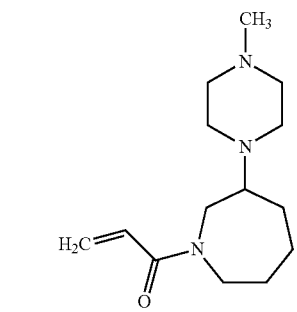 [SMILES: C=CC(=O)N1CCCCC(N2CCN(C)CC2)C1]
EN65
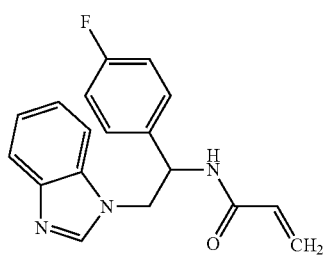 [SMILES: C=CC(=O)NC(Cn1cnc2ccccc21)c1ccc(F)cc1]
EN66
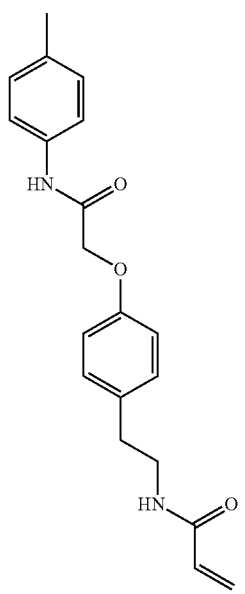 [SMILES: C=CC(=O)NCCc1ccc(OCC(=O)Nc2ccc(C)cc2)cc1]
EN67
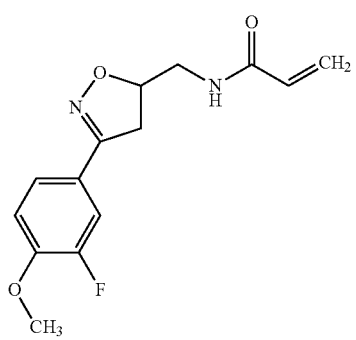 [SMILES: C=CC(=O)NCC1CC(c2ccc(OC)c(F)c2)=NO1]
EN68
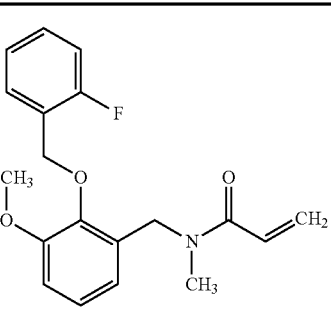
EN69
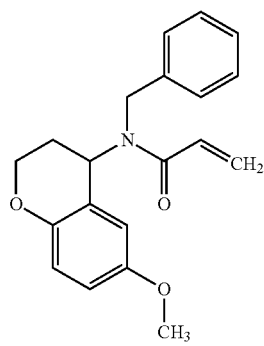 [SMILES: C=CC(=O)N(Cc1ccccc1)C1CCOc2ccc(OC)cc21]
EN70
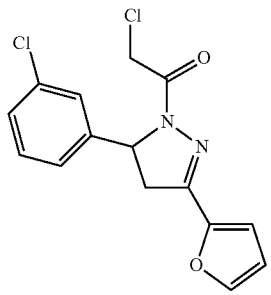 [SMILES: O=C(CCl)N1N=C(c2ccco2)CC1c1cccc(Cl)c1]
EN71
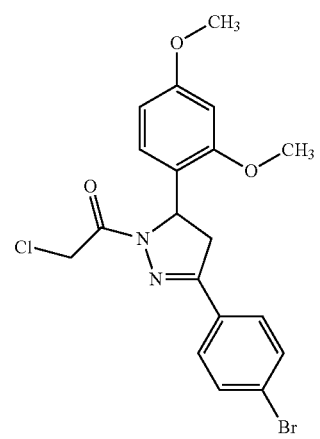 [SMILES: COc1ccc(C2CC(c3ccc(Br)cc3)=NN2C(=O)CCl)c(OC)c1]

TABLE 2-continued
STRUCTURES OF COVALENT LIGANDS SCREENED AGAINST RNF114
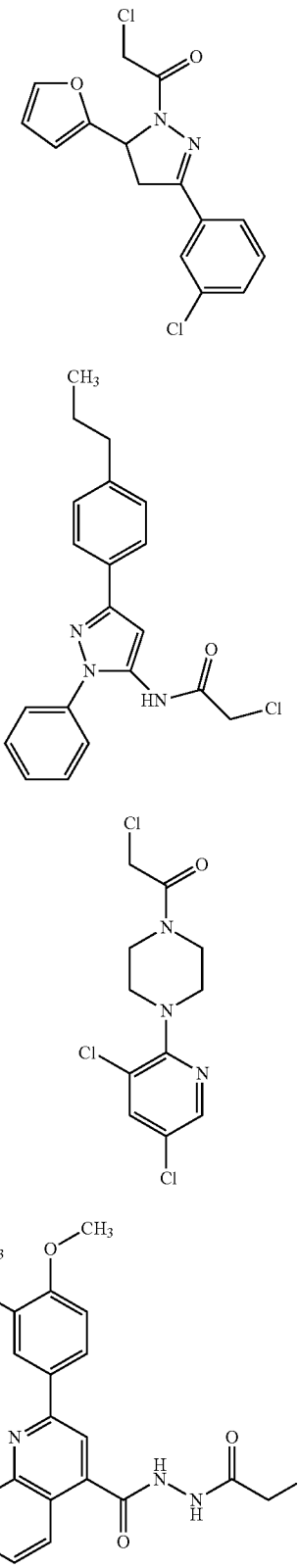
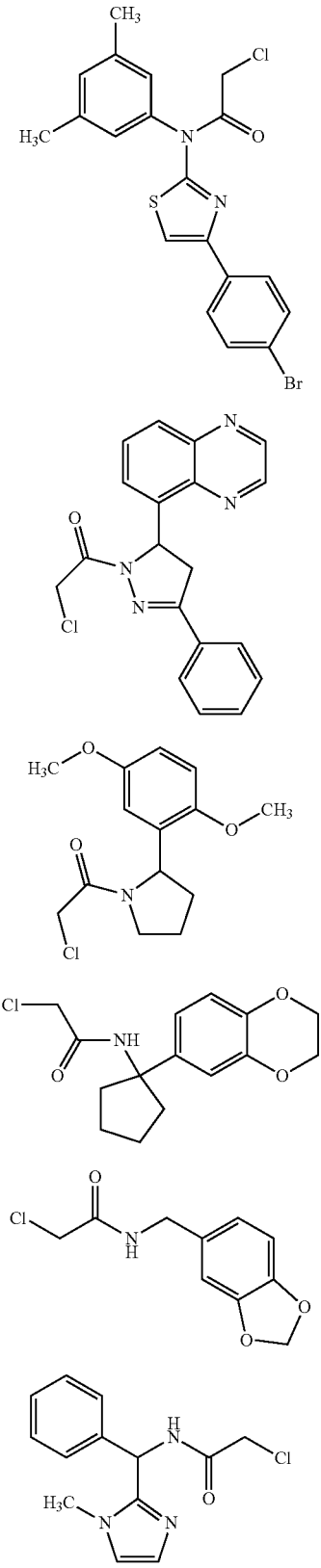

TABLE 2-continued

STRUCTURES OF COVALENT LIGANDS SCREENED
AGAINST RNF114

EN87

EN88

EN89

EN90

EN93

References Pertaining to Examples 4-6

1. Laraia, L., Robke, L. & Waldmann, H. Bioactive Compound Collections: From Design to Target Identification. *Chem* 4, 705-730 (2018). 2. Koehn, F. E. & Carter, G. T. The evolving role of natural products in drug discovery. *Nat. Rev. Drug Discov.* 4, 206-220 (2005). 3. Kingston, D. G. I. Modern Natural Products Drug Discovery and its Relevance to Biodiversity Conservation. *J. Nat. Prod.* 74, 496-511 (2011). 4. Harvey, A. L., Edrada-Ebel, R. & Quinn, R. J. The re-emergence of natural products for drug discovery in the genomics era. *Nat. Rev. Drug Discov.* 14, 111-129 (2015). 5. Nomura, D. K. & Maimone, T. J. Target Identification of Bioactive Covalently Acting Natural Products. *Curr. Top. Microbiol. Immunol.* 420, 351-374 (2019). 6. Wright, M. H. & Sieber, S. A. Chemical proteomics approaches for identifying the cellular targets of natural products. *Nat. Prod. Rep.* 33, 681-708 (2016). 7. Drahl, C., Cravatt, B. F. & Sorensen, E. J. Protein-reactive natural products. *Angew. Chem. Int. Ed Engl.* 44, 5788-5809 (2005). 8. Liu, J. et al. Calcineurin is a common target of cyclophilin-cyclosporin A and FKBP-FK506 complexes. *Cell* 66, 807-815 (1991). 9. Cohen, E., Quistad, G. B. & Casida, J. E. Cytotoxicity of nimbolide, epoxyazadiradione and other limonoids from neem insecticide. *Life Sci.* 58, 1075-1081 (1996). 10. Bodduluru, L. N., Kasala, E. R., Thota, N., Barua, C. C. & Sistla, R. Chemopreventive and therapeutic effects of nimbolide in cancer: the underlying mechanisms. *Toxicol. Vitro Int. J. Publ. Assoc. BIBRA* 28, 1026-1035 (2014). 11. Subramani, R. et al. Nimbolide inhibits pancreatic cancer growth and metastasis through ROS-mediated apoptosis and inhibition of epithelial-to-mesenchymal transition. *Sci. Rep.* 6, 19819 (2016). 12. Hao, F., Kumar, S., Yadav, N. & Chandra, D. Neem components as potential agents for cancer prevention and treatment. *Biochim. Biophys. Acta* 1846, 247-257 (2014). 13. Chien, S.-Y. et al. Nimbolide induces apoptosis in human nasopharyngeal cancer cells. *Environ. Toxicol.* 32, 2085-2092 (2017). 14. Elumalai, P. et al. Nimbolide inhibits invasion and migration, and down-regulates uPAR chemokine gene expression, in two breast cancer cell lines. *Cell Prolif* 47, 540-552 (2014). 15. Elumalai, P., Arunkumar, R., Benson, C. S., Sharmila, G. & Arunakaran, J. Nimbolide inhibits IGF-I-mediated PI3K/Akt and MAPK signalling in human breast cancer cell lines (MCF-7 and MDA-MB-231). *Cell Biochem. Funct.* 32, 476-484 (2014). 16. Kavitha, K. et al. Nimbolide, a neem limonoid abrogates canonical NF-κB and Wnt signaling to induce caspase-dependent apoptosis in human hepatocarcinoma (HepG2) cells. *Eur. J. Pharmacol.* 681, 6-14 (2012). 17. Pooladanda, V., Bandi, S., Mondi, S. R., Gottumukkala, K. M. & Godugu, C. Nimbolide epigenetically regulates autophagy and apoptosis in breast cancer. *Toxicol. Vitro Int. J. Publ. Assoc. BIBRA* 51, 114-128 (2018). 18. Gupta, S. C. et al. Nimbolide, a limonoid triterpene, inhibits growth of human colorectal cancer xenografts by suppressing the proinflammatory microenvironment. *Clin. Cancer Res. Off J. Am. Assoc. Cancer Res.* 19, 4465-4476 (2013). 19. Lin, H., Qiu, S., Xie, L., Liu, C. & Sun, S. Nimbolide suppresses non-small cell lung cancer cell invasion and migration via manipulation of DUSP4 expression and ERK1/2 signaling. *Biomed. Pharmacother. Biomedecine Pharmacother.* 92, 340-346 (2017). 20. Babykutty, S. et al. Nimbolide retards tumor cell migration, invasion, and angiogenesis by downregulating MMP-2/9 expression via inhibiting ERK1/2 and reducing DNA-binding activity of NF-κB in colon cancer cells. *Mol. Carcinog.* 51, 475-490 (2012). 21. Nagini, S. Neem Limonoids as Anticancer Agents: Modulation of Cancer Hallmarks and Oncogenic Signaling. *The Enzymes* 36, 131-147 (2014). 22. Alshammari, G. M., Balakrishnan, A. & Chinnasamy, T. Nimbolide attenuate the lipid accumulation, oxidative stress and antioxidant in primary hepatocytes. *Mol. Biol. Rep.* 44, 463-474 (2017). 23. Leslie, B. J. & Hergenrother, P. J. Identification of the cellular targets of bioactive small organic molecules using affinity reagents. *Chem. Soc. Rev.* 37, 1347-1360 (2008). 24. Pan, S., Zhang, H., Wang, C., Yao, S. C. L. & Yao, S. Q. Target identification of natural products and bioactive compounds using affinity-based probes. *Nat. Prod. Rep.* 33, 612-620 (2016). 25. Ursu, A. & Waldmann, H. Hide and seek: Identification and confirmation of small molecule protein targets. *Bioorg. Med. Chem. Lett.* 25, 3079-3086 (2015). 26. Bianchini, G., Balko, J. M., Mayer, I. A., Sanders, M. E. & Gianni, L. Triple-negative breast cancer: challenges and opportunities of a heterogeneous disease. *Nat. Rev. Clin. Oncol.* 13, 674-690 (2016). 27. Zeichner, S. B., Terawaki, H. & Gogineni, K. A Review of Systemic Treatment in Metastatic Triple-Negative Breast Cancer. *Breast Cancer Basic Clin. Res.* 10, 25-36 (2016). 28. Weerapana, E. et al. Quantitative reactivity profiling predicts functional cysteines in proteomes. *Nature* 468, 790-795 (2010). 29. Evans, M. J. & Cravatt, B. F. Mechanism-based profiling of enzyme families. *Chem. Rev.* 106, 3279-3301 (2006). 30. Roberts, A. M., Ward, C. C. & Nomura, D. K. Activity-based protein profiling for mapping and pharmacologically interrogating proteome-wide ligandable hotspots. *Curr. Opin. Biotechnol.* 43, 25-33 (2017). 31. Grossman, E. A. et al. Covalent Ligand Discovery against Druggable Hotspots Targeted by Anti-cancer Natural Products. *Cell Chem. Biol.* 24, 1368-1376.e4 (2017). 32. Roberts, A. M. et al. Chemoproteomic Screening of Covalent Ligands Reveals UBA5 As a Novel Pancreatic Cancer Target. *ACS Chem. Biol.* 12, 899-904 (2017). 33. Anderson, K. E., To, M., Olzmann, J. A. & Nomura, D. K. Chemoproteomics-Enabled Covalent Ligand Screening Reveals a Thioredoxin-Caspase 3 Interaction Disruptor That Impairs Breast Cancer Pathogenicity. *ACS Chem. Biol.* 12, 2522-2528 (2017). 34. Counihan, J. L., Wiggenhorn, A. L., Anderson, K. E. & Nomura, D. K. Chemoproteomics-Enabled Covalent Ligand Screening Reveals ALDH3A1 as a Lung Cancer Therapy Target. *ACS Chem. Biol.* 13, 1970-1977 (2018). 35. Backus, K. M. et al. Proteome-wide covalent ligand discovery in native biological systems. *Nature* 534, 570-574 (2016). 36. Wang, C., Weerapana, E., Blewett, M. M. & Cravatt, B. F. A chemoproteomic platform to quantitatively map targets of lipid-derived electrophiles. *Nat. Methods* 11, 79-85 (2014). 37. Hacker, S. M. et al. Global profiling of lysine reactivity and ligandability in the human proteome. *Nat. Chem.* 9, 1181-1190 (2017). 38. Ward, C. C., Kleinman, J. I. & Nomura, D. K. NHS-Esters As Versatile Reactivity-Based Probes for Mapping Proteome-Wide Ligandable Hotspots. *ACS Chem. Biol.* 12, 1478-1483 (2017). 39. Han, J. et al. ZNF313 is a novel cell cycle activator with an E3 ligase activity inhibiting cellular senescence by destabilizing p21(WAF1.). *Cell Death Differ.* 20, 1055-1067 (2013). 40. Ma, Y.-X. et al. Identification of a novel human zinc finger protein gene ZNF313. *Sheng Wu Hua Xue Yu Sheng Wu Wu Li Xue Bao Acta Biochim. Biophys. Sin.* 35, 230-237 (2003). 41. Lee, M.-G. et al. XAF1 directs apoptotic switch of p53 signaling through activation of HIPK2 and ZNF313. *Proc. Natl. Acad. Sci. U.S.A.* 111, 15532-15537 (2014). 42. Huang, S. et al. The UbL-UBA Ubiquilin4 protein functions as a tumor suppressor in gastric cancer by p53-dependent and p53-independent regulation of p21. *Cell Death Differ.* 26, 516-530 (2018). Burslem, G. M. & Crews, C. M. Small-Molecule Modulation of Protein Homeostasis. *Chem. Rev.* 117, 11269-11301 (2017). 44. Zengerle, M., Chan, K.-H. & Ciulli, A. Selective Small Molecule Induced Degradation of the BET Bromodomain Protein BRD4. *ACS Chem. Biol.* 10, 1770-1777 (2015). 45. Lai, A. C. & Crews, C. M. Induced protein degradation: an emerging drug discovery paradigm. *Nat. Rev. Drug Discov.* 16, 101-114 (2017). 46. Neklesa, T. K., Winkler, J. D. & Crews, C. M. Targeted protein degradation by PROTACs. *Pharmacol. Ther.* 174, 138-144 (2017). 47. Winter, G. E. et al. DRUG DEVELOPMENT. Phthalimide conjugation as a strategy for in vivo target protein degradation. *Science* 348, 1376-1381 (2015). 48. Shortt, J., Ott, C. J., Johnstone, R. W. & Bradner, J. E. A chemical probe toolbox for dissecting the cancer epigenome. *Nat. Rev. Cancer* 17, 160-183 (2017). 49. Sakamoto, K. M. et al. Protacs: chimeric molecules that target proteins to the Skp1-Cullin-F box complex for ubiquitination and degradation. *Proc. Natl. Acad. Sci. U.S.A.* 98, 8554-8559 (2001). 50. Schneekloth, J. S. et al. Chemical genetic control of protein levels: selective in vivo targeted degradation. *J. Am. Chem. Soc.* 126, 3748-3754 (2004). 51. Lu, J. et al. Hijacking the E3 Ubiquitin Ligase Cereblon to Efficiently Target BRD4. *Chem. Biol.* 22, 755-763 (2015). 52. Havens, C. G. & Walter, J. C. Mechanism of CRL4(Cdt2), a PCNA-dependent E3 ubiquitin ligase. *Genes Dev.* 25, 1568-1582 (2011). 53. Kitagawa, K., Kotake, Y. & Kitagawa, M. Ubiquitin-mediated control of oncogene and tumor suppressor gene products. *Cancer Sci.* 100, 1374-1381 (2009). 54. Biswas, K. et al. The E3 Ligase CHIP Mediates p21 Degradation to Maintain Radioresistance. *Mol. Cancer Res. MCR* 15, 651-659 (2017). 55. Rodriguez, M. S. et al. The RING ubiquitin E3 RNF114 interacts with A20 and modulates NF-κB activity and T-cell activation. *Cell Death Dis.* 5, e1399 (2014). 56. Yang, Y. et al. The E3 ubiquitin ligase RNF114 and TAB1 degradation are required for maternal-to-zygotic transition. *EMBO Rep.* 18, 205-216 (2017). 57. Rape, M. Ubiquitylation at the crossroads of development and disease. *Nat. Rev. Mol. Cell Biol.* 19, 59-70 (2018). 58. Hughes, S. J. & Ciulli, A. Molecular recognition of ternary complexes: a new dimension in the structure-guided design of chemical degraders. *Essays Biochem.* 61, 505-516 (2017). 59. Chamberlain, P. P. et al. Structure of the human Cereblon-DDB1-lenalidomide complex reveals basis for responsiveness to thalidomide analogs. *Nat. Struct. Mol. Biol.* 21, 803-809 (2014). 60. Krönke, J. et al. Lenalidomide induces ubiquitination and degradation of CK1α in del(5q) MDS. *Nature* 523, 183-188 (2015). 61. Jessani, N. et al. Carcinoma and stromal enzyme activity profiles associated with breast tumor growth in vivo. *Proc. Natl. Acad. Sci. U.S.A.* 101, 13756-13761 (2004). 62. Louie, S. M. et al. GSTP1 Is a Driver of Triple-Negative Breast Cancer Cell Metabolism and Pathogenicity. *Cell Chem. Biol.* 23, 567-578 (2016). 63. Bateman, L. A. et al. Chemoproteomics-enabled covalent ligand screen reveals a cysteine hotspot in reticulon 4 that impairs ER morphology and cancer pathogenicity. *Chem. Commun. Camb. Engl.* 53, 7234-7237 (2017). 64. Smith, P. K. et al. Measurement of protein using bicinchoninic acid. *Anal. Biochem.* 150, 76-85 (1985). 65. Xu, T. et al. ProLuCID: An improved SEQUEST-like algorithm with enhanced sensitivity and specificity. *J. Proteomics* 129, 16-24 (2015). 66. Benjamin, D. I. et al. Ether lipid generating enzyme AGPS alters the balance of structural and signaling lipids to fuel cancer pathogenicity. *Proc. Natl. Acad. Sci. U.S.A.* 110, 14912-14917 (2013). 67. Medina-Cleghorn, D. et al. Mapping Proteome-Wide Targets of Environmental Chemicals Using Reactivity-Based Chemoproteomic Platforms. *Chem. Biol.* 22, 1394-1405 (2015). 68. Longo, P. A., Kavran, J. M., Kim, M.-S. & Leahy, D. J. Transient mammalian cell transfection with polyethylenimine (PEI). *Methods Enzymol.* 529, 227-240 (2013). 69. Nomura, D. K. et al. Monoacylglycerol lipase regulates a fatty acid network that promotes cancer pathogenesis. *Cell* 140, 49-61 (2010).

Example 7. Harnessing the Anti-Cancer Natural Product Nimbolide for Targeted Protein Degradation Natural products from organisms such as plants and microbes are a rich source of therapeutic lead compounds[1]. The characterization of their biological activities has resulted in myriad medications for a wide range of pathologies including cancer, bacterial and fungal infections, inflammation, and diabetes[1]. Among natural products there exists a subset of covalently acting molecules that bear electrophilic moieties capable of undergoing essentially irreversible reactions with nucleophilic amino acids within proteins to exert their therapeutic activity. Examples of these natural products include penicillin, which irreversibly inhibits serine transpeptidases inducing anti-bacterial activity, or wortmannin, which covalently modifies a functional lysine on PI3-kinase to inhibit its activity[1,2]. Discovering druggable hotspots targeted by anti-cancer and covalently-acting natural products can not only yield new cancer drugs and therapeutic targets but can also reveal unique insights into modalities accessed by natural products in protein targets that are often considered undruggable or difficult to tackle with standard drug discovery efforts. One example of a druggable modality that would be difficult to predict a priori is FK506 or Tacrolimus that inhibits peptidylprolyl isomerase activity by binding to FKBP12 thus creating a FKBP12-FK506 complex that modulates T cell signaling via inhibition of calcineurin[3]. Gaining insights into nature's strategies for engaging protein targets can thus provide access to new perspectives on what may be considered druggable.

In this study, we investigated the mechanism of action of the natural product nimbolide (1), a limonoid natural product derived from the Neem tree (Azadirachta indica) (FIG. 8A)=[4]. Nimbolide has been shown to exert multiple therapeutic effects and possesses a cyclic enone capable of reacting with cysteines[5-7]. In the context of cancer, nimbolide has been shown to inhibit tumorigenesis and metastasis without causing any toxicity or unwanted side effects across a wide range of cancers[8]. While previous studies suggest that nimbolide impairs cancer pathogenicity through modulating signaling pathways and transcription factors linked to survival, growth, invasion, angiogenesis, inflammation, and oxidative stress the direct targets of nimbolide still remain poorly characterized[8].

Identifying direct protein targets of complex natural products remains challenging and often requires synthesizing analogs of these compounds bearing photoaffinity and enrichment handles, a task which is synthetically challenging and has the potential to alter the activity of the molecule[1]. Even with the generation of such probes, identifying the specific amino acid site targeted by natural products is challenging. In this study, we utilized activity-based protein profiling (ABPP) chemoproteomic approaches to map the proteome-wide targets of nimbolide in breast cancer cell proteomes. Using ABPP platforms, we reveal that one of the primary targets of nimbolide in breast cancer cells is cysteine-8 (C8) of the E3 ubiquitin ligase RNF114. Covalent modification of RNF114 by nimbolide leads to impaired ubiquitination and degradation of its substrate—the tumor suppressor CDKN1A (p21)—leading to its rapid stabilization. Intriguingly, we show that this apparent inhibition of RNF114 activity is through impaired substrate recognition giving rise to the possibility that nimbolide could be used as an E3 ligase recruitment module for targeted protein degradation. Strategies for chemically induced degradation of targets of interest in cells is rapidly gaining interest in drug discovery, including the development of bifunctional molecules referred to as "proteolysis-targeting chimeras" (PROTACs) or "heterobifunctional degraders" that consist of a protein-targeting ligand linked to an E3 ligase recruiter to bring an E3 ligase to a protein of interest to ubiquitinate and mark the target for degradation in a proteasome-dependent manner[9,10]. We demonstrate that nimbolide can be used to recruit RNF114 to other protein substrates for targeted protein degradation applications. Using chemoproteomics-enabled covalent ligand screening platforms, we also identify more synthetically tractable compounds that can similarly react with C8 of RNF114 and phenocopy nimbolide action.

Effects of nimbolide on breast cancer phenotypes. Though nimbolide has been shown to impair cancer pathogenicity across many different types of human cancers, we chose to focus on elucidating the role of nimbolide in triple-negative breast cancers (TNBC). TNBCs are devoid of estrogen, progesterone, and HER2 receptors and are amongst the most aggressive cancers with the worst clinical prognosis[11]. Very few targeted therapies currently exist for TNBC patients. Uncovering new therapeutic modalities in TNBCs would thus potentially contribute significantly to reducing breast cancer-associated mortalities. Consistent with previous reports showing anti-cancer activity in breast cancer cells, nimbolide impaired cell proliferation or serum-free cell survival in 231MFP and HCC38 TNBC cells (FIGS. 17A-17B, FIGS. 18A-18B)[8]. We also show that these effects on 231MFP and HCC38 viability are due to a significant increase in apoptotic cells with nimbolide treatment, assessed by flow cytometry analysis (FIG. 17C, FIGS. 18C-18E).

Figure 19A:
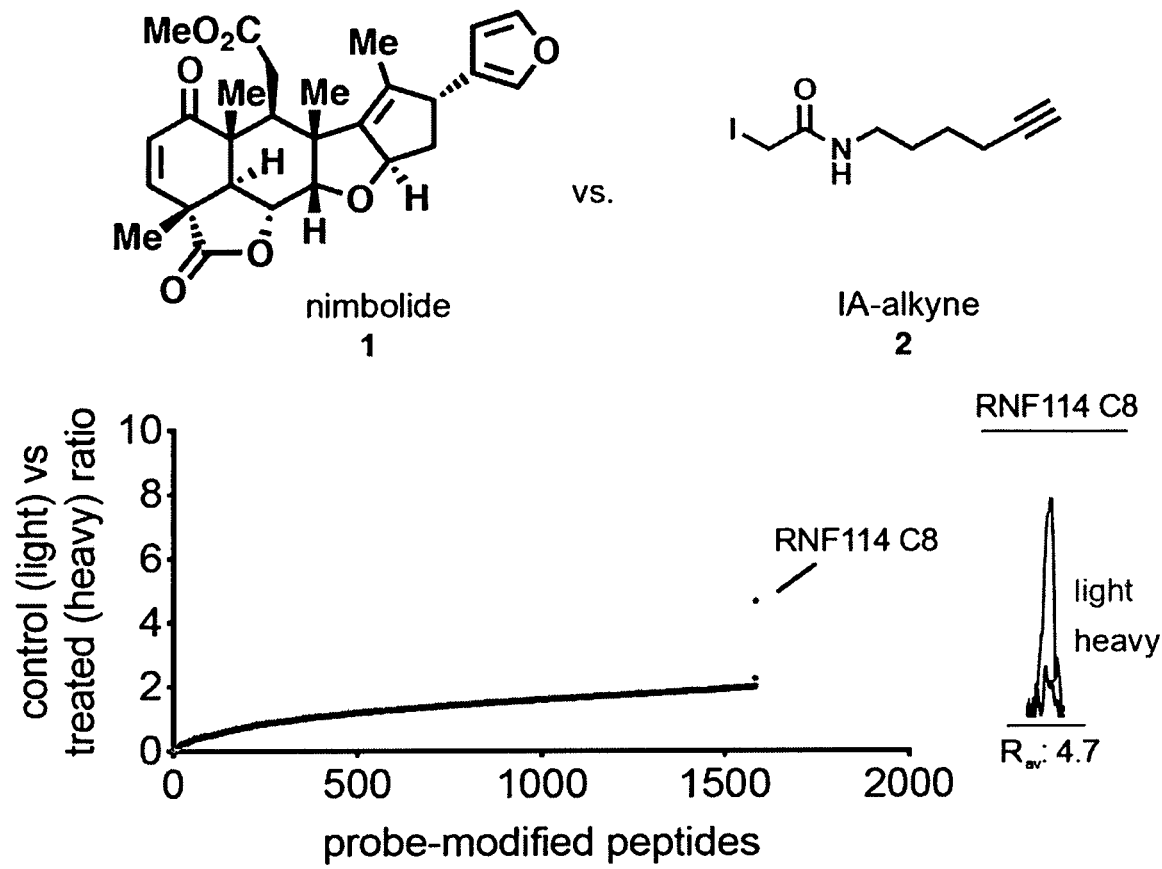
Figure 19B:
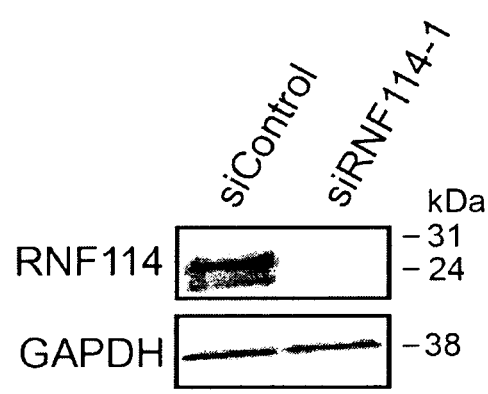
Figure 19C:
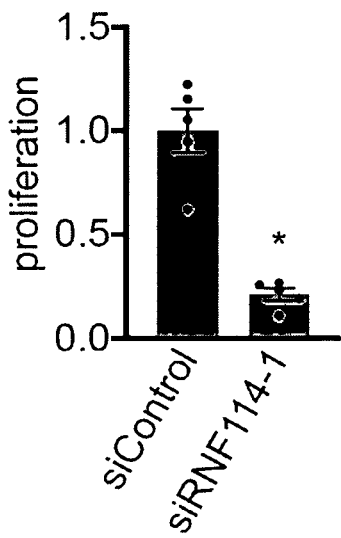

ABPP to map nimbolide targets in breast cancer cells. To interrogate the mechanisms by which nimbolide impairs breast cancer pathogenicity, we applied a chemoproteomic platform termed isotopic tandem orthogonal proteolysis-enabled activity-based protein profiling (isoTOP-ABPP) to determine the specific protein targets of nimbolide. Pioneered by Cravatt and Weerapana, isoTOP-ABPP uses reactivity-based chemical probes to map reactive, functional, and ligandable hotspots directly in complex proteomes[12,13]. When used in a competitive manner, covalently-acting small-molecules can be competed against binding of broad reactivity-based probes to facilitate the rapid discovery of both proteins and ligandable sites targeted by the covalently-acting compound[14-16] (FIG. 9A). In this study, we treated breast cancer cells in situ with vehicle or nimbolide followed by competitive labeling of proteomes with a cysteine-reactive alkyne-functionalized iodoacetamide probe (IA-alkyne) (2), after which isotopically light or heavy cleavable enrichment handles were appended to probe-labeled proteins for isoTOP-ABPP analysis. Probe-modified tryptic peptides were analyzed by liquid chromatography-mass spectrometry (LC-MS/MS) and light to heavy tryptic probe-modified peptide ratios, representing control versus treated IA-alkyne labeled sites, were quantified. IsoTOP-ABPP analysis of ligandable hotspots targeted by in situ nimbolide treatment in 231MFP TNBC cells showed one primary target showing an isotopic ratio >4 that was significantly engaged by nimbolide—the E3 ubiquitin ligase RNF114 (FIG. 19A). Importantly, RNF114 knockdown using three independent small interfering RNA (siRNA) resembled the anti-proliferative effects of nimbolide in 231MFP cells (FIGS. 19B-

19C, FIGS. 20A-20B). Further demonstrating that RNF114 contributes to the anti-proliferative effects of nimbolide, RNF114 knockdown led to significant resistance to nimbolide-mediated anti-proliferative effects (FIG. 19D, FIG. 20C). While nimbolide likely possesses many additional targets beyond RNF114 that are not accessible with isoTOP-ABPP approaches, our results suggested that RNF114 was a novel target of nimbolide and that RNF114 was in-part responsible for the anti-proliferative effects of this natural product. We thus chose to focus further characterization efforts on the interactions between nimbolide and RNF114.

Figure 21A:
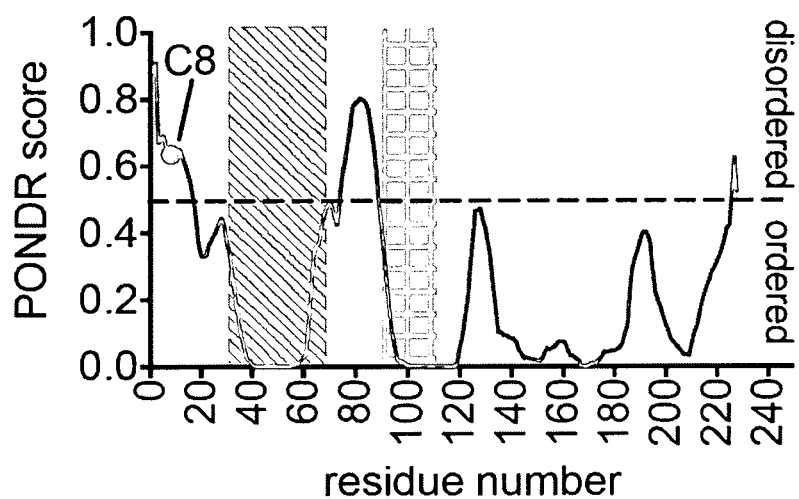
FIGS. 21A-21G. Nimbolide reacts covalently with C8 of RNF114.

Characterization of nimbolide interactions with RNF114. RNF114 is an E3 ubiquitin ligase of the RING family[17]. The site on RNF114 identified by isoTOP-ABPP as the target of nimbolide, C8, falls within the N-terminal region of the protein, predicted to be intrinsically disordered, and resides outside of the two annotated zinc finger domains (FIG. 21A). Intrigued by the apparent targeting of an intrinsically disordered region of a protein by a natural product, we sought to investigate the interaction between nimbolide and RNF114.

Figure 20D:
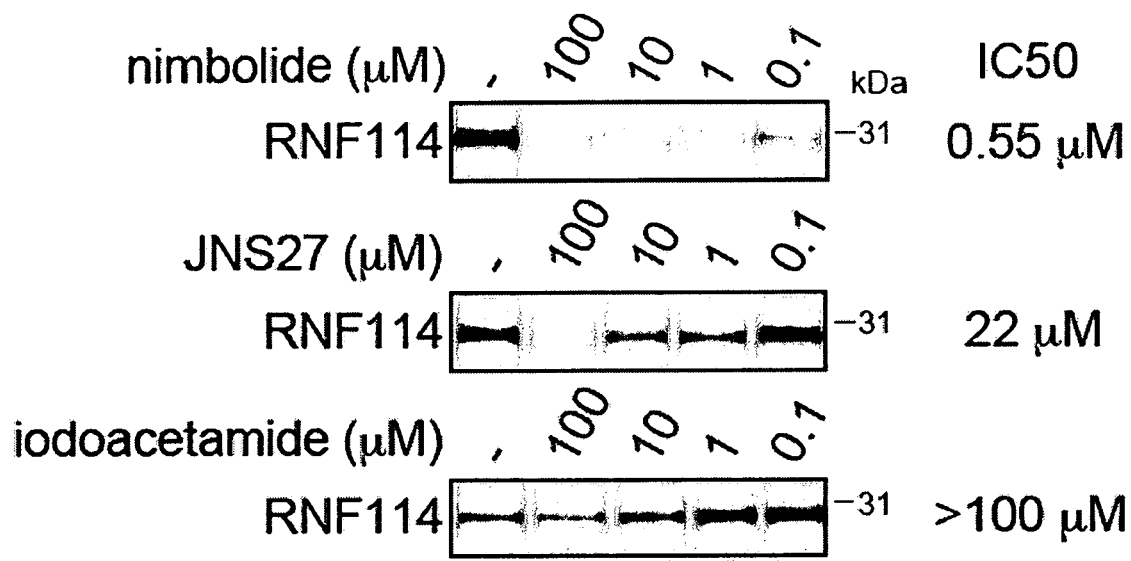
Figure 21B:
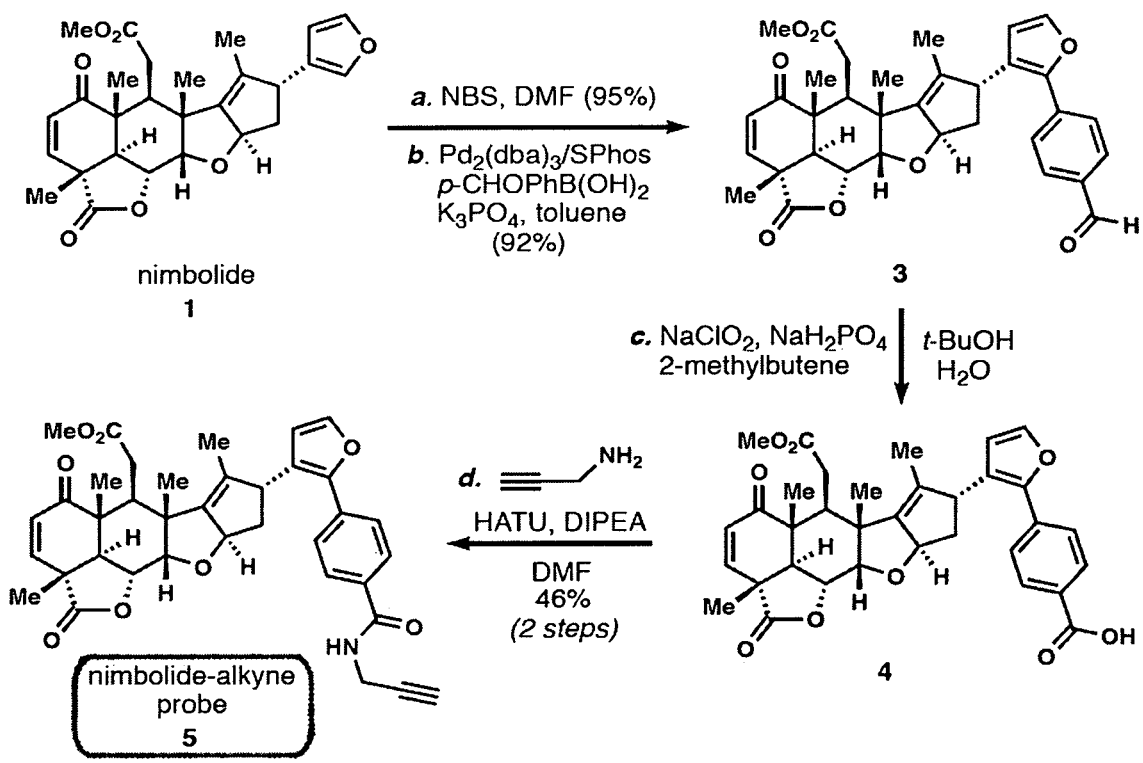
Figure 21C:
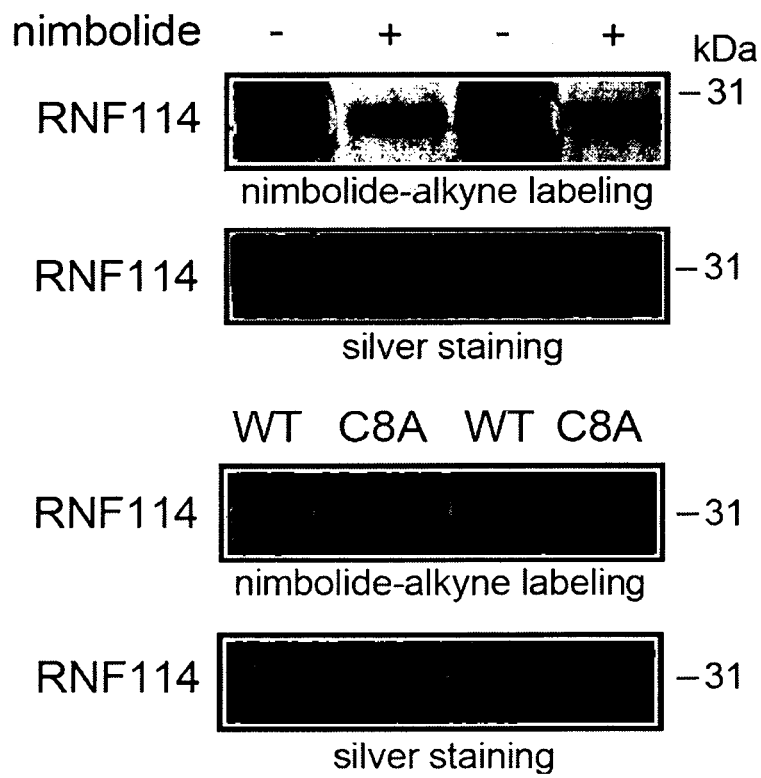
Figure 21D:
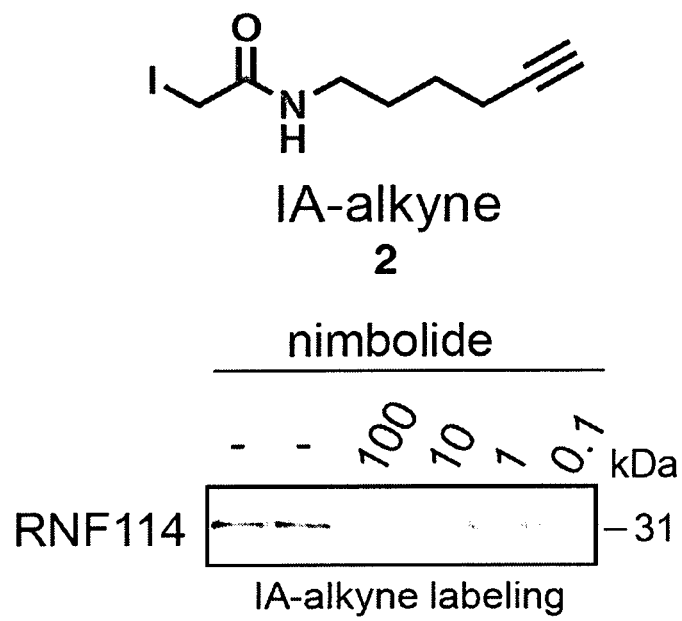
Figure 21E:
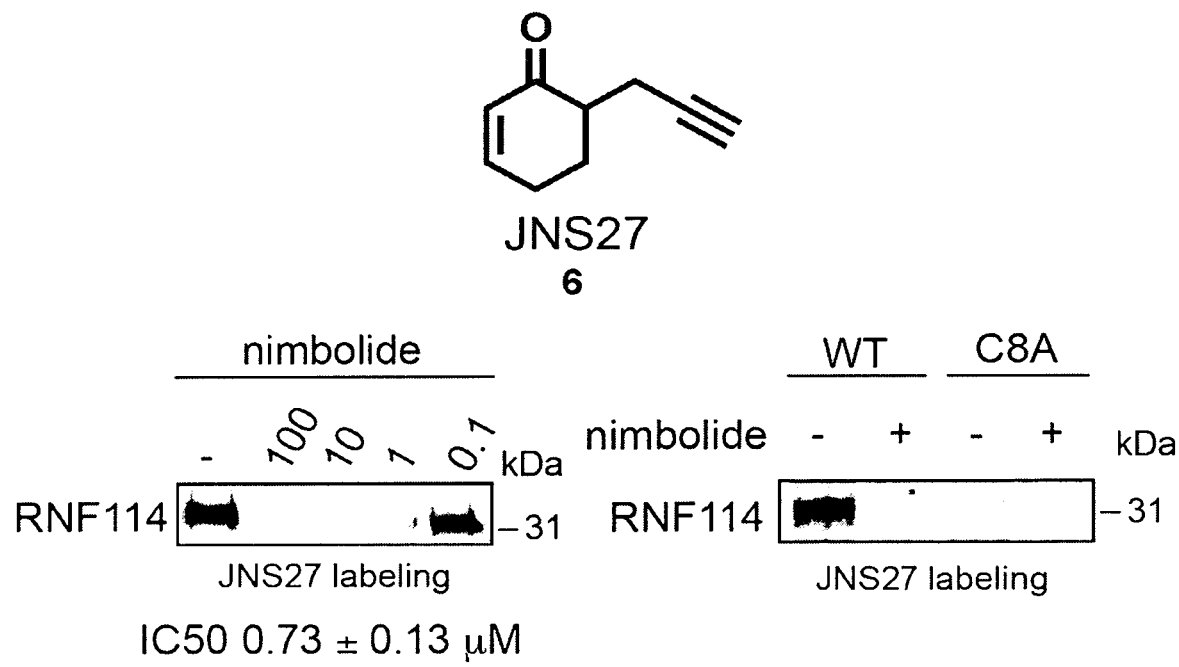

Because isoTOP-ABPP is a competitive assay between the covalently-acting molecule and a broader reactive probe, it is an indirect read-out of potential nimbolide-targeting hotspots. To confirm that nimbolide directly targeted RNF114, we synthesized the alkyne-functionalized probe shown in three steps from nimbolide (FIG. 21B). Selective bromination at C2 of the furan moiety and subsequent Suzuki coupling with 4-Formylphenylboronic acid afforded the aryl-aldehyde (3), which was converted to its corresponding carboxylic acid (4) via Pinnick oxidation. Finally, coupling of (4) and propargyl amine (HATU, DIPEA) afforded the target nimbolide-alkyne probe (5). We confirmed that this nimbolide probe reacts with pure human RNF114 protein as shown by labeling of the protein on a denaturing SDS/PAGE gel. This labeling event was also competed by nimbolide and abrogated in the C8A RNF114 mutant (FIG. 21C). As the nimbolide-alkyne probe is a synthetically laborious probe that requires the rather expensive nimbolide as a starting material, we also sought to develop a simpler probe that could label C8 of RNF114. In initial studies trying to validate RNF114 interactions with nimbolide, where we competed nimbolide against IA-alkyne labeling of RNF114, full inhibition of labeling was not observed, likely due to alkylation of multiple cysteines by IA-alkyne beyond C8 (FIG. 21D). Thus, we synthesized a more tailored alkyne-functionalized cyclic enone probe JNS27 (6), which showed selective labeling of C8 on RNF114 as evidenced by lack of labeling of C8A RNF114 mutant protein (FIG. 21E). With JNS27, we were able to demonstrate full competition of JNS27 labeling with nimbolide with a 50% inhibitory concentration (IC50) of 0.73 µM (FIG. 21E). To demonstrate that nimbolide interactions with RNF114 are not completely driven by reactivity, but rather also through additional interactions with the protein, we show that nimbolide competes against labeling of RNF114 with a rhodamine-functionalized iodoacetamide probe (IA-rhodamine) at far lower concentrations compared to the simpler JNS27 probe or iodoacetamide with an IC50 of 0.55, 22, and >100 µM, respectively (FIG. 20D). Furthermore, a direct mass adduct of nimbolide was detected on the tryptic peptide containing C8 on RNF114 by LC-MS/MS after incubation of pure protein with the natural product. All of these experiments taken together provide evidence that nimbolide modifies an intrinsically disordered region of RNF114 at C8 through a covalent bond formation.

Figure 21F:
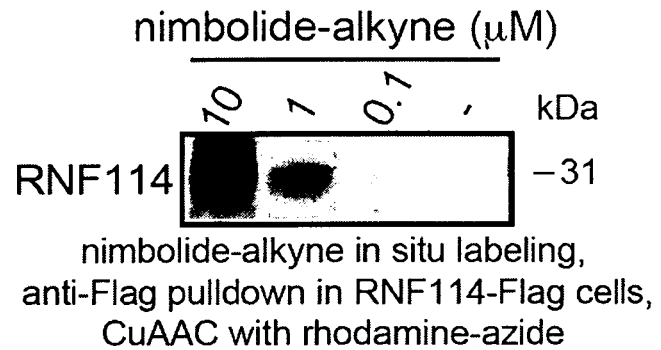
Figure 21G:
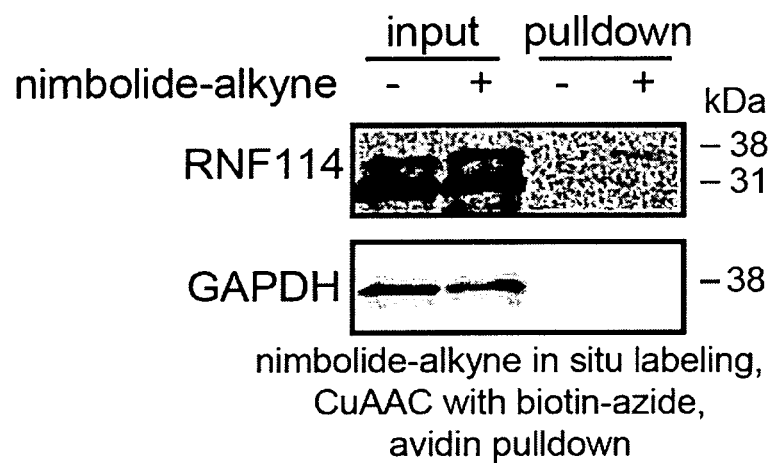

We next performed two complementary experiments to demonstrate that nimbolide directly engaged RNF114 in 231MFP breast cancer cells. First, we showed dose-responsive nimbolide-alkyne labeling of RNF114 in situ by treating Flag-tagged RNF114 expressing cells with the probe, followed by enrichment of Flag-tagged RNF114 and appending rhodamine-azide onto probe-labeled protein by CuAAC and visualizing by gel-based ABPP methods (FIG. 21F). We observed robust in situ nimbolide-alkyne labeling with 10 µM of probe, but also observed lower but significant probe labeling even down to 100 nM (FIG. 21F). Second, we also showed in situ labeling of endogenous RNF114 with the nimbolide-alkyne probe by treating cells with the probe, followed by appending biotin-azide onto probe-labeled proteins by CuAAC and visualizing RNF114 pulldown by Western blotting (FIG. 21G). In this case, significant pulldown was observed at 50 µM of the nimbolide-alkyne probe but not lower concentrations. In this experiment, we show that an unrelated protein such as GAPDH is not enriched by the nimbolide-alkyne probe (FIG. 21G). Using these latter conditions, we also performed a complementary quantitative proteomic profiling study to identify any additional proteins that may be enriched from in situ labeling of 231MFP cells with the nimbolide-alkyne probe. Due to acute cytotoxicity issues, we were not able perform in situ competition studies with higher concentrations of nimbolide itself. In this study, we showed that RNF114 was one of the proteins enriched by the nimbolide-alkyne probe by >10-fold compared to no-probe controls. We also identified 114 additional proteins that were enriched by the probe by >10-fold compared to no-probe controls. These proteins represent additional potential covalent or non-covalent targets that may contribute to the anti-proliferative effects of nimbolide. These enriched targets may also represent proteins with low to partial degrees of engagement with nimbolide, whereas isoTOP-ABPP experiments are meant to identify higher engagement targets. Additionally, these proteins may include probe-specific targets or proteins that may be enriched indirectly through interactions with direct nimbolide-labeled proteins. Nonetheless, we show that RNF114 is engaged by the nimbolide-alkyne probe in breast cancer cells, even down to 100 nM, and that the anti-proliferative effects of nimbolide are at least in-part mediated by RNF114.

Figure 22A:
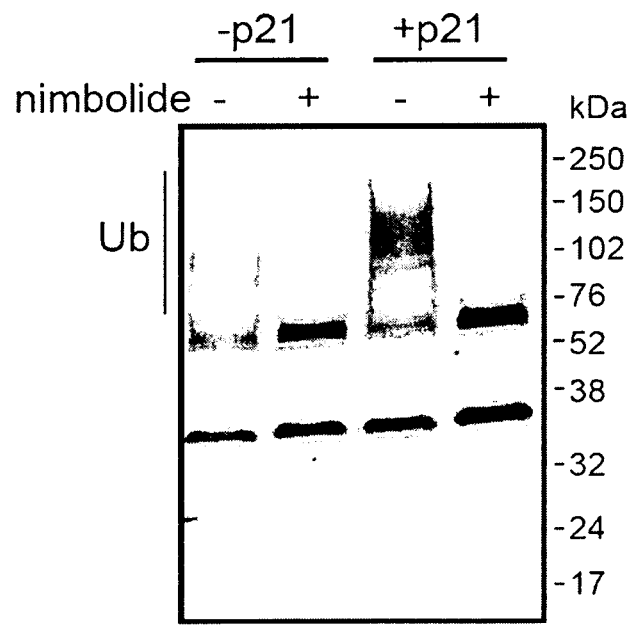
FIGS. 22A-22I. Nimbolide inhibits RNF114 activity through disrupting substrate recognition.
Figure 22B:
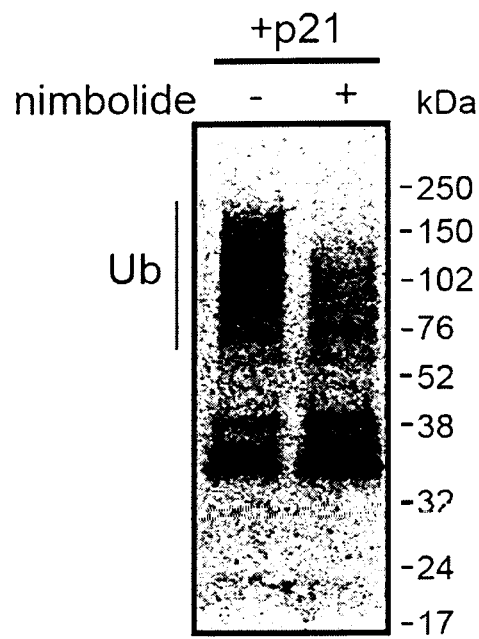
Figure 22C:
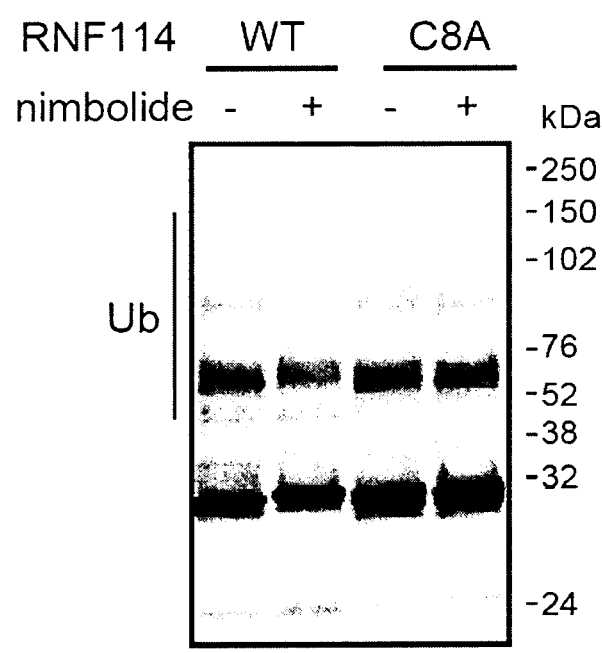
Figure 22D:
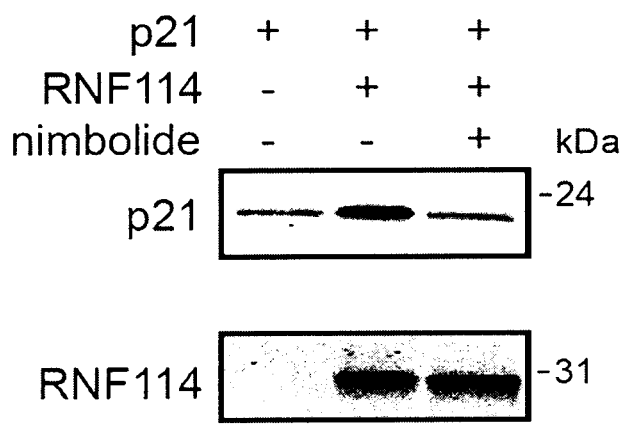
Figure 22E:
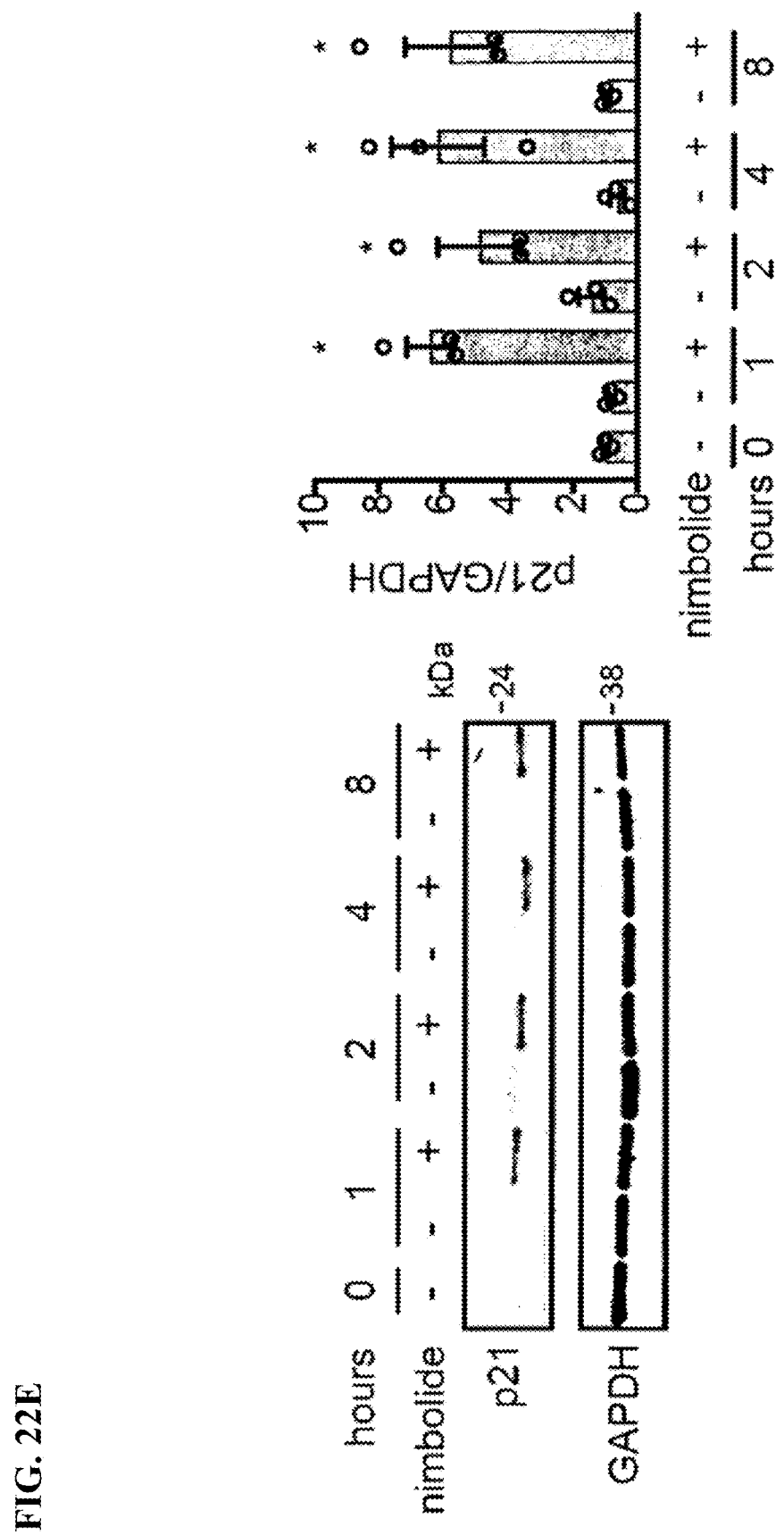
Figure 22F:
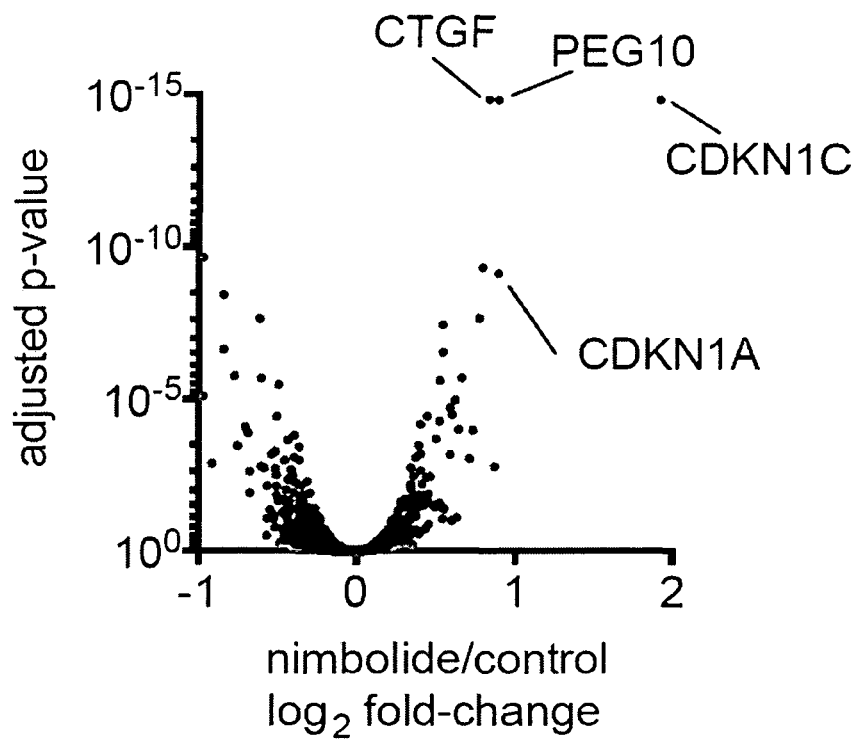
Figure 22G:
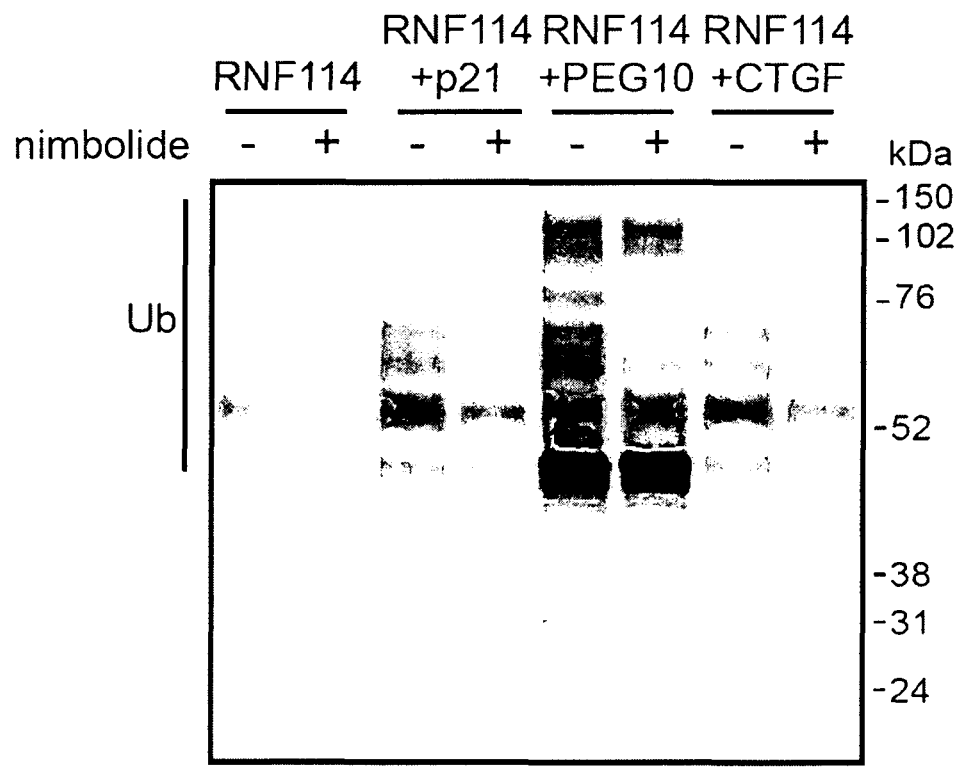
Figure 22H:
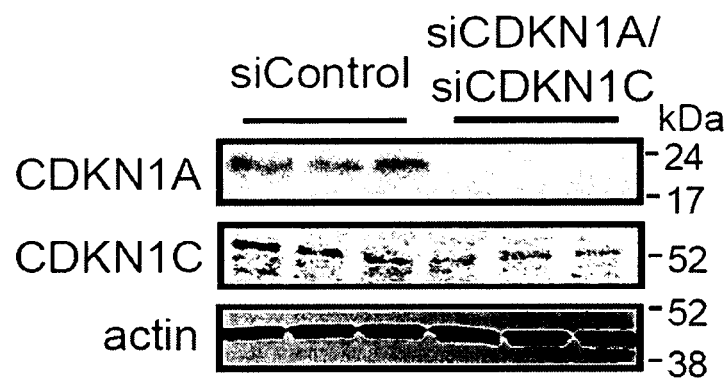
Figure 22I:
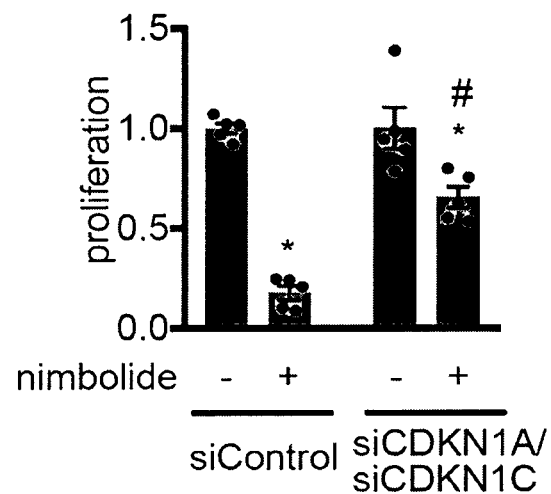

Effects of nimbolide on RNF114 function. RNF114 has been previously shown to ubiquitinate and degrade the tumor suppressor p21, among other substrates[17-19]. In an in vitro reconstituted system, nimbolide inhibited both RNF114 autoubiquitination and p21 ubiquitination activity (FIGS. 22A-22B). The RNF114 C8A mutation did not affect basal RNF114 autoubiquitination activity, but attenuated the inhibition observed with nimbolide treatment (FIG. 22C). Previous characterization of RNF114 suggested that the N-terminus may be involved in substrate recognition[17]. Consistent with this premise, we found that the amount of p21 co-immunoprecipitated with RNF114 was reduced by nimbolide, suggesting that the apparent inhibition of RNF114 may be due to impaired substrate recognition, rather than inhibition of its catalytic activity (FIG. 22D). We further demonstrated that nimbolide treatment in 231MFP cells stabilized CDKN1A (p21) protein expression within 1 hour in a dose-responsive manner, with no significant changes to TP53 (p53) levels (FIG. 22E). The elevated levels of CDKN1A observed were not due to transcriptional downregulation of mRNA levels, as p21 mRNA levels remained unchanged with nimbolide treatment. To identify other potential substrates of RNF114, we also performed a tandem mass tagging (TMT)-based quantitative proteomic experiment on 231MFP cells treated with nimbolide. Consistent with our Western blotting data, we observed CDKN1A (p21) as one of the proteins that were significantly elevated >2-fold with nimbolide treatment (FIG. 22F). We also observed the levels of several other targets that were heightened by nimbolide treatment, including CDKN1C (p57), PEG10, and CTGF. Beyond CDKN1A (p21) and CDKN1C (p57) which have previously been reported as potential RNF114 substrates[17], we conjectured that PEG10 and CTGF may also represent additional novel substrates of RNF114 (FIG. 22F). Consistent with this premise, we demonstrated in an in vitro RNF114 ubiquitination assay that RNF114 ubiquitinates PEG10 and CTGF and that this ubiquitination is inhibited by nimbolide (FIG. 22G). As both p21 and p57 are tumor suppressors that, when elevated, promote cell cycle arrest and apoptosis[20,21], we postulated that the stabilization of both of these tumor suppressors may be responsible for the anti-proliferative effect of nimbolide. We demonstrated that dual knockdown of CDKN1A (p21) and CDKN1C (p57) results in significant attenuation in nimbolide-mediated anti-proliferative effects in 231MFP breast cancer cells (FIGS. 22H-22I). Collectively, these data suggest that nimbolide reacts with an intrinsically disordered C8 of RNF114 in breast cancer cells to disrupt RNF114-substrate recognition, leading to inhibition of ubiquitination of its substrates such as CDKN1A and CDKN1C, leading to their stabilization, and impaired cell proliferation in breast cancer cells.

Figure 23A:
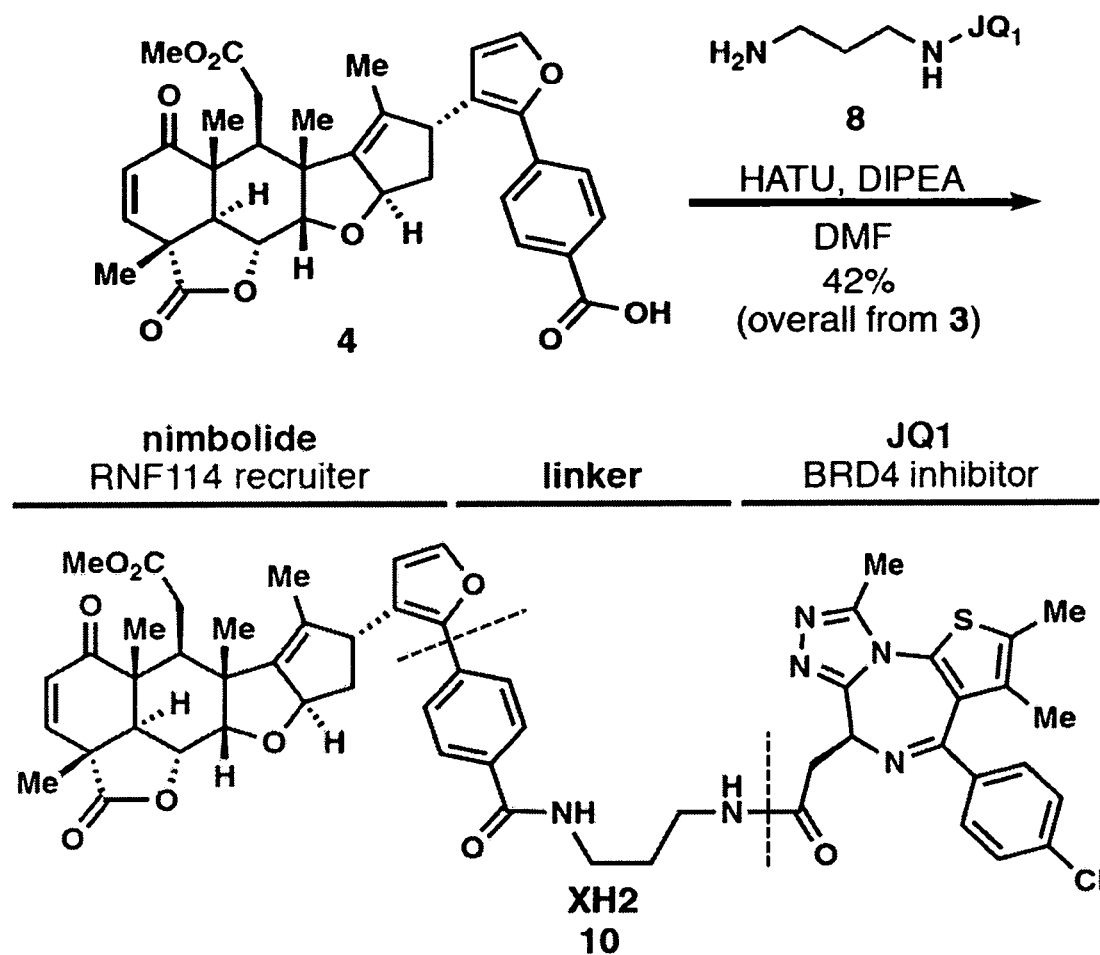
FIGS. 23A-23I. Nimbolide can be used to recruit RNF114 for targeted protein degradation of BRD4.
Figure 23B:
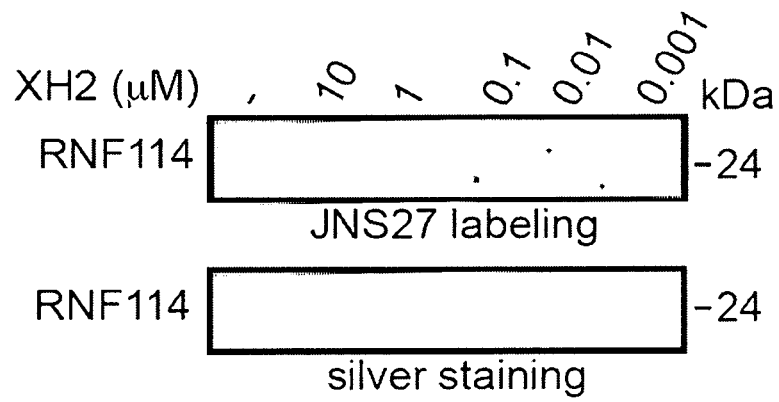
Figure 23C:
Figure 23D:
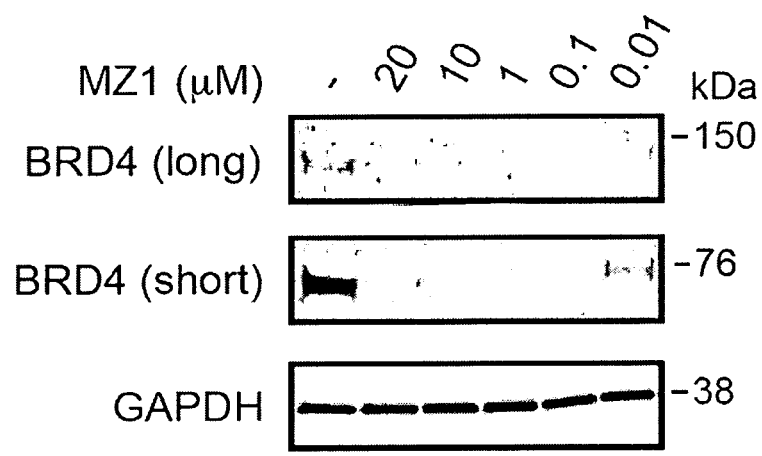
Figure 23E:
Figure 23F:
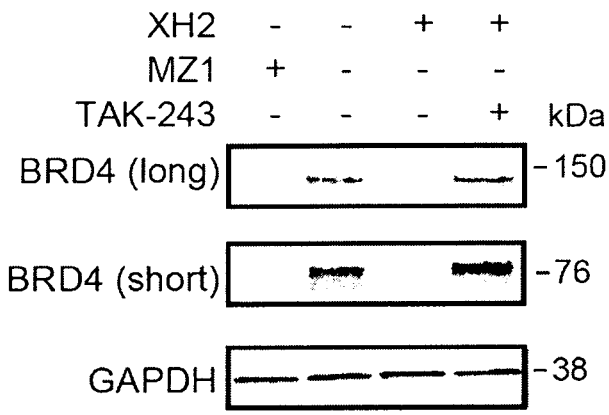
Figure 23G:
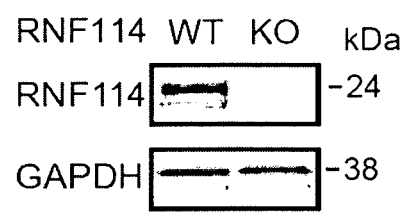
Figure 23H:
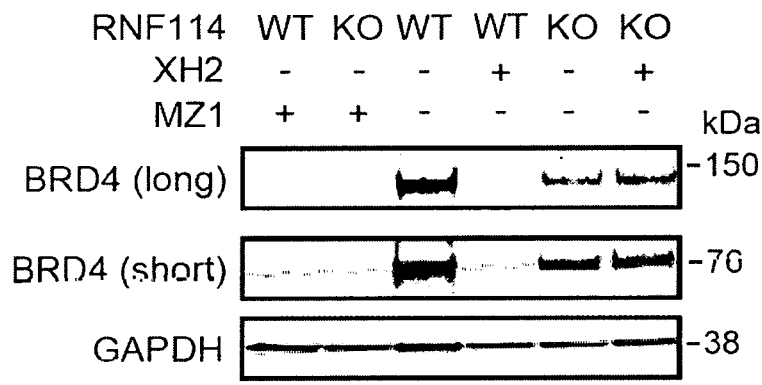
Figure 23I:
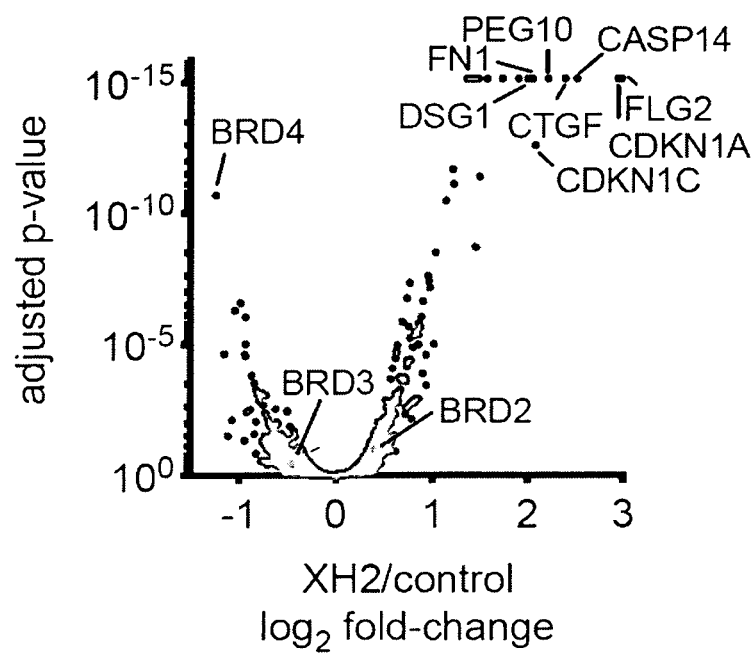

Nimbolide as an RNF114-recruiter. Since nimbolide targets a potential substrate recognition site, we conjectured that nimbolide could be used to recruit RNF114 to other protein substrates for proteasomal degradation through the development of heterobifunctional degraders using nimbolide as an RNF114 recruiter. To demonstrate feasibility, two degraders formed by linking nimbolide to the Bromodomain and extra-terminal (BET) family inhibitor JQ1 were synthesized (FIG. 23A). Prior studies have demonstrated efficient proteasome-dependent degradation of BET family members and in particular BRD 4 with JQ1-based degraders linked to either a CRBN (cereblon)-recruiter thalidomide or a VHL recruiter[22,23] Previously prepared acid (4) was coupled to JQ1-functionalized amines containing both longer (PEG-based) (7) and shorter (alkyl-based) (8) spacer units, arriving at degraders XH1 (9) and XH2 (10) (FIG. 23A). We show that XH2 still binds to RNF114 with an IC50 of 0.24 µM (FIG. 23B). While XH1 did not show appreciable BRD4 degradation, XH2 treatment in 231MFP cells led to BRD4 degradation after a 12 h treatment (FIG. 23C). Interestingly, XH2 showed less degradation at 1 µM compared to 0.1 and 0.01 µM and MZ1 showed less degradation at 20 µM compared to 10, 1, and 0.1 µM, which we attribute to the "hook effect" previously reported with other degraders including the previously reported JQ1-based degrader MZ1 that utilizes a VHL recruiter[9,22] (FIGS. 23C-23D). To confirm proteasome-dependence of BRD4 degradation, we showed that the XH2-mediated degradation of BRD4 was attenuated by pre-treatment of cells with the proteasome inhibitor bortezomib (BTZ) (FIG. 23E). XH2-mediated BRD4 degradation was also prevented by pre-treatment with an E1 ubiquitin-activating enzyme inhibitor (TAK-243) or pre-competing with the BRD4 inhibitor JQ1 (FIG. 23F). However, treatment with a translation inhibitor (emetine) had no effect of the observed degradation of BRD4. To further demonstrate that the degradation of BRD4 by XH2 was through the specific recruitment of RNF114, we showed that degradation of BRD4 by XH2, but not MZ1, was not observed in RNF114 knockout (KO) HAP1 cells compared to wild-type (WT) HAP1 cell counterparts (FIGS. 23G-23H). We further showed that re-expression of wild-type RNF114 in HAP1 RNF114 knockout cells led to the restoration of BRD4 degradation by XH2. The selectivity of XH2-mediated degradation of proteins was demonstrated using TMT-based quantitative proteomic profiling experiment to assess changes in protein expression. We showed that XH2 selectively degrades BRD4 in 231MFP breast cancer cells while sparing the other identified BET family members BRD2 and BRD3 (FIG. 23I). Of note, we also observed several proteins that showed increased levels upon XH2 treatment including CDKN1A, CDKN1C, PEG10, and CTGF, which were observed as elevated in levels with nimbolide treatment alone (FIG. 23I). There were also additional proteins that were upregulated, such as DSG1, FN1, FLG2, and CASP14 (FIG. 23I). These upregulated proteins may be potential substrates of RNF114 with stabilization stemming from the nimbolide portion of XH2, as is likely the case with CDKN1A, CDKN1C, PEG10 and CTGF. The other targets may be downstream transcriptional effects stemming from JQ1-mediated BRD4 inhibition and degradation. Our results indicate that nimbolide reactivity with RNF114 can be exploited to recruit this E3 ligase to other protein substrates, such as BRD4, to ubiquitinate and selectively degrade them.

Covalent ligands against RNF114. With the insight gained that C8 of RNF114 has potential to be exploited for cancer therapy and targeted protein degradation applications, we searched for more synthetically tractable covalent ligands that similarly target RNF114. To achieve this goal, we screened a library of cysteine-reactive covalent ligands against RNF114 using a moderate-throughput gel-based ABPP approach, in which covalent ligands are competed against JNS27 labeling of RNF114, followed by appending a rhodamine-azide and analysis by SDS/PAGE and in-gel fluorescence. Of the approximately 200 cysteine-reactive covalent ligands screened against RNF114, the acrylamide EN62 (11) emerged as a promising hit. EN62 inhibited RNF114 autoubiquitination activity in a C8-dependent manner. While EN62 is an early hit compound that requires substantial improvements to cell permeability, potency, and selectivity, this covalent ligand represents a starting point for more synthetically tractable covalent ligand scaffolds that target C8 of RNF114 for targeted protein degradation applications.

We show compelling evidence that nimbolide impairs breast cancer pathogenicity in-part through targeting a substrate recognition domain at C8 within RNF114 to inhibit p21 ubiquitination and degradation, leading to its stabilization. We demonstrate that nimbolide targeting of C8 on RNF114 can be used to recruit RNF114 for targeted protein degradation applications and degradation of BRD4 with a nimbolide-JQ1 degrader XH2 is possible.

We report here that nimbolide disrupts RNF114 interactions with one of its endogenous substrate p21 and we also show that p21 levels are rapidly stabilized in breast cancer cells in a p53-independent manner. Several other E3 ligases have also been reported to degrade p21, including $SCF^{SKP2}$, $CRL4^{CDT2}$, and CHIP under varying conditions during cell cycle or exogenous stress[24-26]. Previous studies have shown that RNF114 expression is elevated at late G1 phase to regulate p21 and p57 levels and is crucial for G1-to-S phase transition[17]. Other RNF114 substrates that have been reported include TAB1 involved in maternal-to-zygotic transition and A20 involved in NF-κB activity and T cell activation[27,28]. In cancer contexts or other cell and tissue types, nimbolide may thus have additional activities through regulating the levels of other RNF114 protein substrates. Intriguingly, we show CTGF and PEG10 may represent additional substrates of RNF114 as demonstrated by their nimbolide-induced stabilization in situ and polyubiquitination by RNF114 in vitro. Further studies are required to establish these additional proteins as direct and endogenous substrates of RNF114. Furthermore, while we show that RNF114 is one target of nimbolide that at least in-part mediates its effects upon proliferation and targeted protein degradation, we also show with the nimbolide-alkyne probe that nimbolide likely possesses many additional protein targets. These additional targets may include other covalent interactions with cysteines that are not labeled by the IA-alkyne cysteine-reactive probe in isoTOP-ABPP experiments, may represent covalent interactions with other amino acids, may represent reversible interactions with additional protein targets, or may include proteins are indirectly enriched from interactions with direct nimbolide-labeled proteins. Despite nimbolide possessing multiple potential targets, we demonstrate that RNF114 is an important and functional target of nimbolide in breast cancer cells that can be exploited for targeted protein degradation applications. We also convincingly show that the BRD4 degradation observed with the nimbolide-based degrader is driven through RNF114.

Our results also demonstrate that nimbolide functionally targets an intrinsically disordered region within RNF114. Solving the structure of RNF114 covalently modified with nimbolide has thus far proven challenging, but future studies investigating whether nimbolide induces order in the N-terminus would provide insights into the ligandability of intrinsically disordered and undruggable protein targets and strategies for potentially targeting other E3 ligases.

Targeted protein degradation has emerged as a formidable and effective drug discovery paradigm for targeting proteins for elimination through the proteasome[9,10]. One of the challenges, however, is that there are only a small number of E3 ligase recruiters that have been developed among the approximately 600 E3 ligases in the human genome[29]. These E3 ligase recruiters include the thalidomide-type immunomodulatory drugs (IMiD) that recruit cereblon, ligands that recruit VHL, nutlins that recruit MDM2, and ligands that recruit BIRC2 (cIAP)[9,10]. Here, we report that nimbolide can be used as a novel RNF114 recruiter for targeted protein degradation applications. It should be possible to optimize the performance of this degrader class through further linker modifications, an area of the molecule already determined to be important. It may also be possible to utilize more synthetically tractable covalent ligands capable of targeting C8 of RNF114, such as EN62, as RNF114 recruiters. Since nimbolide targets a substrate recognition domain within RNF114, it will also be of future interest to determine whether nimbolide may act as a molecular glue to recruit and degrade neo-substrates, as has been reported for the IMiDs[30].

Interestingly, we did not observe degradation of BRD2 and BRD3 under conditions that led to significant reduction of BRD4 levels despite the high homology in their respective BET bromodomains. Various levels of selectivity within the BET family members and the structural basis thereof have been reported for JQ1-based degraders with Cereblon and VHL-recruiting modules[22,23,31,32]. While a more detailed investigation of the selectivity of XH2 and its structural basis is outside the scope of this study, it serves as another example how availability of additional E3-moieties for a given substrate recognition modules can aid in tuning efficacy and selectivity of degraders targeting a given protein of interest.

Overall, our study further demonstrates the utility of using ABPP-based chemoproteomic platforms to identify unique druggable modalities exploited by natural products. Intriguingly, we show that a natural product can functionally access an E3 ligase protein-protein interaction site for potential cancer therapy and targeted protein degradation applications and remarkably does so in an intrinsically disordered region of the protein. Our study also showcases how covalent ligand screening approaches can be utilized to identify more synthetically tractable small-molecules that act similarly to more complex natural products and that covalent ligands may be able to access other E3 ligases to expand the scope of E3 ligase recruiters.

Example 8. Methods and Assays

Cell Culture. The 231MFP cells were obtained from Prof. Benjamin Cravatt and were generated from explanted tumor xenografts of MDA-MB-231 cells as previously described[33]. HCC38 and HEK293T cells were obtained from the American Type Culture Collection. HEK293T cells were cultured in DMEM containing 10% (v/v) fetal bovine serum (FBS) and maintained at 37° C. with 5% $CO_2$. 231MFP were cultured in L15 medium containing 10% FBS and maintained at 37° C. with 0% $CO_2$. HCC38 cells were cultured in RPMI medium containing 10% FBS and maintained at 37° C. with 5% $CO_2$. HAP1 RNF114 wild-type and knockout cell lines were purchased from Horizon Discovery. The RNF114 knockout cell line was generated by CRISPR/Cas9 to contain a frameshift mutation in a coding exon of RNF114. HAP1 cells were grown in Iscove's Modified Dulbecco's Medium (IMDM) in the presence of 10% FBS and penicillin/streptomycin.

Survival and Proliferation Assays. Cell survival and proliferation assays were performed as previously described using Hoechst 33342 dye (Invitrogen) according to manufacturer's protocol and as previously described[14]. 231MFP cells were seeded into 96-well plates (40,000 for survival and 20,000 for proliferation) in a volume of 150 µl and allowed to adhere overnight. Cells were treated with an additional 50 µL of media containing 1:250 dilution of 1000× compound stock in DMSO. After the appropriate incubation period, media was removed from each well and 100 µl of staining solution containing 10% formalin and Hoechst 33342 dye was added to each well and incubated for 15 min in the dark at room temperature. After incubation, staining solution was removed, and wells were washed with PBS before imaging. Studies with HCC38 cells were also performed as above but were seeded with 20,000 cells for survival and 10,000 cells for proliferation.

Assessing Apoptosis in Breast Cancer Cells. Apoptotic cells were analyzed in cells treated with DMSO vehicle or compound containing serum-free media for 24 or 48 h using flow cytometry. We measured the percentage of Annexin V-positive and propidium iodide-negative early apoptotic cells and Annexin V-positive and propidium iodide-positive late apoptotic cells as previously described 34. Data analysis was performed using FlowJo software.

IsoTOP-ABPP Chemoproteomic Studies. IsoTOP-ABPP studies were done as previously reported[12,14,15]. Cells were lysed by probe sonication in PBS and protein concentrations were measured by BCA assay[35]. For in situ experiments, cells were treated for 90 min with either DMSO vehicle or covalently-acting small molecule (from 1000× DMSO stock) before cell collection and lysis. Proteomes were subsequently labeled with IA-alkyne labeling (100 µM) for 1 h at room temperature. CuAAC was used by sequential addition of tris(2-carboxyethyl)phosphine (1 mM, Sigma), tris[(1-benzyl-1H-1,2,3-triazol-4-yl)methyl]amine (34 µM, Sigma), copper (II) sulfate (1 mM, Sigma), and biotin-linker-azide—the linker functionalized with a TEV protease recognition sequence as well as an isotopically light or heavy valine for treatment of control or treated proteome, respectively. After CuAAC, proteomes were precipitated by centrifugation at 6500×g, washed in ice-cold methanol, combined in a 1:1 control/treated ratio, washed again, then denatured and resolubilized by heating in 1.2% SDS/PBS to 80° C. for 5 minutes. Insoluble components were precipitated by centrifugation at 6500×g and soluble proteome was diluted in 5 ml 0.2% SDS/PBS. Labeled proteins were bound to avidin-agarose beads (170 µl resuspended beads/sample, Thermo Pierce) while rotating overnight at 4° C. Bead-linked proteins were enriched by washing three times each in PBS and water, then resuspended in 6 M urea/PBS (Sigma) and reduced in TCEP (1 mM, Sigma), alkylated with iodoacetamide (IA) (18 mM, Sigma), then washed and resuspended in 2 M urea and trypsinized overnight with 0.5 µg/µl sequencing grade trypsin (Promega). Tryptic peptides were eluted off. Beads were washed three times each in PBS and water, washed in TEV buffer solution (water, TEV buffer, 100 µM dithiothreitol) and resuspended in buffer with Ac-TEV protease and incubated overnight. Peptides were diluted in water and acidified with formic acid (1.2 M, Spectrum) and prepared for analysis.

Mass Spectrometry Analysis. Peptides from all chemoproteomic experiments were pressure-loaded onto a 250 m inner diameter fused silica capillary tubing packed with 4 cm of Aqua C18 reverse-phase resin (Phenomenex #04A-4299) which was previously equilibrated on an Agilent 600 series HPLC using gradient from 100% buffer A to 100% buffer B over 10 min, followed by a 5 min wash with 100% buffer B and a 5 min wash with 100% buffer A. The samples were then attached using a MicroTee PEEK 360 m fitting (Thermo Fisher Scientific #p-888) to a 13 cm laser pulled column packed with 10 cm Aqua C18 reverse-phase resin and 3 cm of strong-cation exchange resin for isoTOP-ABPP studies. Samples were analyzed using an Q Exactive Plus mass spectrometer (Thermo Fisher Scientific) using a 5-step Multidimensional Protein Identification Technology (MudPIT) program, using 0%, 25%, 50%, 80%, and 100% salt bumps of 500 mM aqueous ammonium acetate and using a gradient of 5-55% buffer B in buffer A (buffer A: 95:5 water:acetonitrile, 0.1% formic acid; buffer B 80:20 acetonitrile:water, 0.1% formic acid). Data was collected in data-dependent acquisition mode with dynamic exclusion enabled (60 s). One full MS (MS1) scan (400-1800 m/z) was followed by 15 MS2 scans (ITMS) of the nth most abundant ions. Heated capillary temperature was set to 200° C. and the nanospray voltage was set to 2.75 kV.

Data was extracted in the form of MS1 and MS2 files using Raw Extractor 1.9.9.2 (Scripps Research Institute) and searched against the Uniprot human database using ProLuCID search methodology in IP2 v.3 (Integrated Proteomics Applications, Inc)[36]. Cysteine residues were searched with a static modification for carboxyaminomethylation (+57.02146) and up to two differential modifications for methionine oxidation and either the light or heavy TEV tags (+464.28596 or +470.29977, respectively). Peptides were required to be fully tryptic peptides and to contain the TEV modification. ProLUCID data was filtered through DTASelect to achieve a peptide false-positive rate below 5%. Only those probe-modified peptides that were evident across two out of three biological replicates were interpreted for their isotopic light to heavy ratios. For those probe-modified peptides that showed ratios >2, we only interpreted those targets that were present across all three biological replicates, were statistically significant, and showed good quality MS1 peak shapes across all biological replicates. Light versus heavy isotopic probe-modified peptide ratios are calculated by taking the mean of the ratios of each replicate paired light vs. heavy precursor abundance for all peptide spectral matches (PSM) associated with a peptide. The paired abundances were also used to calculate a paired sample t-test p-value in an effort to estimate constancy within paired abundances and significance in change between treatment and control. P-values were corrected using the Benjamini/Hochberg method.

Knockdown of RNF114, CDKN1A (p21) and CDKN1C (p57) by RNA Interference (RNAi) in 231MFP Cells. RNAi was performed by using siRNA purchased from Dharmacon specific to RNF114 or p21 and p57 for dual knockdown. In brief, 231MFP cells were seeded at a density of 5×10$^4$ cells per mL full media in a 96-well format. On day 0, 231MFP cells were transfected with corresponding small interfering RNA (siRNA) vs. non-targeting negative control (Dharmacon, ON-TARGETplus Non-targeting Pool D-001810-10-05) duplexes at 50 nM using Dharmafect 1 (Dharmacon) as a transfection reagent for 48 h. Thereafter (day 2), transfection media was supplemented with fresh DMSO or compound containing full L15 media and cultured for an additional 24 to 48 h before undergoing cell viability testing as described above. At the time of treatment (day 2), RNA was extracted for analysis by qRT-PCR and lysates were obtained for Western blotting confirmation of knockdown. Targeting Sequences:

```
siRNF114-1:
                                   (SEQ ID NO: 10)
GUGUGAAGGCCACCAUUAA (Dharmacon J-007024-08-0002)

siRNF114-2:
                                   (SEQ ID NO: 11)
GCUUAGAGGUGUACGAGAA (Dharmacon J-007024-05-0002)

siRNF114-3:
                                   (SEQ ID NO: 12)
GCACGGAUACCAAAUCUGU (Dharmacon J-007024-06-0002)

siCDKN1A:
                                   (SEQ ID NO: 13)
AGACCAGCAUGACAGAUUU (Dharmacon J-003471-12-0002)

siCDKN1C:
                                   (SEQ ID NO: 14)
CUGAGAAGUCGUCGGGCGA (Dharmacon J-003244-13-0002)
```

Gene Expression by qPCR. Total RNA was extracted from cells using Trizol (Thermo Fisher Scientific). cDNA was synthesized using MaximaRT (Thermo Fisher Scientific) and gene expression was confirmed by qPCR using the manufacturer's protocol for Fisher Maxima SYBR Green (Thermo Fisher Scientific) on the CFX Connect Real-Time PCR Detection System (BioRad). Primer sequences for Fisher Maxima SYBR Green were derived from Primer Bank. Sequences of primers are as follows:

```
RNF114 Forward:
                                   (SEQ ID NO: 6)
AAT GTT CCA AAC CG
```

-continued
```
RNF114 Reverse:
                                       (SEQ ID NO: 7)
TTG CAG TGT TCC AC CDKN1A Forward:
                                      (SEQ ID NO: 15)
TGT CCG TCA GAA CCC ATG C CDKN1A Reverse:
                                      (SEQ ID NO: 16)
AAA GTC GAA GTT CCA TCG CTC PPIA (Cyclophilin) Forward:
                                       (SEQ ID NO: 8)
CCC ACC GTG TTC TTC GAC ATT PPIA (Cyclophilin) Reverse:
                                       (SEQ ID NO: 9)
GGA CCC GTA TGC TTT AGG ATG A
```

Gene Expression by qPCR. Gene expression was confirmed by qPCR using the manufacturer's protocol for Fisher Maxima SYBR Green. Primer sequences for Fisher Maxima SYBR Green were derived from Primer Bank. Sequences of primers are as follows:

```
RNF114 Forward:
                                       (SEQ ID NO: 6)
AAT GTT CCA AAC CG RNF114 Reverse:
                                       (SEQ ID NO: 7)
TTG CAG TGT TCC AC PPIA (Cyclophilin) Forward:
                                       (SEQ ID NO: 8)
CCC ACC GTG TTC TTC GAC ATT PPIA (Cyclophilin) Reverse:
                                       (SEQ ID NO: 9)
GGA CCC GTA TGC TTT AGG ATG A
```

Gel-Based ABPP. Gel-based ABPP methods were performed as previously described[14]. Recombinant pure human proteins were purchased from Origene. Pure proteins (0.1 µg) were pre-treated with DMSO vehicle or covalently-acting small molecules for 30 min at room temperature in an incubation volume of 50 µL PBS, and were subsequently treated with JNS-1-27 (50 µM final concentration) for 1 h at room temperature. CuAAC was performed to append rhodamine-azide (1 µM final concentration) onto alkyne probe-labeled proteins. Samples were then diluted with 20 µL of 4× reducing Laemmli SDS sample loading buffer (Alfa Aesar) and heated at 90° C. for 5 min. The samples were separated on precast 4-20% TGX gels (Bio-Rad Laboratories, Inc.). Prior to scanning by ChemiDoc MP (Bio-Rad Laboratories, Inc), gels were fixed in a solution of 10% acetic acid, 30% ethanol for 2 hrs. Inhibition of target labeling was assessed by densitometry using ImageJ.

Covalent Ligand Library. The synthesis and characterization of most of the covalent ligands screened against RNF114 have been previously reported[14,37-39]. Synthesis of TRH 1-156, TRH 1-160, TRH 1-167, YP 1-16, YP 1-22, YP 1-26, YP 1-31, YP 1-44 have been previously reported[40-47]. Compounds starting with "EN" were purchased from Enamine LLC. The synthesis and characterization of other covalent ligands not previously reported are described in Example 9.

Western Blotting. Antibodies to RNF114 (Millipore Sigma, HPA021184), p21 (Cell Signaling Technology, 12D1), GAPDH (Proteintech Group Inc., 60004-1-Ig), BRD4 (Abcam plc, Ab128874), DYKDDDDK Tag (Cell Signaling Technology, D6W5B) and beta-actin (Proteintech Group Inc., 6609-1-Ig) were obtained from various commercial sources and dilutions were prepared per recommended manufacturers' procedures. Proteins were resolved by SDS/PAGE and transferred to nitrocellulose membranes using the iBlot system (Invitrogen). Blots were blocked with 5% BSA in Tris-buffered saline containing Tween 20 (TBST) solution for 1 h at room temperature, washed in TBST, and probed with primary antibody diluted in recommended diluent per manufacturer overnight at 4° C. Following washes with TBST, the blots were incubated in the dark with secondary antibodies purchased from Ly-Cor and used at 1:10,000 dilution in 5% BSA in TBST at room temperature. Blots were visualized using an Odyssey Li-Cor scanner after additional washes. If additional primary antibody incubations were required the membrane was stripped using ReBlot Plus Strong Antibody Stripping Solution (EMD Millipore, 2504), washed and blocked again before being reincubated with primary antibody.

Expression and Purification of Wild-type and C8A Mutant RNF114 Protein. RNF14 was expressed and purified using several methods. In each case, RNF114 activity and sensitivity to nimbolide was confirmed. For the first method, we purchased wild-type mammalian expression plasmids with C-terminal FLAG tag were purchased from Origene (Origene Technologies Inc., RC209752). The RNF114 C8A mutant was generated with Q5 site-directed mutagenesis kit according to manufacturer's instructions (New England Biolabs, E0554S). Expression and purification conditions were optimized as reported previously[48]. HEK293T cells were grown to 60% confluency in DMEM (Corning) supplemented with 10% FBS (Corning) and 2 mM L-glutamine (Life Technologies) and maintained at 37° C. with 5% $CO_2$. Immediately prior to transfection, media was replaced with DMEM containing 5% FBS. Each plate was transfected with 20 µg of overexpression plasmid with 100 µg PEI (Sigma). After 48 h cells were collected in TBS, lysed by sonication, and batch bound with anti-DYKDDDDK resin (GenScript, L00432) for 90 min. Lysate and resin was loaded onto a gravity flow column and washed, followed by elution with 250 ng/µL 3×FLAG peptide (ApexBio, A6001). Purity and concentration were verified by PAGE, UV/Spectroscopy, and BCA assay.

For the second method, DNA encoding the complete human isoform of RNF114 (Uniprot id: Q9Y508) was codon optimized for expression in E. coli and synthesized by Integrated DNA Technologies. Constructs containing the complete RNF114 sequence were amplified using primers containing 20 base pair homology to a pET24a plasmid (Novagen) that also contained a $His_8$-MBP-TEV sequence between Nde1 and BamH1 restriction sites. Products for PCR were assessed using 1% agarose gels (Invitrogen), and a QIAquick Gel Extraction kit (Qiagen) was used to purify PCR products of the correct length. Gibson Assembly (NEB Gibson Assembly 2× Master Mix) was used to assemble the purified PCR product into the linearized vector. This vector was then transformed into chemically competent E. coli 10G cells (Lucigen, Middleton, WI). Kanamycin (Kan)-resistant colonies were grown in LB media, and a Miniprep (Qiagen) kit was used to isolate the plasmid before sequence verification with appropriate primers.

pET24a $His_8$-MBP plasmid (100 ng) containing the desired RNF114 construct was transformed into chemically competent E. coli BL21(DE3) cells (NEB product #C2530H). The following day, a single transformed colony was used to inoculate 50 mL of nutrient rich LB medium containing kanamycin (50 µg/mL) and was incubated at 37°

C. overnight, with agitation (250 rpm). The following morning, an overnight starter culture was inoculated to a starting optical density at 500 nM ($OD_{600}$) of 0.1 in Terrific Broth (TB) (1 L) containing 50 mM 3-(N-morpholino)propanesulfonic acid (MOPS) pH 7.5, 1 mM zinc chloride, and Kan (50 μg/mL). Cells were grown until achieving an $OD_{600}$ of 0.8 at 37° C. with agitation at 250 rpm. At this stage, expression of the RNF114 fusion protein was induced with 1 mM isopropyl β-D-1-thiogalactopyranoside (IPTG), and the temperature of the incubator was reduced to 18° C. Cells were harvested by centrifugation after growth for 18 h at 18° C. Cells were subsequently washed with 1× phosphate buffered saline (PBS) buffer and stored at −20° C.

E. coli cells (10 g) containing the overexpressed RNF114 fusion protein were re-suspended in 80 mL of lysis buffer (50 mM Tris, pH 7.5, 150 mM NaCl, 2 Roche protease inhibitor tablets [without EDTA], 200 mM $ZnCl_2$, 1 mM DTT) and sonicated on ice, with a cycling time of 60 seconds on, 60 seconds off, over a total sonication time of three minutes. The cell lysate was centrifuged at 18,000 rpm for 20 minutes and the soluble protein was incubated with agitation for four hours at 4° C. with 2 mL of Ni-NTA resin, which had been pre-equilibrated with wash buffer (50 mM Tris, pH 7.5, 150 mM NaCl, 200 mM $ZnCl_2$, 1 mM DTT, 25 mM imidazole). The cell lysate/Ni-NTA resin mixture was placed into a disposable column and all non-tagged soluble protein, which do not bind to the resin, was collected for a second round of purification. The resin was washed with 25 mL of wash buffer before the His-MBP-RNF114 protein was eluted from the Ni-NTA resin with 25 mL of elution buffer (50 mM tris, pH 7.5, 500 mM imidazole, 200 mM $ZnCl_2$, 150 mM NaCl, 1 mM DTT). This process was repeated incubating the collected flow thorough with an additional 2 mL of pre-equilibrated Ni-NTA resin.

His-MBP-RNF114 protein was simultaneously digested at 4° C. with TEV protease (100 units/mg MBP-RNF114), and dialyzed overnight against dialysis buffer (50 mM tris, pH 7.5, 150 mM NaCl, 200 mM $ZnCl_2$, 1 mM DTT). The following morning two 5 mL His Trap Excel columns assembled in tandem were placed on an Äkta Avant and equilibrated with five column volumes of wash buffer. The TEV cleaved sample was loaded onto the column at a rate of 2 mL/min and the resin was washed with an additional five column volumes of wash buffer. All fractions containing cleaved RNF114 were concentrated to a 5 ml volume. Samples were then loaded onto a pre-equilibrated HiLoad 16/60 Superdex 75 gel filtration column (GE Healthcare). Columns were pre-equilibrated with either 25 mM Tris, pH 7.5, 137 mM NaCl or 20 mM Sodium Phosphate pH 6.8, 150 mM NaCl. The gel filtration column was run using a flow rate of 0.25 mL/min and 2 mL fractions were collected. Fractions corresponding to peaks eluting from the gel filtration column were analyzed using SDS-PAGE and all fractions containing RNF114 were concentrated to a final concentration of 10 mg/mL, flash frozen in liquid nitrogen and stored at −80° C. until needed.

Generation of Stably Expressing FLAG-RNF114 231MFP Cell Lines by Lentiviral Transduction. Human RNF114 with C-terminal FLAG tag was inserted into pLenti vector by FastCloning[49]. FLAG-RNF114 lentivirus was generated by co-transfection of FLAG-RNF114, VSV.G and psPAX2 into HEK 293T cells using Lipfectamine 2000 transfection reagent (ThemoFischer). 24h after transfection media was exchanged for DMEM with 10% heat-inactivated serum (HIS) and after an additional 24 hr virus-containing media was collected and filtered with 0.45 μM filter onto 231MFP cells with equal volume HIS L15 media, in the presence of 10 μg/mL polybrene (Santa Cruz). 24h after transduction, puromycin (2 μg/mL) was added to cells and stably expressing FLAG-RNF114 were obtained after puromycin selection for 72 hr. 231MFP cells stably expressing FLAG-eGFP were generated in parallel as control.

In situ Nimbolide-Alkyne Probe Labeling and FLAG-RNF114 Pulldown. 231MFP cells stably expressing FLAG-RNF114 were treated with either vehicle (DMSO) or 100 nM to 10 μM nimbolide alkyne probe for 2-4 h. Cells were harvested in PBS and lysed by sonication. Total protein concentration of lysates were normalized by BCA assay and normalized lysates were incubated 1.5 hr at 4° C. with 50 μL or FLAG-agarose slurry. After incubation samples were transferred to spin columns and washed 3× with 500 μL PBS. Proteins were eluted using 2 50 μL washes of PBS supplemented with 250 ng/μL 3×FLAG peptide (ApexBio A6001). CuAAC was performed to append rhodamine-azide onto alkyne probe-labeled proteins and after addition of loading buffer samples were separated on precast 4-20% TGX gels (Bio-Rad Laboratories, Inc.) and imaged on ChemiDoc MP (Bio-Rad Laboratories, Inc).

LC-MS/MS Analysis of RNF114. Purified RNF114 (10 μg) in 50 μL PBS were incubated 30 min at room temperature either with DMSO vehicle or covalently acting compound (100 μM). The DMSO control was then treated with light IA while the compound treated sample was incubated with heavy IA for 1 h each at room temperature (200 μM final concentration, Sigma-Aldrich, 721328). The samples were precipitated by additional of 12.5 μL of 100% (w/v) TCA and the treated and control groups were combined pairwise, before cooling to −80° C. for 1 h. The combined sample was then spun for at max speed for 10 min at 4° C., supernatant is carefully removed and the sample is washed with ice cold 0.01 M HCl/90% acetone solution. The pellet was resuspended in 4 M urea containing 0.1% Protease Max (Promega Corp. V2071) and diluted in 40 mM ammonium bicarbonate buffer. The samples were reduced with 10 mM TCEP at 60° C. for 30 min. The sample was then diluted 50% with PBS before sequencing grade trypsin (1 μg per sample, Promega Corp, V5111) was added for an overnight incubation at 37° C. The next day the sample was centrifuged at 13200 rpm for 30 min. The supernatant was transferred to a new tube and acidified to a final concentration of 5% formic acid and stored at −80° C. until MS analysis.

RNF114 Ubiquitination Assay. Recombinant Myc-Flag-RNF114 proteins were either purified from HEK292T cells as described above or purchased from Origene (Origene Technologies Inc., TP309752). For in vitro auto-ubiquitination assay, 0.2 μg of RNF114 in 25 μL of TBS was pre-incubated with DMSO vehicle or the covalently-acting compound for 30 min at room temperature. Subsequently, 0.1 μg of UBE1 (Boston Biochem. Inc, E-305), 0.1 μg UBE2D1 (Boston Bichem. Inc, e2-615), 5 μg of Flag-ubiquitin (Boston Bichem. Inc, u-120) in a total volume of 25 μL Tris buffer containing 2 mM ATP, 10 mM DTT, and 10 mM $MgCl_2$ were added to achieve a final volume of 50 μL. For substrate-protein ubiquitination assays, 0.1 ug of the appropriate substrate protein, purchased from commercial sources, was added at this stage (p21 and PEG10: Origene, CTGF: R&D Systems). The mixture was incubated at 37° C. with agitation for 1.5 h. 20 μL of Laemmli's buffer was added to quench the reaction and proteins were analyzed by western blot assay.

RNF114/p21 Co-Immunoprecipitation. Recombinant Flag-tagged RNF114 was used as bait to precipitate pure recombinant p21 (Origene Technologies Inc., TP309752 and TP720567) using Anti-Flag agarose beads (GenScript Biotech Corp., L00432). One microgram of Flag-RNF114 was added to 50 μL of TBS, followed by the addition of nimbolide (100 μM final concentration, Cayman Chemical Co., 19230) or equivalent volume of DMSO. Samples were incubated at room temperature for 30 min. One microgram of pure p21 was added to each sample, and samples were incubated at room temperature 30 min with agitation. Ten microliters of Flag agarose beads were added to each sample, and samples were agitated at room temperature for 30 min. Washes (3 times, 1 mL TBS) were performed before proteins were eluted using 50 μL of TBS supplemented with 250 ng/μL 3×FLAG peptide (ApexBio A6001). Supernatant (30 μL) were collected and after the addition of Laemmli's reducing agent (10 μL), samples were boiled at 95° C. for 5 min and allowed to cool. Samples were analyzed by Western blotting as described above.

In situ Nimbolide-Alkyne Probe Labeling and Biotin-Azide Pulldown. Experiments were performed following an adaption of a previously described protocol[50]. 231MFP cells were treated with either vehicle (DMSO) or 50 μM nimbolide alkyne probe for 90 min. Cells were harvested in PBS and lysed by sonication. For preparation of Western blotting sample, 195 μL of lysate was aliquoted per sample to which 25 μL of 10% SDS, 5 μL of 5 mM biotin picolylazide (900912 Sigma-Aldrich) and 25 μL of click reaction mix (3 parts TBTA 5 mM TBTA in butanol:DMSO (4:1, v/v), 1 part 50 mM Cu(II)SO4 solution, and 1 part 50 mM TCEP). Samples were incubated for 2 h at 37° C. with gentle agitation after which 1.2 mL ice cold acetone were added. After overnight precipitation at −20° C., samples were spun in a prechilled centrifuge at 1250 g for 10 min allowing for aspiration of excess acetone and subsequent reconstitution of protein pellet in 200 μL PBS containing 1% SDS by probe sonication. At this stage, total protein concentration was determined by BCA assay and samples were normalized to a total volume of 230 μL, with 30 μL reserved as input. 20 μL of prewashed 50% streptavidin agarose bead slurry was added to each sample and samples were incubated overnight at rt with gentle agitation. Supernatant was aspirated from each sample after spinning at 90 g for 2 min at rt. Beads were transferred to spin columns and washed 3× with PBS. To elute, beads were boiled 5 min in 50 μL LDS sample buffer. Eluents were collected by centrifugation and analyzed by immunoblotting. The resulting samples were analyzed as described below in the TMT-based quantitative proteomic profiling section.

TMT-Based Quantitative Proteomic Profiling.

Cell Lysis, Proteolysis and Isobaric Labeling. Treated cell-pellets were lysed and digested using the commercially available Pierce™ Mass Spec Sample Prep Kit for Cultured Cells (Thermo Fisher Scientific, P/N 84840) following manufacturer's instructions. Briefly, 100 μg protein from each sample was reduced, alkylated, and digested overnight using a combination of Endoproteinase Lys-C and trypsin proteases. Individual samples were then labeled with isobaric tags using commercially available Tandem Mass Tag™ 6-plex (TMTsixplex™) (Thermo Fisher Scientific, P/N 90061) or TMT11plex (TMT11plex™) isobaric labeling reagent (Thermo Fisher Scientific, P/N 23275) kits, in accordance with manufacturer's protocols.

High pH Reversed Phase Separation. Tandem mass tag labeled (TMT) samples were then consolidated, and separated using high-pH reversed phase chromatography (RP-10) with fraction collection as previously described[50]. Fractions were speed-vac dried, then reconstituted to produce 24 fractions for subsequent on-line nanoLC-MS/MS analysis.

Protein Identification and Quantitation by nanoLC-MS/MS. Reconstituted RP-10 fractions were analyzed on a Thermo Orbitrap Fusion Lumos Mass Spectrometer (Xcalibur 4.1, Tune Application 3.0.2041) coupled to an EasyLC 1200 HPLC system (Thermo Fisher Scientific). The EasyLC 1200 was equipped with a 20 μL loop, set-up for 96 well plates. A Kasil-fritted trapping column (75 μm ID) packed with ReproSil-Pur 120 C18-AQ, 5 μm material (15 mm bed length) was utilized together with a 160 mm length, 75 μm inner diameter spraying capillary pulled to a tip diameter of approximately 8-10 μm using a P-2000 capillary puller (Sutter Instruments, Novato, CA). The 160 mm separation column was packed with ReproSil-Pur 120 C18-AQ, 3 μm material (Dr. Maisch GmbH, Ammerbuch-Entringen, Germany). Mobile phase consisted of A=0.1% formic acid/2% acetonitrile (v/v), and Mobile phase B=0.1% formic acid/98% acetonitrile (v/v). Samples (18 μL) were injected on to trapping column using Mobile Phase A at a flow rate of 2.5 μL/min. Peptides were then eluted using an 80 minute gradient (2% Mobile Phase B for 5 min, 2%-40% B from 5-65 min, followed by 70% B from 65-70 minutes, then returning to 2% B from 70-80 min) at a flowrate of 300 nL/min on the capillary separation column with direct spraying into the mass spectrometer. Data was acquired on Orbitrap Fusion Lumos Mass Spectrometer in data-dependent mode using synchronous precursor scanning MS$^3$ mode (SPS-MS3), with MS$^2$ triggered for the 12 most intense precursor ions within a mass-to-charge ratio (m/z) range of 300-1500 found in the full MS survey scan event. MS scans were acquired at 60,000 mass resolution (R) at m/z 400, using a target value of $4\times10^5$ ions, and a maximum fill time of 50 ms. MS$^2$ scans were acquired as CID ion trap (IT) rapid type scans using a target value of $1\times10^4$ ions, maximum fill time of 50 ms, and an isolation window of 2 Da. Data-dependent MS$^3$ spectra were acquired as Orbitrap (OT) scans, using Top 10 MS$^2$ daughter selection, automatic gain control (AGC) target of $5\times10^4$ ions, with scan range of m/z 100-500. The MS$^3$ maximum injection time was 86 ms, with HCD collision energy set to 65%. MS$^3$ mass resolution (R) was set to 15,000 at m/z 400 for TMT6plex experiments, and 50,000 at m/z 400 for TMT11-plex experiments. Dynamic exclusion was set to exclude selected precursors for 60 s with a repeat count of 1. Nanospray voltage was set to 2.2 kV, with heated capillary temperature set to 300° C., and an S-lens RF level equal to 30%. No sheath or auxiliary gas flow is applied.

Data Processing and Analysis. Acquired MS data was processed using Proteome Discoverer v. 2.2.0.388 software (Thermo) utilizing Mascot v 2.5.1 search engine (Matrix Science, London, UK) together with Percolator validation node for peptide-spectral match filtering[51]. Data was searched against Uniprot protein database (canonical human and mouse sequences, EBI, Cambridge, UK) supplemented with sequences of common contaminants. Peptide search tolerances were set to 10 ppm for precursors, and 0.8 Da for fragments. Trypsin cleavage specificity (cleavage at K, R except if followed by P) allowed for up to 2 missed cleavages. Carbamidomethylation of cysteine was set as a fixed modification, methionine oxidation, and TMT-modification of N-termini and lysine residues were set as variable modifications. Data validation of peptide and protein identifications was done at the level of the complete dataset consisting of combined Mascot search results for all individual samples per experiment via the Percolator validation node in Proteome Discoverer. Reporter ion ratio calculations were performed using summed abundances with most confident centroid selected from 20 ppm window. Only peptideto-spectrum matches that are unique assignments to a given identified protein within the total dataset are considered for protein quantitation. High confidence protein identifications were reported using a Percolator estimated <1% false discovery rate (FDR) cut-off. Differential abundance significance was estimated using a background-based ANOVA with Benjamini-Hochberg correction to determine adjusted p-values.

Example 9. Additional Synthesis and Characterization Data

Synthesis and characterization of the nimbolide-alkyne probe (5) and degraders XH1 (9) and XH2 (10)

General Procedures. Unless otherwise stated, all reactions were performed in oven-dried or flame-dried Fisherbrand® borosilicate glass tubes (Fisher Scientific, 1495925A, 13×100 mm) with a black phenolic screw cap (13-425) under an atmosphere of dry nitrogen. Dry N,N-dimethylformamide (DMF), toluene, and acetonitrile were obtained by passing these previously degassed solvents through activated alumina columns. Nimbolide was purchased from Sigma-Aldrich or Cayman Chemical, and used directly without further purification. Propargylamine and N-methylpropargylamine were purchased from Fisher Scientific and used directly without further purification. Reactions were monitored by thin layer chromatography (TLC) on TLC silica gel 60 $F_{254}$ glass plates (EMD Millipore) and visualized by UV irradiation and staining with p-anisaldehyde, phosphomolybdic acid, or potassium permanganate. Volatile solvents were removed under reduced pressure using a rotary evaporator. Flash column chromatography was performed using Silicycle F60 silica gel (60A, 230-400 mesh, 40-63 μm). Ethyl acetate and hexanes were purchased from Fisher Chemical and used for chromatography without further purification. Proton nuclear magnetic resonance ($^1$H NMR) and carbon nuclear magnetic resonance ($^{13}$C NMR) spectra were recorded on Bruker AV-600 and AV-700 spectrometers operating at 600 and 700 MHz for $^1$H, and 150 and 175 MHz for $^{13}$C. Chemical shifts are reported in parts per million (ppm) with respect to the residual solvent signal CDCl$_3$ ($^1$H NMR: δ=7.26; $^{13}$C NMR: δ=77.16), CD$_2$Cl$_2$ ($^1$H NMR: δ=5.32; $^{13}$C NMR: δ=53.84). Peak multiplicities are reported as follows: s=singlet, d=doublet, t=triplet, dd=doublet of doublets, tt=triplet of triplets, m=multiplet, br=broad signal, app=apparent. IR spectra were recorded on a Nicolet 380 FT-IR spectrometer. High-resolution mass spectra (HRMS) were obtained by the QB3/chemistry mass spectrometry facility at the University of California, Berkeley. Optical rotations were measured on a Perkin-Elmer 241 polarimeter.

Scheme S1. Synthesis of the nimbolide-alkyne probe (5).

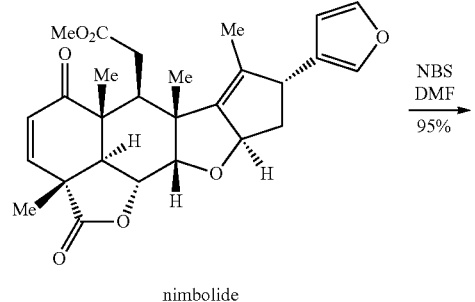

nimbolide

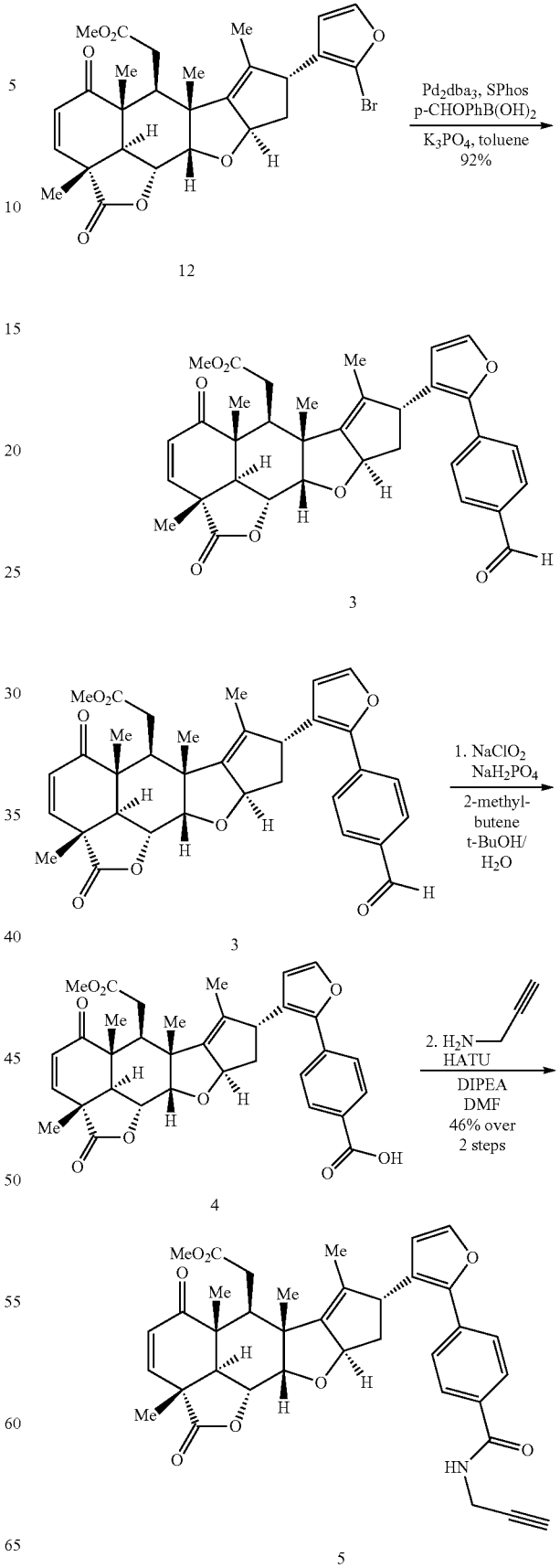

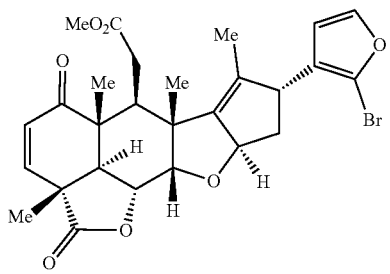

Bromonimbolide (12): Nimbolide (100 mg, 0.214 mmol) was divided evenly into four reaction tubes (Fisher Scientific, 13×100 mm), each charged with a stir bar. The tubes were evacuated and back-filled with nitrogen, dry DMF (0.25 mL each) was added, and the resulting solutions were cooled to 0° C. in an ice bath. Recrystallized N-bromosuccinimide (40.0 mg, 0.225 mmol) was dissolved in dry DMF (4 mL), and the solution was slowly added to each reaction tube (1 mL each). The reaction mixture was stirred at 0° C. for 1 hour and then quenched by the addition of saturated aq. $Na_2S_2O_3$ (5 mL each). The resulting mixtures were combined and extracted with EtOAc (3×20 mL). The combined organic layer was washed with $H_2O$ (50 mL) and brine (50 mL), dried over $MgSO_4$, and concentrated in vacuo. The crude mixture was purified by column chromatography (EtOAc:hexane=1:3 to 1:1), affording (12) (111 mg, 95%) as a white foam: $[\alpha]_D^{20}$=+190.3° (c 0.010 g/ml, $CHCl_3$); $^1$H NMR (700 MHz, $CDCl_3$) δ 7.34 (d, J=2.1 Hz, 1H), 7.28 (d, J=9.7 Hz, 1H), 6.29 (d, J=2.1 Hz, 1H), 5.92 (d, J=9.7 Hz, 1H), 5.56 (app. tt, J=7.4, 1.8 Hz, 1H), 4.62 (dd, J=12.5, 3.7 Hz, 1H), 4.27 (d, J=3.7 Hz, 1H), 3.67 (brd, J=7.0 Hz, 1H), 3.56 (s, 3H), 3.24 (dd, J=16.3, 5.5 Hz, 1H), 3.18 (d, J=12.5 Hz, 1H), 2.75 (dd, J=5.5, 5.5 Hz, 1H), 2.36 (dd, J=16.3, 5.5 Hz, 1H), 2.18-2.13 (m, 2H), 1.66 (d, J=1.4 Hz, 3H), 1.47 (s, 3H), 1.36 (s, 3H), 1.22 (s, 3H); $^{13}$C NMR (175 MHz, $CDCl_3$) δ 200.9, 175.0, 173.2, 149.8, 145.4, 144.2, 136.1, 131.2, 125.2, 120.3, 112.1, 88.5, 83.1, 73.5, 52.0, 50.5, 50.0, 47.9, 45.4, 43.8, 41.2, 40.4, 32.2, 18.7, 17.3, 15.3, 13.0; IR (thin film, cm$^{-1}$) 2974, 2929, 2875, 1783, 1734, 1678, 1594, 1438, 1394, 1373; HRMS (ESI) calcd. for $[C_{27}H_{29}O_7BrNa]^+$ (M+Na)$^+$: m/z 567.0989, found 567.0990.

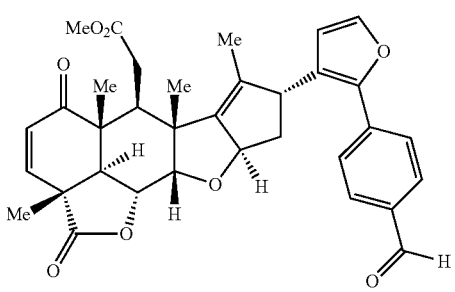

Aldehyde (3): A reaction tube (Fisher Scientific, 13×100 mm) was charged with a stir bar, (12) (12 mg, 0.022 mmol, 1 equiv), $Pd_2(dba)_3$ (10 mg, 0.011 mmol, 0.5 equiv), SPhos (10 mg, 0.024 mmol, 1 equiv), anhydrous $K_3PO_4$ (35 mg, 0.17 mmol, 7.5 equiv) and 4-formylphenylboronic acid (16 mg, 0.11 mmol, 5 equiv). The tube was evacuated and back-filled with nitrogen and dry toluene (0.5 mL) added. The resulting mixture was heated at 60° C. for 48 h, cooled to room temperature, and passed through a plug of Celite®. The filtrate was concentrated in vacuo and purified by column chromatography (EtOAc:hexane=1:3 to 1:1) to afford aldehyde (3) (11.5 mg, 92%) as a light yellow oil: $[\alpha]_D^{20}$=+4.8° (c 0.005 g/mL, $CHCl_3$); $^1$H NMR (600 MHz, $CDCl_3$) δ 10.01 (s, 1H), 7.92 (d, J=8.3 Hz, 2H), 7.71 (d, J=8.3 Hz, 2H), 7.42 (d, J=1.9 Hz, 1H), 7.29 (d, J=9.7 Hz, 1H), 6.39 (d, J=1.9 Hz, 1H), 5.93 (d, J=9.7 Hz, 1H), 5.60 (app. tt, J=7.3, 1.7 Hz, 1H), 4.64 (dd, J=12.5, 3.6 Hz, 1H), 4.32 (d, J=3.6 Hz, 1H), 4.17-4.13 (m, 1H), 3.69 (s, 3H), 3.23 (dd, J=16.4, 5.5 Hz, 1H), 3.20 (d, J=12.5 Hz, 1H), 2.78 (dd, J=5.5, 5.5 Hz, 1H), 2.41 (dd, J=16.4, 5.5 Hz, 1H), 2.31-2.27 (m, 2H), 1.69 (d, J=1.7 Hz, 3H), 1.49 (s, 3H), 1.38 (s, 3H), 1.25 (s, 3H); $^{13}$C NMR (150 MHz, $CDCl_3$) δ 200.8, 191.7, 175.0, 173.2, 149.8, 147.9, 146.3, 143.1, 137.0, 136.1, 134.8, 131.1, 130.3, 126.1, 126.0, 112.6, 88.4, 83.3, 73.4, 52.1, 50.8, 50.0, 47.9, 45.5, 43.8, 41.3, 32.5, 18.8, 17.5, 15.3, 13.4; IR (thin film, cm$^{-1}$) 2977, 2935, 2873, 1782, 1733, 1702, 1677, 1608, 1438, 1393, 1372; HRMS (ESI) calcd. for $[C_{34}H_{34}O_8Na]^+$ (M+Na)$^+$: m/z 593.2146, found 593.2154.

[Note: Aldehyde (3)) is not stable under preparative TLC conditions]

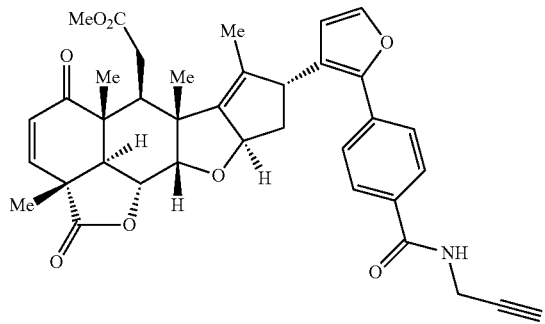

Nimbolide Alkyne Probe (5): i. A reaction tube (Fisher Scientific, 13×100 mm) was charged with a stir bar, aldehyde (3) (7.0 mg, 0.012 mmol, 1 equiv), and a mixture of t-BuOH and 2-methyl-2-butene (0.6 mL, 3:5 v/v). A solution of $NaClO_2$ (3.3 mg, 3 equiv) and $NaH_2PO_4$ (13.2 mg, 9 equiv) in $H_2O$ (0.2 mL) was added in one portion and the resulting mixture was stirred at room temperature for 6 hours. After the reaction was complete as judged by TLC (EtOAc:hexane=2:1), the mixture was diluted with EtOAc (10 mL) and saturated aq. $NH_4Cl$ (10 mL), and the aqueous phase was extracted by EtOAc (10 mL×2). The combined organic layer was washed with brine (20 mL), dried over MgSO$_4$, and concentrated in vacuo. The resulting crude carboxylic acid (4) was used directly without further purification.

ii. A reaction tube (Fisher Scientific, 13×100 mm) charged with a stir bar, crude acid (4) (0.012 mmol assumed), and HATU (13.7 mg, 0.036 mmol, 3 equiv) was added a solution of DIPEA (6.4 µL, 0.036 mmol, 3 equiv) in DMF (0.1 mL). The resulting mixture was cooled to 0° C. and stirred for 10 minutes. A solution of propargylamine (1.6 µL, 0.024 mmol, 2 equiv) in DMF (0.2 mL) was then added and the reaction mixture was further stirred at 0-4° C. for 12 hours. After the reaction was complete, as judged by TLC (EtOAc:hexane=2:1), the mixture was diluted with EtOAc (10 mL) and saturated aq. NH$_4$Cl (10 mL), and the aqueous phase was extracted by EtOAc (10 mL×2). The combined organic layer was washed with H$_2$O (20 mL), brine (20 mL), dried over MgSO$_4$, and concentrated in vacuo. The resulting crude was purified by preparative TLC (EtOAc:hexane=2:1), affording amide (5) (3.5 mg, 46% over 2 steps) as a white solid: $[\alpha]_D^{20}$=+21.5° (c 0.002 g/mL, CHCl$_3$); $^1$H NMR (600 MHz, CDCl$_3$) δ 7.83 (d, J=8.2 Hz, 2H), 7.61 (d, J=8.2 Hz, 2H), 7.39 (d, J=1.8 Hz, 1H), 7.29 (d, J=9.7 Hz, 1H), 6.36 (d, J=1.8 Hz, 1H), 6.27 (t, J=5.2 Hz, 1H), 5.93 (d, J=9.7 Hz, 1H), 5.60 (app. t, J=7.6 Hz, 1H), 4.64 (dd, J=12.6, 3.7 Hz, 1H), 4.31 (d, J=3.7 Hz, 1H), 4.28 (dd, J=5.2, 2.6 Hz, 2H), 4.11 (brd, J=7.6 Hz, 1H), 3.68 (s, 3H), 3.25-3.18 (m, 2H), 2.78 (dd, J=5.5, 5.5 Hz, 1H), 2.40 (dd, J=16.4, 5.5 Hz, 1H), 2.32-2.24 (m, 3H), 1.67 (brs, 3H), 1.49 (s, 3H), 1.38 (s, 3H), 1.24 (s, 3H); $^{13}$C NMR (150 MHz, CDCl$_3$) δ 200.8, 175.0, 173.2, 166.6, 149.8, 148.2, 146.1, 142.5, 136.3, 134.7, 132.1, 131.2, 127.6, 126.1, 124.8, 112.3, 88.5, 83.2, 79.6, 73.5, 72.2, 52.1, 50.8, 50.0, 48.0, 45.5, 43.8, 41.3, 41.3, 32.5, 30.0, 18.8, 17.5, 15.3, 13.4; IR (thin film, cm$^{-1}$) 3337, 2954, 2921, 2852, 1781, 1734, 1663, 1609; HRMS (ESI) calcd. for [C$_{37}$H$_{37}$NO$_8$Na]$^+$ (M+Na)$^+$: m/z 646.2417, found 646.2417.

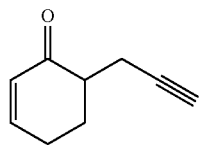

JNS27 (6). i. To a stirring solution of lithium diisopropylamide (6.0 mL, 1.2 equiv) at −78° C. under nitrogen atmosphere, was added a solution of cyclohexenone (0.48 mL, 1 equiv) in THF (5.0 mL) drop wise. After 45 minutes, a solution of 3-bromo-1-(trimethylsilyl)-propyne (0.85 mL, 2.4 equiv) in THF (5.0 mL) was added gradually, before allowing the reaction to come to room temperature overnight. The reaction was quenched with saturated NH$_4$Cl (20 mL) and extracted with EtOAc (20 mL×3). The combined organic layers were washed with brine, dried with Na$_2$SO$_4$, and concentrated in vacuo. Flash chromatography of the crude residue on silica gel (10-20% EtOAc in hexanes) gave the TMS-protected alkyne in 25% yield (261 mg). ii. To a solution of this material (261 mg, 1 equiv) in THF (5.0 mL) under N$_2$ was added a solution of TBAF (0.44 mL, 1 equiv). After 4 hours of stirring at room temperature, the reaction was quenched by the addition of saturated NH$_4$Cl (15 mL). The mixture was extracted with EtOAc (3×15 mL). The combined organic layers were washed with brine, dried with Na$_2$SO$_4$, and concentrated in vacuo. Flash chromatography of the residue on silica gel (0-20% EtOAc in hexanes) gave JNS-27 as a pale-yellow waxy solid in 81% yield (168 mg, 21% over 2 steps). $^1$H NMR (400 MHz, CDCl$_3$) δ 6.99 (m, 1H), 6.03 (dt, J=10.02, 1.97 Hz, 1H), 2.78 (m, 1H), 2.48 (m, 3H), 2.33 (m, 2H), 1.98 (t, J=2.68, 1H), 1.88 (m, 1H); $^{13}$C NMR (400 MHz, CDCl$_3$) δ 150.30, 129.34, 45.74, 27.68, 25.78, 20.27; HRMS (ESI) calcd. for [C$_9$H$_{10}$ONa]$^+$ (M+Na)$^+$: m/z 134.0732, found 134.0728.

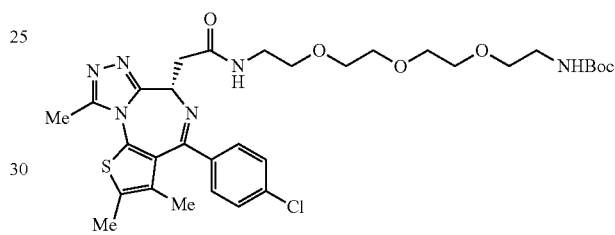

This compound (7) was prepared according to the conditions reported by Bradner and co-workers (PCT Int. Appl. 2017, WO 2017091673 A2).

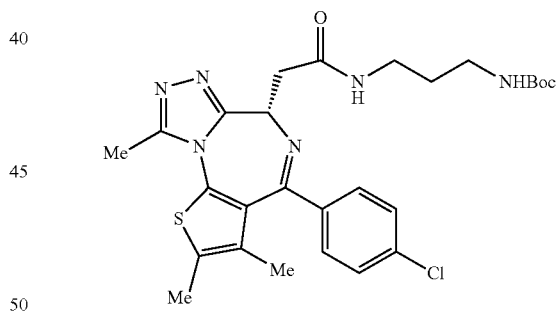

This compound (8) was prepared according to conditions reported by Waring and coworkers (*J. Med. Chem.*, 2016, 59, 7801).

Scheme S2. Synthesis of nimbolide-derived bifunctional degraders XH1 (9) and XH2 (10).

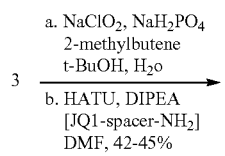

a. NaClO$_2$, NaH$_2$PO$_4$
2-methylbutene
t-BuOH, H$_2$O b. HATU, DIPEA
[JQ1-spacer-NH$_2$]
DMF, 42-45%

-continued
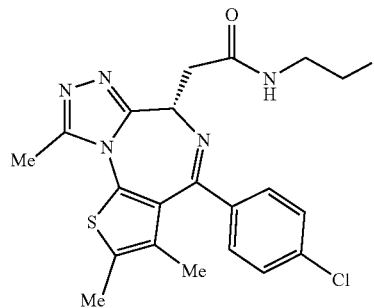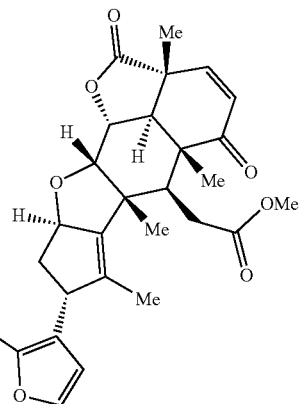
XH1 (9) (45%)
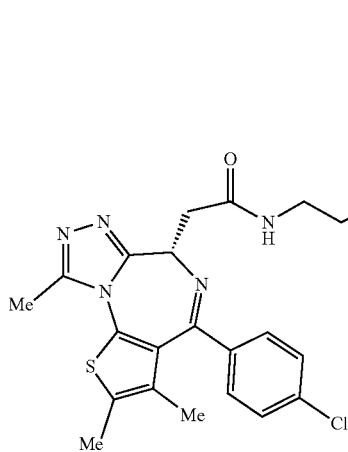
XH2 (10) (42%)
General procedure for the synthesis of bifunctional degraders XH1 (9) and XH2 (10):
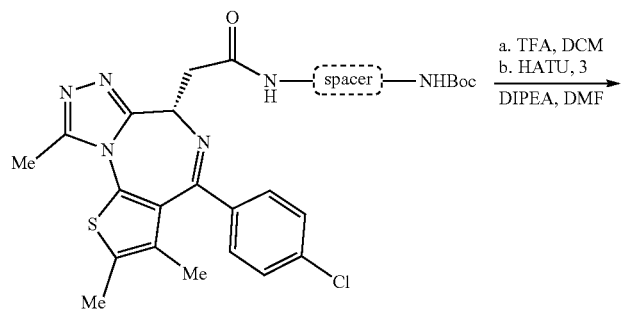

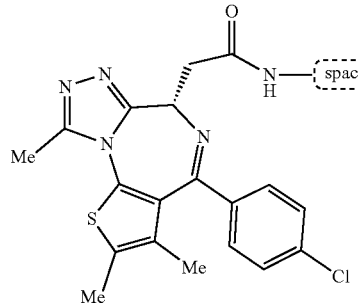
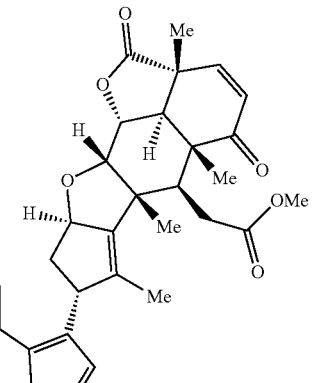

i. A reaction tube (Fisher Scientific, 13×100 mm) was charged with a stir bar, the Boc-protected amine (7) or (8) (0.04 mmol), triethylsilane (12 µL, 0.075 mmol), and DCM concentrated in vacuo. The resulting crude material was purified by preparative TLC (MeOH:DCM=1:15, developed twice), affording the bifunctional degraders XH1 or XH2.

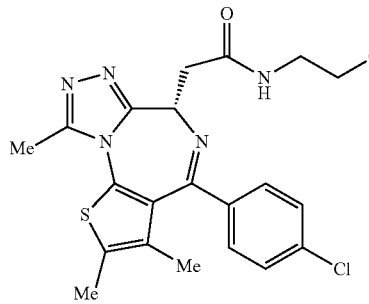
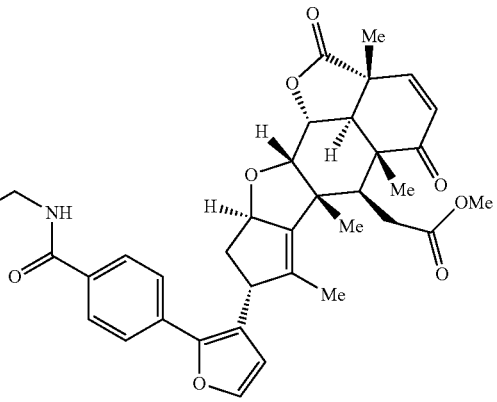

(0.4 mL). The resulting mixture was cooled to 0° C., followed by the dropwise addition of TFA (0.12 mL). The reaction mixture was allowed to warm to room temperature and further stirred for 2 hours. After the reaction was complete as judged by TLC (MeOH:DCM=1:10), the mixture was diluted with toluene (2 mL), and concentrated in vacuo. The resulting crude was dried under high vacuum for 30 minutes, and directly used in the next step without further purification. Carboxylic acid (4) was prepared from aldehyde (3) according to the aforementioned procedure, and used without further purification.

ii. A reaction tube (Fisher Scientific, 13×100 mm) was charged with a stir bar, the crude amine (0.04 mmol assumed), unpurified acid (4) (0.02 mmol assumed), and DMF (0.6 mL). The resulting mixture was cooled to 0° C. in an ice bath, followed by the addition of HATU (23.0 mg, 0.06 mmol) and DIPEA (11 µL, 0.06 mmol). The reaction mixture was stirred at 4° C. for 16 hours. After the reaction was complete as judged by TLC (MeOH:DCM=1:10), the mixture was diluted with EtOAc (10 mL) and saturated aq. NH$_4$Cl (10 mL), and the aqueous phase extracted with EtOAc (2×10 mL). The combined organic layer was washed with H$_2$O (20 mL), brine (20 mL), dried over MgSO$_4$, and XH1 (9) (45% yield from (3)), a white foam: $[\alpha]_D^{20}$=+ 48.7° (c 0.0052 g/mL, CHCl$_3$); $^1$H NMR (600 MHz, CDCl$_3$) δ 7.87 (d, J=8.5 Hz, 2H), 7.53 (d, J=8.5 Hz, 2H), 7.40 (d, J=8.2 Hz, 3H), 7.36 (d, J=1.9 Hz, 1H), 7.34-7.29 (m, 2H), 7.28 (d, J=9.7 Hz, 1H), 6.33 (d, J=1.9 Hz, 1H), 5.93 (d, J=9.7 Hz, 1H), 5.61-5.55 (m, 1H), 4.73 (app. t, J=7.1 Hz, 1H), 4.64 (dd, J=12.5, 3.7 Hz, 1H), 4.30 (d, J=3.6 Hz, 1H), 4.12-4.08 (m, 1H), 3.75-3.64 (m, 15H), 3.64-3.53 (m, 3H), 3.51-3.40 (m, 3H), 3.25-3.16 (m, 2H), 2.77 (app. t, J=5.5 Hz, 1H), 2.70 (s, 3H), 2.42-2.36 (m, 4H), 2.26-2.20 (m, 2H), 1.68-1.65 (m, 3H), 1.65 (d, J=1.8 Hz, 3H), 1.48 (s, 3H), 1.37 (s, 3H), 1.24 (s, 3H); $^{13}$C NMR (150 MHz, CDCl$_3$) δ 200.6, 174.8, 173.0, 170.1, 167.0, 164.4, 155.3, 149.9, 149.6, 148.3, 146.1, 145.6, 142.1, 137.2, 136.3, 135.8, 133.8, 133.0, 131.6, 131.2, 131.0, 130.6, 130.0, 130.0, 128.7, 128.7, 127.6, 127.6, 125.7, 125.7, 124.1, 112.0, 88.3, 83.0, 73.3, 70.5, 70.5, 70.3, 70.2, 69.7, 69.6, 54.1, 51.9, 50.5, 49.7, 47.8, 45.3, 43.6, 41.1, 41.1, 39.7, 39.4, 38.5, 32.3, 18.6, 17.3, 15.1, 14.4, 13.1, 13.1, 11.6; IR (thin film, cm$^{-1}$) 3339, 2923, 2866, 1781, 1734, 1659, 1540, 1487, 1437, 1419, 1300; HRMS (ESI) calcd. for $[C_{61}H_{67}N_6O_{12}Cl_1S_1Na]^+$ (M+Na)$^+$: m/z 1165.4118, found 1165.4142.

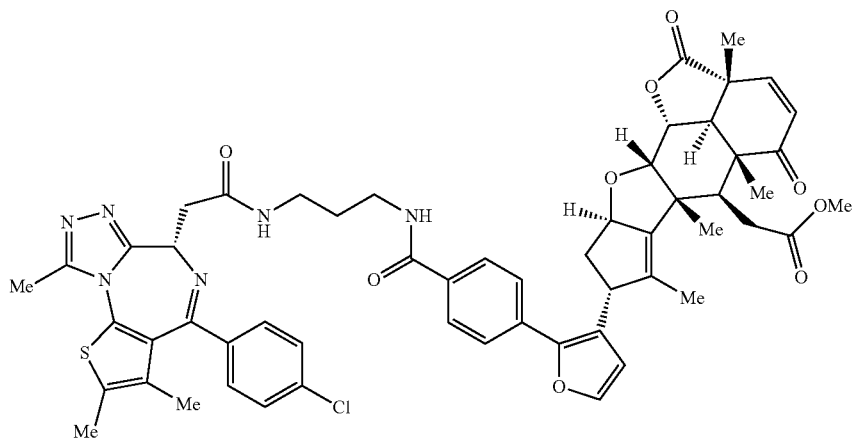

XH2 (10) (42% yield from (3)), a white foam: $[\alpha]_D^{20}$=+ 18.6° (c 0.004 g/mL, CHCl$_3$); $^1$H NMR (600 MHz, CD$_2$Cl$_2$) δ 7.90 (d, J=8.3 Hz, 2H), 7.65-7.57 (m, 3H), 7.44-7.39 (m, 3H), 7.33 (d, J=8.5 Hz, 2H), 7.25 (d, J=9.7 Hz, 1H), 7.07 (t, J=6.5 Hz, 1H), 6.36 (d, J=1.9 Hz, 1H), 5.89 (d, J=9.7 Hz, 1H), 5.52 (app. t, J=7.6 Hz, 1H), 4.66-4.59 (m, 2H), 4.26 (d, J=3.6 Hz, 1H), 4.12 (brd, J=7.6 Hz, 1H), 3.63 (s, 3H), 3.52-3.45 (m, 2H), 3.44-3.34 (m, 4H), 3.20 (dd, J=16.4, 5.5 Hz, 1H), 3.15 (d, J=12.5 Hz, 1H), 2.74 (app. t, J=5.5 Hz, 1H), 2.63 (s, 3H), 2.45-2.37 (m, 4H), 2.25-2.21 (m, 2H), 1.75-1.70 (m, 2H), 1.65 (s, 6H), 1.46 (s, 3H), 1.36 (s, 3H), 1.22 (s, 3H); $^{13}$C NMR (150 MHz, CD$_2$Cl$_2$) δ 201.2, 175.6, 173.5, 171.9, 166.7, 164.5, 156.1, 150.5, 149.9, 148.8, 146.3, 142.5, 137.1, 137.0, 136.6, 134.2, 133.7, 132.7, 131.6, 131.3, 131.2, 130.8, 130.3, 130.3, 129.0, 129.0, 127.8, 127.8, 126.2, 126.2, 124.8, 112.6, 88.6, 83.4, 73.9, 54.9, 52.1, 51.0, 50.2, 48.2, 45.8, 44.1, 41.6, 41.5, 39.7, 36.5, 36.2, 32.7, 29.9, 18.8, 17.5, 15.4, 14.6, 13.4, 13.3, 12.0; IR (thin film, cm$^{-1}$) 3308, 3023, 2930, 2867, 1782, 1734, 1654, 1540, 1488, 1437, 1301; HRMS (ESI) calcd. for [C$_{56}$H$_{57}$ClN$_6$O$_9$S]$^+$ (M+H)$^+$: m/z 1025.3669, found 1025.3669.

Synthesis and Characterization of Cysteine-Reactive Covalent Ligands Previously not Reported General synthetic methods. Chemicals and reagents were purchased from major commercial suppliers and used without further purification. Reactions were performed under a nitrogen atmosphere unless otherwise noted. Silica gel flash column chromatography was performed using EMD or Sigma Aldrich silica gel 60 (230-400 mesh). Proton and carbon nuclear magnetic resonance ($^1$H NMR and $^{13}$C NMR) data was acquired on a Bruker AVB 400, AVQ 400, or AV 600 spectrometer at the University of California, Berkeley. High resolution mass spectrum were obtained from the QB3 mass spectrometry facility at the University of California, Berkeley using positive or negative electrospray ionization (+ESI or −ESI). Yields are reported as a single run.

General Procedure A. The amine (1 eq.) was dissolved in DCM (5 mL/mmol) and cooled to 0° C. To the solution was added acryloyl chloride (1.2 eq.) followed by triethylamine (1.2 eq.). The solution was warmed to room temperature and stirred overnight. The solution was then washed with brine and the crude product was purified by silica gel chromatography (and recrystallization if necessary) to afford the corresponding acrylamide.

General Procedure B. The amine (1 eq.) was dissolved in DCM (5 mL/mmol) and cooled to 0° C. To the solution was added chloroacetyl chloride (1.2 eq.) followed by triethylamine (1.2 eq.). The solution was warmed to room temperature and stirred overnight. The solution was then washed with brine and the crude product was purified by silica gel chromatography (and recrystallization if necessary) to afford the corresponding chloroacetamide.

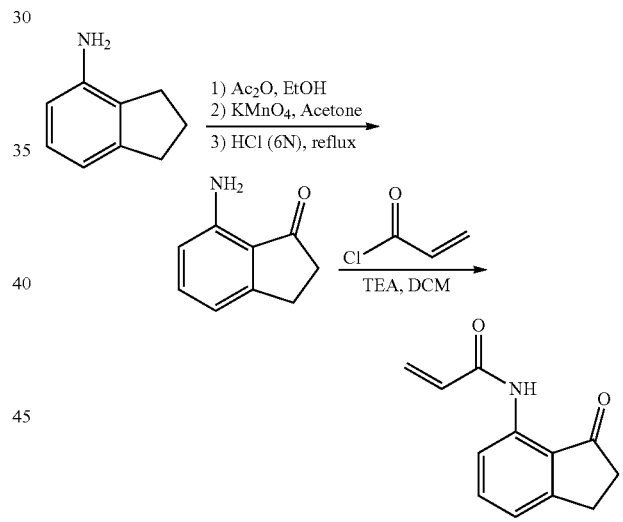

N-(3-oxo-2,3-dihydro-1H-inden-4-yl)acrylamide (TRH 1-129) (13). i. To a solution of 4-aminoindane (1.0 g, 7.5 mmol) in ethanol (20 mL) at 0° C. was added acetic anhydride (1.4 mL, 15.0 mmol). The solution was then warmed to room temperature and stirred overnight at which point the solvent was evaporated in vacuo. The residue was then dissolved in acetone (50 mL) and 15% aqueous magnesium sulfate (1.2 g in 6.75 mL of water) followed by potassium permanganate (3.4 g, 17.0 mmol) were added. The resulting solution was stirred for 24 hours and then filtered through a pad of celite, eluting with chloroform and then water. The eluent was separated, and the aqueous layer was extracted several times with additional chloroform. The combined organics were dried over magnesium sulfate, filtered and evaporated in vacuo. The residue was then dissolved in 6N HCl (20 mL) and heated to 90° C. After stirring for 5 hours, the solution was cooled, neutralized with small portions of potassium carbonate, and extracted with ethyl acetate. The combined organics were dried with magnesium sulfate, filtered, and evaporated in vacuo to give the crude 7-aminoindan-1-one (610 mg, 55% over 3 steps) which was used without further purification.

ii. To a solution of the crude 7-aminoindan-1-one in dichloromethane (15 mL) was added acryloyl chloride (0.39 mL, 4.8 mmol) followed by triethylamine (0.67 mL, 4.8 mmol) at 0° C. under an atmosphere of $N_2$. The reaction mixture was warmed to room temperature and stirred overnight. The reaction mixture was then washed with 1M HCl solution twice, brine, and concentrated in vacuo. The crude material was purified by silica gel chromatography (10% to 20% ethyl acetate in hexanes) to yield (13) the product (390 mg, 47% yield, 26% combined yield over 4 steps) as a white solid.

$^1$H NMR (400 MHz, CDCl$_3$): δ 10.64 (s, 1H), 8.45 (d, J=8.2 Hz, 1H), 7.55 (t, J=7.9 Hz, 1H), 7.12 (d, J=7.6 Hz, 1H), 6.45 (dd, J=1.0, 17.0 Hz, 1H), 6.33 (dd, J=10.1, 17.0 Hz, 1H), 5.82 (dd, J=1.0, 10.1 Hz, 1H), 3.11 (t, J=11.5 Hz, 2H), 2.74-2.71 (m, 2H). $^{13}$C NMR (100 MHz, CDCl$_3$): δ 209.3, 164.4, 155.9, 138.7, 137.0, 131.7, 128.0, 123.1, 120.8, 116.9, 36.5, 25.5. HRMS (+ESI): Calculated: 202.0863 (C$_{12}$H$_{12}$NO$_2$). Observed: 202.0860.

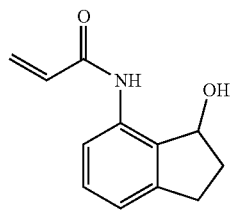

N-(3-hydroxy-2,3-dihydro-1H-inden-4-yl)acrylamide (TRH 1-133) (14). To a solution of (13) (201 mg, 1.0 mmol) in anhydrous methanol (7 mL) under nitrogen atmosphere was added sodium borohydride (46.1 mg, 1.2 mmol). After 30 minutes of stirring, the reaction was quenched with saturated sodium bicarbonate solution and extracted three times with DCM. The combined organic layers were dried with magnesium sulfate, filtered, and concentrated in vacuo. The crude material was purified by silica gel chromatography (30 to 50% ethyl acetate in hexanes) affording (14) (190 mg, 94% yield) as a white solid.

$^1$H NMR (400 MHz, CDCl$_3$): δ 8.93 (s, 1H), 7.98 (d, J=7.8 Hz, 1H), 7.19 (t, J=7.9 Hz, 11H), 6.95 (d, J=7.4 Hz, 1H), 6.29 (d, J=16.8 Hz, 1H), 6.15 (dd, J=10.2, 16.9 Hz, 1H), 5.66 (d, J=10.2 Hz, 1H), 5.32 (q, J=6.9 Hz, 1H), 3.60 (d, J=6.7 Hz, 1H), 2.96 (ddd, J=2.4, 9.0, 15.7 Hz), 2.73 (quint, J=8.1 Hz, 1H), 2.56-2.48 (m, 1H), 1.96-1.86 (m, 1H). $^{13}$C NMR (100 MHz, CDCl$_3$): δ 164.1, 143.7, 135.6, 132.8, 131.6, 129.5, 127.3, 121.0, 118.5, 76.2, 36.0, 29.8. HRMS (–ESI): Calculated: 202.0874 (C$_{12}$H$_{12}$NO$_2$). Observed: 202.0874.

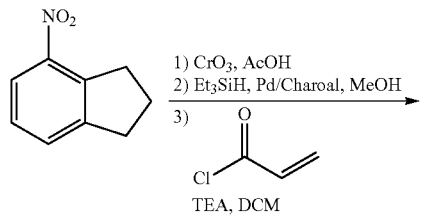

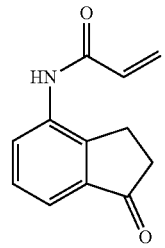

N-(1-oxo-2,3-dihydro-1H-inden-4-yl)acrylamide (TRH 1-134) (15). i. To a solution of 4-nitroindane (5.38 g, 33 mmol) in acetic acid (250 mL) was slowly added chromium trioxide (8.95 g, 90 mmol). After stirring for 24 hours, the reaction was neutralized with 2M NaOH and extracted five times with ethyl acetate. The combined organics were washed with a saturated sodium bicarbonate solution and brine, dried over magnesium sulfate, filtered, and concentrated in vacuo. The crude material was purified by silica gel chromatography (10-20% ethyl acetate in hexanes) to give 1.26 g (ca. 7.1 mmol) of 4-nitroindanone as a white solid.

ii. This intermediate was then combined with palladium on activated charcoal (125 mg, 10 wt %) dissolved in anhydrous methanol (21 mL) under an atmosphere of a nitrogen. Triethylsilane (11.3 mL, 71 mmol) was slowly added by addition funnel over the course of 10 minutes to the reaction in a room temperature water bath. After an additional 20 minutes of stirring, the reaction mixture was filtered through a pad of celite and concentrated in vacuo to give 4-aminoindanone which was used without further purification.

iii. The aforementioned crude aminoindanone was dissolved in DCM (21 mL) under an atmosphere of nitrogen and cooled to 0° C. at which point acryloyl chloride (0.77 mL, 9.5 mmol) and triethylamine (1.19 mL, 8.5 mmol) were slowly added dropwise. The reaction mixture was warmed to room temperature, stirred overnight, washed twice with brine, dried over magnesium sulfate, filtered, and concentrated in vacuo. The crude material was purified by silica gel chromatography (30-50% ethyl acetate in hexanes) affording (15) (989 mg, 15% yield over 3 steps) as a white solid.

$^1$H NMR (400 MHz, CDCl$_3$): δ 8.20 (d, J=5.8 Hz, 1H), 7.63 (s, 1H), 7.56 (d, J=7.5 Hz, 1H), 7.39 (t, J=7.7 Hz, 1H), 6.48 (d, J=16.7 Hz, 1H), 6.37 (dd, J=10.0, 16.8 Hz, 1H), 5.83 (d, J=10.1 Hz, 1H), 3.04 (t, J=5.6 Hz, 2H), 2.70 (t, J=5.7 Hz, 2H). $^{13}$C NMR (100 MHz, CDCl$_3$): δ 206.3, 163.9, 146.0, 138.0, 135.4, 130.7, 128.8, 128.7, 127.6, 120.4, 36.1, 23.4. HRMS (–ESI): Calculated: 200.0717 (C$_{12}$H$_{10}$NO$_2$). Observed: 200.0715.

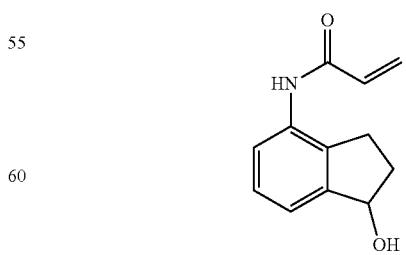

N-(1-hydroxy-2,3-dihydro-1H-inden-4-yl)acrylamide (TRH 1-135) (16). To a solution of (15) (1.26 g, 6.25 mmol) in anhydrous methanol (50 mL) under nitrogen atmosphere was added sodium borohydride (292.7 mg, 7.7 mmol). After 30 minutes of stirring, the reaction was quenched with water and the methanol was removed in vacuo. The residue was saturated with NaCl and extracted five times with a 2:1 chloroform:methanol solution. The combined organic layers were dried over 3Å molecular sieves, filtered, and concentrated in vacuo. The crude material was purified by silica gel chromatography (40 to 70% ethyl acetate in hexanes) to give (16) (1.05 g, 83% yield) as a white solid.

$^1$H NMR (400 MHz, MeOD): δ 7.50 (dd, J=2.3, 6.3 Hz, 1H), 7.25-7.20 (m, 2H), 6.51 (dd, J=10.2, 17.0 Hz, 1H), 6.35 (dd, J=1.7, 17.0 Hz, 1H), 5.77 (dd, J=1.7, 10.2 Hz, 1H), 5.17 (t, J=6.3 Hz, 1H), 2.97 (ddd, J=4.5, 8.6, 16.2, 1H), 2.74 (quint, J=7.8 Hz, 1H), 2.47-2.39 (m, 1H), 1.95-1.86 (m, 1H). $^{13}$C NMR (100 MHz, MeOD): δ 166.3, 148.0, 137.8, 134.8, 132.1, 128.3, 127.9, 124.0, 122.7, 76.9, 36.1, 28.6. HRMS (−ESI): Calculated: 202.0874 ($C_{12}H_{12}NO_2$). Observed: 202.0872.

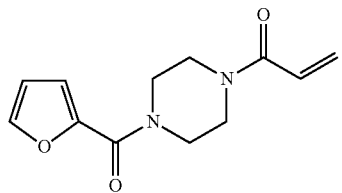 [SMILES: C=CC(=O)N1CCN(C(=O)c2ccco2)CC1]

1-(4-(furan-2-carbonyl)piperazin-1-yl)prop-2-en-1-one (TRH 1-145) (17). To a solution 1-(2-furoyl)piperazine (362 mg, 2.0 mmol) in dichloromethane (10 mL) was added acryloyl chloride (0.20 mL, 2.4 mmol) followed by triethylamine (0.34 mL, 2.4 mmol) at 0° C. under an atmosphere of nitrogen. After stirring for 20 minutes, the reaction mixture was warmed to room temperature and was stirred an additional 24 hours. The reaction mixture was washed twice with brine, dried over magnesium sulfate, and concentrated in vacuo. The resulting crude material was purified by silica gel chromatography (70% to 100% ethyl acetate in hexanes) to yield (17) (446 mg, 95%) as a yellow solid.

$^1$H NMR (400 MHz, CDCl$_3$): δ 7.53 (m, 1H), 7.06 (dd, J=0.7, 3.5 Hz, 1H), 6.61 (dd, J=10.5, 16.8 Hz, 1H), 6.52 (dd, J=1.8, 3.5 Hz, 1H), 6.33 (dd, J=1.9, 16.8 Hz, 1H), 5.75 (dd, J=1.9, 10.5 Hz, 1H), 3.84-3.67 (m, 8H). $^{13}$C NMR (100 MHz, CDCl$_3$): δ 165.5, 159.1, 147.5, 144.0, 128.5, 127.1, 117.0, 111.5, 45.6, 41.9. HRMS (+ESI): Calculated: 235.1077 ($C_{12}H_{15}N_2O_3$). Observed: 235.1075.

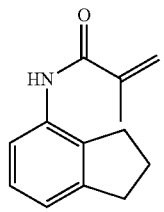

N-(2,3-dihydro-1H-inden-4-yl)methacrylamide (TRH 1-149) (18). To a solution 4-aminoindane (0.24 mL, 2.0 mmol) in dichloromethane (10 mL) was added methacryloyl chloride (0.23 mL, 2.4 mmol) followed by triethylamine (0.34 mL, 2.4 mmol) at 0° C. under an atmosphere of nitrogen. After stirring for 20 minutes, the reaction mixture was warmed to room temperature and stirred for an additional 3.5 hours. The reaction mixture was then washed twice with brine, dried over magnesium sulfate, and concentrated in vacuo. The resulting crude material was purified by silica gel chromatography (35% to 40% ethyl acetate in hexanes) to yield (18) (378 mg, 94%) as an off-white solid.

$^1$H NMR (400 MHz, CDCl$_3$): δ 7.72 (d, J=8.0 Hz, 1H), 7.55 (s, 1H), 7.12 (t, J=7.7 Hz, 1H), 7.01 (d, J=7.4 Hz, 1H), 5.79 (s, 1H), 5.42 (s, 1H), 2.93 (t, J=7.5 Hz, 2H), 2.79 (t, J=7.4 Hz, 2H), 7.12-2.06 (m, 2H), 2.04 (s, 3H). $^{13}$C NMR (100 MHz, CDCl$_3$): δ 166.3, 145.1, 140.6, 134.5, 133.7, 127.0, 120.7, 119.8, 118.9, 33.1, 29.9, 24.7, 18.6. HRMS (+ESI): Calculated: 202.1226 ($C_{13}H_{16}NO$). Observed: 202.1224.

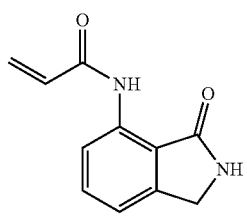

N-(3-oxoisoindolin-4-yl)acrylamide (TRH 1-152) (19). To a solution of 7-aminoisoindolin-1-one (99 mg, 0.67 mmol) in dichloromethane (4 mL) was added acryloyl chloride (0.07 mL, 0.8 mmol) followed by triethylamine (0.11 mL, 0.8 mmol) at 0° C. under N$_2$ atmosphere. After stirring for 20 minutes, the reaction mixture was warmed to room temperature and stirred overnight. The reaction mixture was washed twice with brine, dried over magnesium sulfate, and concentrated in vacuo. The resulting crude material was purified by silica gel chromatography (50 to 60% ethyl acetate in hexanes) to afford the title compound (58 mg, 43%) as a white solid.

$^1$H NMR (400 MHz, CDCl$_3$): δ 10.50 (s, 1H), 8.58 (d, J=8.2 Hz, 1H), 7.55 (t, J=7.9 Hz, 1H), 7.15 (d, J=7.5 Hz, 1H), 6.82 (s, 1H), 6.46 (dd, J=1.3, 17.0 Hz, 1H), 6.36 (dd, J=10.0, 17.0 Hz, 1H), 5.81 (dd, J=1.3, 10.0 Hz, 1H), 4.46 (s, 2H). $^{13}$C NMR (100 MHz, CDCl$_3$): δ 172.9, 164.2, 143.9, 138.2, 133.8, 131.8, 127.8, 118.0, 117.7, 117.6, 45.6. HRMS (+ESI): Calculated: 203.0815 ($C_{11}H_{11}N_2O_2$). Observed: 203.0814.

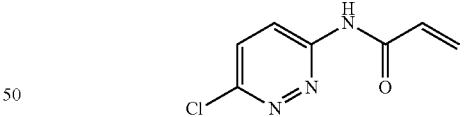

N-(6-chloropyridazin-3-yl)acrylamide (TRH 1-155) (20). To a solution 3-amino-6-chloropyridazine (261 mg, 2.0 mmol) in dichloromethane (10 mL) was added acryloyl chloride (0.20 mL, 2.4 mmol) followed by triethylamine (0.34 mL, 2.4 mmol) at 0° C. under an atmosphere of nitrogen. After stirring for 20 minutes, the reaction mixture was warmed to room temperature and stirred overnight. The solution was washed twice with brine, dried over magnesium sulfate, and concentrated in vacuo. The resulting crude material was purified by silica gel chromatography (40% to 50% ethyl acetate in hexanes) to yield (20) (23 mg, 6%) as a pale-yellow solid.

$^1$H NMR (400 MHz, CDCl$_3$): δ 10.06 (s, 1H), 8.70 (d, J=9.4 Hz, 1H), 7.57 (d, J=9.4 Hz, 1H), 6.73 (dd, J=10.2, 16.8 Hz, 1H) 6.56 (dd, J=1.2, 16.8 Hz, 1H), 5.94 (dd, J=1.2, 10.2 Hz,

1H). ¹³C NMR (100 MHz, CDCl₃): δ 164.8, 155.2, 152.3, 130.7, 130.4, 130.3, 122.0. HRMS (+ESI): Calculated: 182.0127 (C₇H₅N₃OCl). Observed: 182.0126.

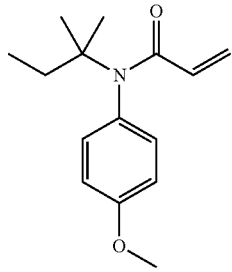 [SMILES: C=CC(=O)N(c1ccc(OC)cc1)C(C)(C)CC]

N-(4-methoxyphenyl)-N-(tert-pentyl)acrylamide (TRH 1-170) (21). To a solution of 4-methoxy-N-(tert-pentyl) aniline (94 mg, 0.49 mmol) in dichloromethane (5 mL) was added acryloyl chloride (0.05 mL, 0.6 mmol) followed by triethylamine (0.09 mL, 0.6 mmol) at 0° C. under an atmosphere of nitrogen. After stirring for 15 minutes, the reaction mixture was warmed to room temperature and stirred an additional 18 hours. The reaction mixture was then washed with saturated aqueous sodium bicarbonate solution, brine, dried over magnesium sulfate, and concentrated in vacuo. The resulting crude material was purified by silica gel chromatography (0% to 20% ethyl acetate in hexanes) to yield the title compound (82 mg, 68%) as a pale-yellow oil.

¹H NMR (400 MHz, CDCl₃): δ 6.99 (d, J=8.7 Hz, 2H), 6.85 (d, J=8.7 Hz, 2H), 6.17 (dd, J=1.9, 16.7 Hz, 1H), 5.76 (dd, J=10.3, 16.7 Hz, 1H), 5.28 (dd, J=1.9, 10.3 Hz, 1H), 3.81 (s, 3H), 2.11 (q, J=7.5 Hz, 2H), 1.20 (s, 6H), 0.91 (t, J=7.5 Hz, 3H). ¹³C NMR (100 MHz, CDCl₃): δ 166.3, 159.0, 134.3, 131.49, 131.45, 125.6, 114.1, 61.7, 55.5, 32.0, 27.4, 9.4. HRMS (+ESI): Calculated: 247.1572 (C₁₅H₂₁NO₂). Observed: 247.1577.

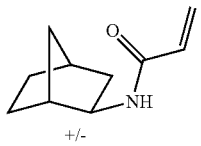

N-(exo-norborn-2-yl)acrylamide (TRH 1-176) (22). To a solution of exo-2-aminonorbornane (0.24 mL, 2 mmol) in dichloromethane (10 mL) was added acryloyl chloride (0.20 mL, 2.4 mmol) followed by triethylamine (0.33 mL, 2.4 mmol) at 0° C. under an atmosphere of nitrogen. After stirring for 20 minutes, the reaction mixture was warmed to room temperature and stirred for an additional 18 hours. The reaction mixture was then washed with saturated aqueous sodium bicarbonate solution, brine, dried over magnesium sulfate, and concentrated in vacuo. The resulting crude material was purified by silica gel chromatography (30% ethyl acetate in hexanes) to yield the title compound (271 mg, 82%) as a white solid.

¹H NMR (400 MHz, CDCl₃): δ 6.42 (s, 1H), 6.25 (dd, J=2.3, 17.0 Hz, 1H), 6.18 (dd, J=9.5, 17.0 Hz, 1H), 5.58 (dd, J=2.3, 9.5 Hz, 1H), 3.8-3.77 (m, 1H), 2.27-2.24 (m, 2H), 1.78 (ddd, J=2.1, 8.1, 13.0 Hz, 1H), 1.55-1.38 (m, 3H), 1.30-1.10 (m, 4H). ¹³C NMR (100 MHz, CDCl₃): δ 165.0, 131.8, 125.8, 52.9, 42.4, 40.0, 35.7, 35.6, 28.2, 26.6. HRMS (+EI): Calculated: 165.1154 (C₁₀H₁₅NO). Observed: 165.1155.

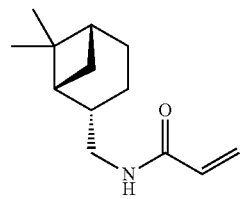

N-(((1R,2S,5R)-6,6-dimethylbicyclo[3.1.1]heptan-2-yl) methyl)acrylamide (TRH 1-178) (23). To a solution of (−)-cis-myrtanylamine (0.34 mL, 2 mmol) in dichloromethane (10 mL) was added acryloyl chloride (0.20 mL, 2.4 mmol) followed by triethylamine (0.33 mL, 2.4 mmol) at 0° C. under an atmosphere of nitrogen. After stirring for 20 minutes, the reaction mixture was warmed to room temperature and stirred for an additional 21 hours. The reaction mixture was then washed with saturated aqueous sodium bicarbonate solution, brine, dried over magnesium sulfate, and concentrated in vacuo. The resulting crude material was purified by silica gel chromatography (20 to 30% ethyl acetate in hexanes) to yield the title compound (369 mg, 89%) as a white solid.

¹H NMR (600 MHz, CDCl₃): δ 6.26 (dd, J=1.5, 17.0 Hz, 1H), 6.11 (dd, J=10.3, 17.0 Hz, 1H) 5.85 (s, 11H), 5.61 (dd, J=1.5, 10.3 Hz, 1H), 3.39-3.29 (m, 2H), 2.38-2.34 (m, 1H), 2.26-2.21 (m, 1H), 1.98-1.90 (m, 4H), 1.88-1.83 (m, 1H), 1.53-1.47 (m, 1H), 1.19 (s, 3H), 1.04 (s, 3H), 0.89 (d, J=9.6 Hz, 1H). ¹³C NMR (150 MHz, CDCl₃): δ 165.7, 131.2, 126.2, 45.3, 43.9, 41.5, 38.8, 33.3, 28.1, 26.1, 23.3, 19.9. HRMS (−ESI): Calculated: 206.1550 (C₁₃H₂₀NO). Observed: 206.1551.

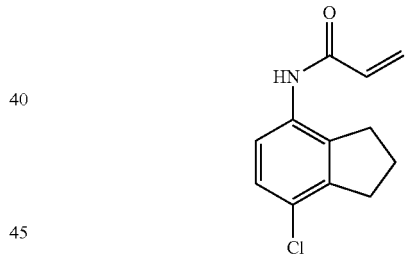

N-(7-chloro-2,3-dihydro-1H-inden-4-yl)acrylamide (YP 1-1) (24). A solution of N-(2,3-dihydro-1H-inden-4-yl)acrylamide (187 mg, 1.0 mmol) in PEG 400 (5.2 mL) was cooled to 0° C. and N-chlorosuccinimide (140 mg, 1.0 mmol) added. After 30 minutes, the mixture was warmed to room temperature and stirred overnight. The reaction mixture was diluted with ethyl acetate, washed with brine twice, and dried over magnesium sulfate. The volatiles were removed in vacuo and the crude product purified by silica gel chromatography (30% ethyl acetate in hexanes). The obtained mixture of isomers were recrystallized to afford the title compound (47 mg, 22% yield) as a white solid.

¹H NMR (400 MHz, CDCl₃): δ 7.78 (d, J=8.8 Hz, 1H), 7.15-7.11 (m, 2H), 6.42 (dd, J=1.4, 16.8 Hz, 1H), 6.26 (dd, J=10.2, 16.8 Hz, 1H), 5.77 (dd, J=1.4, 10.2 Hz, 1H), 2.98 (t, J=7.6 Hz, 2H), 2.87 (t, J=7.5 Hz, 2H), 2.12 (quint, J=7.5 Hz, 2H). ¹³C NMR (100 MHz, CDCl₃): δ 163.4, 143.1, 136.1, 132.2, 131.0, 128.0, 127.2, 126.7, 120.9, 32.7, 31.1, 24.0. HRMS (+ESI): Calculated: 220.0535 (C₁₂H₁₁ClNO). Observed: 220.0533.

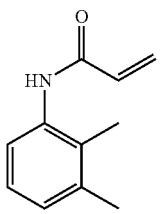

N-(2,3-dimethylphenyl)acrylamide (YP 1-18) (25). A solution of 2,3-dimethylaniline (121 mg, 1.0 mmol) in DCM (10 mL) was cooled to 0° C. and acryloyl chloride (109 mg, 1.2 mmol) and triethylamine (121 mg, 1.2 mmol) were added sequentially. The reaction mixture was maintained at this temperature for 30 minutes and then warmed to room temperature and stirred overnight. The reaction mixture was washed twice with brine and dried over magnesium sulfate. Volatiles were removed in vacuo and the crude material purified by silica gel chromatography (30% to 40% ethyl acetate in hexanes) to afford the product (154 mg, 88%) as a white solid.

$^1$H NMR (400 MHz, CDCl$_3$): δ 7.49 (d, J=7.9 Hz, 1H), 7.29 (s, 1H), 7.11-7.07 (m, 1H), 7.01 (d, J=7.7, 1H) 6.40 (d, J=17.1, 1H), 6.30 (dd, J=7.3, 17.1 Hz, 1H), 5.74 (d, J=10.1 Hz, 1H), 2.29 (s, 1H), 2.13 (s, 1H). $^{13}$C NMR (100 MHz, CDCl$_3$): δ 135.1, 131.2, 127.6, 127.3, 125.9, 122.3, 20.6, 13.9. HRMS (+ESI): Calculated: 176.1070 (C$_{11}$H$_{14}$NO). Observed: 176.1068.

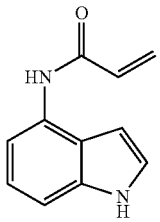

N-(1H-indol-4-yl)acrylamide (YP 1-19) (26). A solution of 4-aminoindole (132 mg, 1 mmol) in DCM/DMF (1:1 v:v, 10 mL) was cooled to 0° C. and acryloyl chloride (109 mg, 1.2 mmol) and triethylamine (121 mg, 1.2 mmol) added sequentially. The reaction mixture was stirred at this temperature for 26 minutes and then warmed to room temperature and stirred overnight. The reaction mixture was washed twice with brine and dried over magnesium sulfate. Volatiles were removed in vacuo and the crude product purified by basic alumina chromatography (60% to 75% ethyl acetate in hexanes) to afford the title compound (56 mg, 30%) as a white-grey solid.

$^1$H NMR (600 MHz, MeOD): δ 7.51 (d, J=7.6 Hz, 1H), 7.24-7.22 (m, 2H), 7.08 (t, J=7.6 Hz, 1H), 6.64 (dd, J=10.1, 16.7 Hz, 2H), 6.38 (dd, J=1.7, 16.9 Hz, 1H), 5.78 (dd, J=1.7, 10.3 Hz, 1H), 4.6 (s, 1H). $^{13}$C NMR (150 MHz, MeOD): δ 165.0, 137.2, 131.1, 129.2, 126.0, 123.8, 121.5, 120.9, 112.2, 108.4, 98.5. HRMS (+ESI): Calculated: 187.0866 (C$_{11}$H$_{11}$N$_2$O). Observed: 187.0865.

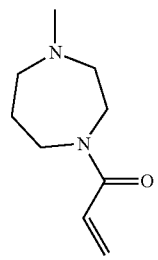

1-(4-methyl-1,4-diazepan-1-yl)prop-2-en-1-one (YP 1-23) (27). A solution of 1-methylhomopiperazine (114 mg, 1.0 mmol) in DCM (10 mL) was cooled to 0° C. and acryloyl chloride (109 mg, 1.2 mmol) and triethylamine (121 mg, 1.2 mmol) added sequentially. The solution was maintained at this temperature for 30 minutes and then warmed to room temperature and stirred overnight. The reaction mixture was washed twice with brine and dried over magnesium sulfate. After removal of the volatiles in vacuo, the crude product was purified via silica gel chromatography (1% to 10% methanol in DCM) affording the title compound (58 mg, 51%) as a yellow oil (mixture of rotamers).

$^1$H NMR (400 MHz, CDCl$_3$): δ 6.61-6.53 (m, 1H), 6.35-6.29 (m, 1H), 5.70-5.66 (m, 1H), 3.74-3.72 (m, 1H), 3.69 (t, J=6.4 Hz, 1H), 3.65-3.61 (m, 2H), 2.66-2.63 (m, 2H), 2.59-2.54 (m, 2H), 2.37 (s, 3H), 1.94 (quint, J=6.2 Hz, 2H). $^{13}$C NMR (100 MHz, CDCl$_3$): δ 166.4, 166.3, 128.0, 127.9, 127.8, 127.6, 59.1, 58.0, 57.1, 56.8, 47.4, 47.1, 46.7, 46.6, 45.3, 44.8, 28.1, 26.9. HRMS (+ESI): Calculated: 169.1335 (C$_9$H$_{17}$N$_2$O). Observed: 169.1333.

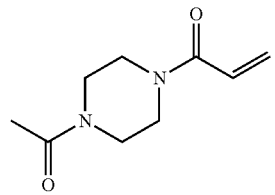

1-(4-acetylpiperazin-1-yl)prop-2-en-1-one (YP 1-24) (28). A solution of 1-acetylpiperazine (128 mg, 1.0 mmol) in DCM (10 mL) was cooled to 0° C. and acryloyl chloride (109 mg, 1.2 mmol) and triethylamine (121 mg, 1.2 mmol) added sequentially. The solution was stirred at this temperature for 23 minutes and then warmed to room temperature and stirred an additional two hours. The reaction mixture was washed twice with brine, dried over magnesium sulfate, and the volatiles removed in vacuo. The crude material was purified via silica gel chromatography (0% to 10% methanol in DCM) to afford the title compound (40 mg, 18%) as a yellow oil.

$^1$H NMR (400 MHz, CDCl$_3$): δ 6.57 (dd, J=10.5, 16.8 Hz, 1H), 6.33 (dd, J=1.8, 16.8 Hz, 1H), 5.75 (dd, J=1.9, 10.5 Hz, 1H), 3.72 (s, 1H), 3.66-3.64 (m, 3H), 3.57 (s, 1H), 3.51-3.49 (m, 2H), 2.13 (s, 3H). $^{13}$C NMR (100 MHz, CDCl$_3$): δ 169.0, 165.6, 128.7, 127.0, 41.9, 41.4, 21.4. HRMS (+ESI): Calculated: 183.1128 (C$_9$H$_{15}$N$_2$O$_2$). Observed: 183.1126.

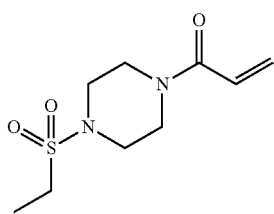

1-(4-(Ethylsulfonyl)piperazin-1-yl)prop-2-en-1-one (YP 1-25) (29). A solution of 1-(ethanesulfonyl)piperazine (178 mg, 1.0 mmol) in DCM (10 mL) was cooled to 0° C. and acryloyl chloride (109 mg, 1.2 mmol) and triethylamine (121 mg, 1.2 mmol) added sequentially. The solution was stirred at this temperature for 27 minutes and then warmed to room temperature and stirred for an additional two hours. The solution was washed twice with brine and dried over magnesium sulfate. The crude material was purified by silica gel chromatography (1% to 10% methanol in DCM) to afford the title compound (163 mg, 70%) as a white-yellow solid.

$^1$H NMR (400 MHz, CDCl$_3$): δ 6.57 (dd, J=10.5, 16.8 Hz, 1H), 6.32 (dd, J=1.9, 16.8 Hz, 1H), 5.76 (dd, J=1.8, 10.5 Hz, 1H), 3.77 (s, 2H), 3.67 (s, 2H), 3.32 (t, J=5.2 Hz, 4H), 2.98 (q, J=7.5 Hz, 2H), 1.37 (t, J=7.4, 3H). $^{13}$C NMR (100 MHz, CDCl$_3$): δ 165.5, 128.8, 127.0, 77.4, 45.9, 45.6, 44.2, 41.9, 7.8. HRMS (+ESI): Calculated: 233.0954 (C$_9$H$_{17}$N$_2$O$_3$S$_1$). Observed: 233.0953.

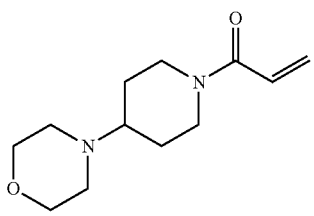 [SMILES: C=CC(=O)N1CCC(N2CCOCC2)CC1]

1-(4-morpholinopiperidin-1-yl)prop-2-en-1-one (YP 1-42) (30). Following General Procedure A using 4-morpholinopiperidine (336 mg, 2.0 mmol), the product was obtained after silica gel chromatography (1% methanol and 80% ethyl acetate in hexanes) as a colorless oil (259 mg, 58%).

$^1$H NMR (400 MHz, CDCl$_3$): δ 6.42 (dd, J=10.6, 16.8 Hz, 1H), 6.06 (dd, J=2.0, 16.8 Hz, 1H), 5.49 (dd, J=2.0, 10.6 Hz, 1H), 4.45 (d, J=12.8 Hz, 1H), 3.86 (d, J=12.8 Hz, 1H), 3.52 (t, J=4.7 Hz, 4H), 2.90 (t, J=12.8 Hz, 1H), 2.55-2.48 (m, 1H), 2.37-2.35 (m, 4H), 2.26 (tt, J=3.7, 11.0 Hz, 1H), 1.72 (d, J=12.8 Hz, 2H), 1.30-1.20 (m, 2H). $^{13}$C NMR (100 MHz, CDCl$_3$): δ 165.0, 127.7, 127.3, 67.1, 61.6, 49.6, 44.9, 41.1, 28.9, 27.8. HRMS (+ESI): Calculated: 225.1598 (C$_{12}$H$_{21}$N$_2$O$_2$). Observed: 225.1595.

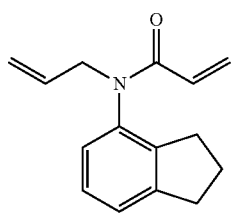 [SMILES: C=CCN(C(=O)C=C)c1cccc2c1CCC2]

N-allyl-N-(2,3-dihydro-1H-inden-4-yl)acrylamide (IGA 1-12) (31). To a solution of sodium hydride (96 mg, 4.0 mmol) in tetrahydrofuran (8 mL) was added N-(2,3-dihydro-1H-inden-4-yl)acrylamide (187 mg, 1.0 mmol) in tetrahydrofuran (2 mL) under an atmosphere of nitrogen. The reaction mixture was cooled to 0° C. and 3-bromoprop-1-ene (484 mg, 4.0 mmol) was and the mixture warmed to room temperature and stirred overnight. The reaction was quenched by the addition of water and extracted with ethyl acetate. The crude product was purified by silica gel chromatography (20% ethyl acetate in hexanes) to afford the product (151 mg, 67%) as a yellow crystalline solid.

$^1$H NMR (400 MHz, CDCl$_3$): δ 7.06-7.18 (m, 2H), 6.80-6.88 (m, 1H), 6.26-6.37 (dd, J=16.8, 2.0 Hz, 1H), 5.76-5.96 (m, 2H), 5.38-5.48 (dd, J=10.3, 2.1 Hz, 1H), 4.98-5.08 (m, 2H), 4.40-4.52 (ddt, J=14.5, 6.3, 1.3 Hz, 1H), 4.00-4.11 (ddt, J=14.5, 6.8, 1.2 Hz, 1H), 2.82-2.98 (m, 2H), 2.59-2.79 (m, 2H), 1.92-2.07 (m, 2H). $^{13}$C NMR (100 MHz, CDCl$_3$): δ 165.1, 146.5, 142.4, 137.9, 133.0, 128.4, 127.8, 127.48, 126.1, 124.3, 118.1, 51.6, 33.3, 30.9, 25.0. HRMS (+ESI): Calculated: 228.13 (C$_{15}$H$_{17}$NO). Observed: 228.1381.

N-allyl-N-(2,3-dihydro-1H-inden-4-yl)acrylamide (IGA 1-15) (32). To a solution of sodium hydride (96 mg, 4.0 mmol) in tetrahydrofuran (8 mL) was added N-(2,3-dihydro-1H-inden-4-yl)acrylamide (187 mg, 1.0 mmol) in tetrahydrofuran (2 mL) under an atmosphere of nitrogen. The solution was cooled to 0° C. and 1-bromohexane (660 mg, 4.0 mmol) was added after which point the solution was warmed to room temperature and stirred overnight. The solution was quenched with water and extracted with ethyl acetate. The crude product was purified via silica gel chromatography (20% ethyl acetate in hexanes) to afford the product in 34% yield as a yellow oil (92 mg).

$^1$H NMR (400 MHz, CDCl$_3$): δ 7.11-7.25 (m, 2H), 6.86-6.96 (dd, J=7.5, 1.2 Hz, 1H), 6.30-6.40 (dd, J=16.8, 2.1 Hz, 1H), 5.86-6.00 (m, 1H), 5.41-5.51 (dd, J=10.3, 2.1 Hz, 1H), 3.82-3.96 (m, 1H), 3.42-3.56 (m, 1H), 2.90-3.04 (m, 2H), 2.65-2.85 (m, 2H), 1.98-2.16 (m, 2H), 1.47-1.63 (m, 2H), 1.20-1.36 (m, 6H), 0.80-0.90 (m, 3H). $^{13}$C NMR (100 MHz, CDCl$_3$): δ 165.2, 146.5, 142.4, 138.2, 128.6, 127.5, 127.4, 126.1, 124.1, 48.7, 33.3, 31.6, 30.9, 27.9, 26.7, 25.0, 22.6, 14.1. HRMS (+ESI): Calculated: 272.19 (C$_{18}$H$_{25}$NO). Observed: 272.2007.

References Pertaining to Examples 7-9

1. Nomura, D. K. & Maimone, T. J. Target Identification of Bioactive Covalently Acting Natural Products. Curr. Top. Microbiol. Immunol. 420, 351-374 (2018). 2. Drahl, C., Cravatt, B. F. & Sorensen, E. J. Protein-reactive natural products. Angew. Chem. Int. Ed Engl. 44, 5788-5809 (2005). 3. Liu, J. et al. Calcineurin is a common target of cyclophilin-cyclosporin A and FKBP-FK506 complexes. Cell 66, 807-815 (1991). 4. Cohen, E., Quistad, G. B. &

Casida, J. E. Cytotoxicity of nimbolide, epoxyazadiradione and other limonoids from neem insecticide. Life Sci. 58, 1075-1081 (1996). 5. Bodduluru, L. N., Kasala, E. R., Thota, N., Barua, C. C. & Sistla, R. Chemopreventive and therapeutic effects of nimbolide in cancer: the underlying mechanisms. Toxicol. Vitro Int. J. Publ. Assoc. BIBRA 28, 1026-1035 (2014). 6. Subramani, R. et al. Nimbolide inhibits pancreatic cancer growth and metastasis through ROS-mediated apoptosis and inhibition of epithelial-to-mesenchymal transition. Sci. Rep. 6, 19819 (2016). 7. Hao, F., Kumar, S., Yadav, N. & Chandra, D. Neem components as potential agents for cancer prevention and treatment. Biochim. Biophys. Acta 1846, 247-257 (2014). 8. Gupta, S. C., Prasad, S., Tyagi, A. K., Kunnumakkara, A. B. & Aggarwal, B. B. Neem (Azadirachta indica): An indian traditional panacea with modern molecular basis. Phytomedicine Int. J. Phytother. Phytopharm. 34, 14-20 (2017). 9. Burslem, G. M. & Crews, C. M. Small-Molecule Modulation of Protein Homeostasis. Chem. Rev. 117, 11269-11301 (2017). 10. Lai, A. C. & Crews, C. M. Induced protein degradation: an emerging drug discovery paradigm. Nat. Rev. Drug Discov. 16, 101-114 (2017). 11. Bianchini, G., Balko, J. M., Mayer, I. A., Sanders, M. E. & Gianni, L. Triple-negative breast cancer: challenges and opportunities of a heterogeneous disease. Nat. Rev. Clin. Oncol. 13, 674-690 (2016). 12. Weerapana, E. et al. Quantitative reactivity profiling predicts functional cysteines in proteomes. Nature 468, 790-795 (2010). 13. Roberts, A. M., Ward, C. C. & Nomura, D. K. Activity-based protein profiling for mapping and pharmacologically interrogating proteome-wide ligandable hotspots. Curr. Opin. Biotechnol. 43, 25-33 (2017). 14. Grossman, E. A. et al. Covalent Ligand Discovery against Druggable Hotspots Targeted by Anti-cancer Natural Products. Cell Chem. Biol. 24, 1368-1376.e4 (2017). 15. Backus, K. M. et al. Proteome-wide covalent ligand discovery in native biological systems. Nature 534, 570-574 (2016). 16. Wang, C., Weerapana, E., Blewett, M. M. & Cravatt, B. F. A chemoproteomic platform to quantitatively map targets of lipid-derived electrophiles. Nat. Methods 11, 79-85 (2014). 17. Han, J. et al. ZNF313 is a novel cell cycle activator with an E3 ligase activity inhibiting cellular senescence by destabilizing p21 (WAF1.). Cell Death Differ. 20, 1055-1067 (2013). 18. Lee, M.-G. et al. XAF1 directs apoptotic switch of p53 signaling through activation of HIPK2 and ZNF313. Proc. Natl. Acad. Sci. U.S.A. 111, 15532-15537 (2014). 19. Huang, S. et al. The UbL-UBA Ubiquilin4 protein functions as a tumor suppressor in gastric cancer by p53-dependent and p53-independent regulation of p21. Cell Death Differ. 26, 516-530 (2019). 20. Abbas, T. & Dutta, A. p21 in cancer: intricate networks and multiple activities. Nat. Rev. Cancer 9, 400-414 (2009). 21. Guo, H., Tian, T., Nan, K. & Wang, W. p57: A multifunctional protein in cancer (Review). Int. J. Oncol. 36, 1321-1329 (2010). 22. Zengerle, M., Chan, K.-H. & Ciulli, A. Selective Small Molecule Induced Degradation of the BET Bromodomain Protein BRD4. ACS Chem. Biol. 10, 1770-1777 (2015). 23. Winter, G. E. et al. DRUG DEVELOPMENT. Phthalimide conjugation as a strategy for in vivo target protein degradation. Science 348, 1376-1381 (2015). 24. Havens, C. G. & Walter, J. C. Mechanism of CRL4(Cdt2), a PCNA-dependent E3 ubiquitin ligase. Genes Dev. 25, 1568-1582 (2011). 25. Kitagawa, K., Kotake, Y. & Kitagawa, M. Ubiquitin-mediated control of oncogene and tumor suppressor gene products. Cancer Sci. 100, 1374-1381 (2009). 26. Biswas, K. et al. The E3 Ligase CHIP Mediates p21 Degradation to Maintain Radioresistance. Mol. Cancer Res. MCR 15, 651-659 (2017). 27. Rodriguez, M. S. et al. The RING ubiquitin E3 RNF114 interacts with A20 and modulates NF-κB activity and T-cell activation. Cell Death Dis. 5, e1399 (2014). 28. Yang, Y. et al. The E3 ubiquitin ligase RNF114 and TAB1 degradation are required for maternal-to-zygotic transition. EMBO Rep. 18, 205-216 (2017). 29. Rape, M. Ubiquitylation at the crossroads of development and disease. Nat. Rev. Mol. Cell Biol. 19, 59-70 (2018). 30. Hughes, S. J. & Ciulli, A. Molecular recognition of ternary complexes: a new dimension in the structure-guided design of chemical degraders. Essays Biochem. 61, 505-516 (2017). 31. Gadd, M. S. et al. Structural basis of PROTAC cooperative recognition for selective protein degradation. Nat. Chem. Biol. 13, 514-521 (2017). 32. Nowak, R. P. et al. Plasticity in binding confers selectivity in ligand-induced protein degradation. Nat. Chem. Biol. 14, 706-714 (2018). 33. Jessani, N. et al. Carcinoma and stromal enzyme activity profiles associated with breast tumor growth in vivo. Proc. Natl. Acad. Sci. U.S.A. 101, 13756-13761 (2004). 34. Anderson, K. E., To, M., Olzmann, J. A. & Nomura, D. K. Chemoproteomics-Enabled Covalent Ligand Screening Reveals a Thioredoxin-Caspase 3 Interaction Disruptor That Impairs Breast Cancer Pathogenicity. ACS Chem. Biol. 12, 2522-2528 (2017). 35. Smith, P. K. et al. Measurement of protein using bicinchoninic acid. Anal. Biochem. 150, 76-85 (1985). 36. Xu, T. et al. ProLuCID: An improved SEQUEST-like algorithm with enhanced sensitivity and specificity. J. Proteomics 129, 16-24 (2015). 37. Bateman, L. A. et al. Chemoproteomics-enabled covalent ligand screen reveals a cysteine hotspot in reticulon 4 that impairs ER morphology and cancer pathogenicity. Chem. Commun. Camb. Engl. 53, 7234-7237 (2017). 38. Counihan, J. L., Wiggenhorn, A. L., Anderson, K. E. & Nomura, D. K. Chemoproteomics-Enabled Covalent Ligand Screening Reveals ALDH3A1 as a Lung Cancer Therapy Target. ACS Chem. Biol. 13(8), 1970-1977 (2018). 39. Roberts, A. M. et al. Chemoproteomic Screening of Covalent Ligands Reveals UBA5 As a Novel Pancreatic Cancer Target. ACS Chem. Biol. 12, 899-904 (2017). 40. Kokosza, K., Balzarini, J. & Piotrowska, D. G. Novel 5-Arylcarbamoyl-2-methylisoxazolidin-3-yl-3-phosphonates as Nucleotide Analogues. Nucleosides Nucleotides Nucleic Acids 33, 552-582 (2014). 41. Talaty, E. R., Young, S. M., Dain, R. P. & Stipdonk, M. J. V. A study of fragmentation of protonated amides of some acylated amino acids by tandem mass spectrometry: observation of an unusual nitrilium ion. Rapid Commun. Mass Spectrom. 25, 1119-1129 (2011). 42. Timokhin, V. I., Gastaldi, S., Bertrand, M. P. & Chatgilialoglu, C. Rate Constants for the β-Elimination of Tosyl Radical from a Variety of Substituted Carbon-Centered Radicals. J. Org. Chem. 68, 3532-3537 (2003). 43. Cee, V. J. et al. Systematic Study of the Glutathione (GSH) Reactivity of N-Arylacrylamides: 1. Effects of Aryl Substitution. J. Med. Chem. 58, 9171-9178 (2015). 44. Le Sann, C., Huddleston, J. & Mann, J. Synthesis and preliminary evaluation of novel analogues of quindolines as potential stabilisers of telomeric G-quadruplex DNA. Tetrahedron 63, 12903-12911 (2007). 45. Ikoma, M., Oikawa, M. & Sasaki, M. Synthesis and domino metathesis of functionalized 7-oxanorbornene analogs toward cis-fused heterocycles. Tetrahedron 64, 2740-2749 (2008). 46. Cho, S.-D. et al. A One-Pot Synthesis of Pyrido[2,3-b][1,4]oxazin-2-ones. J. Org. Chem. 68, 7918-7920 (2003). 47. Magolan, J., Carson, C. A. & Kerr, M. A. Total Synthesis of (±)-Mersicarpine. Org. Lett. 10, 1437-1440 (2008). 48. Longo, P. A., Kavran, J. M., Kim, M.-S. & Leahy, D. J. Transient mammalian cell transfection with polyethylenimine (PEI). Methods Enzymol. 529, 227-240 (2013). 49. Li, C. et al. FastCloning: a highly simplified, purification-free, sequence- and ligation-independent PCR cloning method. BMC Biotechnol. 11, 92 (2011). 50. Thomas, J. R. et al. A Photoaffinity Labeling-Based Chemoproteomics Strategy for Unbiased Target Deconvolution of Small Molecule Drug Candidates. Methods Mol. Biol. Clifton NJ 1647, 1-18 (2017). 51. Käll, L., Canterbury, J. D., Weston, J., Noble, W. S. & MacCoss, M. J. Semi-supervised learning for peptide identification from shotgun proteomics datasets. Nat. Methods 4, 923-925 (2007).

What is claimed is:

1. A targeted protein degrader comprising 1) a targeted protein binder and 2) an E3 Ubiquitin ligase binder, wherein the targeted protein binder is

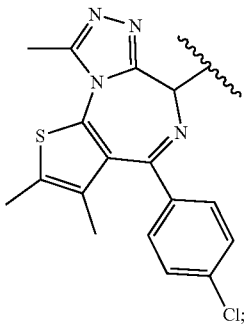 [SMILES: *C1N=C(c2ccc(Cl)cc2)c2c(sc(C)c2C)-n2c(C)nnc21]

wherein the E3 Ubiquitin ligase binder is a monovalent form of the formula:

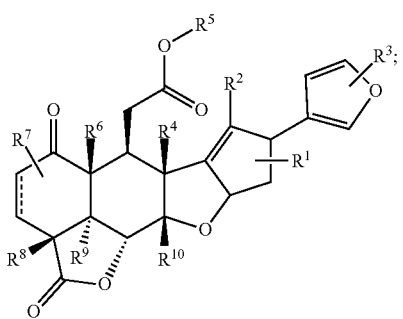

$R^1$, $R^2$, $R^3$, is a single bond or a double bond; and wherein the E3 Ubiquitin ligase is human RNF4 or human RNF114.

2. The targeted protein degrader of claim 1, wherein $R^1$, $R^2$, $R^3$, $R^4$, $R^5$, $R^6$, $R^7$, $R^8$, $R^9$, and $R^{10}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCBr$_2$, —OCHI$_2$, —OCHF$_2$, —OCH$_2$Cl, —OCH$_2$Br, —OCH$_2$I, —OCH$_2$F, —N$_3$, —SF$_5$, $R^{51}$-substituted or unsubstituted C$_1$-C$_8$ alkyl, $R^{51}$-substituted or unsubstituted 2 to 8 membered heteroalkyl, $R^{51}$-substituted or unsubstituted C$_3$-C$_8$ cycloalkyl, $R^{51}$-substituted or unsubstituted 3 to 8 membered heterocycloalkyl, $R^{51}$-substituted or unsubstituted C$_6$-C$_{10}$ aryl, or $R^{51}$-substituted or unsubstituted 5 to 10 membered heteroaryl; or a bond to the binder linker;

wherein only one $R^1$, $R^2$, $R^3$, $R^4$, $R^5$, $R^6$, $R^7$, $R^8$, $R^9$, or $R^{10}$ is a bond to the binder linker; and $R^{51}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 10 membered heteroaryl.

3. The targeted protein degrader of claim 1, wherein the E3 Ubiquitin ligase binder is a monovalent form of the formula:

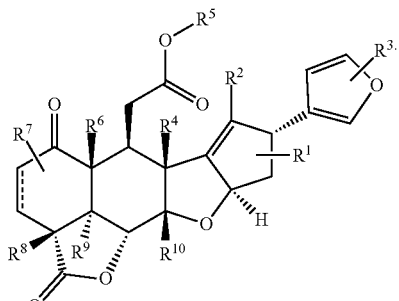

4. The targeted protein degrader of claim 2, wherein the E3 Ubiquitin ligase binder is a monovalent form of the formula:

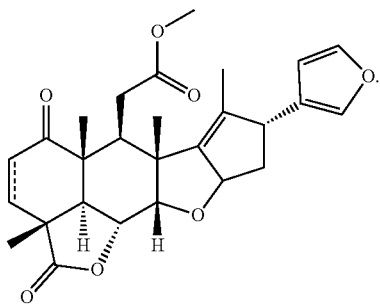

5. The targeted protein degrader of claim 2, wherein the E3 Ubiquitin ligase binder is a monovalent form of the formula:

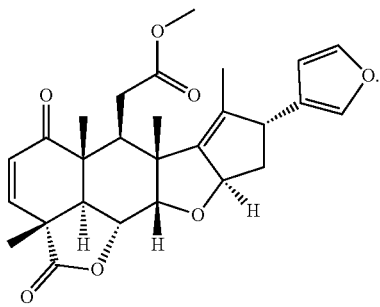

6. The targeted protein degrader of claim 2, wherein the E3 Ubiquitin ligase binder has the formula:

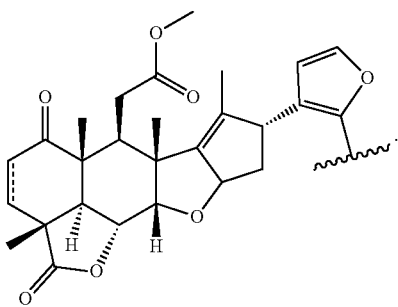

7. The targeted protein degrader of claim 2, wherein the E3 Ubiquitin ligase binder has the formula:

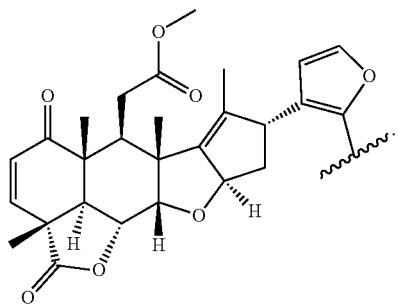

8. The targeted protein degrader of claim 1 wherein the E3 Ubiquitin ligase binder is capable of forming a covalent bond with a cysteine of an E3 Ubiquitin ligase.

9. The targeted protein degrader of claim 1, wherein the targeted protein binder and E3 Ubiquitin ligase binder are covalently bonded by a binder linker, wherein the binder linker is

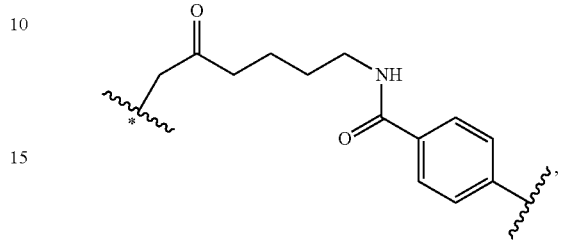

and the * indicates the point of attachment to the targeted protein binder.

10. The targeted protein degrader of claim 1 wherein the E3 Ubiquitin ligase is human RNF4.

11. The targeted protein degrader of claim 1, wherein the E3 Ubiquitin ligase is human RNF114.

12. The targeted protein degrader of claim 1, wherein the targeted protein binder is capable of binding a targeted protein associated with a disease, wherein the disease is breast cancer.

13. A pharmaceutical composition comprising a targeted protein degrader of claim 1 and a pharmaceutically acceptable excipient.

* * * * *